US010285950B2

(12) United States Patent
Frederick et al.

(10) Patent No.: US 10,285,950 B2
(45) **Date of Patent: *May 14, 2019**

(54) COMBINATIONS OF MRNAS ENCODING IMMUNE MODULATING POLYPEPTIDES AND USES THEREOF

(71) Applicant: ModernaTX, Inc., Cambridge, MA (US)

(72) Inventors: Joshua Frederick, Charlestown, MA (US); Ailin Bai, Newton, MA (US); Vladimir Presnyak, Manchester, NH (US); Stephen Hoge, Brookline, MA (US); Kerry Benenato, Sudbury, MA (US); Iain McFadyen, Arlington, MA (US); Ellalahewage Sathyajith Kumarasinghe, Harvard, MA (US); Susannah Hewitt, Jamaica Plain, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/227,810

(22) Filed: Dec. 20, 2018

(65) Prior Publication Data

US 2019/0111003 A1 Apr. 18, 2019

Related U.S. Application Data

(63) Continuation of application No. 15/995,889, filed on Jun. 1, 2018, now Pat. No. 10,172,808, which is a continuation of application No. PCT/US2017/033395, filed on May 18, 2017.

(60) Provisional application No. 62/404,175, filed on Oct. 4, 2016, provisional application No. 62/338,483, filed on May 18, 2016, provisional application No. 62/415,424, filed on Oct. 31, 2016, provisional application No. 62/338,496, filed on May 18, 2016, provisional application No. 62/338,506, filed on May 18, 2016, provisional application No. 62/438,942, filed on Dec. 23, 2016, provisional application No. 62/480,400, filed on Apr. 1, 2017, provisional application No. 62/443,693, filed on Jan. 17, 2017, provisional application No. 62/438,945, filed on Dec. 23, 2016, provisional application No. 62/472,513, filed on Mar. 16, 2017, provisional application No. 62/404,173, filed on Oct. 4, 2016, provisional application No. 62/338,467, filed on May 18, 2016.

(51) Int. Cl.

| | |
|---|---|
| ***A61K 48/00*** | (2006.01) |
| ***A61K 9/51*** | (2006.01) |
| ***C07K 14/54*** | (2006.01) |
| ***A61K 38/17*** | (2006.01) |
| ***A61K 38/20*** | (2006.01) |
| ***C07K 14/705*** | (2006.01) |
| ***A61P 35/00*** | (2006.01) |
| ***A61K 39/395*** | (2006.01) |
| ***A61K 9/00*** | (2006.01) |
| *A61K 39/00* | (2006.01) |

(52) U.S. Cl.

CPC .......... *A61K 9/5123* (2013.01); *A61K 9/0019* (2013.01); *A61K 9/5146* (2013.01); *A61K 38/177* (2013.01); *A61K 38/20* (2013.01); *A61K 38/208* (2013.01); *A61K 39/3955* (2013.01); *A61K 48/005* (2013.01); *A61P 35/00* (2018.01); *C07K 14/54* (2013.01); *C07K 14/5434* (2013.01); *C07K 14/70575* (2013.01); *A61K 2039/505* (2013.01); *A61K 2039/51* (2013.01); *A61K 2039/54* (2013.01); *A61K 2039/545* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 10,172,808 | B2 | 1/2019 | Frederick et al. |
| 2008/0025944 | A1 | 1/2008 | Hoerr et al. |
| 2018/0318229 | A1 | 11/2018 | Frederick et al. |
| 2018/0369374 | A1 | 12/2018 | Frederick et al. |
| 2019/0060246 | A1 | 2/2019 | Frederick et al. |

FOREIGN PATENT DOCUMENTS

| | | | |
|---|---|---|---|
| WO | 2013/053775 | A1 | 4/2013 |
| WO | 2017201325 | A1 | 11/2017 |
| WO | 2017201352 | A1 | 11/2017 |

OTHER PUBLICATIONS

U.S. Appl. No. 15/995,889, filed Jun. 1, 2018, Joshua Frederick.
U.S. Appl. No. 16/184,282, filed Nov. 8, 2018, Joshua Frederick.
U.S. Appl. No. 16/219,418, filed Dec. 13, 2018, Joshua Frederick.
U.S. Appl. No. 16/222,155, filed Dec. 17, 2018, Joshua Frederick.
U.S. Appl. No. 15/996,146, filed Jun. 1, 2018, Joshua P. Frederick.
U.S. Appl. No. 15/995,889, Sep. 21, 2018, J. Angell.
U.S. Appl. No. 15/996,146, Nov. 1, 2018, J. Angell.

(Continued)

*Primary Examiner* — J. E. Angell

(74) *Attorney, Agent, or Firm* — Nelson Mullins Riley & Scarborough LLP; Amy E. Mandragouras, Esq.; Ariana D. Harris

(57) ABSTRACT

The disclosure relates to compositions and methods for the preparation, manufacture and therapeutic use of combinations of immunomodulatory polynucleotides (e.g., mRNAs) encoding an immune response primer polypeptide (e.g., an interleukin 23 (IL-23) polypeptide or an interleukin 36γ (IL-36-gamma) polypeptide), and an immune response co-stimulatory signal polypeptide (e.g., an OX40L polypeptide).

20 Claims, 76 Drawing Sheets
(65 of 76 Drawing Sheet(s) Filed in Color)

Specification includes a Sequence Listing.

(56) References Cited

OTHER PUBLICATIONS

Andarini, S. et al., "Adenovirus Vector-Mediated in Vivo Gene Transfer of OX40 Ligand to Tumor Cells Enhances Antitumor Immunity of Tumor-Bearing Hosts," Cancer Research vol. 64:3281-3287 (2004).
Andries, O. et al., "N1-methyl pseudouridine-incorporated mRNA outperforms pseudouridine-incorporated mRNA by providing enhanced protein expression and reduced immunogenicity in mammalian cell lines and mice," Journal of Controlled Release, vol. 217: 337-344 (2015).
Charoensit, P. et al., "Enhanced growth inhibition of metastatic lung tumors by intravenous injection of ATRA-cationic liposome/IL-12 pDNA complexes in mice," Cancer Gene Therapy, vol. 17(7) 512-522 (2010).
Colombo, M. et al., "Interleukin-12 in anti-tumor immunity and immunotherapy," Cytokine and Growth Factor Reviews, vol. 13 (2):155-168 (2002).
Hara I et al., "Effectiveness of cancer vaccine therapy using cells transduced with the interleukin-12 gene combined with systemic interleukin-18 administration," Cancer Gene Therapy, vol. 7(1):83-90 (2000).
Hu, D. et al., "Immunoglobulin Expression and Its Biological Significance in Cancer Cells," Cellular and Molecular Immunology, vol. 5(5): 319-324 (2008).
International Preliminary Report on Patentability, PCT/US2017/033395, dated Nov. 20, 2018, 9 pages.
International Preliminary Report on Patentability, PCT/US2017/033425, dated Nov. 29, 2018, 12 pages.
International Search Report and Written Opinion, PCT/US2017/033395, dated Sep. 1, 2017, 15 pages.
International Search Report and Written Opinion, PCT/US2017/033425, dated Jul. 25, 2017, 16 pages.
Karkada M. et al., "A liposome-based platform, VacciMae(R), and its modified water-free platform DepoVax(TM) enhance efficacy of in vivo nucleic acid delivery", Vaccine, vol. 28(38):6176-6182 (2010).
Linch S. et al., "0X40 agonists and combination immunotherapy: Putting the pedal to the metal," Frontiers in Oncology, Frontiers Research Foundation, vol. 5:1-14 (2015).
McNamara, M. et al., "RNA-Based Vaccines in Cancer Immunotherapy," Journal of Immunology Research, vol. 2015, pp. 1-9 (2015).
Melero, I. et al., "Evolving synergistic combinations of targeted immunotherapies to combat cancer," Nature Reviews, Cancer, vol. 15(8):457-472 (2015).
Mendiratta, S. et al., "Combination of Interleukin 12 and Interferon [alpha] Gene Therapy Induces a Synergistic Antitumor Response against Colon and Renal Cell Carcinoma", Human Gene Therapy, vol. 11(13):1851-1862 (2000).
Meraz, I. et al., "Adjuvant Cationic Liposomes Presenting MPL and IL-12 Induce Cell Death, Suppress Tumor Growth, and Alter the Cellular Phenotype of Tumors in a Murine Model of Breast Cancer," Molecular Pharmaceutics, vol. 11(10):3484-3491(2014).
Ngiow, S et al."A balance of interleukin-12 and -23 in cancer," Trends in Immunology, vol. 34 (11):548-555 (2013).
Overwijk, W. W. et al., "Immunological and Antitumor Effects of IL-23 as a Cancer Vaccine Adjuvant," The Journal of Immunology, vol. 176 (9):5213-5222 (2006).
Sahin,U. et al., "mRNA-based therapeutics—developing a new class of drugs," Nature Reviews and Discovery, vol. 13 (10):759-780 (2014).
Shim, G. et al., "Application of cationic liposomes for delivery of nucleic acids," Asian Journal of Pharmaceutical Sciences, vol. 8 (2):72-80 (2013).
Tugues, S. et al., "New insights into IL-12-mediated tumor suppression," Call Death and Differentiation, Cell Death and Differentiation, vol. 22(2):237-246 (2014).
Wang J. et al., "Synergistic anti-tumor effect by combinatorial gene-gun therapy using IL-23 and IL-18 cDNA", Journal of Dermatological, vol. 36 (1):66-68 (2004).
Wang X. et al., "IL-36[gamma] Transforms the Tumor Microenvironment and Promotes Type 1 Lymphocyte-Mediated Antitumor Immune Respo," Cancer Cell, vol. 28(3):296-306 (2015).
Wiltrout, J. et al., "IL-12/IL-2 combination cytokine therapy for solid tumours: translation from bench to bedside," The Expert Opinion on Biological, Informa Healthcare, vol. 2 (5):513-524 (2012).
Weiss, J. et al., "Immunotherapy of cancer by IL-12-based cytokine combinations," Expert Opinion on Biological Therapy, vol. 7(11):1705-1721 (2007).
U.S. Appl. No. 16/184,282, Feb. 7, 2019, J. Angell.
U.S. Appl. No. 16/219,418, Feb. 25, 2019, J. Angell.
U.S. Appl. No. 16/222,155, Mar. 8, 2019, J. Angell.
U.S. Appl. No. 15/996,146, Feb. 20, 2019, J. Angell.

FIG. 9B
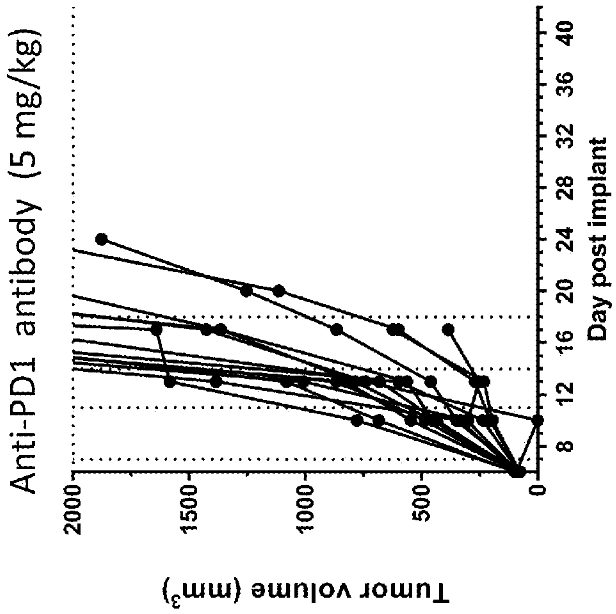
FIG. 9A
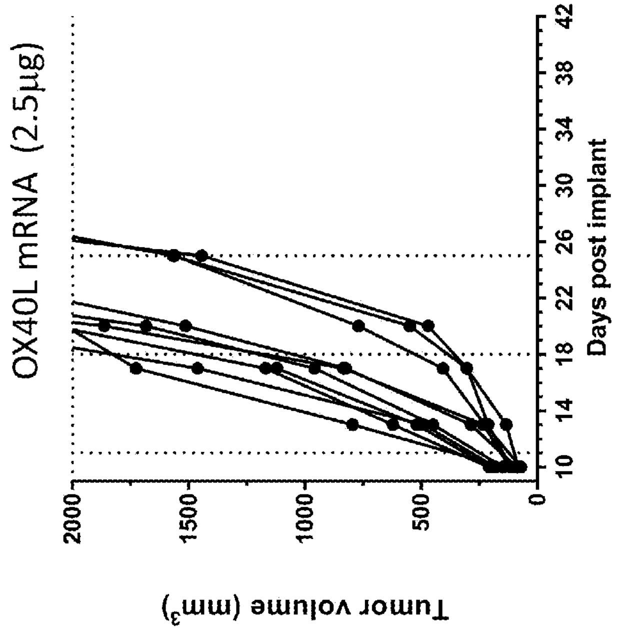
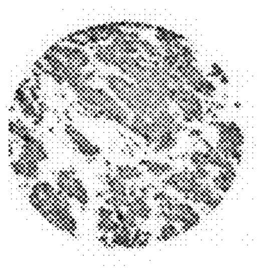
FIG. 9C

IL23 with miR122 (5µg)

IL23_miR122 : IL36γ_miR122 (2.5 µg each)

IL23_miR122 : IL36γ_miR122 : OX40L_miR122 (1.7 μg each)

CD86 activation on CD11b+ cDC2 in dLN iDC in tumor iDC in TdLN

CD86 activation on iDC in dLN

Negative control

No efficacy with αPD-L1 alone

COMBINATIONS OF MRNAS ENCODING IMMUNE MODULATING POLYPEPTIDES AND USES THEREOF

RELATED APPLICATIONS

This application is a Continuation of U.S. Continuation application Ser. No. 15/995,889 filed on Jun. 1, 2018, which is a continuation of International Application No. PCT/US2017/033395, filed May 18, 2017, which claims the benefit of U.S. Provisional Patent Application Ser. No. 62/338,496 filed May 18, 2016; U.S. Provisional Patent Application Ser. No. 62/338,506 filed May 18, 2016; U.S. Provisional Patent Application Ser. No. 62/338,467 filed May 18, 2016; U.S. Provisional Patent Application Ser. No. 62/338,483 filed May 18, 2016; U.S. Provisional Patent Application Ser. No. 62/404,173 filed Oct. 4, 2016; U.S. Provisional Patent Application Ser. No. 62/404,175 filed Oct. 4, 2016; U.S. Provisional Patent Application Ser. No. 62/415,424 filed Oct. 31, 2016; U.S. Provisional Patent Application Ser. No. 62/438,945 filed Dec. 23, 2016; U.S. Provisional Patent Application Ser. No. 62/438,942 filed Dec. 23, 2016; U.S. Provisional Patent Application Ser. No. 62/443,693 filed Jan. 7, 2017; U.S. Provisional Patent Application Ser. No. 62/472,513 filed Mar. 16, 2017 and U.S. Provisional Patent Application Ser. No. 62/480,400 filed Apr. 1, 2017. The entire contents of the above-referenced patent applications are incorporated herein by this reference.

STATEMENT REGARDING SEQUENCE LISTING

The instant application contains a Sequence Listing which has been submitted in ASCII format via EFS-Web and is hereby incorporated by reference in its entirety. Said ASCII copy, created on Dec. 20, 2018, is named MDN_712PCCN2_Sequence_Listing and is 219108 bytes in size.

BACKGROUND

Cancer is a disease characterized by uncontrolled cell division and growth within the body. In the United States, roughly a third of all women and half of all men will experience cancer in their lifetime. With the host of undesired consequences brought about by standard treatments such as chemotherapy and radiotherapy used today, genetic therapy for the manipulation of disease-related peptides and their functions provides a more targeted approach to disease diagnosis, treatment and management. However, gene therapy poses multiple challenges including undesirable immune response and safety concern due to the incorporation of the gene at random locations within the genome. Therefore, there is a need for an improved therapeutic approach to treat tumors.

BRIEF SUMMARY

The present disclosure provides mRNA therapeutics for the treatment of cancer. The mRNA therapeutics of the disclosure are particularly well-suited for the treatment of cancer as the technology provides for the intracellular delivery of mRNA encoding immune modulating polypeptides (for example, oncology-related polypeptides, including immune response stimulators, co-stimulatory factors, checkpoint inhibitors, and the like, useful in immuno-oncology ("IO")), followed by de novo synthesis of functional proteins within target cells, e.g., within target cells in tumors. The disclosure features therapeutic mRNAs having modified nucleotides to (1) minimize unwanted immune activation (e.g., the innate immune response associated with in vivo introduction of foreign nucleic acids) and (2) optimize the translation efficiency of mRNA to protein. Exemplary aspects of the disclosure feature therapeutic mRNAs having a combination of nucleotide modifications to reduce the innate immune response and sequence optimization, in particular, within the open reading frame (ORF) of therapeutic mRNAs encoding immune modulating polypeptides to enhance protein expression.

In other aspects, the mRNA therapeutic technology of the disclosure features delivery of mRNA(s) encoding immune modulating (e.g., oncology-related) polypeptides via a lipid nanoparticle (LNP) delivery system. In exemplary embodiments, the mRNA therapeutic technology of the disclosure features delivery of mRNA(s) encoding immune modulating polypeptides into tumors via a lipid nanoparticle (LNP) delivery system. The disclosure also features novel ionizable lipid-based LNPs which have improved properties when combined with mRNA(s) encoding immune modulating (e.g., oncology-related) polypeptides and administered in vivo, for example, cellular uptake, intracellular transport and/or endosomal release or endosomal escape. The LNP formulations of the disclosure also demonstrate reduced immunogenicity associated with the in vivo administration of LNPs.

Accordingly, the present disclosure features methods and compositions for treating cancer, in particular, immunotherapeutic methods and compositions. In some aspects, the disclosure features methods and compositions for treating cancer using a combination therapy that features two or more immune modulating (e.g., oncology-related) polynucleotides (e.g., mRNAs) encoding a first immune response primer polypeptide and a second, different, immune response primer polypeptide, and, optionally, a polynucleotide encoding an immune response co-stimulatory signal polypeptide and, optionally, a polynucleotide encoding a checkpoint inhibitor polypeptide or a polypeptide comprising a checkpoint inhibitor polypeptide. In some aspects, the disclosure provides an immunomodulatory composition comprising a polynucleotide encoding an Interleukin-23 (IL-23) polypeptide, a polynucleotide encoding an Interleukin-36 gamma (IL-36 gamma) polypeptide and, optionally, a polynucleotide encoding an OX40L polypeptide. In other aspects, the disclosure provides an immunomodulatory composition comprising a polynucleotide encoding an IL-23 polypeptide, a polynucleotide encoding an Interleukin 18 (IL-18) polypeptide and, optionally, a polynucleotide encoding an OX40L polypeptide.

Other aspects of the disclosure feature treatment with a polynucleotide mRNA encoding an IL-23 polypeptide in combination with mRNA encoding an IL-36 polypeptide. Other aspects of the disclosure feature treatment with mRNA encoding an IL-23 polypeptide in combination with mRNA encoding an IL-18 polypeptide. Yet other aspects of the disclosure feature treatment with mRNA encoding immune response primer polypeptides in combination with additional therapeutic agents, such as a checkpoint inhibitor polypeptide (e.g., anti-PD-1 antibody, anti-PDL-1 antibody, anti-CTLA4, or a combination thereof). Exemplary aspects feature treatment with lipid nanoparticle-(LNP-) encapsulated mRNAs. Exemplary aspects feature intratumoral administration of mRNAs in ionizable amino lipid-based LNPs.

In some aspects, the present disclosure provides methods of reducing or decreasing the size of a tumor or inhibiting tumor growth in a subject in need thereof by administering at least two polynucleotides, wherein the at least two polynucleotides are selected from a first polynucleotide encoding a first immune response primer polypeptide (e.g., an IL-23 polypeptide) and a second polynucleotide encoding a second immune response primer polypeptide (different from the first) e.g., an IL-36 gamma polypeptide or an IL-18 polypeptide and, optionally, a third polynucleotide encoding an immune response co-stimulatory signal polypeptide (e.g., an OX40L polypeptide).

In one embodiment, the first polynucleotide comprises an mRNA encoding the first polypeptide, the second polynucleotide comprises an mRNA encoding the second polypeptide, and/or the third polynucleotide comprises an mRNA encoding the third polypeptide. In one embodiment, the first polynucleotide, the second polynucleotide, and/or the third polynucleotide comprise at least one chemically modified nucleoside. In some embodiments, the at least one chemically modified nucleoside is selected from the group consisting of pseudouridine, N1-methylpseudouridine, 5-methylcytosine, 5-methoxyuridine, and a combination thereof.

In one aspect, the disclosure provides a composition, e.g., an immunomodulatory composition, comprising at least two polynucleotides (e.g., at least two mRNAs), wherein the at least two polynucleotides are selected from the group consisting of:

(i) at least one polynucleotide encoding a first immune response primer polypeptide and at least one polynucleotide encoding a second immune response primer polypeptide (different from the first immune response primer polypeptide) ("a doublet");

(ii) at least one polynucleotide encoding a first immune response primer polypeptide, at least one polynucleotide encoding a second immune response primer polypeptide (different from the first), and at least one polynucleotide encoding an immune response co-stimulatory signal polypeptide ("a triplet").

In some aspects, the composition further comprises at least one polynucleotide encoding a checkpoint inhibitor polypeptide. In some aspects, the composition is administered to subjects in need thereof in combination with another cancer therapy, such as a polypeptide comprising a checkpoint inhibitor polypeptide (e.g., an anti-PD-1 antibody, an anti-PDL-1 antibody, an anti-CTLA4 antibody, or a combination thereof).

In one aspect, the composition comprises at least one polynucleotide (e.g., an mRNA) encoding a first immune response primer polypeptide and at least one polynucleotide (e.g., an mRNA) encoding a second immune response primer polypeptide (different from the first immune response primer polypeptide), wherein the first and second immune response primer polypeptides have one or more activities selected from the group consisting of:

(a) priming dendritic cells;

(b) promoting dendritic cell maturation;

(c) promoting antigen presenting cell cytokine and/or chemokine production;

(d) expanding or maintaining Th17 cells;

(e) enhancing Th1 and/or Th9 differentiation; and (f) any combination of (a)-(f).

In one aspect, the immune response primer polypeptide is an IL-12 family member. In one embodiment, the IL-12 family member is a polypeptide selected from the group consisting of IL-12, IL-23, IL-12p40 subunit, IL-23p19 subunit, IL-27, IL-35, and combinations thereof. In one embodiment, the immune response primer polypeptide is IL-23. In one embodiment, the IL-23 polypeptide comprises the amino acid sequence of SEQ ID NO: 1, SEQ ID NO: 5 or SEQ ID NO: 140. In one embodiment, the IL-23 polypeptide is encoded by a nucleotide sequence comprising the nucleotide sequence shown in SEQ ID NO: 141 or 142.

In other aspects, the immune response primer polypeptide is an IL-1 family member. In one embodiment, the IL-1 family member is a polypeptide selected from the group consisting of IL-1α, IL-1β, IL-1Ra, IL-18, IL-33, IL-36Ra, IL-36α, IL-36β, IL-36γ, IL-37, IL-38, and combinations thereof. In one embodiment, the immune response primer polypeptide is an IL-36-gamma polypeptide or an IL-18 polypeptide. In one embodiment, the immune response primer polypeptide is IL-36-gamma polypeptide. In one embodiment, the IL-36-gamma polypeptide comprises the amino acid sequence shown in SEQ ID NO: 16. In one embodiment, the IL-36-gamma polypeptide is encoded by a nucleotide sequence comprising the nucleotide sequence shown in SEQ ID NO: 143 or 144. In one embodiment, the immune response primer polypeptide is IL-18. In one embodiment, the IL-18 polypeptide comprises the amino acid sequence shown in SEQ ID NO: 147, 149, 151 or 153. In one embodiment, the IL-18 polypeptide is encoded by a nucleotide sequence selected from SEQ ID NO: 148 and 155-162.

In one aspect the disclosure provides a composition (e.g., an immune modulatory composition) comprising at least two polynucleotides (e.g., two mRNAs) encoding a first immune response primer polypeptide and a second immune response primer polypeptide, wherein the first immune response primer polypeptide is an IL-12 family member and the second immune response primer polypeptide is an IL-1 family member. In one embodiment, the first immune response primer polypeptide is an IL-23 polypeptide and the second immune response primer polypeptide is an IL-36-gamma polypeptide. In one embodiment, the first immune response primer polypeptide is an IL-23 polypeptide and the second immune response primer polypeptide is an IL-18 polypeptide.

In another aspect, the disclosure provides a composition (e.g., an immune modulatory composition) comprising at least three polynucleotides (e.g., three mRNAs) encoding at least one polynucleotide encoding a first immune response primer polypeptide, at least one polynucleotide encoding a second immune response primer polypeptide (different from the first), and at least one polynucleotide encoding an immune response co-stimulatory signal polypeptide. In some aspects, the immune response co-stimulatory signal polypeptide has at least one activity selected from the group consisting of:

(a) activating, stimulating, promoting or enhancing T cell proliferation, T cell survival, T cell recruitment, or combination thereof; and/or (b) activating, stimulating, promoting or enhancing NK cell proliferation, NK cell survival, NK cell recruitment, or combination thereof.

In some aspects, the immune response co-stimulatory signal polypeptide has at least one activity selected from the group consisting of:

(c) promoting or enhancing T cell expansion and/or function;

(d) promoting or enhancing Th1, Th2 and/or Th9 cell development;

(e) inhibiting or suppressing Treg development and/or activity;

(f) promoting or enhancing development and/or activity of memory cells; and (g) any combination of (c)-(f).

In one embodiment, the immune response co-stimulatory signal polypeptide is selected from the group consisting of OX40L, CD80, IL-15, and combinations thereof. In one embodiment, the immune response co-stimulatory signal polypeptide is selected from the group consisting of OX40L, CD80, IL-15, and combinations thereof. In one embodiment, the immune response co-stimulatory signal polypeptide is OX40L. In one embodiment, the OX40L polypeptide comprises the amino acid sequence shown in SEQ ID NO: 21. In one embodiment, the OX40L polypeptide is encoded by a nucleotide sequence comprising the nucleotide sequence shown in SEQ ID NO: 145 or 146.

In one aspect, the disclosure provides a composition (e.g., an immune modulatory composition) comprising at least three polynucleotides (e.g., three mRNAs) encoding a first immune response primer polypeptide, a second immune response primer polypeptide and an immune response co-stimulatory signal polypeptide, wherein the first immune response primer polypeptide is an IL-23 polypeptide, the second immune response primer polypeptide is an IL-18 polypeptide, and the immune response co-stimulatory signal polypeptide is OX-40L. In another aspect, the disclosure provides a composition (e.g., an immunomodulatory composition) comprising at least three polynucleotides (e.g., three mRNAs) encoding a first immune response primer polypeptide, a second immune response primer polypeptide and an immune response co-stimulatory signal polypeptide, wherein the first immune response primer polypeptide is IL-23 polypeptide, the second immune response primer polypeptide is IL-36-gamma polypeptide, and the immune response co-stimulatory signal polypeptide is OX-40L. In other embodiments, the composition further comprises a polynucleotide (e.g., mRNA) encoding a checkpoint inhibitor polypeptide.

In other embodiments, the disclosure provides a composition for reducing the size of a tumor or inhibiting growth of a tumor, the composition comprising at least two polynucleotides (e.g., two mRNAs) encoding at least a first and a second polypeptide, wherein the at least two polynucleotides are selected from the group consisting of:

(i) a polynucleotide encoding an IL-23 polypeptide, (ii) a polynucleotide encoding an IL-36gamma polypeptide;

(iii) a polynucleotide encoding an IL-18 polypeptide;

(iv) a polynucleotide encoding an OX40L polypeptide;

(v) a polynucleotide encoding a CD80 polypeptide; and (vi) a polynucleotide encoding an anti-CTLA4 antibody; and, (vii) a combination thereof.

In one embodiment, the at least two polynucleotides are selected from the group consisting of:

(i) a polynucleotide encoding an IL-23 polypeptide, (ii) a polynucleotide encoding an IL-36gamma polypeptide;

(iii) a polynucleotide encoding an IL-18 polypeptide;

(iv) a polynucleotide encoding an OX40L polypeptide; and (v) a combination thereof.

In yet another embodiment, the at least two polynucleotides are selected from the group consisting of:

(i) a polynucleotide encoding an IL-23 polypeptide, (ii) a polynucleotide encoding an IL-36gamma polypeptide;

(iii) a polynucleotide encoding an OX40L polypeptide; and (iv) a combination thereof.

In another embodiment, the at least two polynucleotides are selected from the group consisting of:

(i) a polynucleotide encoding an IL23 polypeptide and a polynucleotide encoding an IL36gamma polypeptide;

(ii) a polynucleotide encoding an IL23 polypeptide and a polynucleotide encoding an OX40L polypeptide;

(iii) a polynucleotide encoding IL36gamma polypeptide and polynucleotide encoding an OX40L polypeptide;

(iv) a polynucleotide encoding an IL23 polypeptide and a polynucleotide encoding an IL18 polypeptide;

(v) a polynucleotide encoding an IL36gamma polypeptide and a polynucleotide encoding an IL18 polypeptide; and (vi) a polynucleotide encoding an IL18 polypeptide and a polynucleotide encoding an OX40L polypeptide.

In another embodiment, the disclosure provides a composition for reducing the size of a tumor or inhibiting growth of a tumor, the composition comprising at least three polynucleotides (e.g., three mRNAs) encoding at least a first, second and third polypeptides, wherein the at least three polynucleotides are selected from the group consisting of:

(i) a polynucleotide encoding an IL23 polypeptide, a polynucleotide encoding an IL36gamma polypeptide, and a polynucleotide encoding an OX40L polypeptide; and (ii) a polynucleotide encoding an IL23 polypeptide and a polynucleotide encoding an IL18 polypeptide, and a polynucleotide encoding an OX40L polypeptide.

In some aspects, the polynucleotide encoding an IL-23 polypeptide comprises: (i) an IL-12p40 polypeptide; (ii) an IL-23p19 polypeptide; or (iii) both an IL-12p40 polypeptide and an IL-23p19 polypeptide. In one aspect, the polynucleotide encoding an IL-23 polypeptide comprises an IL-12p40 polypeptide, an IL-23p19 polypeptide and a linker operatively positioned between the IL-12p40 polypeptide and the IL-23p19 polypeptide. In one aspect, the linker is a Gly/Ser linker (e.g., G4S), having an amino acid sequence as shown in any of SEQ ID NOs: 136-139). In one aspect, the polynucleotide encoding an IL-23 polypeptide comprises the amino acid sequence shown in SEQ ID NO: 140. In other aspects, the polynucleotide encoding an IL-23 polypeptide comprises the nucleotide sequence shown in SEQ ID NO: 141.

In some aspects, the polynucleotide encoding an IL-18 polypeptide comprises a heterologous signal sequence. In one aspect, the polynucleotide encoding an IL-18 polypeptide comprises the amino acid sequence shown in SEQ ID NO: 147, 149, 151 or 153. In one aspect, the polynucleotide encoding an IL-18 polypeptide comprises the nucleotide sequence selected from SEQ ID NO: 148 and 155-162.

In some aspects, the polynucleotide encoding an IL-36gamma polypeptide comprises a heterologous signal sequence. In one aspect, the polynucleotide encoding an IL36-gamma polypeptide comprises the amino acid sequence shown in SEQ ID NO: 16. In one aspect, the polynucleotide encoding an IL-36gamma polypeptide comprises the nucleotide sequence shown in SEQ ID NO: 143.

In one aspect, the polynucleotide encoding an OX40L polypeptide comprises the amino acid sequence shown in SEQ ID NO: 21. In one embodiment, the polynucleotide encoding an OX40L polypeptide comprises the nucleotide sequence shown in SEQ ID NO: 145.

In one aspect, the disclosure provides a composition e.g., for reducing the size of a tumor or inhibiting growth of a tumor, the composition comprising at least three polynucleotides (e.g., three mRNAs) encoding at least a first, second and third polypeptides, wherein the at least three polynucleotides comprise a first polynucleotide encoding OX40L, a second polynucleotide encoding an IL-23 polypeptide, and a third polynucleotide encoding IL-36gamma, wherein the first, second and third polynucleotides are present in the composition at a mass ratio of approximately 1:1:2, respectively. In one embodiment, the first and second polynucleotides, encoding OX40L and IL-23 respectively, are present in the composition in approximately equal mass amounts and the third polynucleotide, encoding IL-36gamma, is present in the composition at a higher mass amount than the first and third polynucleotides. Additional mass ratios for the composition are disclosed herein.

Other aspects of the disclosure relate to a lipid nanoparticle comprising any of the foregoing or related compositions. In some aspects, the lipid nanoparticle is formulated with a pharmaceutically acceptable carrier or excipient. In some aspects, the lipid nanoparticle is formulated for intratumoral administration (iTu).

In one aspect the disclosure provides a lipid nanoparticle comprising:

a polynucleotide encoding a human OX40L polypeptide, wherein the polynucleotide comprises an ORF encoding a human OX40L polypeptide; a polynucleotide encoding a human IL23 polypeptide, wherein the polynucleotide comprises an ORF encoding a human IL-12p40 polypeptide operably linked to a human IL-23p19 polypeptide; and a polynucleotide encoding a human IL-36 gamma polypeptide, wherein the polynucleotide comprises an ORF encoding a human IL-36 gamma polypeptide.

In some aspects, the human IL-12p40 polypeptide is operably linked to the human IL-23p19 polypeptide by a peptide linker. In some aspects, the IL-12p40 polypeptide is located at the 5' terminus of the IL-23p19 polypeptide or the linker (e.g., peptide linker). In other aspects, the IL-12p40 polypeptide is located at the 5' terminus of the IL-23p19 polypeptide or the linker (e.g., peptide linker). In some aspects, the linker is a peptide linker, for example, a Gly/Ser linker (e.g., G6S). In some aspects, Gly/Ser linker comprises (GnS)m, wherein n is 1, 2 3, 4, 5, 6, 7, 8, 9, 10, 15, or 20 and m is 1, 2, 3, 4, 5, 6, 7, 8, 9, 10, 15, or 20. In some aspects, the Gly/Ser linker comprises (GnS)m, and wherein n is 6 and m is 1 (i.e., G6S).

In related aspects, a polynucleotide comprising an ORF encoding a human IL23 polypeptide or a polynucleotide comprising an ORF encoding a human IL-36 gamma polypeptide further comprises a signal peptide. In some aspects, the signal peptide is a heterologous signal peptide, for example a signal peptide derived from human immunoglobulin kappa light chain variable region, hIGVK4.

In some aspects, the human OX40L polypeptide comprises an amino acid sequence set forth in SEQ ID NO: 21. In some aspects, the human IL-12p40 polypeptide comprises an amino acid sequence set forth in SEQ ID NO: 1. In some aspects, the human IL-23p19 polypeptide comprises an amino acid sequence set forth in SEQ ID NO: 5. In some aspects, the human IL-36 gamma polypeptide comprises an amino acid sequence set forth in SEQ ID NO: 16.

In some aspects, the disclosure provides any of the foregoing or related polynucleotides further comprising one or more microRNA (miRNA) binding sites. In some aspects, the miRNA binding site is a miR-122 binding site (e.g., a miR-122-3p binding site, a miR-122-5p binding site or both). In some embodiments, the miR binding site is at least one miR-122-5p binding site. In some embodiments the polynucleotide comprises a 3' UTR comprising at least one miR-122-5p binding site. In some aspects, the miR-122-5p binding site comprises the nucleotide sequence shown in SEQ ID NO: 26. In some aspects, the polynucleotide comprises a 3' UTR comprising the nucleotide sequence shown in SEQ ID NO: 120. In one aspect, the polynucleotide comprises a 5' UTR comprising the nucleotide sequence shown in SEQ ID NO: 27.

In other aspects, the disclosure provides use of any of the foregoing or preceding compositions or lipid nanoparticles as described herein in the manufacture of a medicament for treating or delaying progression of cancer in an individual, wherein the medicament comprises the composition or lipid nanoparticle and an optional pharmaceutically acceptable carrier, and wherein the treatment comprises administration of the medicament in combination with a composition comprising a checkpoint inhibitor polypeptide (e.g., an anti-PD-1 antibody, an anti-PDL-1 antibody, an anti-CTLA4 antibody, or a combination thereof), and an optional pharmaceutically acceptable carrier.

In some aspects, the disclosure provides a kit comprising a container comprising a polynucleotide (e.g., an mRNA) composition or a lipid nanoparticle comprising polynucleotides as (e.g., mRNAs) as disclosed herein, and an optional pharmaceutically acceptable carrier, and a package insert comprising instructions for administration of the lipid nanoparticle or pharmaceutical composition for treating or delaying progression of cancer in an individual. In some aspects, the package insert further comprises instructions for administration of the pharmaceutical composition in combination with a composition comprising a checkpoint inhibitor polypeptide and an optional pharmaceutically acceptable carrier for treating or delaying progression of cancer in an individual.

In yet other aspects, the disclosure provides a kit comprising a medicament comprising any of the foregoing or preceding compositions or lipid nanoparticles as described herein and an optional pharmaceutically acceptable carrier, and a package insert comprising instructions for administration of the medicament alone or in combination with a composition comprising a checkpoint inhibitor polypeptide (e.g., an anti-PD-1 antibody, an anti-PDL-1 antibody, an anti-CTLA4 antibody, or a combination thereof), and an optional pharmaceutically acceptable carrier for treating or delaying progression of cancer in an individual. In some aspects, the kit further comprises a package insert comprising instructions for administration of the first medicament and the second medicament for treating or delaying progression of cancer in an individual.

Other aspects of the disclosure relate to a composition comprising any of the foregoing or preceding lipid nanoparticles as described herein and an optional pharmaceutically acceptable carrier for use in treating or delaying progression of cancer in an individual, wherein the treatment comprises administration of the lipid nanoparticle in combination with a second composition, wherein the second composition comprises a checkpoint inhibitor polypeptide (e.g., an anti-PD-1 antibody, an anti-PDL-1 antibody, an anti-CTLA4 antibody, or a combination thereof), and an optional pharmaceutically acceptable carrier.

In some aspects, the checkpoint inhibitor polypeptide inhibits PD1, PD-L1, CTLA4, or a combination thereof. In one embodiment, the checkpoint inhibitor polypeptide is an antibody or a polynucleotide encoding the antibody. In one embodiment, the antibody is an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In one embodiment, the anti-PD-L1 antibody is atezolizumab, avelumab, or durvalumab. In one embodiment, the anti-CTLA-4 antibody is tremelimumab or ipilimumab. In one embodiment, the anti-PD1 antibody is nivolumab or pembrolizumab.

In various embodiments of the composition, the polynucleotides within the composition are mRNA, wherein each mRNA includes at least one chemical modification. In one embodiment, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some aspects, the mRNA comprises at least one chemically modified nucleoside, wherein the at least one chemically modified nucleoside is selected from the group consisting of pseudouridine, N1-methylpseudouridine, 5-methylcytosine, 5-methoxyuridine, and a combination thereof. In some aspects, the at least one chemically modified nucleoside is N1-methylpseudouridine. In some aspects, the polynucleotide is a fully modified N1-methylpseudouridine mRNA. Additional chemical modifications are disclosed herein.

In various embodiments of the composition, the composition is formulated in a lipid nanoparticle carrier. For example, a composition comprising a first and second polynucleotide, and optionally a third polynucleotide, as described herein, are formulated such that all polynucleotides within the composition are carried by the same lipid nanoparticle carrier. In one embodiment, the lipid nanoparticle carrier comprises a molar ratio of about 20-60% ionizable amino lipid: 5-25% phospholipid: 25-55% sterol; and 0.5-15% PEG-modified lipid. In one embodiment, the ionizable amino lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)-heptadecanedioate (L319). In one embodiment, the ionizable amino lipid is Compound 18.

In other aspects, the lipid nanoparticle comprises a molar ratio of about 20-60% ionizable amino lipid: 5-25% phospholipid: 25-55% sterol; and 0.5-15% PEG-modified lipid. In other aspects, the lipid nanoparticle carrier comprises a molar ratio of about 20-60% Compound 18: 5-25% phospholipid: 25-55% cholesterol; and 0.5-15% PEG-modified lipid. In other aspects, the lipid nanoparticle carrier comprises a molar ratio of about 50% ionizable amino lipid: about 10% phospholipid: about 38.5% cholesterol; and about 1.5% PEG-modified lipid. In other aspects, the lipid nanoparticle carrier comprises a molar ratio of about 50% Compound 18: about 10% phospholipid: about 38.5% cholesterol; and about 1.5% PEG-modified lipid. In other aspects, the lipid nanoparticle carrier comprises a molar ratio of about 49.83% ionizable amino lipid: about 9.83% phospholipid: about 30.33% cholesterol; and about 2.0% PEG-modified lipid. In other aspects, the lipid nanoparticle carrier comprises a molar ratio of about 49.83% Compound 18: about 9.83% phospholipid: about 30.33% cholesterol; and about 2.0% PEG-modified lipid.

In another aspect, the invention pertains to a method of reducing or decreasing a size of a tumor or inhibiting a tumor growth in a subject in need thereof comprising administering to the subject any of the compositions described herein. In one embodiment, the composition is administered intratumorally. In another embodiment, the composition is administered regionally (i.e., into the region in which the tumor is growing), for example the composition can be administered intraperitoneally for tumors in the peritoneal cavity. In one embodiment, the tumor is a hepatocellular carcinoma. In another embodiment, the tumor is an ovarian tumor, a colon tumor or a disseminated gastric tumor. Other suitable tumors and cancers for treatment are disclosed herein.

In some embodiments, the IL-23 polypeptide comprises an IL-12p40 subunit comprising an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of binding to an IL-23p19 subunit and forming IL-23, which has an IL-23 activity. In other embodiments, the IL-23 polypeptide comprises an IL-23p19 subunit comprising an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of binding to an IL-12p40 subunit and forming IL-23, which has an IL-23 activity. In some embodiments, the IL-12p40 subunit and the IL-23P19 subunit are on a single polypeptide chain or two different chains.

In some embodiments, the IL-36-gamma polypeptide comprises an amino acid sequence at least 50%, at least 60%, at least 70%, at least 80%, at least 85%, at least 90%, at least 95%, at least 99%, or 100% identical to a sequence listed in Table 1, wherein the amino acid sequence has IL-36-gamma activity.

In some embodiments, the method of the disclosure further comprises administering a third protein or a third polynucleotide encoding the third protein. In one embodiment, the third protein comprises an OX40L polypeptide. In another embodiment, the OX40L polypeptide comprises an amino acid sequence at least 50%, at least 60%, at least 70%, at least 80%, at least 85%, at least 90%, at least 95%, at least 99%, or 100% identical to a sequence listed in Table 1A, wherein the amino acid sequence has a OX40L activity.

In certain embodiments, the first polynucleotide (e.g., mRNA), the second polynucleotide (e.g., mRNA), and/or the third polynucleotide (e.g., mRNA) further comprise a nucleic acid sequence comprising a miRNA binding site, e.g., miR-122, e.g., aacgccauua ucacacuaaa ua (SEQ ID NO: 23) or uggaguguga caaugguguu ug (SEQ ID NO: 25).

The first polynucleotide and/or the second polynucleotide and/or the third polynucleotide can further comprise a 5' UTR, a 3' UTR, a 5' terminal cap, and/or a 3' polyA tail. In other embodiments, the first polynucleotide (e.g., mRNA), the second polynucleotide (e.g., mRNA), and/or the third polynucleotide (e.g., mRNA) are codon optimized, in vitro transcribed, chimeric, or circular.

In some embodiments, the first polynucleotide (e.g., mRNA), the second polynucleotide (e.g., mRNA), and/or the third polynucleotide (e.g., mRNA) is formulated with a delivery agent, e.g., a lipid nanoparticle. In other embodiments, the delivery agent comprises a compound having formula (I)

(I)

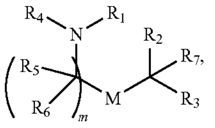

or a salt or stereoisomer thereof, wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —N(R)C(O)$N(R)_2$, —N(R)C(S)$N(R)_2$, —$N(R)R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)S$(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl; each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In other embodiments, the delivery agent comprising a compound having the formula (I)

(I)

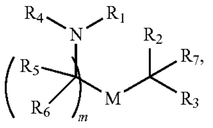

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —N(R)C(O)$N(R)_2$, —N(R)C(S)$N(R)_2$, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, the compound is of Formula (IA):

(IA)

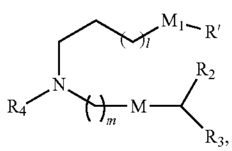

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_n$Q, in which n is 1, 2, 3, 4, or 5 and Q is OH, —NHC(S)$N(R)_2$, or —NHC(O)N(R)$_2$, —NHC(O)N(R)$_2$, —N(R)C(O)R, —N(R)S(O)$_2$R, —N(R)R$_8$, —NHC(═NR$_9$)N(R)$_2$, —NHC(═CHR$_9$)N(R)$_2$, —OC(O)N(R)$_2$, —N(R)C(O)OR, heteroaryl or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (IA), or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_n$Q, in which n is 1, 2, 3, 4, or 5 and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (II):

(II)

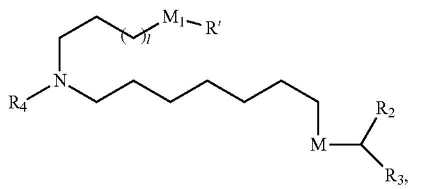

or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_n$Q, in which n is 2, 3, or 4 and Q is OH, —NHC(S)N(R)$_2$, or —NHC(O)N(R)$_2$, —N(R)C(O)R, —N(R)S(O)$_2$R, —N(R)R$_8$, —NHC(═NR$_9$)N(R)$_2$, —NHC(═CHR$_9$)N(R)$_2$, —OC(O)N(R)$_2$, —N(R)C(O)OR, heteroaryl or heterocycloalkyl;

M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the compound is of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or —$(CH_2)_n$Q, in which n is 2, 3, or 4 and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, $M_1$ is M'.

In some embodiments, M and M' are independently —C(O)O— or —OC(O)—.

In some embodiments, l is 1, 3, or 5.

In some embodiments, the compound is selected from the group consisting of Compound 1 to Compound 232, salts and stereoisomers thereof, and any combination thereof. In some embodiments, the compound is selected from the group consisting of Compound 1 to Compound 147, salts and stereoisomers thereof, and any combination thereof.

In certain embodiments, the delivery agent comprises the compound of the Formula (IIa), (IIa)

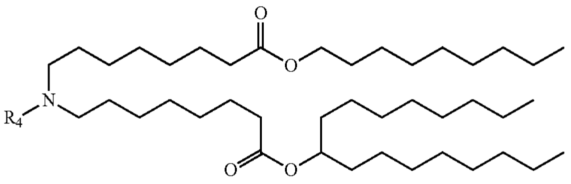

or a salt or stereoisomer thereof.

In certain embodiments, the delivery agent comprises the compound of the Formula (IIb), (IIb)

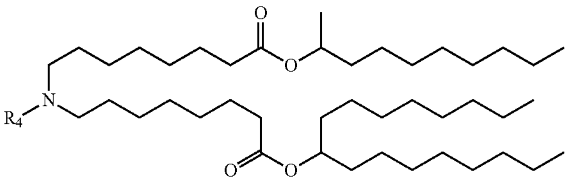

or a salt or stereoisomer thereof.

In certain embodiments, the delivery agent comprises the compound of the Formula (IIc) or (IIe), (IIc)

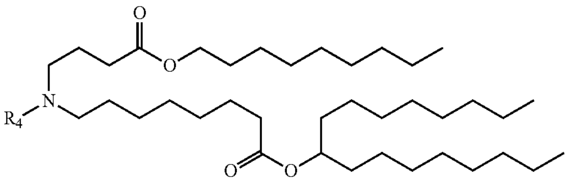

(IIe)

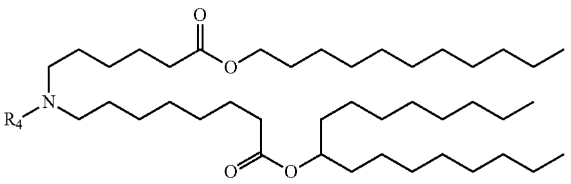

or a salt or stereoisomer thereof.

In some embodiments, $R_4$ is as described herein. In some embodiments, $R_4$ is selected from —$(CH_2)_n$Q and —$(CH_2)_n$CHQR.

In certain embodiments, the delivery agent comprises the compound of the Formula (IId), (IId)

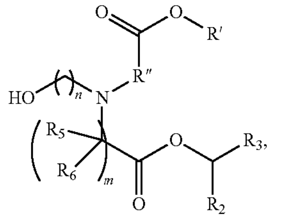

or a salt or stereoisomer thereof, wherein n is selected from 2, 3, and 4, and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound is of the Formula (IId), or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined herein.

In some embodiments, $R_2$ is $C_8$ alkyl.

In some embodiments, $R_3$ is $C_5$ alkyl, $C_6$ alkyl, $C_7$ alkyl, $C_8$ alkyl, or $C_9$ alkyl.

In some embodiments, m is 5, 7, or 9.

In some embodiments, each $R_5$ is H.

In some embodiments, each $R_6$ is H.

In other embodiments, the delivery agent further comprises a phospholipid, a structural lipid, a PEG lipid, an ionizable lipid, and/or a quaternary amine compound.

The disclosure further comprises a composition comprising the first polynucleotide (e.g., mRNA) disclosed herein, the second polynucleotide (e.g., mRNA) disclosed herein, the third polynucleotide (e.g., mRNA) enclosed herein, or combinations thereof, wherein the first polynucleotide, the second polynucleotide, and/or the third polynucleotide are formulated in the delivery agent disclosed herein.

The disclosure further comprises a composition comprising the first polynucleotide (e.g., mRNA) disclosed herein, the second polynucleotide (e.g., mRNA) disclosed herein, and the third polynucleotide (e.g., mRNA) disclosed herein, wherein the first polynucleotide, the second polynucleotide, and the third polynucleotide are formulated in the delivery agent disclosed herein.

The present disclosure also discloses a kit comprising the composition disclosed herein and instructions to use according to the method disclosed herein.

In some embodiments of the method of the present disclosure, the compositions of the present disclosure, or the kit of the present disclosure, the administration of the polynucleotides to a subject in need thereof results in (i) increase in granulocyte level in one or more samples obtained from the subject after administration of doublet or triplet relative to a threshold level or relative to the level after administration of a single polynucleotide encoding an IL-23, an IL-36-gamma, or an OX40L polypeptide; (ii) increase in cross-presenting dendritic cell level in one or more samples obtained from the subject after administration of doublet or triplet relative to a threshold level or relative to the level after administration of a single polynucleotide encoding an IL-23, an IL-36-gamma, or an OX40L polypeptide; (iii) increase in effector to suppressor T cell ratio in one or more samples obtained from the subject after administration of doublet or triplet relative to a threshold level or relative to the ratio after administration of a single polynucleotide encoding an OX40L polypeptide; (iv) increase in effector memory T cell level in one or more samples obtained from the subject after administration of doublet or triplet relative to a threshold level or relative to the level after administration of a single polynucleotide encoding an OX40L polypeptide; (v) increase in PDL1 expression level in one or more samples obtained from the subject after administration of doublet or triplet relative to a threshold level or relative to the level after administration of a single polynucleotide encoding an IL-23, an IL-36-gamma, or an OX40L polypeptide; or (vi) a combination thereof.

The present disclosure also provides a method of reducing or decreasing a size of a tumor or inhibiting a tumor growth in a subject in need thereof comprising administering to the subject a composition comprising (a) two polynucleotides in combination (doublet), wherein the first polynucleotide encodes a first protein comprising an interleukin-23 polypeptide (IL-23), and the second polynucleotide encodes a second protein comprising an interleukin-36-gamma polypeptide (IL-36-gamma); or, (b) three polynucleotides in combination (triplet), where the first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide (OX40L), wherein the administration of the doublet or triplet to the subject results in (i) increase in granulocyte level in one or more samples obtained from the subject after administration of doublet or triplet relative to a threshold level or relative to the level after administration of a single polynucleotide encoding an IL-23, an IL-36-gamma, or an OX40L polypeptide; (ii) increase in cross-presenting dendritic cell level in one or more samples obtained from the subject after administration of doublet or triplet relative to a threshold level or relative to the level after administration of a single polynucleotide encoding an IL-23, an IL-36-gamma, or an OX40L polypeptide; (iii) increase in effector to suppressor T cell ratio in one or more samples obtained from the subject after administration of doublet or triplet relative to a threshold level or relative to the ratio after administration of a single polynucleotide encoding an OX40L polypeptide; (iv) increase in effector memory T cell level in one or more samples obtained from the subject after administration of doublet or triplet relative to a threshold level or relative to the level after administration of a single polynucleotide encoding an OX40L polypeptide; (v) increase in PDL1 expression level in one or more samples obtained from the subject after administration of doublet or triplet relative to a threshold level or relative to the level after administration of a single polynucleotide encoding an IL-23, an IL-36-gamma, or an OX40L polypeptide; or (vi) a combination thereof. In some aspects, wherein the increase in granulocyte level is quantitated as (i) granulocytes as percent of CD45+ cells, or (ii) granulocytes per mg of tumor. In some aspects, the cross-presenting dendritic cells are CD103+ cells. In some aspects, the increase in cross-presenting dendritic cell level is quantitated as (i) cross-presenting dendritic cells per mg of tumor, (ii) cross-presenting CD103+ dendritic cells in tumor draining lymph node (TdLN), or (iii) cross-presenting CD103+ dendritic cells as percentage of CD45+ cells. In some aspects, the effector to suppressor T cell ratio is quantitated as CD8:Treg ratio. In some aspects, the effector memory T cells are CD4+ and/or CD8+ cells. In some aspects, PDL1 expression level is quantitated as (i) number of positive CD11b+ cells, or (ii) PDL1 expression in CD11b+ cells.

The present disclosure also provides a method to increase granulocyte levels in a subject in need thereof comprising administering to the subject a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein granulocyte levels are measured in one or more samples obtained from the subject. In some aspects, the increase in granulocyte level is measured as (i) granulocytes as percent of CD45+ cells, and/or (ii) granulocytes per mg of tumor, relative to a threshold level or relative to the level after administration of a single polynucleotide encoding IL-23 or a single polynucleotide encoding IL-36-gamma.

The present disclosure also provides a method to increase cross-presenting dendritic cell levels in a subject in need thereof comprising administering to the subject a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein cross-presenting dendritic cell levels are measured in one or more samples obtained from the subject. In some aspects, the cross-presenting dendritic cells are CD103+ cells. In some aspects, the increase in cross-presenting CD103+ dendritic cell level is measured as (i) cross-presenting CD103+ dendritic cells per mg of tumor, (ii) cross-presenting CD103+ dendritic cells in TdLN, (iii) cross-presenting CD103+ dendritic cells as percentage of CD45+ cells, or (iv) a combination thereof, relative to a threshold level or relative to the level after administration of a single polynucleotide encoding IL-23, a single polynucleotide encoding IL-36-gamma, or a single polynucleotide encoding OX40L.

The present disclosure also provides a method to increase the effector to suppressor T cell ratio in a subject in need thereof comprising administering to the subject a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the effector to suppressor T cell ratio is measured in one or more samples obtained from the subject. In some aspects, the effector to suppressor T cell ratio is measured as CD8:Treg ratio.

The present disclosure also provides a method to increase effector memory T cells levels in a subject in need thereof comprising administering to the subject a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the effector memory T cells levels are measured in one or more samples obtained from the subject. In some aspects, the effector memory T cells are CD4+ and/or CD8+ cells. In some aspects, the increase in effector memory T cells levels is measured as effector memory T cells within the tumor relative to a threshold level or relative to the level after administration of a single polynucleotide encoding OX40L.

The present disclosure also provides a method to increase PDL1 positive cells levels in a subject in need thereof comprising administering to the subject a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the PDL1 positive cells levels are measured in one or more samples obtained from the subject. In some aspects, the PDL1 positive cells are CD11b+ cells.

In some aspects of the methods disclosed herein, the sample obtained from the subject is selected, for example, from tumoral tissue, tumor infiltrate, blood, plasma, or a combination thereof. A person of skill in the art would understand that any of the cells measured in the methods disclosed herein (e.g., granulocytes, cross-presenting dendritic cells, effector T cells, suppressor T cells, PDL1 positive cells, etc.), and parameters corresponding to those measurements (e.g., absolute or relative levels of cells, ratios to other cells, level of specific subtypes, activation levels, presence/absence of markers, etc.) can be measured in any tissue sample where those cells are present using methods known in the art without undue experimentation.

In some aspects of the methods disclosed herein, the one or more control samples is a sample or samples obtained from a healthy subject or a subject with a tumor. In some aspects, the threshold level is a predetermined value or a value obtained from one or more samples.

The present disclosure also provides a method of determining whether to treat a subject having a tumor disease with a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide; the method comprising (1) administering to the submitted an initial dose of doublet or triplet, and (2) treating the subject if after administration of the initial dose of doublet or triplet the subject is determined to have an increase in (a) level of granulocytes, (b) level of cross-presenting dendritic cells, (c) effector to suppressor T cell ratio, (d) level of effector memory T cells, (e) level of PDL1 positive cells, (f) PDL1 expression, or (g) a combination thereof, with respect to a threshold level.

The present disclosure also provides a method of selecting a subject diagnosed with a tumor as a candidate for treatment with a composition comprising (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide; the method comprising (1) administering to the subject an initial dose of doublet or triplet, and (2) selecting the subject for treatment if after administration of the initial dose of doublet or triplet the subject is determined to have an increase in (a) level of granulocytes, (b) level of cross-presenting dendritic cells, (c) effector to suppressor T cell ratio, (d) level of effector memory T cells, (e) level of PDL1 positive cells, (f) PDL1 expression, or (g) a combination thereof, with respect to a threshold level.

The present disclosure also provides a method of measuring the efficacy of a composition to treat a tumor in a subject in need thereof, wherein the composition comprises (a) two polynucleotides in combination (doublet), wherein first polynucleotide encodes a first protein comprising an IL-23 polypeptide, and the second polynucleotide encodes a second protein comprising an IL-36-gamma polypeptide; or, (b) three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide; wherein the method comprises measuring in at least one sample taken from the subject (a) level of granulocytes, (b) level of cross-presenting dendritic cells, (c) effector to suppressor T cell ratio, (d) level of effector memory T cells, (e) level of PDL1 positive cells, (f) PDL1 expression, or (g) a combination thereof, wherein an increase in at least one of the measurements with respect to a threshold level indicates that the subject is responding to treatment with the doublet or triplet.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

FIGS. 1A and 1B show IL-23 mRNA monotherapy efficacy in the A20 lymphoma animal model. FIG. 1A shows treatment with NST-FIX control (2.5 μg mRNA). Complete response was observed in 1 of 12 subjects (8.3%). FIG. 1B shows treatment with mIL-23 miRless (2.5 μg mRNA). Complete response was observed in 5 of 12 subjects (41.6%). Dosing conditions: 2.5 μg mRNA, intratumoral (iTu) administration, Compound 18-based lipid nanoparticles (SM68 LNP). NST-FIX is negative control mRNA.

FIGS. 2A and 2B show IL-23 mRNA monotherapy efficacy in the MC38-C colon cancer animal model. FIG. 2A shows treatment with NST-OX40L (2.5 μg mRNA). FIG. 2B shows treatment with mIL-23 mRNA lacking miR binding sites in the 3' UTR, "miRless" (2.5 μg mRNA). Complete response was observed in 4 of 10 subjects (40%). Partial response was observed in 2 of 10 subjects (20%). Dosing conditions: 2.5 μg mRNA, iTu, Compound 18-based LNP. NST-OX40L is negative control mRNA.

FIGS. 3A-3F show that addition of mRNA encoding either IL-36-gamma or IL-18 to IL-23 mRNA therapy increases efficacy in the MC38-C colon cancer model. FIG. 3A shows treatment with mRNA encoding IL-23 and NST-FIX (2.5 μg each mRNA). Complete response was observed in 3 of 10 subjects (30%). Partial response was observed in 6 of 10 subjects (60%). FIG. 3B shows treatment with mRNA encoding IL-23 in combination with mRNA encoding IL-36-gamma (2.5 μg each mRNA). Complete response was observed in 9 of 10 subjects (90%). Partial response was observed in 1 of 10 subjects (10%). FIG. 3C shows treatment with mRNA encoding IL-23 in combination with mRNA encoding IL-18 (2.5 μg each mRNA). Complete response was observed in 6 of 10 subjects (60%). Partial response was observed in 3 of 10 subjects (30%). FIG. 3D shows treatment with NST-FIX control (5 μg mRNA). Dosing conditions: 2.5 μg mRNA each mRNA (5 μg for control), iTu, Compound 18-based LNP. NST-FIX is negative control mRNA. FIG. 3E, FIG. 3F, and FIG. 3G show data corresponding to the same experiments presented in FIG. 3A, FIG. 3B, and FIG. 3D, respectively, but extending the time frame of the experiments to day 90.

FIGS. 4A-4C show efficacy of IL-23 and IL-36-gamma or IL-18 combination mRNA therapy in the A20 lymphoma model. FIG. 4A shows treatment with mRNA encoding IL-23 miRless and NST-FIX (2.5 μg each mRNA). Complete response was observed in 8 of 12 subjects (66.6%). Partial response was observed in 1 of 12 subjects (80.3%). FIG. 4B shows treatment with mRNA encoding IL-23 miRless in combination with mRNA encoding IL-36-miR-122 (2.5 μg each mRNA). Complete response was observed in 10 of 12 subjects (83.3%). FIG. 4C shows treatment with IL-23-encoding "miRless" mRNA and IL-18-encoding "miRless" mRNA (2.5 μg each mRNA). Complete response was observed in 6 of 12 subjects (50%). FIG. 4D shows treatment with NST-FIX control (5 μg mRNA). Dosing conditions: 2.5 μg mRNA each RNA (5 μg for control), iTu, Compound 18-based LNP. NST-FIX is negative control mRNA.

FIGS. 5A-5C show early indication of superior efficacy of mRNA encoding IL-36-gamma plus mRNA encoding IL-23 over mRNA encoding IL-23 alone with fixed 5 μg dose of mRNA in the A20 lymphoma model. FIG. 5A shows treatment with mRNA encoding IL-23 (5 μg mRNA). Complete response was observed in 1 of 10 subjects (10%). Partial response was observed in 4 of 10 subjects (40%). FIG. 5B shows treatment with mRNA encoding IL-36-gamma (5 μg mRNA). Complete response was observed in 2 of 10 subjects (20%). Partial response was observed in 1 of 10 subjects (10/%). FIG. 5C shows treatment with mRNA encoding IL-23 and mRNA encoding IL-36-gamma (2.5 μg each mRNA). FIG. 5D shows treatment with NST-FIX mRNA control (5 μg mRNA). Dosing conditions: 2.5 μg mRNA each mRNA (5 μg for control), iTu, Compound 18-based LNP. NST-FIX is negative control mRNA. IL-23/IL-36-gamma combination is superior to mono constituents at fixed 5 μg mRNA dose.

FIGS. 6A-6C show a MC38 colon cancer model comparison of immune infiltrate. FIG. 6A shows a quantification of the infiltration of CD4+, CD8+ and CD11b+ cells in the MC38 model system in cells per mg of tissue. Results are shown for MC38-M (poorly immunogenic) and MC38-C (strongly immunogenic). FIG. 6B shows a tissue micrograph of a poorly immunogenic MC38-M sample) and FIG. 6C shows a tissue micrograph of a strongly immunogenic MC38-C sample.

FIGS. 7A-7D analyzes the efficacy of IL-23 mRNA monotherapy and IL-23/IL-36-gamma or Il-23/IL-18 combination mRNA therapy in the MC38-M colon cancer model. FIG. 7A shows treatment with NST-OX40L (2.5 μg mRNA) in Compound 18-based LNPs. No response was observed. FIG. 7B shows treatment with IL-23 mRNA "miRless" (2.5 μg mRNA) in Compound 18-based LNPs. Only one partial response was observed (1 of 10, 10%). MC38-M is a relatively insensitive model in which OX40L, anti-PD-1 antibody, and IL-23 monotherapies are ineffective. FIG. 7C shows treatment with mRNAs encoding IL-23 and IL-36-gamma (2.5 μg each mRNA). Complete responses were observed in 2 of 10 subjects (20%). Partial responses were observed in 5 of 10 subjects (50%). Thus, IL-23/IL-36-gamma mRNA combination therapy is efficacious in poorly immunogenic MC38-M colon cancer. FIG. 7E shows that treatment with mRNAs encoding IL-23 and IL-18 (2.5 μg each mRNA). Only one partial response was observed (1 of 10, 10%). FIG. 7D shows treatment with NST-FIX control (5 μg mRNA).

FIG. 8 analyzes the efficacy of OX40L mRNA monotherapy in the A20 tumor model. mRNA encoding OX40L (2.5 μg mRNA) was formulated in Compound 18-based LNPs. Two complete responses were observed.

FIGS. 9A-9C show OX40L mRNA "miRless" or anti-PD-1 monotherapy efficacy in MC38-M (poorly immunogenic) colon cancer model. FIG. 9A shows treatment with OX40L mRNA "miRless" (2.5 μg mRNA) in Compound 18-based LNPs. FIG. 9B shows treatment with anti-PD-1 antibody (5 mg/kg 2×/week IP dosing). FIG. 9C shows a microphotography of MC38-M colon cancer model tissue.

FIGS. 10A-10H show the effect of monotherapy, binary combination therapy; and triple combination therapy (including single and multi-dose administration at varying dosage levels) using mRNAs encoding IL-23, IL-36-gamma, and OX40L, wherein each mRNA comprises an miR122 binding site. FIG. 10A shows monotherapy treatment with IL-23_miR-122. No complete responses were observed, but eight escapers. FIG. 10B shows combination treatment with IL-23_miR-122 and IL-36-gamma_miR-122. Three complete responses were observed (25%). Six escapers were observed. FIG. 10C shows treatment with IL-23_miR-122, IL-36-gamma_miR-122 and OX40L_miR-122 triple combination therapy. Three complete responses were observed (25%). Four escapers were observed. For each sample: 5 μg total mRNA/dose was administered intratumorally (iTu). When non-translated control mRNA and IL-36gamma_miR-122 alone were administered, all mice progressed by day 26 (data not shown). FIG. 10D, FIG. 10E, and FIG. 10F show data corresponding to the same experiments presented in FIG. 10A, FIG. 10B, and FIG. 10C, respectively, but extending the time frame of the experiments to day 70. FIG. 10G shows treatment with IL-23_miR-122 and IL-36-gamma_miR-122 doublet therapy at a single dose (8 μg) and IL-23_miR-122, IL-36-gamma_miR-122, and OX40L_miR-122 triplet therapy at a single dose or multiple doses (12 μg) in MC38 luciferase cells relative to a mock control. FIG. 10H shows survival through day 47 following treatment with a single 8 μg dose of IL-23_miR-122 and IL-36-gamma_miR-122 doublet therapy, a single 12 μg dose of IL-23_miR-122, IL-36-gamma_miR-122, and OX40L_miR-122 triplet therapy, or multiple 12 μg doses of IL-23_miR-122, IL-36-gamma_miR-122, and OX40L_miR-122 triplet therapy. Treatment-related deaths were observed with multiple 12 μg doses of IL-23_miR-122, IL-36-gamma_miR-122, and OX40L_miR-122 triplet therapy.

FIG. 11 shows the bioactivity (e.g., induction of murine Interleukin 17 (mIL-17) expression from primary mouse splenocytes) of IL-23 protein produced from an mRNA compared to recombinant IL-23 protein. The solid upper line shows mIL-17 (pg/ml) secreted from primary mouse splenocytes after adding murine IL-23 (mIL-23) obtained from HeLa cells transfected with an mRNA encoding mIL-23; the solid lower line shows mIL-17 (pg/ml) expression after adding human IL-23 (hIL-23) obtained from HeLa cells transfected with an mRNA encoding hIL-23. The dotted black line shows mIL-17 secreted from mouse primary splenocytes after adding recombinant hIL-23; and the dotted gray line shows mIL-17 expression from splenocytes after adding recombinant mIL-23. The IL-23 protein levels used in the experiment were 0.1 ng/ml, 1 ng/ml, 3.3 ng/ml, 10 ng/ml and 100 ng/ml.

FIG. 12A shows murine Interleukin 6 (mIL6) (ng/ml) production in bone marrow derived dendritic cells as induced by murine IL-36gamma (mIL-36γ) protein. The first panel (NT) is a negative control. The second panel shows mIL6 expression after adding recombinant mIL-36γ. The third panel shows mIL6 expression after adding mIL-36γ obtained from HeLa cells transfected with mRNA encoding mIL-36γ. The fourth panel (mock) shows a mock control. FIG. 12B shows Interleukin 8 (IL8) expression (OD450) in A431 cells by recombinant human IL-36-gamma and supernatants from B16F10 cells transfected with three mRNAs encoding hIL-36-gamma.

FIGS. 13A-13E show the costimulatory biological activity of OX40L expressed on the surface of cells treated with OX40L mRNA. FIG. 13A shows a schematic drawing of the T-cell activation assay. OX40L-expressing B16F10 cells or HeLa cells were co-cultured with $CD4^+$ T-cells and anti-mouse CD3 antibody (B16F10 cells) or Dynabeads human T-activator (HeLa cells). IL-2 production was measured using ELISA as a correlate of T-cell activation. FIG. 13B shows results of the T-cell activation assay as measured by mouse IL-2. FIG. 13C shows results of the T-cell activation assay as measured by human IL-2. The y-axis shows mIL-2 expression in ng/ml. FIG. 13D shows the data from FIG. 13C with schematic diagram showing the addition of OX40L expressing cells to the naïve T-cell activation assay. FIG. 13E shows a T-cell activation assay using pre-stimulated T-cells cultured in the presence or absence of OX40L expressing HeLa cells and in the presence or absence of anti-human CD3 antibody.

FIGS. 14A-14D show the different types of immune cells that infiltrate the tumor microenvironment in A20 tumors following administration of a polynucleotide comprising an mRNA encoding an OX40L polypeptide. FIG. 14A shows the percentage of NK cells in the tumor infiltrate 24 hours after treatment, as detected by the DX5 marker. FIG. 14B shows the percentage of $CD4^+$ T-cells in the tumor infiltrate 14 days after treatment, as detected by the CD4 marker. FIG. 14C shows the percentage of $CD8^+$ T-cells in the tumor infiltrate 14 days after treatment, as detected by the CD8 marker. FIG. 14D shows the percentage of $CD8^+$ T-cells in the tumor infiltrate of MC38 tumors 24 and 72 hours after a first and second dose of a polynucleotide comprising an mRNA encoding an OX40L polypeptide.

FIGS. 15A and 15B show in vivo anti-tumor efficacy of mOX40L_miR-122 delivered intratumorally. FIG. 15A shows tumor growth in animals treated intratumorally with control mRNA ("NST-OX40L") (arrows mark injection days). FIG. 15B shows tumor growth in animals treated intratumorally with mOX40L_miR-122 mRNA ("OX40L-miR-122") (arrows mark injection days).

FIGS. 16A-16F show in vivo anti-tumor efficacy of combination therapy comprising a polynucleotide comprising an mRNA encoding an OX40L polypeptide and a miR-122 binding site and an anti-PD-1 antibody. FIG. 16A shows tumor growth in animals treated with intratumoral injections of control mRNA ("NST_mOX40L_122") and control antibody ("Rat IgG2a"). FIG. 16B shows tumor growth in animals treated with intratumoral injections of mOX40L_miR-122 ("mOX40L_122") and control antibody ("Rat IgG2a"). FIG. 16C shows tumor growth in animals treated with intratumoral injections of control mRNA ("NST_mOX40L_122") and anti-PD-1 antibody ("anti-PD-1"). FIG. 16D shows tumor growth in animals treated with intratumoral injections of mOX40L_miR-122 ("mOX40L_122") and anti-PD-1 antibody ("anti-PD-1"). FIG. 16E shows tumor growth in animals treated with intratumoral injections of anti-PD-1 antibody and PBS. FIG. 16F shows tumor growth in animals treated with PBS and control antibody ("Rat IgG2a"). CR=complete responder.

FIG. 17 shows survival curves for animals treated intratumorally with combination therapy comprising control mRNA and control antibody ("NST_mOX40L_122+Rat IgG2a"), mOX40L_miR-122 and control antibody ("mOX40L_122+Rat IgG2a"), control mRNA and anti-PD-1 antibody ("NST_mOX40L_122+anti-PD-1"), mOX40L_miR-122 and anti-PD-1 antibody ("mOX40L_122+anti-PD-1"), anti-PD-1 antibody and PBS ("PBS+anti-PD-1"), and PBS and control antibody ("PBS+Rat IgG2a").

FIGS. 18A and 18B show a memory immune response in animals treated with combination therapy comprising a polynucleotide comprising an mRNA encoding an OX40L polypeptide and a miR-122 binding site and an anti-PD-1 antibody. Animals were initially treated with intratumoral injections of mOX40L_miR-122 and anti-PD-1 antibody as shown in FIG. 16D. Four animals identified as complete responders (CR) were re-challenged with MC38 tumor cells. FIG. 18A shows tumor growth in naïve animals challenged with MC38 tumor cells. FIG. 18B shows tumor growth in the four CR animals re-challenged with MC38 tumor cells.

FIG. 19A-19G show in vivo tumor efficacy in both primary treated and untreated distal tumors with double mRNA therapy (combination of mRNAs encoding IL-23 and IL-36) and triplet mRNA therapy (combination of mRNAs encoding IL-23, IL-36, and OX40L). FIG. 19A shows a schematic description of the MC38-S dual flank model used in the experiments. A tumor implanted in one flank is treated, and the effect is measured in both the primary treated tumor and the untreated tumor in the other flank. FIG. 19B shows the effect of the negative control mRNA (non-translating mRNA encoding for OX40L) on the primary treated tumor. FIG. 19C shows the effect of the negative control mRNA on the untreated tumor. FIG. 19D shows the effect of the double mRNA therapy (mRNA encoding IL-23 and mRNA encoding IL-36-gamma) on the primary treated tumor. FIG. 19E shows the effect of the double mRNA therapy (mRNA encoding IL-23 and mRNA encoding IL-36-gamma) on the distal untreated tumor. FIG. 19F shows the effect of the triplet mRNA therapy (mRNA encoding IL-23, mRNA encoding IL-36-gamma, and mRNA encoding OX40L) on the primary treated tumor. FIG. 19G shows the effect of the triplet mRNA therapy (mRNA encoding IL-23, mRNA encoding IL-36-gamma, and mRNA encoding OX40L) on the distal untreated tumor. In each case, the total dose of mRNA injected in the tumor (control, double, or triplet) was 5 micrograms. mRNAs were administered intratumorally in a single dose.

FIG. 20A-20D show that triplet mRNA therapy combined with an anti-PD-L1 antibody has improved efficacy in a difficult to treat B16F10-AP3 tumor model. FIG. 20A shows tumor growth in animals treated with negative control. FIG. 20B shows tumor growth in animals treated with an anti-PD-L1 antibody. FIG. 20C shows tumor growth in animals treated with triplet mRNA therapy (mRNA encoding IL-23, mRNA encoding IL-36-gamma, and mRNA encoding OX40L). FIG. 20D shows tumor growth in animals treated with triplet mRNA therapy (mRNA encoding IL-23, mRNA encoding IL-36-gamma, and mRNA encoding OX40L) plus the anti-PD-L1 antibody.

FIG. 21A and FIG. 21B show a memory immune response in animals treated with doublet mRNA therapy (mRNA encoding IL-23 plus mRNA encoding IL-36-gamma). Animals were initially treated with 5 ug total mRNA (2.5 ug of mRNA encoding IL-23 and 2.5 ug of mRNA encoding IL-36-gamma) administered intratumorally Q7D. Ten animals identified as complete responders (CR) were re-challenged with MC38-S tumor cells. FIG. 21A shows tumor growth in naïve animals challenged with MC38-S tumor cells. FIG. 21B shows tumor growth in the ten CR animals re-challenged with MC38-S tumor cells.

FIG. 22A and FIG. 22B show an increase in Ly6G+ granulocytes in response to treatment of MC38 tumors with doublet mRNA therapy (mRNA encoding IL-23 plus mRNA encoding IL-36-gamma). FIG. 22A shows the level of granulocytes as percentage of CD45+ cells 24 hours, 72 hours, 7 days, and 14 days after treatment. FIG. 22B shows the level of granulocytes as granulocytes per mg of tumor 24 hours, 72 hours, 7 days, and 14 days after treatment. The measurements presented correspond to treatment with controls ("NoRx" and "NST"), IL-23 and IL-36-gamma monotherapies ("IL23" and "IL36"), and doublet mRNA combination therapy ("Combo," corresponding to mice receiving a single dose of the combination therapy, and "Combo 2 dose" corresponding to mice receiving two doses of the combination therapy). The vertical bars represent mean with S.D. The horizontal bars above the data represent statistical significance.

FIG. 23 shows an increase in Ly6G+ granulocytes as percentage of CD45+ cells 24 hours, 72 hours and 7 days after treatment of MC38 tumors with triplet mRNA combination therapy (mRNA encoding IL-23 plus mRNA encoding IL-36-gamma plus mRNA encoding OX40L). The vertical bars represent mean with S.D. The horizontal bars above the data represent statistical significance.

FIG. 24A and FIG. 24B show an increase in CD103+ dendritic cells (DC) in response to treatment of MC38 tumors with doublet mRNA therapy (mRNA encoding IL-23 plus mRNA encoding IL-36-gamma). FIG. 24A shows the level of CD103+ dendritic cells as percentage of CD45+ cells 7 days after treatment. FIG. 24B shows the level of CD103+ dendritic cells as CD103+ dendritic cells per mg of tumor 7 days after treatment. The measurements presented correspond to treatment with controls ("NoRx" and "NST"), IL-23 and IL-36-gamma monotherapies ("IL23" and "IL36"), and doublet mRNA combination therapy ("Combo"). The vertical bars represent mean with S.D. The horizontal bars above the data represent statistical significance.

FIG. 25A and FIG. 25B show an increase in CD103+ dendritic cells (DC) in response to treatment of MC38 tumors with doublet mRNA therapy (mRNA encoding IL-23 plus mRNA encoding IL-36-gamma) or triplet mRNA therapy (mRNA encoding IL-23 plus mRNA encoding IL-36-gamma plus mRNA encoding OX40L). FIG. 25A shows the level of CD103+ dendritic cells as CD8+ cell per mg of tumor 7 days after treatment. FIG. 25B shows the level of CD8+ dendritic cells in the tumor draining lymph node (TdLN) 7 days after treatment. The measurements presented correspond to treatment with controls ("Naive" and "NST"), OX40L monotherapy ("OX40L"), and doublet and triplet mRNA combination therapies ("Doublet" and "Triplet," respectively). The vertical bars represent mean with S.D. The horizontal bars above the data represent statistical significance.

FIGS. 26A-26D show increase in CD11b+ dendritic cells in MC38 tumors and draining lymph node in response to treatment with triplet mRNA therapy (mRNA encoding IL-23 plus mRNA encoding IL-36-gamma plus mRNA encoding OX40L). FIG. 26A shows the level of CD11+ cDC2 cells as cells per mg of tumor 7 days after treatment. FIG. 26B shows the level of CD11+ cDC2 dendritic cells in the tumor draining lymph node (TdLN) 7 days after treatment. FIG. 26C shows CD86 activation on CD11b+ cDC2 in the draining lymph node 24 h and 72 h post intratumoral administration of triplet mRNA therapy measured as percentage of CD24 cDC2 cells. FIG. 26D shows CD86 activation on CD11b+ cDC2 in the draining lymph node 24 h and 72 h post intratumoral administration of triplet mRNA therapy measured as mean fluorescence intensity (MFI). The vertical bars represent mean with S.D. The horizontal bars above the data represent statistical significance.

FIG. 27A and FIG. 27B show CD86 activation on CD8 cDC1 in the draining lymph node 24 h and 72 h post intratumoral administration of triplet mRNA therapy to MC38 tumors measured as percentage of CD8 cDC1 cells (FIG. 27A) or as mean fluorescence intensity (MFI) (FIG. 27B). The vertical bars represent mean with S.D. The horizontal bars above the data represent statistical significance.

FIGS. 28A-28D show an increase in inflammatory dendritic cells (iDCs) in MC38 tumors and draining lymph nodes in response to treatment with triplet mRNA therapy (mRNA encoding IL-23 plus mRNA encoding IL-36-gamma plus mRNA encoding OX40L). FIG. 28A shows the level of iDCs in tumor as cells per mg of tumor 7 days after treatment. FIG. 28B shows the level of iDCs in the tumor draining lymph node (TdLN) 7 days after treatment. FIG. 28C shows CD86 activation on iDCs in the draining lymph node 24 h and 72 h post intratumoral administration of triplet mRNA therapy measured as percentage of iDCs. FIG. 28D shows CD86 activation on iDCs in the draining lymph node 24 h and 72 h post intratumoral administration of triplet mRNA therapy measured as mean fluorescence intensity (MFI). The vertical bars represent mean with S.D. The horizontal bars above the data represent statistical significance.

FIG. 29 shows an increase in the ratio of effector CD8 (Killer) T cells to regulatory T cells (Treg) in response to treatment of MC38 tumors with doublet mRNA therapy (mRNA encoding IL-23 plus mRNA encoding IL-36-gamma) and triplet mRNA therapy (mRNA encoding IL-23 plus mRNA encoding IL-36-gamma plus mRNA encoding OX40L). Measurements were taken 72 hours and 7 days after treatment. The measurements presented correspond to treatment with controls ("NST"), OX40L monotherapy ("OX40L"), and doublet and triplet mRNA combination therapies ("Doublet" and "Triplet," respectively). The vertical bars represent mean with S.D. The horizontal bars above the data represent statistical significance.

FIG. 30A and FIG. 30B show an increase in central and effector CD4 and CD8 cells in response to treatment of MC38 tumors with doublet mRNA therapy (mRNA encoding IL-23 plus mRNA encoding IL-36-gamma) or triplet mRNA therapy (mRNA encoding IL-23 plus mRNA encoding IL-36-gamma plus mRNA encoding OX40L). FIG. 30A shows the level of CD4 cells as CD4 cells per mg of tumor 7 days and 10 days after treatment. FIG. 30B shows the level of CD8 cells as CD8 cells per mg of tumor 7 days and 10 days after treatment. The measurements presented correspond to treatment with controls ("NST"), OX40L monotherapy ("OX40L"), and doublet and triplet mRNA combination therapies ("Doublet" and "Triplet," respectively). The bars show levels of naïve, central memory, and effector memory CD4 and CD8 cells.

FIG. 31 presents survival curves showing the effect of CD cell depletion on the efficacy of treatment of MC38 tumors with triplet mRNA therapy (mRNA encoding IL-23 plus mRNA encoding IL-36-gamma plus mRNA encoding OX40L). CD4 and CD8 cell levels were depleted by administering anti-CD4 and anti-CD8 antibodies to mice with MC38 tumors. The arrow indicates the administration of the triplet therapy. CD cell depleting doses of antibodies (indicated by circles) were administered prior and after the administration of the triplet therapy.

FIGS. 32A and 32B show the expression of PD-L1 in cancer cells of mice with MC38 tumors in response to the administration of triplet mRNA therapy. FIG. 32A shows the percentage of cancer cells (CD45-, FSchi, MHCII-) positive for PD-L1 7 days after treatment with triplet mRNA therapy. FIG. 32B shows the level of PD-L1 expression in cancer cells (CD45-, FSchi, MHCII-) measured as MFI (mean fluorescence intensity). The vertical bars represent mean with S.D. The horizontal bars above the data represent statistical significance.

FIG. 33A and FIG. 33B show the expression of PD-L1 in mice with MC38 tumors in response to the administration of IL-23 or IL-36-gamma monotherapies or doublet mRNA therapy (mRNA encoding IL-23 plus mRNA encoding IL-36-gamma). FIG. 33A shows the percentage of CD11b+ cells positive for PD-L1. FIG. 33B shows the strength of PD-L1 expression in CD11b+ cells, measured as MFI (mean fluorescence intensity). The measurements presented correspond to treatment with controls ("NoRx" and "NST"), IL-23 and IL-36-gamma monotherapies ("IL23" and "IL36"), and doublet mRNA combination therapy ("Combo"). The vertical bars represent mean with S.D. The horizontal bars above the data represent statistical significance. All the measurements were done 7 days after tumor cells were implanted.

FIG. 34A and FIG. 34B show the expression of PD-L1 in mice with MC38 tumors in response to the administration of OX40L monotherapy or doublet (mRNA encoding IL-23 plus mRNA encoding IL-36-gamma) or triplet (mRNA encoding IL-23 plus mRNA encoding IL-36-gamma plus mRNA encoding OX40L) mRNA therapies. FIG. 34A shows the percentage of CD11b+ cells positive for PD-L1. FIG. 34B shows the strength of PD-L1 expression in CD11b+ cells, measured as MFI (mean fluorescence intensity). The measurements presented correspond to treatment with controls ("NoRx"), OX40L monotherapy ("OX40L"), and doublet and triplet mRNA combination therapies ("doublet" and "triplet," respectively). The vertical bars represent mean with S.D. The horizontal bars above the data represent statistical significance. All the measurements were done 7 days after tumor cells implant were implanted FIGS. 35A-35D show in vivo anti-tumor efficacy of triplet mRNA therapy combined with an anti PD-L1 antibody (10° F.9G2) in immunosuppressive MC38 tumors. FIG. 35A shows tumor growth in animals treated with intratumoral injections of control antibody. FIG. 35B shows tumor growth in animals treated with intratumoral injections of anti PD-L1 antibody (10° F.9G2) alone. FIG. 35C shows tumor growth in animals treated with intratumoral injections of triplet mRNA therapy. FIG. 35D shows tumor growth in animals treated with intratumoral injections of triple mRNA therapy plus anti PD-L1 antibody (1° F.9G2). Vertical dashed lines indicate day of administration of the control antibody, the anti PD-L1 antibody, the triplet mRNA therapy, or the triplet mRNA therapy plus anti PD-L1 antibody.

FIG. 36A and FIG. 36B show the in vivo anti-tumor efficacy of triplet mRNA combination therapy (mRNA encoding IL-23 plus mRNA encoding IL-36-gamma plus mRNA encoding OX40L) in the syngenic H22 (hepatocellular carcinoma (HCC)) model. FIG. 36A shows tumor growth in animals treated with intratumoral injections of control mRNA ("NST-FIX"). FIG. 36B shows tumor growth in animals treated with intratumoral injections of triplet mRNA combination therapy.

FIG. 37 shows mean tumor volume ($mm^3$) for each group of mice treated according to the design outlined in Table 11. The dashed arrows show the lack of efficacy of OX40L administered in Group 8, and the synergistic effect of the combination of OX40L with IL-23 in Group 5.

FIG. 38A shows mean tumor volume ($mm^3$) for groups of mice treated with triplet combinations comprising mouse OX40L, mouse IL-23, and mouse IL-36-gamma. Different amounts of mRNA encoding mouse IL-36-gamma were used in each triplet. The total amount of mRNA in each triplet dose was kept constant by adding the appropriate amount of NST control mRNA.

FIG. 38B shows mean tumor volume ($mm^3$) for groups of mice treated with triplet combinations comprising mouse OX40L, mouse IL-23, and human IL-36-gamma. Different amounts of mRNA encoding human IL-36-gamma were used in each triplet. The total amount of mRNA in each triplet dose was kept constant by adding the appropriate amount of NST control mRNA.

FIG. 39A-39O show tumor volume ($mm^3$) for each group of mice treated according to the study design outlined in Table 11. The dates when mRNAs were administered are indicated by vertical dashed lines. Each drawing indicates the number of animals per group (n), the number of complete responders (CR), and the number of animals with tumors below 100 $mm^3$ in volume at the end of the study. Each drawing also indicates the composition administered to each animal and the ratio between each mRNA in the composition.

Figure 42:
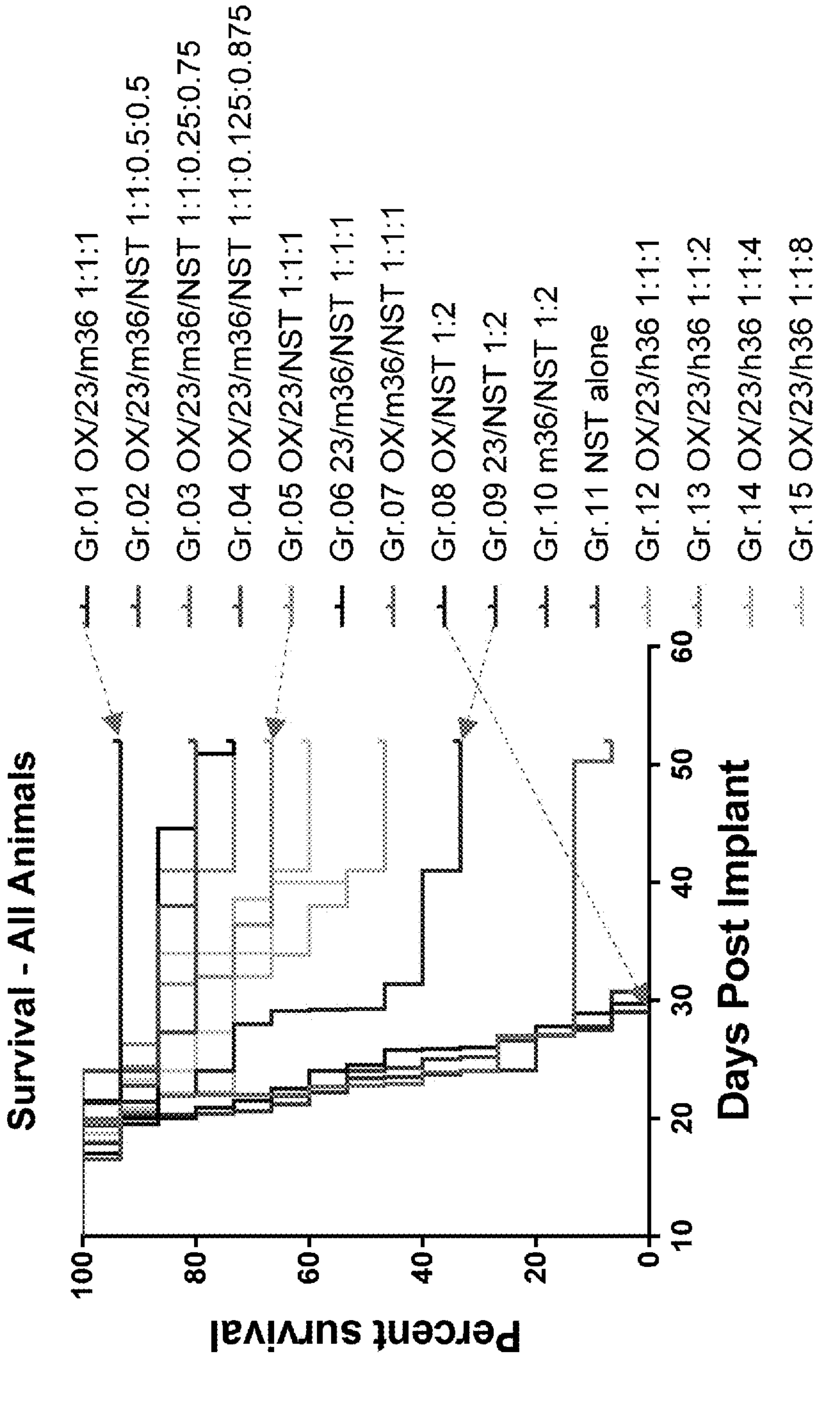

FIG. 42 presents survival curves showing the effect of the treatment of MC38 tumors according to the design outlined in Table 11. The dashed arrows show (i) the lack of efficacy of OX40L administered in Group 8, (ii) the moderate efficacy of IL-23 in Group 9, (iii) the synergistic effect of the combination of OX40L with IL-23 in Group 5, and (iv) the highest efficacy observed, which corresponded to Group 1 (mOX40L/mIL-23/mIL-36-gamma 1:1:1).

Figure 43A:
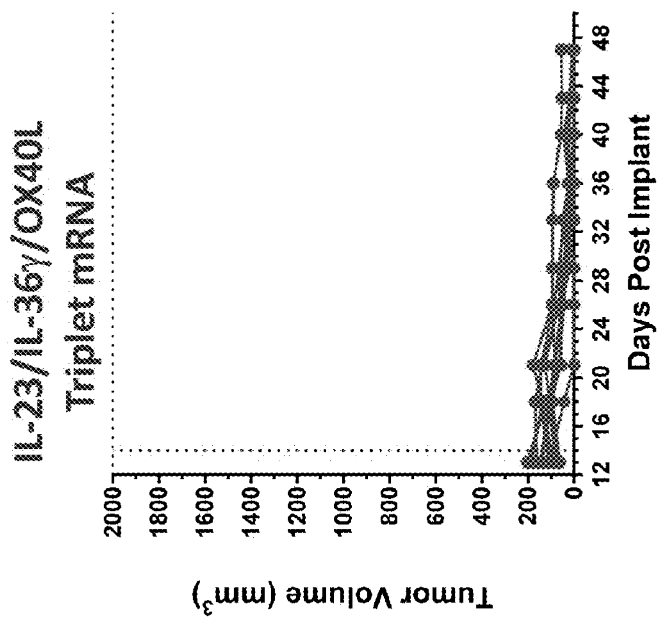

FIG. 43A shows mean tumor volume ($mm^3$) for mice bearing MC38-S tumors and treated with triplet combinations comprising IL-23, IL-36-gamma and OX40L.

Figure 43B:
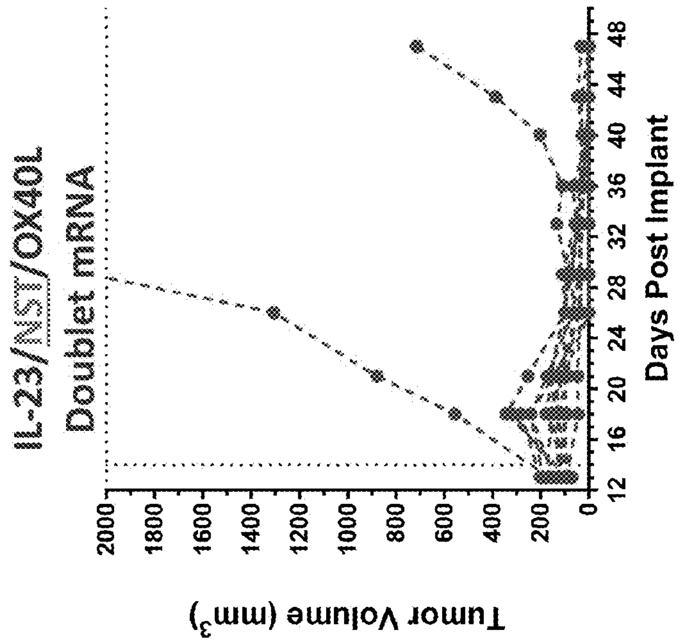

FIG. 43B shows mean tumor volume ($mm^3$) for mice bearing MC38-S tumors and treated with doublet combinations comprising IL-23 and OX40L. The total amount of mRNA in the dose, as compared to mice treated as in FIG. 43A, was kept constant by adding the appropriate amount of NST control mRNA.

Figure 44:
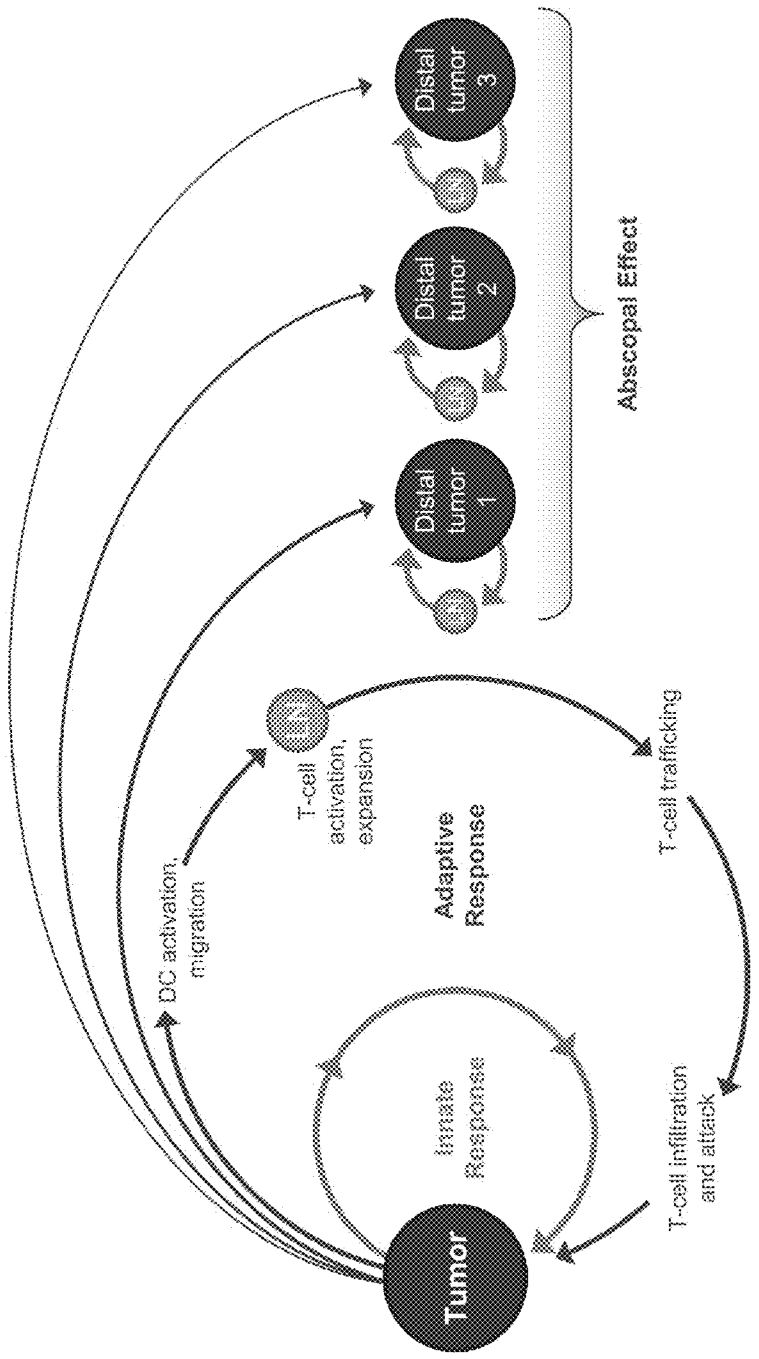

FIG. 44 is a diagram illustrating the abscopal effect for cancer treatment.

DETAILED DESCRIPTION

A particularly exciting approach to treating cancer involves the prevention or treatment of disease with substances that stimulate the immune response, known as immunotherapy. Immunotherapy, also referred to in the art as immuno-oncology, has begun to revolutionize cancer treatment, by introducing therapies that target not the tumor, but the host immune system. These therapies possess unique pharmacological response profiles, and thus represent therapies that might cure many distinct types of cancer. Cancers of the lungs, kidney, bladder and skin are among those that derive substantial efficacy from treatment with immuno-oncology in terms of survival or tumor response, with melanoma possibly showing the greatest benefits. Immunotherapy often features checkpoint inhibitor treatment with an exciting new class of biologic drugs known as checkpoint inhibitor antibodies.

The present disclosure features methods and compositions for treating cancer, in particular, immunotherapeutic methods and compositions. In some aspects, the disclosure features methods and compositions for treating cancer using a combination therapy that features two or more polynucleotides (e.g., mRNAs) encoding a first immune response primer polypeptide and a second, different, immune response primer polypeptide, and, optionally, a polynucleotide encoding an immune response co-stimulatory signal polypeptide and, optionally, a polynucleotide encoding a checkpoint inhibitor polypeptide or a polypeptide comprising a checkpoint inhibitor polypeptide. In some aspects, the disclosure provides an immunomodulatory composition comprising a polynucleotide encoding an Interleukin-23 (IL-23) polypeptide, a polynucleotide encoding an Interleukin-36 gamma (IL-36 gamma) polypeptide and, optionally, a polynucleotide encoding an OX40L polypeptide. In other aspects, the disclosure provides an immunomodulatory composition comprising a polynucleotide encoding an IL-23 polypeptide, a polynucleotide encoding an Interleukin 18 (IL-18) polypeptide and, optionally, a polynucleotide encoding an OX40L polypeptide.

In some aspects, the disclosure relates to methods of treating cancer using a combination approach that features mRNAs encoding IL-23, IL-36 or IL-18 and/or OX40L. Without being bound in theory, it is believed that priming of an anti-cancer immune response is possible by administering, e.g., intratumorally, mRNAs encoding an IL-12 family member (e.g, IL-23) and/or IL-1 family member (e.g., IL-36 or IL-18). IL-23 is important in the stimulation of, for example, T-cells, natural killer cells, macrophages, and or dendritic cells. IL-36 is important in the stimulation of, for example, T-cells, natural killer cells, granulocytes, and/or dendritic cells. IL-18, together with IL-12, induces cell-mediated immunity and is important in the stimulation of, for example, T-cells, natural killer cells, and/or macrophages. mRNA encoding IL-36, or mRNA encoding IL-18, in combination with mRNA encoding IL-23 is believed to provide a first stimulation signal to the immune system, for example, within the tumor environment, e.g., via intratumoral injection of said mRNAs. Administration of mRNA encoding an immune response co-stimulatory signal polypeptide, for example, OX40L is believed to provide a second stimulation signal, when provided in combination with mRNAs encoding IL-23 and IL-36, due at least in part, to the ability of OX40L to stimulate T cells.

In some aspects, the immune therapeutic methods disclosed herein can (1) transform the tumor microenvironment (TME) to optimize immunogenicity, and/or (2) enhance T cell responses to elicit abscopal control and anti-cancer memory. The abscopal effect, i.e., treating a tumor locally yet acting globally is illustrated in FIG. 44.

Some aspects of the disclosure feature treatment with mRNA encoding IL-23 in combination with mRNA encoding IL-36. Other aspects of the disclosure feature treatment with mRNA encoding IL-23 in combination with mRNA encoding IL-18. Exemplary aspects feature treatment with lipid nanoparticle- (LNP-) encapsulated mRNAs. Exemplary aspects feature intratumoral administration of mRNAs in ionizable amino lipid-based LNPs.

Other aspects of the disclosure feature compositions and methods of reducing or decreasing the size of a tumor or inhibiting the growth of a tumor in a subject in need thereof by administering to the subject an effective amount of a combination comprising mRNAs encoding IL-23, IL-36-gamma or IL-18, and OX40L. In some aspects, the mRNA combination comprises a first polynucleotide encoding an IL-23 polypeptide, a second polynucleotide encoding a second protein comprising an IL-36-gamma polypeptide or an IL-18 polypeptide, and a third polynucleotide encoding a third protein comprising an OX40L polypeptide. One aspect of the present disclosure is directed to pharmaceutical compositions comprising two or more polynucleotides (e.g., mRNAs) encoding an IL-23 polypeptide, a polynucleotide (e.g., mRNA) encoding an IL-36-gamma polypeptide or an IL-18 polypeptide, and a polynucleotide (e.g., mRNA) encoding an OX40L polypeptide.

In another aspect, the composition is a lipid composition comprising an ionizable amino lipid, such as a compound of formula (I) as disclosed below, e.g., Compounds 18, 25, 26 or 48. In some aspects of the present disclosure, the lipid composition of the pharmaceutical composition comprises additional lipids/components. For example, the lipid composition can include one or more phospholipids, e.g., MSPC or DSPC. The lipid composition can also comprise a quaternary amine compound such as DOTAP.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); (4) optionally a lipid conjugate (e.g. a PEG-lipid); and (5) optionally a quaternary amine compound.

The headings provided herein are not limitations of the various aspects or aspects of the disclosure, which can be defined by reference to the specification as a whole. Accordingly, the terms defined immediately below are more fully defined by reference to the specification in its entirety. Before describing the present disclosure in detail, it is to be understood that this disclosure is not limited to specific compositions or process steps, as such can vary.

I. Definitions

In order that the present disclosure can be more readily understood, certain terms are first defined. As used in this application, except as otherwise expressly provided herein, each of the following terms shall have the meaning set forth below. Additional definitions are set forth throughout the application.

The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

In this specification and the appended claims, the singular forms “a”, “an” and “the” include plural referents unless the context clearly dictates otherwise. The terms “a” (or “an”), as well as the terms “one or more,” and “at least one” can be used interchangeably herein. In certain aspects, the term “a” or “an” means “single.” In other aspects, the term “a” or “an” includes “two or more” or “multiple.”

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language “comprising,” otherwise analogous aspects described in terms of “consisting of” and/or “consisting essentially of” are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. In general, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Administered in combination: As used herein, the term "administered in combination," "combined administration," or "combination therapy" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type sequence) with another amino acid residue. An amino acid can be substituted in a parent or reference sequence (e.g., a wild type polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association may, but need not, be causatively linked to the disease.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Conservative amino acid substitution: A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an polynucleotide or polypeptide or may apply to a portion, region or feature thereof.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

Controlled Release: As used herein, the term "controlled release" refers to a pharmaceutical composition or compound release profile that conforms to a particular pattern of release to effect a therapeutic outcome.

Covalent Derivative: The term "covalent derivative" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present disclosure can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject may involve administering a nanoparticle composition including the polynucleotide to the subject (e.g., by an intravenous, intramuscular, intradermal, or subcutaneous route). Administration of a nanoparticle composition to a mammal or mammalian cell may involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties that are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels can be located at any position in the peptides or proteins disclosed herein. They can be within the amino acids, the peptides, or proteins, or located at the N- or C-termini.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a tumor, an effective amount of an agent is, for example, an amount sufficient to reduce or decrease a size of a tumor or to inhibit a tumor growth, as compared to the response obtained without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the disclosure, having an optical purity or enantiomeric excess (as determined by methods standard in the art) of at least 80% (i.e., at least 90% of one enantiomer and at most 10% of the other enantiomer), at least 90%, or at least 98%.

Encapsulate. As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency may be given as 97%. As used herein, "encapsulation" may refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the disclosure are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it may be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present disclosure include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full-length protein (e.g., one of the subunits of IL-23) wherein N-terminal, and/or C-terminal, and/or internal subsequences have been deleted. In some preferred aspects of the present disclosure, the fragments of a protein of the present disclosure are functional fragments.

Functional: As used herein, a "functional" biological molecule is a biological molecule in a form in which it exhibits a property and/or activity by which it is characterized. Thus, a functional fragment of a polynucleotide of the present disclosure is a polynucleotide capable of expressing a functional interleukin fragment. As used herein, a functional fragment of an interleukin refers to a fragment of a wild type interleukin (i.e., a fragment of a naturally occurring form of the interleukin), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full-length protein.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is b12seq, part of the BLAST suite of program available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune checkpoint inhibitor: An "immune checkpoint inhibitor" or simply "checkpoint inhibitor" refers to a molecule that prevents immune cells from being turned off by cancer cells. As used herein, the term checkpoint inhibitor refers to polypeptides (e.g., antibodies) or polynucleotides encoding such polypeptides (e.g., mRNAs) that neutralize or inhibit inhibitory checkpoint molecules such as cytotoxic T-lymphocyte-associated protein 4 (CTLA-4), programmed death 1 receptor (PD-1), or PD-1 ligand 1 (PD-L1).

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Immune response co-stimulatory signal: The term "immune response co-stimulatory signal" refers to an immuno-stimulatory molecule that promotes T cell and/or NK cell recruitment, proliferation, activation, survival, or a combination thereof. In some aspects, the immune response co-stimulatory signal is a polypeptide that enhances T-cell expansion, function and memory formation (e.g., OX40L). In some aspects, the co-stimulatory signal promotes Th1, Th2 and/or Th9 development, suppresses Treg development or activity, enhances the expansion and/or survival of CD4 and/or CD8 T cells and/or promotes memory cells. In specific aspects, the immune response co-stimulatory signal polypeptide is selected from the group consisting of: OX40L, CD80, and IL-15. In some specific aspects, the immune response co-stimulatory signal polypeptide is selected from the group consisting of OX40L and CD80.

Immune response primer: The term "immune response primer" refers to an immuno-stimulatory molecule that enhances antigen presentation and/or recognition. In some aspects, an immune response primer is a polypeptide that primes dendritic cells, promotes dendritic cell maturation, promotes antigen presenting cell cytokine/chemokine production, expands and/or maintains Th17 cells, enhances T cell proliferation and/or enhances Th1 and/or Th9 differentiation. In some aspects, the immune response primer is a member of the IL-12 family (e.g., IL-12, IL-23, IL-12p40 subunit, IL-23p19 subunit, IL-27, IL-35). In other aspects, the immune response primer is a member of the IL-1 family (e.g., IL-1α, IL-1β, IL-1Ra, IL-18, IL-33, IL-36Ra, IL-36α, IL-36β, IL-36γ, IL-37, IL-38). In some aspects, the immune response primer is a polypeptide selected from the group consisting of: IL-23, IL-12p40 subunit, IL-23p19 subunit, IL-12, IL-36-gamma, and IL-18.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (IL-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances (e.g., nucleotide sequence or protein sequence) can have varying levels of purity in reference to the substances from which they have been associated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The term "substantially isolated" means that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the disclosure. It is recognized that the compounds of the disclosure can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

Modified: As used herein "modified" refers to a changed state or structure of a molecule of the disclosure. Molecules can be modified in many ways including chemically, structurally, and functionally. In some embodiments, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Nanoparticle Composition: As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the disclosure wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A, C, T and U in the case of a synthetic DNA, or A, C, T, and U in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding RNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a 'P'C codon (RNA map in which U has been replaced with pseudouridine).

Standard A-T and G-C base pairs form under conditions which allow the formation of hydrogen bonds between the N3-H and C4-oxy of thymidine and the N1 and C6-NH$_2$, respectively, of adenosine and between the C2-oxy, N3 and C4-NH$_2$, of cytidine and the C2-NH$_2$, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al. (1993) J. Am. Chem. Soc. 115:4461-4467, and references cited therein; and isoguanine nucleotides can be prepared using the method described by Switzer et al., 1993, supra, and Mantsch et al. (1993) Biochem. 14:5593-5601, or by the method described in U.S. Pat. No. 5,780,610 to Collins et al. Other nonnatural base pairs can be synthesized by the method described in Piccirilli et al. (1990) Nature 343:33-37, for the synthesis of 2,6-diaminopyrimidine and its complement (1-methylpyrazolo-[4,3]pyrimidine-5,7-(4H, 6H)-dione. Other such modified nucleotide units which form unique base pairs are known, such as those described in Leach et al. (1992) J. Am. Chem. Soc. 114:3675-3683 and Switzer et al., supra.

Nucleic acid sequence: The terms "nucleic acid sequence," "nucleotide sequence," or "polynucleotide" are used interchangeably and refer to a contiguous nucleic acid sequence. The sequence can be either single stranded or double stranded DNA or RNA, e.g., an mRNA.

The phrase "nucleotide sequence encoding" and variants thereof refers to the nucleic acid (e.g., an mRNA or DNA molecule) coding sequence that comprises a nucleotide sequence which encodes a polypeptide or functional fragment thereof as set forth herein. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity that is in a form predicate for that substance, molecule or entity to act as a therapeutic upon chemical or physical alteration. Prodrugs may by covalently bonded or sequestered in some way and that release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thiopseudouridine, N1-methyl-pseudouridine, 1-methyl-3-(3-amino-3-carboxypropyl)pseudouridine (acp$^3$ ψ), and 2'-O-methyl-pseudouridine (ψm).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., a mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Repeated transfection: As used herein, the term "repeated transfection" refers to transfection of the same cell culture with a polynucleotide a plurality of times. The cell culture can be transfected at least twice, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times at least 18 times, at least 19 times, at least 20 times, at least 25 times, at least 30 times, at least 35 times, at least 40 times, at least 45 times, at least 50 times or more.

Salts: In some aspects, the pharmaceutical composition for intratumoral delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it may be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of a cancer treatment.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present disclosure can be chemical or enzymatic.

Targeted cells: As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the disclosure can be characterized as having both an N-terminus (terminated by an amino acid with a free amino group ($NH_2$)) and a C-terminus (terminated by an amino acid with a free carboxyl group (COOH)). Proteins of the disclosure are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, a mRNA encoding an IL-36-gamma polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Transcription: As used herein, the term "transcription" refers to methods to introduce exogenous nucleic acids into a cell. Methods of transfection include, but are not limited to, chemical methods, physical treatments and cationic lipids or mixtures.

Transfection: As used herein, "transfection" refers to the introduction of a polynucleotide into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a hyper-proliferative disease, e.g., cancer. For example, "treating" cancer can refer to inhibiting survival, growth, and/or spread of a tumor. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Tumor Microenvironment": As used herein, "tumor microenvironment" refers to the cellular compositions within a tumor with respect to the presence or absence of infiltrating immune and/or inflammatory cells, as well as the type(s) of such cells within the tumor. In one aspect, a tumor microenvironment is an "inflamed tumor microenvironment", which refers to the presence of immune and/or inflammatory cells infiltrated into the tumor, with the predominant cell type being granulocytes. In another aspect, a tumor microenvironment is an "immunosuppressive tumor microenvironment", which refers to the presence of immune and/or inflammatory cells infiltrated into the tumor, with the predominant cell types being monocytic cells and macrophages. In another aspect, a tumor microenvironment is an "immunologically barren tumor microenvironment", which refers to an absence of significant infiltration into the tumor of immune and/or inflammatory cells.

Unmodified: As used herein, "unmodified" refers to any substance, compound or molecule prior to being changed in any way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a β-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

II. Combinations Comprising Polynucleotides Encoding Immune Modulatory Polypeptides The present disclosure provides compositions ("compositions of the disclosure") for the treatment of cancer. In one embodiment, the compositions comprise, in a single formulation, at least two polynucleotides (e.g., mRNAs) or at least three polynucleotides (e.g., mRNAs), each of the compositions selected from a first polynucleotide encoding IL-23, a second polynucleotide encoding IL-36-gamma (or, alternatively, IL-18), and/or a third polynucleotide encoding OX40L. Accordingly, the present disclosure provides, for example, (i) a first polynucleotide (e.g., mRNA) encoding a first protein comprising an IL-23 polypeptide, (ii) a second polynucleotide (e.g., mRNA) encoding a second protein comprising an IL-36-gamma polypeptide (or an IL-18 polypeptide), and (iii) a third polynucleotide (e.g., mRNA) encoding a third protein comprising an OX40L polypeptide, wherein the first polynucleotide, the second polynucleotide, and the third polypeptide are used in various combinations. In one aspect, the composition comprises the first polynucleotide, the second polynucleotide, and the third polynucleotide. The term "polynucleotides of the disclosure" refers to the first polynucleotide, the second polynucleotide, and the third polynucleotide disclosed herein.

As used herein, the term "combinations of the disclosure" comprises, e.g., the combination of (i) a first polynucleotide (e.g., mRNA) encoding a first protein comprising an IL-23 polypeptide, and a second polynucleotide encoding a second protein comprising an IL-36-gamma polypeptide or IL-18 polypeptide; (ii) a first polynucleotide (e.g., mRNA) encoding a first protein comprising an IL-23 polypeptide, and a third polynucleotide (e.g., mRNA) encoding a third protein comprising an OX40L polypeptide; (iii) a second polynucleotide (e.g., mRNA) encoding a second protein comprising an IL-36-gamma polypeptide or IL-18 polypeptide, and a third polynucleotide (e.g., mRNA) encoding a third protein comprising an OX40L polypeptide; or (iv) a first polynucleotide (e.g., mRNA) encoding a first protein comprising an IL-23 polypeptide, a second polynucleotide (e.g., mRNA) encoding a second protein comprising an IL-36-gamma polypeptide or an IL-18 polypeptide, and a third polynucleotide (e.g., mRNA) encoding a third protein comprising an OX40L polypeptide. It is to be understood that the term "combinations of the disclosure" is not limited to the physical combination of a first polynucleotide, a second polynucleotide, and/or a third polynucleotide, but also encompasses the separate administration of both these polynucleotides concurrently or sequentially.

Therefore, in another embodiment, the composition of the present disclosure comprises a polynucleotide (e.g., mRNA) encoding a single polypeptide, IL-23, IL-36-gamma or IL-18, or OX40L, but each of the composition (e.g., a composition comprising a first polynucleotide encoding IL-23, a composition comprising a second polynucleotide encoding IL-36-gamma or IL-18, and a third polynucleotide encoding OX40L) can be used in combination in the methods described herein.

One skilled in the art would also appreciate that alternative embodiments of the present disclosure include a combination therapy of IL-23, IL-36-gamma or IL-18, and/or OX40 as polynucleotides and/or proteins. For example, the present disclosure encompasses combination therapy of (i) a first polynucleotide (e.g., mRNA) encoding IL-23 and a second protein comprising IL-36-gamma or IL-18; a first protein comprising IL-23 and a second polynucleotide (e.g., mRNA) encoding a second protein which comprises IL-36 gamma IL-18; or (iii) a first protein comprising IL-23 and a second protein comprising IL-36 gamma or IL-18. Likewise, the present disclosure further encompasses combination therapy of a IL-23 polynucleotide (e.g., mRNA) or a first protein comprising an IL-23 polypeptide, an IL-36-gamma polynucleotide or an IL-18 polynucleotide (e.g., mRNA) or a second protein comprising an IL-36-gamma polypeptide or an IL-18 polypeptide, an OX40L polynucleotide (e.g., mRNA) or a third protein comprising an OX40L polypeptide, or combinations thereof.

Polynucleotides Encoding IL-23

IL-23 is a pro-inflammatory cytokine that plays an important role in innate and adaptive immunity. Croxford et al. (2012) Eur. J. Immunol. 42:2263-2273. IL-23 functions primarily as a 60 kDa heterodimeric protein consisting of disulfide-linked p19 and p40 subunits. IL-23 is structurally and functionally similar to the pro-inflammatory cytokine IL-12. IL-23 contains the same p40 subunit as IL-12, but includes the p19 subunit rather than IL-12's p35. Oppman et al. (2000) Immunity 13:715-725. The precursor form of the p19 subunit (NCBI Reference Sequence: NP_057668; NM_016584; Uniprot: Q9NPF7; also referred to as IL-23A and IL-23 subunit alpha) is 189 amino acids in length, while its mature form is 170 amino acids long. The precursor form of the p40 subunit (NCBI Reference Sequence: NM_002187; Uniprot:P29460; also referred to as IL-12B, natural killer cell stimulatory factor 2, and cytotoxic lymphocyte maturation factor 2) is 328 amino acids in length, while its mature form is 306 amino acids long.

Many different immune cells, including dendritic cells and macrophages, produce IL-23 upon antigenic stimuli. One difference between IL-12 and IL-23 is that IL-12 is associated with the development and activity of Th1 T cell populations, while IL-23 is associated with the development and activity of Th17 T cell populations. See Vignali et al. (2014) Nat. Immunol. 13:722-728.

Although some early studies implicated IL-23 for anti-tumor therapy (Belladonna et al. (2002) J. Immunol. 168: 5448-5454), more recent studies indicate a potential pro-tumorigenic function for IL-23. See, e.g., Croxford et al. (2012) Eur. J. Immunol. 42:2263-2273. Langowski et al. (2007) Trends Immunol. 28:207-212; Langowski et al. (2006) Nature 442:461-465; Teng et al. (2010) Proc. Natl. Acad. Sci. USA 107:8328-8333; Teng et al. (2012) Cancer Res. 72:3987-3996. Langowski (2006) observed an increase of IL-23 in human tumors. See also Ngiow et al. (2013) Trends Immunol. 34:548-555; Wilke et al. (2011) Carcinogenesis 32:643-649; Xu et al. (2010) Clin. Dev. Immunol. 2010. For example, Wang et al. (2015) Clin. Exp. Rheumatol. 33 (Suppl. 92): S87-S90 teaches that elevated expression of IL-23 has a pathogenic function in cancer. IL-23 has a causal role in tumor development and progression and has been linked to adverse prognostic outcome and rapid progression to metastatic disease, suggesting that inhibition of IL-23 expression may be useful for therapy and prevention of cancer, particularly colorectal cancer. Teng et al. (2015) Nature Medicine 21: 719-29 teaches that IL-23 indirectly or directly promotes tumorigenesis, growth, and metastasis, and indicates that inhibition of IL-23 expression could be used for therapy and prevention of cancer.

As used in the present disclosure, the term "IL-23 polypeptide" refers to, e.g., a IL-12p40 subunit of IL-23, to an IL-23p19 subunit of IL-23, or to a fusion protein comprising an IL-12p40 subunit polypeptide and an IL-23p19 subunit polypeptide. In some aspects, the fusion protein comprises from N-terminus to C-terminus:

(a) an IL-12p40 subunit comprising the IL-12p40 signal peptide, a peptide linker, and a mature IL-23p19 subunit, or (b) an IL-23p19 subunit comprising the IL-23p19 signal peptide, a peptide linker, and a mature IL-12p40.

In one particular aspect, the IL-23 polypeptide comprises, consists of, or consists essentially of a human or murine IL-23 polypeptide of Table 1 (e.g., a precursor or mature IL-12p40 or IL-23p19) or a combination thereon. In one particular aspect, the polynucleotide encoding the IL-23 polypeptide comprises, consists of, or consists essentially of an IL-23-encoding polynucleotide of Table 1.

In some embodiments, the IL-23 polypeptide comprises an amino acid sequence at least 50%, at least 60%, at least 70%, at least 80%, at least 85%, at least 90%, at least 95%, at least 98%, at least 99%, or 100% identical to an IL-23 amino acid sequence listed in Table 1 or an amino acid sequence encoded by a nucleotide sequence listed in Table 1, wherein the IL-23 polypeptide has at least 10% of the activity (e.g., binding to its receptor) of the corresponding wild type IL-23 polypeptide. In a particular embodiment, the IL-23 polypeptide comprises an amino acid sequence at least 50%, at least 60%, at least 70%, at least 80%, at least 85%, at least 90%, at least 95%, at least 98%, at least 99%, or 100% identical to SEQ ID NO: 1, SEQ ID NO: 5 or SEQ ID NO: 140 and has at least 10% of the activity (e.g., binding to its receptor) of the corresponding wild type IL-23 polypeptide. In another particular embodiment, the IL-23 polypeptide consists essentially of SEQ ID NO: 1, SEQ ID NO: 5 or SEQ ID NO: 140 and has at least 10% of the activity (e.g., binding to its receptor) of the corresponding wild type IL-23 polypeptide.

In other embodiments, the IL-23 polypeptide encoded by a polynucleotide of the disclosure comprises an amino acid sequence listed in Table 1 or shown in SEQ ID NOs: 1, 5 or 140 with one or more conservative substitutions, wherein the conservative substitutions do not significantly affect the binding activity of the IL-23 polypeptide to its receptor, i.e., the IL-23 polypeptide binds to the IL-23 receptor after the substitutions.

In some embodiments, a nucleotide sequence (i.e., mRNA) encoding an IL-23 polypeptide comprises a sequence at least 50%, at least 60%, at least 70%, at least 80%, at least 85%, at least 90%, at least 95%, at least 98%, at least 99%, or 100% identical to an IL-23 polypeptide encoding nucleic acid sequence listed in Table 1. In a particular embodiment, the nucleotide sequence (i.e., mRNA) encoding an IL-23 polypeptide comprises a sequence at least 50%, at least 60%, at least 70%, at least 80%, at least 85%, at least 90%, at least 95%, at least 98%, at least 99%, or 100% identical to SEQ ID NO:19, SEQ ID NO:71, SEQ ID NO: 141 or SEQ ID NO: 142. In another particular embodiment, the nucleotide sequence (i.e., mRNA) encoding an IL-23 polypeptide consists essentially of SEQ ID NO: 19, SEQ ID NO:71, SEQ ID NO: 141 or SEQ ID NO: 142. It should be understood that the nucleotide sequence (i.e., mRNA, e.g., SEQ ID NO:19, SEQ ID NO:71 or SEQ ID NO: 141) encoding an IL-23 polypeptide open reading frame (ORF) can be one element within a larger construct, e.g., further including a 5' terminal cap, 5'UTR (e.g., SEQ ID NOs: 27 or 44), 3'UTR (e.g., SEQ ID NOs: 119 or 120), and/or polyA tail.

Polynucleotides Encoding IL-12 Polypeptides

In some aspects, the first polynucleotide encodes a first protein comprising an IL-12 polypeptide. As used in the present disclosure, the term "IL-12 polypeptide" refers to, e.g., a IL-12p40 subunit of IL-12 (i.e., IL12B), to an IL-12p35 subunit of IL-12 (i.e., IL12Aa), or to a fusion protein comprising an IL-12p40 subunit polypeptide and an IL-12p35 subunit polypeptide. In some aspects, the fusion protein comprises an IL12B polypeptide selected from:

(i) the full-length IL12B polypeptide (e.g., having the same or essentially the same length as wild-type IL12B);

(ii) a functional fragment of the full-length IL12B polypeptide (e.g., a truncated (e.g., deletion of carboxy, amino terminal, or internal regions) sequence shorter than an IL12B wild-type; but still retaining IL12B enzymatic activity);

(iii) a variant thereof (e.g., full length or truncated IL12B proteins in which one or more amino acids have been replaced, e.g., variants that retain all or most of the IL12B activity of the polypeptide with respect to the wild type IL12B polypeptide (such as, e.g., V33I, V298F, or any other natural or artificial variants known in the art); or (iv) a fusion protein comprising (i) a full length IL12B wild-type, a functional fragment or a variant thereof, and (ii) a heterologous protein;

and/or an IL12A polypeptide selected from:

(i) the full-length IL12A polypeptide (e.g., having the same or essentially the same length as wild-type IL12A);

(ii) a functional fragment of the full-length IL12A polypeptide (e.g., a truncated (e.g., deletion of carboxy, amino terminal, or internal regions) sequence shorter than an IL12A wild-type; but still retaining IL12A enzymatic activity);

(iii) a variant thereof (e.g., full length or truncated IL12A proteins in which one or more amino acids have been replaced, e.g., variants that retain all or most of the IL12A activity of the polypeptide with respect to the wtIL12A polypeptide (such as natural or artificial variants known in the art); or (iv) a fusion protein comprising (i) a full length IL12A wild-type, a functional fragment or a variant thereof, and (ii) a heterologous protein.

In one particular aspect, the IL-12 polypeptide comprises, consists of, or consists essentially of a human or murine IL-12 polypeptide of Table 1 (e.g., a precursor or mature IL-12p40 or IL-12p35) or a combination thereon. In one particular aspect, the polynucleotide encoding the IL-12 polypeptide comprises, consists of, or consists essentially of an IL-23-encoding polynucleotide of Table 1.

In some embodiments, the IL-12 polypeptide comprises an amino acid sequence at least 50%, at least 60%, at least 70%, at least 80%, at least 85%, at least 90%, at least 95%, at least 98%, at least 99%, or 100% identical to an IL-12 amino acid sequence listed in Table 1 or an amino acid sequence encoded by a nucleotide sequence listed in Table 1, wherein the IL-12 polypeptide has at least 10% of the activity (e.g., binding to its receptor) of the corresponding wild type IL-12 polypeptide.

In other embodiments, the IL-12 polypeptide encoded by a polynucleotide of the disclosure comprises an amino acid sequence listed in Table 1 with one or more conservative substitutions, wherein the conservative substitutions do not significantly affect the binding activity of the IL-12 polypeptide to its receptor, i.e., the IL-12 polypeptide binds to the IL-12 receptor after the substitutions.

In some embodiments, a nucleotide sequence (i.e., mRNA) encoding an IL-12 polypeptide comprises a sequence at least 50%, at least 60%, at least 70%, at least 80%, at least 85%, at least 90%, at least 95%, at least 98%, at least 99%, or 100% identical to an IL-12 polypeptide encoding nucleic acid sequence listed in Table 1. In a particular embodiment, the nucleotide sequence (i.e., mRNA) encoding an IL-12 polypeptide comprises a sequence at least 50%, at least 60%, at least 70%, at least 80%, at least 85%, at least 90%, at least 95%, at least 98%, at least 99%, or 100% identical to SEQ ID NO:183. It should be understood that the nucleotide sequence (i.e., mRNA) encoding an IL-12 polypeptide open reading frame (ORF) can be one element within a larger construct, e.g., further including a 5' terminal cap, 5'UTR (e.g., SEQ ID NOs: 27 or 44), 3'UTR (e.g., SEQ ID NOs: 119 or 120), and/or polyA tail.

Polynucleotides Encoding IL-36-Gamma Polypeptides

In some aspects, the first polynucleotide encoding a first protein comprising an IL-23 polypeptide can be combined with a polynucleotide encoding a second comprising an IL-36 polypeptide.

IL-36-gamma is a member of the Interleukin-1 family of cytokines. Like other members of the interleukin-1 family of cytokines, IL-36-gamma requires N-terminal cleavage for full bioactivity. IL-36-gamma does not have a signal sequence and, therefore, is not secreted through the endoplasmic reticulum Golgi pathway. See Gresnigt and van de Veerdonk (2013) Seminars in Immunology 25:458-465). It is unclear how IL-36-gamma is released from cells to act on, e.g., immune cells, other epithelial cells, and fibroblasts (Gabay et al. (2015) Journal of Leukocyte Biology 97:645-652). In exemplary aspects of the invention, a polynucleotide encoding IL-36, e.g., IL-36-gamma, includes a sequence encoding a heterologous signal peptide. Without being bound in theory, it is believed that polynucleotides encoding such "engineered" signal peptide-interleukin chimeric proteins provide for the generation of active protein when expressed in vivo, in the absence of inflammasome activation.

In one embodiment, the heterologous signal peptide is derived from an immunoglobulin heavy or light chain. In an exemplary embodiment, the heterologous signal peptide is derived from an immunoglobulin light chain, e.g., from the variable region of said light channel. In an exemplary embodiment, the heterologous signal peptide is derived from human immunoglobulin kappa light chain variable region, hIGVK4. In exemplary aspects, a polynucleotide of the invention encodes a heterologous signal peptide, operably linked to sequence encoding an IL-36-gamma polypeptide.

In one particular aspect, the IL-36-gamma polypeptide comprises, consists of, or consists essentially of an IL-36-gamma polypeptide of Table 1. In one particular aspect, the polynucleotide encoding the IL-36-gamma polypeptide comprises, consists of, or consists essentially of an IL-36-gamma-encoding polynucleotide of Table 1.

In some embodiments, the IL-36-gamma polypeptide comprises an amino acid sequence at least 50%, at least 60%, at least 70%, at least 80%, at least 85%, at least 90%, at least 95%, at least 98%, at least 99%, or 100% identical to an IL-36-gamma amino acid sequence listed in Table 1 or an amino acid sequence encoded by a nucleotide sequence listed in Table 1, wherein the IL-36-gamma polypeptide has at least 10% of the activity (e.g., binding to its receptor) of the corresponding wild type IL-36-gamma polypeptide. In a particular embodiment, the IL-36-gamma polypeptide comprises an amino acid sequence at least 50%, at least 60%, at least 70%, at least 80%, at least 85%, at least 90%, at least 95%, at least 98%, at least 99%, or 100% identical to SEQ ID NO: 16 and has at least 10% of the activity (e.g., binding to its receptor) of the corresponding wild type IL-36-gamma polypeptide. In another particular embodiment, the IL-36-gamma polypeptide consists essentially of SEQ ID NO: 16 and has at least 10% of the activity (e.g., binding to its receptor) of the corresponding wild type IL-36-gamma polypeptide.

In other embodiments, the IL-36-gamma polypeptide encoded by a polynucleotide of the disclosure comprises an amino acid sequence listed in Table 1 or shown in SEQ ID NO: 16 with one or more conservative substitutions, wherein the conservative substitutions do not significantly affect the binding activity of the IL-36-gamma polypeptide to its receptor, i.e., the IL-36-gamma polypeptide binds to the IL-36-gamma receptor after the substitutions.

In some embodiments, a nucleotide sequence (i.e., mRNA) encoding an IL-36-gamma polypeptide comprises a sequence at least 50%, at least 60%, at least 70%, at least 80%, at least 85%, at least 90%, at least 95%, at least 98%, at least 99%, or 100% identical to a IL-36-gamma polypeptide encoding nucleic acid sequence listed in Table 1. In a particular embodiment, the nucleotide sequence (i.e., mRNA) encoding an IL-36-gamma polypeptide comprises a sequence at least 50%, at least 60%, at least 70%, at least 80%, at least 85%, at least 90%, at least 95%, at least 98%, at least 99%, or 100% identical to SEQ ID NO:17, SEQ ID NO:94, SEQ ID NO: 143 or SEQ ID NO: 144. In another particular embodiment, the nucleotide sequence (i.e., mRNA) encoding an IL-36-gamma polypeptide consists essentially of SEQ ID NO:17, SEQ ID NO:94, SEQ ID NO: 143 OR SEQ ID NO: 144. It should be understood that the nucleotide sequence (i.e., mRNA, e.g., SEQ ID NO: 17, SEQ ID NO:94 or SEQ ID NO: 143) encoding an IL-23 polypeptide open reading frame (ORF) can be one element within a larger construct, e.g., further including a 5' terminal cap, 5'UTR (e.g., SEQ ID NOs: 27 or 44), 3'UTR (e.g., SEQ ID NOs: 119 or 120), and/or polyA tail.

Polynucleotides Encoding IL-18 Polypeptides

In some aspects, the first polynucleotide encoding a first protein comprising an IL-23 polypeptide can be combined with a second polynucleotide encoding a second protein, wherein the second protein comprises an IL-18 polypeptide.

IL-18, also known as interferon-gamma inducing factor (IGIF) and IFN-γ inducing factor, is a member of the Interleukin-1 family of cytokines. IL-18 has two known isoforms, Isoform 1 and Isoform 2. Isoform 2 differs from Isoform 1 in that it is missing residues 27-30. Like other members of the interleukin-1 family of cytokines, IL-18 requires N-terminal cleavage for full bioactivity (Dinarello et al. (2013) Frontiers in Immunology 4:289). IL-18 does not have a signal sequence and, therefore, is not secreted through the endoplasmic reticulum Golgi pathway. See Gresnigt and van de Veerdonk (2013) Seminars in Immunology 25:458-465).

IL-18 is a pro-inflammatory agonist that signals through the IL-18α and IL-18β co-receptors to induce a signaling cascade activating NFκB and MAPKs (Dinarello et al. (2013). As in the case of IL-23, there are conflicting reports regarding the potential use of IL-18 for anticancer therapy. Ma et al. (2016) Clin. Cancer Res. 22:2969-2680 teaches that co-treatment with IL-18 enhances the antitumor activity elicited by anti-PD-L1 and/or anti-CTLA-4. However, Fabbi et al. (2015) J. Leukoc. Biol. 97:665-675 teaches that IL-18 may play divergent roles in cancer, having anticancer activities in some cases and tumor-promoting activities in other cases. Fabbi indicates that although the preclinical studies and some clinical trials suggest that IL-18 has anti-tumor activities, other studies indicate that IL-18 may exert pro-invasive, proangiogenic, and immune-regulatory activities in different tumor models. For example, Term et al. (2011) Cancer Res. 71: 5393-9 teaches that IL-18 is an immunosuppressive cytokine in cancer, and that IL-18 produced by tumor cells promotes the development of NK-controlled metastases in a PD-1-dependent manner. Kang et al. (2009) Carcinogenesis 30:1987-86 teaches that IL-18 increases metastases and immune escape of stomach cancer.

In exemplary aspects of the invention, a polynucleotide encoding IL-18 includes a sequence encoding a heterologous signal peptide. Without being bound in theory, it is believed that polynucleotides encoding such "engineered" signal peptide-interleukin chimeric proteins provide for the generation of active protein when expressed in vivo, in the absence of inflammasome activation.

In one embodiment, the heterologous signal peptide is derived from an immunoglobulin heavy or light chain. In an exemplary embodiment, the heterologous signal peptide is derived from an immunoglobulin light chain, e.g., from the variable region of said light chain.

In an exemplary embodiment, the heterologous signal peptide is derived from human immunoglobulin kappa light chain variable region, hIGVK4. In exemplary aspects, a polynucleotide of the invention encodes a heterologous signal peptide, operably linked to sequence encoding an IL-18 polypeptide.

In one particular aspect, the IL-18 polypeptide comprises, consists of, or consists essentially of an IL-18 polypeptide of Table 1. In one particular aspect, the polynucleotide encoding the IL-18 polypeptide comprises, consists of, or consists essentially of an IL-18-encoding polynucleotide of Table 1.

In some embodiments, the IL-18 polypeptide comprises an amino acid sequence at least 50%, at least 60%, at least 70%, at least 80%, at least 85%, at least 90%, at least 95%, at least 98%, at least 99%, or 100% identical to an IL-18 amino acid sequence listed in Table 1 or an amino acid sequence encoded by a nucleotide sequence listed in Table 1, wherein the IL-18 polypeptide has at least 10% of the activity (e.g., binding to its receptor) of the corresponding wild type IL-18 polypeptide. In a particular embodiment, the nucleotide sequence (i.e., mRNA) encoding an IL-18 polypeptide comprises a sequence at least 50%, at least 60%, at least 70%, at least 80%, at least 85%, at least 90%, at least 95%, at least 98%, at least 99%, or 100% identical to SEQ ID NO: 148, SEQ ID NO:155, SEQ ID NO: 156, SEQ ID NO: 157, SEQ ID NO: 158, SEQ ID NO: 159, SEQ ID NO: 160, SEQ ID NO: 161 or SEQ ID NO: 162. In another particular embodiment, the nucleotide sequence (i.e., mRNA) encoding an IL18 polypeptide consists essentially of to SEQ ID NO: 148, SEQ ID NO:155, SEQ ID NO: 156, SEQ ID NO: 157, SEQ ID NO: 158, SEQ ID NO: 159, SEQ ID NO: 160, SEQ ID NO: 161 or SEQ ID NO: 162. It should be understood that the nucleotide sequence (i.e., mRNA, e.g., to SEQ ID NO: 148, SEQ ID NO:155, SEQ ID NO: 156, SEQ ID NO: 157, SEQ ID NO: 158, SEQ ID NO: 159, SEQ ID NO: 160, SEQ ID NO: 161 or SEQ ID NO: 162) encoding an IL-18 polypeptide open reading frame (ORF) can be one element within a larger construct, e.g., further including a 5' terminal cap, 5'UTR (e.g., SEQ ID NOs: 27 or 44), 3'UTR (e.g., SEQ ID NOs: 119 or 120), and/or polyA tail.

Polynucleotides Encoding OX40L Polypeptides

In some aspects, the first polynucleotide encoding a first protein comprising an IL-23 polypeptide can be combined with a third polynucleotide encoding a third protein, wherein the third protein comprises an OX40L polypeptide. In other aspects, the second polynucleotide encoding a second protein comprising an IL-36-gamma polypeptide or an IL-18 polypeptide can be combined with a third polynucleotide encoding a third protein, wherein the third protein comprises an OX40L polypeptide. In certain aspects, the first polynucleotide encoding a first protein comprising an IL-23 polypeptide and the second polynucleotide encoding a second protein comprising an IL-36-gamma polypeptide or an IL-18 polypeptide can be combined with a third polynucleotide encoding a third protein, wherein the third protein comprises an OX40L polypeptide.

Human OX40L was first identified on the surface of human lymphocytes infected with human T-cell leukemia virus type-I (HTLV-I) by Tanaka et al. (Tanaka et al., International Journal of Cancer (1985), 36(5):549-55). OX40L is the ligand for OX40 (CD134). OX40L has also been designated CD252 (cluster of differentiation 252), tumor necrosis factor (ligand) superfamily, member 4, tax-transcriptionally activated glycoprotein 1, TXGP1, or gp34. Human OX40L is 183 amino acids in length and contains three domains: a cytoplasmic domain of amino acids 1-23; a transmembrane domain of amino acids 24-50, and an extracellular domain of amino acids 51-183.

In some embodiments, the third polynucleotide comprises an mRNA encoding a mammalian OX40L polypeptide. In some embodiments, the mammalian OX40L polypeptide is a murine OX40L polypeptide. In some embodiments, the mammalian OX40L polypeptide is a human OX40L polypeptide. In some embodiments, the OX40L polypeptide comprises an amino acid sequence set forth in Table 1A.

In some embodiments, each polynucleotide of the disclosure comprises an mRNA, i.e., an mRNA encoding an IL-23 polypeptide, an mRNA encoding an IL-36-gamma polypeptide, and an mRNA encoding an OX40L polypeptide. In some embodiments, the mRNA encoding an IL-23 polypeptide encodes a mammalian IL-23 polypeptide. In some embodiments, the mRNA encoding an IL-36-gamma polypeptide encodes a mammalian IL-36-gamma polypeptide. In some embodiments, the mRNA encoding an OX40L polypeptide encodes a mammalian OX40L polypeptide. In some embodiments, the mRNA encoding an IL-23 polypeptide encodes a murine IL-23 polypeptide. In some embodiments, the mRNA encoding an IL-36-gamma polypeptide encodes a murine IL-36-gamma polypeptide. In some embodiments, the mRNA encoding an OX40L polypeptide encodes a murine OX40L polypeptide. In some embodiments, the mRNA encoding an IL-23 polypeptide encodes a human IL-23 polypeptide. In some embodiments, the mRNA encoding an IL-36-gamma polypeptide encodes a human IL-36-gamma polypeptide. In some embodiments, the mRNA encoding an OX40L polypeptide encodes a human OX40L polypeptide.

In some embodiments, the IL-23 polypeptide comprises a human amino acid sequence set forth in Table 1. In some embodiments, the IL-36-gamma polypeptide comprises a human amino acid sequence set forth in Table 1. In other embodiments, the OX40L polypeptide comprises a human amino acid sequence set forth in Table 1A.

In some embodiments, the OX40L polypeptide comprises an amino acid sequence at least 50%, at least 60%, at least 70%, at least 80%, at least 85%, at least 90%, at least 95%, at least 98%, at least 99%, or 100% identical to an amino acid sequence listed in Table 1A or an amino acid sequence encoded by a nucleotide sequence listed in Table 1A, wherein the amino acid sequence is capable of binding to an OX40 receptor. In a particular embodiment, the OX40L polypeptide comprises an amino acid sequence at least 50%, at least 60%, at least 70%, at least 80%, at least 85%, at least 90%, at least 95%, at least 98%, at least 99%, or 100% identical to SEQ ID NO: 21 and is capable of binding to an OX40 receptor. In another particular embodiment, the OX40L polypeptide consists essentially of SEQ ID NO: 21 and is capable of binding to an OX40 receptor.

In certain embodiments, the OX40L polypeptide encoded by a polynucleotide of the disclosure comprises an amino acid sequence listed in Table 1A or shown in SEQ ID NO: 21 with one or more conservative substitutions, wherein the conservative substitutions do not significantly affect the binding activity of the OX40L polypeptide to its receptor, i.e., the OX40L polypeptide binds to the OX40 receptor after the substitutions.

In other embodiments, a nucleotide sequence (i.e., mRNA) encoding an OX40L polypeptide comprises a sequence at least 50%, at least 60%, at least 70%, at least 80%, at least 85%, at least 90%, at least 95%, at least 98%, at least 99%, or 100% identical to a nucleic acid sequence listed in Table 1A. In a particular embodiment, the nucleotide sequence (i.e., mRNA) encoding an OX40L polypeptide comprises a sequence at least 50%, at least 60%, at least 70%, at least 80%, at least 85%, at least 90%, at least 95%, at least 98%, at least 99%, or 100% identical to SEQ ID NO: 116, SEQ ID NO: 145 or SEQ ID NO: 146. In another particular embodiment, the nucleotide sequence (i.e., mRNA) encoding an OX40L polypeptide consists essentially of SEQ ID NO: 116, SEQ ID NO: 145 or SEQ ID NO: 146. It should be understood that the nucleotide sequence (i.e., mRNA, e.g., SEQ ID NO: 116 or SEQ ID NO: 145) encoding an OX40L polypeptide open reading frame (ORF) can be one element within a larger construct, e.g., further including a 5' terminal cap, 5'UTR (e.g., SEQ ID NOs: 27 or 44), 3'UTR (e.g., SEQ ID NOs: 119 or 120), and/or polyA tail.

In some embodiments, the polynucleotide (e.g., mRNA) useful for the methods and compositions comprises an open reading frame encoding an extracellular domain of OX40L. In other embodiments, the polynucleotide (e.g., mRNA) comprises an open reading frame encoding a cytoplasmic domain of OX40L. In some embodiments, the polynucleotide (e.g., mRNA) comprises an open reading frame encoding a transmembrane domain of OX40L. In certain embodiments, the polynucleotide (e.g., mRNA) comprises an open reading frame encoding an extracellular domain of OX40L and a transmembrane of OX40L. In other embodiments, the polynucleotide (e.g., mRNA) comprises an open reading frame encoding an extracellular domain of OX40L and a cytoplasmic domain of OX40L. In yet other embodiments, the polynucleotide (e.g., mRNA) comprises an open reading frame encoding an extracellular domain of OX40L, a transmembrane of OX40L, and a cytoplasmic domain of OX40L.

Table 1 or Table 1A present, e.g., precursor and mature sequences for IL-23, IL-36-gamma, and OX40L as well as constructs comprising IL-23 or IL-36-gamma. In the context of the present disclosure IL-23 polynucleotide or IL-23 polypeptide encompass both "precursor" and "mature" forms. Furthermore, a construct comprising a polynucleotide encoding IL-23, IL-36-gamma, and OX40L and further comprising components such 3' UTR and 5' UTR would be considered an IL-23, IL-36-gamma, and OX40L encoding polynucleotide. A person of skill in the art would understand that in addition to the native signal sequences and propeptide sequences implicitly disclosed in Table 1 or 1A (sequences present in the precursor for and absent in the mature corresponding form) and the non-native signal peptide disclosed in Table 1 or 1A (IgKV4 signal peptide), other signal sequences can be used. Accordingly, references to an IL-23, IL-36-gamma, and OX40L polypeptide or polynucleotide according to Table 1 encompass variants in which an alternative signal peptide (or encoding sequence) known in the art has been attached to said IL-23, IL-36-gamma, and OX40L polypeptide (or polynucleotide). It is also understood that references to the sequences disclosed in Table 1 through the application are equally applicable and encompass orthologs and functional variants (for example polymorphic variants) and isoforms of those sequences known in the art at the time the application was filed.

TABLE 1

IL-23, IL-36-gamma and IL-18 Polypeptide and Polynucleotide Sequences

| Encoded Polypeptide | Description | Sequence | SEQ ID NO: |
|---|---|---|---|
| hIL-23 IL-12p40 subunit (Precursor) | Amino acid sequence of human IL-23 IL-12p40 subunit (Uniprot: P29460) (Precursor) | MCHQQLVISWFSLVFLASPLVAIWELKKDVYVVELDWYPDAPGEMVVLTC DTPEEDGITWTLDQSSEVLGSGKTLTIQVKEFGDAGQYTCHKGGEVLSHS LLLLHKKEDGIWSTDILKDQKEPKNKTFLRCEAKNYSGRFTCWWLTTIST DLTFSVKSSRGSSDPQGVTCGAATLSAERVRGDNKEYEYSVECQEDSACP AAEESLPIEVMVDAVHKLKYENYTSSFFIRDIIKPDPPKNLQLKPLKNSR QVEVSWEYPDTWSTPHSYFSLTFCVQVQGKSKREKKDRVFTDKTSATVIC RKNASISVRAQDRYYSSSWSEWASVPCS | SEQ ID NO: 1 |
| hIL-23 IL-12p40 subunit (Mature) | Amino acid sequence of human IL-23 IL-12p40 subunit (Uniprot: P29460\|23-328) (Mature) | IWELKKDVYVVELDWYPDAPGEMVVLTCDTPEEDGITWTLDQSSEVLGSG KTLTIQVKEFGDAGQYTCHKGGEVLSHSLLLLHKKEDGIWSTDILKDQKE PKNKTFLRCEAKNYSGRFTCWWLTTISTDLTFSVKSSRGSSDPQGVTCGA ATLSAERVRGDNKEYEYSVECQEDSACPAAEESLPIEVMVDAVHKLKYEN YTSSFFIRDIIKPDPPKNLQLKPLKNSRQVEVSWEYPDTWSTPHSYFSLT FCVQVQGKSKREKKDRVFTDKTSATVICRKNASISVRAQDRYYSSSWSEW ASVPCS | SEQ ID NO: 3 |
| IL-23 IL-23p19 subunit (Precursor) | Amino acid sequence of human IL-23 IL-23p19 subunit (Uniprot: Q9NPF7 (Precursor) | MLGSRAVMLLLLLPWTAQGRAVPGGSSPAWTQCQQLSQKLCTLAWSAHPL VGHMDLREEGDEETTNDVPHIQCGDGCDPQGLRDNSQFCLQRIHQGLIFY EKLLGSDIFTGEPSLLPDSPVGQLHASLLGLSQLLQPEGHHWETQQIPSL SPSQPWQRLLLRFKILRSLQAFVAVAARVFAHGAATLSP | SEQ ID NO: 4 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| IL-23 IL-23p19 subunit (Mature) | Amino acid sequence of human IL-23 IL-23p19 subunit (Uniprot: Q9NPF7 20-189) (Mature) | RAVPGGSSPAWTQCQQLSQKLCTLAWSAHPLVGHMDLREEGDEETTNDVPHIQCGDGCDPQGLRDNSQFCLQRIHQGLIFYEKLLGSDIFTGEPSLLPDSPVGQLHASLLGLSQLLQPEGHHWETQQIPSLSPSQPWQRLLLRFKILRSLQAFVAVAARVFAHGAATLSP | SEQ ID NO: 5 |
| hIL-23 (IL-12p40 subunit and IL-23p19 subunit) | Amino Acid sequence of human IL-23 (IL-12p40 subunit and IL-23p19 subunit linked by GS Linker) | MCHQQLVISWFSLVFLASPLVAIWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCSGGGGGGSRAVPGGSSPAWTQCQQLSQKLCTLAWSAHPLVGHMDLREEGDEETTNDVPHIQCGDGCDPQGLRDNSQFCLQRIHQGLIFYEKLLGSDIFTGEPSLLPDSPVGQLHASLLGLSQLLQPEGHHWETQQIPSLSPSQPWQRLLLRFKILRSLQAFVAVAARVFAHGAATLSP | 140 |
| IL-23 IL-12p40 subunit (Precursor) | Nucleotide sequence of human IL-23 IL-12p40 subunit (Precursor) | ATGTGTCACCAGCAGTTGGTCATCTCTTGGTTTTCCCTGGTTTTTCTGGCATCTCCCCTCGTGGCCATATGGGAACTGAAGAAAGATGTTTATGTCGTAGAATTGGATTGGTATCCGGATGCCCCTGGAGAAATGGTGGTCCTCACCTGTGACACCCCTGAAGAAGATGGTATCACCTGGACCTTGGACCAGAGCAGTGAGGTCTTAGGCTCTGGCAAAACCCTGACCATCCAAGTCAAAGAGTTTGGAGATGCTGGCCAGTACACCTGTCACAAAGGAGGCGAGGTTCTAAGCCATTCGCTCCTGCTGCTTCACAAAAAGGAAGATGGAATTTGGTCCACTGATATTTTAAAGGACCAGAAAGAACCCAAAAATAAGACCTTTCTAAGATGCGAGGCCAAGAATTATTCTGGACGTTTCACCTGCTGGTGGCTGACGACAATCAGTACTGATTTGACATTCAGTGTCAAAAGCAGCAGAGGCTCTTCTGACCCCCAAGGGGTGACGTGCGGAGCTGCTACACTCTCTGCAGAGAGAGTCAGAGGGGACAACAAGGAGTATGAGTACTCAGTGGAGTGCCAGGAGGACAGTGCCTGCCCAGCTGCTGAGGAGAGTCTGCCCATTGAGGTCATGGTGGATGCCGTTCACAAGCTCAAGTATGAAAACTACACCAGCAGCTTCTTCATCAGGGACATCATCAAACCTGACCCACCCAAGAACTTGCAGCTGAAGCCATTAAAGAATTCTCGGCAGGTGGAGGTCAGCTGGGAGTACCCTGACACCTGGAGTACTCCACATTCCTACTTCTCCCTGACATTCTGCGTTCAGGTCCAGGGCAAGAGCAAGAGAGAAAAGAAAGATAGAGTCTTCACGGACAAGACCTCAGCCACGGTCATCTGCCGCAAAAATGCCAGCATTAGCGTGCGGGCCCAGGACCGCTACTATAGCTCATCTTGGAGCGAATGGGCATCTGTGCCCTGCAGTTA | SEQ ID NO: 6 |
| IL-23 IL-12p40 subunit (Mature) | Nucleotide sequence of human IL-23 IL-12p40 subunit (Mature) | ATATGGGAACTGAAGAAAGATGTTTATGTCGTAGAATTGGATTGGTATCCGGATGCCCCTGGAGAAATGGTGGTCCTCACCTGTGACACCCCTGAAGAAGATGGTATCACCTGGACCTTGGACCAGAGCAGTGAGGTCTTAGGCTCTGGCAAAACCCTGACCATCCAAGTCAAAGAGTTTGGAGATGCTGGCCAGTACACCTGTCACAAAGGAGGCGAGGTTCTAAGCCATTCGCTCCTGCTGCTTCACAAAAAGGAAGATGGAATTTGGTCCACTGATATTTTAAAGGACCAGAAAGAACCCAAAAATAAGACCTTTCTAAGATGCGAGGCCAAGAATTATTCTGGACGTTTCACCTGCTGGTGGCTGACGACAATCAGTACTGATTTGACATTCAGTGTCAAAAGCAGCAGAGGCTCTTCTGACCCCCAAGGGGTGACGTGCGGAGCTGCTACACTCTCTGCAGAGAGAGTCAGAGGGGACAACAAGGAGTATGAGTACTCAGTGGAGTGCCAGGAGGACAGTGCCTGCCCAGCTGCTGAGGAGAGTCTGCCCATTGAGGTCATGGTGGATGCCGTTCACAAGCTCAAGTATGAAAACTACACCAGCAGCTTCTTCATCAGGGACATCATCAAACCTGACCCACCCAAGAACTTGCAGCTGAAGCCATTAAAGAATTCTCGGCAGGTGGAGGTCAGCTGGGAGTACCCTGACACCTGGAGTACTCCACATTCCTACTTCTCCCTGACATTCTGCGTTCAGGTCCAGGGCAAGAGCAAGAGAGAAAAGAAAGATAGAGTCTTCACGGACAAGACCTCAGCCACGGTCATCTGCCGCAAAAATGCCAGCATTAGCGTGCGGGCCCAGGACCGCTACTATAGCTCATCTTGGAGCGAATGGGCATCTGTGCCCTGCAGTTA | SEQ ID NO: 7 |
| IL-23 IL-23p19 subunit (Precursor) | Nucleotide sequence of human IL-23 IL-23p19 subunit (Precursor) | ATGCTGGGGAGCAGAGCTGTAATGCTGCTGTTGCTGCTGCCCTGGACAGCTCAGGGCAGAGCTGTGCCTGGGGGCAGCAGCCCTGCCTGGACTCAGTGCCAGCAGCTTTCACAGAAGCTCTGCACACTGGCCTGGAGTGCACATCCACTAGTGGGACACATGGATCTAAGAGAAGAGGGAGATGAAGAGACTACAAATGATGTTCCCCATATCCAGTGTGGAGATGGCTGTGACCCCCAAGGACTCAGGGACAACAGTCAGTTCTGCTTGCAAAGGATCCACCAGGGTCTGATTTTTTATGAGAAGCTGCTAGGATCGGATATTTTCACAGGGGAGCCTTCTCTGCTCCCTGATAGCCCTGTGGCGCAGCTTCATGCCTCCCTACTGGGCCTCAGCCAACTCCTGCAGCCTGAGGGTCACCACTGGGAGACTCAGCAGATTCCAAGCCTCAGTCCCAGCCAGCCATGGCAGCGTCTCCTTCTCCGCTTCAAAATCCTTCGCAGCCTCCAGGCCTTTGTGGCTGTAGCCGCCCGGGTCTTTGCCCATGGAGCAGCAACCCTGAGTCCC | SEQ ID NO: 8 |

TABLE 1-continued

| IL-23, IL-36-gamma and IL-18 Polypeptide and Polynucleotide Sequences | | | |
|---|---|---|---|
| Encoded Polypeptide | Description | Sequence | SEQ ID NO: |
| IL-23 IL-23p19 subunit (Mature) | Nucleotide sequence of human IL-23 IL-23p19 subunit (Mature) | AGAGCTGTGCCTGGGGGCAGCAGCCCTGCCTGGACTCAGTGCC<br>AGCAGCTTTCACAGAAGCTCTGCACACTGGCCTGGAGTGCACATCCACTA<br>GTGGGACACATGGATCTAAGAGAAGAGGGAGATGAAGAGACTACAAATGA<br>TGTTCCCCATATCCAGTGTGGAGATGGCTGTGACCCCCAAGGACTCAGGG<br>ACAACAGTCAGTTCTGCTTGCAAAGGATCCACCAGGGTCTGATTTTTTAT<br>GAGAAGCTGCTAGGATCGGATATTTTCACAGGGGAGCCTTCTCTGCTCCC<br>TGATAGCCCTGTGGCGCAGCTTCATGCCTCCCTACTGGGCCTCAGCCAAC<br>TCCTGCAGCCTGAGGGTCACCACTGGGAGACTCAGCAGATTCCAAGCCTC<br>AGTCCCAGCCAGCCATGGCAGCGTCTCCTTCTCCGCTTCAAAATCCTTCG<br>CAGCCTCCAGGCCTTTGTGGCTGTAGCCGCCCGGGTCTTTGCCCATGGAG<br>CAGCAACCCTGAGTCCC | SEQ ID NO: 9 |
| hIL-23 (IL-12p40 subunit and IL-23p19 subunit) | Nucleotide sequence (ORF) of human IL-23 (IL-12p40 subunit and IL-23p19 subunit linked by GS Linker) | AUGUGUCACCAGCAGUUGGUCAUCUCUUGGUUUUCCCUGGUAUUUCUGGCA<br>UCUCCCCUCGUGGCCAUAUGGGAACUGAAGAAAGAUGUUUAUGUCGUAGAA<br>UUGGAUUGGUAUCCGGAUGCCCCUGGAGAAAUGGUGGUCCUCACCUGUGAC<br>ACCCCUGAAGAAGAUGGUAUCACCUGGACCUUGGACCAGAGCAGUGAGGUC<br>UUAGGCUCUGGCAAGACCCUGACCAUCCAAGUCAAAGAGUUUGGAGAUGCU<br>GGCCAGUACACCUGUCACAAAGGAGGCGAGGUUCUAAGCCAUUCGCUCCUG<br>CUGCUUCACAAGAAGGAAGAUGGAAUUUGGUCCACUGAUAUUUUAAAGGAC<br>CAGAAAGAACCCAAGAAUAAGACCUUUCUAAGAUGCGAGGCCAAGAAUUAU<br>UCUGGACGUUUCACCUGCUGGUGGCUGACGACAAUCAGUACUGAUUUGACA<br>UUCAGUGUCAAGAGCAGCAGAGGCUCUUCUGACCCCCAAGGGGUGACGUGC<br>GGAGCUGCUACACUCUCUGCAGAGAGAGUCAGAGGGGACAACAAGGAGUAU<br>GAGUACUCAGUGGAGUGCCAGGAGGACAGUGCCUGCCCAGCUGCUGAGGAG<br>AGUCUGCCCAUUGAGGUCAUGGUGGAUGCCGUUCACAAGCUCAAGUAUGAG<br>AACUACACCAGCAGCUUCUUCAUCAGGGACAUCAUCAAACCUGACCCACCC<br>AAGAACUUGCAGCUGAAGCCAUUAAAGAAUUCUCGGCAGGUGGAGGUCAGC<br>UGGGAGUACCCUGACACCUGGAGUACUCCACAUUCCUACUUCUCCCUGACA<br>UUCUGCGUUCAGGUCCAGGGCAAGAGCAAGAGAGAGAAGAAAGAUAGAGUC<br>UUCACGGACAAGACCUCAGCCACGGUCAUCUGCCGCAAGAAUGCCAGCAUU<br>AGCGUGCGGGCCCAGGACCGCUACUAUAGCUCAUCUUGGAGCGAAUGGGCA<br>UCUGUGCCCUGCAGUGGCGGAGGGGGCGGAGGGAGCAGAGCUGUGCCUGGG<br>GGCAGCAGCCCUGCCUGGACUCAGUGCCAGCAGCUUUCACAGAAGCUCUGC<br>ACACUGGCCUGGAGUGCACAUCCACUAGUGGGACACAUGGAUCUAAGAGAA<br>GAGGGAGAUGAAGAGACUACAAAUGAUGUUCCCCAUAUCCAGUGUGGAGAU<br>GGCUGUGACCCCCAAGGACUCAGGGACAACAGUCAGUUCUGCUUGCAAAGG<br>AUCCACCAGGGUCUGAUCUUUUAUGAGAAGCUGCUAGGAUCGGAUAUUUUC<br>ACAGGGGAGCCUUCUCUGCUCCCUGAUAGCCCUGUGGGCCAGCUUCAUGCC<br>UCCCUACUGGGCCUCAGCCAACUCCUGCAGCCUGAGGGUCACCACUGGGAG<br>ACUCAGCAGAUUCCAAGCCUCAGUCCCAGCCAGCCAUGGCAGCGUCUCCUU<br>CUCCGCUUCAAGAUCCUUCGCAGCCUCCAGGCCUUUGUGGCUGUAGCCGCC<br>CGGGUCUUUGCCCAUGGAGCAGCAACCCUGAGUCCC | 141 |
| hIL-23 (IL-12p40 subunit and IL-23p19 subunit) | Full-length mRNA Nucleotide sequence (5' UTR, ORF, 3' UTR, mir-122-5p (underlined) polyA tail) of human IL-23 (IL-12p40 subunit and IL-23p19 subunit linked by GS Linker) | 5'$^{7Me}G_{ppp}G_{2'OMe}$GGAAAUAAGAGAGAAAAGAAGAGUAAGAAGAAAUAUAAGA<br>GCCACCAUGUGUCACCAGCAGUUGGUCAUCUCUUGGUUUUCCCUGGUAUUU<br>CUGGCAUCUCCCCUCGUGGCCAUAUGGGAACUGAAGAAAGAUGUUUAUGUC<br>GUAGAAUUGGAUUGGUAUCCGGAUGCCCCUGGAGAAAUGGUGGUCCUCACC<br>UGUGACACCCCUGAAGAAGAUGGUAUCACCUGGACCUUGGACCAGAGCAGU<br>GAGGUCUUAGGCUCUGGCAAGACCCUGACCAUCCAAGUCAAAGAGUUUGGA<br>GAUGCUGGCCAGUACACCUGUCACAAAGGAGGCGAGGUUCUAAGCCAUUCG<br>CUCCUGCUGCUUCACAAGAAGGAAGAUGGAAUUUGGUCCACUGAUAUUUUA<br>AAGGACCAGAAAGAACCCAAGAAUAAGACCUUUCUAAGAUGCGAGGCCAAG<br>AAUUAUUCUGGACGUUUCACCUGCUGGUGGCUGACGACAAUCAGUACUGAU<br>UUGACAUUCAGUGUCAAGAGCAGCAGAGGCUCUUCUGACCCCCAAGGGGUG<br>ACGUGCGGAGCUGCUACACUCUCUGCAGAGAGAGUCAGAGGGGACAACAAG<br>GAGUAUGAGUACUCAGUGGAGUGCCAGGAGGACAGUGCCUGCCCAGCUGCU<br>GAGGAGAGUCUGCCCAUUGAGGUCAUGGUGGAUGCCGUUCACAAGCUCAAG<br>UAUGAGAACUACACCAGCAGCUUCUUCAUCAGGGACAUCAUCAAACCUGAC<br>CCACCCAAGAACUUGCAGCUGAAGCCAUUAAAGAAUUCUCGGCAGGUGGAG<br>GUCAGCUGGGAGUACCCUGACACCUGGAGUACUCCACAUUCCUACUUCUCC<br>CUGACAUUCUGCGUUCAGGUCCAGGGCAAGAGCAAGAGAGAGAAGAAAGAU<br>AGAGUCUUCACGGACAAGACCUCAGCCACGGUCAUCUGCCGCAAGAAUGCC<br>AGCAUUAGCGUGCGGGCCCAGGACCGCUACUAUAGCUCAUCUUGGAGCGAA<br>UGGGCAUCUGUGCCCUGCAGUGGCGGAGGGGGCGGAGGGAGCAGAGCUGUG<br>CCUGGGGGCAGCAGCCCUGCCUGGACUCAGUGCCAGCAGCUUUCACAGAAG<br>CUCUGCACACUGGCCUGGAGUGCACAUCCACUAGUGGGACACAUGGAUCUA<br>AGAGAAGAGGGAGAUGAAGAGACUACAAAUGAUGUUCCCCAUAUCCAGUGU<br>GGAGAUGGCUGUGACCCCCAAGGACUCAGGGACAACAGUCAGUUCUGCUUG<br>CAAAGGAUCCACCAGGGUCUGAUCUUUUAUGAGAAGCUGCUAGGAUCGGAU<br>AUUUUCACAGGGGAGCCUUCUCUGCUCCCUGAUAGCCCUGUGGGCCAGCUU<br>CAUGCCUCCCUACUGGGCCUCAGCCAACUCCUGCAGCCUGAGGGUCACCAC<br>UGGGAGACUCAGCAGAUUCCAAGCCUCAGUCCCAGCCAGCCAUGGCAGCGU<br>CUCCUUCUCCGCUUCAAGAUCCUUCGCAGCCUCCAGGCCUUUGUGGCUGUA<br>GCCGCCCGGGUCUUUGCCCAUGGAGCAGCAACCCUGAGUCCCUGAUAAUAG<br>GCUGGAGCCUCGGUGGCCAUGCUUCUUGCCCCUUGGGCCUCCCCCCAGCCC | 142 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | CUCCUCCCCUUCCUGCACCCGUACCCCCCAAACACCAUUGUCACACUCCAG<br>UGGUCUUUGAAUAAAGUCUGAGUGGGCGGCAAAAAAAAAAAAAAAAAAAAA<br>AAAAAAAAAAAAAAAAAAAAAAAAAAAAAAAAAAAAAAAAAAAAAAAAAAA<br>AAAAAAAAAAAAAAAAAAAAAAAAAAAAUCUAG$_{OH}$3'<br>Where: A, C G & U = AMP, CMP, GMP & N1-ΨUMP, respectively; Me = methyl; p = inorganic phosphate | |
| IL-36-gamma (Precursor) | Amino acid sequence of IL-36-gamma (Precursor) | MRGTPGDADGGGRAVYQSMCKPITGTINDLNQQVWTLQGQNLVAVPRSDS<br>VTPVTVAVITCKYPEALEQGRGDPIYLGIQNPEMCLYCEKVGEQPTLQLK<br>EQKIMDLYGQPEPVKPFLFYRAKTGRTSTLESVAFPDWFIASSKRDQPII<br>LTSELGKSYNTAFELNIND | SEQ ID NO: 10 |
| IL-36-gamma (Precursor) | Nucleotide sequence of IL-36-gamma (Precursor) | ATGAGAGGCACTCCAGGAGACGCTGATGGTGGAGGAAGGGCCGTCTATCA<br>ATCAATGTGTAAACCTATTACTGGGACTATTAATGATTTGAATCAGCAAG<br>TGTGGACCCTTCAGGGTCAGAACCTTGTGGCAGTTCCACGAAGTGACAGT<br>GTGACCCCAGTCACTGTTGCTGTTATCACATGCAAGTATCCAGAGGCTCT<br>TGAGCAAGGCAGAGGGGATCCCATTTATTTGGGAATCCAGAATCCAGAAA<br>TGTGTTTGTATTGTGAGAAGGTTGGAGAACAGCCCACATTGCAGCTAAAA<br>GAGCAGAAGATCATGGATCTGTATGGCCAACCCGAGCCCGTGAAACCCTT<br>CCTTTTCTACCGTGCCAAGACTGGTAGGACCTCCACCCTTGAGTCTGTGG<br>CCTTCCCGGACTGGTTCATTGCCTCCTCCAAGAGAGACCAGCCCATCATT<br>CTGACTTCAGAACTTGGGAAGTCATACAACACTGCCTTTGAATTAAATAT<br>AAATGAC | SEQ ID NO: 11 |
| IL-36-gamma (Mature) | Amino acid sequence of IL-36-gamma (Mature) (Uniprot Q9NZH8, aa 18-169) | SMCKPITGTINDLNQQVWTLQGQNLVAVPRSDSVTPVTVAVITCKYPEAL<br>EQGRGDPIYLGIQNPEMCLYCEKVGEQPTLQLKEQKIMDLYGQPEPVKPF<br>LFYRAKTGRTSTLESVAFPDWFIASSKRDQPIILTSELGKSYNTAFELNI<br>ND | SEQ ID NO: 12 |
| IL-36-gamma (Mature) | Nucleotide sequence of IL-36-gamma (Mature) (CCDS2108.1, nt 52-507) | TCAATGTGTAAACCTATTACTGGGACTATTAATGATTTGAATCAGCAAGT<br>GTGGACCCTTCAGGGTCAGAACCTTGTGGCAGTTCCACGAAGTGACAGTG<br>TGACCCCAGTCACTGTTGCTGTTATCACATGCAAGTATCCAGAGGCTCTTG<br>AGCAAGGCAGAGGGGATCCCATTTATTTGGGAATCCAGAATCCAGAAATGT<br>GTTTGTATTGTGAGAAGGTTGGAGAACAGCCCACATTGCAGCTAAAAGAGC<br>AGAAGATCATGGATCTGTATGGCCAACCCGAGCCCGTGAAACCCTTCCTTT<br>TCTACCGTGCCAAGACTGGTAGGACCTCCACCCTTGAGTCTGTGGCCTTCC<br>CGGACTGGTTCATTGCCTCCTCCAAGAGAGACCAGCCCATCATTCTGACTT<br>CAGAACTTGGGAAGTCATACAACACTGCCTTTGAATTAAATATAAATGAC | SEQ ID NO: 13 |
| IgKV4 signal peptide | Amino acid sequence of IgKV4 signal peptide (Uniprot P06212, aa 1-20) | MVLQTQVFISLLLWISGAYG | SEQ ID NO: 14 |
| IgKV4 signal peptide | Nucleotide sequence of IgKV4 signal peptide (IMGTZ00023, nt 1-60) | ATGGTGTTGCAGACCCAGGTCTTCATTTCTCTGTTGCTCTGGATCTCTGG<br>TGCCTACGGG | SEQ ID NO: 15 |
| hIGKV4-hIL-36g construct (protein) | hIGKV4-hIL-36g construct (protein) | MVLQTQVFISLLLWISGAYGSMCKPITGTINDLNQQVWTLQGQNLVAVPR<br>SDSVTPVTVAVITCKYPEALEQGRGDPIYLGIQNPEMCLYCEKVGEQPTL<br>QLKEQKIMDLYGQPEPVKPFLFYRAKTGRTSTLESVAFPDWFIASSKRDQ<br>PIILTSELGKSYNTAFELNIND | SEQ ID NO: 16 |
| hIGKV4-hIL-36g construct (RNA) | hIGKV4-hIL-36g construct (RNA) | ATGGTGTTGCAGACCCAGGTCTTCATTTCTCTGTTGCTCTGGATCTCTGG<br>TGCCTACGGGTCAATGTGTAAACCTATTACTGGGACTATTAATGATTTGA<br>ATCAGCAAGTGTGGACCCTTCAGGGTCAGAACCTTGTGGCAGTTCCACGA<br>AGTGACAGTGTGACCCCAGTCACTGTTGCTGTTATCACATGCAAGTATCC<br>AGAGGCTCTTGAGCAAGGCAGAGGGGATCCCATTTATTTGGGAATCCAGA<br>ATCCAGAAATGTGTTTGTATTGTGAGAAGGTTGGAGAACAGCCCACATTG<br>CAGCTAAAAGAGCAGAAGATCATGGATCTGTATGGCCAACCCGAGCCCGT<br>GAAACCCTTCCTTTTCTACCGTGCCAAGACTGGTAGGACCTCCACCCTTG<br>AGTCTGTGGCCTTCCCGGACTGGTTCATTGCCTCCTCCAAGAGAGACCAG | SEQ ID NO: 17 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | CCCATCATTCTGACTTCAGAACTTGGGAAGTCATACAACACTGCCTTTGA<br>ATTAAATATAAATGAC | |
| Human IL-36 gamma | Human IL-36-gamma mRNA (ORF) | AUGGUGUUGCAGACCCAGGUCUUCAUUUCUCUGUUGCUCUGGAUCUCUGGU<br>GCCUACGGGUCAAUGUGUAAACCUAUUACUGGGACUAUUAAUGAUUUGAAU<br>CAGCAAGUGUGGACCCUUCAGGGUCAGAACCUUGUGGCAGUUCCACGAAGU<br>GACAGUGUGACCCCAGUCACUGUUGCUGUUAUCACAUGCAAGUAUCCAGAG<br>GCUCUUGAGCAAGGCAGAGGGGAUCCCAUUUAUUUGGGAAUCCAGAAUCCA<br>GAAAUGUGUUUGUAUUGUGAGAAGGUUGGAGAACAGCCCACAUUGCAGCUA<br>AAAGAGCAGAAGAUCAUGGAUCUGUAUGGCCAACCCGAGCCCGUGAAACCC<br>UUCCUUUUCUACCGUGCCAAGACUGGUAGGACCUCCACCCUUGAGUCUGUG<br>GCCUUCCCGGACUGGUUCAUUGCCUCCUCCAAGAGAGACCAGCCCAUCAUU<br>CUGACUUCAGAACUUGGGAAGUCAUACAACACUGCCUUUGAAUUAAAUAUA<br>AAUGAC | 143 |
| Human IL-36-gamma | Full-length mRNA Nucleotide sequence (5' UTR, ORF, 3' UTR, mir-122-5p (underlined) polyA tail) of human IL-36-gamma | 5'$^{7Me}G_{ppp}G_{2'OMe}$GGAAAUAAGAGAGAAAAGAAGAGUAAGAAGAAAUAUAAGA<br>GCCACCAUGGUGUUGCAGACCCAGGUCUUCAUUUCUCUGUUGCUCUGGAUC<br>UCUGGUGCCUACGGGUCAAUGUGUAAACCUAUUACUGGGACUAUUAAUGAU<br>UUGAAUCAGCAAGUGUGGACCCUUCAGGGUCAGAACCUUGUGGCAGUUCCA<br>CGAAGUGACAGUGUGACCCCAGUCACUGUUGCUGUUAUCACAUGCAAGUAU<br>CCAGAGGCUCUUGAGCAAGGCAGAGGGGAUCCCAUUUAUUUGGGAAUCCAG<br>AAUCCAGAAAUGUGUUUGUAUUGUGAGAAGGUUGGAGAACAGCCCACAUUG<br>CAGCUAAAAGAGCAGAAGAUCAUGGAUCUGUAUGGCCAACCCGAGCCCGUG<br>AAACCCUUCCUUUUCUACCGUGCCAAGACUGGUAGGACCUCCACCCUUGAG<br>UCUGUGGCCUUCCCGGACUGGUUCAUUGCCUCCUCCAAGAGAGACCAGCCC<br>AUCAUUCUGACUUCAGAACUUGGGAAGUCAUACAACACUGCCUUUGAAUUA<br>AAUAUAAAUGACUGAUAAUAGGCUGGAGCCUCGGUGGCCAUGCUUCUUGCC<br>CCUUGGGCCUCCCCCCAGCCCCUCCUCCCCUUCCUGCACCCGUACCCCCA<br>AACACCAUUGUCACACUCCAGUGGUCUUUGAAUAAAGUCUGAGUGGGCGGC<br>AAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAUC<br>UAG$_{OH}$3'<br>Where: A, C G & U = AMP, CMP, GMP & N1-ΨUMP, respectively; Me = methyl; p = inorganic phosphate | 144 |
| hIL-23_miR-122 Construct 1 | Codon optimized human IL-23 sequence | ATGTGTCACCAGCAGTTGGTCATCTCTTGGTTTTCCCTGGTATTTCTGGC<br>ATCTCCCCTCGTGGCCATATGGGAACTGAAGAAAGATGTTTATGTCGTAG<br>AATTGGATTGGTATCCGGATGCCCCTGGAGAAATGGTGGTCCTCACCTGT<br>GACACCCCTGAAGAAGATGGTATCACCTGGACCTTGGACCAGAGCAGTGA<br>GGTCTTAGGCTCTGGCAAGACCCTGACCATCCAAGTCAAAGAGTTTGGAG<br>ATGCTGGCCAGTACACCTGTCACAAAGGAGGCGAGGTTCTAAGCCATTCG<br>CTCCTGCTGCTTCACAAGAAGGAAGATGGAATTTGGTCCACTGATATTTT<br>AAAGGACCAGAAAGAACCCAAGAATAAGACCTTTCTAAGATGCGAGGCCA<br>AGAATTATTCTGGACGTTTCACCTGCTGGTGGCTGACGACAATCAGTACT<br>GATTTGACATTCAGTGTCAAGAGCAGCAGAGGCTCTTCTGACCCGCAAGG<br>GGTGACGTGCGGAGCTGCTACACTCTCTGCAGAGAGAGTCAGAGGGGACA<br>ACAAGGAGTATGAGTACTCAGTGGAGTGCCAGGAGGACAGTGCCTGCCCA<br>GCTGCTGAGGAGAGTCTGCCCATTGAGGTCATGGTGGATGCCGTTCACAA<br>GCTCAAGTATGAGAACTACACCAGCAGCTTCTTCATCAGGGACATCATCA<br>AACCTGACCCACCCAAGAACTTGCAGCTGAAGCCATTAAAGAATTCTCGG<br>CAGGTGGAGGTCAGCTGGGAGTACCCTGACACCTGGAGTACTCCACATTC<br>CTACTTCTCCCTGACATTCTGCGTTCAGGTCCAGGGCAAGAGCAAGAGAG<br>AGAAGAAAGATAGAGTCTTCACGGACAAGACCTCAGCCACGGTCATCTGC<br>CGCAAGAATGCCAGCATTAGCGTGCGGGCCCAGGACCGCTACTATAGCTC<br>ATCTTGGAGCGAATGGGCATCTGTGCCCTGCAGTGGCGGAGGTGGCGGAG<br>GGAGCAGAGCTGTGCCTGGCGGCAGCAGCCCTGCCTGGACTCAGTGCCAG<br>CAGCTTTCACAGAAGCTCTGCACACTGGCCTGGAGTGCACATCCACTAGT<br>GGGACACATGGATCTAAGAGAAGAGGGAGATGAAGAGACTACAAATGATG<br>TTCCCCATATCCAGTGTGGAGATGGCTGTGACCCGCAAGGACTCAGGGAC<br>AACAGTCAGTTCTGCTTGCAAAGGATCCACCAGGGTCTGATCTTTTATGA<br>GAAGCTGCTAGGATCGGATATTTTCACAGGGGAGCCTTCTCTGCTCCCTG<br>ATAGCCCTGTGGGCCAGCTTCATGCCTCCCTACTGGGCCTCAGCCAACTC<br>CTGCAGCCTGAGGGTCACCACTGGGAGACTCAGCAGATTCCAAGCCTCAG<br>TCCCAGCCAGCCATGGCAGCGTCTCCTTCTCCGCTTCAAGATCCTTCGCA<br>GCCTCCAGGCCTTTGTGGCTGTAGCCGCCCGGGTCTTTGCCCATGGAGCA<br>GCAACCCTGAGTCCC | SEQ ID NO: 18 |
| hIL-23_miR-122 Construct 2 | Codon optimized human IL-23 sequence | ATGTGTCACCAGCAGTTGGTCATCTCTTGGTTTTCCCTGGTATTTCTGGC<br>ATCTCCCCTCGTGGCCATATGGGAACTGAAGAAAGATGTTTATGTCGTAG<br>AATTGGATTGGTATCCGGATGCCCCTGGAGAAATGGTGGTCCTCACCTGT<br>GACACCCCTGAAGAAGATGGTATCACCTGGACCTTGGACCAGAGCAGTGA<br>GGTCTTAGGCTCTGGCAAGACCCTGACCATCCAAGTCAAAGAGTTTGGAG<br>ATGCTGGCCAGTACACCTGTCACAAAGGAGGCGAGGTTCTAAGCCATTCG<br>CTCCTGCTGCTTCACAAGAAGGAAGATGGAATTTGGTCCACTGATATTTT<br>AAAGGACCAGAAAGAACCCAAGAATAAGACCTTTCTAAGATGCGAGGCCA | SEQ ID NO: 19 |

TABLE 1-continued

| IL-23, IL-36-gamma and IL-18 Polypeptide and Polynucleotide Sequences | | | |
|---|---|---|---|
| Encoded Polypeptide | Description | Sequence | SEQ ID NO: |
| | | AGAATTATTCTGGACGTTTCACCTGCTGGTGGCTGACGACAATCAGTACT GATTTGACATTCAGTGTCAAGAGCAGCAGAGGCTCTTCTGACCCCCAAGG GGTGACGTGCGGAGCTGCTACACTCTCTGCAGAGAGAGTCAGAGGGGACA ACAAGGAGTATGAGTACTCAGTGGAGTGCCAGGAGGACAGTGCCTGCCCA GCTGCTGAGGAGAGTCTGCCCATTGAGGTCATGGTGGATGCCGTTCACAA GCTCAAGTATGAGAACTACACCAGCAGCTTCTTCATCAGGGACATCATCA AACCTGACCCACCCAAGAACTTGCAGCTGAAGCCATTAAAGAATTCTCGG CAGGTGGAGGTCAGCTGGGAGTACCCTGACACCTGGAGTACTCCACATTC CTACTTCTCCCTGACATTCTGCGTTCAGGTCCAGGGCAAGAGCAAGAGAG AGAAGAAAGATAGAGTCTTCACGGACAAGACCTCAGCCACGGTCATCTGC CGCAAGAATGCCAGCATTAGCGTGCGGGCCCAGGACCGCTACTATAGCTC ATCTTGGAGCGAATGGGCATCTGTGCCCTGCAGTGGCGGAGGGGGCGGAG GGAGCAGAGCTGTGCCTGGGGGCAGCAGCCCTGCCTGGACTCAGTGCCAG CAGCTTTCACAGAAGCTCTGCACACTGGCCTGGAGTGCACATCCACTAGT GGGACACATGGATCTAAGAGAAGAGGGAGATGAAGAGACTACAAATGATG TTCCCCATATCCAGTGTGGAGATGGCTGTGACCCCCAAGGACTCAGGGAC AACAGTCAGTTCTGCTTGCAAAGGATCCACCAGGGTCTGATCTTTTATGA GAAGCTGCTAGGATCGGATATTTTCACAGGGGAGCCTTCTCTGCTCCCTG ATAGCCCTGTGGGCCAGCTTCATGCCTCCCTACTGGGCCTCAGCCAACTC CTGCAGCCTGAGGGTCACCACTGGGAGACTCAGCAGATTCCAAGCCTCAG TCCCAGCCAGCCATGGCAGCGTCTCCTTCTCCGCTTCAAGATCCTTCGCA GCCTCCAGGCCTTTGTGGCTGTAGCCGCCCGGGTCTTTGCCCATGGAGCA GCAACCCTGAGTCCC | |
| hIL-23_miR-122 Construct 3 | Codon optimized human IL-23 sequence | ATGTGTCACCAGCAGTTGGTCATCTCTTGGTTTTCCCTGGTTTTTCTGGC ATCTCCCCTCGTGGCCATATGGGAACTGAAGAAAGATGTTTATGTCGTAG AATTGGATTGGTATCCGGATGCCCCTGGAGAAATGGTGGTCCTCACCTGT GACACCCCTGAAGAAGATGGTATCACCTGGACCTTGGACCAGAGCAGTGA GGTCTTAGGCTCTGGCAAAACCCTGACCATCCAAGTCAAAGAGTTTGGAG ATGCTGGCCAGTACACCTGTCACAAAGGAGGCGAGGTTCTAAGCCATTCG CTCCTGCTGCTTCACAAAAAGGAAGATGGAATTTGGTCCACTGATATTTT AAAGGACCAGAAAGAACCCAAAAATAAGACCTTTCTAAGATGCGAGGCCA AGAATTATTCTGGACGTTTCACCTGCTGGTGGCTGACGACAATCAGTACT GATTTGACATTCAGTGTCAAAAGCAGCAGAGGCTCTTCTGACCCCCAAGG GGTGACGTGCGGAGCTGCTACACTCTCTGCAGAGAGAGTCAGAGGGGACA ACAAGGAGTATGAGTACTCAGTGGAGTGCCAGGAGGACAGTGCCTGCCCA GCTGCTGAGGAGAGTCTGCCCATTGAGGTCATGGTGGATGCCGTTCACAA GCTCAAGTATGAAAACTACACCAGCAGCTTCTTCATCAGGGACATCATCA AACCTGACCCACCCAAGAACTTGCAGCTGAAGCCATTAAAGAATTCTCGG CAGGTGGAGGTCAGCTGGGAGTACCCTGACACCTGGAGTACTCCACATTC CTACTTCTCCCTGACATTCTGCGTTCAGGTCCAGGGCAAGAGCAAGAGAG AAAAGAAAGATAGAGTCTTCACGGACAAGACCTCAGCCACGGTCATCTGC CGCAAAAATGCCAGCATTAGCGTGCGGGCCCAGGACCGCTACTATAGCTC ATCTTGGAGCGAATGGGCATCTGTGCCCTGCAGTGGCGGAGGGGGCGGAG GGAGCAGAGCTGTGCCTGGGGGCAGCAGCCCTGCCTGGACTCAGTGCCAG CAGCTTTCACAGAAGCTCTGCACACTGGCCTGGAGTGCACATCCACTAGT GGGACACATGGATCTAAGAGAAGAGGGAGATGAAGAGACTACAAATGATG TTCCCCATATCCAGTGTGGAGATGGCTGTGACCCCCAAGGACTCAGGGAC AACAGTCAGTTCTGCTTGCAAAGGATCCACCAGGGTCTGATTTTTTATGA GAAGCTGCTAGGATCGGATATTTTCACAGGGGAGCCTTCTCTGCTCCCTG ATAGCCCTGTGGGCCAGCTTCATGCCTCCCTACTGGGCCTCAGCCAACTC CTGCAGCCTGAGGGTCACCACTGGGAGACTCAGCAGATTCCAAGCCTCAG TCCCAGCCAGCCATGGCAGCGTCTCCTTCTCCGCTTCAAAATCCTTCGCA GCCTCCAGGCCTTTGTGGCTGTAGCCGCCCGGGTCTTTGCCCATGGAGCA GCAACCCTGAGTCCC | SEQ ID NO: 20 |
| hIL-23_miR-122 Construct 4 | Codon optimized human IL-23 sequence | ATGTGTCACCAGCAGTTGGTCATCTCTTGGTTTTCCCTGGTATTTCTGGCA TCTCCCCTCGTGGCCATATGGGAACTGAAGAAAGATGTTTATGTCGTAGAA TTGGATTGGTATCCGGATGCCCCTGGAGAAATGGTGGTCCTCACCTGTGAC ACCCCTGAAGAAGATGGTATCACCTGGACCTTGGACCAGAGCAGTGAGGTC TTAGGCTCTGGCAAGACCCTGACCATCCAAGTCAAAGAGTTTGGAGATGCT GGCCAGTACACCTGTCACAAAGGAGGCGAGGTTCTAAGCCATTCGCTCCTG CTGCTTCACAAGAAGGAAGATGGAATTTGGTCCACTGATATTTTAAAGGAC CAGAAAGAACCCAAGAATAAGACCTTTCTAAGATGCGAGGCCAAGAATTAT TCTGGACGTTTCACCTGCTGGTGGCTGACGACAATCAGTACTGATTTGACA TTCAGTGTCAAGAGCAGCAGAGGCTCTTCTGACCCCCAAGGGGTGACGTGC GGAGCTGCTACACTCTCTGCAGAGAGAGTCAGAGGGGACAACAAGGAGTAT GAGTACTCAGTGGAGTGCCAGGAGGACAGTGCCTGCCCAGCTGCTGAGGAG AGTCTGCCCATTGAGGTCATGGTGGATGCCGTTCACAAGCTCAAGTATGAG AACTACACCAGCAGCTTCTTCATCAGGGACATCATCAAACCTGACCCACCC AAGAACTTGCAGCTGAAGCCATTAAAGAATTCTCGGCAGGTGGAGGTCAGC TGGGAGTACCCTGACACCTGGAGTACTCCACATTCCTACTTCTCCCTGACA TTCTGCGTTCAGGTCCAGGGCAAGAGCAAGAGAGAGAAGAAAGATAGAGTC TTCACGGACAAGACCTCAGCCACGGTCATCTGCCGCAAGAATGCCAGCATT AGCGTGCGGGCCCAGGACCGCTACTATAGCTCATCTTGGAGCGAATGGGCA | SEQ ID NO: 71 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TCTGTGCCCTGCAGTGGCGGAGGGGGCGGAGGGAGCAGAGCTGTGCCTGGG<br>GGCAGCAGCCCTGCCTGGACTCAGTGCCAGCAGCTTTCACAGAAGCTCTGC<br>ACACTGGCCTGGAGTGCACATCCACTAGTGGGACACATGGATCTAAGAGAA<br>GAGGGAGATGAAGAGACTACAAATGATGTTCCCCATATCCAGTGTGGAGAT<br>GGCTGTGACCCCCAAGGACTCAGGGACAACAGTCAGTTCTGCTTGCAAAGG<br>ATCCACCAGGGTCTGATCTTTTATGAGAAGCTGCTAGGATCGGATATTTTC<br>ACAGGGGAGCCTTCTCTGCTCCCTGATAGCCCTGTGGGCCAGCTTCATGCC<br>TCCCTACTGGGCCTCAGCCAACTCCTGCAGCCTGAGGGTCACCACTGGGAG<br>ACTCAGCAGATTCCAAGCCTCAGTCCCAGCCAGCCATGGCAGCGTCTCCTT<br>CTCCGCTTCAAGATCCTTCGCAGCCTCCAGGCCTTTGTGGCTGTAGCCGCC<br>CGGGTCTTTGCCCATGGAGCAGCAACCCTGAGTCCC | |
| hIL-23 | Codon optimized human IL-23 sequence | ATGTGTCACCAGCAGTTGGTCATCTCTTGGTTTTCCCTGGTATTTCTGGCA<br>TCTCCCCTCGTGGCCATATGGGAACTGAAGAAAGATGTTTATGTCGTAGAA<br>TTGGATTGGTATCCGGATGCCCCTGGAGAAATGGTGGTCCTCACCTGTGAC<br>ACCCCTGAAGAAGATGGTATCACCTGGACCTTGGACCAGAGCAGTGAGGTC<br>TTAGGCTCTGGCAAGACCCTGACCATCCAAGTCAAAGAGTTTGGAGATGCT<br>GGCCAGTACACCTGTCACAAAGGAGGCGAGGTTCTAAGCCATTCGCTCCTG<br>CTGCTTCACAAGAAGGAAGATGGAATTTGGTCCACTGATATTTTAAAGGAC<br>CAGAAAGAACCCAAGAATAAGACCTTTCTAAGATGCGAGGCCAAGAATTAT<br>TCTGGACGTTTCACCTGCTGGTGGCTGACGACAATCAGTACTGATTTGACA<br>TTCAGTGTCAAGAGCAGCAGAGGCTCTTCTGACCCGCAAGGGGTGACGTGC<br>GGAGCTGCTACACTCTCTGCAGAGAGAGTCAGAGGGGACAACAAGGAGTAT<br>GAGTACTCAGTGGAGTGCCAGGAGGACAGTGCCTGCCCAGCTGCTGAGGAG<br>AGTCTGCCCATTGAGGTCATGGTGGATGCCGTTCACAAGCTCAAGTATGAG<br>AACTACACCAGCAGCTTCTTCATCAGGGACATCATCAAACCTGACCCACCC<br>AAGAACTTGCAGCTGAAGCCATTAAAGAATTCTCGGCAGGTGGAGGTCAGC<br>TGGGAGTACCCTGACACCTGGAGTACTCCACATTCCTACTTCTCCCTGACA<br>TTCTGCGTTCAGGTCCAGGGCAAGAGCAAGAGAGAGAAGAAAGATAGAGTC<br>TTCACGGACAAGACCTCAGCCACGGTCATCTGCCGCAAGAATGCCAGCATT<br>AGCGTGCGGGCCCAGGACCGCTACTATAGCTCATCTTGGAGCGAATGGGCA<br>TCTGTGCCCTGCAGTGGCGGAGGTGGCGGAGGGAGCAGAGCTGTGCCTGGC<br>GGCAGCAGCCCTGCCTGGACTCAGTGCCAGCAGCTTTCACAGAAGCTCTGC<br>ACACTGGCCTGGAGTGCACATCCACTAGTGGGACACATGGATCTAAGAGAA<br>GAGGGAGATGAAGAGACTACAAATGATGTTCCCCATATCCAGTGTGGAGAT<br>GGCTGTGACCCGCAAGGACTCAGGGACAACAGTCAGTTCTGCTTGCAAAGG<br>ATCCACCAGGGTCTGATCTTTTATGAGAAGCTGCTAGGATCGGATATTTTC<br>ACAGGGGAGCCTTCTCTGCTCCCTGATAGCCCTGTGGGCCAGCTTCATGCC<br>TCCCTACTGGGCCTCAGCCAACTCCTGCAGCCTGAGGGTCACCACTGGGAG<br>ACTCAGCAGATTCCAAGCCTCAGTCCCAGCCAGCCATGGCAGCGTCTCCTT<br>CTCCGCTTCAAGATCCTTCGCAGCCTCCAGGCCTTTGTGGCTGTAGCCGCC<br>CGGGTCTTTGCCCATGGAGCAGCAACCCTGAGTCCC | SEQ ID NO: 72 |
| mIL-23AB + miR-122 | Codon optimized murine IL-23 sequence | ATGTGTCCTCAGAAGCTAACCATCTCCTGGTTTGCCATCGTTTTGCTGGTG<br>TCTCCACTCATGGCCATGTGGGAGCTGGAGAAAGACGTTTATGTTGTAGAG<br>GTGGACTGGACTCCCGATGCCCCTGGAGAAACAGTGAACCTCACCTGTGAC<br>ACGCCTGAAGAAGATGACATCACCTGGACCTCAGACCAGAGACATGGAGTC<br>ATAGGCTCTGGAAAGACCCTGACCATCACTGTCAAAGAGTTCCTAGATGCT<br>GGCCAGTACACCTGCCACAAAGGAGGCGAGACTCTGAGCCACTCACATCTG<br>CTGCTCCACAAGAAGGAAAATGGAATTTGGTCCACTGAAATTTTAAAAAAT<br>TTCAAAAACAAGACTTTCCTGAAGTGTGAAGCACCAAATTACTCCGGACGG<br>TTCACGTGCTCATGGCTGGTGCAAAGAAACATGGACTTGAAGTTCAACATC<br>AAGAGCAGTAGCAGTTCCCCTGACTCTCGGGCAGTGACATGTGGAATGGCG<br>TCTCTGTCTGCAGAGAAGGTCACACTGGACCAAAGGGACTATGAGAAGTAT<br>TCAGTGTCCTGCCAGGAGGATGTCACCTGCCCAACTGCCGAGGAGACCCTG<br>CCCATTGAACTGGCGTTGGAAGCACGGCAGCAGAATAAATATGAGAACTAC<br>AGCACCAGCTTCTTCATCAGGGACATCATCAAACCAGACCCGCCCAAGAAC<br>TTGCAGATGAAGCCTTTGAAGAACTCACAGGTGGAGGTCAGCTGGGAGTAC<br>CCTGACTCCTGGAGCACTCCCCATTCCTACTTCTCCCTCAAGTTCTTTGTT<br>CGAATCCAGCGCAAGAAAGAAAAGATGAAGGAGACAGAGGAGGGGTGTAAC<br>CAGAAAGGTGCGTTCCTCGTAGAGAAGACATCTACCGAAGTCCAATGCAAA<br>GGCGGGAATGTCTGCGTGCAAGCTCAGGATCGCTATTACAATTCCTCATGC<br>AGCAAGTGGGCATGTGTTCCCTGCAGGGTCCGATCCGGAGGCGGAGGGAGC<br>GGAGGCGGAGGGAGCGGAGGCGGAGGGAGCGTGCCTAGGAGTAGCAGTCCT<br>GACTGGGCTCAGTGCCAGCAGCTCTCTCGGAATCTCTGCATGCTAGCCTGG<br>AACGCACATGCACCAGCGGGACATATGAATCTACTAAGAGAAGAAGAGGAT<br>GAAGAGACTAAAAATAATGTGCCCCGTATCCAGTGTGAAGATGGTTGTGAC<br>CCACAAGGACTCAAGGACAACAGCCAGTTCTGCTTGCAAAGGATCCGCCAA<br>GGTCTGGCTTTTTATAAGCACCTGCTTGACTCTGACATCTTCAAAGGGGAG<br>CCTGCTCTACTCCCTGATAGCCCCATGGAGCAACTTCACACCTCCCTACTA<br>GGACTCAGCCAACTCCTCCAGCCAGAGGATCACCCCCGGGAGACCCAACAG<br>ATGCCCAGCCTGAGTTCTAGTCAGCAGTGGCAGCGCCCCCTTCTCCGTTCC<br>AAGATCCTTCGAAGCCTCCAGGCCTTTTTGGCCATAGCTGCCCGGGTCTTT<br>GCCCACGGAGCAGCAACTCTGACTGAGCCCTTAGTGCCAACAGCT | SEQ ID NO: 73 |

TABLE 1-continued

| IL-23, IL-36-gamma and IL-18 Polypeptide and Polynucleotide Sequences | | | |
|---|---|---|---|
| Encoded Polypeptide | Description | Sequence | SEQ ID NO: |
| SE_IL-23_026 | Codon optimized human IL-23 sequence | ATGTGCCACCAGCAGCTCGTGATCAGCTGGTTCAGCCTAGTGTTCCTCGCC AGCCCACTCGTGGCCATCTGGGAGCTCAAGAAGGACGTCTACGTAGTAGAG CTCGACTGGTACCCGGACGCCCCGGGAGAGATGGTCGTGCTCACCTGCGAC ACCCCGGAAGAGGACGGCATCACCTGGACCCTCGACCAGAGCTCCGAGGTG CTCGGCAGCGGTAAGACCCTGACCATCCAGGTGAAGGAGTTCGGCGACGCC GGCCAATACACCTGCCACAAGGGCGGCGAGGTGCTGAGCCACTCCCTGCTG CTCCTGCATAAGAAGGAGGATGGAATCTGGTCCACCGACATCCTCAAGGAC CAGAAGGAGCCTAAGAACAAGACCTTCCTCCGGTGCGAGGCCAAGAACTAC TCGGGCCGATTCACCTGTTGGTGGCTGACTACCATTAGCACCGACCTCACC TTCAGCGTCAAGAGCAGCAGGGGCAGCAGCGACCCTCAGGGCGTGACCTGC GGCGCCGCCACCCTGAGCGCCGAAAGGGTGAGGGGCGACAACAAGGAGTAC GAATATAGCGTGGAGTGCCAGGAGGACAGCGCCTGCCCGGCCGCCGAGGAG AGCCTGCCTATCGAGGTCATGGTCGACGCCGTGCACAAGCTGAAGTACGAG AACTACACCAGCAGCTTCTTCATCCGGGACATCATCAAGCCGGACCCACCG AAGAACCTGCAACTCAAGCCACTGAAGAACAGCCGGCAGGTGGAGGTGTCC TGGGAGTACCCTGACACCTGGAGCACACCGCACTCCTATTTCTCCCTGACC TTCTGTGTGCAAGTGCAGGGCAAGAGCAAGAGGGAGAAGAAGGACCGGGTG TTCACCGATAAGACCTCCGCCACCGTGATCTGCAGGAAGAACGCCTCCATC AGCGTGAGGGCCCAAGACAGATATTACAGCAGCTCATGGTCCGAGTGGGCC TCCGTCCCATGCTCCGGCGGCGGAGGAGGAGGAAGCAGGGCCGTCCCAGGC GGCTCTAGCCCTGCCTGGACCCAATGCCAGCAGCTGAGCCAGAAGCTGTGC ACTCTGGCCTGGTCCGCCCACCCGCTGGTGGGCCACATGGATCTGCGCGAG GAGGGCGACGAGGAAACCACCAACGACGTCCCGCATATCCAGTGCGGCGAC GGCTGCGATCCACAGGGCCTGAGGGACAACTCCCAGTTCTGCCTGCAGAGA ATCCACCAGGGACTGATCTTCTACGAGAAGCTGCTGGGCAGCGACATATTC ACCGGCGAACCGAGCCTGCTCCCTGACAGCCCGGTGGGCCAGCTGCATGCC AGCCTGCTGGGCCTGTCACAGCTGCTGCAGCCGGAGGGCCATCACTGGGAG ACTCAACAGATCCCTAGCCTCAGCCCTAGCCAGCCGTGGCAGCGGCTGCTG CTCAGGTTCAAGATCCTGAGGAGCCTGCAGGCCTTCGTGGCGGTGGCCGCC CGAGTGTTCGCCCACGGCGCCGCGACCCTGTCCCCG | SEQ ID NO: 74 |
| SE_IL-23_027 | Codon optimized human IL-23 sequence | ATGTGCCACCAACAACTCGTGATCTCCTGGTTCAGCCTCGTTTTCCTCGCA AGCCCACTCGTGGCTATCTGGGAACTCAAGAAGGACGTGTACGTGGTGGAG CTCGACTGGTACCCGGACGCCCCGGGCGAGATGGTGGTGCTCACCTGCGAT ACCCCGGAGGAGGACGGCATCACCTGGACCCTCGACCAGTCCAGCGAAGTG CTGGGATCCGGCAAGACCCTGACCATCCAGGTGAAGGAGTTCGGCGATGCC GGCCAATACACCTGCCACAAGGGCGGCGAGGTCCTCTCCCACAGCCTGCTG CTGCTCCACAAGAAGGAGGACGGCATATGGAGCACCGACATCCTGAAGGAC CAGAAGGAACCTAAGAACAAGACCTTCCTGCGATGCGAGGCCAAGAACTAC AGCGGCAGATTCACCTGCTGGTGGTTAACTACCATAAGCACAGACCTGACC TTCAGCGTAAAGAGCAGCAGAGGCAGCAGCGACCCGCAGGGCGTGACCTGC GGCGCCGCCACCCTGTCCGCCGAGCGGGTGCGGGGCGACAACAAGGAGTAT GAGTACTCAGTGGAATGCCAGGAGGACAGCGCCTGCCCGGCCGCCGAGGAA AGCCTGCCTATCGAGGTGATGGTGGACGCCGTGCACAAGCTGAAGTACGAG AACTACACCAGCAGCTTCTTCATCAGGGACATCATCAAGCCGGACCCGCCG AAGAACCTGCAACTGAAGCCGCTGAAGAACAGCCGGCAAGTGGAGGTGTCC TGGGAGTACCCGGACACCTGGAGCACCCCGCATAGCTATTTCAGCCTCACC TTCTGCGTGCAAGTCCAGGGCAAGTCCAAGCGGGAGAAGAAGGACAGGGTG TTCACCGACAAGACTTCCGCCACTGTGATCTGCCGCAAGAACGCGAGCATC TCCGTGAGGGCGCAGGATAGGTATTATAGCAGCAGCTGGTCGGAGTGGGCC TCCGTGCCTTGCTCCGGCGGAGGCGGCGGAGGCTCGAGAGCCGTCCCAGGC GGCAGCTCCCCAGCCTGGACCCAGTGCCAGCAGCTGAGCCAGAAGCTCTGC ACCCTCGCCTGGAGTGCCCACCCACTGGTGGGCCACATGGACCTCCGCGAG GAAGGCGACGAGGAAACCACCAATGACGTGCCGCATATCCAGTGTGGCGAC GGCTGCGACCCTCAGGGTCTGAGGGATAACAGCCAGTTCTGCCTCCAGCGG ATCCATCAGGGCCTGATCTTCTACGAGAAGCTGCTGGGCAGCGATATCTTC ACCGGCGAGCCGTCCCTGCTGCCGGACAGCCCGGTGGGCCAGCTCCACGCC AGCCTGCTGGGCCTCAGCCAGCTGCTCCAGCCTGAAGGCCACCATTGGGAG ACTCAGCAGATCCCGAGCCTGAGCCCGAGCCAGCCGTGGCAGAGACTGCTG CTCCGTTTCAAGATCCTCAGGTCGCTGCAGGCCTTCGTGGCCGTGGCCGCT AGGGTGTTCGCCCACGGCGCCGCCACCCTGTCCCCT | SEQ ID NO: 75 |
| SE_IL-23_028 | Codon optimized human IL-23 sequence | ATGTGTCATCAGCAGCTCGTGATCAGCTGGTTCAGCCTCGTGTTCCTCGCA AGCCCGCTCGTCGCCATCTGGGAGCTCAAGAAGGACGTGTACGTTGTGGAG CTCGACTGGTACCCGGACGCCCCGGGCGAGATGGTGGTGCTCACCTGCGAC ACCCCGGAGGAGGACGGCATCACCTGGACGCTGGACCAGAGCAGCGAGGTG CTGGGCAGCGGCAAGACGCTGACCATCCAGGTGAAGGAATTCGGCGATGCC GGCCAGTACACCTGCCACAAGGGCGGCGAGGTTCTGAGCCACTCACTGCTG CTCCTCCACAAGAAGGAGGACGGCATCTGGAGCACCGACATCCTGAAGGAC CAGAAGGAGCCTAAGAACAAGACCTTCCTGCGGTGCGAGGCCAAGAATTAC AGCGGACGGTTCACATGCTGGTGGCTGACCACCATCAGCACCGACCTGACC TTCAGCGTCAAGTCCAGCCGGGGCTCAAGCGACCCGCAGGGCGTGACCTGC GGCGCCGCCACCCTGAGCGCCGAGAGGGTCAGAGGCGACAACAAGGAGTAC GAATACAGCGTGGAGTGTCAGGAGGACTCGGCCTGCCCGGCCGCTGAGGAA TCCCTGCCGATCGAAGTAATGGTGGACGCTGTGCACAAGCTGAAGTACGAG | SEQ ID NO: 76 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | AACTACACCAGCAGCTTCTTCATCAGGGACATCATCAAGCCAGACCCTCCT AAGAACCTCCAGCTGAAGCCTCTGAAGAACAGCCGGCAGGTGGAGGTGAGC TGGGAGTATCCGGACACCTGGTCCACCCCGCACTCCTACTTCAGCCTTACA TTCTGCGTGCAGGTGCAGGGCAAGAGCAAGAGGGAGAAGAAGGATAGGGTC TTCACCGACAAGACCAGCGCCACCGTCATCTGCAGAAAGAACGCCTCTATC TCCGTCAGGGCCCAGGATCGCTACTACAGCAGCAGCTGGAGCGAGTGGGCT TCCGTCCCTTGCTCAGGTGGCGGTGGCGGCGGCAGCAGGGCCGTCCCGGGT GGCAGCTCGCCGGCCTGGACCCAGTGCCAGCAACTCTCGCAGAAGCTGTGT ACCCTGGCCTGGTCGGCCCATCCGCTGGTGGGCCACATGGACCTGAGGGAG GAGGGCGATGAGGAGACGACCAATGATGTGCCTCACATCCAGTGTGGCGAC GGCTGCGACCCTCAAGGCCTGAGGGACAATAGCCAGTTCTGCCTGCAGAGG ATCCATCAGGGCCTGATCTTCTACGAGAAGCTGCTGGGCAGCGACATTTTC ACCGGCGAGCCGAGCCTCCTGCCGGACAGCCCTGTGGGTCAACTGCACGCC AGCCTCCTGGGCCTGTCCCAACTGCTGCAGCCGGAGGGCCACCACTGGGAA ACCCAGCAGATCCCAAGCCTGTCCCCGAGCCAACCGTGGCAGCGCCTGCTG CTGCGGTTCAAGATCCTGAGAAGCCTCCAGGCTTTCGTGGCAGTCGCCGCC AGGGTGTTCGCCCACGGCGCCGCCACCCTGTCCCCT | |
| SE_IL-23_029 | Codon optimized human IL-23 sequence | ATGTGCCACCAGCAGCTCGTGATTAGCTGGTTCAGCCTCGTGTTCCTCGCC AGCCCGCTCGTGGCCATCTGGGAGCTTAAGAAGGACGTGTACGTGGTGGAG CTCGACTGGTACCCAGACGCGCCGGGCGAGATGGTGGTCCTTACCTGCGAC ACCCCGGAAGAGGACGGTATTACCTGGACCCTGGATCAGTCTAGCGAGGTG CTGGGATCAGGCAAGACCCTCACCATCCAGGTCAAGGAGTTCGGCGACGCC GGCCAGTATACGTGCCACAAGGGAGGCGAGGTGCTGAGCCATTCGCTGCTG CTCCTGCACAAGAAGGAGGATGGCATCTGGAGCACCGACATTCTCAAGGAC CAGAAGGAGCCGAAGAACAAGACCTTCCTCAGGTGCGAAGCAAAGAATTAC TCCGGACGCTTCACCTGCTGGTGGCTGACAACCATCAGCACCGACCTGACG TTCAGCGTCAAGTCCAGCAGGGGCAGCAGCGACCCGCAGGGCGTGACCTGC GGCGCTGCCACCCTCAGCGCCGAGCGAGTTAGGGGCGACAACAAGGAGTAC GAGTACTCCGTGGAGTGCCAGGAGGACTCCGCTTGCCCGGCCGCCGAGGAG TCCCTCCCTATCGAGGTGATGGTCGACGCCGTGCACAAGCTGAAGTATGAG AACTACACCAGCTCATTCTTCATCAGAGACATCATCAAGCCAGACCCGCCG AAGAACCTCCAGCTGAAGCCTCTGAAGAACAGCAGGCAGGTGGAGGTGTCC TGGGAGTACCCGGACACCTGGTCCACCCCGCACTCCTACTTCAGCCTGACC TTCTGCGTGCAGGTCCAAGGCAAGAGCAAGCGGGAGAAGAAGGACCGCGTG TTCACCGACAAGACCTCCGCCACGGTCATATGCAGGAAGAACGCCAGCATC AGCGTCAGAGCCCAGGATAGATACTACTCGAGCTCCTGGTCCGAGTGGGCG AGCGTGCCGTGCAGCGGCGGAGGCGGTGGCGGCTCCCGAGCCGTTCCAGGC GGCTCTAGCCCGGCATGGACGCAGTGCCAGCAGCTCTCCCAGAAGCTGTGT ACCCTGGCCTGGAGCGCCCACCCACTGGTGGGTCACATGGACCTGAGGGAG GAGGGCGACGAGGAAACCACCAATGATGTGCCGCACATCCAGTGCGGCGAC GGCTGCGATCCTCAGGGCCTGCGGGACAACTCCCAGTTCTGCTTACAAAGG ATCCACCAGGGCCTGATCTTCTACGAGAAGCTCCTGGGCTCCGACATCTTC ACCGGCGAGCCAAGCCTCCTGCCGGACAGTCCGGTGGGCCAGCTGCACGCC TCCCTGCTGGGCCTGAGCCAACTGCTGCAGCCGGAGGGCCACCACTGGGAG ACACAGCAGATACCTAGCCTGTCCCCAAGCCAGCCTTGGCAGCGCCTGCTG CTGCGCTTCAAGATCCTGAGAAGCTTGCAGGCCTTCGTGGCCGTGGCCGCC CGGGTGTTCGCCCACGGCGCCGCAACCCTGAGCCCA | SEQ ID NO: 77 |
| SE_IL-23_030 | Codon optimized human IL-23 sequence | ATGTGTCACCAGCAGCTCGTAATCTCCTGGTTCAGCCTCGTGTTCCTCGCC TCCCCGCTCGTGGCTATCTGGGAGCTCAAGAAGGACGTGTACGTGGTCGAG CTCGACTGGTACCCAGACGCGCCGGGCGAGATGGTGGTGCTCACCTGCGAC ACCCCTGAGGAGGACGGCATCACCTGGACCTTAGACCAGAGCTCCGAGGTG CTCGGCAGCGGCAAGACACTCACTATCCAAGTGAAGGAGTTCGGCGATGCC GGCCAGTACACGTGCCACAAGGGCGGCGAGGTGCTGAGCCATAGCCTGCTG CTGCTGCACAAGAAGGAAGACGGCATTTGGAGCACCGACATCCTGAAGGAC CAGAAGGAGCCGAAGAACAAGACCTTCCTGCGCTGCGAGGCCAAGAACTAC TCCGGCCGATTCACCTGTTGGTGGCTGACAACCATCAGCACTGACCTGACC TTCTCCGTCAAGTCATCCCGCGGCAGCAGCGATCCGCAGGGCGTCACCTGC GGAGCCGCCACCCTGTCCGCCGAGAGGGTGCGCGGCGACAACAAGGAGTAC GAGTACTCCGTGGAGTGCCAGGAGGATAGCGCCTGCCCAGCCGCCGAGGAG TCCCTGCCAATCGAGGTGATGGTGGACGCCGTGCATAAGCTCAAGTATGAG AACTACACCAGCAGCTTCTTCATAAGGGACATCATCAAGCCGGACCCTCCG AAGAACCTGCAACTGAAGCCGCTCAAGAACAGCAGGCAAGTGGAGGTGTCC TGGGAATACCCGGATACCTGGAGCACCCCGCACTCCTACTTCTCCCTGACC TTCTGCGTTCAGGTGCAAGGAAAGAGCAAGCGGGAGAAGAAGGACCGGGTG TTCACCGACAAGACCAGCGCCACCGTGATCTGCCGCAAGAATGCCAGCATC AGCGTAAGAGCCCAGGACAGGTACTACAGCTCGTCCTGGTCCGAGTGGGCC TCGGTGCCGTGTAGCGGCGGCGGAGGCGGTGGCAGCAGGGCCGTCCCAGGC GGCTCCTCACCAGCCTGGACACAGTGCCAGCAACTGAGCCAGAAGCTGTGT ACCCTGGCCTGGAGCGCCCACCCGCTGGTGGGCCATATGGACCTGCGGGAG GAGGGCGACGAGGAGACGACCAACGATGTGCCACACATCCAGTGCGGTGAT GGATGCGATCCACAGGGCCTGAGGGACAACAGCCAGTTCTGCCTGCAGAGA ATCCACCAGGGCCTGATCTTCTACGAGAAGCTGCTGGGAAGCGATATTTTC ACTGGAGAACCGAGCCTTTTGCCGGATAGCCCTGTGGGTCAGCTCCACGCC | |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | AGCCTGCTGGGTCTGTCCCAGCTGCTCCAGCCGGAGGGCCACCACTGGAA<br>ACCCAGCAGATCCCGAGCCTGTCCCCAAGCCAGCCATGGCAACGGCTGCTG<br>CTTAGGTTCAAGATCCTGAGAAGCTTACAGGCCTTCGTGGCCGTGGCCGCC<br>AGGGTGTTCGCCCACGGCGCCGCGACCCTGAGCCCG | |
| SE_IL-23_031 | Codon optimized human IL-23 sequence | ATGTGCCACCAGCAGTTGGTGATCAGCTGGTTCAGCCTCGTGTTCCTCGCC<br>AGCCCACTCGTCGCCATCTGGGAGTTGAAGAAGGACGTGTACGTGGTGGAG<br>CTCGACTGGTACCCGGACGCCCCGGGCGAGATGGTGGTGCTCACCTGCGAC<br>ACCCCGGAGGAGGACGGCATCACGTGGACCCTGGACCAGAGCAGCGAGGTC<br>CTGGGCAGCGGCAAGACCCTCACCATCCAGGTGAAGGAGTTCGGCGACGCC<br>GGCCAGTACACCTGCCACAAGGGCGGAGAAGTGCTGAGCCATTCCCTGCTG<br>CTGCTGCATAAGAAGGAGGATGGCATTTGGAGCACTGACATCCTCAAGGAC<br>CAGAAGGAGCCGAAGAACAAGACATTCCTGCGATGCGAGGCCAAGAATTAC<br>AGCGGTAGGTTCACCTGCTGGTGGCTTACGACCATCAGCACAGACCTGACG<br>TTCTCCGTGAAGTCCAGCAGGGGCAGCAGCGATCCGCAGGGCGTGACCTGC<br>GGCGCCGCCACCCTGAGCGCCGAGCGGGTGAGAGGAGACAACAAGGAGTAT<br>GAATACAGCGTGGAATGTCAGGAGGACTCGGCCTGCCCGGCTGCCGAGGAG<br>AGCCTGCCAATCGAGGTGATGGTGGATGCCGTGCACAAGCTGAAGTACGAG<br>AACTACACCAGCAGCTTCTTCATCCGTGACATCATCAAGCCGGACCCGCCG<br>AAGAACCTGCAGCTGAAGCCGCTCAAGAACTCCCGACAGGTGGAAGTGTCC<br>TGGGAGTATCCAGACACCTGGTCAACCCCGCACTCCTACTTCTCCCTCACA<br>TTCTGCGTGCAGGTGCAGGGCAAGAGCAAGCGCGAGAAGAAGGATAGGGTG<br>TTCACCGACAAGACGAGCGCGACCGTGATCTGCAGGAAGAACGCCAGCATC<br>AGCGTGCGGGCCCAGGACAGGTACTACAGCTCCTCCTGGAGCGAATGGGCC<br>TCCGTCCCGTGCTCAGGCGGTGGCGGCGGCTCGCGGGCCGTGCCGGGA<br>GGCAGCAGTCCTGCATGGACCCAGTGCCAACAGCTGAGCCAGAAGCTCTGC<br>ACATTGGCCTGGAGCGCCCACCCGCTGGTGGGCCACATGGACCTCAGAGAG<br>GAGGGCGACGAAGAAACCACCAACGACGTGCCGCACATCCAGTGCGGCGAC<br>GGCTGCGACCCTCAGGGTCTGCGGGACAATAGCCAATTCTGCCTCCAGCGC<br>ATCCATCAGGGCCTGATCTTCTACGAGAAGCTTCTGGGAAGCGACATCTTC<br>ACCGGCGAGCCGAGCCTGCTGCCGGACAGCCCGGTGGGCCAGCTGCACGCC<br>TCCCTCCTGGGCCTGAGCCAGCTGCTGCAACCAGAGGGCCATCACTGGAA<br>ACCCAGCAGATCCCTAGCCTGAGCCCGAGCCAGCCGTGGCAGAGGCTGCTC<br>CTGCGGTTCAAGATCCTCAGGAGCCTGCAGGCCTTCGTGGCCGTGGCGGCC<br>CGGGTGTTCGCCCACGGCGCCGCCACCCTCAGCCCA | SEQ ID NO: 79 |
| SE_IL-23_032 | Codon optimized human IL-23 sequence | ATGTGCCACCAACAGCTCGTGATCAGCTGGTTCAGCCTCGTGTTCCTCGCC<br>AGCCCGCTCGTGGCCATCTGGGAGCTCAAGAAGGACGTGTACGTCGTCGAA<br>CTCGACTGGTACCCGGACGCGCCGGGCGAAATGGTGGTGCTAACCTGCGAC<br>ACCCCGGAAGAGGACGGCATCACCTGGACCCTGGACCAATCAAGCGAGGTG<br>CTGGGTAGCGGAAAGACCCTCACCATCCAGGTGAAGGAGTTCGGCGACGCC<br>GGCCAATACACGTGTCACAAGGGCGGCGAGGTGCTGAGCCACAGCCTCCTA<br>CTGCTGCACAAGAAGGAGGACGGTATCTGGAGCACCGACATACTGAAGGAC<br>CAGAAGGAGCCGAAGAACAAGACCTTCCTGCGCTGCGAGGCCAAGAACTAC<br>TCTGGCAGGTTCACCTGCTGGTGGCTCACCACCATCAGCACCGACCTGACC<br>TTCAGCGTCAAGAGCTCCCGGGGCAGTAGCGATCCGCAGGGCGTGACCTGC<br>GGCGCCGCCACCCTCAGCGCCGAGCGCGTCCGCGGCGACAACAAGGAGTAC<br>GAGTACAGCGTGGAGTGCCAGGAGGACTCCGCCTGCCCGGCCGCCGAGGAG<br>AGCCTCCCGATCGAGGTCATGGTGGACGCCGTGCACAAGCTGAAGTATGAG<br>AATTACACCTCCTCCTTCTTCATCCGGGATATCATAAAGCCGGACCCGCCG<br>AAGAACTTACAGCTGAAGCCTCTGAAGAACAGCAGGCAGGTGGAGGTGAGC<br>TGGGAGTATCCGGACACCTGGAGCACCCCGCACTCCTATTTCAGCCTGACC<br>TTCTGCGTCCAAGTGCAGGGCAAGAGCAAGAGGGAGAAGAAGGACAGGGTG<br>TTCACGGACAAGACCAGCGCCACCGTAATCTGTAGGAAGAACGCCAGCATC<br>AGCGTGCGAGCCCAGGACAGGTACTACTCCAGTAGCTGGTCCGAGTGGGCC<br>TCCGTGCCATGTAGCGGAGGCGGCGGCGGCGGCAGCCGGGCCGTGCCAGGA<br>GGAAGCTCTCCGGCCTGGACCCAGTGCCAACAGCTGAGCCAGAAGCTGTGC<br>ACCCTGGCCTGGAGCGCCCACCCGCTCGTGGGCCACATGGATCTGCGGGAG<br>GAGGGCGACGAGGAAACTACCAACGACGTGCCACACATCCAGTGCGGCGAC<br>GGCTGCGACCCACAGGGACTGAGGGACAATTCCCAGTTCTGCCTCCAGCGG<br>ATCCACCAGGGCCTGATCTTCTACGAGAAGCTCCTGGGCAGCGATATCTTC<br>ACCGGTGAGCCTTCCCTGCTGCCGGATTCCCCTGTGGGCCAGCTCCATGCC<br>TCTCTGCTGGGCCTCAGCCAGCTGCTGCAACCGGAGGGACACCATTGGGAG<br>ACGCAGCAAATCCCTAGCCTGAGCCCGAGCCAACCATGGCAAAGGCTCCTG<br>CTGAGGTTCAAGATCCTGCGCAGCCTGCAGGCCTTCGTGGCCGTCGCCGCC<br>CGGGTGTTCGCCCACGGCGCCGCCACGCTGAGCCCG | SEQ ID NO: 80 |
| SE_IL-23_033 | Codon optimized human IL-23 sequence | ATGTGCCACCAGCAGCTCGTGATAAGCTGGTTCAGCCTCGTCTTCCTCGCG<br>AGCCCGCTCGTCGCCATCTGGGAACTCAAGAAGGACGTGTACGTGGTGGAG<br>CTCGATTGGTACCCGGACGCCCCGGGTGAAATGGTGGTCCTCACCTGCGAC<br>ACCCCGGAGGAGGACGGCATCACGTGGACTCTGGACCAGAGCAGCGAAGTG<br>CTCGGCTCGGGTAAGACTCTGACCATCCAGGTGAAGGAGTTCGGTGACGCC<br>GGCCAGTACACCTGCCATAAGGGCGGAGAGGTGCTCTCCCACAGCCTGCTG<br>CTGCTGCACAAGAAGGAAGACGGTATCTGGAGCACCGATATCCTGAAGGAC | SEQ ID NO: 81 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | CAGAAGGAGCCGAAGAACAAGACCTTCCTGCGGTGTGAGGCCAAGAACTAC AGCGGCAGATTCACCTGTTGGTGGCTGACCACCATCTCGACCGACCTGACA TTCAGCGTGAAGTCCTCCAGGGGTAGCAGCGACCCGCAGGGCGTGACCTGC GGCGCCGCCACCCTGTCCGCCGAGCGGGTGCGCGGCGACAACAAGGAGTAC GAGTACTCCGTGGAGTGCCAGGAGGACAGCGCCTGCCCAGCGGCGGAGGAG AGCCTCCCTATCGAAGTGATGGTGGACGCCGTACACAAGCTGAAGTATGAG AATTACACCAGCAGCTTCTTCATCCGGGACATAATCAAGCCGGATCCACCG AAGAATCTGCAGCTGAAGCCACTGAAGAACAGCCGGCAGGTGGAGGTGAGC TGGGAGTACCCGGACACCTGGTCCACCCCTCACAGCTACTTCAGCCTGACC TTCTGTGTGCAGGTCCAGGGCAAGTCCAAGCGCGAGAAGAAGGACCGAGTG TTCACCGACAAGACCTCGGCCACCGTGATCTGCCGTAAGAACGCATCTATC AGCGTGCGGGCCCAGGACCGGTACTACAGCTCCAGTTGGAGCGAATGGGCC AGCGTGCCTTGCTCCGGCGGCGGCGGCGGCGGAAGCAGGGCCGTGCCGGGC GGCAGCTCCCCAGCATGGACCCAGTGCCAGCAACTGAGCCAGAAGCTGTGC ACCCTCGCCTGGTCTGCCCACCCGCTGGTGGGCCACATGGATCTGCGGGAG GAGGGCGATGAGGAAACCACCAACGACGTGCCGCACATCCAGTGCGGCGAC GGATGCGACCCTCAAGGCCTGAGAGACAACAGCCAGTTCTGCCTGCAGCGA ATCCACCAGGGCCTGATCTTCTACGAGAAGCTGCTGGGCAGCGACATCTTC ACCGGCGAGCCGAGCCTGCTGCCGGACAGCCCGGTGGGCCAACTGCACGCC AGCCTGCTGGGACTGTCCCAACTGCTGCAGCCGGAAGGCCACCACTGGGAG ACACAGCAGATCCCGAGCCTGAGCCCTTCCCAGCCGTGGCAGAGGCTGCTG CTGAGGTTCAAGATCCTCCGTTCTCTACAGGCCTTCGTGGCCGTGGCGGCC AGAGTGTTCGCCCACGGCGCCGCTACGCTCTCCCCG | |
| SE_IL-23_034 | Codon optimized human IL-23 sequence | ATGTGCCACCAGCAGCTCGTGATCAGCTGGTTCTCCTTGGTGTTCCTCGCA TCCCCACTCGTGGCCATCTGGGAGCTCAAGAAGGACGTGTACGTGGTGGAG CTCGACTGGTACCCGGACGCCCCAGGCGAGATGGTGGTGCTCACCTGTGAC ACCCCGGAGGAGGACGGCATCACTTGGACCCTGGACCAAAGCTCTGAGGTC CTGGGCTCCGGCAAGACGCTCACCATCCAGGTGAAGGAGTTCGGCGATGCC GGCCAGTACACCTGCCACAAGGGCGGCGAGGTGCTGAGCCACAGCCTGCTG CTGCTGCACAAGAAGGAGGACGGCATCTGGTCCACCGATATTCTTAAGGAC CAGAAGGAGCCGAAGAACAAGACGTTCCTGCGGTGCGAGGCCAAGAACTAC AGCGGCAGATTCACCTGCTGGTGGCTCACTACCATCAGCACCGACCTGACC TTCAGCGTGAAGTCCTCCAGGGGCAGCTCCGACCCGCAGGGAGTCACCTGC GGCGCCGCCACCCTGAGTGCGGAACGGGTGAGAGGAGACAACAAGGAGTAC GAGTACTCCGTGGAATGTCAGGAGGACAGCGCCTGCCCGGCCGCCGAGGAG AGCCTGCCGATCGAGGTCATGGTGGACGCCGTGCATAAGCTGAAGTACGAG AACTACACCAGCAGCTTCTTCATCCGGGACATCATCAAGCCGGACCCGCCG AAGAACCTGCAGCTGAAGCCGCTGAAGAACTCCCGACAGGTGGAGGTTAGC TGGGAGTACCCGGACACCTGGAGCACCCCACACAGCTACTTCAGCCTCACC TTCTGCGTGCAGGTCCAGGGCAAGAGCAAGAGGGAGAAGAAGGACAGGGTG TTCACCGACAAGACCAGCGCCACAGTGATCTGTAGAAAGAACGCCAGCATC TCCGTGCGCGCCCAGGACCGCTACTACAGCAGCAGCTGGAGCGAGTGGGCT AGCGTCCCATGCTCCGGTGGCGGTGGCGGCGGCAGCAGAGCCGTGCCGGGC GGCAGCAGCCCAGCCTGGACACAGTGTCAGCAGCTCTCCCAGAAGCTGTGC ACCCTCGCCTGGAGCGCCCACCCGCTGGTGGGCCACATGGATCTCAGGGAG GAGGGCGACGAAGAAACCACCAACGACGTGCCGCACATCCAGTGTGGCGAT GGATGCGACCCGCAGGGCCTGAGGGACAACAGCCAGTTCTGCCTGCAGCGG ATCCACCAGGGCCTGATCTTCTATGAGAAGCTGCTGGGCTCAGACATTTTC ACCGGCGAACCAAGCCTCCTGCCGGACAGCCCGGTGGGACAGCTGCACGCC TCCCTGCTGGGCCTGAGCCAGCTGCTCCAGCCGGAGGGCCACCACTGGGAA ACGCAGCAGATCCCGAGCCTCTCCCCAAGCCAGCCATGGCAGAGGCTCCTG CTCCGCTTCAAGATCCTGCGGTCCCTGCAGGCCTTCGTGGCCGTGGCCGCG AGGGTCTTCGCCCACGGCGCCGCCACCCTGAGCCCT | SEQ ID NO: 82 |
| SE_IL-23_035 | Codon optimized human IL-23 sequence | ATGTGCCACCAGCAGCTCGTGATCAGCTGGTTCAGCCTCGTGTTCCTTGCC TCCCCGCTCGTGGCCATCTGGGAGCTCAAGAAGGACGTCTACGTGGTGGAG TTGGACTGGTATCCAGACGCCCCGGGCGAGATGGTGGTGCTTACCTGCGAT ACCCCAGAGGAGGATGGCATTACCTGGACCCTGGACCAGAGCAGCGAAGTG CTGGGCAGCGGCAAGACCCTGACCATCCAGGTGAAGGAGTTCGGCGACGCC GGCCAATACACCTGCCACAAGGGCGGCGAGGTGCTGAGCCACAGCCTGCTG CTTCTGCACAAGAAGGAGGATGGCATCTGGAGCACAGACATCCTCAAGGAC CAGAAGGAGCCGAAGAACAAGACCTTCCTTAGGTGCGAGGCCAAGAACTAC TCCGGCCGGTTCACCTGCTGGTGGCTCACCACCATTTCCACCGACCTGACC TTCAGCGTCAAGAGCAGCCGGGGATCCTCTGATCCGCAGGGCGTGACCTGC GGCGCCGCCACCCTGAGCGCCGAACGCGTGAGGGGCGACAACAAGGAGTAC GAGTATTCAGTCGAGTGCCAGGAGGACAGCGCCTGCCCGGCCGCCGAGGAG AGCCTGCCGATCGAAGTCATGGTGGACGCCGTGCACAAGCTAAAGTACGAG AACTACACCAGCTCCTTCTTCATCAGGGACATCATCAAGCCTGACCCGCCA AAGAACCTGCAGCTGAAGCCGCTGAAGAACTCCAGGCAGGTGGAGGTCAGC TGGGAGTACCCTGACACCTGGAGCACCCCGCACTCCTACTTCTCGCTCACC TTCTGCGTGCAAGTGCAGGGCAAGTCCAAGAGGGAGAAGAAGGACCGGGTG TTCACCGACAAGACCAGCGCCACCGTGATATGCAGGAAGAACGCCAGCATC TCCGTCCGGGCTCAGGACAGGTACTACAGCTCCAGCTGGAGCGAATGGGCC | SEQ ID NO: 83 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TCCGTCCCGTGCAGCGGCGGCGGTGGCGGCGGTAGCCGTGCCGTCCCAGGC GGAAGCTCCCCTGCCTGGACACAGTGTCAGCAGCTGTCCCAGAAGCTGTGC ACCCTGGCCTGGTCCGCCCATCCGCTCGTGGGCCATATGGACCTCAGGGAG GAGGGCGACGAGGAAACAACCAACGATGTGCCGCATATCCAATGCGGCGAC GGCTGCGATCCGCAGGGCCTGCGGGATAACAGCCAATTCTGCCTGCAGAGA ATCCACCAGGGACTGATCTTCTACGAGAAGCTGCTGGGCAGCGACATCTTC ACAGGCGAACCTAGCCTGCTGCCAGACTCTCCTGTGGGTCAGCTGCACGCC AGCCTGCTGGGCCTCTCCCAGCTCCTGCAACCGGAGGGCCACCACTGGGAG ACGCAGCAGATCCCAAGCCTCAGCCCGTCCCAGCCGTGGCAGAGGCTGCTC CTGCGCTTCAAGATCCTGCGCAGCCTGCAGGCCTTCGTCGCGGTGGCGGCC CGTGTGTTCGCGCACGGCGCCGCCACCCTGTCCCCA | |
| SE_IL-23_036 | Codon optimized human IL-23 sequence | ATGTGCCACCAGCAGCTCGTCATCAGCTGGTTCAGCCTCGTGTTCCTCGCC AGCCCGCTCGTGGCCATTTGGGAGCTCAAGAAGGACGTGTACGTGGTCGAG CTCGATTGGTACCCGGACGCCCCAGGAGAGATGGTCGTCCTCACCTGCGAC ACCCCGGAGGAGGACGGCATCACCTGGACCCTCGACCAAAGCTCCGAGGTG CTCGGCAGCGGCAAGACCCTGACAATCCAGGTGAAGGAGTTCGGTGACGCC GGCCAGTACACCTGCCATAAGGGCGGCGAGGTGCTGAGCCACAGCCTGCTG CTGCTGCACAAGAAGGAGGACGGCATCTGGTCTACCGACATCCTGAAGGAC CAGAAGGAGCCGAAGAATAAGACTTTCCTGAGGTGCGAGGCCAAGAACTAC TCCGGCCGCTTCACCTGTTGGTGGCTGACCACTATCTCGACCGACCTGACC TTCAGCGTGAAGTCCTCGCGGGGCTCCTCCGACCCGCAGGGCGTGACCTGC GGCGCCGCCACTCTGTCCGCTGAGAGGGTCAGGGGCGACAACAAGGAGTAC GAGTACAGCGTCGAGTGTCAGGAGGACAGCGCCTGCCCGGCCGCCGAGGAG TCCCTGCCGATTGAGGTCATGGTGGACGCGGTGCACAAGCTGAAGTATGAG AACTATACCAGCTCCTTCTTCATCCGGGACATTATCAAGCCGGACCCGCCG AAGAACCTGCAGCTGAAGCCGCTGAAGAACTCCCGCCAGGTCGAGGTGTCC TGGGAGTATCCTGACACCTGGTCCACCCCGCACTCCTACTTCAGCCTGACC TTCTGCGTGCAGGTGCAAGGCAAGAGCAAGCGAGAGAAGAAGGATAGAGTG TTCACCGACAAGACCAGCGCCACCGTGATTTGCAGAAAGAACGCCAGCATC TCCGTGCGCGCCCAGGACCGCTACTACAGCAGCAGCTGGTCCGAGTGGGCC AGCGTGCCATGCAGCGGCGGAGGCGGAGGCGGTAGCCGCGCCGTGCCAGGC GGAAGCTCCCCGGCGTGGACCCAGTGCCAGCAGCTGAGCCAGAAGCTCTGC ACACTGGCCTGGTCCGCCCATCCACTCGTGGGCCACATGGACCTCCGGGAG GAGGGAGACGAGGAAACGACGAACGACGTGCCGCACATCCAGTGCGGCGAC GGCTGCGACCCGCAGGGACTGCGGGACAACTCCCAGTTCTGCCTGCAGAGG ATCCATCAGGGTCTGATCTTCTACGAGAAGCTGCTGGGCAGCGACATCTTC ACCGGCGAACCAAGCCTGCTGCCTGACTCCCCTGTGGGCCAGCTGCACGCC TCCCTGCTGGGCCTGTCCCAGCTGCTCCAGCCGGAGGGCCACCACTGGGAA ACCCAACAAATCCCGAGCCTGAGCCCATCCCAGCCGTGGCAGCGCCTGCTG CTGAGGTTCAAGATCCTGCGCTCCCTGCAGGCCTTCGTCGCCGTGGCCGCC AGAGTATTCGCCCACGGCGCCGCCACCCTGAGCCCG | SEQ ID NO: 84 |
| SE_IL-23_037 | Codon optimized human IL-23 sequence | ATGTGCCACCAGCAGCTCGTCATCAGCTGGTTCTCCCTCGTGTTCCTCGCG AGCCCTCTCGTGGCCATCTGGGAACTCAAGAAGGACGTGTACGTGGTGGAG CTCGACTGGTATCCAGACGCCCCGGGCGAAATGGTGGTGCTCACTTGTGAC ACCCCGGAGGAGGACGGTATCACCTGGACCCTGGACCAGTCCAGCGAGGTC CTGGGCAGCGGCAAGACGCTGACCATCCAGGTGAAGGAGTTCGGCGACGCC GGACAGTACACCTGCCATAAGGGCGGAGAGGTGCTCAGCCATTCCCTGCTC CTGCTGCACAAGAAGGAGGACGGCATATGGAGCACGGACATACTGAAGGAC CAGAAGGAGCCTAAGAACAAGACCTTCCTGAGATGCGAGGCCAAGAACTAC TCCGGTCGGTTCACCTGTTGGTGGCTCACCACCATCTCCACCGACCTGACC TTCAGCGTGAAGTCCTCCAGAGGCTCCAGCGACCCGCAGGGCGTCACCTGC GGCGCCGCCACCCTGTCCGCCGAGAGGGTGAGGGGCGACAATAAGGAGTAC GAGTACAGCGTGGAATGTCAAGAGGATAGCGCCTGCCCGGCCGCCGAGGAA AGCCTGCCAATCGAGGTGATGGTGGATGCCGTGCACAAGCTGAAGTATGAG AACTACACCAGCTCCTTCTTCATCAGGGACATCATCAAGCCGGACCCGCCG AAGAACCTGCAGCTCAAGCCACTGAAGAACAGCAGACAGGTGGAGGTGTCC TGGGAGTACCCGGACACATGGAGCACCCCGCACTCCTACTTCTCCCTCACC TTCTGCGTCCAGGTGCAGGGCAAGAGCAAGCGGGAGAAGAAGGACAGGGTG TTCACCGATAAGACCTCCGCCACAGTGATCTGCCGCAAGAACGCCTCCATC AGCGTGAGGGCCCAGGACAGATACTACAGCTCCAGCTGGAGCGAGTGGGCC AGCGTCCCATGCAGCGGCGGCGGAGGCGGCGGCAGCAGAGCCGTGCCGGGC GGCAGCTCCCCAGCATGGACACAGTGCCAGCAGCTGAGCCAGAAGCTCTGC ACCCTCGCCTGGTCGGCCCACCCGCTGGTGGGCCACATGGACCTGCGCGAG GAAGGCGACGAGGAAACCACGAACGACGTGCCGCACATCCAGTGCGGCGAC GGCTGCGACCCGCAGGGCCTCCGTGATAACAGCCAGTTCTGCCTGCAGAGG ATCCACCAGGGCCTGATCTTCTACGAGAAGCTGCTGGGCTCCGACATCTTC ACTGGCGAGCCGAGCCTGCTCCCAGATAGCCCAGTGGGACAGCTGCACGCC AGCCTGCTGGGCCTCTCCCAGCTGCTCCAACCGGAGGGCCATCACTGGGAA ACCCAGCAGATCCCGAGCCTGTCCCCGAGTCAGCCATGGCAGAGACTGCTG CTGAGGTTCAAGATCCTGCGGTCCCTGCAGGCCTTCGTGGCCGTGGCCGCC AGAGTGTTCGCCCACGGCGCCGCCACCCTCAGCCCA | SEQ ID NO: 85 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| SE_IL-23_038 | Codon optimized human IL-23 sequence | ATGTGCCACCAGCAGCTCGTGATCAGCTGGTTCAGCCTTGTGTTCTTGGCC<br>AGCCCCCTTGTGGCCATCTGGGAGTTAAAGAAGGACGTGTACGTGGTGGAG<br>TTAGACTGGTACCCCGACGCCCCCGGCGAGATGGTGGTGCTCACCTGCGAC<br>ACCCCCGAGGAGGACGGCATCACCTGGACCCTGGACCAGAGCAGCGAGGTG<br>CTGGGCAGCGGCAAGACCCTGACCATCCAGGTGAAGGAGTTCGGCGACGCC<br>GGCCAGTACACCTGCCACAAGGGCGGCGAAGTGCTGAGCCACAGCCTGCTG<br>CTCCTGCACAAGAAGGAAGATGGCATCTGGAGCACCGACATCCTGAAGGAC<br>CAGAAGGAGCCCAAGAACAAGACCTTCCTGCGGTGCGAGGCCAAGAACTAC<br>AGCGGCCGGTTCACCTGCTGGTGGCTGACCACCATCAGCACCGATCTGACC<br>TTCAGCGTCAAGTCCAGCCGGGGCAGCAGCGACCCCCAGGGCGTGACCTGT<br>GGCGCCGCCACCCTGAGCGCCGAGCGGGTGCGGGGCGACAACAAGGAGTAC<br>GAGTACAGCGTGGAGTGCCAGGAGGACAGCGCCTGCCCCGCCGCCGAGGAG<br>AGCCTGCCCATCGAGGTGATGGTGGACGCCGTGCACAAGCTGAAGTACGAG<br>AACTACACCTCCAGCTTCTTCATCCGGGACATCATCAAGCCCGACCCCCCT<br>AAGAACCTGCAGCTGAAGCCCCTGAAGAACAGCCGGCAGGTGGAGGTGAGC<br>TGGGAGTACCCAGACACATGGAGCACACCCCACAGCTACTTCTCCTTGACC<br>TTCTGCGTGCAGGTGCAGGGCAAGAGCAAGCGGGAGAAGAAGGATCGGGTG<br>TTCACCGACAAGACCAGCGCCACCGTGATCTGCCGGAAGAACGCCAGCATC<br>AGCGTGCGGGCCCAGGACCGGTACTACTCTTCTTCGTGGAGCGAGTGGGCC<br>AGCGTGCCCTGCAGCGGCGGCGGAGGAGGCGGCAGCAGAGCCGTGCCGGGC<br>GGCAGTTCCCCCGCCTGGACTCAGTGCCAGCAACTGAGCCAGAAGCTGTGC<br>ACCCTGGCCTGGAGCGCCCACCCACTGGTGGGCCACATGGACCTGAGAGAG<br>GAGGGCGACGAGGAGACGACCAACGACGTGCCCCACATCCAGTGCGGCGAC<br>GGCTGCGACCCACAGGGTCTGCGAGACAACAGCCAGTTCTGCCTGCAGAGG<br>ATCCACCAGGGCTTGATCTTCTACGAGAAGCTGCTGGGAAGCGACATCTTC<br>ACCGGCGAGCCTTCCCTGCTGCCCGACAGCCCCGTCGGCCAGCTGCACGCC<br>AGCCTCCTGGGCCTGTCCCAGCTGCTCCAGCCCGAGGGCCACCACTGGAA<br>ACCCAGCAGATCCCAAGCCTGAGCCCCAGCCAGCCCTGGCAGAGACTGCTG<br>CTGCGGTTCAAGATCCTGCGGAGCCTGCAGGCCTTCGTGGCCGTGGCCGCC<br>AGAGTCTTCGCCCACGGAGCCGCCACACTAAGCCCC | SEQ ID NO: 86 |
| SE_IL-23_039 | Codon optimized human IL-23 sequence | ATGTGCCACCAGCAGCTTGTGATCAGCTGGTTCAGCCTTGTGTTCCTCGCC<br>AGCCCCTTAGTGGCCATCTGGGAGCTCAAGAAGGACGTGTACGTGGTGGAG<br>CTCGACTGGTACCCCGACGCCCCCGGCGAGATGGTGGTGCTAACCTGCGAC<br>ACCCCCGAGGAGGACGGCATCACCTGGACCCTGGACCAGAGCAGCGAGGTG<br>CTGGGCAGCGGCAAGACCCTGACCATCCAGGTGAAGGAGTTCGGCGACGCC<br>GGCCAGTACACCTGCCACAAGGGCGGCGAGGTCCTGAGCCACAGCCTGTTG<br>CTCCTGCACAAGAAGGAAGACGGTATCTGGAGCACCGACATCCTGAAGGAC<br>CAGAAGGAGCCCAAGAACAAGACCTTCCTGCGGTGCGAGGCCAAGAACTAC<br>AGCGGCCGGTTCACCTGCTGGTGGCTGACCACCATCTCCACCGACCTGACC<br>TTCAGCGTGAAGTCCAGCCGGGGCAGCAGCGACCCCCAGGGCGTGACATGC<br>GGCGCCGCCACCCTGAGCGCCGAGCGGGTGCGGGGCGACAACAAGGAGTAC<br>GAGTACAGCGTGGAGTGCCAGGAGGACAGCGCCTGCCCCGCCGCCGAGGAG<br>AGCCTGCCCATCGAGGTGATGGTGGACGCCGTGCACAAGCTGAAGTACGAG<br>AACTACACAAGCAGCTTCTTCATCCGGGACATCATCAAGCCCGACCCCCCT<br>AAGAACCTGCAGCTGAAGCCCCTGAAGAACAGCCGGCAGGTGGAGGTGAGC<br>TGGGAGTACCCTGACACCTGGTCTACCCCCCACAGCTACTTCAGCCTCACC<br>TTCTGCGTGCAGGTGCAGGGCAAGAGCAAGCGGGAGAAGAAGGATCGGGTG<br>TTCACCGACAAGACCAGCGCCACCGTGATCTGCCGGAAGAACGCCAGCATC<br>AGCGTGCGGGCCCAGGACCGGTACTACAGCAGCTCTTGGAGCGAGTGGGCC<br>AGCGTGCCCTGCAGCGGCGGTGGCGGCGGCGGAAGCAGAGCCGTGCCAGGC<br>GGCTCTAGCCCCGCATGGACCCAGTGTCAACAGCTGAGCCAGAAGCTGTGC<br>ACCCTGGCCTGGAGCGCCCACCCTTTGGTGGGCCACATGGACCTGAGAGAG<br>GAGGGCGACGAGGAAACGACCAACGACGTGCCCCACATCCAGTGCGGCGAC<br>GGCTGTGACCCTCAGGGCCTGCGGGACAACAGCCAGTTCTGCCTGCAGAGG<br>ATCCACCAGGGATTGATCTTCTACGAGAAGCTCCTGGGCTCTGACATCTTC<br>ACCGGCGAGCCAAGCCTGCTCCCCGACAGCCCCGTGGGACAGCTGCACGCC<br>TCCCTGCTGGGCCTGTCACAGCTCCTTCAGCCCGAGGGCCACCACTGGGAG<br>ACACAGCAGATCCCATCTCTGAGCCCCAGCCAGCCCTGGCAGAGACTGTTG<br>CTGCGGTTCAAGATCCTGCGGAGCCTGCAGGCCTTCGTGGCCGTGGCCGCC<br>AGGGTGTTCGCCCACGGAGCAGCCACACTGTCCCCC | SEQ ID NO: 87 |
| SE_IL-23_040 | Codon optimized human IL-23 sequence | ATGTGCCACCAGCAGCTTGTGATCAGCTGGTTCAGCTTAGTGTTCCTCGCC<br>AGCCCCTTAGTGGCCATCTGGGAGCTCAAGAAGGACGTGTACGTGGTGGAG<br>CTTGACTGGTACCCCGACGCCCCCGGCGAGATGGTGGTGCTCACCTGCGAC<br>ACCCCCGAGGAGGACGGCATCACCTGGACCCTGGACCAGAGCAGCGAGGTG<br>CTGGGCAGCGGCAAGACCCTGACCATCCAGGTGAAGGAGTTCGGCGACGCC<br>GGCCAGTACACCTGCCACAAGGGCGGCGAGGTTCTTAGCCACAGCCTGCTG<br>CTTCTGCACAAGAAGGAGGATGGCATCTGGAGCACCGACATCCTGAAGGAC<br>CAGAAGGAGCCCAAGAACAAGACCTTCCTGCGGTGCGAGGCCAAGAACTAC<br>AGCGGCCGGTTCACCTGCTGGTGGCTGACCACCATCTCTACCGACCTGACC<br>TTCAGCGTTAAGAGCAGCCGGGGCAGCAGCGACCCCCAGGGCGTAACCTGC<br>GGCGCCGCCACCCTGAGCGCCGAGCGGGTGCGGGGCGACAACAAGGAGTAC<br>GAGTACAGCGTGGAGTGCCAGGAGGACAGCGCCTGCCCCGCCGCCGAGGAG<br>AGCCTGCCCATCGAGGTGATGGTGGACGCCGTGCACAAGCTGAAGTACGAG | SEQ ID NO: 88 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | AACTATACCTCTAGCTTCTTCATCCGGGACATCATCAAGCCCGACCCCCCA<br>AAGAACCTGCAGCTGAAGCCCCTGAAGAACAGCCGGCAGGTGGAGGTGAGC<br>TGGGAGTACCCTGACACATGGAGCACACCCCACAGCTACTTCAGTCTGACA<br>TTCTGCGTGCAGGTGCAGGGCAAGAGCAAGCGGGAGAAGAAGGATCGGGTG<br>TTCACCGACAAGACCAGCGCCACCGTGATCTGCCGGAAGAACGCCAGCATC<br>AGCGTGCGGGCCCAGGACCGGTACTACAGCAGCTCCTGGAGCGAGTGGGCC<br>AGCGTGCCCTGCAGCGGCGGCGGAGGAGGCGGCAGCAGAGCCGTGCCAGGC<br>GGCTCCTCTCCCGCGTGGACCCAGTGCCAGCAGTTGAGCCAGAAGCTGTGC<br>ACCCTGGCATGGTCCGCCCACCCACTGGTGGGCCACATGGACCTCAGGGAG<br>GAGGGCGACGAGGAGACAACCAACGACGTGCCCCACATCCAGTGCGGCGAC<br>GGCTGCGACCCACAGGGCCTGAGAGACAACAGCCAGTTCTGTCTGCAGAGA<br>ATCCACCAGGGACTGATCTTCTACGAGAAGCTGCTCGGCTCCGACATCTTC<br>ACCGGCGAGCCTAGCCTCCTGCCCGACAGCCCCGTGGGACAGCTGCACGCC<br>AGTTTGTTGGGCCTGTCACAACTGCTGCAGCCCGAGGGCCACCACTGGGAG<br>ACGCAGCAGATCCCTAGCCTGAGCCCCAGCCAGCCCTGGCAGCGGTTACTG<br>CTGCGGTTCAAGATCCTGCGGAGCCTGCAGGCCTTCGTGGCCGTGGCCGCC<br>CGCGTGTTCGCCCACGGAGCGGCCACACTGAGCCCC | |
| SE_IL-23_041 | Codon optimized human IL-23 sequence | ATGTGCCACCAGCAGCTCGTGATCAGCTGGTTCAGCCTTGTGTTCCTCGCC<br>AGCCCCCTCGTGGCCATCTGGGAGCTCAAGAAGGACGTGTACGTCGTCGAG<br>CTCGACTGGTACCCCGACGCCCCCGGCGAGATGGTCGTCCTCACCTGCGAC<br>ACCCCCGAGGAGGACGGCATCACCTGGACCCTCGACCAGTCCTCCGAGGTC<br>CTCGGCTCCGGCAAGACCCTCACCATCCAGGTCAAGGAGTTCGGCGACGCC<br>GGCCAGTACACCTGCCACAAGGGCGGAGAGGTTCTGTCCCACTCCCTGCTG<br>CTACTCCACAAGAAGGAGGATGGCATCTGGTCCACCGACATCCTCAAGGAC<br>CAGAAGGAGCCCAAGAACAAGACCTTCCTCCGCTGCGAGGCCAAGAACTAC<br>TCCGGCCGCTTCACCTGCTGGTGGCTCACCACCATCTCCACAGACCTCACC<br>TTCTCCGTCAAGTCCTCCCGCGGCTCCTCCGACCCCCAGGGCGTTACCTGC<br>GGCGCCGCCACCCTCTCCGCCGAGCGCGTCCGCGGCGACAACAAGGAGTAC<br>GAGTACTCCGTCGAGTGCCAGGAGGACTCCGCCTGCCCCGCCGCCGAGGAG<br>TCCCTCCCCATCGAGGTCATGGTCGACGCCGTCCACAAGCTCAAGTACGAG<br>AACTACACCAGCTCCTTCTTCATCCGCGACATCATCAAGCCTGACCCTCCT<br>AAGAATCTCCAGCTCAAGCCCCTCAAGAACTCCCGCCAGGTCGAGGTGTCC<br>TGGGAATATCCAGACACCTGGAGCACCCCCCACTCCTACTTCTCCCTGACC<br>TTCTGCGTCCAGGTCCAGGGCAAGTCCAAGCGCGAGAAGAAGGATCGCGTC<br>TTCACCGACAAGACATCCGCCACCGTCATCTGCCGCAAGAACGCCTCCATC<br>TCCGTCCGCGCCCAGGACCGCTACTACTCCTCCTCTTGGTCCGAGTGGGCC<br>TCCGTCCCCTGCTCCGGCGGAGGCGGCGGTGGATCCCGCGCCGTCCCTGGC<br>GGCAGCTCCCCAGCTTGGACCCAGTGTCAGCAGCTCTCCCAGAAGCTCTGC<br>ACCCTCGCCTGGAGCGCCCACCCCCTCGTCGGCCACATGGACCTCAGGGAG<br>GAGGGCGACGAGGAGACAACCAACGACGTCCCCCACATCCAGTGCGGCGAC<br>GGCTGCGACCCACAGGGACTTAGAGACAACTCCCAGTTCTGCCTCCAGCGC<br>ATCCACCAGGGCCTCATCTTCTACGAGAAGCTTTTGGGATCCGACATCTTC<br>ACTGGCGAGCCTAGCCTGCTGCCGGACTCCCCTGTGGGCCAGCTCCACGCG<br>TCTCTGCTGGGCCTGAGTCAGCTCCTCCAGCCCGAGGGCCACCACTGGGAA<br>ACCCAGCAGATCCCTTCCTTGTCCCCCTCCCAGCCCTGGCAGCGCCTCCTG<br>CTGCGGTTCAAGATCCTGAGATCCCTCCAGGCCTTCGTCGCCGTCGCCGCC<br>CGGGTCTTCGCCCATGGCGCTGCTACACTGAGCCCC | SEQ ID NO: 89 |
| SE_IL-23_042 | Codon optimized human IL-23 sequence | ATGTGCCACCAGCAGCTCGTGATCAGCTGGTTCAGCCTCGTGTTCCTAGCC<br>AGCCCCCTTGTGGCCATCTGGGAGCTCAAGAAGGACGTGTACGTCGTCGAG<br>CTCGACTGGTACCCCGACGCCCCCGGCGAGATGGTCGTCCTCACCTGCGAC<br>ACCCCCGAGGAGGACGGCATCACCTGGACCCTCGACCAGTCCTCCGAGGTC<br>CTCGGCTCCGGCAAGACCCTCACCATCCAGGTCAAGGAGTTCGGCGACGCC<br>GGCCAGTACACCTGCCACAAGGGCGGCGAGGTGCTGTCCCACTCCCTGCTG<br>CTGCTCCACAAGAAGGAGGATGGCATCTGGTCCACCGACATCCTCAAGGAC<br>CAGAAGGAGCCCAAGAACAAGACCTTCCTCCGCTGCGAGGCCAAGAACTAC<br>TCCGGCCGCTTCACCTGCTGGTGGCTCACCACCATCAGCACCGACCTCACC<br>TTCTCCGTCAAGTCCTCCCGCGGCTCCTCCGACCCCCAGGGCGTGACATGC<br>GGCGCCGCCACCCTCTCCGCCGAGCGCGTCCGCGGCGACAACAAGGAGTAC<br>GAGTACTCCGTCGAGTGCCAGGAGGACTCCGCCTGCCCCGCCGCCGAGGAG<br>TCCCTCCCCATCGAGGTCATGGTCGACGCCGTCCACAAGCTCAAGTACGAG<br>AACTACACCAGTAGCTTCTTCATCCGCGACATCATCAAGCCTGACCCTCCA<br>AAGAACCTCCAGCTCAAGCCCCTCAAGAACTCCCGCCAGGTCGAAGTGTCC<br>TGGGAGTACCCAGACACCTGGTCAACTCCCCACTCCTACTTCAGCCTTACG<br>TTCTGCGTCCAGGTCCAGGGCAAGTCCAAGCGCGAGAAGAAGGATCGCGTC<br>TTCACCGACAAGACTTCCGCCACCGTCATCTGCCGCAAGAACGCCTCCATC<br>TCCGTCCGCGCCCAGGACCGCTACTACAGCTCCTCTTGGTCCGAGTGGGCC<br>TCCGTCCCCTGCTCCGGAGGCGGTGGCGGCGGATCCCGCGCCGTCCCAGGC<br>GGAAGCTCCCCCGCATGGACCCAGTGTCAGCAGCTCTCCCAGAAGCTCTGC<br>ACCCTCGCCTGGTCCGCCCACCCCCTCGTCGGCCACATGGACCTGCGCGAG<br>GAGGGCGACGAGGAGACAACCAACGACGTCCCCCACATCCAGTGCGGCGAC<br>GGCTGCGATCCACAGGGCCTGAGGGACAACTCCCAGTTCTGCCTCCAGCGC<br>ATCCACCAGGGACTCATCTTCTACGAGAAGCTGCTGGGAAGCGACATATTC<br>ACCGGCGAGCCTTCCTTGCTGCCAGACTCCCCTGTGGGCCAGCTCCACGCC | SEQ ID NO: 90 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TCCCTCCTGGGCCTCTCCCAACTGCTCCAGCCCGAGGGCCACCACTGGGAG<br>ACACAGCAGATCCCATCCCTGTCCCCCTCCCAGCCCTGGCAGCGCCTGCTA<br>CTGCGCTTCAAGATCCTGAGATCCCTCCAGGCCTTCGTCGCCGTCGCCGCC<br>AGAGTGTTCGCCCATGGAGCCGCCACACTGAGCCCC | |
| SE_IL-23_043 | Codon optimized human IL-23 sequence | ATGTGCCACCAGCAGCTGGTGATCAGCTGGTTCAGCCTGGTGTTCCTGGCC<br>AGCCCCCTGGTGGCCATCTGGGAGCTGAAGAAGGACGTGTACGTGGTGGAG<br>CTGGACTGGTACCCCGACGCCCCCGGCGAGATGGTGGTGCTGACCTGCGAC<br>ACCCCCGAGGAGGACGGCATCACCTGGACCCTGGACCAGAGCAGCGAGGTG<br>CTGGGCAGCGGCAAGACCCTGACCATCCAGGTGAAGGAGTTCGGCGACGCC<br>GGCCAGTACACCTGCCACAAGGGCGGCGAGGTGCTGAGCCACAGCCTGCTG<br>CTGCTGCACAAGAAGGAGGACGGCATCTGGAGCACCGACATCCTGAAGGAC<br>CAGAAGGAGCCCAAGAACAAGACCTTCCTGCGGTGCGAGGCCAAGAACTAC<br>AGCGGCCGGTTCACCTGCTGGTGGCTGACCACCATCAGCACCGACCTGACC<br>TTCAGCGTGAAGAGCAGCCGGGGCAGCAGCGACCCCCAGGGCGTGACCTGC<br>GGCGCCGCCACCCTGAGCGCCGAGCGGGTGCGGGGCGACAACAAGGAGTAC<br>GAGTACAGCGTGGAGTGCCAGGAGGACAGCGCCTGCCCCGCCGCCGAGGAG<br>AGCCTGCCCATCGAGGTGATGGTGGACGCCGTGCACAAGCTGAAGTACGAG<br>AACTACACCAGCAGCTTCTTCATCCGGGACATCATCAAGCCCGACCCCCCC<br>AAGAACCTGCAGCTGAAGCCCCTGAAGAACAGCCGGCAGGTGGAGGTGAGC<br>TGGGAGTACCCCGACACCTGGAGCACCCCCCACAGCTACTTCAGCCTGACC<br>TTCTGCGTGCAGGTGCAGGGCAAGAGCAAGCGGGAGAAGAAGGACCGGGTG<br>TTCACCGACAAGACCAGCGCCACCGTGATCTGCCGGAAGAACGCCAGCATC<br>AGCGTGCGGGCCCAGGACCGGTACTACAGCAGCAGCTGGAGCGAGTGGGCC<br>AGCGTGCCCTGCAGCGGCGGCGGCGGCGGCGGCAGCCGGGCCGTGCCCGGC<br>GGCAGCAGCCCCGCCTGGACCCAGTGCCAGCAGCTGAGCCAGAAGCTGTGC<br>ACCCTGGCCTGGAGCGCCCACCCCCTGGTGGGCCACATGGACCTGCGGGAG<br>GAGGGCGACGAGGAGACCACCAACGACGTGCCCCACATCCAGTGCGGCGAC<br>GGCTGCGACCCCCAGGGCCTGCGGGACAACAGCCAGTTCTGCCTGCAGCGG<br>ATCCACCAGGGCCTGATCTTCTACGAGAAGCTGCTGGGCAGCGACATCTTC<br>ACCGGCGAGCCCAGCCTGCTGCCCGACAGCCCCGTGGGCCAGCTGCACGCC<br>AGCCTGCTGGGCCTGAGCCAGCTGCTGCAGCCCGAGGGCCACCACTGGGAG<br>ACCCAGCAGATCCCCAGCCTGAGCCCCAGCCAGCCCTGGCAGCGGCTGCTG<br>CTGCGGTTCAAGATCCTGCGGAGCCTGCAGGCCTTCGTGGCCGTGGCCGCC<br>CGGGTGTTCGCCCACGGCGCCGCCACCCTGAGCCCC | SEQ ID NO: 91 |
| SE_IL-23_044 | Codon optimized human IL-23 sequence | ATGTGCCACCAGCAGCTGGTGATCAGCTGGTTCAGCCTGGTGTTCCTGGCC<br>AGCCCCCTGGTGGCCATCTGGGAGCTGAAGAAGGACGTGTACGTGGTGGAG<br>CTGGACTGGTACCCGGACGCGCCGGGGGAGATGGTGGTGCTGACGTGCGAC<br>ACGCCGGAGGAGGACGGGATCACGTGGACGCTGGACCAGAGCAGCGAGGTG<br>CTGGGGAGCGGGAAGACGCTGACGATCCAGGTGAAGGAGTTCGGGGACGCG<br>GGGCAGTACACGTGCCACAAGGGGGGGGAGGTGCTGAGCCACAGCCTGCTG<br>CTGCTGCACAAGAAGGAGGACGGGATCTGGAGCACGGACATCCTGAAGGAC<br>CAGAAGGAGCCGAAGAACAAGACGTTCCTGAGGTGCGAGGCGAAGAACTAC<br>AGCGGGAGGTTCACGTGCTGGTGGCTGACGACGATCAGCACGGACCTGACG<br>TTCAGCGTGAAGAGCAGCAGGGGGAGCAGCGACCCGCAGGGGGTGACGTGC<br>GGGGCGGCGACGCTGAGCGCGGAGAGGGTGAGGGGGGACAACAAGGAGTAC<br>GAGTACAGCGTGGAGTGCCAGGAGGACAGCGCGTGCCCGGCGGCGGAGGAG<br>AGCCTGCCGATCGAGGTGATGGTGGACGCGGTGCACAAGCTGAAGTACGAG<br>AACTACACGAGCAGCTTCTTCATCAGGGACATCATCAAGCCGGACCCGCCG<br>AAGAACCTGCAGCTGAAGCCGCTGAAGAACAGCAGGCAGGTGGAGGTGAGC<br>TGGGAGTACCCGGACACGTGGAGCACGCCGCACAGCTACTTCAGCCTGACG<br>TTCTGCGTGCAGGTGCAGGGGAAGAGCAAGAGGGAGAAGAAGGACAGGGTG<br>TTCACGGACAAGACGAGCGCGACGGTGATCTGCAGGAAGAACGCGAGCATC<br>AGCGTGAGGGCGCAGGACAGGTACTACAGCAGCAGCTGGAGCGAGTGGGCG<br>AGCGTGCCGTGCAGCGGGGGGGGGGGGGGGGGGAGCAGGGCGGTGCCGGGG<br>GGGAGCAGCCCGGCGTGGACGCAGTGCCAGCAGCTGAGCCAGAAGCTGTGC<br>ACGCTGGCGTGGAGCGCGCACCCGCTGGTGGGGCACATGGACCTGAGGGAG<br>GAGGGGGACGAGGAGACGACGAACGACGTGCCGCACATCCAGTGCGGGGAC<br>GGGTGCGACCCGCAGGGGCTGAGGGACAACAGCCAGTTCTGCCTGCAGAGG<br>ATCCACCAGGGGCTGATCTTCTACGAGAAGCTGCTGGGGAGCGACATCTTC<br>ACGGGGGAGCCGAGCCTGCTGCCGGACAGCCCGGTGGGGCAGCTGCACGCG<br>AGCCTGCTGGGGCTGAGCCAGCTGCTGCAGCCGGAGGGGCACCACTGGGAG<br>ACGCAGCAGATCCCGAGCCTGAGCCCGAGCCAGCCGTGGCAGAGGCTGCTG<br>CTGAGGTTCAAGATCCTGAGGAGCCTGCAGGCGTTCGTGGCGGTGGCGGCG<br>AGGGTGTTCGCGCACGGGGCGGCGACGCTGAGCCCG | SEQ ID NO: 92 |
| SE_IL-23_045 | Codon optimized human IL-23 sequence | ATGTGCCACCAGCAGCTGGTGATCAGCTGGTTCAGCCTGGTGTTCCTGGCC<br>AGCCCCCTGGTGGCCATCTGGGAGCTGAAGAAGGACGTGTACGTCGTCGAG<br>CTCGACTGGTACCCCGACGCCCCCGGCGAGATGGTCGTCCTCACCTGCGAC<br>ACCCCCGAGGAGGACGGCATCACCTGGACCCTCGACCAGTCCTCCGAGGTC<br>CTCGGCTCCGGCAAGACCCTCACCATCCAGGTCAAGGAGTTCGGCGACGCC<br>GGCCAGTACACCTGCCACAAGGGCGGCGAGGTCCTCTCCCACTCCCTCCTC<br>CTCCTCCACAAGAAGGAGGACGGCATCTGGTCCACCGACATCCTCAAGGAC<br>CAGAAGGAGCCCAAGAACAAGACCTTCCTCCGCTGCGAGGCCAAGAACTAC | SEQ ID NO: 93 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TCCGGCCGCTTCACCTGCTGGTGGCTCACCACCATCTCCACCGACCTCACC<br>TTCTCCGTCAAGTCCTCCCGCGGCTCCTCCGACCCCCAGGGCGTCACCTGC<br>GGCGCCGCCACCCTCTCCGCCGAGCGCGTCCGCGGCGACAACAAGGAGTAC<br>GAGTACTCCGTCGAGTGCCAGGAGGACTCCGCCTGCCCCGCCGCCGAGGAG<br>TCCCTCCCCATCGAGGTCATGGTCGACGCCGTCCACAAGCTCAAGTACGAG<br>AACTACACCTCCTCCTTCTTCATCCGCGACATCATCAAGCCCGACCCCCCC<br>AAGAACCTCCAGCTCAAGCCCCTCAAGAACTCCCGCCAGGTCGAGGTCTCC<br>TGGGAGTACCCCGACACCTGGTCCACCCCCCACTCCTACTTCTCCCTCACC<br>TTCTGCGTCCAGGTCCAGGGCAAGTCCAAGCGCGAGAAGAAGGACCGCGTC<br>TTCACCGACAAGACCTCCGCCACCGTCATCTGCCGCAAGAACGCCTCCATC<br>TCCGTCCGCGCCCAGGACCGCTACTACTCCTCCTCCTGGTCCGAGTGGGCC<br>TCCGTCCCCTGCTCCGGCGGCGGCGGCGGCGGCTCCCGCGCCGTCCCCGGC<br>GGCTCCTCCCCCGCCTGGACCCAGTGCCAGCAGCTCTCCCAGAAGCTCTGC<br>ACCCTCGCCTGGTCCGCCCACCCCCTCGTCGGCCACATGGACCTCCGCGAG<br>GAGGGCGACGAGGAGACCACCAACGACGTCCCCCACATCCAGTGCGGCGAC<br>GGCTGCGACCCCCAGGGCCTCCGCGACAACTCCCAGTTCTGCCTCCAGCGC<br>ATCCACCAGGGCCTCATCTTCTACGAGAAGCTCCTCGGCTCCGACATCTTC<br>ACCGGCGAGCCCTCCCTCCTCCCCGACTCCCCCGTCGGCCAGCTCCACGCC<br>TCCCTCCTCGGCCTCTCCCAGCTCCTCCAGCCCGAGGGCCACCACTGGGAG<br>ACCCAGCAGATCCCCTCCCTCTCCCCCTCCCAGCCCTGGCAGCGCCTCCTC<br>CTCCGCTTCAAGATCCTCCGCTCCCTCCAGGCCTTCGTCGCCGTCGCCGCC<br>CGCGTCTTCGCCCACGGCGCCGCCACCCTCTCCCCC | |
| hIGKV4-IL-36g | Codon optimized hIGKV4-hIL-36g | ATGGTGTTGCAGACCCAGGTCTTCATTTCTCTGTTGCTCTGGATCTCTGGT<br>GCCTACGGGTCAATGTGTAAACCTATTACTGGGACTATTAATGATTTGAAT<br>CAGCAAGTGTGGACCCTTCAGGGTCAGAACCTTGTGGCAGTTCCACGAAGT<br>GACAGTGTGACCCCAGTCACTGTTGCTGTTATCACATGCAAGTATCCAGAG<br>GCTCTTGAGCAAGGCAGAGGGGATCCCATTTATTTGGGAATCCAGAATCCA<br>GAAATGTGTTTGTATTGTGAGAAGGTTGGAGAACAGCCCACATTGCAGCTA<br>AAAGAGCAGAAGATCATGGATCTGTATGGCCAACCCGAGCCCGTGAAACCC<br>TTCCTTTTCTACCGTGCCAAGACTGGTAGGACCTCCACCCTTGAGTCTGTG<br>GCCTTCCCGGACTGGTTCATTGCCTCCTCCAAGAGAGACCAGCCCATCATT<br>CTGACTTCAGAACTTGGGAAGTCATACAACACTGCCTTTGAATTAAATATA<br>AATGAC | SEQ ID NO: 94 |
| SE_IL-36_001 | Codon optimized hIGKV4-hIL-36g | ATGGTGCTCCAGACCCAGGTGTTCATCTCCTTGCTCTTGTGGATCAGTGGC<br>GCTTACGGATCAATGTGCAAGCCTATTACCGGCACCATCAACGACTTAAAC<br>CAGCAGGTTTGGACCCTCCAGGGCCAGAACCTCGTTGCCGTGCCTCGCAGC<br>GACAGCGTGACCCCTGTCACCGTGGCCGTGATCACGTGTAAGTACCCTGAA<br>GCACTGGAGCAGGGCAGAGGCGACCCAATTTATCTCGGAATCCAGAACCCG<br>GAGATGTGCCTGTACTGCGAGAAGGTGGGCGAACAGCCTACCCTGCAGCTG<br>AAGGAGCAGAAGATCATGGATCTGTATGGACAGCCTGAGCCGGTGAAGCCG<br>TTCCTGTTCTACAGAGCGAAGACTGGAAGGACAAGCACCCTAGAGAGCGTC<br>GCCTTCCCGGACTGGTTCATCGCCAGCTCAAAGAGGGATCAGCCTATCATT<br>CTGACGTCAGAGCTTGGCAAGAGCTACAACACCGCCTTCGAGCTTAATATC<br>AACGAC | SEQ ID NO: 95 |
| SE_IL-36_002 | Codon optimized hIGKV4-hIL-36g | ATGGTGCTTCAGACCCAGGTGTTCATCAGCCTACTCCTCTGGATCAGCGGC<br>GCCTACGGCAGCATGTGCAAGCCCATCACCGGCACCATCAACGACTTAAAC<br>CAGCAGGTGTGGACCCTCCAGGGCCAGAACCTTGTGGCCGTGCCCCGGAGC<br>GACAGCGTGACCCCGGTGACCGTTGCTGTGATCACCTGCAAGTACCCCGAG<br>GCCCTGGAGCAGGGCCGGGGCGACCCCATCTACCTGGGCATCCAGAACCCC<br>GAGATGTGCCTGTACTGCGAGAAGGTGGGCGAGCAGCCCACTTTGCAGCTG<br>AAGGAGCAGAAGATCATGGACCTGTACGGCCAGCCCGAGCCCGTGAAGCCC<br>TTCCTGTTCTACCGGGCCAAGACCGGCCGGACCAGCACCCTGGAGAGCGTG<br>GCCTTCCCCGACTGGTTCATCGCCAGCAGCAAGCGGGACCAGCCGATCATC<br>CTGACCAGCGAGCTGGGCAAGAGCTACAACACCGCCTTCGAGCTGAATATC<br>AATGAC | SEQ ID NO: 96 |
| SE_IL-36_003 | Codon optimized hIGKV4-hIL-36g | ATGGTGCTCCAGACGCAGGTGTTCATCAGCTTGCTTCTTTGGATCAGCGGA<br>GCCTACGGCTCCATGTGCAAGCCTATCACAGGCACCATCAACGACTTAAAC<br>CAGCAGGTGTGGACCCTCCAGGGTCAGAACTTAGTGGCCGTGCCTCGGAGC<br>GACAGCGTCACGCCTGTGACCGTGGCCGTAATAACCTGTAAGTATCCTGAG<br>GCCCTGGAACAGGGCAGGGGAGATCCAATATACCTGGGCATCCAGAACCCT<br>GAGATGTGTCTCTACTGCGAGAAGGTGGGCGAACAGCCTACCTTGCAGCTG<br>AAGGAGCAGAAGATAATGGACCTGTACGGACAGCCAGAACCAGTCAAGCCG<br>TTCCTGTTCTATAGAGCCAAGACCGGTAGAACCTCCACGCTCGAGTCCGTG<br>GCATTCCCTGACTGGTTCATCGCCTCCAGCAAGCGCGACCAGCCGATCATA<br>CTGACCTCTGAGTTGGGCAAGAGCTATAACACCGCCTTCGAGCTGAATATC<br>AATGAC | SEQ ID NO: 97 |
| SE_IL-36_004 | Codon optimized: hIGKV4-hIL-36g | ATGGTGCTTCAGACCCAGGTGTTCATCAGCTTGCTCCTCTGGATCAGCGGC<br>GCCTACGGCAGCATGTGCAAGCCCATCACCGGCACCATCAACGACCTCAAC<br>CAGCAGGTCTGGACCCTCCAGGGCCAGAACCTCGTCGCCGTGCCTCGCTCC<br>GACTCCGTCACCCCTGTCACGGTGGCCGTGATCACCTGCAAGTACCCCGAG | SEQ ID NO: 98 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | GCCCTCGAGCAGGGCCGCGGCGACCCCATCTACCTCGGCATCCAGAACCCC GAGATGTGCCTCTACTGCGAGAAGGTCGGCGAGCAGCCCACTCTGCAGCTC AAGGAGCAGAAGATCATGGACCTCTACGGCCAGCCCGAGCCCGTCAAGCCC TTCCTCTTCTACCGCGCCAAGACCGGCCGCACCTCCACCCTCGAGTCCGTC GCCTTCCCCGACTGGTTCATCGCCTCCTCCAAGCGCGACCAGCCTATTATC CTCACCTCCGAGCTCGGCAAGTCCTACAACACCGCCTTCGAGCTCAACATC AATGAC | |
| SE_IL-36_005 | Codon optimized hIGKV4-hIL-36g | ATGGTGCTCCAGACCCAGGTGTTCATTAGCCTATTACTTTGGATATCCGGC GCTTACGGCAGCATGTGCAAGCCTATCACCGGCACCATCAACGACCTCAAC CAGCAGGTTTGGACACTCCAGGGCCAGAACCTTGTGGCCGTGCCTAGATCC GACTCTGTTACCCCTGTTACAGTGGCTGTGATCACTTGCAAGTACCCGGAA GCCCTGGAGCAGGGCAGGGGAGATCCTATCTATCTGGGTATCCAGAACCCA GAAATGTGCCTTTATTGCGAGAAGGTGGGCGAGCAGCCTACACTTCAGCTG AAGGAACAGAAGATCATGGACCTCTACGGACAGCCAGAACCAGTGAAGCCT TTCCTGTTCTACCGAGCCAAGACCGGCCGGACCAGCACCCTGGAGAGCGTG GCGTTCCCTGATTGGTTCATCGCCTCTAGCAAGAGGGACCAACCTATCATC TTAACCAGTGAGCTGGGCAAGAGCTACAACACGGCCTTCGAGCTCAACATT AATGAT | SEQ ID NO: 99 |
| SE_IL-36_006 | Codon optimized hIGKV4-hIL-36g | ATGGTGCTCCAGACCCAGGTGTTCATCAGCCTATTGCTCTGGATCAGCGGC GCCTACGGCAGCATGTGCAAGCCCATCACCGGCACCATCAACGACTTGAAC CAGCAGGTGTGGACCTTGCAGGGCCAGAACCTCGTGGCCGTGCCCCGGAGC GACAGCGTGACGCCAGTGACCGTGGCGGTCATCACCTGCAAGTACCCCGAG GCCCTGGAGCAGGGCCGGGGCGACCCCATCTACCTGGGCATCCAGAACCCC GAGATGTGCCTGTACTGCGAGAAGGTGGGCGAGCAGCCCACCCTTCAGCTG AAGGAGCAGAAGATCATGGACCTGTACGGCCAGCCCGAGCCCGTGAAGCCC TTCCTGTTCTACCGGGCCAAGACCGGCCGGACCAGCACCCTGGAGAGCGTG GCCTTCCCCGACTGGTTCATCGCCAGCAGCAAGCGGGACCAGCCTATCATC CTGACCAGCGAGCTGGGCAAGAGCTACAACACCGCCTTCGAGCTGAATATC AATGAC | SEQ ID NO: 100 |
| SE_IL-36_007 | Codon optimized hIGKV4-hIL-36g | ATGGTGCTCCAGACACAGGTGTTCATCTCTCTCCTCCTCTGGATATCCGGA GCCTACGGCTCAATGTGTAAGCCTATCACCGGCACTATCAACGATTTAAAT CAGCAGGTGTGGACCCTTCAGGGCCAGAACCTCGTGGCAGTGCCGAGAAGC GACAGCGTGACCCCGGTGACCGTGGCCGTGATCACTTGTAAGTACCCAGAG GCCCTGGAGCAGGGTCGCGGCGACCCAATCTATCTGGGTATTCAGAACCCT GAGATGTGCCTGTATTGCGAGAAGGTGGGCGAACAGCCGACGCTGCAGCTC AAGGAGCAGAAGATCATGGATTTATACGGCCAGCCTGAGCCGGTGAAGCCA TTCCTGTTCTACAGGGCCAAGACGGGCAGGACTTCCACCTTGGAGAGCGTG GCTTTCCCGGACTGGTTCATTGCATCTTCCAAGAGGGACCAGCCTATTATC CTGACAAGCGAGCTGGGCAAGTCATACAACACCGCCTTCGAGCTGAACATT AATGAC | SEQ ID NO: 101 |
| SE_IL-36_008 | Codon optimized hIGKV4-hIL-36g | ATGGTGCTCCAGACCCAGGTGTTCATCAGCTTGCTCCTCTGGATCAGCGGC GCCTACGGCAGCATGTGCAAGCCCATCACCGGCACCATCAACGACTTGAAC CAGCAGGTGTGGACCTTGCAGGGCCAGAACCTCGTGGCCGTGCCCCGGAGC GACAGCGTGACTCCTGTGACCGTGGCGGTGATCACCTGCAAGTACCCCGAG GCCCTGGAGCAGGGCCGGGGCGACCCCATCTACCTGGGCATCCAGAACCCC GAGATGTGCCTGTACTGCGAGAAGGTGGGCGAGCAGCCCACCCTCCAGCTG AAGGAGCAGAAGATCATGGACCTGTACGGCCAGCCCGAGCCCGTGAAGCCC TTCCTGTTCTACCGGGCCAAGACCGGCCGGACCAGCACCCTGGAGAGCGTG GCCTTCCCCGACTGGTTCATCGCCAGCAGCAAGCGGGACCAGCCTATCATC CTGACCAGCGAGCTGGGCAAGAGCTACAACACCGCCTTCGAGCTGAATATC AACGAC | SEQ ID NO: 102 |
| SE_IL-36_009 | Codon optimized hIGKV4-hIL-36g | ATGGTGCTTCAGACACAGGTCTTCATTAGCCTCTTATTATGGATATCCGGC GCTTACGGCTCTATGTGCAAGCCTATTACCGGCACAATCAACGATTTGAAC CAGCAAGTGTGGACCCTCCAGGGCCAGAATTTGGTGGCCGTGCCGAGATCC GATAGCGTGACCCCAGTGACCGTGGCTGTGATTACCTGTAAGTACCCTGAA GCTCTGGAGCAGGGCAGGGGCGACCCAATTTACCTCGGCATCCAGAACCCT GAGATGTGTCTGTACTGTGAGAAGGTGGGCGAGCAGCCAACTTTACAACTC AAGGAACAGAAGATCATGGACCTCTACGGCCAGCCAGAGCCGGTTAAGCCT TTCCTGTTCTATAGAGCCAAGACTGGCAGGACCAGTACCCTGGAGTCAGTG GCTTTCCCTGATTGGTTCATTGCCTCCAGCAAGCGGGATCAGCCAATTATT CTGACCAGCGAGCTGGGAAAGAGCTACAACACCGCGTTCGAGCTGAACATC AACGAT | SEQ ID NO: 103 |
| SE_IL-36_010 | Codon optimized hIGKV4-hIL-36g | ATGGTGCTCCAGACCCAGGTGTTCATCAGCTTGCTCTTGTGGATCAGCGGC GCCTACGGCAGCATGTGCAAGCCCATCACCGGCACCATCAACGACCTCAAC CAGCAGGTCTGGACCCTCCAGGGCCAGAACCTCGTCGCCGTGCCTCGCTCC GACTCCGTCACTCCAGTCACAGTGGCTGTGATCACCTGCAAGTACCCCGAG GCCCTCGAGCAGGGCCGCGGCGACCCCATCTACCTCGGCATCCAGAACCCC GAGATGTGCCTCTACTGCGAGAAGGTCGGCGAGCAGCCCACCTTGCAGCTC AAGGAGCAGAAGATCATGGACCTCTACGGCCAGCCCGAGCCCGTCAAGCCC | SEQ ID NO: 104 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TTCCTCTTCTACCGCGCCAAGACCGGCCGCACCTCCACCCTCGAGTCCGTC GCCTTCCCCGACTGGTTCATCGCCTCCTCCAAGCGCGACCAGCCTATTATC CTCACCTCCGAGCTCGGCAAGTCCTACAACACCGCCTTCGAGCTCAATATC AACGAC | |
| SE_IL-36_041 | Codon optimized hIGKV4-hIL-36g | ATGGTCCTCCAGACCCAAGTCTTCATCTCCTTGTTGCTCTGGATCAGCGGG GCCTACGGCTCTATGTGTAAGCCCATTACCGGCACCATCAACGACCTCAAC CAACAGGTCTGGACCCTTCAGGGTCAGAACCTCGTCGCCGTGCCCAGATCC GACTCCGTGACCCCTGTCACCGTGGCCGTGATCACCTGCAAATATCCCGAG GCCCTGGAGCAGGGGCGCGGCGACCCCATATACCTGGGCATCCAGAACCCC GAGATGTGCCTCTACTGCGAGAAGGTGGGCGAACAGCCCACCCTCCAGCTG AAGGAGCAGAAGATCATGGACCTGTACGGCCAGCCCGAGCCCGTGAAGCCC TTCCTGTTCTATAGGGCCAAGACCGGCCGCACCTCCACCCTGGAGTCCGTG GCCTTCCCCGATTGGTTTATTGCCAGTAGCAAGAGGGACCAGCCCATCATC CTCACCAGCGAACTGGGCAAGAGCTACAACACCGCCTTCGAGCTGAACATC AATGAC | SEQ ID NO: 105 |
| SE_IL-36_042 | Codon optimized hIGKV4-hIL-36g | ATGGTGCTCCAGACACAGGTGTTCATCAGCCTCCTCCTCTGGATCAGCGGG GCCTACGGCAGCATGTGCAAGCCCATCACAGGCACCATCAACGACCTCAAT CAGCAAGTCTGGACCCTCCAGGGTCAGAACCTCGTGGCCGTGCCCCGCAGC GACAGCGTGACGCCCGTGACAGTGGCCGTCATCACGTGCAAATACCCCGAA GCCCTGGAGCAGGGCCGTGGCGACCCTATCTACCTGGGCATACAGAACCCC GAGATGTGCCTGTACTGCGAGAAGGTGGGTGAGCAGCCCACCCTGCAACTG AAGGAGCAGAAGATCATGGACCTCTACGGACAACCGGAGCCCGTGAAACCC TTCCTGTTCTACAGGGCCAAGACCGGGAGGACCTCCACCCTGGAAAGCGTG GCCTTTCCCGACTGGTTTATCGCCAGCTCCAAGAGGGACCAACCCATCATC CTCACCAGCGAGCTGGGCAAGTCTTACAACACCGCCTTTGAGCTGAACATC AATGAT | SEQ ID NO: 106 |
| SE_IL-36_043 | Codon optimized hIGKV4-hIL-36g | ATGGTGCTCCAGACCCAGGTGTTCATCAGCCTCCTCCTCTGGATCAGCGGG GCCTACGGGAGCATGTGCAAGCCCATCACCGGGACCATCAACGACCTCAAC CAGCAGGTCTGGACGCTCCAGGGGCAGAATCTCGTGGCCGTGCCCAGATCC GACAGCGTGACCCCGGTGACCGTGGCCGTCATCACCTGTAAGTACCCGGAG GCCCTGGAACAGGGCCGAGGTGACCCCATCTATCTGGGTATCCAGAATCCG GAGATGTGCCTGTACTGCGAGAAGGTGGGCGAGCAGCCCACCCTGCAGCTG AAGGAGCAGAAGATCATGGACCTGTACGGCCAACCCGAGCCCGTGAAGCCC TTCCTGTTTTACAGGGCCAAGACCGGCCGGACGAGCACCCTGGAGAGCGTG GCCTTTCCCGACTGGTTCATCGCCAGTAGCAAGAGGGACCAACCCATCATC CTGACCTCCGAGCTGGGCAAGAGCTACAATACCGCCTTCGAGCTCAACATC AATGAT | SEQ ID NO: 107 |
| SE_IL-36_044 | Codon optimized hIGKV4-hIL-36g | ATGGTCCTACAGACCCAAGTGTTCATCAGCCTCCTTCTCTGGATCAGCGGA GCCTACGGCTCCATGTGTAAGCCCATCACCGGCACTATCAACGACCTCAAT CAGCAGGTGTGGACACTCCAGGGCCAGAACCTCGTGGCCGTGCCCAGAAGC GACAGCGTGACCCCGGTCACCGTCGCCGTGATCACCTGCAAATATCCCGAG GCCCTGGAGCAGGGCCGAGGGGACCCCATCTACCTCGGGATCCAGAACCCG GAGATGTGTCTGTATTGTGAGAAGGTCGGCGAGCAACCTACCCTGCAGCTG AAGGAGCAGAAGATCATGGACCTGTACGGCCAGCCCGAGCCGGTGAAACCG TTCCTGTTCTACCGGGCCAAGACCGGCAGAACCAGCACCCTGGAAAGCGTG GCCTTTCCCGACTGGTTCATCGCGAGCAGTAAACGGGACCAACCCATCATC CTGACCAGCGAGCTGGGCAAGAGCTACAACACCGCGTTTGAGCTGAACATC AACGAC | SEQ ID NO: 108 |
| SE_IL-36_045 | Codon optimized hIGKV4-hIL-36g | ATGGTGCTACAGACCCAGGTGTTCATCAGCCTCCTACTTTGGATCAGCGGG GCGTACGGCAGCATGTGCAAACCCATCACAGGAACCATCAACGACCTTAAC CAGCAGGTCTGGACACTCCAGGGCCAGAACCTCGTGGCCGTGCCCAGGAGC GATTCCGTCACGCCCGTGACCGTGGCTGTGATCACCTGCAAGTACCCCGAG GCCCTGGAGCAGGGGCGAGGGGACCCCATCTACCTGGGCATCCAGAACCCC GAGATGTGCCTGTACTGCGAGAAGGTCGGTGAACAGCCCACCCTCCAACTC AAGGAGCAGAAGATTATGGACCTGTACGGCCAGCCAGAGCCCGTGAAGCCA TTTCTGTTCTATAGGGCCAAGACCGGCCGCACCTCCACCCTGGAGTCCGTG GCCTTCCCCGACTGGTTCATCGCCAGCAGCAAACGGGACCAGCCCATCATT CTGACCAGCGAACTGGGCAAGAGCTACAATACCGCCTTCGAGCTTAATATC AATGAC | SEQ ID NO: 109 |
| SE_IL-36_046 | Codon optimized hIGKV4-hIL-36g | ATGGTGCTCCAAACTCAGGTGTTCATCAGCCTCCTCCTCTGGATCAGCGGG GCGTACGGCAGCATGTGTAAGCCCATCACCGGCACCATCAACGACCTCAAC CAGCAAGTGTGGACCTTGCAGGGCCAGAATCTCGTGGCCGTGCCCAGGTCC GACAGCGTGACGCCCGTGACTGTGGCCGTCATCACCTGCAAATATCCGGAG GCGCTGGAGCAGGGCAGAGGCGATCCCATCTATCTCGGGATCCAGAACCCC GAGATGTGCCTGTATTGCGAGAAGGTCGGCGAGCAGCCCACCCTCCAGCTG AAGGAGCAGAAGATCATGGACCTGTATGGCCAGCCCGAGCCCGTGAAGCCC TTCCTGTTCTACCGGGCGAAGACCGGCCGCACCTCCACCCTGGAAAGCGTG GCCTTCCCCGATTGGTTCATCGCGTCCAGCAAGAGGGACCAGCCGATCATC | SEQ ID NO: 110 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | CTGACCTCAGAGCTGGGCAAGTCCTACAACACCGCCTTCGAGCTGAATATC AACGAC | |
| SE_IL-36_047 | Codon optimized hIGKV4-hIL-36g | ATGGTGCTCCAGACCCAGGTGTTCATAAGCCTCCTCCTCTGGATCAGCGGC GCCTACGGCTCTATGTGCAAGCCCATCACCGGGACCATCAACGACCTCAAC CAGCAGGTGTGGACCCTACAGGGCCAGAACCTCGTGGCCGTGCCCCGGAGC GACTCTGTGACTCCCGTCACCGTGGCCGTCATCACCTGCAAGTACCCCGAG GCCCTGGAGCAGGGCAGGGGCGACCCGATCTATCTGGGCATCCAGAATCCC GAGATGTGCCTCTACTGCGAGAAGGTGGGCGAACAGCCCACCCTCCAGCTG AAGGAGCAGAAGATAATGGATCTGTACGGTCAGCCCGAGCCCGTGAAGCCG TTCCTGTTCTACCGGGCCAAGACGGGAAGGACAAGCACCCTGGAGAGCGTG GCATTTCCCGACTGGTTCATCGCCAGCTCCAAGAGGGATCAGCCCATAATC CTGACCAGCGAGCTGGGCAAGAGCTACAACACCGCCTTCGAGCTGAATATC AACGAC | SEQ ID NO: 111 |
| SE_IL-36_048 | Codon optimized hIGKV4-hIL-36g | ATGGTGCTCCAGACCCAAGTCTTCATCAGCCTCCTCCTCTGGATCTCCGGC GCCTACGGGAGCATGTGCAAGCCCATCACGGGCACCATCAACGACCTCAAT CAGCAGGTCTGGACCCTCCAGGGTCAGAACCTCGTGGCCGTCCCCAGGTCC GACAGCGTGACCCCGGTGACCGTGGCCGTGATCACCTGCAAGTACCCCGAG GCGCTGGAGCAAGGCCGGGGCGACCCCATCTACCTGGGTATCCAGAACCCC GAGATGTGCCTGTACTGTGAGAAAGTGGGCGAGCAGCCCACACTGCAGCTG AAGGAGCAGAAGATCATGGATCTGTACGGTCAGCCCGAGCCCGTGAAACCC TTCCTGTTTTACAGGGCCAAGACCGGCAGGACCAGCACCCTGGAGAGCGTG GCCTTCCCGGACTGGTTCATCGCCAGCAGTAAGAGGGACCAACCCATAATA CTGACCAGCGAGCTCGGCAAGAGCTACAATACCGCCTTCGAGCTGAATATC AACGAC | SEQ ID NO: 112 |
| SE_IL-36_049 | Codon optimized hIGKV4-hIL-36g | ATGGTGTTGCAGACACAGGTGTTCATCAGCCTCCTCCTCTGGATCAGCGGC GCTTACGGCAGCATGTGCAAGCCCATCACCGGCACCATCAACGATCTCAAT CAGCAGGTGTGGACCCTCCAGGGCCAGAATCTCGTAGCCGTTCCCAGAAGC GACAGCGTGACGCCCGTCACGGTGGCTGTGATCACGTGCAAATACCCAGAG GCACTCGAGCAGGGCAGAGGCGATCCTATCTACCTGGGAATCCAGAACCCC GAGATGTGCCTGTACTGCGAGAAGGTCGGAGAGCAGCCTACCCTGCAACTG AAGGAGCAGAAGATAATGGACCTGTACGGACAGCCCGAGCCCGTGAAGCCA TTTCTGTTCTACAGAGCCAAGACCGGAAGAACAAGCACACTGGAAAGCGTG GCATTTCCTGACTGGTTCATTGCCAGCTCCAAGCGGGACCAGCCCATAATC CTCACCTCTGAGCTGGGCAAGAGCTACAACACCGCCTTCGAGCTGAACATC AACGAC | SEQ ID NO: 113 |
| SE_IL-36_050 | Codon optimized hIGKV4-hIL-36g | ATGGTGCTCCAGACACAGGTGTTCATCAGCCTCCTCCTCTGGATCAGTGGC GCGTACGGATCAATGTGCAAGCCCATCACAGGCACCATTAACGATCTCAAC CAGCAGGTGTGGACCCTCCAGGGCCAGAACCTCGTGGCCGTGCCCAGGTCC GACAGCGTGACTCCTGTCACAGTAGCCGTGATCACCTGCAAGTACCCCGAG GCACTTGAGCAGGGCCGGGGCGACCCCATCTACCTGGGGATCCAGAACCCT GAGATGTGTCTGTACTGCGAGAAAGTGGGCGAGCAGCCCACACTGCAGCTC AAGGAGCAGAAGATCATGGATCTGTATGGCCAGCCCGAGCCCGTGAAGCCT TTCCTGTTTTATCGCGCCAAGACAGGACGGACTTCAACCTTGGAATCCGTG GCTTTCCCCGACTGGTTCATCGCGTCTTCCAAGAGGGACCAGCCTATCATT CTTACCTCAGAGCTGGGCAAATCATATAACACAGCTTTCGAGCTGAACATC AATGAC | SEQ ID NO: 114 |
| mIL-2sp_mIL-36g_nopoly | Codon optimized murine mIL-2-mIL-36g | ATGTACAGCATGCAGCTCGCATCCTGTGTCACATTGACACTTGTGCTCCTT GTCAACAGCGGAAGAGAAACTCCTGACTTTGGGGAGGTTTTTGACTTGGAC CAGCAGGTGTGGATCTTTCGTAATCAGGCCCTTGTGACAGTTCCACGAAGC CACAGAGTAACCCCAGTCAGCGTGACTATCCTCCCATGCAAGTACCCAGAG TCTCTTGAACAGGACAAAGGGATTGCCATTTATTTGGGAATTCAGAATCCA GATAAATGCCTGTTTTGTAAGGAAGTTAATGGACACCCTACTTTGCTGCTA AAGGAAGAGAAGATTTTGGATTTGTACCACCACCCTGAGCCAATGAAGCCA TTCCTGTTTTACCACACCCGGACAGGTGGAACATCCACCTTTGAATCAGTG GCTTTCCCTGGCCACTATATTGCCTCCTCCAAGACTGGCAACCCCATCTTC CTCACATCAAAGAAGGGAGAATATTACAACATTAACTTCAATTTAGATATA AAGTCT | SEQ ID NO: 115 |
| IL-18 isoform 1 (Precursor) | Human IL 18 isoform 1 (Uniprot: Q14116) (Precursor) | MAAEPVEDNCINFVAMKFIDNTLYFIAEDDENLESDYFGKLESKLSVIRN LNDQVLFIDQGNRPLFEDMTDSDCRDNAPRTIFIISMYKDSQPRGMAVTI SVKCEKISTLSCENKIISFKEMNPPDNIKDTKSDIIFFQRSVPGHDNKMQ FESSSYEGYFLACEKERDLFKLILKKEDELGDRSIMFTVQNED | SEQ ID NO: 147 |
| IL-18 isoform 1 (Precursor) | Nucleotide sequence of IL-18 isoform 1 (Precursor) | ATGGCTGCTGAACCAGTAGAAGACAATTGCATCAACTTTGTGGCAATGAA ATTTATTGACAATACGCTTTACTTTATAGCTGAAGATGATGAAAACCTGG AATCAGATTACTTTGGCAAGCTTGAATCTAAATTATCAGTCATAAGAAAT TTGAATGACCAAGTTCTCTTCATTGACCAAGGAAATCGGCCTCTATTTGA AGATATGACTGATTCTGACTGTAGAGATAATGCACCCCGGACCATATTTA TTATAAGTATGTATAAAGATAGCCAGCCTAGAGGTATGGCTGTAACTATC | SEQ ID NO: 148 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| | | TCTGTGAAGTGTGAGAAAATTTCAACTCTCTCCTGTGAGAACAAAATTAT<br>TTCCTTTAAGGAAATGAATCCTCCTGATAACATCAAGGATACAAAAAGTG<br>ACATCATATTCTTTCAGAGAAGTGTCCCAGGACATGATAATAAGATGCAA<br>TTTGAATCTTCATCATACGAAGGATACTTTCTAGCTTGTGAAAAAGAGAG<br>AGACCTTTTTAAACTCATTTTGAAAAAAGAGGATGAATTGGGGGATAGAT<br>CTATAATGTTCACTGTTCAAAACGAAGAC | |
| IL-18 isoform 1 (Mature) | Amino acid sequence of IL-18 isoform 1 (Uniprot: Q14116 37-193) (Mature) | YFGKLESKLSVIRNLNDQVLFIDQGNRPLFEDMTDSDCRDNAPRTIFIIS<br>MYKDSQPRGMAVTISVKCEKISTLSCENKIISFKEMNPPDNIKDTKSDII<br>FFQRSVPGHDNKMQFESSSYEGYFLACEKERDLFKLILKKEDELGDRSIM<br>FTVQNED | SEQ ID NO: 149 |
| IL-18 isoform 1 (Mature) | Nucleotide sequence of IL-18 isoform 1 (Mature) | Subsequence of precursor sequence encoding IL-18 Isoform 1 which encodes the mature amino acid sequence above | SEQ ID NO: 150 |
| IL-18 isoform 2 (Precursor) | Amino acid sequence of isoform 2 (Uniprot: Q14116-2) Delta3pro- IL-18, 27-30 missing (Precursor) | MAAEPVEDNCINFVAMKFIDNTLYFIENLESDYFGKLESKLSVIRNLNDQ<br>VLFIDQGNRPLFEDMTDSDCRDNAPRTIFIISMYKDSQPRGMAVTISVKC<br>EKISTLSCENKIISFKEMNPPDNIKDTKSDIIFFQRSVPGHDNKMQFESS<br>SYEGYFLACEKERDLFKLILKKEDELGDRSIMFTVQNED | SEQ ID NO: 151 |
| IL-18 isoform 2 (Precursor) | Nucleotide sequence of isoform 2 (Precursor) | Subsequence of precursor sequence encoding IL-18 Isoform 1 which encodes the precursor amino acid sequence above | SEQ ID NO: 152 |
| IL-18 isoform 2 (Mature) | Amino acid sequence of IL-18 isoform 2 (Uniprot: Q14116 37-193) (Mature) | YFGKLESKLSVIRNLNDQVLFIDQGNRPLFEDMTDSDCRDNAPRTIFIIS<br>MYKDSQPRGMAVTISVKCEKISTLSCENKIISFKEMNPPDNIKDTKSDII<br>FFQRSVPGHDNKMQFESSSYEGYFLACEKERDLFKLILKKEDELGDRSIM<br>FTVQNED | SEQ ID NO: 153 |
| IL-18 isoform 2 (Mature) | Nucleotide sequence of IL-18 isoform 2 (Mature) | Subsequence of precursor sequence encoding IL-18 Isoform 1 which encodes the mature amino acid sequence above | SEQ ID NO: 154 |
| hIL-2sp-hIL- 18_miR122 | Codon optimized sequence | ATGTACAGGATGCAACTCCTGTCTTGCATTGCACTAAGTCTTGCACTTGTC<br>ACAAACAGTTACTTTGGCAAGCTTGAATCTAAATTATCAGTCATAAGAAAT<br>TTGAATGACCAAGTTCTCTTCATTGACCAAGGAAATCGGCCTCTATTTGAA<br>GATATGACTGATTCTGACTGTAGAGATAATGCACCCCGGACCATATTTATT<br>ATAAGTATGTATAAAGATAGCCAGCCTAGAGGTATGGCTGTAACTATCTCT<br>GTGAAGTGTGAGAAGATTTCAACTCTCTCCTGTGAGAACAAGATTATTTCC<br>TTTAAGGAAATGAATCCTCCTGATAACATCAAGGATACAAAGAGTGACATC<br>ATATTCTTTCAGAGAAGTGTCCCAGGACATGATAATAAGATGCAATTTGAA<br>TCTTCATCATACGAAGGATACTTTCTAGCTTGTGAGAAAGAGAGAGACCTG<br>TTTAAACTCATTTTGAAGAAAGAGGATGAATTGGGCGATAGATCTATAATG<br>TTCACTGTTCAGAACGAAGAC | SEQ ID NO: 155 |
| hIL1ra-hIL- 18_miR122 | Codon optimized sequence | ATGGAAATCTGCAGAGGCCTCCGCAGTCACCTAATCACTCTCCTCCTCTTC<br>CTGTTCCATTCAGAGACGATCTGCTACTTTGGCAAGCTTGAATCTAAATTA<br>TCAGTCATAAGAAATTTGAATGACCAAGTTCTCTTCATTGACCAAGGAAAT<br>CGGCCTCTATTTGAAGATATGACTGATTCTGACTGTAGAGATAATGCACCC<br>CGGACCATATTTATTATAAGTATGTATAAAGATAGCCAGCCTAGAGGTATG<br>GCTGTAACTATCTCTGTGAAGTGTGAGAAGATTTCAACTCTCTCCTGTGAG<br>AACAAGATTATTTCCTTTAAGGAAATGAATCCTCCTGATAACATCAAGGAT<br>ACAAAGAGTGACATCATATTCTTTCAGAGAAGTGTCCCAGGACATGATAAT<br>AAGATGCAATTTGAATCTTCATCATACGAAGGATACTTTCTAGCTTGTGAG<br>AAAGAGAGAGACCTGTTTAAACTCATTTTGAAGAAAGAGGATGAATTGGGC<br>GATAGATCTATAATGTTCACTGTTCAGAACGAAGAC | SEQ ID NO: 156 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| hIL1ra-hIL8_miR122 | Codon optimized sequence | ATGGAAATCTGCAGAGGCCTCCGCAGTCACCTAATCACTCTCCTCCTCTTC CTGTTCCATTCAGAGACGATCTGCTACTTTGGCAAGCTTGAATCTAAATTA TCAGTCATAAGAAATTTGAATGACCAAGTTCTCTTCATTGACCAAGGAAAT CGGCCTCTATTTGAAGATATGACTGATTCTGACTGTAGAGATAATGCACCC CGGACCATATTTATTATAAGTATGTATAAAGATAGCCAGCCTAGAGGTATG GCTGTAACTATCTCTGTGAAGTGTGAGAAAATTTCAACTCTCTCCTGTGAG AACAAAATTATTTCCTTTAAGGAAATGAATCCTCCTGATAACATCAAGGAT ACAAAGAGTGACATCATATTCTTTCAGAGAAGTGTCCCAGGACATGATAAT AAGATGCAATTTGAATCTTCATCATACGAAGGATACTTTCTAGCTTGTGAG AAAGAGAGAGACCTTTTTAAACTCATTTTGAAGAAAGAGGATGAATTGGGG GATAGATCTATAATGTTCACTGTTCAAAACGAAGAC | SEQ ID NO: 157 |
| hIGLV3-21-hIL-18 | Codon optimized sequence | ATGGCCTGGACCGTTCTCCTCCTCGGCCTCCTCTCTCACTGCACAGGCTCT GTGACCTCCTACTTTGGCAAGCTTGAATCTAAATTATCAGTCATAAGAAAT TTGAATGACCAAGTTCTCTTCATTGACCAAGGAAATCGGCCTCTATTTGAA GATATGACTGATTCTGACTGTAGAGATAATGCACCCCGGACCATATTTATT ATAAGTATGTATAAAGATAGCCAGCCTAGAGGTATGGCTGTAACTATCTCT GTGAAGTGTGAGAAAATTTCAACTCTCTCCTGTGAGAACAAAATTATTTCC TTTAAGGAAATGAATCCTCCTGATAACATCAAGGATACAAAGAGTGACATC ATATTCTTTCAGAGAAGTGTCCCAGGACATGATAATAAGATGCAATTTGAA TCTTCATCATACGAAGGATACTTTCTAGCTTGTGAGAAAGAGAGAGACCTT TTTAAACTCATTTTGAAGAAAGAGGATGAATTGGGGGATAGATCTATAATG TTCACTGTTCAAAACGAAGAC | SEQ ID NO: 158 |
| hIL-2-hIL-18_mod_miR122 | Codon optimized sequence | ATGTACAGGATGCAACTCCTGTCTTGCATTGCACTAAGTCTTGCACTTGTC ACAAACAGTTACTTTGGCAAGCTTGAATCTAAATTATCAGTCATAAGAAAT TTGAATGACCAAGTTCTCTTCATTGACCAAGGAAATCGGCCTCTATTTGAA GATATGACTGATTCTGACTGTAGAGATAATGCACCCCGGACCATATTTATT ATAAGTATGTATAAAGATAGCCAGCCTAGAGGTATGGCTGTAACTATCTCT GTGAAGTGTGAGAAAATTTCAACTCTCTCCTGTGAGAACAAAATTATTTCC TTTAAGGAAATGAATCCTCCTGATAACATCAAGGATACAAAGAGTGACATC ATATTCTTTCAGAGAAGTGTCCCAGGACATGATAATAAGATGCAATTTGAA TCTTCATCATACGAAGGATACTTTCTAGCTTGTGAGAAAGAGAGAGACCTT TTTAAACTCATTTTGAAGAAAGAGGATGAATTGGGGGATAGATCTATAATG TTCACTGTTCAAAACGAAGAC | SEQ ID NO: 159 |
| hIL-2sp-hIL-18 | Codon optimized sequence | ATGTACAGGATGCAACTCCTGTCTTGCATTGCACTAAGTCTTGCACTTGTC ACAAACAGTTACTTTGGCAAGCTTGAATCTAAATTATCAGTCATAAGAAAT TTGAATGACCAAGTTCTCTTCATTGACCAAGGAAATCGGCCTCTATTTGAA GATATGACTGATTCTGACTGTAGAGATAATGCACCCCGGACCATATTTATT ATAAGTATGTATAAAGATAGCCAGCCTAGAGGTATGGCTGTAACTATCTCT GTGAAGTGTGAGAAAATTTCAACTCTCTCCTGTGAGAACAAAATTATTTCC TTTAAGGAAATGAATCCTCCTGATAACATCAAGGATACAAAAAGTGACATC ATATTCTTTCAGAGAAGTGTCCCAGGACATGATAATAAGATGCAATTTGAA TCTTCATCATACGAAGGATACTTTCTAGCTTGTGAAAAAGAGAGAGACCTT TTTAAACTCATTTTGAAAAAAGAGGATGAATTGGGGGATAGATCTATAATG TTCACTGTTCAAAACGAAGAC | SEQ ID NO: 160 |
| Hs IL-18 WT | human IL-18 nucleotide sequence | ATGGCTGCTGAACCAGTAGAAGACAATTGCATCAACTTTGTGGCAATGAAA TTTATTGACAATACGCTTTACTTTATAGCTGAAGATGATGAAAACCTGGAA TCAGATTACTTTGGCAAGCTTGAATCTAAATTATCAGTCATAAGAAATTTG AATGACCAAGTTCTCTTCATTGACCAAGGAAATCGGCCTCTATTTGAAGAT ATGACTGATTCTGACTGTAGAGATAATGCACCCCGGACCATATTTATTATA AGTATGTATAAAGATAGCCAGCCTAGAGGTATGGCTGTAACTATCTCTGTG AAGTGTGAGAAAATTTCAACTCTCTCCTGTGAGAACAAAATTATTTCCTTT AAGGAAATGAATCCTCCTGATAACATCAAGGATACAAAAAGTGACATCATA TTCTTTCAGAGAAGTGTCCCAGGACATGATAATAAGATGCAATTTGAATCT TCATCATACGAAGGATACTTTCTAGCTTGTGAAAAAGAGAGAGACCTTTTT AAACTCATTTTGAAAAAAGAGGATGAATTGGGGGATAGATCTATAATGTTC ACTGTTCAAAACGAAGAC | SEQ ID NO: 161 |
| mIL-2sp-mIL-18 + miR122 | Codon optimized murine IL-18 | ATGTACAGCATGCAGCTCGCATCCTGTGTCACATTGACACTTGTGCTCCTT GTCAACAGCAACTTTGGCCGACTTCACTGTACAACCGCAGTAATACGGAAT ATAAATGACCAAGTTCTCTTCGTTGACAAAAGACAGCCTGTGTTCGAGGAT ATGACTGATATTGATCAAAGTGCCAGTGAACCCCAGACCAGACTGATAATA TACATGTACAAAGACAGTGAAGTAAGAGGACTGGCTGTGACCCTCTCTGTG AAGGATAGTAAAATGTCTACCCTCTCCTGTAAGAACAAGATCATTTCCTTT GAGGAAATGGATCCACCTGAAAATATTGATGATATACAAAGTGATCTCATA TTCTTTCAGAAACGTGTTCCAGGACACAACAAGATGGAGTTTGAATCTTCA CTGTATGAAGGACACTTTCTTGCTTGCCAAAAGGAAGATGATGCTTTCAAA CTCATTCTGAAAAAAAAGGATGAAAATGGGGATAAATCTGTAATGTTCACT CTCACTAACTTACATCAAAGT | SEQ ID NO: 162 |

TABLE 1-continued

IL-23, IL-36-gamma and IL-18 Polypeptide and Polynucleotide Sequences

| Encoded Polypeptide | Description | Sequence | SEQ ID NO: |
|---|---|---|---|
| hIL12AB_002 | mRNA ORF for human IL-12 | AUGUGCCACCAGCAGCUGGUGAUCAGCUGGUUCAGCCUGGUGUUCCUGGCCAGCCCC<br>CUGGUGGCCAUCUGGGAGCUGAAGAAGGACGUGUACGUGGUGGAGUUGGAUUGGUAC<br>CCCGACGCCCCCGGCGAGAUGGUGGUGCUGACCUGCGACACCCCCGAGGAGGACGGC<br>AUCACCUGGACCCUGGACCAGAGCAGCGAGGUGCUGGGCAGCGGCAAGACCCUGACC<br>AUCCAGGUGAAGGAGUUCGGCGACGCCGGCCAGUACACCUGCCACAAGGGCGGCGAG<br>GUGCUGAGCCACAGCCUGCUGCUGCUGCACAAGAAGGAGGACGGCAUCUGGAGCACC<br>GACAUCCUGAAGGACCAGAAGGAGCCCAAGAACAAGACCUUCCUGAGAUGCGAGGCC<br>AAGAACUACAGCGGCAGAUUCACCUGCUGGUGGCUGACCACCAUCAGCACCGACCUG<br>ACCUUCAGCGUGAAGAGCAGCAGAGGCAGCAGCGACCCCCAGGGCGUGACCUGCGGC<br>GCCGCCACCCUGAGCGCCGAGAGAGUGAGAGGCGACAACAAGGAGUACGAGUACAGC<br>GUGGAGUGCCAGGAAGAUAGCGCCUGCCCCGCCGCCGAGGAGAGCCUGCCCAUCGAG<br>GUGAUGGUGGACGCCGUGCACAAGCUGAAGUACGAGAACUACACCAGCAGCUUCUUC<br>AUCAGAGAUAUCAUCAAGCCCGACCCCCCCAAGAACCUGCAGCUGAAGCCCCUGAAG<br>AACAGCCGGCAGGUGGAGGUGAGCUGGGAGUACCCCGACACCUGGAGCACCCCCCAC<br>AGCUACUUCAGCCUGACCUUCUGCGUGCAGGUGCAGGGCAAGAGCAAGAGAGAGAAG<br>AAAGAUAGAGUGUUCACCGACAAGACCAGCGCCACCGUGAUCUGCAGAAAGAACGCC<br>AGCAUCAGCGUGAGAGCCCAAGAUAGAUACUACAGCAGCAGCUGGAGCGAGUGGGCC<br>AGCGUGCCCUGCAGCGGCGGCGGCGGCGGCGGCAGCAGAAACCUGCCCGUGGCCACC<br>CCCGACCCCGGCAUGUUCCCCUGCCUGCACCACAGCCAGAACCUGCUGAGAGCCGUG<br>AGCAACAUGCUGCAGAAGGCCCGGCAGACCCUGGAGUUCUACCCCUGCACCAGCGAG<br>GAGAUCGACCACGAAGAUAUCACCAAAGAUAAGACCAGCACCGUGGAGGCCUGCCUG<br>CCCCUGGAGCUGACCAAGAACGAGAGCUGCCUGAACAGCAGAGAGACCAGCUUCAUC<br>ACCAACGGCAGCUGCCUGGCCAGCAGAAAGACCAGCUUCAUGAUGGCCCUGUGCCUG<br>AGCAGCAUCUACGAGGACCUGAAGAUGUACCAGGUGGAGUUCAAGACCAUGAACGCC<br>AAGCUGCUGAUGGACCCCAAGCGGCAGAUCUUCCUGGACCAGAACAUGCUGGCCGUG<br>AUCGACGAGCUGAUGCAGGCCCUGAACUUCAACAGCGAGACCGUGCCCCAGAAGAGC<br>AGCCUGGAGGAGCCCGACUUCUACAAGACCAAGAUCAAGCUGUGCAUCCUGCUGCAC<br>GCCUUCAGAAUCAGAGCCGUGACCAUCGACAGAGUGAUGAGCUACCUGAACGCCAGC | SEQ ID NO: 183 |
| IL12B | Wildtype IL12B without signal amino acids | IWELKKDVYVVELDWYPDAPGEMVVLTCDTPEEDGITWTLDQSSEVLGSGKTLTIQV<br>KEFGDAGQYTCHKGGEVLSHSLLLLHKKEDGIWSTDILKDQKEPKNKTFLRCEAKNY<br>SGRFTCWWLTTISTDLTFSVKSSRGSSDPQGVTCGAATLSAERVRGDNKEYEYSVEC<br>QEDSACPAAEESLPIEVMVDAVHKLKYENYTSSFFIRDIIKPDPPKNLQLKPLKNSR<br>QVEVSWEYPDTWSTPHSYFSLTFCVQVQGKSKREKKDRVFTDKTSATVICRKNASIS<br>VRAQDRYYSSS<br>WSEWASVPCS | SEQ ID NO: 184 |
| IL12B | Wildtype IL12B without signal nucleic acids | ATATGGGAACTGAAGAAAGATGTTTATGTCGTAGAATTGGATTGGTATCCGGATGCC<br>CCTGGAGAAATGGTGGTCCTCACCTGTGACACCCCTGAAGAAGATGGTATCACCTGG<br>ACCTTGGACCAGAGCAGTGAGGTCTTAGGCTCTGGCAAAACCCTGACCATCCAAGTC<br>AAAGAGTTTGGAGATGCTGGCCAGTACACCTGTCACAAAGGAGGCGAGGTTCTAAGC<br>CATTCGCTCCTGCTGCTTCACAAAAAGGAAGATGGAATTTGGTCCACTGATATTTTA<br>AAGGACCAGAAAGAACCCAAAAATAAGACCTTTCTAAGATGCGAGGCCAAGAATTAT<br>TCTGGACGTTTCACCTGCTGGTGGCTGACGACAATCAGTACTGATTTGACATTCAGT<br>GTCAAAAGCAGCAGAGGCTCTTCTGACCCCCAAGGGGTGACGTGCGGAGCTGCTACA<br>CTCTCTGCAGAGAGAGTCAGAGGGGACAACAAGGAGTATGAGTACTCAGTGGAGTGC<br>CAGGAGGACAGTGCCTGCCCAGCTGCTGAGGAGAGTCTGCCCATTGAGGTCATGGTG<br>GATGCCGTTCACAAGCTCAAGTATGAAAACTACACCAGCAGCTTCTTCATCAGGGAC<br>ATCATCAAACCTGACCCACCCAAGAACTTGCAGCTGAAGCCATTAAAGAATTCTCGG<br>CAGGTGGAGGTCAGCTGGGAGTACCCTGACACCTGGAGTACTCCACATTCCTACTT<br>CTCCCTGACATTCTGCGTTCAGGTCCAGGGCAAGAGCAAGAGAGAAAAGAAAGATAG<br>AGTCTTCACGGACAAGACCTCAGCCACGGTCATCTGCCGCAAAAATGCCAGCATTAG<br>CGTGCGGGCCCAGGACCGCTACTATAGCTCATCTTGGAGCGAATGGGCATCTGTGCC<br>CTGCAGT | SEQ ID NO: 185 |
| IL12A | Wildtype IL12A without signal amino acids | RNLPVATPDPGMFPCLHHSQNLLRAVSNMLQKARQTLEFYPCTSEEIDHEDITKDKT<br>STVEACLPLELTKNESCLNSRETSFITNGSCLASRKTSFMMALCLSSIYEDLKMYQV<br>EFKTMNAKLLMDPKRQIFLDQNMLAVIDELMQALNFNSETVPQKSSLEEPDFYKTKI<br>KLCILLHAFRIRAVTIDRVMSYLNAS | SEQ ID NO: 186 |
| IL12A | Wildtype IL12A without signal nucleic acids | AGAAACCTCCCCGTGGCCACTCCAGACCCAGGAATGTTCCCATGCCTTCACCACTCC<br>CAAAACCTGCTGAGGGCCGTCAGCAACATGCTCCAGAAGGCCAGACAAACTCTAGAA<br>TTTTACCCTTGCACTTCTGAAGAGATTGATCATGAAGATATCACAAAAGATAAAACC<br>AGCACAGTGGAGGCCTGTTTACCATTGGAATTAACCAAGAATGAGAGTTGCCTAAAT<br>TCCAGAGAGACCTCTTTCATAACTAATGGGAGTTGCCTGGCCTCCAGAAAGACCTCT<br>TTTATGATGGCCCTGTGCCTTAGTAGTATTTATGAAGACTTGAAGATGTACCAGGTG<br>GAGTTCAAGACCATGAATGCAAAGCTTCTGATGGATCCTAAGAGGCAGATCTTTCTA<br>GATCAAAACATGCTGGCAGTTATTGATGAGCTGATGCAGGCCCTGAATTTCAACAGT<br>GAGACTGTGCCACAAAAATCCTCCCTTGAAGAACCGGATTTTTATAAAACTAAAATC<br>AAGCTCTGCATACTTCTTCATGCTTTCAGAATTCGGGCAGTGACTATTGATAGAGTG<br>ATGAGCTATCTGAATGCTTCC | SEQ ID NO: 187 |

TABLE 1-continued

| IL-23, IL-36-gamma and IL-18 Polypeptide and Polynucleotide Sequences | | | |
|---|---|---|---|
| Encoded Polypeptide | Description | Sequence | SEQ ID NO: |
| IL12B | Wildtype IL12B signal peptide amino acids | MCHQQLVISWFSLVFLASPLVA | SEQ ID NO: 188 |
| IL12B | Wildtype IL12B signal peptide nucleoic acids | ATGTGTCACCAGCAGTTGGTCATCTCTTGGTTTTCCCTGGTTTTTCTGGCATCTCCC<br>CTCGTGGCC | SEQ ID NO: 189 |

TABLE 1A

| OX40L Polypeptide and Polynucleotide sequences | | | |
|---|---|---|---|
| Encoded Polypeptide | Description | Sequence | SEQ ID NO: |
| OX40L (TNFSF4) | Tumor necrosis factor ligand superfamily member 4 isoform 1 [Homo sapiens] NP_003317 | MERVQPLEENVGNAARPRFERNKLLLVASVIQGLGLLLCFTYICLHFSA<br>LQVSHRYPRIQSIKVQFTEYKKEKGFILTSQKEDEIMKVQNNSVIINCD<br>GFYLISLKGYFSQEVNISLHYQKDEEPLFQLKKVRSVNSLMVASLTYKD<br>KVYLNVTTDNTSLDDFHVNGGELILIHQNPGEFCVL | SEQ ID NO: 21 183 aa |
| OX40L (TNFSF4) | TNFSF4 isoform 2 [Homo sapiens] NP_001284491 | MVSHRYPRIQSIKVQFTEYKKEKGFILTSQKEDEIMKVQNNSVIINCDG<br>FYLISLKGYFSQEVNISLHYQKDEEPLFQLKKVRSVNSLMVASLTYKDK<br>VYLNVTTDNTSLDDFHVNGGELILIHQNPGEFCVL | SEQ ID NO: 2 133 aa |
| OX40L (TNFSF4) | TNFSF4 [Mus musculus] NP_033478 | MEGEGVQPLDENLENGSRPRFKWKKTLRLVVSGIKGAGMLLCFIYVCLQ<br>LSSSPAKDPPIQRLRGAVTRCEDGQLFISSYKNEYQTMEVQNNSVVIKC<br>DGLYIIYLKGSFFQEVKIDLHFREDHNPISIPMLNDGRRIVFTVVASLA<br>FKDKVYLTVNAPDTLCEHLQINDGELIVVQLTPGYCAPEGSYHSTVNQV<br>PL | SEQ ID NO: 65 198 aa |
| Human OX40L | Human OX40L mRNA (ORF) | AUGGAAAGGGUCCAACCCCUGGAAGAGAAUGUGGGAAAUGCAGCCAGGC<br>CAAGAUUCGAGAGGAACAAGCUAUUGCUGGUGGCCUCUGUAAUUCAGGG<br>ACUGGGGCUGCUCCUGUGCUUCACCUACAUCUGCCUGCACUUCUCUGCU<br>CUUCAGGUAUCACAUCGGUAUCCUCGAAUUCAAAGUAUCAAAGUACAAU<br>UUACCGAAUAUAAGAAGGAGAAAGGUUUCAUCCUCACUUCCCAAAAGGA<br>GGAUGAAAUCAUGAAGGUGCAGAACAACUCAGUCAUCAUCAACUGUGAU<br>GGGUUUUAUCUCAUCUCCCUGAAGGGCUACUUCUCCCAGGAAGUCAACA<br>UUAGCCUUCAUUACCAGAAGGAUGAGGAGCCCCUCUUCCAACUGAAGAA<br>GGUCAGGUCUGUCAACUCCUUGAUGGUGGCCUCUCUGACUUACAAAGAC<br>AAAGUCUACUUGAAUGUGACCACUGACAAUACCUCCCUGGAUGACUUCC<br>AUGUGAAUGGCGGAGAACUGAUUCUUAUCCAUCAAAAUCCUGGUGAAUU<br>CUGUGUCCUU | 145 |
| Human OX40L | Full-length mRNA Nucleotide sequence (5' UTR, ORF, 3' UTR, miR-122-5p (underlined) polyA tail) of human OX40L | 5' $^{7Me}G_{ppp}G_{2'OMe}$GGAAAUAAGAGAGAAAAGAAGAGUAAGAAGAAAUAUAA<br>GAGCCACCAUGGAAAGGGUCCAACCCCUGGAAGAGAAUGUGGGAAAUGC<br>AGCCAGGCCAAGAUUCGAGAGGAACAAGCUAUUGCUGGUGGCCUCUGUA<br>AUUCAGGGACUGGGGCUGCUCCUGUGCUUCACCUACAUCUGCCUGCACU<br>UCUCUGCUCUUCAGGUAUCACAUCGGUAUCCUCGAAUUCAAAGUAUCAA<br>AGUACAAUUUACCGAAUAUAAGAAGGAGAAAGGUUUCAUCCUCACUUCC<br>CAAAAGGAGGAUGAAAUCAUGAAGGUGCAGAACAACUCAGUCAUCAUCA<br>ACUGUGAUGGGUUUUAUCUCAUCUCCCUGAAGGGCUACUUCUCCCAGGA<br>AGUCAACAUUAGCCUUCAUUACCAGAAGGAUGAGGAGCCCCUCUUCCAA<br>CUGAAGAAGGUCAGGUCUGUCAACUCCUUGAUGGUGGCCUCUCUGACUU<br>ACAAAGACAAAGUCUACUUGAAUGUGACCACUGACAAUACCUCCCUGGA<br>UGACUUCCAUGUGAAUGGCGGAGAACUGAUUCUUAUCCAUCAAAAUCCU<br>GGUGAAUUCUGUGUCCUUUGAUAAUAGGCUGGAGCCUCGGUGGCCAUGC<br>UUCUUGCCCCUUGGGCCUCCCCCCAGCCCCUCCUCCCCUUCCUGCACCC<br>GUACCCCCCAAACACCAUUGUCACACUCCAGUGGUCUUUGAAUAAAGUC | 146 |

TABLE 1A-continued

OX40L Polypeptide and Polynucleotide sequences

| Encoded Polypeptide | Description | Sequence | SEQ ID NO: |
|---|---|---|---|
| | | UGAGUGGGCGGCAAAAAAAAAAAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAUCUAG$_{OH}$3'<br>Where: A, C G & U = AMP, CMP, GMP & N1-ΨUMP, respectively; Me = methyl; p = inorganic phosphate | |
| OX40L (TNFSF4) | TNFSF4, ORF [Homo sapiens] | AUGGAAAGGGUCCAACCCCUGGAAGAGAAUGUG<br>GGAAAUGCAGCCAGGCCAAGAUUCGAGAGGAAC<br>AAGCUAUUGCUGGUGGCCUCUGUAAUUCAGGGA<br>CUGGGGCUGCUCCUGUGCUUCACCUACAUCUGC<br>CUGCACUUCUCUGCUCUUCAGGUAUCACAUCGG<br>UAUCCUCGAAUUCAAAGUAUCAAAGUACAAUUU<br>ACCGAAUAUAAGAAGGAGAAAGGUUUCAUCCUC<br>ACUUCCCAAAAGGAGGAUGAAAUCAUGAAGGUG<br>CAGAACAACUCAGUCAUCAUCAACUGUGAUGGG<br>UUUUAUCUCAUCUCCCUGAAGGGCUACUUCUCC<br>CAGGAAGUCAACAUUAGCCUUCAUUACCAGAAG<br>GAUGAGGAGCCCCUCUUCCAACUGAAGAAGGUC<br>AGGUCUGUCAACUCCUUGAUGGUGGCCUCUCUG<br>ACUUACAAAGACAAAGUCUACUUGAAUGUGACC<br>ACUGACAAUACCUCCCUGGAUGACUUCCAUGUG<br>AAUGGCGGAGAACUGAUUCUUAUCCAUCAAAAU<br>CCUGGUGAAUUCUGUGUCCUU | SEQ ID NO: 66 552nts |
| OX40L (TNFSF4) | TNFSF4, transcript variant 1, mRNA NM_003326 | GGCCCUGGGACCUUUGCCUAUUUUCUGAUUGAU<br>AGGCUUUGUUUUGUCUUUACCUCCUUCUUUCUG<br>GGGAAAACUUCAGUUUUAUCGCACGUUCCCCUU<br>UUCCAUAUCUUCAUCUUCCCUCUACCCAGAUUG<br>UGAAGAUGGAAAGGGUCCAACCCCUGGAAGAGA<br>AUGUGGGAAAUGCAGCCAGGCCAAGAUUCGAGA<br>GGAACAAGCUAUUGCUGGUGGCCUCUGUAAUUC<br>AGGGACUGGGGCUGCUCCUGUGCUUCACCUACA<br>UCUGCCUGCACUUCUCUGCUCUUCAGGUAUCAC<br>AUCGGUAUCCUCGAAUUCAAAGUAUCAAAGUAC<br>AAUUUACCGAAUAUAAGAAGGAGAAAGGUUUCA<br>UCCUCACUUCCCAAAAGGAGGAUGAAAUCAUGA<br>AGGUGCAGAACAACUCAGUCAUCAUCAACUGUG<br>AUGGGUUUUAUCUCAUCUCCCUGAAGGGCUACU<br>UCUCCCAGGAAGUCAACAUUAGCCUUCAUUACC<br>AGAAGGAUGAGGAGCCCCUCUUCCAACUGAAG<br>AAGGUCAGGUCUGUCAACUCCUUGAUGGUGGC<br>CUCUCUGACUUACAAAGACAAAGUCUACUUGA<br>AUGUGACCACUGACAAUACCUCCCUGGAUGAC<br>UUCCAUGUGAAUGGCGGAGAACUGAUUCUUAU<br>CCAUCAAAAUCCUGGUGAAUUCUGUGUCCUUU<br>GAGGGGCUGAUGGCAAUAUCUAAAACCAGGCA<br>CCAGCAUGAACACCAAGCUGGGGGUGGACAGG<br>GCAUGGAUUCUUCAUUGCAAGUGAAGGAGCCU<br>CCCAGCUCAGCCACGUGGGAUGUGACAAGAAG<br>CAGAUCCUGGCCCUCCCGCCCCCACCCCUCAG<br>GGAUAUUUAAAACUUAUUUUAUAUACCAGUUA<br>AUCUUAUUUAUCCUUAUAUUUUCUAAAUUGCC<br>UAGCCGUCACACCCCAAGAUUGCCUUGAGCCU<br>ACUAGGCACCUUUGUGAGAAAGAAAAAAUAGA<br>UGCCUCUUCUUCAAGAUGCAUUGUUUCUAUUG<br>GUCAGGCAAUUGUCAUAAUAAACUUAUGUCAU<br>UGAAAACGGUACCUGACUACCAUUUGCUGGAA<br>AUUUGACAUGUGUGUGGCAUUAUCAAAAUGAA<br>GAGGAGCAAGGAGUGAAGGAGUGGGGUUAUGA<br>AUCUGCCAAAGGUGGUAUGAACCAACCCCUGG<br>AAGCCAAAGCGGCCUCUCCAAGGUUAAAUUGA<br>UUGCAGUUUGCAUAUUGCCUAAAUUUAAACUU<br>UCUCAUUUGGUGGGGGUUCAAAAGAAGAAUCA<br>GCUUGUGAAAAAUCAGGACUUGAAGAGAGCCG<br>UCUAAGAAAUACCACGUGCUUUUUUUCUUUAC<br>CAUUUUGCUUUCCCAGCCUCCAAACAUAGUUA<br>AUAGAAAUUUCCCUUCAAAGAACUGUCUGGGG<br>AUGUGAUGCUUUGAAAAAUCUAAUCAGUGACU<br>UAAGAGAGAUUUUCUUGUAUACAGGGAGAGUG<br>AGAUAACUUAUUGUGAAGGGUUAGCUUUACUG<br>UACAGGAUAGCAGGGAACUGGACAUCUCAGGG<br>UAAAAGUCAGUACGGAUUUUAAUAGCCUGGGG<br>AGGAAAACACAUUCUUUGCCACAGACAGGCAA<br>AGCAACACAUGCUCAUCCUCCUGCCUAUGCUG<br>AGAUACGCACUCAGCUCCAUGUCUUGUACACA | SEQ ID NO: 67 3484 nts |

TABLE 1A-continued

| OX40L Polypeptide and Polynucleotide sequences | | | |
|---|---|---|---|
| Encoded Polypeptide | Description | Sequence | SEQ ID NO: |
| | | CAGAAACAUUGCUGGUUUCAAGAAAUGAGGUG AUCCUAUUAUCAAAUUCAAUCUGAUGUCAAAU AGCACUAAGAAGUUAUUGUGCCUUAUGAAAAA UAAUGAUCUCUGUCUAGAAAUACCAUAGACCA UAUAUAGUCUCACAUUGAUAAUUGAAACUAGA AGGGUCUAUAAUCAGCCUAUGCCAGGGCUUCA AUGGAAUAGUAUCCCCUUAUGUUUAGUUGAAA UGUCCCCUUAACUUGAUAUAAUGUGUUAUGCU UAUGGCGCUGUGGACAAUCUGAUUUUUCAUGU CAACUUUCCAGAUGAUUUGUAACUUCUCUGUG CCAAACCUUUUAUAAACAUAAAUUUUUGAGAU AUGUAUUUUAAAAUUGUAGCACAUGUUUCCCU GACAUUUUCAAUAGAGGAUACAACAUCACAGA AUCUUUCUGGAUGAUUCUGUGUUAUCAAGGAA UUGUACUGUGCUACAAUUAUCUCUAGAAUCUC CAGAAAGGUGGAGGGCUGUUCGCCCUUACACU AAAUGGUCUCAGUUGGAUUUUUUUUCCUGUU UUCUAUUUCCUCUUAAGUACACCUUCAACUAU AUUCCCAUCCCUCUAUUUUAAUCUGUUAUGAA GGAAGGUAAAUAAAAAUGCUAAAUAGAAGAAA UUGUAGGUAAGGUAAGAGGAAUCAAGUUCUGA GUGGCUGCCAAGGCACUCACAGAAUCAUAAUC AUGGCUAAAUAUUUAUGGAGGGCCUACUGUGG ACCAGGCACUGGGCUAAAUACUUACAUUUACA AGAAUCAUUCUGAGACAGAUAUUCAAUGAUAU CUGGCUUCACUACUCAGAAGAUUGUGUGUGUG UUUGUGUGUGUGUGUGUGUGUGUAUUUCACUU UUUGUUAUUGACCAUGUUCUGCAAAAUUGCAG UUACUCAGUGAGUGAUAUCCGAAAAAGUAAAC GUUUAUGACUAUAGGUAAUAUUUAAGAAAAUG CAUGGUUCAUUUUUAAGUUUGGAAUUUUUAUC UAUAUUUCUCACAGAUGUGCAGUGCACAUGCA GGCCUAAGUAUAUGUUGUGUGUGUUGUUUGUC UUUGAUGUCAUGGUCCCCUCUCUUAGGUGCUC ACUCGCUUUGGGUGCACCUGGCCUGCUCUUCC CAUGUUGGCCUCUGCAACCACACAGGGAUAUU UCUGCUAUGCACCAGCCUCACUCCACCUUCCU UCCAUCAAAAAUAUGUGUGUGUGUCUCAGUCC CUGUAAGUCAUGUCCUUCACAGGGAGAAUUAA CCCUUCGAUAUACAUGGCAGAGUUUUGUGGGA AAAGAAUUGAAUGAAAAGUCAGGAGAUCAGAA UUUUAAAUUUGACUUAGCCACUAACUAGCCAU GUAACCUUGGGAAAGUCAUUUCCCAUUUCUGG GUCUUGCUUUUCUUUCUGUUAAAUGAGAGGAA UGUUAAAUAUCUAACAGUUUAGAAUCUUAUGC UUACAGUGUUAUCUGUGAAUGCACAUAUUAAA UGUCUAUGUUCUUGUUGCUAUGAGUCAAGGAG UGUAACCUUCUCCUUUACUAUGUUGAAUGUAU UUUUUUCUGGACAAGCUUACAUCUUCCCUCAGC CAUCUUUGUGAGUCCUUCAAGAGCAGUUAUCA AUUGUUAGUUAGAUAUUUUCUAUUUAGAGAAU GCUUAAGGGAUUCCAAUCCCGAUCCAAAUCAU AAUUUGUUCUUAAGUAUACUGGGCAGGUCCCC UAUUUUAAGUCAUAAUUUUGUAUUUAGUGCUU UCCUGGCUCUCAGAGAGUAUUAAUAUUGAUAU UAAUAAUAUAGUUAAUAGUAAUAUUGCUAUUU ACAUGGAAACAAAUAAAAGAUCUCAGAAUUCA CUAAAAAAAAAAA | |
| OX40L (TNFSF4) | Mus musculus Tnfsf4, mRNA NM_009452 | AUUGCUUUUUGUCUCCUGUUCUGGGACCUUUA UCUUCUGACCCGCAGGCUUGACUUUGCCCUUA UUGGCUCCUUUGUGGUGAAGAGCAGUCUUCCC CCAGGUUCCCCGCCACAGCUGUAUCUCCUCUG CACCCCGACUGCAGAGAUGGAAGGGGAAGGGG UUCAACCCCUGGAUGAGAAUCUGGAAAACGGA UCAAGGCCAAGAUUCAAGUGGAAGAAGACGCU AAGGCUGGUGGUCUCUGGGAUCAAGGGAGCAG GGAUGCUUCUGUGCUUCAUCUAUGUCUGCCUG CAACUCUCUUCCUCUCCGGCAAAGGACCCUCC AAUCCAAAGACUCAGAGGAGCAGUUACCAGAU GUGAGGAUGGGCAACUAUUCAUCAGCUCAUAC AAGAAUGAGUAUCAAACUAUGGAGGUGCAGAA CAAUUCGGUUGUCAUCAAGUGCGAUGGGCUUU AUAUCAUCUACCUGAAGGGCUCCUUUUUCCAG GAGGUCAAGAUUGACCUUCAUUUCCGGGAGGA | SEQ ID NO: 68 1609 nts |

TABLE 1A-continued

OX40L Polypeptide and Polynucleotide sequences

| Encoded Polypeptide | Description | Sequence | SEQ ID NO: |
|---|---|---|---|
| | | UCAUAAUCCCAUCUCUAUUCCAAUGCUGAACG<br>AUGGUCGAAGGAUUGUCUUCACUGUGGUGGCC<br>UCUUUGGCUUUCAAAGAUAAAGUUUACCUGAC<br>UGUAAAUGCUCCUGAUACUCUCUGCGAACACC<br>UCCAGAUAAAUGAUGGGGAGCUGAUUGUUGUC<br>CAGCUAACGCCUGGAUACUGUGCUCCUGAAGG<br>AUCUUACCACAGCACUGUGAACCAAGUACCAC<br>UGUGAAUUCCACUCUGAGGGUGGACGGGACAC<br>AGGUUCUUUCUCGAGAGAGAUGAGUGCAUCCU<br>GCUCAUGAGAUGUGACUGAAUGCAGAGCCUAC<br>CCUACUUCCUCACUCAGGGAUAUUUAAAUCAU<br>GUCUUACAUAACAGUUGACCUCUCAUUCCCAG<br>GAUUGCCUUGAGCCUGCUAAGAGCUGUUCUGG<br>GAAUGAAAAAAAAAAUAAAUGUCUCUUCAAGA<br>CACAUUGCUUCUGUCGGUCAGAAGCUCAUCGU<br>AAUAAACAUCUGCCACUGAAAAUGGCGCUUGA<br>UUGCUAUCUUCUAGAAUUUUGAUGUUGUCAAA<br>AGAAAGCAAAACAUGGAAAGGGUGGUGUCCAC<br>CGGCCAGUAGGAGCUGGAGUGCUCUCUUCAAG<br>GUUAAGGUGAUAGAAGUUUACAUGUUGCCUAA<br>AACUGUCUCUCAUCUCAUGGGGGGCUUGGAAA<br>GAAGAUUACCCCGUGGAAAGCAGGACUUGAAG<br>AUGACUGUUUAAGCAACAAGGUGCACUCUUUU<br>CCUGGCCCCUGAAUACACAUAAAAGACAACUU<br>CCUUCAAAGAACUACCUAGGGACUAUGAUACC<br>CACCAAAGAACCACGUCAGCGAUGCAAAGAAA<br>ACCAGGAGAGCUUUGUUUAUUUUGCAGAGUAU<br>ACGAGAGAUUUUACCCUGAGGGCUAUUUUUAU<br>UAUACAGGAUGAGAGUGAACUGGAUGUCUCAG<br>GAUAAAGGCCAAGAAGGAUUUUUCACAGUCUG<br>AGCAAGACUGUUUUUGUAGGUUCUCUCUCCAA<br>AACUUUUAGGUAAAUUUUUGAUAAUUUUAAAA<br>UUUUUAGUUAUAUUUUUGGACCAUUUUCAAUA<br>GAAGAUUGAAACAUUUCCAGAUGGUUUCAUAU<br>CCCCACAAG | |
| Human OX40L | mRNA sequence: Human OX40L with 5'-UTR, 3'-UTR, and miR-122 binding site | GGGAAAUAAGAGAGAAAAGAAGAGUAAGAAGA<br>AAUAUAAGAGCCACCAUGGAAAGGGUCCAACC<br>CCUGGAAGAGAAUGUGGGAAAUGCAGCCAGGC<br>CAAGAUUCGAGAGGAACAAGCUAUUGCUGGUG<br>GCCUCUGUAAUUCAGGGACUGGGGCUGCUCCU<br>GUGCUUCACCUACAUCUGCCUGCACUUCUCUG<br>CUCUUCAGGUAUCACAUCGGUAUCCUCGAAUU<br>CAAAGUAUCAAAGUACAAUUUACCGAAUAUAA<br>GAAGGAGAAAGGUUUCAUCCUCACUUCCCAAA<br>AGGAGGAUGAAAUCAUGAAGGUGCAGAACAAC<br>UCAGUCAUCAUCAACUGUGAUGGGUUUUAUCU<br>CAUCUCCCUGAAGGGCUACUUCUCCCAGGAAG<br>UCAACAUUAGCCUUCAUUACCAGAAGGAUGAG<br>GAGCCCCUCUUCCAACUGAAGAAGGUCAGGUC<br>UGUCAACUCCUUGAUGGUGGCCUCUCUGACUU<br>ACAAAGACAAAGUCUACUUGAAUGUGACCACU<br>GACAAUACCUCCCUGGAUGACUUCCAUGUGAA<br>UGGCGGAGAACUGAUUCUUAUCCAUCAAAAUC<br>CUGGUGAAUUCUGUGUCCUUUGAUAAUAGGCU<br>GGAGCCUCGGUGGCCAUGCUUCUUGCCCCUUG<br>GGCCUCCCCCCAGCCCCUCCUCCCCUUCCUGC<br>ACCCGUACCCCCCAAACACCAUUGUCACACUC<br>CAGUGGUCUUUGAAUAAAGUCUGAGUGGGCGG<br>C | SEQ ID NO: 69 |
| Murine OX40L | mRNA sequence: murine OX40L with 5'-UTR, 3'-UTR, and miR-122 binding site | GGGAAAUAAGAGAGAAAAGAAGAGUAAGAAGAA<br>AUAUAAGAGCCACCAUGGAAGGGGAAGGGGUUC<br>AACCCCUGGAUGAGAAUCUGGAAAACGGAUCAA<br>GGCCAAGAUUCAAGUGGAAGAAGACGCUAAGGC<br>UGGUGGUCUCUGGGAUCAAGGGAGCAGGGAUGC<br>UUCUGUGCUUCAUCUAUGUCUGCCUGCAACUCU<br>CUUCCUCUCCGGCAAAGGACCCUCCAAUCCAAA<br>GACUCAGAGGAGCAGUUACCAGAUGUGAGGAUG<br>GGCAACUAUUCAUCAGCUCAUACAAGAAUGAGU<br>AUCAAACUAUGGAGGUGCAGAACAAUUCGGUUG<br>UCAUCAAGUGCGAUGGGCUUUAUAUCAUCUACC<br>UGAAGGGCUCCUUUUUCCAGGAGGUCAAGAUUG<br>ACCUUCAUUUCCGGGAGGAUCAUAAUCCCAUCU<br>CUAUUCCAAUGCUGAACGAUGGUCGAAGGAUUG | SEQ ID NO: 70 |

TABLE 1A-continued

| OX40L Polypeptide and Polynucleotide sequences | | | |
|---|---|---|---|
| Encoded Polypeptide | Description | Sequence | SEQ ID NO: |
| | | UCUUCACUGUGGUGGCCUCUUUGGCUUUCAAAG AUAAAGUUUACCUGACUGUAAAUGCUCCUGAUA CUCUCUGCGAACACCUCCAGAUAAAUGAUGGGG AGCUGAUUGUUGUCCAGCUAACGCCUGGAUACU GUGCUCCUGAAGGAUCUUACCACAGCACUGUGA ACCAAGUACCACUGUGAUAAUAGGCUGGAGCCU CGGUGGCCAUGCUUCUUGCCCCUUGGGCCUCCC CCCAGCCCCUCCUCCCCUUCCUGCACCCGUACC CCCCAAACACCAUUGUCACACUCCAGUGGUCUU UGAAUAAAGUCUGAGUGGGCGGC | |
| hOX40L miR-122 | Codon optimized human OX40L sequences | ATGGAAAGGGTCCAACCCCTGGAAGAGAATGTGGGAAATGCAGCCAGGC CAAGATTCGAGAGGAACAAGCTATTGCTGGTGGCCTCTGTAATTCAGGG ACTGGGGCTGCTCCTGTGCTTCACCTACATCTGCCTGCACTTCTCTGCT CTTCAGGTATCACATCGGTATCCTCGAATTCAAAGTATCAAAGTACAAT TTACCGAATATAAGAAGGAGAAAGGTTTCATCCTCACTTCCCAAAAGGA GGATGAAATCATGAAGGTGCAGAACAACTCAGTCATCATCAACTGTGAT GGGTTTTATCTCATCTCCCTGAAGGGCTACTTCTCCCAGGAAGTCAACA TTAGCCTTCATTACCAGAAGGATGAGGAGCCCCTCTTCCAACTGAAGAA GGTCAGGTCTGTCAACTCCTTGATGGTGGCCTCTCTGACTTACAAAGAC AAAGTCTACTTGAATGTGACCACTGACAATACCTCCCTGGATGACTTCC ATGTGAATGGCGGAGAACTGATTCTTATCCATCAAAATCCTGGTGAATT CTGTGTCCTT | SEQ ID NO: 116 |
| mOX40L + miR-122 | Codon optimized mouse OX40L sequences | ATGGAAGGGGAAGGGGTTCAACCCCTGGATGAGAATCTGGAAAACGGAT CAAGGCCAAGATTCAAGTGGAAGAAGACGCTAAGGCTGGTGGTCTCTGG GATCAAGGGAGCAGGGATGCTTCTGTGCTTCATCTATGTCTGCCTGCAA CTCTCTTCCTCTCCGGCAAAGGACCCTCCAATCCAAAGACTCAGAGGAG CAGTTACCAGATGTGAGGATGGGCAACTATTCATCAGCTCATACAAGAA TGAGTATCAAACTATGGAGGTGCAGAACAATTCGGTTGTCATCAAGTGC GATGGGCTTTATATCATCTACCTGAAGGGCTCCTTTTTCCAGGAGGTCA AGATTGACCTTCATTTCCGGGAGGATCATAATCCCATCTCTATTCCAAT GCTGAACGATGGTCGAAGGATTGTCTTCACTGTGGTGGCCTCTTTGGCT TTCAAAGATAAAGTTTACCTGACTGTAAATGCTCCTGATACTCTCTGCG AACACCTCCAGATAAATGATGGGGAGCTGATTGTTGTCCAGCTAACGCC TGGATACTGTGCTCCTGAAGGATCTTACCACAGCACTGTGAACCAAGTA CCACTG | SEQ ID NO: 117 |
| OX40L (TNFSF4) | Codon-optimized sequence 1 for ENSP 281834 | AUGGAGAGAGUGCAGCCCCUGGAGGAGAACGUG GGCAACGCCGCCAGACCCAGAUUCGAGAGAAAC AAGCUGCUGCUGGUGGCCAGCGUGAUCCAGGGC CUGGGCCUGCUGCUGUGCUUCACCUACAUCUGC CUGCACUUCAGCGCCCUGCAGGUGAGCCACAGA UACCCCAGAAUCCAGAGCAUCAAGGUGCAGUUC ACCGAGUACAAGAAGGAGAAGGGCUUCAUCCUG ACCAGCCAGAAGGAGGACGAGAUCAUGAAGGUG CAGAACAACAGCGUGAUCAUCAACUGCGACGGC UUCUACCUGAUCAGCCUGAAGGGCUACUUCAGC CAGGAGGUGAACAUCAGCCUGCACUACCAGAAG GACGAGGAGCCCCUGUUCCAGCUGAAGAAGGUG AGAAGCGUGAACAGCCUGAUGGUGGCCAGCCUG ACCUACAAGGACAAGGUGUACCUGAACGUGACC ACCGACAACACCAGCCUGGACGACUUCCACGUG AACGGCGGCGAGCUGAUCCUGAUCCACCAGAAC CCCGGCGAGUUCUGCGUGCUG | SEQ ID NO: 121 |
| OX40L (TNFSF4) | Codon-optimized sequence 2 for ENSP 281834 | AUGGAGCGUGUGCAGCCUCUUGAGGAGAAUGUG GGAAAUGCAGCCCGGCCUCGAUUCGAACGUAAU AAACUCCUGCUCGUGGCCUCCGUGAUCCAGGGU CUCGGUUUAUUGCUGUGUUUUACCUAUAUAUGC UUACACUUUAGUGCAUUACAGGUCUCACACCGG UACCCUCGCAUUCAGUCUAUAAAAGUGCAGUUU ACCGAGUAUAAGAAGGAGAAAGGUUUUAUACUG ACUUCUCAGAAAGAGGACGAGAUCAUGAAGGUG CAGAAUAAUAGCGUCAUUAUCAACUGCGAUGGA UUCUAUCUAAUUUCCCUAAAGGGGUACUUCAGC CAGGAGGUCAAUAUAUCACUGCACUAUCAAAAG GACGAGGAGCCCCUGUUUCAACUGAAGAAAGUG CGAUCAGUUAACUCUCUGAUGGUUGCCUCUCUG ACCUAUAAGGACAAAGUCUACUUGAACGUGACA ACUGACAACACCUCACUGGAUGACUUUCAUGUG AAUGGGGGGGAACUGAUUCUUAUCCAUCAGAAU CCAGGAGAAUUCUGUGUGCUC | SEQ ID NO: 122 |

TABLE 1A-continued

OX40L Polypeptide and Polynucleotide sequences

| Encoded Polypeptide | Description | Sequence | SEQ ID NO: |
|---|---|---|---|
| OX40L (TNFSF4) | Codon-optimized sequence 3 for ENSP 281834 | AUGGAGCGGGUGCAGCCCCUGGAGGAGAAUGUG GGCAAUGCUGCCCGGCCCAGGUUUGAAAGAAAC AAGCUGCUGCUGGUGGCCAGCGUCAUCCAGGGC CUGGGCCUGCUGCUGUGCUUCACCUACAUCUGC CUGCACUUCAGCGCCCUGCAGGUGAGCCACCGC UACCCCCGCAUCCAGAGCAUCAAGGUGCAGUUC ACAGAGUACAAGAAGGAGAAGGGCUUCAUCCUG ACCAGCCAGAAGGAGGAUGAGAUCAUGAAGGUG CAGAACAACAGCGUCAUCAUCAACUGUGAUGGC UUCUACCUGAUCAGCCUGAAGGGCUACUUCAGC CAGGAGGUGAACAUCAGCCUGCACUACCAGAAG GAUGAGGAGCCCCUCUUCCAGCUGAAGAAGGUG CGCUCUGUGAACAGCCUGAUGGUGGCCAGCCUG ACCUACAAGGACAAGGUGUACCUGAAUGUGACC ACAGACAACACCAGCCUGGAUGACUUCCACGUG AAUGGAGGAGAGCUGAUCCUGAUCCACCAGAAC CCUGGAGAGUUCUGUGUGCUG | SEQ ID NO: 123 |
| OX40L (TNFSF4) | Codon-optimized sequence 4 for ENSP 281834 | AUGGAGCGGGUGCAGCCCCUGGAGGAGAACGUG GGCAACGCCGCCCGCCCGCGUUUUGAGCGAAAU AAGUUACUGCUUGUUGCAUCUGUGAUACAGGGG UUGGGUUUACUUCUUUGCUUUACAUAUAUUUGU CUCCACUUUAGUGCGCUUCAGGUAUCCCAUCGG UACCCGCGCAUCCAGUCAAUCAAGGUCCAGUUC ACUGAAUAUAAAAAGGAGAAAGGAUUCAUUCUG ACUUCACAAAAAGAGGACGAAAUCAUGAAAGUG CAGAACAACUCUGUAAUUAUAAACUGCGAUGGG UUCUAUCUGAUCAGUCUGAAGGGAUAUUUUAGC CAGGAAGUAAAUAUUUCACUACAUUAUCAGAAG GACGAAGAACCACUUUUUCAACUGAAGAAAGUC CGGUCCGUGAACUCCCUGAUGGUUGCUAGCCUU ACCUACAAGGAUAAAGUCUAUUUAAACGUCACA ACAGAUAACACUAGCCUCGACGAUUUCCAUGUG AACGGAGGUGAACUGAUAUUGAUCCAUCAAAAC CCCGGCGAGUUCUGCGUUUUA | SEQ ID NO: 124 |
| OX40L (TNFSF4) | Codon-optimized sequence 5 for ENSP 281834 | AUGGAGCGGGUCCAGCCCCUCGAGGAGAACGUU GGUAAUGCCGCACGUCCCAGGUUUGAACGCAAC AAGCUGCUGUUGGUGGCCAGCGUCAUUCAGGGG CUGGGUUUGUUGCUGUGCUUCACUUACAUCUGU CUGCAUUUUAGUGCACUCCAGGUGUCCCACCGC UACCCCCGUAUCCAAUCCAUUAAAGUCCAAUUU ACCGAAUACAAAAAAGAGAAGGGUUUCAUUCUU ACCUCCCAGAAGGAGGAUGAAAUUAUGAAGGUG CAGAACAAUUCUGUUAUCAUCAACUGUGACGGA UUCUAUCUGAUUUCACUGAAGGGAUACUUUUCC CAGGAGGUGAACAUCAGUCUGCAUUAUCAGAAG GACGAAGAACCGCUUUUUCAACUGAAGAAGGUU AGGAGUGUGAACUCCUUAAUGGUAGCCAGCCUG ACAUAUAAGGACAAGGUAUAUCUGAACGUCACC ACUGAUAACACCUCUUUAGACGAUUUUCAUGUA AAUGGGGGAGAAUUGAUACUCAUUCACCAGAA UCCGGGUGAGUUUUGUGUUCUG | SEQ ID NO: 125 |
| OX40L (TNFSF4) | Codon-optimized sequence 1 for ENSP 356691 | AUGGUGAGCCACAGAUACCCCAGAAUCCAGAGCA UCAAGGUGCAGUUCACCGAGUACAAGAAGGAGAA GGGCUUCAUCCUGACCAGCCAGAAGGAGGACGAG AUCAUGAAGGUGCAGAACAACAGCGUGAUCAUCA ACUGCGACGGCUUCUACCUGAUCAGCCUGAAGGG CUACUUCAGCCAGGAGGUGAACAUCAGCCUGCAC UACCAGAAGGACGAGGAGCCCCUGUUCCAGCUGA AGAAGGUGAGAAGCGUGAACAGCCUGAUGGUGGC CAGCCUGACCUACAAGGACAAGGUGUACCUGAAC GUGACCACCGACAACACCAGCCUGGACGACUUCC ACGUGAACGGCGGCGAGCUGAUCCUGAUCCACCA GAACCCCGGCGAGUUCUGCGUGCUG | SEQ ID NO: 126 |
| OX40L (TNFSF4) | Codon-optimized sequence 2 for ENSP 356691 | AUGGUUUCUCACCGUUACCCACGGAUCCAGUCUA UCAAGGUUCAGUUUACCGAGUACAAAAAGGAAAA AGGGUUCAUCCUCACCUCUCAGAAAGAGGACGAA AUCAUGAAGGUGCAGAAUAACUCUGUAAUCAUUA AUUGCGACGGUUUUUAUCUGAUUUCACUGAAGGG CUACUUUAGUCAGGAAGUUAAUAUUAGUUUGCAC UACCAAAAGGACGAGGAGCCUCUCUUCCAACUAA AAAAGGUAAGAUCCGUUAAUUCCCUUAUGGUGGC | SEQ ID NO: 127 |

TABLE 1A-continued

OX40L Polypeptide and Polynucleotide sequences

| Encoded Polypeptide | Description | Sequence | SEQ ID NO: |
|---|---|---|---|
| | | CUCCUUAACUUAUAAGGACAAGGUGUAUCUGAAU GUGACCACAGAUAACACAUCCCUGGACGACUUUC AUGUAAAUGGCGGCGAGUUAAUUCUGAUACACCA GAACCCUGGCGAGUUCUGCGUGCUG | |
| OX40L (TNFSF4) | Codon-optimized sequence 3 for ENSP 356691 | AUGGUGAGCCACCGCUACCCCCGCAUCCAGAGCA UCAAGGUGCAGUUCACAGAGUACAAGAAGGAGAA GGGCUUCAUCCUGACCAGCCAGAAGGAGGAUGAG AUCAUGAAGGUGCAGAACAACAGCGUCAUCAUCA ACUGUGAUGGCUUCUACCUGAUCAGCCUGAAGGG CUACUUCAGCCAGGAGGUGAACAUCAGCCUGCAC UACCAGAAGGAUGAGGAGCCCCUCUUCCAGCUGA AGAAGGUGCGCUCUGUGAACAGCCUGAUGGUGGC CAGCCUGACCUACAAGGACAAGGUGUACCUGAAU GUGACCACAGACAACACCAGCCUGGAUGACUUCC ACGUGAAUGGAGGAGAGCUGAUCCUGAUCCACCA GAACCCUGGAGAGUUCUGUGUGCUG | SEQ ID NO: 128 |
| OX40L (TNFSF4) | Codon-optimized sequence 4 for ENSP 356691 | AUGGUGAGCCACCGGUACCCCCGGAUCCAGAGCA UCAAGGUGCAGUUCACCGAAUACAAGAAGGAGAA GGGUUUUAUCCUGACGAGCCAGAAGGAAGACGAG AUUAUGAAGGUCCAAAACAACUCAGUCAUCAUAA ACUGCGAUGGAUUUUACCUGAUCUCUCUGAAAGG GUACUUCUCCCAGGAAGUGAAUAUUAGCUUGCAC UAUCAAAAAGAUGAGGAGCCUCUAUUCCAGCUCA AGAAGGUCAGAAGCGUCAAUAGUCUGAUGGUCGC AUCAUUAACCUAUAAAGACAAAGUAUAUCUAAAU GUGACGACAGACAAUACAUCCCUCGAUGAUUUUC ACGUCAACGGAGGCGAACUCAUUCUGAUCCACCA GAAUCCAGGGGAAUUUUGCGUGCUG | SEQ ID NO: 129 |
| OX40L (TNFSF4) | Codon-optimized sequence 5 for ENSP 356691 | AUGGUCUCACACCGGUACCCCCGUAUCCAGAGUA UUAAGGUGCAAUUCACGGAGUAUAAAAAAGAAAA GGGAUUCAUUCUGACGUCUCAGAAGGAAGAUGAG AUCAUGAAGGUCCAGAACAAUUCUGUGAUCAUUA AUUGCGAUGGAUUUUAUCUGAUUUCACUUAAAGG AUAUUUUUCCCAGGAGGUUAAUAUCAGUUUGCAC UAUCAGAAAGACGAGGAGCCAUUAUUCCAGCUGA AGAAGGUGAGAUCAGUGAAUAGCCUGAUGGUUGC GUCACUGACGUAUAAAGACAAAGUUUAUCUAAAC GUUACCACUGAUAAUACAUCCCUUGAUGAUUUUC AUGUGAACGGGGGUGAACUGAUCCUUAUACACCA GAACCCCGGAGAGUUCUGUGUGUUG | SEQ ID NO: 130 |
| OX40L (TNFSF4) | Codon-optimized sequence 1 for ENSP 439704 | AUGGUGAGCCACAGAUACCCCAGAAUCCAGAGCAU CAAGGUGCAGUUCACCGAGUACAAGAAGGAGAAG GGCUUCAUCCUGACCAGCCAGAAGGAGGACGAGA UCAUGAAGGUGCAGAACAACAGCGUGAUCAUCAA CUGCGACGGCUUCUACCUGAUCAGCCUGAAGGGC UACUUCAGCCAGGAGGUGAACAUCAGCCUGCACU ACCAGAAGGACGAGGAGCCCCUGUUCCAGCUGAA GAAGGUGAGAAGCGUGAACAGCCUGAUGGUGGCC AGCCUGACCUACAAGGACAAGGUGUACCUGAACG UGACCACCGACAACACCAGCCUGGACGACUUCCA CGUGAACGGCGGCGAGCUGAUCCUGAUCCACCAG AACCCCGGCGAGUUCUGCGUGCUG | SEQ ID NO: 131 |
| OX40L (TNFSF4) | Codon-optimized sequence 2 for ENSP 439704 | AUGGUGUCACACCGGUACCCUCGGAUCCAGUCUA UUAAAGUUCAAUUUACGGAGUACAAGAAAGAAAA AGGCUUUAUCCUUACAAGCCAAAAGGAAGACGAG AUCAUGAAAGUGCAAAACAACAGUGUGAUUAUAA AUUGUGAUGGCUUCUACCUUAUUAGUCUGAAGGG CUACUUUAGUCAGGAAGUCAAUAUUAGCCUACAC UACCAGAAAGACGAGGAGCCCCUCUUUCAACUGA AAAAGGUGCGCUCCGUGAAUUCGUUGAUGGUCGC CUCUCUGACCUACAAAGAUAAGGUGUAUCUUAAC GUUACUACCGACAAUACUAGUCUGGACGACUUUC ACGUCAACGGAGGCGAACUUAUUCUGAUCCACCA GAACCCCGGCGAAUUCUGCGUGCUG | SEQ ID NO: 132 |
| OX40L (TNFSF4) | Codon-optimized sequence 3 for ENSP 439704 | AUGGUGAGCCACCGCUACCCCCGCAUCCAGAGCA UCAAGGUGCAGUUCACAGAGUACAAGAAGGAGAA GGGCUUCAUCCUGACCAGCCAGAAGGAGGAUGAG AUCAUGAAGGUGCAGAACAACAGCGUCAUCAUCA ACUGUGAUGGCUUCUACCUGAUCAGCCUGAAGGG | SEQ ID NO: 133 |

TABLE 1A-continued

OX40L Polypeptide and Polynucleotide sequences

| Encoded Polypeptide | Description | Sequence | SEQ ID NO: |
|---|---|---|---|
| | | CUACUUCAGCCAGGAGGUGAACAUCAGCCUGCAC UACCAGAAGGAUGAGGAGCCCCUCUUCCAGCUGA AGAAGGUGCGCUCUGUGAACAGCCUGAUGGUGGC CAGCCUGACCUACAAGGACAAGGUGUACCUGAAU GUGACCACAGACAACACCAGCCUGGAUGACUUCC ACGUGAAUGGAGGAGAGCUGAUCCUGAUCCACCA GAACCCUGGAGAGUUCUGUGUGCUG | |
| OX40L (TNFSF4) | Codon-optimized sequence 4 for ENSP 439704 | AUGGUGAGCCACCGGUACCCCCGGAUCCAGAGCA UCAAGGUGCAGUUCACAGAGUACAAGAAGGAGAA GGGAUUUAUUCUCACAAGUCAGAAAGAAGAUGAG AUCAUGAAGGUUCAGAACAACUCAGUCAUUAUUA AUUGCGACGGAUUCUAUCUCAUUAGCCUCAAAGG CUAUUUCAGCCAGGAGGUCAAUAUCAGCCUGCAC UACCAGAAGGAUGAGGAACCUCUCUUUCAGCUGA AAAAAGUCCGCUCUGUGAAUUCCCUCAUGGUCGC UUCCCUGACCUACAAGGAUAAAGUUUAUUUGAAC GUUACAACAGAUAAUACAUCGCUGGACGACUUCC AUGUGAAUGGUGGCGAACUAAUUCUAAUACACCA AAAUCCAGGCGAAUUUUGUGUCCUU | SEQ ID NO: 134 |
| OX40L (TNFSF4) | Codon-optimized sequence 5 for ENSP 439704 | AUGGUAUCCCAUAGAUACCCACGUAUUCAAAGCA UUAAGGUGCAGUUCACAGAGUACAAAAAGGAGAA GGGUUUCAUACUGACGUCACAGAAGGAGGACGAG AUAAUGAAGGUGCAGAAUAAUAGUGUGAUCAUCA AUUGUGAUGGAUUCUAUUUGAUCAGCCUCAAAGG UUAUUUCUCACAGGAAGUCAACAUUUCCCUGCAC UACCAGAAGGACGAAGAGCCUUUGUUUCAGCUGA AGAAGGUGCGCUCAGUGAACAGUUUGAUGGUAGC CUCCCUAACUUAUAAAGAUAAAGUUUAUCUGAAC GUGACAACCGAUAACACAUCCCUGGACGACUUUC ACGUCAAUGGAGGUGAGUUAAUCCUGAUCCAUCA GAAUCCCGGAGAAUUCUGCGUUCUU | SEQ ID NO: 135 |

Based on the RNA sequences provided herein, and in particular in Table 1 and Table 1A, a person of ordinary skill in the art would understand the corresponding DNA sequence (e.g., conversion of uracil to thymine). Likewise, based on the DNA sequences provided, a person of ordinary skill in the art would understand the corresponding RNA sequence (e.g., conversion of thymine to uracil).

In some embodiments, the first polynucleotide comprises an mRNA (e.g., SEQ ID NO: 141) comprising a codon optimized sequence encoding an IL-23 polypeptide. In some embodiments, the second polynucleotide comprises an mRNA (e.g., SEQ ID NO: 143) comprising a codon optimized sequence encoding an IL-36-gamma polypeptide. In other embodiments, the third polynucleotide comprises an mRNA (e.g., SEQ ID NO: 145) comprising a codon optimized sequence encoding an OX40L polypeptide.

In some embodiments, the first polynucleotide comprises an mRNA encoding an IL-23 polypeptide which is full length. In some embodiments, the first polynucleotide comprises an mRNA encoding a human IL-23 polypeptide which lacks at least one, at least two, at least three, at least four, at least five, at least six, at least seven, at least eight, at least nine, at least 10, at least 14, or at least 15 amino acids at the N-terminus or C-terminus of the wild type IL-23 polypeptide.

In some embodiments, the second polynucleotide comprises an mRNA encoding an IL-36-gamma polypeptide which is full length. In some embodiments, the second polynucleotides comprise an mRNA encoding a human IL-36-gamma polypeptide which lacks at least one, at least two, at least three, at least four, at least five, at least six, at least seven, at least eight, at least nine, at least 10, at least 14, or at least 15 amino acids at the N-terminus or C-terminus of the wild type IL-36-gamma polypeptide.

In some embodiments, the polynucleotide comprises an mRNA encoding an OX40L polypeptide which is full length. In some embodiments, the polynucleotide comprises an mRNA encoding a human OX40L polypeptide which is 183 amino acids in length. In certain embodiments, the OX40L polypeptide can lack at least one, at least two, at least three, at least four, at least five, at least six, at least seven, at least eight, at least nine, at least 10, at least 14, or at least 15 amino acids at the N-terminus or C-terminus of the OX40L polypeptide.

In some embodiments, the polynucleotides (e.g., mRNA) of the present disclosure are "structurally modified" or "chemically modified." As used herein, a "structural" modification is one in which two or more linked nucleosides are inserted, deleted, duplicated, inverted or randomized in a polynucleotide without significant chemical modification to the mRNA themselves. Because chemical bonds will necessarily be broken and reformed to effect a structural modification, structural modifications are of a chemical nature and hence are chemical modifications. However, structural modifications will result in a different sequence of nucleotides. For example, the mRNA "AUCG" can be chemically modified to "AU-5meC-G". The same mRNA can be structurally modified from "AUCG" to "AUCCCG". Here, the dinucleotide "CC" has been inserted, resulting in a structural modification to the polynucleotide.

In some embodiments, the polynucleotides (e.g., mRNA) of the present disclosure, can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotide (e.g., an mRNA encoding an IL-23 polypeptide, an mRNA encoding an IL-36-gamma polypeptide and/or an mRNA encoding an OX40L polypeptide) can have a uniform chemical modification of two, three, or four of the same nucleoside type throughout the entire polynucleotide (e.g., mRNA) (such as all uridines and all cytosines, etc. are modified in the same way). When a polynucleotide (e.g., an mRNA encoding an IL-23 polypeptide, an mRNA encoding an IL-36-gamma polypeptide and/or an mRNA encoding an OX40L polypeptide) of the present disclosure is chemically and/or structurally modified, the mRNA can be referred to as a "modified mRNA." Non-limiting examples of chemical modifications are described elsewhere herein.

In some embodiments, the first polynucleotide and/or the second polynucleotide comprise at least one chemically modified nucleoside. In some embodiments, the at least one chemically modified nucleoside is selected from the group consisting of any of the chemically modified nucleoside disclosed herein and a combination thereof.

In some embodiments, the at least one chemically modified nucleoside is selected from the group consisting of pseudouridine, N1-methylpseudouridine, 5-methylcytosine, 5-methoxyuridine, and a combination thereof.

In some embodiments, wherein the nucleosides in the first polynucleotide, the second polynucleotide and/or the third polynucleotide are chemically modified by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100%.

In some embodiments, the chemically modified nucleosides in the first polynucleotide, the second polynucleotide and/or the third polynucleotide are selected from the group consisting of uridine, adenine, cytosine, guanine, and any combination thereof. In some embodiments, the uridine nucleosides in the first polynucleotide, the second polynucleotide and/or the third polynucleotide are chemically modified by at least about 10%, at least about 15%, at least about 20%, at least about 25%, at least about 30%, at least about 35%, at least about 40%, at least about 45%, at least 50%, at least about 55%, at least about 60%, at least about 65%, at least about 70%, at least about 75%, at least about 80%, at least about 85%, at least about 90%, at least about 95%, at least about 99%, or 100%.

In some embodiments, the adenosine nucleosides in the first polynucleotide, the second polynucleotide and/or the third polynucleotide are chemically modified by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100%.

In some embodiments, the cytidine nucleosides in the first polynucleotide, the second polynucleotide and/or the third polynucleotide are chemically modified by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100%.

In some embodiments, the guanosine nucleosides in the first polynucleotide, the second polynucleotide and/or the third polynucleotide are chemically modified by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100%.

In some embodiments, each of the mRNA encoding the first protein, the mRNA encoding the second protein, and the mRNA encoding the third protein comprises an open reading frame.

In some embodiments, the IL-23 polypeptide comprises an IL-12p40 subunit comprising an amino acid sequence at least about 50%, at least about 55%, at least about 60%, at least about 65%, at least about 70%, at least about 75%, at least about 80%, at least about 85%, at least about 90%, at least about 95%, at least about 99%, or 100% to an IL-23 polypeptide sequence listed in Table 1, wherein the amino acid sequence is capable of binding to an IL-23p19 subunit and forming IL-23, which has an IL-23 activity.

In some embodiments, the IL-12p40 subunit is encoded by a nucleic acid sequence at least about 70%, at least about 75%, at least about 80%, at least about 85%, at least about 90%, at least about 95%, at least 99%, or 100% identical to an IL-23 polypeptide encoding sequence listed in Table 1.

In some embodiments, the IL-23 polypeptide comprises an IL-23p19 subunit comprising an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to an IL-23 polypeptide sequence listed in Table 1, wherein the amino acid sequence is capable of binding to an IL-12p40 subunit and forming IL-23, which has an IL-23 activity.

In some embodiments, the IL-23p19 subunit is encoded by a nucleic acid sequence at least about 70%, at least about 75%, at least about 80%, at least about 85%, at least about 90%, at least about 95%, at least about 99%, or 100% identical to a IL-23 polypeptide encoding sequence listed in Table 1.

In some embodiments, the IL-12p40 subunit and the IL-23p19 subunit of the IL-23 protein are on a single polypeptide chain or two different chains. In some embodiments, the IL-12p40 subunit and the IL-23p19 subunit are fused by a linker. In some embodiments, the IL-12p40 subunit comprises a signal peptide. In some embodiments, the IL-23p19 subunit comprises a signal peptide. In some embodiments, the IL-12p40 subunit is a mature IL-12p40 (i.e., it does not comprise a signal peptide). In some embodiments, the IL-23p19 subunit is a mature IL-23p19 (i.e., it does not comprise a signal peptide). In some embodiments, the IL-12p40 subunit comprises a non-native signal peptide. In some aspects, the IL-23p19 subunit comprises a non-native signal peptide.

In some embodiments, the IL-23 is a fusion polypeptide comprising an IL-12p40 subunit and an IL-23p19 subunit according to any of the following alternative formulas:

[signal peptide 1]-[IL-12p40]-[linker]-[IL-23p19]

[signal peptide 2]-[IL-23p19]-[linker]-[IL-12p40]

wherein [signal peptide 1] can be an IL-12p40 signal peptide or a non-native signal peptide, [signal peptide 2] can be an IL-23p19 signal peptide or a non-native signal peptide, [IL-12p40] is a mature IL-12p40, [IL-23p19] is a mature IL-23p29, and [linker] is a peptide linker.

In some embodiments, the peptide linker comprises a (GS) linker. In some embodiments, the (GS) linker comprises a (GnS)m (SEQ ID NO: 193) sequence, wherein n is 1-20 and m is 1-100. In some embodiments, the (GS) linker comprises the sequence GGS, GGGS (SEQ ID NO: 194), GGGGS (SEQ ID NO: 136), GGGGGS (SEQ ID NO: 137), GGGGGGS (SEQ ID NO: 138), GGGGGGGS (SEQ ID NO: 139) GGSGGGGSGG (SEQ ID NO: 190), GGSGGGG (SEQ ID NO: 191), or GSGSGSGS (SEQ ID NO: 192). In some embodiments, the linker can comprise $(EAAAK)_q$ (SEQ ID NO: 163), wherein q is an integer from 1 to 5. In one embodiment, the linker can comprise $(EAAAK)_3$ (SEQ ID NO: 195), i.e., EAAAKEAAAKEAAAK (SEQ ID NO: 164). In some embodiments, the linker can be a Gly-rich linker, for example, comprising $(Gly)_p$ (SEQ ID NO: 196), wherein p is an integer from 1 to 40. In some embodiments, a Gly-rich linker can comprise GGGGG (SEQ ID NO: 165), GGGGGG (SEQ ID NO: 166), GGGGGGG (SEQ ID NO: 167) or GGGGGGGG (SEQ ID NO: 168). Further exemplary linkers include, but not limited to, GGGGSLVPRGSGGGGS (SEQ ID NO: 169), GSGSGS (SEQ ID NO: 170), GGGGSLVPRGSGGGG (SEQ ID NO: 171), GGSGGHMGSGG (SEQ ID NO: 172), GGSGGSGGSGG (SEQ ID NO: 173), GGSGG (SEQ ID NO: 174), GSGSGSGS (SEQ ID NO: 175), GGGSEGGGSEGGGSEGGG (SEQ ID NO: 176), AAGAATAA (SEQ ID NO: 177), GGSSG (SEQ ID NO: 178), GSGGGTGGGSG (SEQ ID NO: 179), GSGSGSGSGGSG (SEQ ID NO: 180), GSGGSGSGGSGGSG (SEQ ID NO: 181), and GSGGSGGSGGSGGS (SEQ ID NO: 182). The linkers described herein can be used in any of the polynucleotides described herein.

In some embodiments, the IL-23 polypeptide according to formulas above (i.e., an IL-23 polypeptide comprising an IL-12p40 subunit and an IL-23p19 subunit) comprises an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to an IL-23 polypeptide sequence listed in Table 1, wherein the amino acid sequence is capable of having at least one IL-23 activity (e.g., binding to an IL-23 receptor).

In some embodiments, the IL-23 polypeptide according to the formulas above (i.e., an IL-23 polypeptide comprising an IL-12p40 subunit and an IL-23p19 subunit) is encoded by a nucleic acid sequence at least about 70%, at least about 75%, at least about 80%, at least about 85%, at least about 90%, at least about 95%, at least about 99%, or 100% identical to a sequence listed in Table 1.

In some embodiments, the IL-36-gamma polypeptide comprises an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to a IL-36-gamma polypeptide sequence listed in Table 1, wherein the polypeptide is capable of having an IL-36-gamma activity (e.g., binding to an IL-36 receptor)

In some embodiments, the IL-36-gamma polypeptide is encoded by a nucleic acid sequence at least about 70%, at least about 75%, at least about 80%, at least about 85%, at least about 90%, at least about 95%, at least about 99%, or 100% identical to a IL-36-gamma polypeptide encoding sequence listed in Table 1.

In some embodiments, the IL-18 polypeptide comprises an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to a IL-18 polypeptide sequence listed in Table 1, wherein the polypeptide is capable of having an IL-18 activity (e.g., binding to an IL-18 receptor)

In some embodiments, the IL-18 polypeptide is encoded by a nucleic acid sequence at least about 70%, at least about 75%, at least about 80%, at least about 85%, at least about 90%, at least about 95%, at least about 99%, or 100% identical to a IL-18 polypeptide encoding sequence listed in Table 1.

In other embodiments, the composition of the disclosure further comprises a third polynucleotide encoding a third protein. In one embodiment, the third polynucleotide comprises an mRNA encoding the third protein. In another embodiment, the third polynucleotide encodes an OX40L polypeptide.

In some embodiments, the OX40L polypeptide comprises an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to an OX40L polypeptide sequence listed in Table 1A, wherein the polypeptide is capable of having an OX40L activity (e.g., binding to an OX40L receptor).

In some embodiments, the OX40L polypeptide is encoded by a nucleic acid sequence at least about 70%, at least about 75%, at least about 80%, at least about 85%, at least about 90%, at least about 95%, at least about 99%, or 100% identical to an OX40L polypeptide encoding sequence listed in Table 1A.

In certain embodiments, the composition further comprises a fourth polynucleotide encoding the fourth protein. In some embodiments, the fourth polynucleotide comprises an mRNA encoding the fourth protein. In some embodiments, the first polynucleotide, the second polynucleotide, the third polynucleotide, and/or the fourth polynucleotide further comprise a nucleic acid sequence comprising a miRNA binding site.

In some embodiments, the miRNA binding site binds to miR-122. In some embodiments, the miRNA binding site binds to miR-122-3p or to miR-122-5p. In some embodiments, the miRNA binding site comprises a nucleotide sequence at least about 80%, at least about 85%, at least about 90%, at least about 95%, or 100% identical to SEQ ID NO: 24, wherein the miRNA binding site binds to miR-122 (miR-122-3p, 22 nts—aacgccauuaucacacuaaaua). In some embodiments, the miRNA binding site comprises a nucleotide sequence at least about 80%, at least about 85%, at least about 90%, at least about 95%, or 100% identical to SEQ ID NO: 26 wherein the miRNA binding site binds to miR-122

(miR-122-5p, 22 nts—uggaguguga caaugguguuug). In some embodiments, the first polynucleotide, the second polynucleotide, the third polynucleotide, and/or the fourth polynucleotide comprise two different miRNA binding sites or the same miRNA binding site. In some embodiments, the first polynucleotide, the second polynucleotide, the third polynucleotide, and/or the fourth polynucleotide comprise at least two, at least three, at least four, at least five, at least six, at least seven, at least eight, at least nine, or at least ten miRNA binding sites.

In some embodiments, the first polynucleotide, the second polynucleotide, the third polynucleotide, and/or the fourth polynucleotide further comprise a 5' UTR. In some embodiments, the 5' UTR comprises a nucleic acid sequence at least about 90%, at least about 95%, at least about 96%, at least about 97%, at least about 98%, at least about 99%, or 100% identical to a 5' UTR sequence listed in Table 3. In a particular embodiment, the 5' UTR comprises a nucleic acid sequence at least about 90%, at least about 95%, at least about 96%, at least about 97%, at least about 98%, at least about 99%, or 100% identical to SEQ ID NO: 27 or SEQ ID NO: 44. In another particular embodiment, the 5' UTR consists essentially of a nucleic acid sequence of SEQ ID NO: 27 or SEQ ID NO: 44. It should be understood that the 5' UTR can be one element within a larger construct, e.g., further including a 5' terminal cap, OFR (e.g., SEQ ID NOs: 17, 19, 71, 94, and 116), 3'UTR (e.g., SEQ ID NOs: 119 or 120), and/or polyA tail. In some embodiments, one or more miRNA binding sites can be positioned within the 5' UTR at one or more possible insertion sites.

In some embodiments, the first polynucleotide, the second polynucleotide, the third polynucleotide, and/or the fourth polynucleotide comprise a 3' UTR. In some embodiments, the 3' UTR comprises a nucleic acid sequence at least about 90%, at least about 95%, at least about 96%, at least about 97%, at least about 98%, at least about 99%, or 100% identical to a 3' UTR sequence listed in Table 4A or 4B. In a particular embodiment, the 3' UTR comprises a nucleic acid sequence at least about 90%, at least about 95%, at least about 96%, at least about 97%, at least about 98%, at least about 99%, or 100% identical to SEQ ID NO: 119 or 120. In another particular embodiment, the 3' UTR consists essentially of a nucleic acid sequence of SEQ ID NO: 119 or SEQ ID NO: 120. It should be understood that the 3' UTR can be one element within a larger construct, e.g., further including a 5' terminal cap, 5' UTR (e.g., SEQ ID NO: 27 or 44), OFR (e.g., SEQ ID NOs: 17, 19, 71, 94, and 116), and/or polyA tail.

In some embodiments, the miRNA binding site (e.g., a miR-122 binding site) is inserted within the 3' UTR. In some embodiments, a miRNA binding site (e.g., miR-122 binding site) is inserted within the 3' UTR downstream of the stop codon of the coding region within the polyribonucleotide of the invention, e.g., mRNA, in which case there are 3' UTR bases between the stop codon and the miR binding site(s). In some embodiments, if there are multiple copies of a stop codon in the construct, a miRNA binding site (e.g., miR-122 binding site) is inserted downstream of the final stop codon. In some embodiments, a miRNA binding site (e.g., miR-122 binding site) is inserted about 10, about 20, about 30, about 40, about 50, about 60, about 70, about 80, about 90, or about 100 bases downstream of the stop codon (or the final stop codon if there are multiple stop codons in the construct). In a particular embodiment, a miRNA binding site (e.g., miR-122 binding site) is inserted downstream of the stop codon (or the final stop codon if there are multiple stop codons in the construct) such that there are 79 3' UTR bases between the stop codon and the miR binding site(s).

In some embodiments, the first polynucleotide, the second polynucleotide, the third polynucleotide, and/or the fourth polynucleotide further comprise a spacer sequence fused to the miRNA binding site. In some embodiments, the spacer sequence comprises at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides.

In some embodiments, the first polynucleotide, the second polynucleotide, the third polynucleotide, and/or the fourth polynucleotide further comprise a 5' terminal cap. In some embodiments, the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the first polynucleotide, the second polynucleotide, the third polynucleotide, and/or the fourth polynucleotide comprise a 3' polyA tail. In some embodiments, the first polynucleotide, the second polynucleotide, the third polynucleotide, and/or the fourth polynucleotide are codon optimized. In some embodiments, the first polynucleotide, the second polynucleotide, the third polynucleotide, and/or the fourth polynucleotide are in vitro transcribed (IVT). In some embodiments, the first polynucleotide, the second polynucleotide, the third polynucleotide, and/or the fourth polynucleotide are chimeric. In some embodiments, the first polynucleotide, the second polynucleotide, the third polynucleotide, and/or the fourth polynucleotide are circular.

In some embodiments, the IL-23 polypeptide IL-12p40 subunit, the IL-23 polypeptide IL-23p19 subunit, the IL-36-gamma polypeptide, and/or the OX40L polypeptide are fused to a heterologous polypeptide.

In some embodiments, the first polynucleotide (e.g., mRNA), the second polynucleotide (e.g., mRNA), and the third polynucleotide (e.g., mRNA) comprise, consist essentially of, or consist of a 5' terminal cap, a 5' UTR, an open reading frame (ORF), a 3' UTR, and a polyA tail. In one embodiment, the first polynucleotide (e.g., mRNA) comprises, consists essentially of, or consists of a nucleic acid sequence of SEQ ID NO: 27 or 44, SEQ ID NO: 19, 71 or 141, and SEQ ID NO: 119 or 120. In another embodiment, the second polynucleotide (e.g., mRNA) comprises, consists essentially of, or consists of a nucleic acid sequence of SEQ ID NO: 27 or 44, SEQ ID NO: 17, 94 or 143, and SEQ ID NO: 119 or 120. In yet another embodiment, the third polynucleotide (e.g., mRNA) comprises, consists essentially of, or consists of a nucleic acid sequence of SEQ ID NO: 27 or 44, SEQ ID NO: 116 or 145, and SEQ ID NO: 119 or 120.

In a particular embodiment, the first polynucleotide comprises a nucleic acid sequence at least 50%, at least 60%, at least 70%, at least 80%, at least 85%, at least 90%, at least 95%, at least about 96%, at least about 97%, at least about 98%, at least about 99%, or 100% identical to SEQ ID NO: 142. In another particular embodiment, the first polynucleotide consists essentially of a nucleic acid sequence of SEQ ID NO: 142. In yet another particular embodiment, the first polynucleotide consists of a nucleic acid sequence of SEQ ID NO: 142.

In a particular embodiment, the second polynucleotide comprises a nucleic acid sequence at least 50%, at least 60%, at least 70%, at least 80%, at least 85%, at least 90%, at least 95%, at least about 96%, at least about 97%, at least about 98%, at least about 99%, or 100% identical to SEQ ID NO: 144. In another particular embodiment, the second polynucleotide consists essentially of a nucleic acid sequence of SEQ ID NO: 144. In yet another particular embodiment, the second polynucleotide consists of a nucleic acid sequence of SEQ ID NO: 144.

In a particular embodiment, the third polynucleotide comprises a nucleic acid sequence at least 50%, at least 60%, at least 70%, at least 80%, at least 85%, at least 90%, at least 95%, at least about 96%, at least about 97%, at least about 98%, at least about 99%, or 100% identical to SEQ ID NO: 146. In another particular embodiment, the third polynucleotide consists essentially of a nucleic acid sequence of SEQ ID NO: 146. In yet another particular embodiment, the third polynucleotide consists of a nucleic acid sequence of SEQ ID NO: 146.

In some embodiments, the first polynucleotide comprises a nucleotide sequence at least about 50%, at least about 55%, at least about 60%, at least about 65%, at least about 70%, at least about 75%, at least about 80%, at least about 85%, at least about 90%, at least about 95%, at least about 99%, or 100% identical to any of the IL-23-encoding sequences disclosed in Table 1.

In some embodiments, the second polynucleotide comprises a nucleotide sequence at least about 50%, at least about 55%, at least about 60%, at least about 65%, at least about 70%, at least about 75%, at least about 80%, at least about 85%, at least about 90%, at least about 95%, at least about 99%, or 100% identical to any of the IL-36-gamma-encoding sequences disclosed in Table 1.

In some embodiments, the second polynucleotide comprises a nucleotide sequence at least about 50%, at least about 55%, at least about 60%, at least about 65%, at least about 70%, at least about 75%, at least about 80%, at least about 85%, at least about 90%, at least about 95%, at least about 99%, or 100% identical to a sequence encoding IL-18, wherein said sequence comprises the an IL-18-encoding sequence disclosed in Table 1.

In some embodiments, the third polynucleotide comprises a nucleotide sequence at least 50%, at least 60%, at least 70%, at least 80%, at least 85%, at least 90%, at least 95%, at least 99%, or 100% identical to an OX40L-encoding sequence or OX40L_miR-122 construct of Table 1A.

In other embodiments, the composition for the disclosure comprises a fourth protein or a fourth polynucleotide encoding the fourth protein. For example, the fourth polynucleotide can comprise an mRNA encoding the fourth protein.

In some embodiments, the compositions disclosed herein are for use in reducing or decreasing a size of a tumor or inhibiting a tumor growth in a subject in need thereof. In some embodiments, the compositions disclosed herein are for use in reducing or decreasing a size of a tumor or inhibiting a tumor growth in a subject in need thereof.

In some embodiments, the compositions disclosed herein are administered to a subject in need thereof to treat cancer, and the administration of the composition treats or ameliorates the symptoms of the cancer.

In some embodiments, the cancer is selected from the group consisting of adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

In some embodiments, the first polynucleotide, the second polynucleotide and/or the third polynucleotide are formulated for delivery by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof. In some embodiments, the effective amount of a composition disclosed herein is between about 0.10 mg/kg to about 1000 mg/kg. In some embodiments, the compositions disclosed herein are formulated for administration to a human subject.

In some embodiments, the compositions and formulations disclosed herein are for use in the treatment of cancer. In some embodiments, the compositions and formulations disclosed are used for the manufacture of a medicament for the treatment of cancer.

It should be understood that there is no intent to limit the polynucleotide combinations disclosed herein (e.g., a first polynucleotide comprising an mRNA encoding an IL-23 polypeptide, a second polynucleotide comprising an mRNA encoding an IL-36-gamma polypeptide or an IL-18 polypeptide and a third polynucleotide comprising an mRNA encoding an OX40L polypeptide) to the particular forms disclosed. In this respect, the disclosures related to a particular polynucleotide and its respective encoded polypeptide in this section are equally applicable to additional polynucleotides and their respective encoded polypeptides, e.g., a third, fourth, fifth, etc. polypeptide, to be combined with the IL-23, IL-36-gamma, IL-18, and/or OX40L-encoding polynucleotides disclosed herein. Thus, disclosures related to a "first polynucleotide" or "second polynucleotide" (or respective encoded polypeptides) are equally applicable to a "third polynucleotide" and successive polynucleotides (or their respective encoded polypeptides).

In addition, specific disclosures related to a particular protein encoded by first or second polynucleotide, e.g., the disclosure that "the second polynucleotides comprise an mRNA encoding a human IL-36-gamma polypeptide which lacks at least one, at least two, at least three, at least four, at least five, at least six, at least seven, at least eight, at least nine, at least 10, at least 14, or at least 15 amino acids at the N-terminus or C-terminus of the wild type IL-36-gamma polypeptide," would be equally applicable to third and successive proteins. Accordingly, a person of skill in the art would understand that if the third protein was, for example, OX40L, the third polynucleotide could comprise an mRNA encoding a human OX40L polypeptide lacking at least one, at least two, at least three, at least four, at least five, at least six, at least seven, at least eight, at least nine, at least 10, at least 14, or at least 15 amino acids at the N-terminus or C-terminus of the wild type OX40L polypeptide, as disclosed above with respect to the first or second polypeptides of the present disclosure.

III. Methods of Use of Combinations of Polynucleotides Encoding Immune Modulatory Polypeptides Immunotherapy, also known as immuno-oncology, has revolutionized cancer treatment, by introducing therapies that target not the tumor, but the host immune system, therapies that possess unique adverse event profiles, and therapies that might cure many types of cancer. As used herein, the term "immunotherapy" refers to the treatment of disease by inducing, enhancing, or suppressing an immune response. Immunotherapies designed to elicit or amplify an immune response are referred to as "activation immunotherapies", while immunotherapies that reduce or suppress an immune response are referred to as "suppression immunotherapies".

Cancers of the lungs, kidney, bladder and skin are among those that derive substantial efficacy from treatment with immuno-oncology in terms of survival or tumor response, with melanoma possibly showing the greatest benefits. Immunotherapy often features checkpoint inhibitor treatment with an exciting new class of biologic drugs known as checkpoint inhibitor antibodies. Targets include, for example, PD-1, PD-L1, and CTLA-4.

Monoclonal antibodies that target PD-1, PD-L1, or CTLA4 can boost the immune response against cancer cells and have shown a great deal of promise in treating certain cancers. For example, pembrolizumab (Keytruda®) and nivolumab (Opdivo®) target PD-1; atezolizumab (Tecentriq®) targets PD-L1; and ipilimumab (Yervoy®) binds to and inhibits CTLA-4.

One concern with these drugs is that they can allow the immune system to attack some normal organs in the body, which can lead to serious or even life-threatening side effects in some people. One avenue to reduce such side effects is to administer other agents in combination with these checkpoint inhibitor antibodies, ideally enabling physicians to lower the treatment dose of the antibody.

Therefore, the present disclosure provides methods for treating cancer (e.g., reducing or decreasing a size of a tumor or inhibiting a tumor growth in a subject in need thereof) comprising the administration of any of the compositions disclosed in Section II, supra. In particular, the present disclosure provides methods for treating cancer (e.g., reducing or decreasing a size of a tumor or inhibiting a tumor growth in a subject in need thereof) comprising administering to a subject in need thereof:

(i) at least one polynucleotide comprising an mRNA encoding a protein comprising a IL-23 polypeptide, (ii) at least one polynucleotide comprising an mRNA encoding a protein comprising an IL-36-gamma polypeptide or an IL-18 polypeptide, and/or (iii) at least one polynucleotide comprising an mRNA encoding a protein comprising an OX40L polypeptide.

In some embodiments, the present disclosure provides a method of reducing or decreasing the size of a tumor and/or inhibiting a tumor growth in a subject in need thereof comprising administering to the subject at least two polynucleotides, wherein the at least two polynucleotides are selected from a first polynucleotide encoding an IL-23 polypeptide, a second polynucleotide encoding an IL-36-gamma polypeptide or an IL-18 polypeptide, and a third polynucleotide encoding an OX40L polypeptide. In one particular aspect, the method of reducing or decreasing the size of a tumor and/or inhibiting a tumor growth in a subject in need thereof comprises administering to the subject (i) a first polynucleotide encoding a first protein comprising an IL-23 polypeptide, (ii) a second polynucleotide encoding a second protein comprising an IL-36-gamma polypeptide or an IL-18 polypeptide, (iii) a third polypeptide encoding a third protein comprising an OX40L polypeptide, and/or (iv) any combination thereof. In another particular embodiment, the method of reducing or decreasing the size of a tumor and/or inhibiting a tumor growth in a subject in need thereof comprises administering to the subject (i) a first polynucleotide encoding a first protein comprising an IL-23 polypeptide (e.g., SEQ ID NO: 141), (ii) a second polynucleotide encoding a second protein comprising an IL-36-gamma polypeptide (e.g., SEQ ID NO: 143), and (iii) a third polypeptide encoding a third protein comprising an OX40L polypeptide (e.g., SEQ ID NO: 145), preferably in a mass ratio of 1:2:1 w/w. In some particular aspects, the method of reducing or decreasing the size of a tumor and/or inhibiting a tumor growth in a subject in need thereof comprises further comprises administering to the subject effective amounts of additional polynucleotide, e.g., a fourth or fifth polynucleotide encoding a fourth or fifth protein.

In other embodiments, the present disclosure provides methods of promoting an anti-tumor effect (e.g., induce T cell proliferation, induce T cell infiltration in a tumor, induce a memory T cell response, increasing the number of NK cells, etc.) by administering the first, second, and/or third polynucleotides (e.g., mRNAs) disclosed herein.

In one embodiment, the present disclosure provides a method of activating T cells in a subject in need thereof, inducing T cell proliferation in a subject in need thereof, inducing T cell infiltration in a tumor of a subject in need thereof, and/or inducing a memory T cell response in a subject in need thereof, comprising administering to the subject a first polynucleotide encoding IL-23, a second polynucleotide encoding IL-36-gamma or IL-18, a third polynucleotide encoding OX40L, or combinations thereof. In a particular embodiment, the method of activating T cells in a subject in need thereof, inducing T cell proliferation in a subject in need thereof, inducing T cell infiltration in a tumor of a subject in need thereof, and/or inducing a memory T cell response in a subject in need thereof comprises administering to the subject (i) a first polynucleotide encoding a first protein comprising an IL-23 polypeptide (e.g., SEQ ID NO: 141), (ii) a second polynucleotide encoding a second protein comprising an IL-36-gamma polypeptide (e.g., SEQ ID NO: 143), and (iii) a third polypeptide encoding a third protein comprising an OX40L polypeptide (e.g., SEQ ID NO: 145), preferably in a mass ratio of 1:2:1 w/w. In certain embodiments, the intratumoral administration of the first polynucleotide (e.g., mRNA), second polynucleotide (e.g., mRNA), and/or third polynucleotide (e.g., mRNA) can increase the efficacy of the anti-tumor effect (e.g., T cell infiltration in a tumor) compared to other routes of administration.

In one embodiment, activated T cells in the subject reduce or decrease the size of a tumor or inhibit the growth of a tumor in the subject. Activation of T cells can be measured using applications in the art such as measuring T cell proliferation; measuring cytokine production with enzyme-linked immunosorbant assays (ELISA) or enzyme-linked immunospot assays (ELISPOT); or detection of cell-surface markers associated with T cell activation (e.g., CD69, CD40L, CD137, CD25, CD71, CD26, CD27, CD28, CD30, CD154, and CD134) with techniques such as flow cytometry.

In one embodiment, T cell proliferation in the subject is directed to an anti-tumor immune response in the subject. In another aspect, the T cell proliferation in the subject reduces or decreases the size of a tumor or inhibits the growth of a tumor in the subject. T cell proliferation can be measured using applications in the art such as cell counting, viability staining, optical density assays, or detection of cell-surface markers associated with T cell activation (e.g., CD69, CD40L, CD137, CD25, CD71, CD26, CD27, CD28, CD30, CD154, and CD134) with techniques such as flow cytometry.

In one embodiment, T cell infiltration in a tumor of the subject is directed to an anti-tumor immune response in the subject. In another aspect, the T cell infiltration in a tumor of the subject reduces or decreases the size of a tumor or inhibits the growth of a tumor in the subject. T cell infiltration in a tumor can be measured using applications in the art such as tissue sectioning and staining for cell markers, measuring local cytokine production at the tumor site, or detection of T cell-surface markers with techniques such as flow cytometry.

In one embodiment, the memory T cell response in the subject is directed to an anti-tumor immune response in the subject. In another aspect, the memory T cell response in the subject reduces or decreases the size of a tumor or inhibits the growth of a tumor in the subject. A memory T cell response can be measured using applications in the art such as measuring T cell markers associated with memory T cells, measuring local cytokine production related to memory immune response, or detecting memory T cell-surface markers with techniques such as flow cytometry.

In certain embodiments, the activated T cells by the present methods are $CD4^+$ cells, $CD8^+$ cells, $CD62^+$ (L-selectin$^+$) cells, $CD69^+$ cells, $CD40L^+$ cells, $CD137^+$ cells, $CD25^+$ cells, $CD71^+$ cells, $CD26^+$ cells, $CD27^+$ cells, $CD28^+$ cells, $CD30^+$ cells, $CD45^+$ cells, $CD45RA^+$ cells, $CD45RO^+$ cells, $CD11b^+$ cells, $CD154^+$ cells, $CD134^+$ cells, $CXCR3^+$ cells, $CCR4^+$ cells, $CCR6^+$ cells, $CCR7^+$ cells, $CXCR5^+$ cells, $Crth2^+$ cells, gamma delta T cells, or any combination thereof. In some embodiments, the activated T cells by the present methods are $Th_1$ cells. In other embodiments, the T cells activated by the present methods are $Th_2$ cells. In other embodiments, the T cells activated by the present disclosure are cytotoxic T cells.

In some embodiments, the infiltrating T cells by the present methods are $CD4^+$ cells, $CD8^+$ cells, $CD62^+$ (L-selectin$^+$) cells, $CD69^+$ cells, $CD40L^+$ cells, $CD137^+$ cells, $CD25^+$ cells, $CD71^+$ cells, $CD26^+$ cells, $CD27^+$ cells, $CD28^+$ cells, $CD30^+$ cells, $CD45^+$ cells, $CD45RA^+$ cells, $CD45RO^+$ cells, $CD11b^+$ cells, $CD154^+$ cells, $CD134^+$ cells, $CXCR3^+$ cells, $CCR4^+$ cells, $CCR6^+$ cells, $CCR7^+$ cells, $CXCR5^+$ cells, $Crth2^+$ cells, gamma delta T cells, or any combination thereof. In some embodiments, the infiltrating T cells by the present methods are $Th_1$ cells. In other embodiments, the infiltrating T cells by the present methods are $Th_2$ cells. In other embodiments, the infiltrating T cells by the present disclosure are cytotoxic T cells.

In some embodiments, the memory T cells induced by the present methods are $CD4^+$ cells, $CD8^+$ cells, $CD62^+$ (L-selectin$^+$) cells, $CD69^+$ cells, $CD40L^+$ cells, $CD137^+$ cells, $CD25^+$ cells, $CD71^+$ cells, $CD26^+$ cells, $CD27^+$ cells, $CD28^+$ cells, $CD30^+$ cells, $CD45^+$ cells, $CD45RA^+$ cells, $CD45RO^+$ cells, $CD11b^+$ cells, $CD154^+$ cells, $CD134^+$ cells, $CXCR3^+$ cells, $CCR4^+$ cells, $CCR6^+$ cells, $CCR7^+$ cells, $CXCR5^+$ cells, $Crth2^+$ cells, gamma delta T cells, or any combination thereof. In some embodiments, the memory T cells by the present methods are $Th_1$ cells. In other embodiments, the memory T cells by the present methods are $Th_2$ cells. In other embodiments, the memory T cells by the present disclosure are cytotoxic T cells.

The present disclosure further provides a method of increasing the number of Natural Killer (NK) cells in a subject in need thereof comprising administering a polynucleotide comprising an mRNA encoding an OX40L polypeptide, a polynucleotide comprising an mRNA encoding IL-23, and/or a polynucleotide comprising an mRNA encoding IL-36-gamma or IL-18. In a particular embodiment, the method of increasing the number of Natural Killer (NK) cells in a subject in need thereof in need thereof comprises administering to the subject (i) a first polynucleotide encoding a first protein comprising an IL-23 polypeptide (e.g., SEQ ID NO: 141), (ii) a second polynucleotide encoding a second protein comprising an IL-36-gamma polypeptide (e.g., SEQ ID NO: 143), and (iii) a third polypeptide encoding a third protein comprising an OX40L polypeptide (e.g., SEQ ID NO: 145), preferably in a mass ratio of 1:2:1 w/w. In one aspect, the increase in the number of NK cells in the subject is directed to an anti-tumor immune response in the subject. In another aspect, the increase in the number of NK cells in the subject reduces or decreases the size of a tumor or inhibits the growth of a tumor in the subject. Increases in the number of NK cells in a subject can be measured using applications in the art such as detection of NK cell-surface markers (e.g., CD335/NKp46; CD336/NKp44; CD337/NPp30) or intracellular NK cell markers (e.g., perforin; granzymes; granulysin).

In certain embodiments, administration of at least two mRNAs selected from the mRNA encoding IL-23, the mRNA encoding IL-36-gamma or the mRNA encoding IL-18, and the mRNA encoding an OX40L polypeptide increases the total number of NK cells in the subject compared to the number of NK cells in a subject who is not administered with the at least two mRNAs or who is administered with the mRNA encoding IL-23 alone, the mRNA encoding IL-36-gamma alone, the mRNA encoding 11-18, or the mRNA encoding OX40L alone. In other embodiments, administration of at least two mRNAs selected from the mRNA encoding IL-23, the mRNA encoding IL-36-gamma, the mRNA encoding IL-18, and the mRNA encoding an OX40L polypeptide increases the total number of NK cells in the subject compared to a subject who is administered a dendritic cell transduced with the mRNA encoding an OX40L polypeptide alone, the mRNA encoding IL-23 alone, or the mRNA encoding IL-36-gamma alone, or the mRNA encoding IL-18. In other embodiments, administration of at least two mRNAs selected from the mRNA encoding IL-23, the mRNA encoding IL-36-gamma, the mRNA encoding IL-18, and the mRNA encoding an OX40L polypeptide increases the number of NK cells in the subject within the tumor microenvironment compared to that of a subject who is not administered with the at least two mRNAs or who is administered with the mRNA encoding IL-23 alone, the mRNA encoding IL-36-gamma alone, the mRNA encoding IL-18 alone, or the mRNA encoding the OX40L polypeptide alone. In other embodiments, administration of at least two mRNAs selected from the mRNA encoding IL-23, the mRNA encoding IL-36-gamma, the mRNA encoding IL-18, and the mRNA encoding an OX40L polypeptide increases the number of NK cells in a subject within the tumor microenvironment compared to that of a subject who is administered a dendritic cell transduced with the mRNA encoding an OX40L polypeptide alone, the mRNA encoding IL-23 alone, the mRNA encoding IL-18 alone, or the mRNA encoding IL-36-gamma alone. In other embodiments, the concentration of NK cells within the tumor microenvironment is increased while the total number of NK cells in the subject remains the same.

In certain embodiments of the disclosure, the number of NK cells is increased at least about two-fold, at least about three-fold, at least about four-fold, at least about five-fold, at least about six-fold, at least about seven-fold, at least about eight-fold, at least about nine-fold, or at least about ten-fold compared to a control (e.g., saline or an mRNA without IL-23, IL-36-gamma, or OX40L expression). In a particular embodiment, the number of NK cells is increased by at least two mRNAs selected from the mRNA encoding IL-23, the mRNA encoding IL-36-gamma, the mRNA encoding IL-18, and the mRNA encoding an OX40L polypeptide at least about two-fold compared to a control (e.g., saline or an mRNA without IL-23, IL-36-gamma, IL-18, or OX40L expression).

In one aspect, the administration of the combinations disclosed herein reduces or decreases a size of a tumor or inhibits a tumor growth at least 1.5 fold, at least 2 fold, at least 2.5 fold, at least 3 fold, at least 3.5 fold, at least 4 fold, at least 4.5 fold, or at least 5 fold better than (i) an administration of the first polynucleotide encoding the first protein alone (e.g., a polynucleotide encoding a protein comprising an IL-23 polypeptide), (ii) an administration of the second polynucleotide encoding the second protein alone (e.g., a polynucleotide encoding a protein comprising an IL-36-gamma polypeptide or an IL-18 polypeptide), or (iii) an administration of the third polynucleotide encoding the third protein alone (e.g., a polynucleotide encoding a protein comprising an OX40L polypeptide). The reduction or decrease in size or the inhibition of tumor growth can be measured using any method known in the art without undue experimentation.

In some aspects, the reduction or decrease a size of the tumor, or inhibition of tumor growth is at least 1.5 fold, at least 2 fold, at least 2.5 fold, at least 3 fold, at least 3.5 fold, at least 4 fold, at least 4.5 fold, or at least 5 fold higher than a control (e.g., treatment with PBS, treatment with a polynucleotide encoding a control protein, or treatment with a control protein).

In some aspects, the first polynucleotide administered according to the methods disclosed herein comprises a RNA, e.g., an mRNA, encoding the first protein (e.g., a protein comprising an IL-23 polypeptide). In some aspects, the second polynucleotide administered according to the methods disclosed herein comprises a RNA, e.g., an mRNA, encoding the second protein (e.g., a protein comprising an IL-36-gamma polypeptide or IL-18 polypeptide). In some aspects, the third polynucleotide administered according to the methods disclosed herein comprises a RNA, e.g., an mRNA, encoding the third protein (e.g., a protein comprising an OX40L polypeptide).

The methods disclosed herein comprise administering any of the compositions of the present disclosure by any route available, including, but not limited to, intratumoral, enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraperitoneal (into the peritoneum), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops.

In some aspects, the methods disclosed herein comprise administering the first polynucleotide, the second polynucleotide, and/or the third polynucleotide subcutaneously, intravenously, intramuscularly, intra-articularly, intra-synovially, intrasternally, intrathecally, intrahepatically, intralesionally, intracranially, intraventricularly, orally, by inhalation spray, topically, rectally, nasally, buccally, vaginally or via an implanted reservoir.

In some aspects, the methods disclosed herein comprise administering the first polynucleotide, the second polynucleotide, and/or the third polynucleotide as a formulation for intramuscular, subcutaneous, intratumoral, or intradermal delivery. In some embodiments, the formulation for intramuscular, subcutaneous, intratumoral, or intradermal delivery comprises additional polynucleotides, e.g., a third, a forth or a fifth polynucleotide. In certain embodiments, the intratumoral administration of the first polynucleotide, the second polynucleotide, and/or the third polynucleotide can increase the efficacy of the anti-tumor effect compared to other routes of administration. In some embodiments, additional polynucleotides, e.g., a third, a forth or a fifth polynucleotide, are administered intratumorally increasing the efficacy of the anti-tumor effect compared to other routes of administration.

In some aspects of the methods disclosed herein, the first polynucleotide, the second polynucleotide, and/or the third polynucleotide are formulated for in vivo delivery. In some embodiments, the first polynucleotide, the second polynucleotide, and the third polynucleotide can be co-formulated at varying weight ratios, for example, with equivalent amounts (by weight) of each polynucleotide or with any one of the polynucleotides present at 2, 3, 4, 5, 6, 7, 8, 9, 10, 11, 12, 13, 14, 15, 16, 17, 18, 19, 20, 25, 30, 35, 40, 45, or 50 times the amount (by weight) of the other polynucleotides. In one embodiment, the IL-23:IL-36gamma:OX40L polynucleotides are co-formulated at a weight (mass) ratio such that the IL-23 and OX40L polynucleotides are at about equal amounts and the IL-36gamma polynucleotide is present at a higher weight (mass) amount, such as 1.5, 2.0, 2.5, 3.0, 3.5, 4.0, 4.5 or 5.0 times greater weight (mass) amount. In one particular embodiment, the IL-23:IL-36gamma:OX40L polynucleotides are co-formulated at a weight (mass) ratio of 1:2:1. In used herein, the mass ratio can also be referred to by reference to a composition comprising polynucleotides (e.g., mRNAs) encoding OX40L:IL-23:IL-36gamma formulated at a weight (mass) ratio of 1:1:2.

In other embodiments, the IL-23:IL-36gamma:OX40L polynucleotides are co-formulated at a weight (mass) ratio of 1:1:1, 2:1:1, 1:2:1, 1:1:2, 3:1:1, 1:3:1, 1:1:3, 4:1:1, 1:4:1, 1:1:4, 5:1:1, 1:5:1, 1:1:5, 6:1:1, 1:6:1, 1:1:6, 7:1:1, 1:7:1, 1:1:8, 9:1:1, 1:9:1, 1:1:9, 10:1:1, 1:10:1, 1:1:10, 11:1:1, 1:11:1, 1:1:11, 12:1:1, 1:12:1, 1:1:12, 13:1:1, 1:13:1, 1:1:13, 14:1:1, 1:14:1, 1:1:14, 15:1:1, 1:15:1, 1:1:15, 16:1:1, 1:16:1, 1:1:16, 17:1:1, 1:17:1, 1:1:17, 18:1:1, 1:18:1, 1:1:18, 19:1:1, 1:19:1, 1:1:19, 20:1:1, 1:20:1, 1:1:20, 25:1:1, 1:25:1, 1:1:25, 30:1:1, 1:30:1, 1:1:30, 35:1:1, 1:35:1, 1:1:35, 40:1:1, 1:40:1, 1:1:40, 45:1:1, 1:45:1, 1:1:45, 50:1:1, 1:50:1, or 1:1:50. In other embodiments, each of the three polynucleotides can be present in the co-formulation at a different weight. By way of example only, the IL-23:IL-36gamma:OX40L polynucleotides can be co-formulated at a weight (mass) ratio of 1:2:3, 1:3:2, 2:1:3, 2:3:1, 3:1:2, or 3:2:1; or alternative at a weight (mass) ratio of 1:3:5, 1:5:3, 3:5:1, 3:1:5, 5:1:3, or 5:3:1; or alternative at a weight (mass) ratio of 1:5:10, 1:10:5, 5:1:10, 5:10:1, 10:1:5, or 10:5:1. In a particular embodiment, (i) a first polynucleotide encoding a first protein comprising an IL-23 polypeptide (e.g., SEQ ID NO: 140), (ii) a second polynucleotide encoding a second protein comprising an IL-36-gamma polypeptide (e.g., SEQ ID NO: 16), and (iii) a third polypeptide encoding a third protein comprising an OX40L polypeptide (e.g., SEQ ID NO: 21) are formulated in a weight (mass) ratio of 1:2:1. While this is a preferred formulation, the skilled artisan will readily appreciate that amounts of any one of the three constituents outside of this ratio may also provide formulations which are suitable for use in any of the methods disclosed herein.

The polynucleotide co-formulation can be administered as a single dose or as multiple doses. Co-formulations with varying weight (mass) ratios, e.g., co-formulation #1 in which the first polynucleotide, the second polynucleotide, and the third polynucleotide are present at 1:2:1 w/w and co-formulation #2 in which the first polynucleotide, the second polynucleotide, and the third polynucleotide are present at 1:1:2 w/w, can each be administered once or multiple times sequentially, concurrently, or simultaneously.

In one embodiment, the 1:2:1 co-formulation of (i) a first polynucleotide encoding a first protein comprising an IL-23 polypeptide (e.g., SEQ ID NO: 140), (ii) a second polynucleotide encoding a second protein comprising an IL-36-gamma polypeptide (e.g., SEQ ID NO: 16), and (iii) a third polypeptide encoding a third protein comprising an OX40L polypeptide (e.g., SEQ ID NO: 21) is administered as a single dose or as multiple doses.

In some aspects of the methods disclosed herein, the administration of a composition disclosed herein treats a cancer.

In certain aspects of the method disclosed herein, the compositions disclosed herein are administered to treat a cancer selected from the group consisting of adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

In some aspects of the methods disclosed herein, the first polynucleotide, the second polynucleotide, and/or the third polynucleotide are delivered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof. In other aspects of the methods disclosed herein, additional polynucleotides, e.g., a third, fourth or fifth polynucleotide are also delivered by a delivered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof In some embodiments, the effective amount of the compositions disclosed herein used in the methods of the present disclosure is between about 0.10 mg/kg to about 1000 mg/kg. In some embodiments, the subject is a human.

In some embodiments of the methods disclosed herein, the first polynucleotide encoding a first protein comprising an IL-23 polypeptide, the second polynucleotide encoding the second protein comprising an IL-36-gamma polypeptide or an IL-18 polypeptide, and the third polynucleotide encoding a third protein comprising an OX40L polypeptide are part of the same composition (e.g., a solution contains both the first, second, and third polynucleotide). In some embodiments of the methods disclosed herein, the first polynucleotide encoding a first protein comprising an IL-23 polypeptide, the second polynucleotide encoding the second protein comprising an IL-36-gamma polypeptide or an IL-18 polypeptide, and the third polynucleotide encoding a third protein comprising an OX40L polypeptide are part of different compositions (e.g., each polynucleotide can be in a different solution, or they can be combined in different solutions).

In some embodiments of the methods disclosed herein, the first polynucleotide encoding the first protein comprising an IL-23 polypeptide, and the second polynucleotide encoding the second protein comprising an IL-36-gamma polypeptide or an IL-18 polypeptide, are administered simultaneously. In some embodiments of the methods disclosed herein, the first polynucleotide encoding the first protein comprising an IL-23 polypeptide, and the second polynucleotide encoding the second protein comprising an IL-36-gamma polypeptide or an IL-18 polypeptide, are administered concurrently. In some embodiments of the methods disclosed herein, the first polynucleotide encoding the first protein comprising an IL-23 polypeptide, and a second polynucleotide encoding the second protein comprising an IL-36-gamma polypeptide or an IL-18 polypeptide, are administered sequentially (i.e., the first polynucleotide can be administered first, followed by the administration of the second polynucleotide, or vice versa).

In some embodiments of the methods disclosed herein, the polynucleotide encoding the first protein comprising an OX40L polypeptide, and the polynucleotide encoding the second protein comprising an IL-36-gamma polypeptide or an IL-18 polypeptide, are administered simultaneously. In some embodiments of the methods disclosed herein, the polynucleotide encoding the protein comprising an OX40L polypeptide, and the polynucleotide encoding the protein comprising an IL-36-gamma polypeptide or an IL-18 polypeptide, are administered concurrently. In some embodiments of the methods disclosed herein, the polynucleotide encoding the protein comprising an OX40L polypeptide, and a polynucleotide encoding the protein comprising an IL-36-gamma polypeptide, are administered sequentially (i.e., the OX40L polynucleotide can be administered first, followed by the administration of the IL-36-gamma polynucleotide or an IL-18 polynucleotide, or vice versa).

In some embodiments of the methods disclosed herein, the first polynucleotide encoding the first protein comprising an IL-23 polypeptide, the second polynucleotide encoding the second protein comprising an IL-36-gamma polypeptide or an IL-18 polypeptide, and the third polynucleotide encoding the third protein comprising an OX40L polypeptide are administered simultaneously. In some embodiments of the methods disclosed herein, the first polynucleotide encoding the first protein comprising an IL-23 polypeptide, the second polynucleotide encoding the second protein comprising an IL-36-gamma polypeptide or an IL-18 polypeptide, and the third polynucleotide encoding the third protein comprising an OX40L polypeptide are administered concurrently. In some embodiments of the methods disclosed herein, the first polynucleotide encoding the first protein comprising an IL-23 polypeptide, the second polynucleotide encoding the second protein comprising an IL-36-gamma polypeptide or an IL-18 polypeptide, and the third polynucleotide encoding the third protein comprising an OX40L polypeptide are administered sequentially (i.e., the first, second, and third polynucleotide can be administered according to any administration sequence). In a particular embodiment, the first protein comprising an IL-23 polypeptide (e.g., SEQ ID NO: 140, encoded by SEQ ID NO: 141), the second polynucleotide encoding the second protein comprising an IL-36-gamma polypeptide (e.g., SEQ ID NO: 16, encoded by SEQ ID NO: 143), and the third polynucleotide encoding the third protein comprising an OX40L polypeptide (e.g., SEQ ID NO: 21, encoded by SEQ ID NO: 145) are administered at a final weight (mass) ratio of 1:2:1 regardless of administration sequence.

In some embodiments, the present disclosure provides a method to treat a tumor (e.g., reduce the size of a tumor) located distally with respect to a treated tumor (proximal tumor). In some embodiments, the proximal tumor is treated with a first polynucleotide (e.g., an mRNA) encoding the first protein comprising an IL-23 polypeptide, a second polynucleotide (e.g., an mRNA) encoding a second protein comprising an IL-36-gamma polypeptide or an IL-18 polypeptide, and a third polynucleotide (e.g., an mRNA) encoding a third protein comprising an OX40L polypeptide, or a combination thereof. The methods disclosed herein can be used, for example, to treat tumors at locations where administration of a therapy intratumorally would be unsafe or impractical by administering a composition disclosed herein (e.g., an mRNA encoding an IL-23 polypeptide (e.g., SEQ ID NO: 141), a mRNA an IL-36-gamma polypeptide (e.g., SEQ ID NO: 143), and a third mRNA encoding an OX40L polypeptide (e.g., SEQ ID NO: 145) intratumorally to one or more accessible tumors. In some embodiments, the administration of a therapy disclosed herein to a proximal tumor can be used to treat metastases.

In some embodiments, the present disclosure provides a method to treat a tumor that is not responsive or it is poorly responsive to checkpoint inhibitors (e.g., a molecule targeting PD-1 or PD-L1 such as an anti-PD-L1 antibody) comprising the administration of a first polynucleotide (e.g., an mRNA) encoding the first protein comprising an IL-23 polypeptide, a second polynucleotide (e.g., an mRNA) encoding a second protein comprising an IL-36-gamma polypeptide or an IL-18 polypeptide, and a third polynucleotide (e.g., an mRNA) encoding a third protein comprising an OX40L polypeptide, or a combination thereof, together with a checkpoint inhibitor (e.g., an anti-PD-L1 antibody and/or an anti-PD-1 antibody and/or an anti-CTLA-4 antibody). In a particular embodiment, the first protein comprising an IL-23 polypeptide (e.g., SEQ ID NO: 140, encoded by SEQ ID NO: 141), the second polynucleotide encoding the second protein comprising an IL-36-gamma polypeptide (e.g., SEQ ID NO: 16, encoded by SEQ ID NO: 143), and the third polynucleotide encoding the third protein comprising an OX40L polypeptide (e.g., SEQ ID NO: 21, encoded by SEQ ID NO: 145) are administered together with a checkpoint inhibitor (e.g., an anti-PD-L1 antibody and/or an anti-PD-1 antibody and/or an anti-CTLA-4 antibody).

As used herein the terms "doublet," "doublet therapy," "doublet combination therapy," "doublet mRNA therapy" and grammatical variants thereof refer to a combination treatment in which two mRNAs encoding two proteins selected from an IL-23 polypeptide, an IL-36-gamma polypeptide or an IL-18 polypeptide, and an OX40L polypeptide are administered to a patient in need thereof. In some embodiments, the doublet therapy consists essentially of or consists of two mRNAs encoding an IL-23 polypeptide and an IL-36-gamma polypeptide or an IL-18 polypeptide, respectively. The doublet therapy can be administered, e.g., (i) as a single composition comprising both mRNAs, or (ii) as separate compositions each one comprising one mRNA. In some embodiments, the mRNAs in the doublet therapy are administered simultaneously. In other embodiments, the mRNAs in the doublet therapy are administered sequentially.

As used herein the terms "triplet," "triplet therapy," "triplet combination therapy," "triplet mRNA therapy" and grammatical variants thereof are used interchangeably and refer to a combination treatment in which three mRNAs encoding an IL-23 polypeptide, an IL-36-gamma polypeptide or an IL-18 polypeptide, and an OX40L polypeptide are administered to a patient in need thereof. In some embodiments, the triplet therapy consists essentially of or consists of three mRNAs encoding an IL-23 polypeptide, an IL-36-gamma polypeptide or an IL-18 polypeptide, and an OX40L polypeptide, respectively. The triplet therapy can be administered, e.g., (i) as a single composition comprising the three mRNAs (e.g., at a final weight (mass) ratio of 1:2:1 w/w IL-23:IL-36gamma:OX40L), or (ii) as separate compositions each one comprising one or two mRNAs (e.g., at a final weight (mass) ratio of 1:2:1 w/w IL-23:IL-36gamma:OX40L). In some embodiments, the mRNAs in the triplet therapy are administered simultaneously. In other embodiments, each mRNAs in the triplet therapy, or combinations thereof are administered sequentially. In a particular embodiment, the triplet therapy comprises or consists essentially of (i) a first polynucleotide encoding a first protein comprising an IL-23 polypeptide (e.g., SEQ ID NO: 140, encoded by SEQ ID NO: 141), (ii) a second polynucleotide encoding a second protein comprising an IL-36-gamma polypeptide (e.g., SEQ ID NO: 16, encoded by SEQ ID NO: 143), and (iii) a third polypeptide encoding a third protein comprising an OX40L polypeptide (e.g., SEQ ID NO: 145, encoded by SEQ ID NO: 145), preferably formulated in a weight (mass) ratio of 1:2:1, administered according to any administration sequence (e.g., sequential, concurrent, or simultaneous).

In some embodiments, the present disclosure provides methods of treatment wherein the administration of polynucleotides or combination of polynucleotides (e.g., mRNAs) disclosed herein to a subject in need thereof (e.g., a cancer patient) results in:

(a) increase in granulocyte level in one or more samples obtained from the subject after administration of doublet or triplet relative to a threshold level or relative to the level after administration of a single polynucleotide encoding an IL-23, an IL-36-gamma or an IL-18 polypeptide, or an OX40L polypeptide;

(b) increase in cross-presenting dendritic cell level in one or more samples obtained from the subject after administration of doublet or triplet relative to a threshold level or relative to the level after administration of a single polynucleotide encoding an IL-23, an IL-36-gamma or an IL-18 polypeptide, or an OX40L polypeptide;

(c) increase in effector to suppressor T cell ratio in one or more samples obtained from the subject after administration of doublet or triplet relative to a threshold level or relative to the ratio after administration of a single polynucleotide encoding an OX40L polypeptide;

(d) increase in effector memory T cell level in one or more samples obtained from the subject after administration of doublet or triplet relative to a threshold level or relative to the level after administration of a single polynucleotide encoding an OX40L polypeptide;

(e) increase in PDL1 expression level in one or more samples obtained from the subject after administration of doublet or triplet relative to a threshold level or relative to the level after administration of a single polynucleotide encoding an IL-23, an IL-36-gamma or an IL-18 polypeptide, or an OX40L polypeptide; or (f) a combination thereof.

The present disclosure provides a method of reducing or decreasing a size of a tumor or inhibiting a tumor growth in a subject in need thereof comprising administering to the subject a composition comprising (i) two polynucleotides (e.g., mRNAs) in combination (doublet), wherein the first polynucleotide encodes a first protein comprising an interleukin-23 polypeptide (IL-23), and the second polynucleotide encodes a second protein comprising an interleukin-36-gamma polypeptide (IL-36-gamma) or an IL-18 polypeptide; or, (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide (OX40L), wherein the administration of the doublet or triplet to the subject results in:

(a) increase in granulocyte level in one or more samples obtained from the subject after administration of doublet or triplet relative to a threshold level or relative to the level after administration of a single polynucleotide encoding an IL-23, an IL-36-gamma or an IL-18 polypeptide, or an OX40L polypeptide;

(b) increase in cross-presenting dendritic cell level in one or more samples obtained from the subject after administration of doublet or triplet relative to a threshold level or relative to the level after administration of a single polynucleotide encoding an IL-23, an IL-36-gamma or an IL-18 polypeptide, or an OX40L polypeptide;

(c) increase in effector to suppressor T cell ratio in one or more samples obtained from the subject after administration of doublet or triplet relative to a threshold level or relative to the ratio after administration of a single polynucleotide encoding an OX40L polypeptide;

(d) increase in effector memory T cell level in one or more samples obtained from the subject after administration of doublet or triplet relative to a threshold level or relative to the level after administration of a single polynucleotide encoding an OX40L polypeptide;

(e) increase in PDL1 expression level in one or more samples obtained from the subject after administration of doublet or triplet relative to a threshold level or relative to the level after administration of a single polynucleotide encoding an IL-23, an IL-36-gamma, or an OX40L polypeptide; or (f) a combination thereof.

Levels of granulocytes, cross-presenting dendritic cells (e.g., CD103+ cells), effector T cells (e.g., CD4+ or CD8+ cells), suppressor T cells (e.g., Treg cells), effector memory T cells (e.g., CD4+ or CD8+ cells), CD11b+ cells, expression of PD-L1, etc. can be measured in one or more samples obtained from the subject according to any methods known in the art.

In some embodiments, the increase in granulocyte level is quantitated as (i) granulocytes as percent of CD45+ cells, or (ii) granulocytes per mg of tumor. In some embodiments, the cross-presenting dendritic cells are CD103+ cells. In some embodiments, the increase in cross-presenting dendritic cell level is quantitated as (i) cross-presenting dendritic cells per mg of tumor, (ii) cross-presenting CD103+ dendritic cells in tumor draining lymph node (TdLN), (iii) cross-presenting CD103+ dendritic cells as percentage of CD45+ cells, or any combination thereof. In some embodiments, the effector to suppressor T cell ratio is quantitated as CD8:Treg ratio. In embodiments, the effector memory T cells are CD4+ and/or CD8+ cells. In some embodiments, PD-L1 expression level is quantitated as (i) number of positive CD11b+ cells, or (ii) PD-L1 expression in CD11b+ cells.

The present disclosure also provides a method to increase granulocyte levels in a subject in need thereof comprising administering to the subject a composition comprising (i) two polynucleotides (e.g., mRNAs) in combination (doublet), wherein first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs) in combination (triplet), where first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, wherein granulocyte levels are measured in one or more samples obtained from the subject. In some embodiments, the increase in granulocyte level is measured as (i) granulocytes as percent of CD45+ cells, and/or (ii) granulocytes per mg of tumor, relative to a threshold level or relative to the level after administration of a single polynucleotide encoding IL-23 or a single polynucleotide encoding IL-36-gamma or an IL-18 polypeptide.

Also provided is a method to increase cross-presenting dendritic cell levels in a subject in need thereof comprising administering to the subject a composition comprising (i) two polynucleotides (e.g., mRNAs) in combination (doublet), wherein first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs:141, 143 and 145) in combination (triplet), where first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, wherein cross-presenting dendritic cell levels are measured in one or more samples obtained from the subject. In some embodiments, the cross-presenting dendritic cells are CD103+ cells. In some embodiments, the increase in cross-presenting CD103+ dendritic cell level is measured as (i) cross-presenting CD103+ dendritic cells per mg of tumor, (ii) cross-presenting CD103+ dendritic cells in TdLN, (iii) cross-presenting CD103+ dendritic cells as percentage of CD45+ cells, or (iv) a combination thereof, relative to a threshold level or relative to the level after administration of a single polynucleotide encoding IL-23, a single polynucleotide encoding IL-36-gamma or an IL-18 polypeptide, or a single polynucleotide encoding OX40L.

The present disclosure also provides a method to increase the effector to suppressor T cell ratio in a subject in need thereof comprising administering to the subject a composition comprising (i) two polynucleotides (e.g., mRNAs) in combination (doublet), wherein first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, wherein the effector to suppressor T cell ratio is measured in one or more samples obtained from the subject. In some embodiments, the effector T cell to suppressor T cell ratio is measured as the ratio between CD8+ cells and regulatory T cells (Treg), i.e., the CD8:Treg ratio.

The present disclosure also provides a method to increase effector memory T cells levels in a subject in need thereof comprising administering to the subject a composition comprising (i) two polynucleotides (e.g., mRNAs) in combination (doublet), wherein the first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, wherein the effector memory T cells levels are measured in one or more samples obtained from the subject. In some embodiments, the effector memory T cells are CD4+ and/or CD8+ cells. In some embodiments, the increase in effector memory T cells levels is measured as effector memory T cells within the tumor relative to a threshold level or relative to the level after administration of a single polynucleotide encoding OX40L.

The present disclosure also provides a method to increase PD-L1 positive cells levels in a subject in need thereof comprising administering to the subject a composition comprising (i) two polynucleotides (e.g., mRNAs) in combination (doublet), wherein the first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, wherein the PD-L1 positive cells levels are measured in one or more samples obtained from the subject. In some embodiments, the PD-L1 positive cells are CD11b+ cells.

In some aspects of the methods disclosed herein, the sample or samples obtained from the subject are selected from the group consisting of tumoral tissue, tumor infiltrate, blood, plasma, and any combination thereof. In some embodiments, the one or more control samples are a sample or samples obtained from a healthy subject or a subject with a tumor.

In some embodiments, the threshold level is a predetermined value or a value obtained from one or more samples, e.g., a value obtained from a pool of samples from a population of healthy individuals or a population of subjects with a tumor.

The present disclosure also provides a method of determining whether to treat a subject having a tumor disease with a composition comprising (i) two polynucleotides (e.g., mRNAs) in combination (doublet), wherein the first polynucleotide encodes a first protein comprising an IL-23 polypeptide, and the second polynucleotide encodes a second protein comprising an IL-36-gamma polypeptide or an IL-18 polypeptide; (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, or (iii) any composition disclosed herein, the method comprising (i) administering to the submitted an initial dose of doublet or triplet, and
(ii) treating the subject if after administration of the initial dose of doublet or triplet the subject is determined to have an increase in
 (a) level of granulocytes,
 (b) level of cross-presenting dendritic cells,
 (c) effector to suppressor T cell ratio,
 (d) level of effector memory T cells,
 (e) level of PD-L1 positive cells,
 (f) PD-L1 expression, or
 (g) a combination thereof,
with respect to a threshold level.

Also provided is a method of selecting a subject diagnosed with a tumor as a candidate for treatment with a composition comprising (i) two polynucleotides (e.g., mRNAs) in combination (doublet), wherein the first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs: 141, 143 and 145) in combination (triplet), where the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, or (iii) any composition disclosed herein, the method comprising (i) administering to the subject an initial dose of doublet or triplet, and
(ii) selecting the subject for treatment if after administration of the initial dose of doublet or triplet the subject is determined to have an increase in
  (a) level of granulocytes,
  (b) level of cross-presenting dendritic cells,
  (c) effector to suppressor T cell ratio,
  (d) level of effector memory T cells,
  (e) level of PD-L1 positive cells,
  (f) PD-L1 expression, or
  (g) a combination thereof, with respect to a threshold level.

The present disclosure also provides a method of measuring the efficacy of a composition to treat a tumor in a subject in need thereof, wherein the composition comprises (i) two polynucleotides (e.g., mRNAs) in combination (doublet), wherein the first polynucleotide encodes a first protein comprising an IL-23 polypeptide, and the second polynucleotide encodes a second protein comprising an IL-36-gamma polypeptide or an IL-18 polypeptide; or, (ii) three polynucleotides (e.g., mRNAs, e.g., SEQ ID NOs: 141, 143 and 145) in combination (triplet), wherein the first polynucleotide encodes a first protein comprising an IL-23 polypeptide, the second polynucleotide encodes a second protein comprising an IL-36-gamma polypeptide or an IL-18 polypeptide, and the third polynucleotide encodes a third protein comprising an OX40L polypeptide, or (iii) any composition disclosed herein, wherein the method comprises measuring in at least one sample taken from the subject (a) level of granulocytes, (b) level of cross-presenting dendritic cells, (c) effector to suppressor T cell ratio, (d) level of effector memory T cells, (e) level of PD-L1 positive cells, (f) PD-L1 expression, or (g) a combination thereof, wherein an increase in at least one of the measurements with respect to a threshold level indicates that the subject is responding to treatment with the doublet or triplet.

IV. Diseases, Disorders and/or Conditions

In some embodiments, the polynucleotides (e.g., mRNA) of the present disclosure, e.g., a first polynucleotide comprising an mRNA encoding a first protein comprising an IL-23 polypeptide, a second polynucleotide comprising an mRNA encoding a second protein comprising an IL-36-gamma polypeptide or an IL-18 polypeptide, and/or a third polynucleotide comprising an mRNA encoding a third protein comprising an OX40L polypeptide can be used to reduce or decrease a size of a tumor or inhibit a tumor growth in a subject in need thereof.

In some embodiments, additional polynucleotides (e.g., a forth polynucleotide) can be administered in combination with a first polynucleotide comprising an mRNA encoding a first protein comprising an IL-23 polypeptide, a second polynucleotide comprising an mRNA encoding a second protein comprising an IL-36-gamma polypeptide or an IL-18 polypeptide, and/or a third polynucleotide comprising an mRNA encoding a third protein comprising an OX40L polypeptide to reduce or decrease a size of a tumor or inhibit a tumor growth in a subject in need thereof.

Accordingly, in some embodiments, the polynucleotides (e.g., mRNA) of the present disclosure, i.e., a first polynucleotide comprising an mRNA encoding a first protein comprising an IL-23 polypeptide, a second polynucleotide comprising an mRNA encoding a second protein comprising an IL-36-gamma polypeptide or an IL-18 polypeptide, and a third polynucleotide comprising an mRNA encoding a third protein comprising an OX40L polypeptide can be used to reduce or decrease a size of a tumor or inhibit a tumor growth in a subject in need thereof.

In some embodiments, the tumor is associated with a disease, disorder, and/or condition. In a particular embodiment, the disease, disorder, and/or condition is a cancer. Thus, in one aspect, the administration of a first polynucleotide comprising an mRNA encoding a first protein comprising an IL-23 polypeptide, a second polynucleotide comprising an mRNA encoding an IL-36-gamma polypeptide or an IL-18 polypeptide, and/or a third polynucleotide comprising an mRNA encoding an OX40L polypeptide, treats a cancer.

In another aspect, the administration of a first polynucleotide comprising an mRNA encoding a first protein comprising an IL-23 polypeptide, a second polynucleotide comprising an mRNA encoding an IL-36-gamma polypeptide or an IL-18 polypeptide, and further in combination with a third polynucleotide comprising an mRNA encoding third protein, wherein the third protein comprises an OX40L polypeptide, treats a cancer.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor at various stages. In certain embodiments, the cancer or tumor is stage 0, such that, e.g., the cancer or tumor is very early in development and has not metastasized. In some embodiments, the cancer or tumor is stage I, such that, e.g., the cancer or tumor is relatively small in size, has not spread into nearby tissue, and has not metastasized. In other embodiments, the cancer or tumor is stage II or stage III, such that, e.g., the cancer or tumor is larger than in stage 0 or stage I, and it has grown into neighboring tissues but it has not metastasized, except potentially to the lymph nodes. In other embodiments, the cancer or tumor is stage IV, such that, e.g., the cancer or tumor has metastasized. Stage IV can also be referred to as advanced or metastatic cancer.

In some aspects, the cancer can include, but is not limited to, adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment.

In some aspects, the tumor is a solid tumor. A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas include, e.g., acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum.

Additional cancers that can be treated include, e.g., Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

Cancers and/or tumors amenable to treatment in accordance with the methods of the instant invention include those accessible via direct intratumoral and/or regional administration, i.e., administration in the region of a target tumor. For example, tumors accessible to administration with a simple syringe injection are readily amenable to treatment. Also amenable to treatment are tumors in which injection requires some imaging and/or guided administration, and/or those in which injection is possible via image-guided percutaneous injection, or catheter/cannula directly into site, or endoscopy.

Exemplary cancers and/or tumors amenable to treatment include melanoma, breast cancer, e.g., TNBC, head & neck cancer, sarcoma, CTLC, NHL, basal cell carcinoma, non-small cell lung carcinoma (NSCLC), hepatocellular carcinoma (HCC), glioma, gastric cancer, and pancreatic cancer. Particularly amenable to treatment are melanoma, breast cancer, e.g., TNBC, and head & neck cancer.

Melanoma

Melanoma is one of the most aggressive forms of skin cancer. Furthermore, incidence rates are increasing and there are few treatment options available. Melanoma is detected at a rate of 132,000 new cases per year worldwide (76,000 new cases per year in the United States) accounting for approximately 10,000 deaths per year in the US. About 25% are in patients <40 years. PD-1 inhibitors (e.g., nivolumab, pembrolizumab) are currently the standard of care and evidence a durable response rate of 37%, and progression-free survival of 30% at 2 years. However, there is also observed a rapid progression for non-responders (median 4m) and overall survival of only 40% is observed at 3 years with no evidence of plateau, i.e., treated patients continue to regress.

Thus, there is a clear need for new, more effective treatments in this setting. Melanoma also serves as a model tumor for understanding immunity to cancer. Melanoma tumor-associated antigens were among the first cancer antigens to be identified and classified, with further studies showing that many of these are also expressed by other tumor types. In addition, melanoma regression has been associated with vitiligo, visibly confirming an active role of the immune system in this type of cancer, and spontaneous regression of primary melanomas has also been observed in some cases. These observations, relating to the activity of the immune system in melanoma, provided strong evidence that this tumor should prove to be amenable to immunotherapy. Against this background, melanoma has long been at the cutting edge of immuno-oncology research and will likely continue to be used as a model tumor to increase our understanding of immuno-oncology and to inform treatment options in other types of immune-therapy responsive cancers.

Triple Negative Breast Cancer

Breast cancers display different characteristics that require different types of treatment. Most breast cancers are hormone receptor-positive, meaning that the cancer cells are stimulated to grow from exposure to the female hormones estrogen and/or progesterone. Other breast cancers are referred to as HER2-positive, which means that they overexpress the human epidermal growth factor receptor 2, a biologic pathway that is involved in replication and growth of a cell. HER2-positive breast cancers account for approximately 25% of breast cancers and are treated with agents that target the receptor to slow growth and replication. Breast cancers that are not stimulated to grow from exposure to estrogen or progesterone and are HER2-negative are called triple-negative breast cancers. Triple-negative breast cancers tend to be more aggressive than other breast cancers and have fewer treatment options as compared to other breast cancers. Although breast cancer has historically been considered immunologically silent, several preclinical and clinical studies suggest that immunotherapy has the potential to improve clinical outcomes for patients with breast cancer. Overall, immunotherapy holds several key advantages over conventional chemotherapeutic and targeted treatments directed at the tumor itself. First, immunotherapy generally results in fewer side effects, enabling it to be administered for longer periods of time and/or in combination with other agents without added toxicity. Patients may also be less likely to develop resistance to immunotherapy because of the immune system's ability to target multiple cancer antigens simultaneously, and adapt to changing cancer cells.

Head and Neck Cancer

Head and neck squamous cell carcinoma (HNSCC) induces an immune suppressive state via various mechanisms. Patients with HNSCC have altered lymphocyte homeostasis (mainly reduced levels of CD3+, CD4+, and CD8+ T cells) compared to healthy controls. This imbalance even remains 2 years after treatment with curative intent. Consistently, a higher number of tumor infiltrating CD4+ and CD8+ lymphocytes is associated with better overall survival in HNSCC patients. Additionally, natural killer cell (NK) function is impaired in HNSCC patients.

HNSCC cells apply certain strategies to escape immunosurveillance and subsequent elimination. For example, they interact indirectly with the immune system to maintain an immunosuppressive microenvironment. In essence, HNSCC exploit the fact that the immune system is tightly regulated through immune checkpoints to avoid autoimmunity or immune system over-activation under physiological circumstances.

Tumor-Directed Immuno-Therapy

Important goals for the field of immuno-oncology are to improve the response rate and increase the number of tumor indications that respond to immunotherapy, without increasing adverse side effects. One approach to achieve these goals is to use tumor-directed immunotherapy, i.e., to focus the immune activation to the most relevant part of the immune system. This may improve anti-tumor efficacy as well as reduce immune-related adverse events. Tumor-directed immune activation can be achieved by local injections of immune modulators directly into the tumor or into the tumor area. Therapies focused on targeting checkpoint inhibitors and co-stimulatory receptors can generate tumor-specific T cell responses through localized immune activation.

Modulation of Tumor Microenvironments

In certain embodiments, a composition of the invention (e.g., doublet or triplet mRNA composition) can be used to modulate tumor microenvironments and/or can be selected for treatment based on the tumor microenvironment in the subject to be treated. In one embodiment, a composition of the invention is used to treat a tumor that has an inflamed tumor microenvironment. In another embodiment, a composition of the invention is used to treat a tumor that has an immunosuppressive tumor microenvironment. In yet another embodiment, a composition of the invention is used to treat a tumor that has an immunologically barren tumor microenvironment. In situations in which the tumor has an inflamed tumor microenvironment, i.e., the tumor microenvironment already exhibits infiltration of immune and/or inflammatory cells, treatment with doublet mRNA therapy may be sufficient rather than treatment with triplet mRNA therapy (see e.g., Example 23, FIG. 45A-B). For example, for treatment of a tumor with an inflamed tumor microenvironment, in one embodiment, the tumor is treated with a polynucleotide encoding an IL-12 family member (e.g., IL-23) and a polynucleotide encoding an immune response co-stimulatory signal (e.g., OX40L).

V. Combination Therapies

In certain embodiments, the methods of treatment disclosed herein comprise administering a first polynucleotide encoding a first protein comprising an IL-23 polypeptide, a second polynucleotide encoding an IL-36-gamma polypeptide or an IL-18 polypeptide, and/or a third polynucleotide encoding a third protein comprising an OX40L polypeptide and further comprise administering one or more anti-cancer agents to the subject. In certain embodiments, the methods of treatment disclosed herein comprise administering a first polynucleotide encoding a first protein comprising an IL-23 polypeptide, a second polynucleotide encoding an IL-36-gamma polypeptide or an IL-18 polypeptide, a third polynucleotide encoding an OX40L polypeptide, and further comprise administering one or more anti-cancer agents to the subject.

In some embodiments, the one or more anti-cancer agents are an mRNA. In certain embodiments, the one or more anti-cancer agents are an mRNA encoding a tumor antigen. In other embodiments, the one or more anti-cancer agents are not a tumor antigen or an mRNA encoding a tumor antigen. In some embodiments, the one or more anti-cancer agents is an approved agent by the United States Food and Drug Administration. In other embodiments, the one or more anti-cancer agents is a pre-approved agent by the United States Food and Drug Administration.

In some aspects, the subject for the present methods or compositions has been treated with one or more standard of care therapies. In other aspects, the subject for the present methods or compositions has not been responsive to one or more standard of care therapies or anti-cancer therapies.

In recent years, the introduction of immune checkpoint inhibitors for therapeutic purposes has revolutionized cancer treatment. Of interest are therapies featuring combinations of checkpoint inhibitors with other costimulatory or inhibitory molecules.

T cell regulation, i.e., activation or inhibition is mediated via co-stimulatory or co-inhibitory signals. This interaction is exerted via ligand/receptor interaction. T cells harbor a myriad of both activating receptors, such as OX40, and inhibitory receptors (i.e., immune checkpoints) such as programmed death receptor 1 (PD-1) or cytotoxic T lymphocyte-associated protein 4 (CTLA-4) (Mellman et al. 2011 Nature.; 480:480-489). Activation of this immune checkpoints results in T cell deactivation and commandeering these pathways by tumor cells contributes to their successful immune escape.

Immune checkpoint inhibitors such as pembrolizumab or nivolumab, which target the interaction between programmed death receptor 1/programmed death ligand 1 (PD-1/PD-L1) and PD-L2, have been recently approved for the treatment of various malignancies and are currently being investigated in clinical trials for cancers including melanoma, head and neck squamous cell carcinoma (HNSCC). Data available from these trials indicate substantial activity accompanied by a favorable safety and toxicity profile in these patient populations.

For example, checkpoint inhibitors have been tested in clinical trials for the treatment of melanoma. In particular, phase III clinical trials have revealed that therapies such as ipilimumab and pembrolizumab, which target the CTLA4 and PD-1 immune checkpoints, respectively, have raised the three-year survival of patients with melanoma to ~70%, and overall survival (>5 years) to ~30%.

Likewise, checkpoint inhibitors have been tested in clinical trials for the treatment of head and neck cancer. In preclinical studies, it had been shown that that 45-80% of HNSCC tumors express programmed death ligand 1 (PD-L1) (Zandberg et al. (2014) Oral Oncol. 50:627-632). Currently there are dozens of clinical trials evaluating the efficacy and safety of immune checkpoint inhibitors as monotherapy or in combination regimens in HNSCC. For example, clinical trials with PD 1, PD-L1, and CTLA-4 inhibitors are being tested in HNSCC. Data that the PD-1 antibody pembrolizumab might be effective in metastatic/recurrent (R/M) HNSCC patients were generated in the phase 1b Keynote-012 phase I/II trial (Cheng. ASCO 2015, oral presentation). More recently the data of the randomized CheckMate-141 phase III clinical trial were presented (Gillison. AACR 2016, oral presentation). This study investigated the efficacy of the monoclonal PD 1 antibody nivolumab given every 2 weeks in platinum-refractory R/M HNSCC patients. The study was stopped early due to superiority of the nivolumab arm of the study.

In one aspect, the subject has been previously treated with a PD-1 antagonist prior to the polynucleotide of the present disclosure. In another aspect, the subject has been treated with a monoclonal antibody that binds to PD-1 prior to the polynucleotide of the present disclosure. In another aspect, the subject has been treated with an anti-PD-1 monoclonal antibody therapy prior to the polynucleotide of the present methods or compositions. In other aspects, the anti-PD-1 monoclonal antibody therapy comprises nivolumab, pembrolizumab, pidilizumab, or any combination thereof. In another aspect, the subject has been treated with a monoclonal antibody that binds to PD-L1 prior to the polynucleotide of the present disclosure. In another aspect, the subject has been treated with an anti-PD-L1 monoclonal antibody therapy prior to the polynucleotide of the present methods or compositions. In other aspects, the anti-PD-L1 monoclonal antibody therapy comprises durvalumab, avelumab, MEDI473, BMS-936559, aezolizumab, or any combination thereof.

In some aspects, the subject has been treated with a CTLA-4 antagonist prior to treatment with the compositions of present disclosure. In another aspect, the subject has been previously treated with a monoclonal antibody that binds to CTLA-4 prior to the compositions of the present disclosure. In another aspect, the subject has been treated with an anti-CTLA-4 monoclonal antibody prior to the polynucleotide of the present disclosure. In other aspects, the anti-CTLA-4 antibody therapy comprises ipilimumab or tremelimumab.

In some aspects, the disclosure is directed to a method of treating cancer and/or a method of immunotherapy in a subject in need thereof comprising administering to the subject (e.g., intratumorally, intraperitoneally, or intravenously) the first, second, and/or third polynucleotide (e.g., RNA, e.g., mRNA) encoding an IL-23 polypeptide, or an IL-36gamma polypeptide, an IL-18 polypeptide, and an OX40L polypeptide, respectively, in combination with a PD-1 antagonist, e.g., an antibody or antigen-binding portion thereof that specifically binds to PD-1, e.g., an anti-PD-1 monoclonal antibody.

In one embodiment, the anti-PD-1 antibody (or an antigen-binding portion thereof) useful for the disclosure is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www-.cancer.gov/drugdictionary?cdrid=695789 (last accessed: Dec. 14, 2014). Pembrolizumab has been approved by the FDA for the treatment of relapsed or refractory melanoma and advanced NSCLC.

In another embodiment, the anti-PD-1 antibody useful for the disclosure is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223.

In other embodiments, the anti-PD-1 antibody is MEDI0680 (formerly AMP-514), which is a monoclonal antibody against the PD-1 receptor. MEDI0680 is described, for example, in U.S. Pat. No. 8,609,089B2 or in http://www.cancer.gov/drugdictionary?cdrid=756047 (last accessed Dec. 14, 2014).

In certain embodiments, the anti-PD-1 antibody is BGB-A317, which is a humanized monoclonal antibody. BGB-A317 is described in U.S. Publ. No. 2015/0079109.

In certain embodiments, a PD-1 antagonist is AMP-224, which is a B7-DC Fc fusion protein. AMP-224 is discussed in U.S. Publ. No. 2013/0017199 or in http://www.cancer-.gov/publications/dictionaries/cancer-drug?cdrid=700595 (last accessed Jul. 8, 2015).

In other embodiments, the disclosure includes a method of treating cancer and/or a method of immunotherapy in a subject in need thereof comprising administering to the subject (e.g., intratumorally, intraperitoneally, or intravenously) the first, second, and/or third polynucleotide (e.g., RNA, e.g., mRNA) encoding an IL-23 polypeptide, or an IL-36gamma polypeptide, an IL-18 polypeptide, and an OX40L polypeptide, respectively, together with an antibody or an antigen binding portion thereof that specifically binds to PD-1, e.g., an anti-PD-1 monoclonal antibody, e.g., an anti-PD-1 monoclonal antibody comprises Nivolumab, Pembrolizumab, Pidilizumab, or any combination thereof.

In some aspects, the disclosure is directed to a method of treating cancer and/or a method of immunotherapy in a subject in need thereof comprising administering to the subject (e.g., intratumorally, intraperitoneally, or intravenously) the first, second, and/or third polynucleotide (e.g., RNA, e.g., mRNA) encoding an IL-23 polypeptide, or an IL-36gamma polypeptide, an IL-18 polypeptide, and an OX40L polypeptide, respectively, in combination with a PD-L1 antagonist, e.g., an antibody or antigen-binding portion thereof that specifically binds to PD-L1, e.g., an anti-PD-L1 monoclonal antibody, e.g., an anti-PD-L1 monoclonal antibody comprises Durvalumab, Avelumab, MEDI473, BMS-936559, Atezolizumab, or any combination thereof.

In certain embodiments, the anti-PD-L1 antibody useful for the disclosure is MSB0010718C (also called Avelumab; See US 2014/0341917) or BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) J Clin Oncol 31(suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands.

In other aspects, the disclosure is directed to a method of treating cancer and/or a method of immunotherapy in a subject in need thereof comprising administering to the subject (e.g., intratumorally, intraperitoneally, or intravenously) the first, second, and/or third polynucleotide (e.g., RNA, e.g., mRNA) encoding an IL-23 polypeptide, or an IL-36gamma polypeptide, an IL-18 polypeptide, and an OX40L polypeptide, respectively, in combination with a CTLA-4 antagonist, e.g., an antibody or antigen-binding portion thereof that specifically binds to CTLA-4, e.g., an anti-CTLA-4 monoclonal antibody, e.g., an anti-CTLA-4 monoclonal antibody comprises Ipilimumab or Tremelimumab, or any combination thereof.

An exemplary clinical anti-CTLA-4 antibody is the human mAb 10D1 (now known as ipilimumab and marketed as YERVOY®) as disclosed in U.S. Pat. No. 6,984,720. Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

In one embodiment, a first polynucleotide encoding a first protein comprising an IL-23 polypeptide, a second polynucleotide encoding a second protein comprising an IL-36 gamma polypeptide or an IL-18 polypeptide, and a third polypeptide encoding a third protein comprising an OX40L polypeptide are administered in combination with an antibody or an antigen-binding portion thereof which specifically binds to CTLA-4, an antibody or antigen-binding portion thereof which specifically binds to a PD-1 receptor, an antibody or antigen-binding portion thereof which specifically binds to a PD-L1 receptor, a polynucleotide encoding the same, or any combination thereof.

In one embodiment, a first polynucleotide encoding a first protein comprising an IL-23 polypeptide, a second polynucleotide encoding a second protein comprising an IL-36 gamma polypeptide or an IL-18 polypeptide, and a third polypeptide encoding a third protein comprising an OX40L polypeptide are administered in combination with an antibody or an antigen-binding portion thereof that specifically binds to a PD-1 or PD-L1 receptor or a polynucleotide encoding the same.

In another embodiment, a first polynucleotide encoding a first protein comprising an IL-23 polypeptide, a second polynucleotide encoding a second protein comprising an IL-36 gamma polypeptide or an IL-18 polypeptide, and a third polypeptide encoding a third protein comprising an OX40L polypeptide are administered in combination with an antibody or an antigen-binding portion thereof that specifically binds to a CTLA-4 or a polynucleotide encoding the same.

In yet another embodiment, a first polynucleotide encoding a first protein comprising an IL-23 polypeptide, a second polynucleotide encoding a second protein comprising an IL-36 gamma polypeptide or an IL-18 polypeptide, and a third polypeptide encoding a third protein comprising an OX40L polypeptide are administered in combination with an antibody or an antigen-binding portion thereof that specifically binds to a PD-1 or PD-L1 receptor and an antibody or an antigen-binding portion thereof that specifically binds to a CTLA-4 (or polynucleotides of the same).

VI. Sequence-Optimized Polynucleotide Sequences Encoding Immune Modulatory Polypeptides In some embodiments, a polynucleotide of the disclosure comprises a sequence-optimized nucleotide sequence encoding a polypeptide disclosed herein, e.g., IL-23 (at least one subunit of IL-23 or a fusion protein comprising both subunits of IL-23), IL-36-gamma, IL-18 and/or OX40L. In some embodiments, the polynucleotide of the disclosure comprises an open reading frame (ORF) encoding an IL-23 polypeptide, wherein the ORF has been sequence optimized (e.g., SEQ ID NO:141). In some embodiments, the polynucleotide of the disclosure comprises an open reading frame (ORF) encoding an IL-36-gamma polypeptide or an IL-18 polypeptide, wherein the ORF has been sequence optimized (e.g., SEQ ID NO: 143). In some embodiments, the polynucleotide of the disclosure comprises an open reading frame (ORF) encoding an OX40L polypeptide, wherein the ORF has been sequence optimized (e.g., SEQ ID NO: 145).

In some embodiments, the sequence optimized IL-23, IL-36-gamma or an IL-18 polypeptide and/or OX40L sequences, fragments, and variants thereof are used to practice the methods disclosed herein. In some embodiments, the sequence optimized IL-23, IL-36-gamma or an IL-18 polypeptide and/or OX40L fragments and variants thereof are combined with or alternatives to their respective wild-type sequences (show in TABLES 1 and 1A).

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding an IL-23, IL-36-gamma or an IL-18 polypeptide and/or OX40L polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the disclosure is greater than the uracil or thymine content in the reference wild-type sequence and still maintain beneficial effects, e.g., increased expression and/or signaling response when compared to the reference wild-type sequence.

In some embodiments, the optimized sequences of the present disclosure contain unique ranges of uracils or thymine (if DNA) in the sequence. The uracil or thymine content of the optimized sequences can be expressed in various ways, e.g., uracil or thymine content of optimized sequences relative to the theoretical minimum (% $U_{TM}$ or % $T_{TM}$), relative to the wild-type (% $U_{WT}$ or % $T_{WT}$), and relative to the total nucleotide content (% $U_{TL}$ or % $T_{TL}$). For DNA it is recognized that thymine is present instead of uracil, and one would substitute T where U appears. Thus, all the disclosures related to, e.g., % $U_{TM}$, % $U_{WT}$, or $_{\%}U_{TL}$, with respect to RNA are equally applicable to % $T_{TM}$, % $T_{WT}$, or $_{\%}T_{TL}$ with respect to DNA.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

A uracil- or thymine-modified sequence encoding an IL-23, IL-36-gamma and/or OX40L polypeptide of the disclosure can also be described according to its uracil or thymine content relative to the uracil or thymine content in the corresponding wild-type nucleic acid sequence (% $U_{WT}$ or % $T_{WT}$). The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, a uracil-modified sequence encoding an IL-23, IL-36-gamma, IL-18 and/or OX40L polypeptide of the disclosure has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster. Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide.

In some embodiments, a uracil-modified sequence encoding an IL-23, IL-36-gamma, IL-18 and/or OX40L polypeptide of the disclosure has a reduced number of uracil triplets (UUU) with respect to the wild-type nucleic acid sequence. In some embodiments, a uracil-modified sequence encoding an IL-23, IL-36-gamma, IL-18 and/or OX40L polypeptide has a reduced number of uracil pairs (UU) with respect to the number of uracil pairs (UU) in the wild-type nucleic acid sequence. In some embodiments, a uracil-modified sequence encoding an IL-23, IL-36-gamma, IL-18 and/or OX40L polypeptide of the disclosure has a number of uracil pairs (UU) corresponding to the minimum possible number of uracil pairs (UU) in the wild-type nucleic acid sequence.

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$. In some embodiments, a uracil-modified sequence encoding an IL-23, IL-36-gamma, IL-18 and/or OX40L polypeptide has a % $UU_{wt}$ between below 100%.

In some embodiments, the polynucleotide of the disclosure comprises a uracil-modified sequence encoding an IL-23, IL-36-gamma, IL-18 and/or OX40L polypeptide disclosed herein. In some embodiments, the uracil-modified sequence encoding IL-23, IL-36-gamma, IL-18 and/or OX40L polypeptide comprises at least one chemically modified nucleobase, e.g., 5-methoxyuracil. In some embodiments, at least 95% of a nucleobase (e.g., uracil) in a uracil-modified sequence encoding an IL-23, IL-36-gamma, IL-18 and/or OX40L polypeptide of the disclosure are modified nucleobases. In some embodiments, at least 95% of uracil in a uracil-modified sequence encoding an IL-23, IL-36-gamma, IL-18 and/or OX40L polypeptide is 5-methoxyuracil. In some embodiments, the polynucleotide comprising a uracil-modified sequence further comprises a miRNA binding site, e.g., a miRNA binding site that binds to miR-122. In some embodiments, the polynucleotide comprising a uracil-modified sequence is formulated with a delivery agent, e.g., a compound having Formula (I), e.g., any of Compounds 1-147, or any of Compounds 1-232.

VII. Methods for Sequence Optimization

In some embodiments, a polynucleotide of the disclosure (e.g., a polynucleotide comprising a nucleotide sequence encoding an IL-23, IL-36-gamma, IL-18 and/or OX40L polypeptide (e.g., the wild-type sequence, functional fragment, or variant thereof) is sequence optimized.

A sequence optimized nucleotide sequence (nucleotide sequence is also referred to as "nucleic acid" herein) comprises at least one codon modification with respect to a reference sequence (e.g., a wild-type sequence encoding an IL-23, IL-36-gamma, IL-18 and/or OX40L polypeptide. Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active IL-23, IL-36-gamma, IL-18 and/or OX40L polypeptide.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active IL-23, IL-36-gamma, IL-18 and/or OX40L polypeptide or compositions or formulations comprising the same to a patient suffering from cancer, so the synthesis and delivery of the IL-23, IL-36-gamma, IL-18 and/or OX40L polypeptide to treat cancer takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn may correspond to a ΨΨC codon (RNA map in which U has been replaced with pseudouridine).

In one embodiment, a reference sequence encoding an IL-23, IL-36-gamma, IL-18 and/or OX40L polypeptide can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the disclosure can be generated using one or more codon optimization methods, or a combination thereof. Sequence optimization methods which may be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising IL-23, IL-36-gamma, IL-18 and/or OX40L polypeptide, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:

(i) Sequential: Each sequence optimization method or set of design rules applies to a different subsequence of the overall sequence, for example reducing uridine at codon positions 1 to 30 and then selecting high frequency codons for the remainder of the sequence;

(ii) Hierarchical: Several sequence optimization methods or sets of design rules are combined in a hierarchical, deterministic fashion. For example, use the most GC-rich codons, breaking ties (which are common) by choosing the most frequent of those codons.

(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., an IL-23, IL-36-gamma, IL-18 and/or OX40L polypeptide), with a specific rule or set of rules indicating how to select a specific codon for each amino acid position.

a Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:

(i) increase or decrease in global uridine content;

(ii) increase or decrease in local uridine content (i.e., changes in uridine content are limited to specific subsequences);

(iii) changes in uridine distribution without altering the global uridine content;

(iv) changes in uridine clustering (e.g., number of clusters, location of clusters, or distance between clusters); or (v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases may be uridines in the reference sequence and 10% of nucleobases may be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence may have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.rna.albany.edu). Human rRNA, for example, has ten times more pseudouridine (Ψ) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or locally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) Immunity 23:165-175; Kormann et al. (2010) Nature Biotechnology 29:154-157; or Sahin et al. (2014) Nature Reviews Drug Discovery|AOP, published online 19 Sep. 2014m doi:10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding an IL-23, IL-36-gamma and/or OX40L polypeptide comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding an IL-23, IL-36-gamma, IL-18 and/or OX40L polypeptide comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding an IL-23, IL-36-gamma, IL-18 and/or OX40L polypeptide comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding an IL-23, IL-36-gamma, IL-18 and/or OX40L polypeptide comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding an IL-23, IL-36-gamma, IL-18 and/or OX40L polypeptide disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguade (1998) J. Mol. Evol. 47: 268-74. Methods such as the 'frequency of optimal codons' (Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding an IL-23, IL-36-gamma and/or OX40L polypeptide disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding an IL-23, IL-36-gamma, IL-18 and/or OX40L polypeptide are substituted with alternative codons, each alternative codon having a codon frequency higher than the codon frequency of the substituted codon in the synonymous codon set.

In some embodiments, at least one codon in the reference nucleic acid sequence encoding an IL-23, IL-36-gamma, IL-18 and/or OX40L polypeptide is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding IL-23, IL-36-gamma, IL-18 and/or OX40L polypeptide are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding an IL-23, IL-36-gamma, IL-18 and/or OX40L polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding an IL-23, IL-36-gamma and/or OX40L polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding an IL-23 and/or IL-36-gamma, IL-18 polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding an IL-23, IL-36-gamma, IL-18 and/or OX40L polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding an IL-23, IL-36-gamma, IL-18 and/or OX40L polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding an IL-23, IL-36-gamma, IL-18 and/or OX40L polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, an sequence optimized nucleic acid encoding an IL-23, IL-36-gamma, IL-18 and/or OX40L polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al. (2009) PLoS ONE 4(9): e7002; Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.

(ii) Structural motifs: Motifs encoded by an arrangement of nucleotides that tends to form a certain secondary structure.

(iii) Local motifs: Motifs encoded in one contiguous subsequence.

(iv) Distributed motifs: Motifs encoded in two or more disjoint subsequences.

(v) Advantageous motifs: Motifs which improve nucleotide structure or function.

(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for Xbal (TCTAGA), EcoRI (GAATTC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWnCRnCTCnCnnWnD, wherein n means any nucleotide, R means A or G, W means A or T, D means A or G or T but not C) (SEQ ID NO: 197); structural motifs, such as GGGG repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding an IL-23, IL-36-gamma, IL-18 and/or OX40L polypeptide e disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization may generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding an IL-23, IL-36-gamma, IL-18 and/or OX40L polypeptide and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding an IL-23, IL-36-gamma, IL-18 and/or OX40L polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence.

In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:

(i) the optimized codon set has a higher average G/C content than the original or native codon set; or, (ii) the optimized codon set has a lower average U content than the original or native codon set; or, (iii) the optimized codon set is composed of codons with the highest frequency; or, (iv) the optimized codon set is composed of codons with the lowest frequency; or, (v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

VIII. Characterization of Sequence Optimized Nucleic Acids

In some embodiments of the disclosure, the polynucleotide (e.g., a RNA, e.g., an mRNA) comprising a sequence optimized nucleic acid disclosed herein encoding an IL-23, IL-36-gamma, IL-18 and/or OX40L polypeptide can be can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding an IL-23, IL-36-gamma, IL-18 and/or OX40L polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding an IL-23, IL-36-gamma, IL-18 and/or OX40L polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the disclosure, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the disclosure, the desired property of the polynucleotide is the level of expression of an IL-23, IL-36-gamma, IL-18 and/or OX40L polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the disclosure, the sequence optimization of a nucleic acid sequence disclosed herein, e.g., a nucleic acid sequence encoding an IL-23, IL-36-gamma, IL-18 and/or OX40L polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding an IL-23, IL-36-gamma, IL-18 and/or OX40L polypeptide or a functional fragment thereof may trigger an immune response, which could be caused by (i) the therapeutic agent (e.g., an mRNA encoding an IL-23, IL-36-gamma, IL-18 and/or OX40L polypeptide), or (ii) the expression product of such therapeutic agent (e.g., the IL-23, IL-36-gamma, IL-18 and/or OX40L polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding an IL-23, IL-36-gamma, IL-18 and/or OX40L polypeptide or by the expression product of IL-23, IL-36-gamma, IL-18 and/or OX40L polypeptide encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-13 (IL-13), interferon α (IFN-α), etc.

IX. Polynucleotides Encoding Immune Modulatory Polypeptides Comprising microRNA Binding Sites The polynucleotide (e.g., mRNA) encoding an IL-23, IL-36-gamma, IL-18 and/or OX40L polypeptide can further comprise one or more microRNA binding sites. microRNAs (or miRNA) are 19-25 nucleotides long noncoding RNAs that bind to the 3'UTR of nucleic acid molecules and down-regulate gene expression either by reducing nucleic acid molecule stability or by inhibiting translation.

The present invention also provides pharmaceutical compositions and formulations that comprise any of the polyribonucleotides described above. In some embodiments, the composition or formulation further comprises a delivery agent.

In some embodiments, the composition or formulation can contain a polyribonucleotide comprising a sequence optimized nucleic acid sequence disclosed herein which encodes a polypeptide. In some embodiments, the composition or formulation can contain a polyribonucleotide (e.g., a RNA, e.g., an mRNA) comprising a polyribonucleotide (e.g., an ORF) having significant sequence identity to a sequence optimized nucleic acid sequence disclosed herein which encodes a polypeptide. In some embodiments, the polyribonucleotide further comprises a miRNA binding site, e.g., a miRNA binding site that binds miR-122.

By engineering microRNA target sequences into the polynucleotides (e.g., in a 3'UTR like region or other region) of the disclosure, one can target the molecule for degradation or reduced translation, provided the microRNA in question is available. This can reduce off-target effects upon delivery of the polyribonucleotide. For example, if a polyribonucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polyribonucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polyribonucleotide sequences in which they naturally occur in order to increase protein expression in specific tissues. For example, a binding site for a specific miRNA can be removed from a polyribonucleotide to improve protein expression in tissues or cells containing the miRNA.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

In one embodiment, the miRNA binding site (e.g., miR-122 binding site) binds to the corresponding mature miRNA that is part of an active RNA-induced silencing complex (RISC) containing Dicer. In another embodiment, binding of the miRNA binding site to the corresponding miRNA in RISC degrades the mRNA containing the miRNA binding site or prevents the mRNA from being translated.

As used herein, the term "microRNA binding site" refers to a microRNA target site or a microRNA recognition site, or any nucleotide sequence to which a microRNA binds or associates. It should be understood that "binding" can follow traditional Watson-Crick hybridization rules or can reflect any stable association of the microRNA with the target sequence at or adjacent to the microRNA site.

Some microRNAs, e.g., miR-122, are abundant in normal tissue but are present in much lower levels in cancer or tumor tissue. Thus, engineering microRNA target sequences (i.e., microRNA binding site) into the polynucleotides encoding an IL-23 and/or IL-36-gamma, IL-18 and/or a third protein (e.g., OX40L polypeptide) (e.g., in a 3'UTR like region or other region) can effectively target the molecule for degradation or reduced translation in normal tissue (where the microRNA is abundant) while providing high levels of translation in the cancer or tumor tissue (where the microRNA is present in much lower levels). This provides a tumor-targeting approach for the methods and compositions of the disclosure.

In some embodiments, the microRNA binding site (e.g., miR-122 binding site) is fully complementary to miRNA (e.g., miR-122), thereby degrading the mRNA fused to the miRNA binding site. In other embodiments, the miRNA binding site is not fully complementary to the corresponding miRNA. In certain embodiments, the miRNA binding site (e.g., miR-122 binding site) is the same length as the corresponding miRNA (e.g., miR-122). In other embodiments, the microRNA binding site (e.g., miR-122 binding site) is one nucleotide shorter than the corresponding microRNA (e.g., miR-122, which has 22 nts) at the 5' terminus, the 3' terminus, or both. In still other embodiments, the microRNA binding site (e.g., miR-122 binding site) is two nucleotides shorter than the corresponding microRNA (e.g., miR-122) at the 5' terminus, the 3' terminus, or both. In yet other embodiments, the microRNA binding site (e.g., miR-122 binding site) is three nucleotides shorter than the corresponding microRNA (e.g., miR-122) at the 5' terminus, the 3' terminus, or both. In some embodiments, the microRNA binding site (e.g., miR-122 binding site) is four nucleotides shorter than the corresponding microRNA (e.g., miR-122) at the 5' terminus, the 3' terminus, or both. In other embodiments, the microRNA binding site (e.g., miR-122 binding site) is five nucleotides shorter than the corresponding microRNA (e.g., miR-122) at the 5' terminus, the 3' terminus, or both. In some embodiments, the microRNA binding site (e.g., miR-122 binding site) is six nucleotides shorter than the corresponding microRNA (e.g., miR-122) at the 5' terminus, the 3' terminus, or both. In other embodiments, the microRNA binding site (e.g., miR-122 binding site) is seven nucleotides shorter than the corresponding microRNA (e.g., miR-122) at the 5' terminus or the 3' terminus. In other embodiments, the microRNA binding site (e.g., miR-122 binding site) is eight nucleotides shorter than the corresponding microRNA (e.g., miR-122) at the 5' terminus or the 3' terminus. In other embodiments, the microRNA binding site (e.g., miR-122 binding site) is nine nucleotides shorter than the corresponding microRNA (e.g., miR-122) at the 5' terminus or the 3' terminus. In other embodiments, the microRNA binding site (e.g., miR-122 binding site) is ten nucleotides shorter than the corresponding microRNA (e.g., miR-122) at the 5' terminus or the 3' terminus. In other embodiments, the microRNA binding site (e.g., miR-122 binding site) is eleven nucleotides shorter than the corresponding microRNA (e.g., miR-122) at the 5' terminus or the 3' terminus. In other embodiments, the microRNA binding site (e.g., miR-122 binding site) is twelve nucleotides shorter than the corresponding microRNA (e.g., miR-122) at the 5' terminus or the 3' terminus. The miRNA binding sites that are shorter than the corresponding miRNAs are still capable of degrading the mRNA incorporating one or more of the miRNA binding sites or preventing the mRNA from translation.

In some embodiments, the microRNA binding site (e.g., miR-122 binding site) has sufficient complementarity to miRNA (e.g., miR-122) so that a RISC complex comprising the miRNA (e.g., miR-122) cleaves the polynucleotide comprising the microRNA binding site. In other embodiments, the microRNA binding site (e.g., miR-122 binding site) has imperfect complementarity so that a RISC complex comprising the miRNA (e.g., miR-122) induces instability in the polynucleotide comprising the microRNA binding site. In another embodiment, the microRNA binding site (e.g., miR-122 binding site) has imperfect complementarity so that a RISC complex comprising the miRNA (e.g., miR-122) represses transcription of the polynucleotide comprising the microRNA binding site.

A miRNA binding site having sufficient complementarity to a miRNA refers to a degree of complementarity sufficient to facilitate miRNA-mediated regulation of a polyribonucleotide, e.g., miRNA-mediated translational repression or degradation of the polyribonucleotide. In exemplary aspects of the invention, a miRNA binding site having sufficient complementarity to the miRNA refers to a degree of complementarity sufficient to facilitate miRNA-mediated degradation of the polyribonucleotide, e.g., miRNA-guided RNA-induced silencing complex (RISC)-mediated cleavage of mRNA. The miRNA binding site can have complementarity to, for example, a 19-25 nucleotide long miRNA sequence, to a long 19-23 nucleotide miRNA sequence, or to a long 22 nucleotide miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence (such an miRNA binding site has "imperfect complementarity"). Full or complete complementarity (e.g., full complementarity or complete complementarity over all or a significant portion of the length of a naturally-occurring miRNA) is preferred when the desired regulation is mRNA degradation.

In one embodiment, the miRNA binding site (e.g., miR-122 binding site) has one mismatch from the corresponding miRNA (e.g., miR-122). In another embodiment, the miRNA binding site has two mismatches from the corresponding miRNA. In other embodiments, the miRNA binding site has three mismatches from the corresponding miRNA. In other embodiments, the miRNA binding site has four mismatches from the corresponding miRNA. In some embodiments, the miRNA binding site has five mismatches from the corresponding miRNA. In other embodiments, the miRNA binding site has six mismatches from the corresponding miRNA. In certain embodiments, the miRNA binding site has seven mismatches from the corresponding miRNA. In other embodiments, the miRNA binding site has eight mismatches from the corresponding miRNA. In other embodiments, the miRNA binding site has nine mismatches from the corresponding miRNA. In other embodiments, the miRNA binding site has ten mismatches from the corresponding miRNA. In other embodiments, the miRNA binding site has eleven mismatches from the corresponding miRNA. In other embodiments, the miRNA binding site has twelve mismatches from the corresponding miRNA.

In certain embodiments, the miRNA binding site (e.g., miR-122 binding site) has at least about ten contiguous nucleotides complementary to at least about ten contiguous nucleotides of the corresponding miRNA (e.g., miR-122), at least about eleven contiguous nucleotides complementary to at least about eleven contiguous nucleotides of the corresponding miRNA, at least about twelve contiguous nucleotides complementary to at least about twelve contiguous nucleotides of the corresponding miRNA, at least about thirteen contiguous nucleotides complementary to at least about thirteen contiguous nucleotides of the corresponding miRNA, or at least about fourteen contiguous nucleotides complementary to at least about fourteen contiguous nucleotides of the corresponding miRNA. In some embodiments, the miRNA binding sites have at least about fifteen contiguous nucleotides complementary to at least about fifteen contiguous nucleotides of the corresponding miRNA, at least about sixteen contiguous nucleotides complementary to at least about sixteen contiguous nucleotides of the corresponding miRNA, at least about seventeen contiguous nucleotides complementary to at least about seventeen contiguous nucleotides of the corresponding miRNA, at least about eighteen contiguous nucleotides complementary to at least about eighteen contiguous nucleotides of the corresponding miRNA, at least about nineteen contiguous nucleotides complementary to at least about nineteen contiguous nucleotides of the corresponding miRNA, at least about twenty contiguous nucleotides complementary to at least about twenty contiguous nucleotides of the corresponding miRNA, or at least about twenty one contiguous nucleotides complementary to at least about twenty one contiguous nucleotides of the corresponding miRNA.

In some embodiments, the polynucleotides comprise an mRNA encoding an IL-23, IL-36-gamma, IL-18 and/or OX40L polypeptide and at least one miR-122 binding site, at least two miR-122 binding sites, at least three miR-122 binding sites, at least four miR-122 binding sites, or at least five miR-122 binding sites. In one aspect, the miRNA binding site binds miR-122 or is complementary to miR-122. In another aspect, the miRNA binding site binds to miR-122-3p or miR-122-5p. In a particular aspect, the miRNA binding site comprises a nucleotide sequence at least 80%, at least 85%, at least 90%, at least 95%, or 100% identical to SEQ ID NO: 24, wherein the miRNA binding site binds to miR-122. In another particular aspect, the miRNA binding site comprises a nucleotide sequence at least 80%, at least 85%, at least 90%, at least 95%, or 100% identical to SEQ ID NO: 26, wherein the miRNA binding site binds to miR-122. These sequences are shown below in TABLE 2.

TABLE 2 miR-122 and miR-122 binding sites

| SEQ ID NO. | Description | Sequence |
|---|---|---|
| SEQ ID NO: 22 | miR-122 | CCUUAGCAGAGCUGUGGAG UGUGACAAUGGUGUUUGUG UCUAAACUAUCAAACGCCA UUAUCACACUAAAUAGCUA CUGCUAGGC |
| SEQ ID NO: 23 | miR-122-3p | AACGCCAUUAUCACACUAAAUA |
| SEQ ID NO: 24 | miR-122-3p binding site | UAUUUAGUGUGAUAAUGGCGUU |
| SEQ ID NO: 25 | miR-122-5p | UGGAGUGUGACAAUGGUGUUUG |
| SEQ ID NO: 26 | miR-122-5p binding site | CAAACACCAUUGUCACACUCCA |

In some embodiments, a miRNA binding site (e.g., miR-122 binding site) is inserted in the polynucleotide of the disclosure in any position of the polynucleotide (e.g., 3' UTR); the insertion site in the polynucleotide can be anywhere in the polynucleotide as long as the insertion of the miRNA binding site in the polynucleotide does not interfere with the translation of the functional IL-23, IL-36-gamma, IL-18 and/or OX40L polypeptide in the absence of the corresponding miRNA (e.g., miR-122); and in the presence of the miRNA (e.g., miR-122), the insertion of the miRNA binding site in the polynucleotide and the binding of the miRNA binding site to the corresponding miRNA are capable of degrading the polynucleotide or preventing the translation of the polynucleotide. In one embodiment, a miRNA binding site is inserted in a 3'UTR of the polynucleotide.

In certain embodiments, a miRNA binding site is inserted in at least about 30 nucleotides downstream from the stop codon of the IL-23, IL-36-gamma, IL-18 and/or OX40L polypeptide encoding mRNA. In other embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of the polynucleotide, e.g., the IL-23, IL-36-gamma, IL-18 and/or OX40L polypeptide encoding mRNA. In other embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of the polynucleotide, e.g., the IL-23, IL-36-gamma, IL-18 and/or OX40L polypeptide encoding mRNA.

IVT Polynucleotide Architecture

In some embodiments, the polynucleotide of the present disclosure comprising an mRNA encoding an IL-23, IL-36-gamma, IL-18 and/or OX40L polypeptide is an IVT polynucleotide. Traditionally, the basic components of an mRNA molecule include at least a coding region, a 5'UTR, a 3'UTR, a 5' cap and a poly-A tail. The IVT polynucleotides of the present disclosure can function as mRNA but are distinguished from wild-type mRNA in their functional and/or structural design features which serve, e.g., to overcome existing problems of effective polypeptide production using nucleic-acid based therapeutics.

The primary construct of an IVT polynucleotide comprises a first region of linked nucleotides that is flanked by a first flanking region and a second flaking region. This first region can include, but is not limited to, the encoded IL-23, IL-36-gamma, IL-18 and/or OX40L polypeptide. The first flanking region can include a sequence of linked nucleosides which function as a 5' untranslated region (UTR) such as the 5' UTR of any of the nucleic acids encoding the native 5' UTR of the polypeptide or a non-native 5'UTR such as, but not limited to, a heterologous 5' UTR or a synthetic 5' UTR. The IVT encoding an IL-23, IL-36-gamma, IL-18 and/or OX40L polypeptide can comprise at its 5 terminus a signal sequence region encoding one or more signal sequences. The flanking region can comprise a region of linked nucleotides comprising one or more complete or incomplete 5' UTRs sequences. The flanking region can also comprise a 5' terminal cap. The second flanking region can comprise a region of linked nucleotides comprising one or more complete or incomplete 3' UTRs which can encode the native 3' UTR of IL-23, IL-36-gamma, IL-18 and/or OX40L polypeptide or a non-native 3' UTR such as, but not limited to, a heterologous 3' UTR or a synthetic 3' UTR. The flanking region can also comprise a 3' tailing sequence. The 3' tailing sequence can be, but is not limited to, a polyA tail, a polyA-G quartet and/or a stem loop sequence.

Bridging the 5' terminus of the first region and the first flanking region is a first operational region. Traditionally, this operational region comprises a Start codon. The operational region can alternatively comprise any translation initiation sequence or signal including a Start codon.

Bridging the 3' terminus of the first region and the second flanking region is a second operational region. Traditionally this operational region comprises a Stop codon. The operational region can alternatively comprise any translation initiation sequence or signal including a Stop codon. Multiple serial stop codons can also be used in the IVT polynucleotide. In some embodiments, the operation region of the present disclosure can comprise two stop codons. The first stop codon can be "TGA" or "UGA" and the second stop codon can be selected from the group consisting of "TAA," "TGA," "TAG," "UAA," "UGA" or "UAG."

The IVT polynucleotide primary construct comprises a first region of linked nucleotides that is flanked by a first flanking region and a second flaking region. As used herein, the "first region" can be referred to as a "coding region" or "region encoding" or simply the "first region." This first region can include, but is not limited to, the encoded polypeptide of interest. In one aspect, the first region can include, but is not limited to, the open reading frame encoding at least one polypeptide of interest. The open reading frame can be codon optimized in whole or in part. The flanking region can comprise a region of linked nucleotides comprising one or more complete or incomplete 5' UTRs sequences which can be completely codon optimized or partially codon optimized. The flanking region can include at least one nucleic acid sequence including, but not limited to, miR sequences, TERZAK™ sequences and translation control sequences. The flanking region can also comprise a 5' terminal cap 138. The 5' terminal capping region can include a naturally occurring cap, a synthetic cap or an optimized cap. The second flanking region can comprise a region of linked nucleotides comprising one or more complete or incomplete 3' UTRs. The second flanking region can be completely codon optimized or partially codon optimized. The flanking region can include at least one nucleic acid sequence including, but not limited to, miR sequences and translation control sequences. After the second flanking region the polynucleotide primary construct can comprise a 3' tailing sequence. The 3' tailing sequence can include a synthetic tailing region and/or a chain terminating nucleoside. Non-liming examples of a synthetic tailing region include a polyA sequence, a polyC sequence, a polyA-G quartet. Non-limiting examples of chain terminating nucleosides include 2'-O methyl, F and locked nucleic acids (LNA).

Bridging the 5' terminus of the first region and the first flanking region is a first operational region. Traditionally this operational region comprises a Start codon. The operational region can alternatively comprise any translation initiation sequence or signal including a Start codon.

Bridging the 3' terminus of the first region and the second flanking region is a second operational region. Traditionally this operational region comprises a Stop codon. The operational region can alternatively comprise any translation initiation sequence or signal including a Stop codon. According to the present disclosure, multiple serial stop codons can also be used.

In some embodiments, the first and second flanking regions of the IVT polynucleotide can range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, 900, 1,000, 1,500, 2,000, 2,500, 3,000, 3,500, 4,000, 4,500, 5,000, 5,500 nucleotides or at least 30, 40, 45, 50, 55, 60, 70, 80, 90, 100, 120, 140, 160, 180, 200, 250, 300, 350, 400, 450, 500, 600, 700, 800, 900, 1,000, 1,500, 2,000, 2,500, 3,000, 3,500, 4,000, 4,500, 5,000, 5,500 nucleotides).

In some embodiments, the tailing sequence of the IVT polynucleotide can range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length can be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

In some embodiments, the capping region of the IVT polynucleotide can comprise a single cap or a series of nucleotides forming the cap. In this embodiment the capping region can be from 1 to 10, e.g. 2-9, 3-8, 4-7, 1-5, 5-10, or at least 2, or 10 or fewer nucleotides in length. In some embodiments, the cap is absent.

In some embodiments, the first and second operational regions of the IVT polynucleotide can range from 3 to 40, e.g., 5-30, 10-20, 15, or at least 4, or 30 or fewer nucleotides in length and can comprise, in addition to a Start and/or Stop codon, one or more signal and/or restriction sequences.

In some embodiments, the IVT polynucleotides can be structurally modified or chemically modified. When the IVT polynucleotides are chemically and/or structurally modified the polynucleotides can be referred to as "modified IVT polynucleotides."

In some embodiments, if the IVT polynucleotides are chemically modified they can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the IVT polynucleotides can have a uniform chemical modification of two, three, or four of the same nucleoside type throughout the entire polynucleotide (such as all uridines and all cytosines, etc. are modified in the same way).

In some embodiments, the IVT polynucleotides can include a sequence encoding a self-cleaving peptide, described herein, such as but not limited to the 2A peptide. The polynucleotide sequence of the 2A peptide in the IVT polynucleotide can be modified or codon optimized by the methods described herein and/or are known in the art. In some embodiments, this sequence can be used to separate the coding region of two or more polypeptides of interest in the IVT polynucleotide.

Chimeric Polynucleotide Architecture

In some embodiments, the polynucleotide of the present disclosure is a chimeric polynucleotide. The chimeric polynucleotides or RNA constructs disclosed herein maintain a modular organization similar to IVT polynucleotides, but the chimeric polynucleotides comprise one or more structural and/or chemical modifications or alterations which impart useful properties to the polynucleotide. As such, the chimeric polynucleotides which are modified mRNA molecules of the present disclosure are termed “chimeric modified mRNA” or “chimeric mRNA.”

Chimeric polynucleotides have portions or regions which differ in size and/or chemical modification pattern, chemical modification position, chemical modification percent or chemical modification population and combinations of the foregoing.

Examples of parts or regions, where the chimeric polynucleotide functions as an mRNA and encodes an IL-23, IL-36-gamma, IL-18 and/or OX40L polypeptide, but is not limited to, untranslated regions (UTRs, such as the 5' UTR or 3' UTR), coding regions, cap regions, polyA tail regions, start regions, stop regions, signal sequence regions, and combinations thereof. Regions or parts that join or lie between other regions can also be designed to have subregions.

In some embodiments, the chimeric polynucleotides of the disclosure have a structure comprising Formula X.

5'[An]x-L1-[Bo]y-L2-[Cp]z-L3 3' Formula X wherein:

each of A and B independently comprise a region of linked nucleosides;

either A or B or both A and B encode an IL-23, IL-36-gamma, IL-18 and/or OX40L polypeptide described elsewhere herein;

C is an optional region of linked nucleosides;

at least one of regions A, B, or C is positionally modified, wherein said positionally modified region comprises at least two chemically modified nucleosides of one or more of the same nucleoside type of adenosine, thymidine, guanosine, cytidine, or uridine, and wherein at least two of the chemical modifications of nucleosides of the same type are different chemical modifications;

n, o and p are independently an integer between 15-1000;

x and y are independently 1-20;

z is 0-5;

L1 and L2 are independently optional linker moieties, said linker moieties being either nucleic acid based or non-nucleic acid based; and L3 is an optional conjugate or an optional linker moiety, said linker moiety being either nucleic acid based or non-nucleic acid based.

In some embodiments, at least one of the regions of linked nucleosides of A comprises a sequence of linked nucleosides which can function as a 5' untranslated region (UTR). The sequence of linked nucleosides can be a natural or synthetic 5' UTR. As a non-limiting example, the chimeric polynucleotide can encode an IL-23, IL-36-gamma, IL-18 and/or OX40L polypeptide, and the sequence of linked nucleosides of A can encode the native 5' UTR of the IL-23, IL-36-gamma, IL-18 and/or OX40L polypeptide or a non-heterologous 5' UTR such as, but not limited to a synthetic UTR.

In another embodiment, at least one of the regions of linked nucleosides of A is a cap region. The cap region can be located 5' to a region of linked nucleosides of A functioning as a 5'UTR. The cap region can comprise at least one cap such as, but not limited to, Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azido-guanosine, Cap2 and Cap4.

In some embodiments, the polynucleotide of the disclosure comprises a Cap1 5'UTR. In some embodiments, a polynucleotide comprising 5'UTR sequence, e.g., Cap1, for encoding an IL-23, IL-36-gamma, IL-18 and/or OX40L polypeptide disclosed herein increases expression of IL-23, IL-36-gamma, IL-18 and/or OX40L polypeptide compared to polynucleotides encoding IL-23, IL-36-gamma, IL-18 and/or OX40L polypeptide comprising a different 5'UTR (e.g., Cap0, ARCA, inosine, N1-methyl-guanosine, 2'fluoro-guanosine, 7-deaza-guanosine, 8-oxo-guanosine, 2-amino-guanosine, LNA-guanosine, 2-azido-guanosine, Cap2 or Cap4). In some embodiments, a polynucleotide comprises the Cap1 5'UTR, wherein the polynucleotide encodes an IL-23, IL-36-gamma and/or OX40L polypeptide. In some embodiments, polynucleotide comprising the Cap1 5'UTR, increases IL-23, IL-36-gamma and/or OX40L polypeptide expression.

In some embodiments, at least one of the regions of linked nucleosides of B comprises at least one open reading frame of a nucleic acid sequence encoding an IL-23, IL-36-gamma, IL-18 and/or OX40L polypeptide. The nucleic acid sequence can be codon optimized and/or comprise at least one modification.

In some embodiments, at least one of the regions of linked nucleosides of C comprises a sequence of linked nucleosides which can function as a 3' UTR. The sequence of linked nucleosides can be a natural or synthetic 3' UTR. As a non-limiting example, the chimeric polynucleotide can encode an IL-23, IL-36-gamma, IL-18 and/or OX40L polypeptide, and the sequence of linked nucleosides of C can encode the native 3' UTR of an IL-23, IL-36-gamma, IL-18 and/or OX40L polypeptide or a non-heterologous 3' UTR such as, but not limited to a synthetic UTR.

In some embodiments, at least one of the regions of linked nucleosides of A comprises a sequence of linked nucleosides which functions as a 5' UTR and at least one of the regions of linked nucleosides of C comprises a sequence of linked nucleosides which functions as a 3' UTR. In some embodiments, the 5' UTR and the 3' UTR can be from the same or different species. In another embodiment, the 5' UTR and the 3' UTR can encode the native untranslated regions from different proteins from the same or different species.

Chimeric polynucleotides, including the parts or regions thereof, of the present disclosure can be classified as hemimers, gapmers, wingmers, or blockmers.

As used herein, a “hemimer” is a chimeric polynucleotide comprising a region or part which comprises half of one pattern, percent, position or population of a chemical modification(s) and half of a second pattern, percent, position or population of a chemical modification(s). Chimeric polynucleotides of the present disclosure can also comprise hemimer subregions. In some embodiments, a part or region is 50% of one and 50% of another.

In some embodiments, the entire chimeric polynucleotide is 50% of one and 50% of the other. Any region or part of any chimeric polynucleotide of the disclosure can be a hemimer. Types of hemimers include pattern hemimers, population hemimers or position hemimers. By definition, hemimers are 50:50 percent hemimers.

As used herein, a “gapmer” is a chimeric polynucleotide having at least three parts or regions with a gap between the parts or regions. The “gap” can comprise a region of linked nucleosides or a single nucleoside which differs from the chimeric nature of the two parts or regions flanking it. The two parts or regions of a gapmer can be the same or different from each other.

As used herein, a "wingmer" is a chimeric polynucleotide having at least three parts or regions with a gap between the parts or regions. Unlike a gapmer, the two flanking parts or regions surrounding the gap in a wingmer are the same in degree or kind. Such similarity can be in the length of number of units of different modifications or in the number of modifications. The wings of a wingmer can be longer or shorter than the gap. The wing parts or regions can be 20, 30, 40, 50, 60 70, 80, 90 or 95% greater or shorter in length than the region which comprises the gap.

As used herein, a "blockmer" is a patterned polynucleotide where parts or regions are of equivalent size or number and type of modifications. Regions or subregions in a blockmer can be 50, 51, 52, 53, 54, 55, 56, 57, 58, 59, 60, 61 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 310, 320, 330, 340, 350, 360, 370, 380, 390, 400, 410, 420, 430, 440, 450, 460, 470, 480, 490 or 500, nucleosides long.

Chimeric polynucleotides, including the parts or regions thereof, of the present disclosure having a chemical modification pattern are referred to as "pattern chimeras." Pattern chimeras can also be referred to as blockmers. Pattern chimeras are those polynucleotides having a pattern of modifications within, across or among regions or parts.

Patterns of modifications within a part or region are those which start and stop within a defined region. Patterns of modifications across a part or region are those patterns which start in on part or region and end in another adjacent part or region. Patterns of modifications among parts or regions are those which begin and end in one part or region and are repeated in a different part or region, which is not necessarily adjacent to the first region or part.

The regions or subregions of pattern chimeras or blockmers can have simple alternating patterns such as ABAB [AB]n where each "A" and each "B" represent different chemical modifications (at least one of the base, sugar or backbone linker), different types of chemical modifications (e.g., naturally occurring and non-naturally occurring), different percentages of modifications or different populations of modifications. The pattern can repeat n number of times where n=3-300. Further, each A or B can represent from 1-2500 units (e.g., nucleosides) in the pattern. Patterns can also be alternating multiples such as AABBAABB[AABB]n (an alternating double multiple) or AAABBBAAABBB [AAABBB]n (an alternating triple multiple) pattern. The pattern can repeat n number of times where n=3-300.

Different patterns can also be mixed together to form a second order pattern. For example, a single alternating pattern can be combined with a triple alternating pattern to form a second order alternating pattern A'B'. One example would be [ABABAB][AAABBBAAABBB][ABABAB] [AAABBBAAABBB] [ABABAB][AAABBBAAABBB], where [ABABAB] is A' and [AAABBBAAABBB] is B'. In like fashion, these patterns can be repeated n number of times, where n=3-300.

Patterns can include three or more different modifications to form an ABCABC[ABC]n pattern. These three component patterns can also be multiples, such as AABBCCAABBCC[AABBCC]n and can be designed as combinations with other patterns such as ABCABCAABBCCABCABCAABBCC, and can be higher order patterns.

Regions or subregions of position, percent, and population modifications need not reflect an equal contribution from each modification type. They can form series such as "1-2-3-4", "1-2-4-8", where each integer represents the number of units of a particular modification type. Alternatively, they can be odd only, such as "1-3-3-1-3-1-5" or even only "2-4-2-4-6-4-8" or a mixture of both odd and even number of units such as "1-3-4-2-5-7-3-3-4".

Pattern chimeras can vary in their chemical modification by degree (such as those described above) or by kind (e.g., different modifications).

Chimeric polynucleotides, including the parts or regions thereof, of the present disclosure having at least one region with two or more different chemical modifications of two or more nucleoside members of the same nucleoside type (A, C, G, T, or U) are referred to as "positionally modified" chimeras. Positionally modified chimeras are also referred to herein as "selective placement" chimeras or "selective placement polynucleotides". As the name implies, selective placement refers to the design of polynucleotides which, unlike polynucleotides in the art where the modification to any A, C, G, T or U is the same by virtue of the method of synthesis, can have different modifications to the individual As, Cs, Gs, Ts or Us in a polynucleotide or region thereof. For example, in a positionally modified chimeric polynucleotide, there can be two or more different chemical modifications to any of the nucleoside types of As, Cs, Gs, Ts, or Us. There can also be combinations of two or more to any two or more of the same nucleoside type. For example, a positionally modified or selective placement chimeric polynucleotide can comprise 3 different modifications to the population of adenines in the molecule and also have 3 different modifications to the population of cytosines in the construct—all of which can have a unique, non-random, placement.

Chimeric polynucleotides, including the parts or regions thereof, of the present disclosure having a chemical modification percent are referred to as "percent chimeras." Percent chimeras can have regions or parts which comprise at least 1%, at least 2%, at least 5%, at least 8%, at least 10%, at least 20%, at least 30%, at least 40%, at least 50%, at least 60%, at least 70%, at least 80%, at least 90%, at least 95%, or at least 99% positional, pattern or population of modifications. Alternatively, the percent chimera can be completely modified as to modification position, pattern, or population. The percent of modification of a percent chimera can be split between naturally occurring and non-naturally occurring modifications.

Chimeric polynucleotides, including the parts or regions thereof, of the present disclosure having a chemical modification population are referred to as "population chimeras."

A population chimera can comprise a region or part where nucleosides (their base, sugar or backbone linkage, or combination thereof) have a select population of modifications. Such modifications can be selected from functional populations such as modifications which induce, alter or modulate a phenotypic outcome. For example, a functional population can be a population or selection of chemical modifications which increase the level of a cytokine. Other functional populations can individually or collectively function to decrease the level of one or more cytokines. Use of a selection of these like-function modifications in a chimeric polynucleotide would therefore constitute a "functional population chimera." As used herein, a "functional population chimera" can be one whose unique functional feature is defined by the population of modifications as described above or the term can apply to the overall function of the chimeric polynucleotide itself. For example, as a whole the chimeric polynucleotide can function in a different or superior way as compared to an unmodified or non-chimeric polynucleotide.

It should be noted that polynucleotides which have a uniform chemical modification of all of any of the same nucleoside type or a population of modifications produced by mere downward titration of the same starting modification in all of any of the same nucleoside type, or a measured percent of a chemical modification of all any of the same nucleoside type but with random incorporation, such as where all uridines are replaced by a uridine analog, e.g., pseudouridine or 5-methoxyuridine, are not considered chimeric polynucleotides. Likewise, polynucleotides having a uniform chemical modification of two, three, or four of the same nucleoside type throughout the entire polynucleotide (such as all uridines and all cytosines, etc. are modified in the same way) are not considered chimeric polynucleotides. One example of a polynucleotide which is not chimeric is the canonical pseudouridine/5-methyl cytosine modified polynucleotide. These uniform polynucleotides are arrived at entirely via in vitro transcription (IVT) enzymatic synthesis; and due to the limitations of the synthesizing enzymes, they contain only one kind of modification at the occurrence of each of the same nucleoside type, i.e., adenosine (A), thymidine (T), guanosine (G), cytidine (C) or uridine (U), found in the polynucleotide. Such polynucleotides can be characterized as IVT polynucleotides.

The chimeric polynucleotides of the present disclosure can be structurally modified or chemically modified. When the chimeric polynucleotides of the present disclosure are chemically and/or structurally modified the polynucleotides can be referred to as "modified chimeric polynucleotides."

The regions or parts of the chimeric polynucleotides can be separated by a linker or spacer moiety. Such linkers or spaces can be nucleic acid based or non-nucleosidic.

In some embodiments, the chimeric polynucleotides can include a sequence encoding a self-cleaving peptide described herein, such as, but not limited to, a 2A peptide. The polynucleotide sequence of the 2A peptide in the chimeric polynucleotide can be modified or codon optimized by the methods described herein and/or are known in the art.

Notwithstanding the foregoing, the chimeric polynucleotides of the present disclosure can comprise a region or part which is not positionally modified or not chimeric as defined herein. For example, a region or part of a chimeric polynucleotide can be uniformly modified at one or more A, T, C, G, or U, but the polynucleotides will not be uniformly modified throughout the entire region or part.

Chimeric polynucleotides of the present disclosure can be completely positionally modified or partially positionally modified. They can also have subregions which can be of any pattern or design.

In some embodiments, regions or subregions of the polynucleotides can range from absent to 500 nucleotides in length (e.g., at least 60, 70, 80, 90, 100, 110, 120, 130, 140, 150, 160, 170, 180, 190, 200, 250, 300, 350, 400, 450, or 500 nucleotides). Where the region is a polyA tail, the length can be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides to about 160 nucleotides are functional. The chimeric polynucleotides of the present disclosure which function as an mRNA need not comprise a polyA tail.

According to the present disclosure, chimeric polynucleotides which function as an mRNA can have a capping region. The capping region can comprise a single cap or a series of nucleotides forming the cap. In this embodiment the capping region can be from 1 to 10, e.g. 2-9, 3-8, 4-7, 1-5, 5-10, or at least 2, or 10 or fewer nucleotides in length. In some embodiments, the cap is absent.

The present disclosure contemplates chimeric polynucleotides which are circular or cyclic. As the name implies circular polynucleotides are circular in nature meaning that the termini are joined in some fashion, whether by ligation, covalent bond, common association with the same protein or other molecule or complex or by hybridization.

Chimeric polynucleotides, formulations and compositions comprising chimeric polynucleotides, and methods of making, using and administering chimeric polynucleotides are also described in International Patent Application No. PCT/US2014/53907.

In some embodiments, the chimeric polynucleotide encodes an IL-23, IL-36-gamma, IL-18 and/or OX40L polypeptide. In some embodiments, the chimeric polynucleotides of the disclosure comprise any one of the IL-23 and/or IL-36-gamma, IL-18 nucleic acid sequences listed in Table 1 and/or an OX40L nucleic acid sequence listed in Table 1A. In some embodiments the chimeric polynucleotide of the disclosure encodes any one of the IL-23 and/or IL-36-gamma, IL-18 listed in Table 1 and/or OX40L polypeptides listed in Table 1A.

Circular Polynucleotide

The polynucleotide (e.g., mRNA) encoding an IL-23, IL-36-gamma, IL-18 and/or OX40L polypeptide can be circular or cyclic. As used herein, "circular polynucleotides" or "circP" means a single stranded circular polynucleotide which acts substantially like, and has the properties of, an RNA. The term "circular" is also meant to encompass any secondary or tertiary configuration of the circP. Circular polynucleotides are circular in nature meaning that the termini are joined in some fashion, whether by ligation, covalent bond, common association with the same protein or other molecule or complex or by hybridization.

Circular polynucleotides, formulations and compositions comprising circular polynucleotides, and methods of making, using and administering circular polynucleotides are also disclosed in International Patent Application No. PCT/US2014/53904 (published as WO2015034925, see also, US 2016-0194368).

In some embodiments, the circular polynucleotide encodes an IL-23 polypeptide, an IL-36-gamma polypeptide, or an OX40L polypeptide. In some embodiments, the circular polynucleotides of the disclosure comprise any one of the IL-23, IL-36-gamma, IL-18 nucleic acid sequences listed in TABLE 1, or OX40L nucleic acid sequences listed in TABLE 1A. In some embodiments, the circular polynucleotides of the disclosure encode any one of the IL-23 polypeptide, IL-36-gamma, IL-18 polypeptides sited in TABLE 1, or OX40L polypeptides listed in TABLE 1A. In some embodiments, the circular polynucleotide increases IL-23 polypeptide, IL-36-gamma polypeptide, IL-18 or OX40L polypeptide expression.

Multimers of Polynucleotides

In some embodiments, multiple distinct chimeric polynucleotides and/or IVT polynucleotides can be linked together through the 3'-end using nucleotides which are modified at the 3'-terminus. Chemical conjugation can be used to control the stoichiometry of delivery into cells. This can be controlled by chemically linking chimeric polynucleotides and/or IVT polynucleotides using a 3'-azido terminated nucleotide on one polynucleotides species and a C5-ethynyl or alkynyl-containing nucleotide on the opposite polynucleotide species. The modified nucleotide is added post-transcriptionally using terminal transferase (New England Biolabs, Ipswich, Mass.) according to the manufacturer's protocol. After the addition of the 3'-modified nucleotide, the two polynucleotides species can be combined in an aqueous solution, in the presence or absence of copper, to form a new covalent linkage via a click chemistry mechanism as described in the literature.

In another example, more than two chimeric polynucleotides and/or IVT polynucleotides can be linked together using a functionalized linker molecule. For example, a functionalized saccharide molecule can be chemically modified to contain multiple chemical reactive groups (SH—, $NH_2$—, $N_3$, etc.) to react with the cognate moiety on a 3'-functionalized mRNA molecule (i.e., a 3'-maleimide ester, 3'-NHS-ester, alkynyl). The number of reactive groups on the modified saccharide can be controlled in a stoichiometric fashion to directly control the stoichiometric ratio of conjugated chimeric polynucleotides and/or IVT polynucleotides.

In some embodiments, the chimeric polynucleotides and/or IVT polynucleotides can be linked together in a pattern. The pattern can be a simple alternating pattern such as CD[CD]x where each "C" and each "D" represent a chimeric polynucleotide, IVT polynucleotide, different chimeric polynucleotides or different IVT polynucleotides. The pattern can repeat x number of times, where x=1-300. Patterns can also be alternating multiples such as CCDD[CCDD] x (an alternating double multiple) or CCCDDD[CCCDDD] x (an alternating triple multiple) pattern. The alternating double multiple or alternating triple multiple can repeat x number of times, where x=1-300.

Conjugates and Combinations of Polynucleotides

The polynucleotide (e.g., mRNA) encoding an IL-23 polypeptide, an IL-36-gamma polypeptide, an IL-18 polypeptide, or an OX40L polypeptide of the present disclosure can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugation can result in increased stability and/or half-life and can be particularly useful in targeting the polynucleotides to specific sites in the cell, tissue or organism.

A polynucleotide (e.g., mRNA) encoding an IL-23 polypeptide, an IL-36-gamma polypeptide, an IL-18 polypeptide, or an OX40L polypeptide of the disclosure can further comprise a nucleotide sequence encoding one or more heterologous polypeptides. In one embodiment, the one or more heterologous polypeptides improves a pharmacokinetic property or pharmacodynamics property of the IL-23 polypeptide, IL-36-gamma polypeptide, an IL-18 polypeptide, or OX40L polypeptide, or a polynucleotide (e.g., at least one mRNA) encoding the IL-23 polypeptide, IL-36-gamma polypeptide, an IL-18 polypeptide, or OX40L polypeptide. In another embodiment, the one or more heterologous polypeptides comprise a polypeptide that can extend a half-life of the IL-23 polypeptide, IL-36-gamma polypeptide, an IL-18 polypeptide, or OX40L polypeptide.

A polynucleotide (e.g., mRNA) encoding an IL-23 polypeptide, an IL-36-gamma polypeptide, an IL-18 polypeptide, or an OX40L polypeptide of the present disclosure can further comprise one or more regions or parts which act or function as an untranslated region. By definition, wild type untranslated regions (UTRs) of a gene are transcribed but not translated. In mRNA, the 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. TABLE 3 and TABLES 4A and 4B provide a listing of exemplary UTRs which can be utilized in the polynucleotides of the present disclosure.

5' UTR and Translation Initiation

In certain embodiments, the polynucleotide (e.g., mRNA) encoding an IL-23 polypeptide, an IL-36-gamma polypeptide an IL-18 polypeptide, or an OX40L polypeptide of the present disclosure further comprises a 5' UTR and/or a translation initiation sequence. Natural 5'UTRs bear features which play roles in translation initiation. They harbor signatures like Kozak sequences which are commonly known to be involved in the process by which the ribosome initiates translation of many genes. 5'UTR also have been known to form secondary structures which are involved in elongation factor binding.

By engineering the features typically found in abundantly expressed genes of specific target organs, one can enhance the stability and protein production of the polynucleotides of the disclosure. For example, introduction of 5' UTR of mRNA known to be upregulated in cancers, such as c-myc, could be used to enhance expression of a nucleic acid molecule, such as a polynucleotide, in cancer cells. Untranslated regions useful in the design and manufacture of polynucleotides include, but are not limited, to those disclosed in International Patent Publication No. WO 2014/164253 (see also US20160022840).

Shown in TABLE 3 is a listing of a 5'-untranslated region of the disclosure. Variants of 5' UTRs can be utilized wherein one or more nucleotides are added or removed to the termini, including A, U, C or G.

TABLE 3

5'-Untranslated Regions

| 5' UTR Identifier | Name/ Description | Sequence | SEQ ID NO. |
|---|---|---|---|
| 5UTR-001 | Upstream UTR | GGGAAAUAAGAGAGAAAAGAAGAGUAAGAAGAAAUAU AAGAGCCACC | SEQ ID NO: 27 |
| 5UTR-002 | Upstream UTR | GGGAGAUCAGAGAGAAAAGAAGAGUAAGAAGAAAUAU AAGAGCCACC | SEQ ID NO: 28 |
| 5UTR-003 | Upstream UTR | GGAAUAAAAGUCUCAACACAACAUAUACAAAACAAAC GAAUCUCAAGCAAUCAAGCAUUCUACUUCUAUUGCAG CAAUUUAAAUCAUUUCUUUUAAAGCAAAAGCAAUUUU CUGAAAAUUUUCACCAUUUACGAACGAUAGCAAC | SEQ ID NO: 29 |
| 5UTR-004 | Upstream UTR | GGGAGACAAGCUUGGCAUUCCGGUACUGUU GGUAAAGCCACC | SEQ ID NO: 30 |
| 5UTR-005 | Upstream UTR | GGGAGAUCAGAGAGAAAAGAAGAGUAAGAAGAAAUAU AAGAGCCACC | SEQ ID NO: 31 |
| 5UTR-006 | Upstream UTR | GGAAUAAAAGUCUCAACACAACAUAUACAAAACAAAC GAAUCUCAAGCAAUCAAGCAUUCUACUUCUAUUGCAG CAAUUUAAAUCAUUUCUUUUAAAGCAAAAGCAAUUUU CUGAAAAUUUUCACCAUUUACGAACGAUAGCAAC | SEQ ID NO: 32 |
| 5UTR-007 | Upstream UTR | GGGAGACAAGCUUGGCAUUCCGGUACUGUU GGUAAAGCCACC | SEQ ID NO: 33 |
| 5UTR-008 | Upstream UTR | GGGAAUUAACAGAGAAAAGAAGAGUAAGAAGAAAUAU AAGAGCCACC | SEQ ID NO: 34 |
| 5UTR-009 | Upstream UTR | GGGAAAUUAGACAGAAAAGAAGAGUAAGAAGAAAUAU AAGAGCCACC | SEQ ID NO: 35 |
| 5UTR-010 | Upstream UTR | GGGAAAUAAGAGAGUAAAGAACAGUAAGAAGAAAUAU AAGAGCCACC | SEQ ID NO: 36 |
| 5UTR-011 | Upstream UTR | GGGAAAAAAGAGAGAAAAGAAGACUAAGAAGAAAUAU AAGAGCCACC | SEQ ID NO: 37 |
| 5UTR-012 | Upstream UTR | GGGAAAUAAGAGAGAAAAGAAGAGUAAGAAGAUAUAU AAGAGCCACC | SEQ ID NO: 38 |
| 5UTR-013 | Upstream UTR | GGGAAAUAAGAGACAAAACAAGAGUAAGAAGAAAUAU AAGAGCCACC | SEQ ID NO: 39 |
| 5UTR-014 | Upstream UTR | GGGAAAUUAGAGAGUAAAGAACAGUAAGUAGAAUUAA AAGAGCCACC | SEQ ID NO: 40 |
| 5UTR-015 | Upstream UTR | GGGAAAUAAGAGAGAAUAGAAGAGUAAGAAGAAAUAU AAGAGCCACC | SEQ ID NO: 41 |
| 5UTR-016 | Upstream UTR | GGGAAAUAAGAGAGAAAAGAAGAGUAAGAAGAAAAUU AAGAGCCACC | SEQ ID NO: 42 |
| 5UTR-017 | Upstream UTR | GGGAAAUAAGAGAGAAAAGAAGAGUAAGAAGAAAUUU AAGAGCCACC | SEQ ID NO: 43 |
| 5UTR-018 | Upstream UTR | GGGAAAUAAGAGAGAAAAGAAGAGUAAGAAGAAAUAU AAGAGCCACC | SEQ ID NO: 44 |
| 5UTR-019 | Upstream UTR | UCAAGCUUUUGGACCCUCGUACAGAAGCUAAUACGAC UCACUAUAGGGAAAUAAGAGAGAAAAGAAGAGUAAGA AGAAAUAUAAGAGCCACC | SEQ ID NO: 118 |

Other non-UTR sequences can also be used as regions or subregions within the polynucleotides. For example, introns or portions of introns sequences can be incorporated into regions of the polynucleotides. Incorporation of intronic sequences can increase protein production as well as polynucleotide levels.

Combinations of features can be included in flanking regions and can be contained within other features. For example, the ORF can be flanked by a 5' UTR which can contain a strong Kozak translational initiation signal and/or a 3' UTR which can include an oligo(dT) sequence for templated addition of a poly-A tail. 5'UTR can comprise a first polynucleotide fragment and a second polynucleotide fragment from the same and/or different genes such as the 5'UTRs described in U.S. Patent Application Publication No. 2010-0293625.

These UTRs or portions thereof can be placed in the same orientation as in the transcript from which they were selected or can be altered in orientation or location. Hence a 5' or 3' UTR can be inverted, shortened, lengthened, made with one or more other 5' UTRs or 3' UTRs.

In some embodiments, the UTR sequences can be changed in some way in relation to a reference sequence. For example, a 3' or 5' UTR can be altered relative to a wild type or native UTR by the change in orientation or location as taught above or can be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' or 3' UTR can be used. As used herein, a "double" UTR is one in which two copies of the same UTR are encoded either in series or substantially in series. For example, a double beta-globin 3' UTR can be used as described in U.S. Patent Application Publication No. 2010-0129877.

In some embodiments, flanking regions can be heterologous. In some embodiments, the 5' untranslated region can be derived from a different species than the 3' untranslated region. The untranslated region can also include translation enhancer elements (TEE). As a non-limiting example, the TEE can include those described in U.S. Patent Application Publication No. 2009-0226470.

3' UTR and the AU Rich Elements

In certain embodiments, the polynucleotide (e.g., mRNA) encoding an IL-23 polypeptide, an IL-36-gamma polypeptide, an IL-18 polypeptide, or an OX40L polypeptide further comprises a 3' UTR. 3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the disclosure comprises a binding site for regulatory proteins or microRNAs. In some embodiments, the 3'-UTR has a silencer region, which binds to repressor proteins and inhibits the expression of the mRNA. In other embodiments, the 3'-UTR comprises an AU-rich element. Proteins bind AREs to affect the stability or decay rate of transcripts in a localized manner or affect translation initiation. In other embodiments, the 3'-UTR comprises the sequence AAUAAA that directs addition of several hundred adenine residues called the poly(A) tail to the end of the mRNA transcript.

Table 4A shows a listing of 3'-untranslated regions useful for the mRNAs encoding an IL-23 polypeptide, an IL-36-gamma polypeptide, or an OX40L polypeptide. Variants of 3' UTRs can be utilized wherein one or more nucleotides are added or removed to the termini, including A, U, C or G.

TABLE 4A

Exemplary 3'-Untranslated Regions

| 3' UTR Identifier | Name/ Description | Sequence | SEQ ID NO. |
|---|---|---|---|
| 3UTR-001 | Creatine Kinase | GCGCCUGCCCACCUGCCACCGACUGCUGGAACCCAGCCA<br>GUGGGAGGGCCUGGCCCACCAGAGUCCUGCUCCCUCACU<br>CCUCGCCCCGCCCCCUGUCCCAGAGUCCCACCUGGGGGC<br>UCUCUCCACCCUUCUCAGAGUUCCAGUUUCAACCAGAGU<br>UCCAACCAAUGGGCUCCAUCCUCUGGAUUCUGGCCAAUG<br>AAAUAUCUCCCUGGCAGGGUCCUCUUCUUUUCCCAGAGC<br>UCCACCCCAACCAGGAGCUCUAGUUAAUGGAGAGCUCCC<br>AGCACACUCGGAGCUUGUGCUUUGUCUCCACGCAAAGCG<br>AUAAAUAAAAGCAUUGGUGGCCUUUGGUCUUUGAAUAAA<br>GCCUGAGUAGGAAGUCUAGA | SEQ ID NO: 45 |
| 3UTR-002 | Myoglobin | GCCCCUGCCGCUCCCACCCCCACCCAUCUGGGCCCCGGG<br>UUCAAGAGAGAGCGGGGUCUGAUCUCGUGUAGCCAUAUA<br>GAGUUUGCUUCUGAGUGUCUGCUUUGUUUAGUAGAGGUG<br>GGCAGGAGGAGCUGAGGGGCUGGGGCUGGGGUGUUGAAG<br>UUGGCUUUGCAUGCCCAGCGAUGCGCCUCCCUGUGGGAU<br>GUCAUCACCCUGGGAACCGGGAGUGGCCCUUGGCUCACU<br>GUGUUCUGCAUGGUUUGGAUCUGAAUUAAUUGUCCUUUC<br>UUCUAAAUCCCAACCGAACUUCUUCCAACCUCCAAACUG<br>GCUGUAACCCCAAAUCCAAGCCAUUAACUACACCUGACA<br>GUAGCAAUUGUCUGAUUAAUCACUGGCCCCUUGAAGACA<br>GCAGAAUGUCCCUUUGCAAUGAGGAGGAGAUCUGGGCUG<br>GGCGGGCCAGCUGGGGAAGCAUUUGACUAUCUGGAACUU<br>GUGUGUGCCUCCUCAGGUAUGGCAGUGACUCACCUGGUU<br>UUAAUAAAACAACCUGCAACAUCUCAUGGUCUUUGAAUA<br>AAGCCUGAGUAGGAAGUCUAGA | SEQ ID NO: 46 |
| 3UTR-003 | α-actin | ACACACUCCACCUCCAGCACGCGACUUCUCAGGACGACG<br>AAUCUUCUCAAUGGGGGGGCGGCUGAGCUCCAGCCACCC<br>CGCAGUCACUUUCUUUGUAACAACUUCCGUUGCUGCCAU<br>CGUAAACUGACACAGUGUUUAUAACGUGUACAUACAUUA<br>ACUUAUUACCUCAUUUUGUUAUUUUUCGAAACAAAGCCC<br>UGUGGAAGAAAAUGGAAAACUUGAAGAAGCAUUAAAGUC<br>AUUCUGUUAAGCUGCGUAAAUGGUCUUUGAAUAAAGCCU<br>GAGUAGGAAGUCUAGA | SEQ ID NO: 47 |
| 3UTR-004 | Albumin | CAUCACAUUUAAAAGCAUCUCAGCCUACCAUGAGAAUAA<br>GAGAAAGAAAAUGAAGAUCAAAAGCUUAUUCAUCUGUUU<br>UUCUUUUUCGUUGGUGUAAAGCCAACACCCUGUCUAAAA<br>AACAUAAAUUUCUUUAAUCAUUUUGCCUCUUUUCUCUGU<br>GCUUCAAUUAAUAAAAAAUGGAAAGAAUCUAAUAGAGUG<br>GUACAGCACUGUUAUUUUUCAAAGAUGUGUUGCUAUCCU<br>GAAAAUUCUGUAGGUUCUGUGGAAGUUCCAGUGUUCUCU<br>CUUAUUCCACUUCGGUAGAGGAUUUCUAGUUUCUUGUGG | SEQ ID NO: 48 |

TABLE 4A-continued

| Exemplary 3'-Untranslated Regions | | | |
|---|---|---|---|
| 3' UTR Identifier | Name/ Description | Sequence | SEQ ID NO. |
| | | GCUAAUUAAAUAAAUCAUUAAUACUCUUCUAAUGGUCUU UGAAUAAAGCCUGAGUAGGAAGUCUAGA | |
| 3UTR-005 | α-globin | GCUGCCUUCUGCGGGGCUUGCCUUCUGGCCAUGCCCUUC UUCUCUCCCUUGCACCUGUACCUCUUGGUCUUUGAAUAA AGCCUGAGUAGGAAGGCGGCCGCUCGAGCAUGCAUCUAG A | SEQ ID NO: 49 |
| 3UTR-006 | G-CSF | GCCAAGCCCUCCCCAUCCCAUGUAUUUAUCUCUAUUUAA UAUUUAUGUCUAUUUAAGCCUCAUAUUUAAAGACAGGGA AGAGCAGAACGGAGCCCCAGGCCUCUGUGUCCUUCCCUG CAUUUCUGAGUUUCAUUCUCCUGCCUGUAGCAGUGAGAA AAAGCUCCUGUCCUCCCAUCCCCUGGACUGGGAGGUAGA UAGGUAAAUACCAAGUAUUUAUUACUAUGACUGCUCCCC AGCCCUGGCUCUGCAAUGGGCACUGGGAUGAGCCGCUGU GAGCCCCUGGUCCUGAGGGUCCCCACCUGGGACCCUUGA GAGUAUCAGGUCUCCCACGUGGGAGACAAGAAAUCCCUG UUUAAUAUUUAAACAGCAGUGUUCCCCAUCUGGGUCCUU GCACCCCUCACUCUGGCCUCAGCCGACUGCACAGCGGCC CCUGCAUCCCCUUGGCUGUGAGGCCCCUGGACAAGCAGA GGUGGCCAGAGCUGGGAGGCAUGGCCCUGGGGUCCCACG AAUUUGCUGGGGAAUCUCGUUUUUCUUCUUAAGACUUUU GGGACAUGGUUUGACUCCCGAACAUCACCGACGCGUCUC CUGUUUUUCUGGGUGGCCUCGGGACACCUGCCCUGCCCC CACGAGGGUCAGGACUGUGACUCUUUUUAGGGCCAGGCA GGUGCCUGGACAUUUGCCUUGCUGGACGGGGACUGGGGA UGUGGGAGGGAGCAGACAGGAGGAAUCAUGUCAGGCCUG UGUGUGAAAGGAAGCUCCACUGUCACCCUCCACCUCUUC ACCCCCCACUCACCAGUGUCCCCUCCACUGUCACAUUGU AACUGAACUUCAGGAUAAUAAAGUGUUUGCCUCCAUGGU CUUUGAAUAAAGCCUGAGUAGGAAGGCGGCCGCUCGAGC AUGCAUCUAGA | SEQ ID NO: 50 |
| 3UTR-007 | Col1a2; collagen, type I, alpha 2 | ACUCAAUCUAAAUUAAAAAAGAAAGAAAUUUGAAAAAAC UUUCUCUUUGCCAUUUCUUCUUCUUCUUUUUUAACUGAA AGCUGAAUCCUUCCAUUUCUUCUGCACAUCUACUUGCUU AAAUUGUGGGCAAAAGAGAAAAAGAAGGAUUGAUCAGAG CAUUGUGCAAUACAGUUUCAUUAACUCCUUCCCCCGCUC CCCCAAAAAUUUGAAUUUUUUUUUCAACACUCUUACACC UGUUAUGGAAAAUGUCAACCUUUGUAAGAAAACCAAAAU AAAAAUUGAAAAAUAAAAACCAUAAACAUUUGCACCACU UGUGGCUUUUGAAUAUCUUCCACAGAGGGAAGUUUAAAA CCCAAACUUCCAAAGGUUUAAACUACCUCAAAACACUUU CCCAUGAGUGUGAUCCACAUUGUUAGGUGCUGACCUAGA CAGAGAUGAACUGAGGUCCUUGUUUUGUUUUGUUCAUAA UACAAAGGUGCUAAUUAAUAGUAUUUCAGAUACUUGAAG AAUGUUGAUGGUGCUAGAAGAAUUUGAGAAGAAAUACUC CUGUAUUGAGUUGUAUCGUGUGGUGUAUUUUUUAAAAAA UUUGAUUUAGCAUUCAUAUUUUCCAUCUUAUUCCCAAUU AAAAGUAUGCAGAUUAUUUGCCCAAAUCUUCUUCAGAUU CAGCAUUUGUUCUUUGCCAGUCUCAUUUUCAUCUUCUUC CAUGGUUCCACAGAAGCUUUGUUUCUUGGGCAAGCAGAA AAAUUAAAUUGUACCUAUUUUGUAUAUGUGAGAUGUUUA AAUAAAUUGUGAAAAAAAUGAAAUAAAGCAUGUUUGGUU UUCCAAAAGAACAUAU | SEQ ID NO: 51 |
| 3UTR-008 | Col6a2; collagen, type VI, alpha 2 | CGCCGCCGCCCGGGCCCCGCAGUCGAGGGUCGUGAGCCC ACCCCGUCCAUGGUGCUAAGCGGGCCCGGGUCCCACACG GCCAGCACCGCUGCUCACUCGGACGACGCCCUGGGCCUG CACCUCUCCAGCUCCUCCCACGGGGUCCCCGUAGCCCCG GCCCCCGCCCAGCCCCAGGUCUCCCCAGGCCCUCCGCAG GCUGCCCGGCCUCCCUCCCCCUGCAGCCAUCCCAAGGCU CCUGACCUACCUGGCCCCUGAGCUCUGGAGCAAGCCCUG ACCCAAUAAAGGCUUUGAACCCAU | SEQ ID NO: 52 |
| 3UTR-009 | RPN1; ribophorin I | GGGGCUAGAGCCCUCUCCGCACAGCGUGGAGACGGGGCA AGGAGGGGGGUUAUUAGGAUUGGUGGUUUUGUUUUGCUU UGUUUAAAGCCGUGGGAAAAUGGCACAACUUUACCUCUG UGGGAGAUGCAACACUGAGAGCCAAGGGGUGGGAGUUGG GAUAAUUUUUAUAUAAAAGAAGUUUUUCCACUUUGAAUU GCUAAAAGUGGCAUUUUUCCUAUGUGCAGUCACUCCUCU CAUUUCUAAAAUAGGGACGUGGCCAGGCACGGUGGCUCA UGCCUGUAAUCCCAGCACUUUGGGAGGCCGAGGCAGGCG GCUCACGAGGUCAGGAGAUCGAGACUAUCCUGGCUAACA CGGUAAAACCCUGUCUCUACUAAAAGUACAAAAAAUUAG | SEQ ID NO: 53 |

TABLE 4A-continued

Exemplary 3'-Untranslated Regions

| 3' UTR Identifier | Name/ Description | Sequence | SEQ ID NO. |
|---|---|---|---|
| | | CUGGGCGUGGUGGUGGGCACCUGUAGUCCCAGCUACUCG GGAGGCUGAGGCAGGAGAAAGGCAUGAAUCCAAGAGGCA GAGCUUGCAGUGAGCUGAGAUCACGCCAUUGCACUCCAG CCUGGGCAACAGUGUUAAGACUCUGUCUCAAAUAUAAAU AAAUAAAUAAAUAAAUAAAUAAAUAAAUAAAAAUAAAGC GAGAUGUUGCCCUCAAA | |
| 3UTR-010 | LRP1; low density lipoprotein receptor-related protein 1 | GGCCCUGCCCCGUCGGACUGCCCCCAGAAAGCCUCCUGC CCCCUGCCAGUGAAGUCCUUCAGUGAGCCCCUCCCCAGC CAGCCCUUCCCUGGCCCCGCCGGAUGUAUAAAUGUAAAA AUGAAGGAAUUACAUUUUAUAUGUGAGCGAGCAAGCCGG CAAGCGAGCACAGUAUUAUUUCUCCAUCCCCUCCCUGCC UGCUCCUUGGCACCCCCAUGCUGCCUUCAGGGAGACAGG CAGGGAGGGCUUGGGGCUGCACCUCCUACCCUCCCACCA GAACGCACCCCACUGGGAGAGCUGGUGGUGCAGCCUUCC CCUCCCUGUAUAAGACACUUUGCCAAGGCUCUCCCCUCU CGCCCCAUCCCUGCUUGCCCGCUCCCACAGCUUCCUGAG GGCUAAUUCUGGGAAGGGAGAGUUCUUUGCUGCCCCUGU CUGGAAGACGUGGCUCUGGGUGAGGUAGGCGGGAAAGGA UGGAGUGUUUUAGUUCUUGGGGGAGGCCACCCCAAACCC CAGCCCCAACUCCAGGGGCACCUAUGAGAUGGCCAUGCU CAACCCCCCUCCCAGACAGGCCCUCCCUGUCUCCAGGGC CCCCACCGAGGUUCCCAGGGCUGGAGACUUCCUCUGGUA AACAUUCCUCCAGCCUCCCCUCCCCUGGGGACGCCAAGG AGGUGGGCCACACCCAGGAAGGGAAAGCGGGCAGCCCCG UUUUGGGGACGUGAACGUUUUAAUAAUUUUUGCUGAAUU CCUUUACAACUAAAUAACACAGAUAUUGUUAUAAAUAAA AUUGU | SEQ ID NO: 54 |
| 3UTR-011 | Nnt1; cardiotrophin-like cytokine factor 1 | AUAUUAAGGAUCAAGCUGUUAGCUAAUAAUGCCACCUCU GCAGUUUUGGGAACAGGCAAAUAAAGUAUCAGUAUACAU GGUGAUGUACAUCUGUAGCAAAGCUCUUGGAGAAAAUGA AGACUGAAGAAAGCAAAGCAAAAACUGUAUAGAGAGAUU UUUCAAAAGCAGUAAUCCCUCAAUUUUAAAAAAGGAUUG AAAAUUCUAAAUGUCUUUCUGUGCAUAUUUUUUGUGUUA GGAAUCAAAAGUAUUUUAUAAAAGGAGAAAGAACAGCCU CAUUUUAGAUGUAGUCCUGUUGGAUUUUUUAUGCCUCCU CAGUAACCAGAAAUGUUUUAAAAAACUAAGUGUUUAGGA UUUCAAGACAACAUUAUACAUGGCUCUGAAAUAUCUGAC ACAAUGUAAACAUUGCAGGCACCUGCAUUUUAUGUUUUU UUUUUCAACAAAUGUGACUAAUUUGAAACUUUUAUGAAC UUCUGAGCUGUCCCCUUGCAAUUCAACCGCAGUUUGAAU UAAUCAUAUCAAAUCAGUUUUAAUUUUUUAAAUUGUACU UCAGAGUCUAUAUUUCAAGGGCACAUUUUCUCACUACUA UUUUAAUACAUUAAAGGACUAAAUAAUCUUUCAGAGAUG CUGGAAACAAAUCAUUUGCUUUAUAUGUUUCAUUAGAAU ACCAAUGAAACAUACAACUUGAAAAUUAGUAAUAGUAUU UUUGAAGAUCCCAUUUCUAAUUGGAGAUCUCUUUAAUUU CGAUCAACUUAUAAUGUGUAGUACUAUAUUAAGUGCACU UGAGUGGAAUUCAACAUUUGACUAAUAAAAUGAGUUCAU CAUGUUGGCAAGUGAUGUGGCAAUUAUCUCUGGUGACAA AAGAGUAAAAUCAAAUAUUUCUGCCUGUUACAAAUAUCA AGGAAGACCUGCUACUAUGAAAUAGAUGACAUUAAUCUG UCUUCACUGUUUAUAAUACGGAUGGAUUUUUUUUCAAAU CAGUGUGUGUUUUGAGGUCUUAUGUAAUUGAUGACAUUU GAGAGAAAUGGUGGCUUUUUUUAGCUACCUCUUUGUUCA UUUAAGCACCAGUAAAGAUCAUGUCUUUUUAUAGAAGUG UAGAUUUUCUUUGUGACUUUGCUAUCGUGCCUAAAGCUC UAAAUAUAGGUGAAUGUGUGAUGAAUACUCAGAUUAUUU GUCUCUCUAUAUAAUUAGUUUGGUACUAAGUUUCUCAAA AAAUUAUUAACACAUGAAAGACAAUCUCUAAACCAGAAA AAGAAGUAGUACAAAUUUUGUUACUGUAAUGCUCGCGUU UAGUGAGUUUAAAACACACAGUAUCUUUUGGUUUUAUAA UCAGUUUCUAUUUUGCUGUGCCUGAGAUUAAGAUCUGUG UAUGUGUGUGUGUGUGUGUGUGCGUUUGUGUGUUAAAGC AGAAAAGACUUUUUUAAAAGUUUUAAGUGAUAAAUGCAA UUUGUUAAUUGAUCUUAGAUCACUAGUAAACUCAGGGCU GAAUUAUACCAUGUAUAUUCUAUUAGAAGAAAGUAAACA CCAUCUUUAUUCCUGCCCUUUUUCUUCUCUCAAAGUAGU UGUAGUUAUAUCUAGAAAGAAGCAAUUUUGAUUUCUUGA AAAGGUAGUUCCUGCACUCAGUUUAAACUAAAAAUAAUC AUACUUGGAUUUUAUUUAUUUUUGUCAUAGUAAAAAUUU UAAUUUAUAUAUAUUUUUAUUUAGUAUUAUCUUAUUCUU UGCUAUUUGCCAAUCCUUUGUCAUCAAUUGUGUUAAAUG AAUUGAAAAUUCAUGCCCUGUUCAUUUUAUUUUACUUUA | SEQ ID NO: 55 |

TABLE 4A-continued

Exemplary 3'-Untranslated Regions

| 3' UTR Identifier | Name/ Description | Sequence | SEQ ID NO. |
|---|---|---|---|
| | | UUGGUUAGGAUAUUUAAAGGAUUUUUGUAUAUAUAAUUU<br>CUUAAAUUAAUAUUCCAAAAGGUUAGUGGACUUAGAUUA<br>UAAAUUAUGGCAAAAAUCUAAAAACAACAAAAAUGAUUU<br>UUAUACAUUCUAUUUCAUUAUUCCUCUUUUUCCAAUAAG<br>UCAUACAAUUGGUAGAUAUGACUUAUUUUAUUUUUGUAU<br>UAUUCACUAUAUCUUUAUGAUAUUUAAGUAUAAAUAAUU<br>AAAAAAAUUUAUUGUACCUUAUAGUCUGUCACCAAAAAA<br>AAAAAAUUAUCUGUAGGUAGUGAAAUGCUAAUGUUGAUU<br>UGUCUUUAAGGGCUUGUUAACUAUCCUUUAUUUUCUCAU<br>UUGUCUUAAAUUAGGAGUUUGUGUUUAAAUUACUCAUCU<br>AAGCAAAAAAUGUAUAUAAAUCCCAUUACUGGGUAUAUA<br>CCCAAAGGAUUAUAAAUCAUGCUGCUAUAAAGACACAUG<br>CACACGUAUGUUUAUUGCAGCACUAUUCACAAUAGCAAA<br>GACUUGGAACCAACCCAAAUGUCCAUCAAUGAUAGACUU<br>GAUUAAGAAAAUGUGCACAUAUACACCAUGGAAUACUAU<br>GCAGCCAUAAAAAAGGAUGAGUUCAUGUCCUUUGUAGGG<br>ACAUGGAUAAAGCUGGAAACCAUCAUUCUGAGCAAACUA<br>UUGCAAGGACAGAAAACCAAACACUGCAUGUUCUCACUC<br>AUAGGUGGGAAUUGAACAAUGAGAACACUUGGACACAAG<br>GUGGGGAACACCACACACCAGGGCCUGUCAUGGGGUGGG<br>GGGAGUGGGGAGGGAUAGCAUUAGGAGAUAUACCUAAUG<br>UAAAUGAUGAGUUAAUGGGUGCAGCACACCAACAUGGCA<br>CAUGUAUACAUAUGUAGCAAACCUGCACGUUGUGCACAU<br>GUACCCUAGAACUUAAAGUAUAAUUAAAAAAAAAAAAGAA<br>AACAGAAGCUAUUUAUAAAGAAGUUAUUUGCUGAAAUAA<br>AUGUGAUCUUUCCCAUUAAAAAAAUAAAGAAAUUUUGGG<br>GUAAAAAAACACAAUAUAUUGUAUUCUUGAAAAAUUCUA<br>AGAGAGUGGAUGUGAAGUGUUCUCACCACAAAAGUGAUA<br>ACUAAUUGAGGUAAUGCACAUAUUAAUUAGAAAGAUUUU<br>GUCAUUCCACAAUGUAUAUAUACUUAAAAAUAUGUUAUA<br>CACAAUAAAUACAUACAUUAAAAAAUAAGUAAAUGUA | |
| 3UTR-012 | Col6a1; collagen, type VI, alpha 1 | CCCACCCUGCACGCCGGCACCAAACCCUGUCCUCCCACC<br>CCUCCCCACUCAUCACUAAACAGAGUAAAAUGUGAUGCG<br>AAUUUUCCCGACCAACCUGAUUCGCUAGAUUUUUUUUAA<br>GGAAAAGCUUGGAAAGCCAGGACACAACGCUGCUGCCUG<br>CUUUGUGCAGGGUCCUCCGGGGCUCAGCCCUGAGUUGGC<br>AUCACCUGCGCAGGGCCCUCUGGGGCUCAGCCCUGAGCU<br>AGUGUCACCUGCACAGGGCCCUCUGAGGCUCAGCCCUGA<br>GCUGGCGUCACCUGUGCAGGGCCCUCUGGGGCUCAGCCC<br>UGAGCUGGCCUCACCUGGGUUCCCCACCCCGGGCUCUCC<br>UGCCCUGCCCUCCUGCCCGCCCUCCCUCCUGCCUGCGCA<br>GCUCCUUCCCUAGGCACCUCUGUGCUGCAUCCCACCAGC<br>CUGAGCAAGACGCCCUCUCGGGGCCUGUGCCGCACUAGC<br>CUCCCUCUCCUCUGUCCCCAUAGCUGGUUUUUCCCACCA<br>AUCCUCACCUAACAGUUACUUUACAAUUAAACUCAAAGC<br>AAGCUCUUCUCCUCAGCUUGGGGCAGCCAUUGGCCUCUG<br>UCUCGUUUUGGGAAACCAAGGUCAGGAGGCCGUUGCAGA<br>CAUAAAUCUCGGCGACUCGGCCCCGUCUCCUGAGGGUCC<br>UGCUGGUGACCGGCCUGGACCUUGGCCCUACAGCCCUGG<br>AGGCCGCUGCUGACCAGCACUGACCCCGACCUCAGAGAG<br>UACUCGCAGGGGCGCUGGCUGCACUCAAGACCCUCGAGA<br>UUAACGGUGCUAACCCCGUCUGCUCCUCCCUCCCGCAGA<br>GACUGGGGCCUGGACUGGACAUGAGAGCCCCUUGGUGCC<br>ACAGAGGGCUGUGUCUUACUAGAAACAACGCAAACCUCU<br>CCUUCCUCAGAAUAGUGAUGUGUUCGACGUUUUAUCAAA<br>GGCCCCCUUUCUAUGUUCAUGUUAGUUUUGCUCCUUCUG<br>UGUUUUUUUCUGAACCAUAUCCAUGUUGCUGACUUUUCC<br>AAAUAAAGGUUUUCACUCCUCUC | SEQ ID NO: 56 |
| 3UTR-013 | Calr; calreticulin | AGAGGCCUGCCUCCAGGGCUGGACUGAGGCCUGAGCGCU<br>CCUGCCGCAGAGCUGGCCGCGCCAAAUAAUGUCUCUGUG<br>AGACUCGAGAACUUUCAUUUUUUUCCAGGCUGGUUCGGA<br>UUUGGGGUGGAUUUUGGUUUUGUUCCCCUCCUCCACUCU<br>CCCCCACCCCCUCCCCGCCCUUUUUUUUUUUUUUUUUUA<br>AACUGGUAUUUUAUCUUUGAUUCUCCUUCAGCCCUCACC<br>CCUGGUUCUCAUCUUUCUUGAUCAACAUCUUUUCUUGCC<br>UCUGUCCCCUUCUCUCAUCUCUUAGCUCCCCUCCAACCU<br>GGGGGGCAGUGGUGUGGAGAAGCCACAGGCCUGAGAUUU<br>CAUCUGCUCUCCUUCCUGGAGCCCAGAGGAGGGCAGCAG<br>AAGGGGGUGGUGUCUCCAACCCCCCAGCACUGAGGAAGA<br>ACGGGGCUCUUCUCAUUUCACCCCUCCCUUUCUCCCCUG<br>CCCCCAGGACUGGGCCACUUCUGGGUGGGGCAGUGGGUC<br>CCAGAUUGGCUCACACUGAGAAUGUAAGAACUACAAACA<br>AAAUUUCUAUUAAAUUAAAUUUUGUGUCUCC | SEQ ID NO: 57 |

TABLE 4A-continued

Exemplary 3'-Untranslated Regions

| 3' UTR Identifier | Name/ Description | Sequence | SEQ ID NO. |
|---|---|---|---|
| 3UTR-014 | Col1a1; collagen, type I, alpha 1 | CUCCCUCCAUCCCAACCUGGCUCCCUCCCACCCAACCAA<br>CUUUCCCCCCAACCCGGAAACAGACAAGCAACCCAAACU<br>GAACCCCCUCAAAAGCCAAAAAAUGGGAGACAAUUUCAC<br>AUGGACUUUGGAAAAUAUUUUUUUCCUUUGCAUUCAUCU<br>CUCAAACUUAGUUUUUAUCUUUGACCAACCGAACAUGAC<br>CAAAAACCAAAAGUGCAUUCAACCUUACCAAAAAAAAAA<br>AAAAAAAAAGAAUAAAUAAAUAACUUUUUAAAAAAGGAA<br>GCUUGGUCCACUUGCUUGAAGACCCAUGCGGGGGUAAGU<br>CCCUUUCUGCCCGUUGGGCUUAUGAAACCCCAAUGCUGC<br>CCUUUCUGCUCCUUUCUCCACACCCCCCUUGGGGCCUCC<br>CCUCCACUCCUUCCCAAAUCUGUCUCCCCAGAAGACACA<br>GGAAACAAUGUAUUGUCUGCCCAGCAAUCAAAGGCAAUG<br>CUCAAACACCCAAGUGGCCCCCACCCUCAGCCCGCUCCU<br>GCCCGCCCAGCACCCCCAGGCCCUGGGGGACCUGGGGUU<br>CUCAGACUGCCAAAGAAGCCUUGCCAUCUGGCGCUCCCA<br>UGGCUCUUGCAACAUCUCCCCUUCGUUUUUGAGGGGGUC<br>AUGCCGGGGGAGCCACCAGCCCCUCACUGGGUUCGGAGG<br>AGAGUCAGGAAGGGCCACGACAAAGCAGAAACAUCGGAU<br>UUGGGGAACGCGUGUCAAUCCCUUGUGCCGCAGGGCUGG<br>GCGGGAGAGACUGUUCUGUUCCUUGUGUAACUGUGUUGC<br>UGAAAGACUACCUCGUUCUUGUCUUGAUGUGUCACCGGG<br>GCAACUGCCUGGGGGCGGGGAUGGGGGCAGGGUGGAAGC<br>GGCUCCCCAUUUUAUACCAAAGGUGCUACAUCUAUGUGA<br>UGGGUGGGGUGGGGAGGGAAUCACUGGUGCUAUAGAAAU<br>UGAGAUGCCCCCCCAGGCCAGCAAAUGUUCCUUUUUGUU<br>CAAAGUCUAUUUUUAUUCCUUGAUAUUUUUCUUUUUUUU<br>UUUUUUUUUUGUGGAUGGGGACUUGUGAAUUUUUCUAA<br>AGGUGCUAUUUAACAUGGGAGGAGAGCGUGUGCGGCUCC<br>AGCCCAGCCCGCUGCUCACUUUCCACCCUCUCUCCACCU<br>GCCUCUGGCUUCUCAGGCCUCUGCUCUCCGACCUCUCUC<br>CUCUGAAACCCUCCUCCACAGCUGCAGCCCAUCCUCCCG<br>GCUCCCUCCUAGUCUGUCCUGCGUCCUCUGUCCCCGGGU<br>UUCAGAGACAACUUCCCAAAGCACAAAGCAGUUUUUCCC<br>CCUAGGGGUGGGAGGAAGCAAAAGACUCUGUACCUAUUU<br>UGUAUGUGUAUAAUAAUUUGAGAUGUUUUUAAUUAUUUU<br>GAUUGCUGGAAUAAAGCAUGUGGAAAUGACCCAAACAUA<br>AUCCGCAGUGGCCUCCUAAUUUCCUUCUUUGGAGUUGGG<br>GGAGGGGUAGACAUGGGGAAGGGGCUUUGGGGUGAUGGG<br>CUUGCCUUCCAUUCCUGCCCUUUCCCUCCCCACUAUUCU<br>CUUCUAGAUCCCUCCAUAACCCCACUCCCCUUUCUCUCA<br>CCCUUCUUAUACCGCAAACCUUUCUACUUCCUCUUUCAU<br>UUUCUAUUCUUGCAAUUUCCUUGCACCUUUUCCAAAUCC<br>UCUUCUCCCCUGCAAUACCAUACAGGCAAUCCACGUGCA<br>CAACACACACACACACUCUUCACAUCUGGGGUUGUCCAA<br>ACCUCAUACCCACUCCCCUUCAAGCCCAUCCACUCUCCA<br>CCCCCUGGAUGCCCUGCACUUGGUGGCGGUGGGAUGCUC<br>AUGGAUACUGGGAGGGUGAGGGGAGUGGAACCCGUGAGG<br>AGGACCUGGGGGCCUCUCCUUGAACUGACAUGAAGGGUC<br>AUCUGGCCUCUGCUCCCUUCUCACCCACGCUGACCUCCU<br>GCCGAAGGAGCAACGCAACAGGAGAGGGGUCUGCUGAGC<br>CUGGCGAGGGUCUGGGAGGGACCAGGAGGAAGGCGUGCU<br>CCCUGCUCGCUGUCCUGGCCCUGGGGGAGUGAGGGAGAC<br>AGACACCUGGGAGAGCUGUGGGGAAGGCACUCGCACCGU<br>GCUCUUGGGAAGGAAGGAGACCUGGCCCUGCUCACCACG<br>GACUGGGUGCCUCGACCUCCUGAAUCCCCAGAACACAAC<br>CCCCCUGGGCUGGGGUGGUCUGGGGAACCAUCGUGCCCC<br>CGCCUCCCGCCUACUCCUUUUUAAGCUU | SEQ ID NO: 58 |
| 3UTR-015 | Plod1; procollagen-lysine, 2-oxoglutarate 5-dioxygenase 1 | UUGGCCAGGCCUGACCCUCUUGGACCUUUCUUCUUUGCC<br>GACAACCACUGCCCAGCAGCCUCUGGGACCUCGGGGUCC<br>CAGGGAACCCAGUCCAGCCUCCUGGCUGUUGACUUCCCA<br>UUGCUCUUGGAGCCACCAAUCAAAGAGAUUCAAAGAGAU<br>UCCUGCAGGCCAGAGGCGGAACACACCUUUAUGGCUGGG<br>GCUCUCCGUGGUGUUCUGGACCCAGCCCCUGGAGACACC<br>AUUCACUUUUACUGCUUUGUAGUGACUCGUGCUCUCCAA<br>CCUGUCUUCCUGAAAAACCAAGGCCCCCUUCCCCCACCU<br>CUUCCAUGGGGUGAGACUUGAGCAGAACAGGGGCUUCCC<br>CAAGUUGCCCAGAAAGACUGUCUGGGUGAGAAGCCAUGG<br>CCAGAGCUUCUCCCAGGCACAGGUGUUGCACCAGGGACU<br>UCUGCUUCAAGUUUUGGGGUAAAGACACCUGGAUCAGAC<br>UCCAAGGGCUGCCCUGAGUCUGGGACUUCUGCCUCCAUG<br>GCUGGUCAUGAGAGCAAACCGUAGUCCCCUGGAGACAGC<br>GACUCCAGAGAACCUCUUGGGAGACAGAAGAGGCAUCUG<br>UGCACAGCUCGAUCUUCUACUUGCCUGUGGGGAGGGGAG<br>UGACAGGUCCACACACCACACUGGGUCACCCUGUCCUGG | SEQ ID NO: 59 |

TABLE 4A-continued

| Exemplary 3'-Untranslated Regions | | | |
|---|---|---|---|
| 3' UTR Identifier | Name/ Description | Sequence | SEQ ID NO. |
| | | AUGCCUCUGAAGAGAGGGACAGACCGUCAGAAACUGGAG AGUUUCUAUUAAAGGUCAUUUAAACCA | |
| 3UTR-016 | Nucb1; nucleobindin 1 | UCCUCCGGGACCCCAGCCCUCAGGAUUCCUGAUGCUCCA AGGCGACUGAUGGGCGCUGGAUGAAGUGGCACAGUCAGC UUCCCUGGGGGCUGGUGUCAUGUUGGGCUCCUGGGGCGG GGGCACGGCCUGGCAUUUCACGCAUUGCUGCCACCCCAG GUCCACCUGUCUCCACUUUCACAGCCUCCAAGUCUGUGG CUCUUCCCUUCUGUCCUCCGAGGGGCUUGCCUUCUCUCG UGUCCAGUGAGGUGCUCAGUGAUCGGCUUAACUUAGAGA AGCCCGCCCCCUCCCCUUCUCCGUCUGUCCCAAGAGGGU CUGCUCUGAGCCUGCGUUCCUAGGUGGCUCGGCCUCAGC UGCCUGGGUUGUGGCCGCCCUAGCAUCCUGUAUGCCCAC AGCUACUGGAAUCCCCGCUGCUGCUCCGGGCCAAGCUUC UGGUUGAUUAAUGAGGGCAUGGGGUGGUCCCUCAAGACC UUCCCCUACCUUUUGUGGAACCAGUGAUGCCUCAAAGAC AGUGUCCCCUCCACAGCUGGGUGCCAGGGGCAGGGGAUC CUCAGUAUAGCCGGUGAACCCUGAUACCAGGAGCCUGGG CCUCCCUGAACCCCUGGCUUCCAGCCAUCUCAUCGCCAG CCUCCUCCUGGACCUCUUGGCCCCCAGCCCCUUCCCCAC ACAGCCCCAGAAGGGUCCCAGAGCUGACCCCACUCCAGG ACCUAGGCCCAGCCCCUCAGCCUCAUCUGGAGCCCCUGA AGACCAGUCCCACCCACCUUUCUGGCCUCAUCUGACACU GCUCCGCAUCCUGCUGUGUGUCCUGUUCCAUGUUCCGGU UCCAUCCAAAUACACUUUCUGGAACAAA | SEQ ID NO: 60 |
| 3UTR-017 | α-globin | GCUGGAGCCUCGGUGGCCAUGCUUCUUGCCCCUUGGGCC UCCCCCCAGCCCCUCCUCCCCUUCCUGCACCCGUACCCC CGUGGUCUUUGAAUAAAGUCUGAGUGGGCGGC | SEQ ID NO: 61 |
| 3UTR-018 | Downstream UTR | UAAUAGGCUGGAGCCUCGGUGGCCAUGCUUCUUGCCCCU UGGGCCUCCCCCCAGCCCCUCCUCCCCUUCCUGCACCCG UACCCCCGUGGUCUUUGAAUAAAGUCUGAGUGGGCGGC | SEQ ID NO: 62 |
| 3UTR-019 | Downstream UTR | UGAUAAUAGGCUGGAGCCUCGGUGGCCAUGCUUCUUGCC CCUUGGGCCUCCCCCCAGCCCCUCCUCCCCUUCCUGCAC CCGUACCCCCUGGUCUUUGAAUAAAGUCUGAGUGGGCGG C | SEQ ID NO: 119 |

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NOS: 45-62 and any combination thereof. In a particular embodiment, the 3' UTR sequence further comprises a miRNA binding site, e.g., miR-122 binding site. In other embodiments, a 3'UTR sequence useful for the disclosure comprises 3' UTR-018 (SEQ ID NO: 62).

In certain embodiments, the 3' UTR sequence comprises one or more miRNA binding sites, e.g., miR-122 binding sites, or any other heterologous nucleotide sequences therein, without disrupting the function of the 3' UTR. Some examples of 3' UTR sequences comprising a miRNA binding site are listed in Table 4B.

TABLE 4B

| Exemplary 3' UTR with miRNA Binding Sites | | | |
|---|---|---|---|
| 3' UTR Identifier/ miRNA BS | Name/ Description | Sequence | SEQ ID NO. |
| 3UTR-018 + miR-122-5p binding site | Downstream UTR | UAAUAGGCUGGAGCCUCGGUGGCCAUGCUUCUUGCC CCUUGGGCCUCCCCCCAGCCCCUCCUCCCCUUCCUG CACCCGUACCCCC**CAAACACCAUUGUCACACUCCA**G UGGUCUUUGAAUAAAGUCUGAGUGGGCGGC | SEQ ID NO: 63 |
| 3UTR-018 + miR-122-3p binding site | Downstream UTR | UAAUAGGCUGGAGCCUCGGUGGCCAUGCUUCUUGCC CCUUGGGCCUCCCCCCAGCCCCUCCUCCCCUUCCUG CACCCGUACCCCC**UAUUUAGUGUGAUAAUGGCGUU**G UGGUCUUUGAAUAAAGUCUGAGUGGGCGGC | SEQ ID NO: 64 |

TABLE 4B-continued

Exemplary 3' UTR with miRNA Binding Sites

| 3' UTR Identifier/ miRNA BS | Name/ Description | Sequence | SEQ ID NO. |
|---|---|---|---|
| 3UTR-019 + miR-122 binding site | Downstream UTR | UGAUAAUAGGCUGGAGCCUCGGUGGCCAUGCUUCUU GCCCCUUGGGCCUCCCCCCAGCCCCUCCUCCCCUUC CUGCACCCGUACCCCCCAAACACCAUUGUCACACUC CAGUGGUCUUUGAAUAAAGUCUGAGUGGGCGGC | SEQ ID NO: 120 |

*miRNA binding site is boxed or underlined.

In certain embodiments, the 3' UTR sequence useful for the disclosure comprises a nucleotide sequence at least about 60%, at least about 70%, at least about 80%, at least about t90%, at least about 95%, at least about 96%, at least about 97%, at least about 98%, at least about 99%, or about 100% identical to the sequence set forth as SEQ ID NO: 63 or 64.

Regions Having a 5' Cap

The polynucleotide comprising an mRNA encoding an IL-23 polypeptide, an IL-36-gamma polypeptide, an IL-18 polypeptide, or an OX40L polypeptide of the present disclosure can further comprise a 5' cap. The 5' cap useful for the IL-23, IL-36-gamma an IL-18 polypeptide, and/or OX40L polypeptide encoding mRNA can bind the mRNA Cap Binding Protein (CBP), thereby increasing mRNA stability. The cap can further assist the removal of 5' proximal introns removal during mRNA splicing.

In some embodiments, the polynucleotide comprising an mRNA encoding an IL-23 polypeptide, an IL-36-gamma polypeptide, an IL-18 polypeptide, or an OX40L polypeptide of the present disclosure comprises a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

In certain embodiments, the 5' cap comprises 2'-O-methylation of the ribose sugars of 5'-terminal and/or 5'-anteterminal nucleotides on the 2'-hydroxyl group of the sugar ring. In other embodiments, the caps for the IL-23 polypeptide, IL-36-gamma polypeptide, or an OX40L polypeptide-encoding mRNA include cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs can be chemically (i.e. non-enzymatically) or enzymatically synthesized and/or linked to the polynucleotides of the disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3-O}$G(5')ppp(5')G cap analog. See, e.g., the various cap analogs and the methods of synthesizing cap analogs described in Kore et al. (2013) Bioorganic & Medicinal Chemistry 21:4570-4574. In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

The IL-23 polypeptide, IL-36-gamma polypeptide, an IL-18 polypeptide, and/or an OX40L polypeptide encoding mRNA of the present disclosure can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects.

Non-limiting examples of more authentic 5' cap structures of the present disclosure are those which, among other things, have enhanced binding of cap binding proteins, increased half-life, reduced susceptibility to 5' endonucleases and/or reduced 5' decapping, as compared to synthetic 5' cap structures known in the art (or to a wild-type, natural or physiological 5' cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5' cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

In some embodiments, a polynucleotide comprising an mRNA encoding an IL-23 polypeptide, an IL-36-gamma polypeptide, an IL-18 polypeptide, or an OX40L polypeptide of the present disclosure further comprises a poly A tail. In further embodiments, terminal groups on the poly-A tail can be incorporated for stabilization. In other embodiments, a poly-A tail comprises des-3' hydroxyl tails. The useful poly-A tails can also include structural moieties or 2'-Omethyl modifications as taught by Li et al. (2005) Current Biology 15:1501-1507.

In one embodiment, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

Start Codon Region

In some embodiments, the polynucleotide comprising an mRNA encoding an IL-23 polypeptide, an IL-36-gamma polypeptide, an IL-18 polypeptide, or an OX40L polypeptide of the present disclosure further comprises regions that are analogous to or function like a start codon region.

In some embodiments, the translation of a polynucleotide initiates on a codon which is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG. See Touriol et al. (2003) Biology of the Cell 95:169-178 and Matsuda and Mauro (2010) PLoS ONE 5:11. As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. See, e.g., Matsuda and Mauro (2010) PLoS ONE 5:11. Masking any of the nucleotides flanking a codon that initiates translation can be used to alter the position of translation initiation, translation efficiency, length and/or structure of a polynucleotide.

In some embodiments, a masking agent is used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs). See, e.g., Matsuda and Mauro (2010) PLoS ONE 5:11, describing masking agents LNA polynucleotides and EJCs.

In another embodiment, a masking agent is used to mask a start codon of a polynucleotide in order to increase the likelihood that translation will initiate on an alternative start codon. In some embodiments, a masking agent is used to mask a first start codon or alternative start codon in order to increase the chance that translation will initiate on a start codon or alternative start codon downstream to the masked start codon or alternative start codon.

In some embodiments, a start codon or alternative start codon is located within a perfect complement for a miR binding site. The perfect complement of a miR binding site can help control the translation, length and/or structure of the polynucleotide similar to a masking agent. As a non-limiting example, the start codon or alternative start codon is located in the middle of a perfect complement for a miR-122 binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide is removed from the polynucleotide sequence in order to have the translation of the polynucleotide begin on a codon which is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

Stop Codon Region

In some embodiments, the polynucleotide comprising an mRNA encoding an IL-23 polypeptide, an IL-36-gamma polypeptide, an IL-18 polypeptide, or an OX40L polypeptide of the present disclosure can further comprise at least one stop codon or at least two stop codons before the 3' untranslated region (UTR). The stop codon can be selected from UGA, UAA, and UAG. In some embodiments, the polynucleotides of the present disclosure include the stop codon UGA and one additional stop codon. In a further embodiment the addition stop codon can be UAA. In another embodiment, the polynucleotides of the present disclosure include three stop codons, four stop codons, or more.

X. Methods of Making Polynucleotides

The present disclosure also provides methods for making a polynucleotide disclosed herein or a complement thereof. In some aspects, a polynucleotide (e.g., an mRNA) disclosed herein, and encoding an IL-23 polypeptide, an IL-36-gamma polypeptide, or an OX40L polypeptide can be constructed using in vitro transcription.

In other aspects, a polynucleotide (e.g., an mRNA) disclosed herein, and encoding an IL-23 polypeptide, an IL-36-gamma polypeptide, an IL-18 polypeptide, or an OX40L polypeptide can be constructed by chemical synthesis using an oligonucleotide synthesizer. In other aspects, a polynucleotide (e.g., an mRNA) disclosed herein, and encoding an IL-23 polypeptide, an IL-36-gamma polypeptide, an IL-18 polypeptide, or an OX40L polypeptide is made by using a host cell. In certain aspects, a polynucleotide (e.g., an mRNA) disclosed herein, and encoding an IL-23 polypeptide, an IL-36-gamma polypeptide, an IL-18 polypeptide, or an OX40L polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., an mRNA) encoding an IL-23 polypeptide, an IL-36-gamma polypeptide, an IL-18 polypeptide, or an OX40L polypeptide. The resultant mRNAs can then be examined for their ability to produce protein and/or produce a therapeutic outcome.

In Vitro Transcription-Enzymatic Synthesis

A polynucleotide disclosed herein can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate modified nucleic acids. See U.S. Publ. No. US2013-0259923.

The IVT system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein.

Any number of RNA polymerases or variants can be used in the synthesis of the polynucleotides of the present disclosure.

RNA polymerases can be modified by inserting or deleting amino acids of the RNA polymerase sequence. As a non-limiting example, the RNA polymerase is modified to exhibit an increased ability to incorporate a 2'-modified nucleotide triphosphate compared to an unmodified RNA polymerase. See International Publication WO2008078180 and U.S. Pat. No. 8,101,385.

Variants can be obtained by evolving an RNA polymerase, optimizing the RNA polymerase amino acid and/or nucleic acid sequence and/or by using other methods known in the art. As a non-limiting example, T7 RNA polymerase variants are evolved using the continuous directed evolution system set out by Esvelt et al. (2011) Nature 472:499-503, where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. Cheng et al. (1994) Proc. Natl. Acad. Sci. USA 91:5695-5699. RNA polymerases from bacteriophage T3, T7, and SP6 have been widely used to prepare RNAs for biochemical and biophysical studies. RNA polymerases, capping enzymes, and poly-A polymerases are disclosed in International Publication No. WO2014028429 (see also US 20150211039).

In one aspect, the RNA polymerase which can be used in the synthesis of the polynucleotides described herein is a Syn5 RNA polymerase. See Zhu et al. (2013) Nucleic Acids Research 288:3545-3552. The Syn5 RNA polymerase was recently characterized from marine cyanophage Syn5 by Zhu et al. where they also identified the promoter sequence. See Zhu et al. (2013) Nucleic Acids Research 288:3545-3552. Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-termini.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 198) as described by Zhu et al. (2013) Nucleic Acids Research 288:3545-3552.

In one aspect, a Syn5 RNA polymerase can be used in the synthesis of polynucleotides comprising at least one chemical modification described herein and/or known in the art. (see e.g., the incorporation of pseudo-UTP and 5Me-CTP described in Zhu et al. (2013) Nucleic Acids Research 288:3545-3552.

In one aspect, the polynucleotides described herein can be synthesized using a Syn5 RNA polymerase which has been purified using modified and improved purification procedure described by Zhu et al. (2013) Nucleic Acids Research 288:3545-3552.

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the disclosure.

Polymerase chain reaction (PCR) has wide applications in rapid amplification of a target gene, as well as genome mapping and sequencing. The key components for synthesizing DNA comprise target DNA molecules as a template, primers complementary to the ends of target DNA strands, deoxynucleoside triphosphates (dNTPs) as building blocks, and a DNA polymerase. As PCR progresses through denaturation, annealing and extension steps, the newly produced DNA molecules can act as a template for the next circle of replication, achieving exponentially amplification of the target DNA. PCR requires a cycle of heating and cooling for denaturation and annealing. Variations of the basic PCR include asymmetric PCR (Innis et al. (1988) Proc. Natl. Acad. Sci. USA 85:9436-9440), inverse PCR (Ochman et al. (1988) Genetics 120:621-623), reverse transcription PCR (RT-PCR) (Freeman et al. (1999) BioTechniques 26:112-22, 124-5). In RT-PCR, a single stranded RNA is the desired target and is converted to a double stranded DNA first by reverse transcriptase.

A variety of isothermal in vitro nucleic acid amplification techniques have been developed as alternatives or complements of PCR. For example, strand displacement amplification (SDA) is based on the ability of a restriction enzyme to form a nick. Walker et al. (1992) Proc. Natl. Acad. Sci. USA 89:392-396, the contents of which are incorporated herein by reference in their entirety.

A restriction enzyme recognition sequence is inserted into an annealed primer sequence. Primers are extended by a DNA polymerase and dNTPs to form a duplex. Only one strand of the duplex is cleaved by the restriction enzyme. Each single strand chain is then available as a template for subsequent synthesis. SDA does not require the complicated temperature control cycle of PCR.

Nucleic acid sequence-based amplification (NASBA), also called transcription mediated amplification (TMA), is also an isothermal amplification method that utilizes a combination of DNA polymerase, reverse transcriptase, RNAse H, and T7 RNA polymerase. Compton (1991) Nature 350:91-92. A target RNA is used as a template and a reverse transcriptase synthesizes its complementary DNA strand. RNAse H hydrolyzes the RNA template, making space for a DNA polymerase to synthesize a DNA strand complementary to the first DNA strand which is complementary to the RNA target, forming a DNA duplex. T7 RNA polymerase continuously generates complementary RNA strands of this DNA duplex. These RNA strands act as templates for new cycles of DNA synthesis, resulting in amplification of the target gene.

Rolling-circle amplification (RCA) amplifies a single stranded circular polynucleotide and involves numerous rounds of isothermal enzymatic synthesis where <29 DNA polymerase extends a primer by continuously progressing around the polynucleotide circle to replicate its sequence over and over again. Therefore, a linear copy of the circular template is achieved. A primer can then be annealed to this linear copy and its complementary chain can be synthesized. See Lizardi et al. (1998) Nature Genetics 19:225-232. A single stranded circular DNA can also serve as a template for RNA synthesis in the presence of an RNA polymerase. Daubendiek et al. (1995) JACS 117:7818-7819. An inverse rapid amplification of cDNA ends (RACE) RCA is described by Polidoros et al. A messenger RNA (mRNA) is reverse transcribed into cDNA, followed by RNAse H treatment to separate the cDNA. The cDNA is then circularized by CircLigase into a circular DNA. The amplification of the resulting circular DNA is achieved with RCA. Polidoros et al. (2006) BioTechniques 41:35-42.

Any of the foregoing methods can be utilized in the manufacture of one or more regions of the polynucleotides of the present disclosure.

Assembling polynucleotides or nucleic acids by a ligase is also widely used. DNA or RNA ligases promote intermolecular ligation of the 5' and 3' ends of polynucleotide chains through the formation of a phosphodiester bond. Ligase chain reaction (LCR) is a promising diagnosing technique based on the principle that two adjacent polynucleotide probes hybridize to one strand of a target gene and couple to each other by a ligase. If a target gene is not present, or if there is a mismatch at the target gene, such as a single-nucleotide polymorphism (SNP), the probes cannot ligase. Wiedmann et al. (1994) PCR Methods and Application 3(4):s51-s64. LCR can be combined with various amplification techniques to increase sensitivity of detection or to increase the amount of products if it is used in synthesizing polynucleotides and nucleic acids.

Several library preparation kits for nucleic acids are now commercially available. They include enzymes and buffers to convert a small amount of nucleic acid samples into an indexed library for downstream applications. For example, DNA fragments can be placed in a NEBNEXT® ULTRA™ DNA Library Prep Kit by NEWENGLAND BIOLABS® for end preparation, ligation, size selection, clean-up, PCR amplification and final clean-up.

Continued development is going on to improvement the amplification techniques. For example, U.S. Pat. No. 8,367,328 to Asada et al., teaches utilizing a reaction enhancer to increase the efficiency of DNA synthesis reactions by DNA polymerases. The reaction enhancer comprises an acidic substance or cationic complexes of an acidic substance. U.S. Pat. No. 7,384,739 to Kitabayashi et al., teaches a carboxylate ion-supplying substance that promotes enzymatic DNA synthesis, wherein the carboxylate ion-supplying substance is selected from oxalic acid, malonic acid, esters of oxalic acid, esters of malonic acid, salts of malonic acid, and esters of maleic acid. U.S. Pat. No. 7,378,262 to Sobek et al., discloses an enzyme composition to increase fidelity of DNA amplifications. The composition comprises one enzyme with 3' exonuclease activity but no polymerase activity and another enzyme that is a polymerase. Both of the enzymes are thermostable and are reversibly modified to be inactive at lower temperatures.

U.S. Pat. No. 7,550,264 to Getts et al. teaches multiple round of synthesis of sense RNA molecules are performed by attaching oligodeoxynucleotides tails onto the 3' end of cDNA molecules and initiating RNA transcription using RNA polymerase. U.S. Pat. Publication No. 2013/0183718 to Rohayem teaches RNA synthesis by RNA-dependent RNA polymerases (RdRp) displaying an RNA polymerase activity on single-stranded DNA templates. Oligonucleotides with non-standard nucleotides can be synthesized with enzymatic polymerization by contacting a template comprising non-standard nucleotides with a mixture of nucleotides that are complementary to the nucleotides of the template as disclosed in U.S. Pat. No. 6,617,106 to Benner.

Chemical Synthesis

Standard methods can be applied to synthesize an isolated polynucleotide sequence encoding an IL-23 polypeptide, an IL-36-gamma polypeptide, an IL-18 polypeptide, and/or an OX40L polypeptide. For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., mRNA) can be chemically synthesized using chemical synthesis methods and potential nucleobase substitutions known in the art. See, for example, International Publication Nos. WO2014093924 (see also US20150307542), WO2013052523 (see also US20130115272); WO2013039857, WO2012135805 (see also US20120251618), WO2013151671 (see also US20150044277); U.S. Publ. No. US20130115272; or U.S. Pat. Nos. 8,999,380, 8,710,200.

Purification

Purification of the polynucleotides (e.g., mRNA) encoding an IL-23 polypeptide, an IL-36-gamma polypeptide, an IL-18 polypeptide, and/or an OX40L polypeptide described herein can include, but is not limited to, polynucleotide clean-up, quality assurance and quality control. Clean-up can be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a polynucleotide such as a "purified polynucleotide" refers to one that is separated from at least one contaminant. As used herein, a "contaminant" is any substance which makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide (e.g., mRNA) encoding an IL-23 polypeptide, an IL-36-gamma polypeptide, an IL-18 polypeptide, and/or an OX40L polypeptide of the disclosure removes impurities that can reduce or remove an unwanted immune response, e.g., reducing cytokine activity.

In some embodiments, the polynucleotide (e.g., mRNA) encoding an IL-23 polypeptide, an IL-36-gamma polypeptide, an IL-18 polypeptide, and/or an OX40L polypeptide of the disclosure is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)). In some embodiments, a column chromatography (e.g., strong anion exchange HPLC, weak anion exchange HPLC, reverse phase HPLC (RP-HPLC), and hydrophobic interaction HPLC (HIC-HPLC), or (LCMS)) purified polynucleotide, which encodes an IL-23 polypeptide, an IL-36-gamma polypeptide, an IL-18 polypeptide, and/or an OX40L polypeptide disclosed herein increases expression of the IL-23 polypeptide, the IL-36-gamma polypeptide, an IL-18 polypeptide, and/or an OX40L polypeptide compared to polynucleotides encoding the IL-23 polypeptide, an IL-36-gamma polypeptide, an IL-18 polypeptide, and/or an OX40L polypeptide purified by a different purification method.

In some embodiments, a column chromatography (e.g., strong anion exchange HPLC, weak anion exchange HPLC, reverse phase HPLC (RP-HPLC), and hydrophobic interaction HPLC (HIC-HPLC), or (LCMS)) purified polynucleotide encodes a encodes a mammalian IL-23 polypeptide, a mammalian IL-36-gamma polypeptide, an IL-18 polypeptide, and/or a mammalian OX40L polypeptide. In some embodiments, the purified polynucleotide encodes an IL-23 polypeptide, an IL-36-gamma polypeptide, an IL-18 polypeptide, and/or an OX40L polypeptide. In some embodiments, the purified polynucleotide encodes a human IL-23 polypeptide, a human IL-36-gamma polypeptide, an IL-18 polypeptide, and/or a human OX40L polypeptide.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC.

In another embodiment, the polynucleotides can be sequenced by methods including, but not limited to reverse-transcriptase-PCR.

XI. Chemical Modifications

As used herein in polynucleotides comprising an mRNA encoding an IL-23 polypeptide, polynucleotides comprising an mRNA encoding an IL-36-gamma polypeptide an IL-18 polypeptide, polynucleotides comprising an mRNA encoding an OX40L polypeptide, or combinations thereof according to the present disclosure, the terms "chemical modification" or, as appropriate, "chemically modified" refer to modification with respect to adenosine (A), guanosine (G), uridine (U), thymidine (T) or cytidine (C) ribo- or deoxyribonucleotides in one or more of their position, pattern, percent or population. Generally, herein, these terms are not intended to refer to the ribonucleotide modifications in naturally occurring 5'-terminal mRNA cap moieties.

In a polypeptide, the term "modification" refers to a modification as compared to the canonical set of 20 amino acids.

The modifications can be various distinct modifications. In some embodiments, the regions can contain one, two, or more (optionally different) nucleoside or nucleotide (nucleobase) modifications. In some embodiments, a modified polynucleotide, introduced to a cell can exhibit reduced degradation in the cell, as compared to an unmodified polynucleotide. In other embodiments, the modification is in the nucleobase and/or the sugar structure. In yet other embodiments, the modification is in the backbone structure.

Chemical Modifications

Some embodiments of the present disclosure provide a first polynucleotide comprising an mRNA encoding an IL-23 polypeptide, and a second polynucleotide comprising an mRNA encoding an IL-36-gamma polypeptide or an IL-18 polypeptide, or a third polynucleotide comprising an mRNA encoding an OX40L polypeptide, wherein the mRNA includes at least one chemical modification.

Other embodiments of the present disclosure provide a first polynucleotide comprising an mRNA encoding an IL-23 polypeptide, a second polynucleotide comprising an mRNA encoding an IL-36-gamma polypeptide, oran IL-18 polypeptide, and a third polynucleotide comprising an mRNA encoding an OX40L polypeptide wherein the mRNA includes at least one chemical modification.

In some embodiments, the chemical modification is selected from pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine,), 5-methoxyuridine, and 2'-O-methyl uridine.

A "nucleoside" as used herein refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" as used herein refers to a nucleoside, including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the polynucleotides, compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl) cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2' O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine;

7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethyl aminomethyl-2-thiouridine; 5-carboxymethylaminomethyluridine; 5-carboxymethyl aminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenyl aminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonyl ethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio)pseudouracil; 2' methyl, 2'amino, 2'azido, 2'fluoro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methyl aminomethyl)-2,4 (dithio)uracil; 5 (methylaminomethyl)-4 (thio)uracil; 5 (propynyl)uracil; 5 (trifluoromethyl)uracil; 5-(2-aminopropyl)uracil; 5-(alkyl)-2-(thio) pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouri dine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluoro-cytidine; 2' methyl, 2'amino, 2'azido, 2'fluoro-adenine; 2'methyl, 2'amino, 2'azido, 2'fluoro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl)isocarbostyrilyl; 3-(methyl)isocarbostyrilyl; 4-(fluoro)-6-(methyl)benzimidazole; 4-(methyl) benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl) isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines;

N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an OX40L polypeptide, or any combination thereof, include a combination of at least two (e.g., 2, 3, 4 or more) of the aforementioned modified nucleobases.

In some embodiments, modified nucleobases in the polynucleotide comprising an mRNA encoding an IL-23 polypeptide, the polynucleotide comprising an mRNA encoding an IL-36-gamma polypeptide, the polynucleotide comprising an mRNA encoding an OX40L polypeptide, or any combination thereof, are selected from the group consisting of pseudouridine (ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine,), 5-methoxyuridine, 2'-O-methyl uridine 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methyl aminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methylcytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the disclosure (e.g., an mRNA polynucleotide encoding an IL-23 polypeptide, an IL-36-gamma polypeptide, an IL-18 polypeptide, and/or an OX40L polypeptide) are modified nucleobases. In some embodiments, at least 95% of uracil in a polynucleotide of the present disclosure (e.g., an mRNA polynucleotide encoding an IL-23 polypeptide, an IL-36-gamma polypeptide, an IL-18 polypeptide, and/or, an OX40L polypeptide) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding an IL-23 polypeptide, an IL-36-gamma polypeptide, an OX40L polypeptide, or any combination thereof, are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding an IL-23 polypeptide, an IL-36-gamma polypeptide, an OX40L polypeptide, or any combination thereof, are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding an IL-23 polypeptide, an IL-36-gamma polypeptide, an IL-18 polypeptide, an OX40L polypeptide, or any combination thereof, are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding an IL-23 polypeptide, an IL-36-gamma polypeptide, an IL-18 polypeptide, an OX40L polypeptide, or any combination thereof, are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding an IL-23 polypeptide, an IL-36-gamma polypeptide, an IL-18 polypeptide, an OX40L polypeptide, or any combination thereof, are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, $—CH_2—O—N(CH_3)—CH_2—$, $—CH_2—N(CH_3)—N(CH_3)—CH_2—$, $—CH_2—NH—CH_2—$, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, $—N(CH_3)—CH_2—CH_2—$, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

In some embodiments, modified nucleobases in the polynucleotide comprising an mRNA encoding an IL-23 polypeptide, the polynucleotide comprising an mRNA encoding an IL-36-gamma polypeptide, or an IL-18 polypeptide, the polynucleotide comprising an mRNA encoding an OX40L polypeptide, or any combination thereof, are selected from the group consisting of 1-methyl-pseudouridine (m1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide comprising an mRNA encoding an IL-23 polypeptide, the polynucleotide comprising an mRNA encoding an IL-36-gamma polypeptide, or an IL-18 polypeptide, the polynucleotide comprising an mRNA encoding an OX40L polypeptide, or any combination thereof, comprise pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise 1-methyl-pseudouridine (m1ψ) and 5-methyl-cytidine (m5C).

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an OX40L polypeptide, or any combination thereof, comprise 2-thiouridine (s2U). In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise 2-thiouridine and 5-methyl-cytidine (m5C).

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise methoxy-uridine (mo5U). In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine.

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise 2'-O-methyl uridine and 5-methyl-cytidine (m5C). In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise N6-methyl-adenosine (m6A). In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, comprise N6-methyl-adenosine (m6A) and 5-methyl-cytidine (m5C).

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenosine (m6A), and 2,6-diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, or 7-methyl-8-oxo-guanosine.

Other modifications which can be useful in the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure are listed in Table 5.

TABLE 5

| Additional Modification types | |
|---|---|
| Name | Type |
| 2,6-(diamino)purine | Other |
| 1-(aza)-2-(thio)-3-(aza)-phenoxazin-1-yl | Other |

TABLE 5-continued

| Additional Modification types | |
|---|---|
| Name | Type |
| 1,3-(diaza)-2-(oxo)-phenthiazin-l-yl | Other |
| 1,3-(diaza)-2-(oxo)-phenoxazin-1-yl | Other |
| 1,3,5-(triaza)-2,6-(dioxa)-naphthalene | Other |
| 2 (amino)purine | Other |
| 2,4,5-(trimethyl)phenyl | Other |
| 2' methyl, 2'amino, 2'azido, 2'fluro-cytidine | Other |
| 2' methyl, 2'amino, 2'azido, 2'fluro-adenine | Other |
| 2'methyl, 2'amino, 2'azido, 2'fluro-uridine | Other |
| 2'-amino-2'-deoxyribose | Other |
| 2-amino-6-Chloro-purine | Other |
| 2-aza-inosinyl | Other |
| 2'-azido-2'-deoxyribose | Other |
| 2'fluoro-2'-deoxyribose | Other |
| 2'-fluoro-modified bases | Other |
| 2'-O-methyl-ribose | Other |
| 2-oxo-7-aminopyridopyrimidin-3-yl | Other |
| 2-oxo-pyridopyrimidine-3-yl | Other |
| 2-pyridinone | Other |
| 3 nitropyrrole | Other |
| 3-(methyl)-7-(propynyl)isocarbostyrilyl | Other |
| 3-(methyl)isocarbostyrilyl | Other |
| 4-(fluoro)-6-(methyl)benzimidazole | Other |
| 4-(methyl)benzimidazole | Other |
| 4-(methyl)indolyl | Other |
| 4,6-(dimethyl)indolyl | Other |
| 5 nitroindole | Other |
| 5 substituted pyrimidines | Other |
| 5-(methyl)isocarbostyrilyl | Other |
| 5-nitroindole | Other |
| 6-(aza)pyrimidine | Other |
| 6-(azo)thymine | Other |
| 6-(methyl)-7-(aza)indolyl | Other |
| 6-chloro-purine | Other |
| 6-phenyl-pyrrolo-pyrimidin-2-on-3-yl | Other |
| 7-(aminoalkylhydroxy)-1-(aza)-2-(thio)-3-(aza)-phenthiazin-l-yl | Other |
| 7-(aminoalkylhydroxy)-1-(aza)-2-(thio)-3-(aza)-phenoxazin-1-yl | Other |
| 7-(aminoalkylhydroxy)-1,3-(diaza)-2-(oxo)-phenoxazin-1-yl | Other |
| 7-(aminoalkylhydroxy)-l,3-(diaza)-2-(oxo)-phenthiazin-l-yl | Other |
| 7-(aminoalkylhydroxy)-l,3-(diaza)-2-(oxo)-phenoxazin-l-yl | Other |
| 7-(aza)indolyl | Other |
| 7-(guanidiniumalkylhydroxy)-1-(aza)-2-(thio)-3-(aza)-phenoxazinl-yl | Other |
| 7-(guanidiniumalkylhydroxy)-1-(aza)-2-(thio)-3-(aza)-phenthiazin-l-yl | Other |
| 7-(guanidiniumalkylhydroxy)-1-(aza)-2-(thio)-3-(aza)-phenoxazin-1-yl | Other |
| 7-(guanidiniumalkylhydroxy)-1,3-(diaza)-2-(oxo)-phenoxazin-1-yl | Other |
| 7-(guanidiniumalkyl-hydroxy)-l,3-(diaza)-2-(oxo)-phenthiazin-l-yl | Other |
| 7-(guanidiniumalkylhydroxy)-l,3-(diaza)-2-(oxo)-phenoxazin-l-yl | Other |
| 7-(propynyl)isocarbostyrilyl | Other |
| 7-(propynyl)isocarbostyrilyl, propynyl-7-(aza)indolyl | Other |
| 7-deaza-inosinyl | Other |
| 7-substituted 1-(aza)-2-(thio)-3-(aza)-phenoxazin-1-yl | Other |
| 7-substituted 1,3-(diaza)-2-(oxo)-phenoxazin-1-yl | Other |
| 9-(methyl)-imidizopyridinyl | Other |
| aminoindolyl | Other |
| anthracenyl | Other |
| bis-ortho-(aminoalkylhydroxy)-6-phenyl-pyrrolo-pyrimidin-2-on-3-yl | Other |
| bis-ortho-substituted-6-phenyl-pyrrolo-pyrimidin-2-on-3-yl | Other |
| difluorotolyl | Other |
| hypoxanthine | Other |
| imidizopyridinyl | Other |
| Inosinyl | Other |
| isocarbostyrilyl | Other |
| isoguanisine | Other |
| N2-substituted purines | Other |
| N6-methyl-2-amino-purine | Other |
| N6-substituted purines | Other |
| N-alkylated derivative | Other |
| napthalenyl | Other |
| nitrobenzimidazolyl | Other |
| nitroimidazolyl | Other |
| nitroindazolyl | Other |
| nitropyrazolyl | Other |
| nubularine | Other |
| O6-substituted purines | Other |
| O-alkylated derivative | Other |
| ortho-(aminoalkylhydroxy)-6-phenyl-pyrrolo-pyrimidin-2-on-3-yl | Other |
| ortho-substituted-6-phenyl-pyrrolo-pyrimidin-2-on-3-yl | Other |

TABLE 5-continued

| Additional Modification types | |
|---|---|
| Name | Type |
| Oxoformycin TP | Other |
| para-(aminoalkylhydroxy)-6-phenyl-pyrrolo-pyrimidin-2-on-3-yl | Other |
| para-substituted-6-phenyl-pyrrolo-pyrimidin-2-on-3-yl | Other |
| pentacenyl | Other |
| phenanthracenyl | Other |
| Phenyl | Other |
| propynyl-7-(aza)indolyl | Other |
| Pyrenyl | Other |
| pyridopyrimidin-3-yl | Other |
| pyridopyrimidin-3-yl, 2-oxo-7-amino-pyridopyrimidin-3-yl | Other |
| pyrrolo-pyrimidin-2-on-3-yl | Other |
| Pyrrolopyrimidinyl | Other |
| Pyrrolopyrizinyl | Other |
| Stilbenzyl | Other |
| substituted 1,2,4-triazoles | Other |
| Tetracenyl | Other |
| Tubercidine | Other |
| Xanthine | Other |
| Xanthosine-5'-TP | Other |
| 2-thio-zebularine | Other |
| 5-aza-2-thio-zebularine | Other |
| 7-deaza-2-amino-purine | Other |
| pyridin-4-one ribonucleoside | Other |
| 2-Amino-riboside-TP | Other |
| Formycin A TP | Other |
| Formycin B TP | Other |
| Pyrrolosine TP | Other |
| 2'-OH-ara-adenosine TP | Other |
| 2'-OH-ara-cytidine TP | Other |
| 2'-OH-ara-uridine TP | Other |
| 2'-OH-ara-guanosine TP | Other |
| 5-(2-carbomethoxyvinyl)uridine TP | Other |
| N6-(19-Amino-pentaoxanonadecyl)adenosine TP | Other |

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure can include any useful linker between the nucleosides. Such linkers, including backbone modifications are given in TABLE 6.

TABLE 6

| Linker modifications | |
|---|---|
| Name | TYPE |
| 3'-alkylene phosphonates | Linker |
| 3'-amino phosphoramidate | Linker |
| alkene containing backbones | Linker |
| Aminoalkylphosphoramidates | Linker |
| Aminoalkylphosphotriesters | Linker |
| Boranophosphates | Linker |
| —CH2-0-N(CH3)—CH2— | Linker |
| —CH2—N(CH3)—N(CH3)—CH2— | Linker |
| —CH2—NH—CH2— | Linker |
| chiral phosphonates | Linker |
| chiral phosphorothioates | Linker |
| formacetyl and thioformacetyl backbones | Linker |
| methylene (methylimino) | Linker |
| methylene formacetyl and thioformacetyl backbones | Linker |
| methyleneimino and methylenehydrazino backbones | Linker |
| morpholino linkages | Linker |
| —N(CH3)—CH2—CH2— | Linker |
| oligonucleosides with heteroatom internucleoside linkage | Linker |
| Phosphinates | Linker |
| phosphoramidates | Linker |
| Phosphorodithioates | Linker |
| phosphorothioate internucleoside linkages | Linker |
| Phosphorothioates | Linker |

TABLE 6-continued

| Linker modifications | |
|---|---|
| Name | TYPE |
| Phosphotriesters | Linker |
| PNA | Linker |
| siloxane backbones | Linker |
| sulfamate backbones | Linker |
| sulfide sulfoxide and sulfone backbones | Linker |
| sulfonate and sulfonamide backbones | Linker |
| Thionoalkylphosphonates | Linker |
| Thionoalkylphosphotriesters | Linker |
| Thionophosphoramidates | Linker |

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure, or any combination thereof, can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase can be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present disclosure can be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs), hexitol nucleic acids (HNAs), or hybrids thereof. Additional modifications are described herein. Modified nucleic acids and their synthesis are disclosed in International Patent Publication No. WO2013052523 (see also US20130115272).

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide of the present disclosure, or any combination thereof, do not substantially induce an innate immune response of a cell into which the mRNA is introduced. Features of an induced innate immune response include 1) increased expression of pro-inflammatory cytokines, 2) activation of intracellular PRRs (RIG-I, MDA5, etc, and/or 3) termination or reduction in protein translation.

Any of the regions of the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising and mRNA encoding an OX40L polypeptide of the present disclosure, or any combination thereof, can be chemically modified as taught herein or as taught in International Patent Publication No. WO2013052523 (see also US20130115272).

In some embodiments, a modified polynucleotide, e.g., mRNA comprising at least one modification described herein, of the disclosure encodes an IL-23, IL-36-gamma, the polynucleotide comprising an mRNA encoding an IL-18 polypeptide and/or OX40L. In some embodiments, the modified polynucleotide, e.g., mRNA comprising at least one modification described herein, of the disclosure encodes a human IL-23, IL-36-gamma, IL18 and/or OX40L.

In some embodiments, the modified polynucleotide, e.g., mRNA comprising at least one modification described herein, of the disclosure encodes a polypeptide comprising the amino acid sequence set forth in Table 1. In some embodiments, the modified polynucleotide, e.g., mRNA comprising at least one modification described herein, of the disclosure encodes a polypeptide comprising the amino acid sequence set forth in Table 1.

In some embodiments, the modified polynucleotide, e.g., mRNA comprising at least one modification described herein, of the disclosure encodes at least one IL-23, IL-36-gamma, IL-18 and/or OX40L mutant, a fragment, or variant thereof, e.g., an IL-23, IL-36-gamma, IL-18 and/or OX40L functional fragment of IL-23, IL-36-gamma, IL-18 and/or OX40L.

In some embodiments, the modified polynucleotide, e.g., mRNA comprising at least one modification described herein, of the disclosure is selected from the IL-23, IL-36-gamma, IL-18 and/or OX40L nucleic acid sequences listed in Table 1.

The polynucleotide comprising an mRNA encoding an IL-23 polypeptide, the polynucleotide comprising an mRNA encoding an IL-36-gamma polypeptide, mRNA encoding an IL-18 polypeptide and the polynucleotide comprising an mRNA encoding an OX40L polypeptide of the present disclosure can also include building blocks, e.g., modified ribonucleosides, and modified ribonucleotides, of polynucleotide molecules. For example, these building blocks can be useful for preparing the polynucleotides of the disclosure. Such building blocks are taught in International Patent Publication No. WO2013052523 (see also US20130115272) and International Application Publication No. WO2014093924 (see also US20150307542).

Modifications on the Sugar

The modified nucleosides and nucleotides (e.g., building block molecules), which can be incorporated into a polynucleotide (e.g., RNA or mRNA, as described herein) comprising an mRNA encoding an IL-23 polypeptide, a polynucleotide (e.g., RNA or mRNA, as described herein) comprising an mRNA encoding an IL-36-gamma polypeptide, mRNA encoding an IL-18 polypeptide or a polynucleotide (e.g., RNA or mRNA, as described herein) comprising an mRNA encoding an OX40L polypeptide of the present disclosure, can be modified on the sugar of the ribonucleic acid.

For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $-O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught in International Patent Publication No. WO2013052523 (see also US20130115272) and International Application Publication No. WO2014093924 (see also US20150307542).

Combinations of Modified Sugars, Nucleobases, and Internucleoside Linkages

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide of the disclosure, or any combination thereof, can include a combination of modifications to the sugar, the nucleobase, and/or the internucleoside linkage. These combinations can include any one or more modifications described herein.

Examples of modified nucleotides and modified nucleotide combinations are provided below in TABLE 7. These combinations of modified nucleotides can be used to form the polynucleotides of the disclosure. Unless otherwise noted, the modified nucleotides can be completely substituted for the natural nucleotides of the polynucleotides of the disclosure. As a non-limiting example, the natural nucleotide uridine can be substituted with a modified nucleoside described herein. In another non-limiting example, the natural nucleotide uridine can be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker can be incorporated into the polynucleotides of the disclosure and such modifications are taught in International Patent Publication No. WO2013052523 (see also US20130115272) and International Application Publication No. WO2014093924 (see also US20150307542).

TABLE 7

| Combinations | |
|---|---|
| Modified Nucleotide | Modified Nucleotide Combination |
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | a-thio-cytidine/pseudo-uridine |
| | about 50% of the cytosines are α-thio-cytidine |

TABLE 7-continued

| Combinations | |
|---|---|
| Modified Nucleotide | Modified Nucleotide Combination |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/ about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/ about 50% of uridines are 2-thio-uridine |

Additional examples of modified nucleotides and modified nucleotide combinations are provided below in TABLE 8.

TABLE 8

| Additional combinations | | | |
|---|---|---|---|
| Uracil | Cytosine | Adenine | Guanine |
| 5-methoxy-UTP | CTP | ATP | GTP |
| 5-Methoxy-UTP | N4Ac-CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4Ac-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4-Ac-CTP | ATP | GTP |
| 5-Methoxy-UTP | 5-Iodo-CTP | ATP | GTP |
| 5-Methoxy-UTP | 5-Bromo-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |

TABLE 8-continued

| Additional combinations | | | |
|---|---|---|---|
| Uracil | Cytosine | Adenine | Guanine |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | CTP | Alpha-thio-ATP | GTP |
| 5-Methoxy-UTP | 5-Methyl-CTP | Alpha-thio-ATP | GTP |
| 5-Methoxy-UTP | CTP | ATP | Alpha-thio-GTP |
| 5-Methoxy-UTP | 5-Methyl-CTP | ATP | Alpha-thio-GTP |
| 5-Methoxy-UTP | CTP | N6-Me-ATP | GTP |
| 5-Methoxy-UTP | 5-Methyl-CTP | N6-Me-ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |

TABLE 8-continued

| Additional combinations | | | |
|---|---|---|---|
| Uracil | Cytosine | Adenine | Guanine |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | 5-Ethyl-CTP | ATP | GTP |
| 5-Methoxy-UTP | 5-Methoxy-CTP | ATP | GTP |
| 5-Methoxy-UTP | 5-Ethynyl-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% 1-Methyl-pseudo-UTP | 5-Methyl-CTP | ATP | GTP |
| 50% 5-Methoxy-UTP + 50% 1-Methyl-pseudo-UTP | 5-Methyl-CTP | ATP | GTP |
| 25% 5-Methoxy-UTP + 75% 1-Methyl-pseudo-UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% 1-Methyl-pseudo-UTP | 75% 5-Methyl-CTP + 25% CTP | ATP | GTP |
| 75% 5-Methoxy-UTP + 25% 1-Methyl-pseudo-UTP | 50% 5-Methyl-CTP + 50% CTP | ATP | GTP |
| 75% 5-Methoxy-UTP + 25% 1-Methyl-pseudo-UTP | 25% 5-Methyl-CTP + 75% CTP | ATP | GTP |
| 50% 5-Methoxy-UTP + 50% 1-Methyl-pseudo-UTP | 75% 5-Methyl-CTP + 25% CTP | ATP | GTP |
| 50% 5-Methoxy-UTP + 50% 1-Methyl-pseudo-UTP | 50% 5-Methyl-CTP + 50% CTP | ATP | GTP |
| 50% 5-Methoxy-UTP + 50% 1-Methyl-pseudo-UTP | 25% 5-Methyl-CTP + 75% CTP | ATP | GTP |
| 25% 5-Methoxy-UTP + 75% 1-Methyl-pseudo-UTP | 75% 5-Methyl-CTP + 25% CTP | ATP | GTP |
| 25% 5-Methoxy-UTP + 75% 1-Methyl-pseudo-UTP | 50% 5-Methyl-CTP + 50% CTP | ATP | GTP |
| 25% 5-Methoxy-UTP + 75% 1-Methyl-pseudo-UTP | 25% 5-Methyl-CTP + 75% CTP | ATP | GTP |
| 75% 5-Methoxy-UTP + 25% 1-Methyl-pseudo-UTP | CTP | ATP | GTP |
| 50% 5-Methoxy-UTP + 50% 1-Methyl-pseudo-UTP | CTP | ATP | GTP |
| 25% 5-Methoxy-UTP + 75% 1-Methyl-pseudo-UTP | CTP | ATP | GTP |
| 5-methoxy-UTP (In House) | CTP | ATP | GTP |
| 5-methoxy-UTP (Hongene) | CTP | ATP | GTP |
| 5-methoxy-UTP (Hongene) | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |

TABLE 8-continued

| Additional combinations | | | |
|---|---|---|---|
| Uracil | Cytosine | Adenine | Guanine |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |

TABLE 8-continued

| Additional combinations | | | |
|---|---|---|---|
| Uracil | Cytosine | Adenine | Guanine |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | 5-Fluoro-CTP | ATP | GTP |
| 5-Methoxy-UTP | 5-Phenyl-CTP | ATP | GTP |
| 5-Methoxy-UTP | N4-Bz-CTP | ATP | GTP |
| 5-Methoxy-UTP | CTP | N6-Isopentenyl-ATP | GTP |
| 5-Methoxy-UTP | N4-Ac-CTP | ATP | GTP |
| 25% 5-Methoxy-UTP + 75% UTP | 25% N4-Ac-CTP + 75% CTP | ATP | GTP |
| 25% 5-Methoxy-UTP + 75% UTP | 75% N4-Ac-CTP + 25% CTP | ATP | GTP |
| 75% 5-Methoxy-UTP + 25% UTP | 25% N4-Ac-CTP + 75% CTP | ATP | GTP |
| 75% 5-Methoxy-UTP + 25% UTP | 75% N4-Ac-CTP + 25% CTP | ATP | GTP |
| 5-Methoxy-UTP | 5-Hydroxymethyl-CTP | ATP | GTP |
| 25% 5-Methoxy-UTP + 75% UTP | 25% 5-Hydroxymethyl-CTP + 75% CTP | ATP | GTP |
| 25% 5-Methoxy-UTP + 75% UTP | 75% 5-Hydroxymethyl-CTP + 25% CTP | ATP | GTP |
| 75% 5-Methoxy-UTP + 25% UTP | 25% 5-Hydroxymethyl-CTP + 75% CTP | ATP | GTP |
| 75% 5-Methoxy-UTP + 25% UTP | 75% 5-Hydroxymethyl-CTP + 25% CTP | ATP | GTP |
| 5-Methoxy-UTP | N4-Methyl CTP | ATP | GTP |
| 25% 5-Methoxy-UTP + 75% UTP | 25% N4-Methyl CTP + 75% CTP | ATP | GTP |
| 25% 5-Methoxy-UTP + 75% UTP | 75% N4-Methyl CTP + 25% CTP | ATP | GTP |
| 75% 5-Methoxy-UTP + 25% UTP | 25% N4-Methyl CTP + 75% CTP | ATP | GTP |
| 75% 5-Methoxy-UTP + 25% UTP | 75% N4-Methyl CTP + 25% CTP | ATP | GTP |
| 5-Methoxy-UTP | 5-Trifluoromethyl-CTP | ATP | GTP |
| 25% 5-Methoxy-UTP + 75% UTP | 25% 5-Trifluoromethyl-CTP + 75% CTP | ATP | GTP |
| 25% 5-Methoxy-UTP + 75% UTP | 75% 5-Trifluoromethyl-CTP + 25% CTP | ATP | GTP |
| 75% 5-Methoxy-UTP + 25% UTP | 25% 5-Trifluoromethyl-CTP + 75% CTP | ATP | GTP |

TABLE 8-continued

| Additional combinations | | | |
|---|---|---|---|
| Uracil | Cytosine | Adenine | Guanine |
| 75% 5-Methoxy-UTP + 25% UTP | 75% 5-Trifluoromethyl-CTP + 25% CTP | ATP | GTP |
| 5-Methoxy-UTP | 5-Bromo-CTP | ATP | GTP |
| 25% 5-Methoxy-UTP + 75% UTP | 25% 5-Bromo-CTP + 75% CTP | ATP | GTP |
| 25% 5-Methoxy-UTP + 75% UTP | 75% 5-Bromo-CTP + 25% CTP | ATP | GTP |
| 75% 5-Methoxy-UTP + 25% UTP | 25% 5-Bromo-CTP + 75% CTP | ATP | GTP |
| 75% 5-Methoxy-UTP + 25% UTP | 75% 5-Bromo-CTP + 25% CTP | ATP | GTP |
| 5-Methoxy-UTP | 5-Iodo-CTP | ATP | GTP |
| 25% 5-Methoxy-UTP + 75% UTP | 25% 5-Iodo-CTP + 75% CTP | ATP | GTP |
| 25% 5-Methoxy-UTP + 75% UTP | 75% 5-Iodo-CTP + 25% CTP | ATP | GTP |
| 75% 5-Methoxy-UTP + 25% UTP | 25% 5-Iodo-CTP + 75% CTP | ATP | GTP |
| 75% 5-Methoxy-UTP + 25% UTP | 75% 5-Iodo-CTP + 25% CTP | ATP | GTP |
| 5-Methoxy-UTP | 5-Ethyl-CTP | ATP | GTP |
| 25% 5-Methoxy-UTP + 75% UTP | 25% 5-Ethyl-CTP + 75% CTP | ATP | GTP |
| 25% 5-Methoxy-UTP + 75% UTP | 75% 5-Ethyl-CTP + 25% CTP | ATP | GTP |
| 75% 5-Methoxy-UTP + 25% UTP | 25% 5-Ethyl-CTP + 75% CTP | ATP | GTP |
| 75% 5-Methoxy-UTP + 25% UTP | 75% 5-Ethyl-CTP + 25% CTP | ATP | GTP |
| 5-Methoxy-UTP | 5-Methoxy-CTP | ATP | GTP |
| 25% 5-Methoxy-UTP + 75% UTP | 25% 5-Methoxy-CTP + 75% CTP | ATP | GTP |
| 25% 5-Methoxy-UTP + 75% UTP | 75% 5-Methoxy-CTP + 25% CTP | ATP | GTP |
| 75% 5-Methoxy-UTP + 25% UTP | 25% 5-Methoxy-CTP + 75% CTP | ATP | GTP |
| 75% 5-Methoxy-UTP + 25% UTP | 75% 5-Methoxy-CTP + 25% CTP | ATP | GTP |
| 5-Methoxy-UTP | 5-Ethynyl-CTP | ATP | GTP |
| 25% 5-Methoxy-UTP + 75% UTP | 25% 5-Ethynyl-CTP + 75% CTP | ATP | GTP |
| 25% 5-Methoxy-UTP + 75% UTP | 75% 5-Ethynyl-CTP + 25% CTP | ATP | GTP |
| 75% 5-Methoxy-UTP + 25% UTP | 25% 5-Ethynyl-CTP + 75% CTP | ATP | GTP |
| 75% 5-Methoxy-UTP + 25% UTP | 75% 5-Ethynyl-CTP + 25% CTP | ATP | GTP |
| 5-Methoxy-UTP | 5-Pseudo-iso-CTP | ATP | GTP |
| 25% 5-Methoxy-UTP + 75% UTP | 25% 5-Pseudo-iso-CTP + 75% CTP | ATP | GTP |
| 25% 5-Methoxy-UTP + 75% UTP | 75% 5-Pseudo-iso-CTP + 25% CTP | ATP | GTP |
| 75% 5-Methoxy-UTP + 25% UTP | 25% 5-Pseudo-iso-CTP + 75% CTP | ATP | GTP |
| 75% 5-Methoxy-UTP + 25% UTP | 75% 5-Pseudo-iso-CTP + 25% CTP | ATP | GTP |
| 5-Methoxy-UTP | 5-Formyl-CTP | ATP | GTP |
| 25% 5-Methoxy-UTP + 75% UTP | 25% 5-Formyl-CTP + 75% CTP | ATP | GTP |
| 25% 5-Methoxy-UTP + 75% UTP | 75% 5-Formyl-CTP + 25% CTP | ATP | GTP |
| 75% 5-Methoxy-UTP + 25% UTP | 25% 5-Formyl-CTP + 75% CTP | ATP | GTP |
| 75% 5-Methoxy-UTP + 25% UTP | 75% 5-Formyl-CTP + 25% CTP | ATP | GTP |
| 5-Methoxy-UTP | 5-Aminoallyl-CTP | ATP | GTP |
| 25% 5-Methoxy-UTP + 75% UTP | 25% 5-Aminoallyl-CTP + 75% CTP | ATP | GTP |
| 25% 5-Methoxy-UTP + 75% UTP | 75% 5-Aminoallyl-CTP + 25% CTP | ATP | GTP |
| 75% 5-Methoxy-UTP + 25% UTP | 25% 5-Aminoallyl-CTP + 75% CTP | ATP | GTP |
| 75% 5-Methoxy-UTP + 25% UTP | 75% 5-Aminoallyl-CTP + 25% CTP | ATP | GTP |

XII. Pharmaceutical Compositions: Formulation, Administration, Delivery and Dosing The present disclosure provides pharmaceutical formulations comprising any of the compositions disclosed herein, e.g., a first polynucleotide comprising an mRNA encoding a first protein comprising an IL-23 polypeptide, a second polynucleotide comprising an mRNA encoding a second protein comprising an IL-36-gamma polypeptide, or a polynucleotide comprising an mRNA encoding an IL-18 polypeptide, and/or a third polynucleotide comprising an mRNA encoding a third protein, wherein the third protein comprises an OX40L polypeptide as described elsewhere herein.

In some embodiments of the disclosure, the polynucleotide are formulated in compositions and complexes in combination with one or more pharmaceutically acceptable excipients. Pharmaceutical compositions can optionally comprise one or more additional active substances, e.g. therapeutically and/or prophylactically active substances. Pharmaceutical compositions of the present disclosure can be sterile and/or pyrogen-free. General considerations in the formulation and/or manufacture of pharmaceutical agents can be found, for example, in *Remington: The Science and Practice of Pharmacy* $21^{st}$ ed., Lippincott Williams & Wilkins, 2005.

In some embodiments, compositions are administered to humans, human patients or subjects. For the purposes of the present disclosure, the phrase "active ingredient" generally refers to polynucleotides to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals.

In some embodiments, the polynucleotide of the present disclosure is formulated for subcutaneous, intravenous, intraperitoneal, intratumoral, intramuscular, intra-articular, intra-synovial, intrasternal, intrathecal, intrahepatic, intralesional, intracranial, intraventricular, oral, inhalation spray, topical, rectal, nasal, buccal, vaginal, intratumoral, or implanted reservoir intramuscular, subcutaneous, intratumoral, or intradermal delivery. In other embodiments, the polynucleotide is formulated for intratumoral, intraperitoneal, or intravenous delivery. In a particular embodiment, the polynucleotide of the present disclosure is formulated for intratumoral delivery.

Formulations of the pharmaceutical compositions described herein can be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition can comprise between 0.1% and 100%, e.g., between 0.5% and 50%, between 1% and 30%, between 5% and 80%, or at least 80% (w/w) active ingredient.

Formulations

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the disclosure can be formulated using one or more excipients.

The function of the one or more excipients is, e.g., to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles, polymers, lipoplexes, core-shell nanoparticles, peptides, proteins, cells transfected with polynucleotides (e.g., for transplantation into a subject), hyaluronidase, nanoparticle mimics and combinations thereof. Accordingly, the formulations of the disclosure can include one or more excipients, each in an amount that together increases the stability of the polynucleotide, increases cell transfection by the polynucleotide, increases the expression of polynucleotides encoded protein, and/or alters the release profile of polynucleotide encoded proteins. Further, the polynucleotides of the present disclosure can be formulated using self-assembled nucleic acid nanoparticles.

Formulations of the pharmaceutical compositions described herein can be prepared by any method known or hereafter developed in the art of pharmacology. In general, such preparatory methods include the step of associating the active ingredient with an excipient and/or one or more other accessory ingredients.

A pharmaceutical composition in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered. For example, the composition can comprise between 0.1% and 99% (w/w) of the active ingredient. By way of example, the composition can comprise between 0.1% and 100%, e.g., between 0.5 and 50%, between 1-30%, between 5-80%, at least 80% (w/w) active ingredient.

In some embodiments, the formulations described herein contain at least one polynucleotide. As a non-limiting example, the formulations contain 1, 2, 3, 4 or 5 polynucleotides. In other embodiments, the polynucleotide of the disclosure is formulated for intratumoral delivery in a tumor of a patient in need thereof.

Pharmaceutical formulations can additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006). The use of a conventional excipient medium can be contemplated within the scope of the present disclosure, except insofar as any conventional excipient medium can be incompatible with a substance or its derivatives, such as by producing any undesirable biological effect or otherwise interacting in a deleterious manner with any other component(s) of the pharmaceutical composition.

In some embodiments, the particle size of the lipid nanoparticle is increased and/or decreased. The change in particle size can be able to help counter biological reaction such as, but not limited to, inflammation or can increase the biological effect of the modified mRNA delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients can optionally be included in the pharmaceutical formulations of the disclosure.

In some embodiments, the polynucleotides is administered in or with, formulated in or delivered with nanostructures that can sequester molecules such as cholesterol. Non-limiting examples of these nanostructures and methods of making these nanostructures are described in US Patent Publication No. US20130195759. Exemplary structures of these nanostructures are shown in US Patent Publication No. US20130195759, and can include a core and a shell surrounding the core.

Lipidoids

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide can be formulated with lipidoids. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010), the present disclosure describes their formulation and use in delivering polynucleotides.

Complexes, micelles, liposomes or particles can be prepared containing these lipidoids and therefore, can result in an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intraperitoneal, intratumoral, intramuscular, or subcutaneous routes.

In vivo delivery of nucleic acids can be affected by many parameters, including, but not limited to, the formulation composition, nature of particle PEGylation, degree of loading, polynucleotide to lipid ratio, and biophysical parameters such as, but not limited to, particle size (Akinc et al., Mol Ther. 2009 17:872-879). As an example, small changes in the anchor chain length of poly(ethylene glycol) (PEG) lipids can result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), and MD1, can be tested for in vivo activity.

The lipidoid referred to herein as "98N12-5" is disclosed by Akinc et al., Mol Ther. (2009) 17:872-879.

The lipidoid referred to herein as "C12-200" is disclosed by Love et al., Proc. Natl. Acad. Sci. USA (2010) 107:1864-1869 and Liu and Huang (2010) Molecular Therapy. 2010: 669-670. The lipidoid formulations can include particles comprising either 3 or 4 or more components in addition to polynucleotides.

Lipidoids and polynucleotide formulations comprising lipidoids are described in International Application Publication No. WO2014093924 (see also US20150307542).

Liposomes, Lipoplexes, and Lipid Nanoparticles

The polynucleotides of the disclosure can be formulated using one or more liposomes, lipoplexes, or lipid nanoparticles. In one embodiment, pharmaceutical compositions of the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide include liposomes. Liposomes are artificially-prepared vesicles which can primarily be composed of a lipid bilayer and can be used as a delivery vehicle for the administration of pharmaceutical formulations. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the pharmaceutical formulations.

The formation of liposomes can depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles are prepared by the methods, apparatus and devices described in US Patent Publication No. US20130177638, US20130177637, US20130177636, US20130177635, US20130177634, US20130177633, US20130183375, US20130183373 and US20130183372.

In one embodiment, pharmaceutical compositions described herein include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (as described in US20100324120) and liposomes which can deliver small molecule drugs such as, but not limited to, DOXIL® from Janssen Biotech, Inc. (Horsham, Pa.).

In one embodiment, pharmaceutical compositions described herein can include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations contain, but are not limited to, 48% cholesterol, 20% DSPC, 2% PEG-c-DMA, and 30% ionizable lipid, where the ionizable lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In other embodiments, formulations comprise a percentage of cholesterol selected from the group consisting of 28.5%, 31.5%, 33.5%, 36.5%, 37.0%, 38.5%, 39.0% and 43.5%. In some embodiments, formulations comprise from about 5.0% to about 10.0% DSPC and/or from about 7.0% to about 15.0% DSPC.

In one embodiment, pharmaceutical compositions include liposomes which are formed to deliver a polynucleotide comprising an mRNA encoding an IL-23 polypeptide, a polynucleotide comprising an mRNA encoding an IL-36-gamma polypeptide, the polynucleotide comprising an mRNA encoding an IL-18 polypeptide, and/or a polynucleotide comprising an mRNA encoding an OX40L polypeptide. The polynucleotides can be encapsulated by the liposome and/or it can be contained in an aqueous core which can then be encapsulated by the liposome. See International Pub. Nos. WO2012031046 (see also US20130189351), WO2012031043 (see also US20130202684), WO2012030901 (see also US20130195969) and WO2012006378 (see also US20130171241) and US Patent Publication No. US20130189351, US20130195969 and US20130202684).

In another embodiment, liposomes is formulated for targeted delivery. As a non-limiting example, the liposome is formulated for targeted delivery to the liver. The liposome used for targeted delivery can include, but is not limited to, the liposomes described in and methods of making liposomes described in US Patent Publication No. US20130195967.

In another embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a cationic oil-in-water emulsion where the emulsion particle comprises an oil core and a cationic lipid which can interact with the polynucleotide anchoring the molecule to the emulsion particle. See International Pub. No. WO2012006380 (see also US20160256541).

In one embodiment, the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide are formulated in a water-in-oil emulsion comprising a continuous hydrophobic phase in which the hydrophilic phase is dispersed. As a non-limiting example, the emulsion can be made by the methods described in International Publication No. WO2013087791 (see also US20140294904).

In another embodiment, the lipid formulation includes at least ionizable lipid, a lipid which can enhance transfection and a least one lipid which contains a hydrophilic head group linked to a lipid moiety. See International Pub. No. WO2011076807 and U.S. Pub. No. 20110200582. In another embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a lipid vesicle which can have crosslinks between functionalized lipid bilayers (see U.S. Pub. No. 20120177724).

In one embodiment, the polynucleotides are formulated in a liposome as described in International Patent Publication No. WO2013086526 (see also US20140356416). The polynucleotides can be encapsulated in a liposome using reverse pH gradients and/or optimized internal buffer compositions as described in International Patent Publication No. WO2013086526.

In one embodiment, the polynucleotide pharmaceutical compositions are formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine)

based liposomes (e.g., siRNA delivery for ovarian cancer (Landen et al. Cancer Biology & Therapy 2006 5(12)1708-1713)) and hyaluronan-coated liposomes (Quiet Therapeutics, Israel).

In one embodiment, the cationic lipid is a low molecular weight cationic lipid such as those described in US Patent Application No. 20130090372. In another embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a lipid vesicle which can have crosslinks between functionalized lipid bilayers.

In other embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a liposome comprising a cationic lipid. The liposome can have a molar ratio of nitrogen atoms in the cationic lipid to the phosphates in the polynucleotide (N:P ratio) of between 1:1 and 20:1 as described in International Publication No. WO2013006825. In another embodiment, the liposome can have a N:P ratio of greater than 20:1 or less than 1:1.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a lipid-polycation complex. The formation of the lipid-polycation complex can be accomplished by methods known in the art and/or as described in U.S. Pub. No. 20120178702. As a non-limiting example, the polycation includes a cationic peptide or a polypeptide such as, but not limited to, polylysine, polyornithine and/or polyarginine and the cationic peptides described in International Pub. No. WO2012013326 or US Patent Pub. No. US20130142818. In another embodiment, the polynucleotides are formulated in a lipid-polycation complex which can further include a non-cationic lipid such as, but not limited to, cholesterol or dioleoyl phosphatidylethanolamine (DOPE).

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in an aminoalcohol lipidoid. Aminoalcohol lipidoids which can be used in the present disclosure can be prepared by the methods described in U.S. Pat. No. 8,450,298.

The liposome formulation can be influenced by, but not limited to, the selection of the ionizable lipid component, the degree of ionizable lipid saturation, the nature of the PEGylation, ratio of all components and biophysical parameters such as size. In one example by Semple et al. (Semple et al. Nature Biotech. 2010 28:172-176), the liposome formulation was composed of 57.1% ionizable lipid, 7.1% dipalmitoylphosphatidylcholine, 34.3% cholesterol, and 1.4% PEG-c-DMA. As another example, changing the composition of the ionizable lipid could more effectively deliver siRNA to various antigen presenting cells (Basha et al. Mol Ther. 2011 19:2186-2200). In some embodiments, liposome formulations comprise from about 35 to about 45% ionizable lipid, from about 40% to about 50% ionizable lipid, from about 50% to about 60% ionizable lipid and/or from about 55% to about 65% ionizable lipid. In some embodiments, the ratio of lipid to mRNA in liposomes is from about 5:1 to about 20:1, from about 10:1 to about 25:1, from about 15:1 to about 30:1 and/or at least 30:1.

In some embodiments, the ratio of PEG in the lipid nanoparticle (LNP) formulations is increased or decreased and/or the carbon chain length of the PEG lipid is modified from C14 to C18 to alter the pharmacokinetics and/or biodistribution of the LNP formulations. As a non-limiting example, LNP formulations contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(co-methoxy-poly(ethyleneglycol)2000)carbamoyl)]-1,2-dimyristyloxypropyl-3-amine) (also referred to herein as PEG-DOMG) as compared to the ionizable lipid, DSPC and cholesterol. In another embodiment the PEG-c-DOMG can be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The ionizable lipid can be selected from any lipid known in the art such as, but not limited to, DLin-MC3-DMA, DLin-DMA, C12-200 and DLin-KC2-DMA.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide are formulated in a lipid nanoparticle such as those described in International Publication No. WO2012170930 (see also US20140294938).

In another embodiment, the formulation comprising the polynucleotide(s) is a nanoparticle which can comprise at least one lipid. The lipid can be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid is a cationic lipid such as, but not limited to, DLin-DMA, DLin-D-DMA, DLin-MC3-DMA, DLin-KC2-DMA, DODMA and amino alcohol lipids. The amino alcohol cationic lipid can be the lipids described in and/or made by the methods described in U.S. Patent Application Publication No. US20130150625. As a non-limiting example, the cationic lipid can be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl} propan-1-ol (Compound 4 in US20130150625); or any pharmaceutically acceptable salt or stereoisomer thereof.

The present disclosure provides pharmaceutical compositions with advantageous properties. In particular, the present application provides pharmaceutical compositions comprising:

(i) a polynucleotide comprising an mRNA encoding an IL-23 polypeptide; or, (ii) a polynucleotide comprising an mRNA encoding an IL-36-gamma polypeptide or a polynucleotide comprising an mRNA encoding an IL-18 polypeptide; or, (iii) a polynucleotide comprising an mRNA encoding an IL-23 polypeptide and a polynucleotide comprising an mRNA encoding an IL-36-gamma polypeptide or a polynucleotide comprising an mRNA encoding an IL-18 polypeptide; or, (iv) a polynucleotide comprising an mRNA encoding an IL-23 polypeptide and a polynucleotide comprising an mRNA encoding an OX40L polypeptide; or, (v) a polynucleotide comprising an mRNA encoding an IL-36-gamma polypeptide or a polynucleotide comprising an mRNA encoding an IL-18 polypeptide, and a polynucleotide comprising an mRNA encoding an OX40L polypeptide; or (vi) a polynucleotide comprising an mRNA encoding an IL-23 polypeptide, a polynucleotide comprising an mRNA encoding an IL-36-gamma polypeptide, or a polynucleotide comprising an mRNA encoding an IL-18 polypeptide, and a polynucleotide comprising an mRNA encoding an OX40L polypeptide;

and, (b) a delivery agent.

In some embodiments, the delivery agent comprises a compound having the formula (I)

(I)

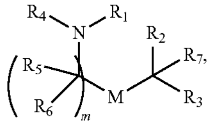

wherein $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, C1-14 alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)N$(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-$1_2$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, C1-14 alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S$(O)_2$R, —N(OR)C(O) OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=N $R_9$)R, —C(O)N(R)OR, and —C(=$NR_9$)N$(R)_2$, and each n is independently selected from 1, 2, 3, 4, and 5; and when Q is a 5- to 14-membered heterocycle and (i) $R_4$ is —$(CH_2)_n$Q in which n is 1 or 2, or (ii) $R_4$ is —$(CH_2)_n$CHQR in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted C1-6 alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, C1-14 alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted C1-6 alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)O R, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is $—(CH_2)_nQ$ or $—(CH_2)_nCHQR$, where Q is $—N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, C2-14 alkyl, $C_{2-14}$ alkenyl, —R*YR", —YR", and —R*OR", or $R_2$ and $R_3$, together with the atom to which they are attached, form a heterocycle or carbocycle;

$R_4$ is $—(CH_2)_nQ$ or $—(CH_2)_nCHQR$, where Q is $—N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of C1-12 alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of C1-$1_2$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In certain embodiments, a subset of compounds of Formula (I) includes those of Formula (IA):

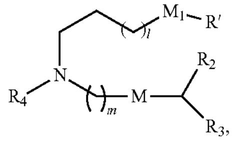

(IA)

or a salt or stereoisomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;
$M_1$ is a bond or M';
$R_4$ is unsubstituted $C_{1-3}$ alkyl, or $—(CH_2)_nQ$, in which Q is OH, $—NHC(S)N(R)_2$, or $—NHC(O)N(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

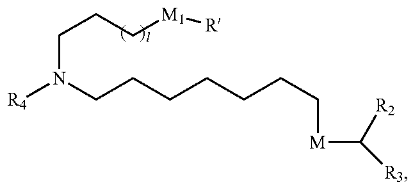

(II)

or a salt or stereoisomer thereof, wherein l is selected from 1, 2, 3, 4, and 5; $M_1$ is a bond or M'; $R_4$ is unsubstituted $C_{1-3}$ alkyl, or $—(CH_2)_nQ$, in which n is 2, 3, or 4, and Q is OH, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;
$M_1$ is a bond or M';
$R_4$ is unsubstituted $C_{1-3}$ alkyl, or $—(CH_2)_nQ$, in which n is 2, 3, or 4, and Q is OH, $—NHC(S)N(R)_2$, or $—NHC(O)N(R)_2$;
M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, the compound of formula (I) is of the formula (IIa), (IIa)

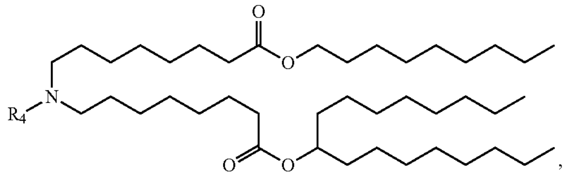

or a salt thereof, wherein $R_4$ is as described above.

In some embodiments, the compound of formula (I) is of the formula (IIb), (IIb)

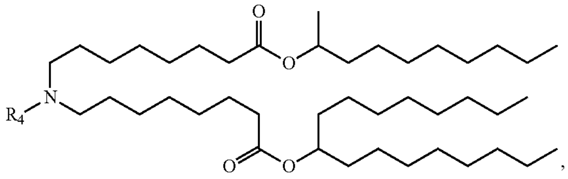

or a salt thereof, wherein $R_4$ is as described above.

In some embodiments, the compound of formula (I) is of the formula (IIc), (IIc)

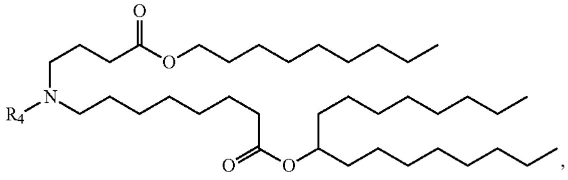

or a salt thereof, wherein $R_4$ is as described above.

In some embodiments, the compound of formula (I) is of the formula (IIe):

(IIe)

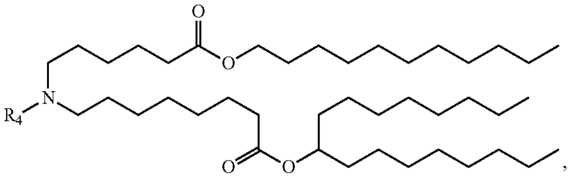

or a salt thereof, wherein $R_4$ is as described above.

In some embodiments, the compound of formula (IIa), (IIb), (IIc), or (IIe) comprises an $R_4$ which is selected from $—(CH_2)_nQ$ and $—(CH_2)_nCHQR$, wherein Q, R and n are as defined above.

In some embodiments, Q is selected from the group consisting of —OR, —OH, $—O(CH_2)_nN(R)_2$, —OC(O)R, $—CX_3$, —CN, —N(R)C(O)R, —N(H)C(O)R, $—N(R)S(O)_2R$, $—N(H)S(O)_2R$, $—N(R)C(O)N(R)_2$, $—N(H)C(O)N(R)_2$, —N(H)C(O)N(H)(R), $—N(R)C(S)N(R)_2$, $—N(H)C(S)N(R)_2$, —N(H)C(S)N(H)(R), and a heterocycle, wherein R is as defined above. In some aspects, n is 1 or 2. In some embodiments, Q is OH, $—NHC(S)N(R)_2$, or $—NHC(O)N(R)_2$.

In some embodiments, the compound of formula (I) is of the formula (IId), (IId)

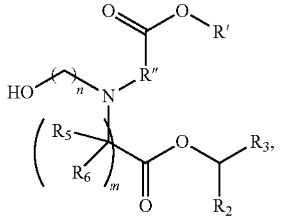

or a salt thereof, wherein $R_2$ and $R_3$ are independently selected from the group consisting of $C_{5-14}$ alkyl and $C_{5-14}$ alkenyl, n is selected from 2, 3, and 4, and R', R'', $R_5$, $R_6$ and m are as defined above.

In some aspects of the compound of formula (IId), $R_2$ is $C_8$ alkyl. In some aspects of the compound of formula (IId), $R_3$ is $C_5$-$C_9$ alkyl. In some aspects of the compound of formula (IId), m is 5, 7, or 9. In some aspects of the compound of formula (IId), each $R_5$ is H. In some aspects of the compound of formula (IId), each $R_6$ is H.

In another aspect, the present application provides a lipid composition (e.g., a lipid nanoparticle (LNP)) comprising: (1) a compound having the formula (I); (2) optionally a helper lipid (e.g. a phospholipid); (3) optionally a structural lipid (e.g. a sterol); (4) optionally a lipid conjugate (e.g. a PEG-lipid); and (5) optionally a quaternary amine compound. In exemplary embodiments, the lipid composition (e.g., LNP) further comprises a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or a combination thereof, e.g., a polynucleotide or polynucleotides encapsulated therein.

In one particular embodiment, the lipid composition (e.g., LNP) further comprises a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, or a polynucleotide comprising an mRNA encoding an OX40L polypeptide. In another particular embodiment, the lipid composition (e.g., LNP) further comprises a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and a polynucleotide comprising an mRNA encoding an OX40L polypeptide.

As used herein, the term “alkyl” or “alkyl group” means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation “$C_{1-14}$ alkyl” means a linear or branched, saturated hydrocarbon including 1-14 carbon atoms. An alkyl group may be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{2-14}$ alkenyl" means a linear or branched hydrocarbon including 2-14 carbon atoms and at least one double bond. An alkenyl group may include one, two, three, four, or more double bonds. For example, $C_{18}$ alkenyl may include one or more double bonds. A $C_{18}$ alkenyl group including two double bonds may be a linoleyl group. An alkenyl group may be optionally substituted.

As used herein, the term "carbocycle" or "carbocyclic group" means a mono- or multicyclic system including one or more rings of carbon atoms. Rings may be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles may include one or more double bonds and may be aromatic (e.g., aryl groups). Examples of carbocycles include cyclopropyl, cyclopentyl, cyclohexyl, phenyl, naphthyl, and 1,2-dihydronaphthyl groups. Carbocycles may be optionally substituted.

As used herein, the term "heterocycle" or "heterocyclic group" means a mono- or multicyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, or twelve membered rings. Heterocycles may include one or more double bonds and may be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles may be optionally substituted.

As used herein, a "biodegradable group" is a group that may facilitate faster metabolism of a lipid in a subject. A biodegradable group may be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''$, in which each OR are alkoxy groups that can be the same or different and R" is an alkyl or alkenyl group), a phosphate (e.g., $P(O)_{43}$), a thiol (e.g., —SH), a sulfoxide (e.g., —S(O)R), a sulfinic acid (e.g., —S(O)OH), a sulfonic acid (e.g., $—S(O)_2OH$), a thial (e.g., —C(S)H), a sulfate (e.g., $S(O)_4^{2-}$), a sulfonyl (e.g., $—S(O)_2—$), an amide (e.g., $—C(O)NR_2$, or —N(R)C(O)R), an azido (e.g., $—N_3$), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, $—(CH_2)_nQ$, $—CH_2)_nCHQR$, —CHQR, and $—CQ(R)_2$, where Q is selected from a $C_{3-6}$ carbocycle, 5- to 14-membered aromatic or non-aromatic heterocycle having one or more heteroatoms selected from N, O, S, and P, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5.

In another embodiment, $R_4$ is selected from the group consisting of a $C_{3-6}$ carbocycle, $—CH_2)_nQ$, $—CH_2)_nCHQR$, —CHQR, and $—CQ(R)_2$, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and a 5- to 14-membered heterocycloalkyl having one or more heteroatoms selected from N, O, and S which is substituted with one or more substituents selected from oxo (═O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, $—CH_2)_nQ$, $—CH_2)_nCHQR$, —CHQR, and $—CQ(R)_2$, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—C(R)N(R)_2C(O)OR$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl.

In another embodiment, $R_4$ is selected from the group consisting of a $C_{3-6}$ carbocycle, —$(CH_2)_nQ$, —$(CH_2)_nCHQR$, —CHQR, and —$CQ(R)_2$, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$C(R)N(R)_2C(O)OR$, and each n is independently selected from 1, 2, 3, 4, and 5.

In another embodiment, $R_4$ is unsubstituted $C_{14}$ alkyl, e.g., unsubstituted methyl.

In certain embodiments, the disclosure provides a compound having the Formula (I), wherein $R_4$ is —$CH_2)_nQ$ or —$CH_2)_nCHQR$, where Q is —$N(R)_2$, and n is selected from 3, 4, and 5.

In certain embodiments, the disclosure provides a compound having the Formula (I), wherein $R_4$ is selected from the group consisting of —$CH_2)_nQ$, —$CH_2)_nCHQR$, —CHQR, and —$CQ(R)_2$, where Q is —$N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle, and $R_4$ is —$CH_2)_nQ$ or —$CH_2)_nCHQR$, where Q is —$N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_5$-20 alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" may be $C_3$ alkyl. For example, R" may be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

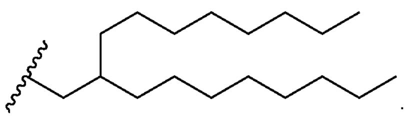 [SMILES: *CC(CCCCCCCC)CCCCCCCC]

.

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

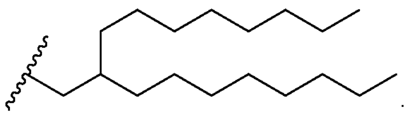 [SMILES: *CC(CCCCCCCC)CCCCCCCC]

.

In certain embodiments, R' is unsubstituted $C_{1-8}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' may be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M may be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_nQ$ and —$(CH_2)_nCHQR$.

In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)$S(O)_2R$, —N(H)$S(O)_2R$, —N(R)C(O)$N(R)_2$, —N(H)C(O)$N(R)_2$, —N(H)C(O)N(H)(R), —N(R)C(S)$N(R)_2$, —N(H)C(S)$N(R)_2$, —N(H)C(S)N(H)(R), —C(R)$N(R)_2$C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (═O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ may be —$(CH_2)_2OH$. For example, $R_4$ may be —$(CH_2)_3OH$. For example, $R_4$ may be —$(CH_2)_4OH$. For example, $R_4$ may be benzyl. For example, $R_4$ may be 4-methoxybenzyl.

In some embodiments, $R_4$ is a $C_{3-6}$ carbocycle. In some embodiments, $R_4$ is a $C_{3-6}$ cycloalkyl. For example, $R_4$ may be cyclohexyl optionally substituted with e.g., OH, halo, $C_{1-6}$ alkyl, etc. For example, $R_4$ may be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ may be —$CH_2CH(OH)CH_3$ or —$CH_2CH(OH)CH_2CH_3$.

In some embodiments, R is substituted $C_{1-3}$ alkyl, e.g., $CH_2OH$. For example, $R_4$ may be —$CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, may form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, may form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —$(CH_2)_nQ$ and —$(CH_2)_nCHQR$. In some embodiments, Q is selected from the group consisting of —OR, —OH, —$O(CH_2)_nN(R)_2$, —OC(O)R, —$CX_3$, —CN, —N(R)C(O)R, —N(H)C(O)R, —N(R)$S(O)_2R$, —N(H)$S(O)_2R$, —N(R)C(O)$N(R)_2$, —N(H)C(O)$N(R)_2$, —N(H)C(O)N(H)(R), —N(R)C(S)$N(R)_2$, —N(H)C(S)$N(R)_2$, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, may form a phenyl group bearing one or more $C_5$ alkyl substitutions.

In some embodiments, the pharmaceutical compositions of the present disclosure, the compound of formula (I) is selected from the group consisting of:

(Compound 1)

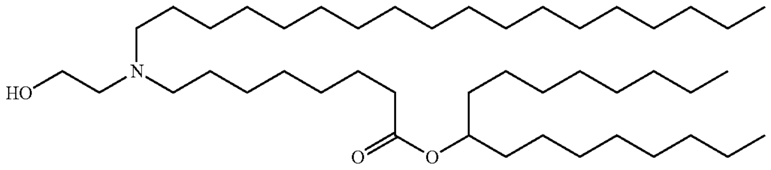

, (Compound 2)

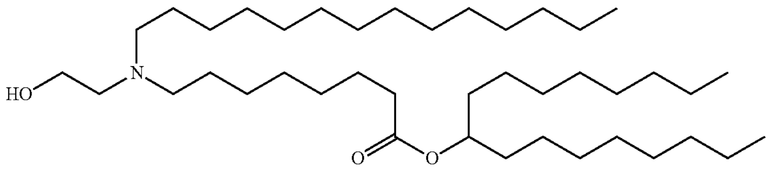

,

-continued
(Compound 3)
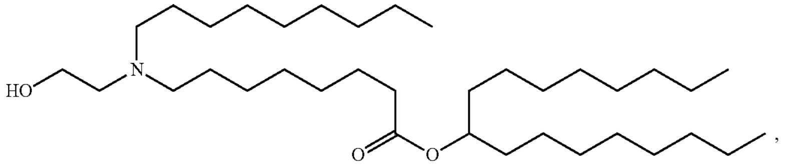
(Compound 4)
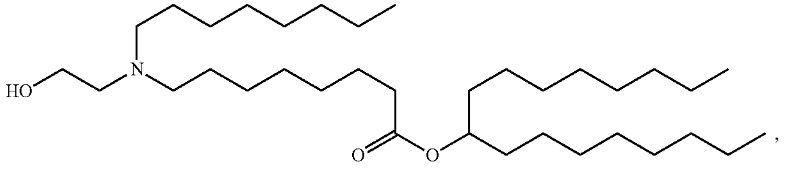
(Compound 5)
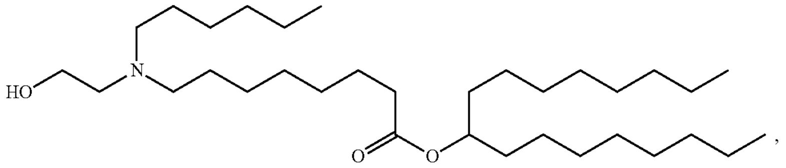
(Compound 6)
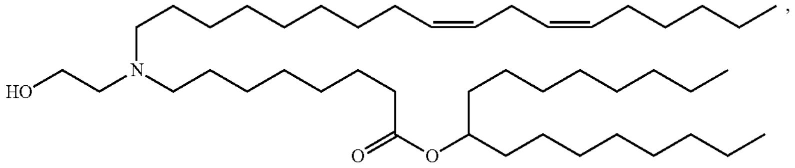
(Compound 7)
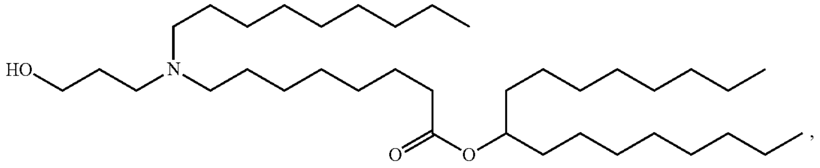
(Compound 8)
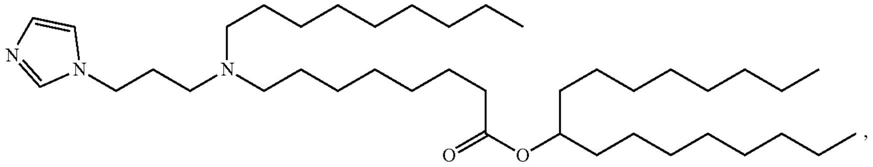
(Compound 9)
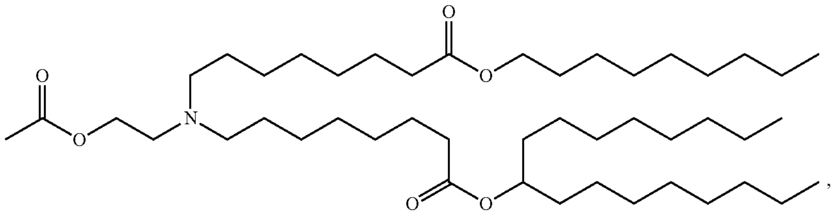
(Compound 10)
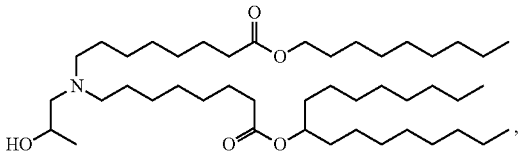
(Compound 11)
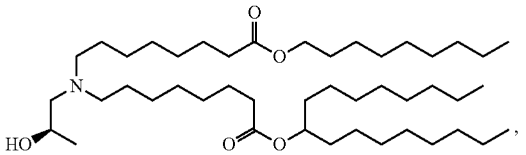

-continued
(Compound 12)
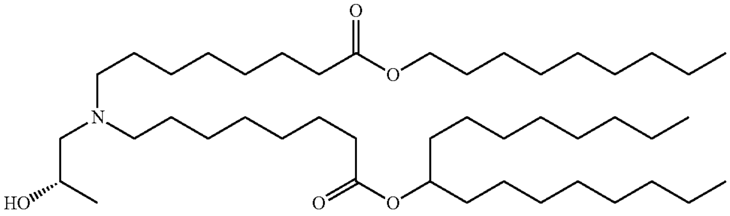
,
(Compound 13)
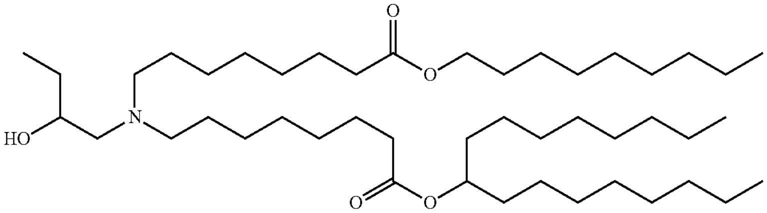
,
(Compound 14)
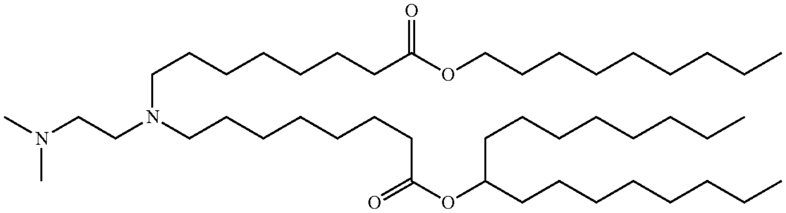
,
(Compound 15)
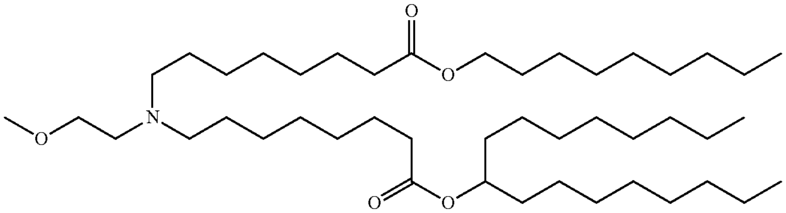
,
(Compound 16)
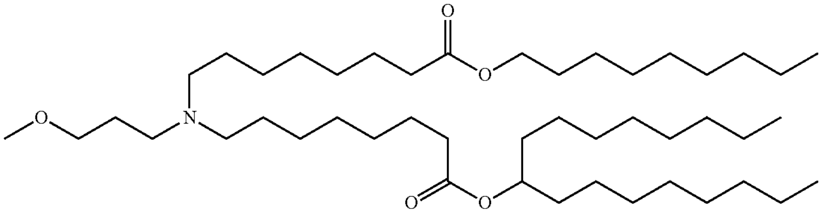
,
(Compound 17)
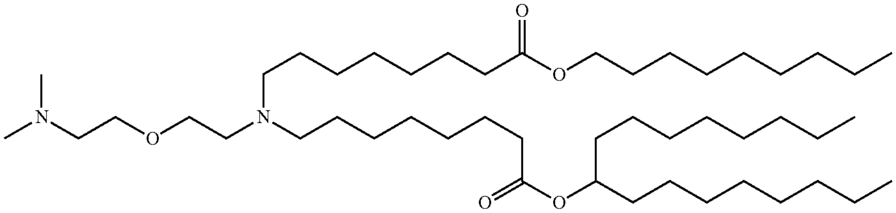
,
(Compound 18)
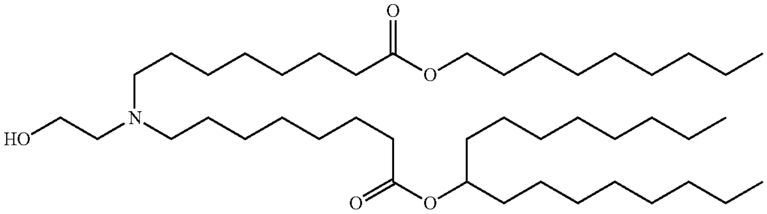
, -continued
(Compound 19)
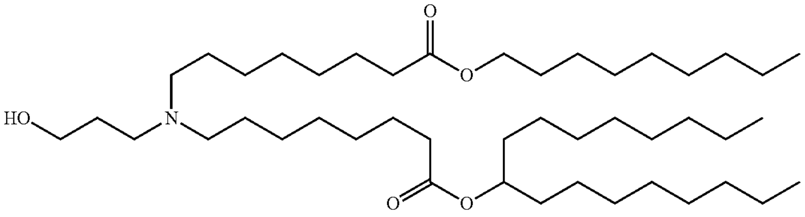
,
(Compound 20)
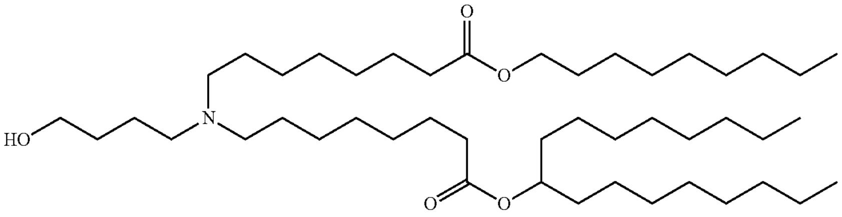
,
(Compound 21)
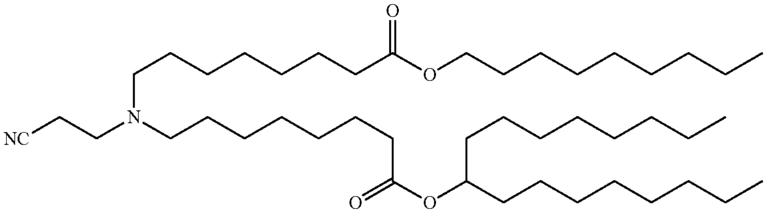
,
(Compound 22)
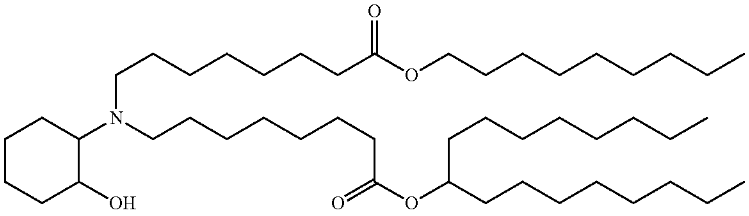
,
(Compound 23)
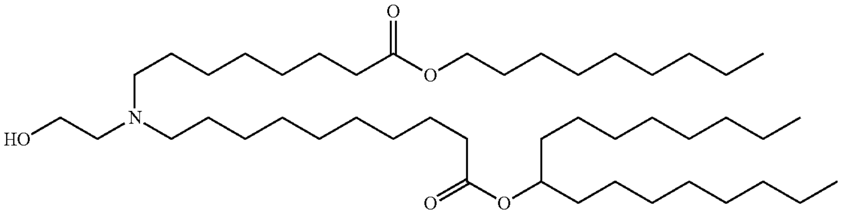
,
(Compound 24)
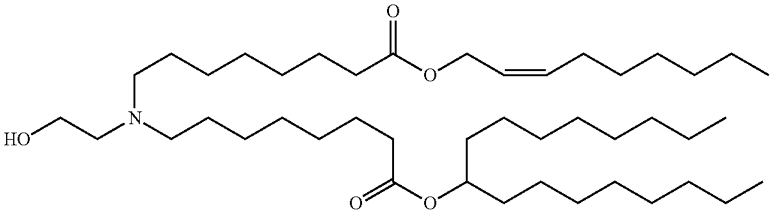
,
(Compound 25)
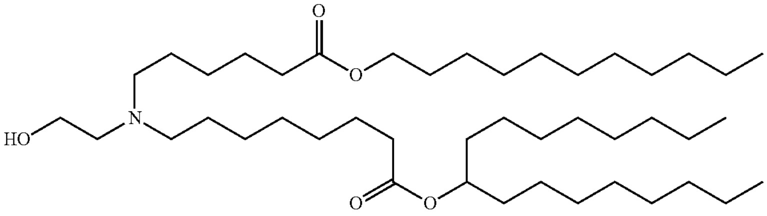
, -continued
(Compound 26)
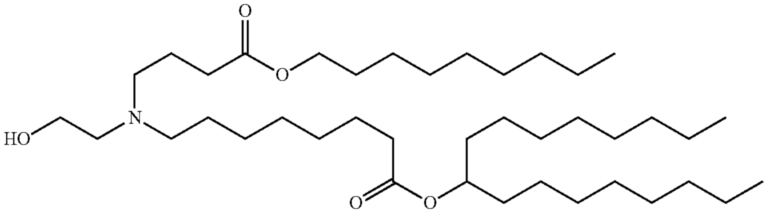
,
(Compound 27)
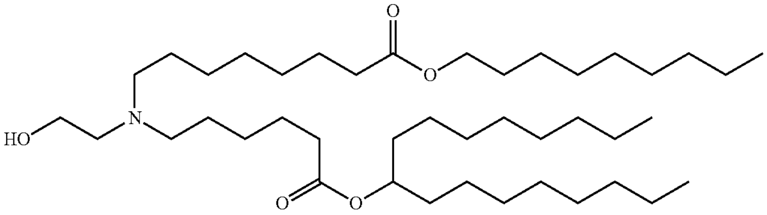
,
(Compound 28)
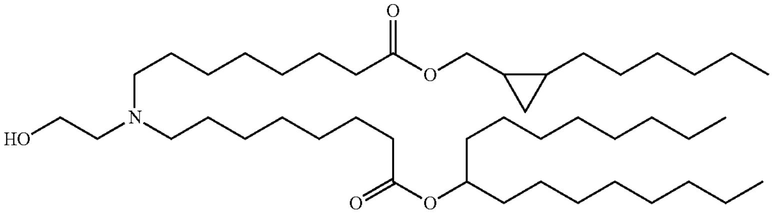
,
(Compound 29)
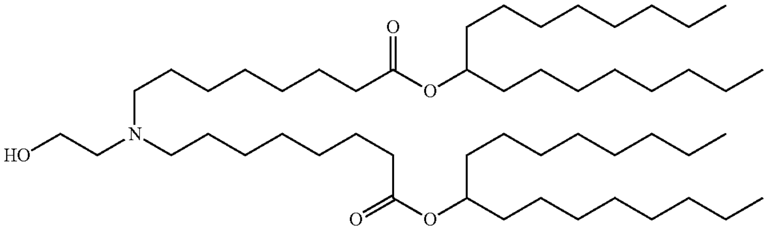
,
(Compound 30)
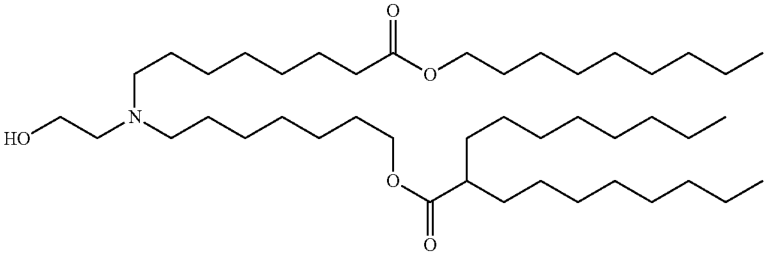
,
(Compound 31)
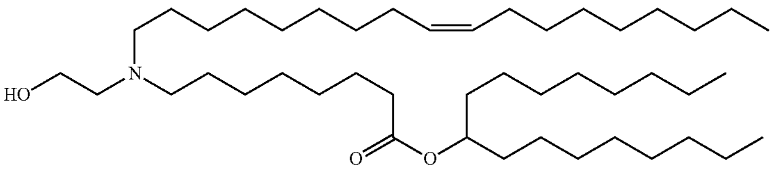
,
(Compound 32)
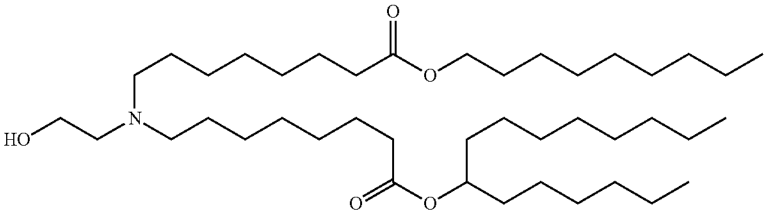
, -continued
(Compound 33)
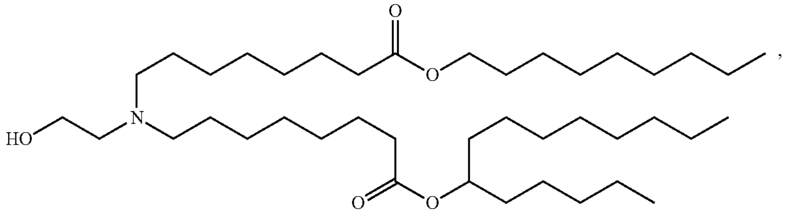
(Compound 34)
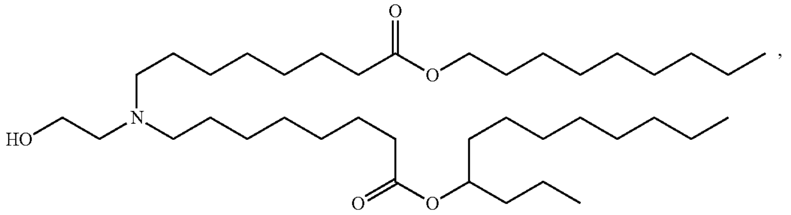
(Compound 35)
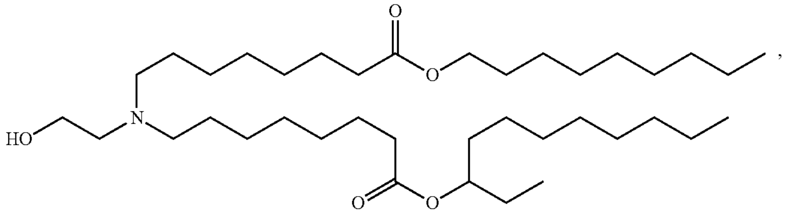
(Compound 36)
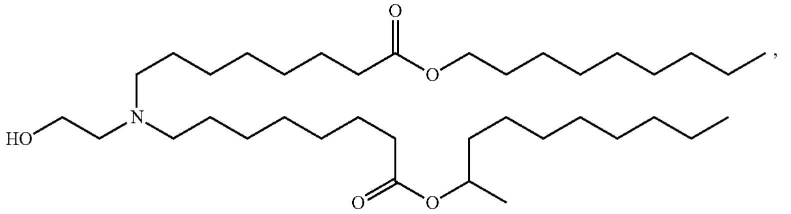
(Compound 37)
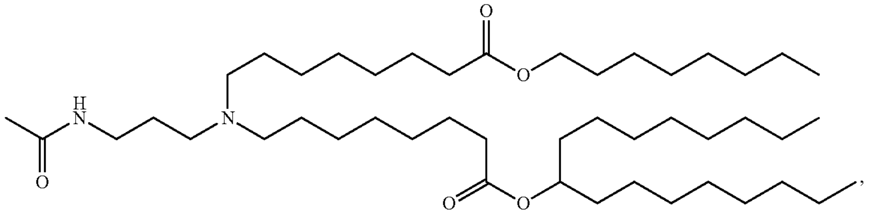
(Compound 38)
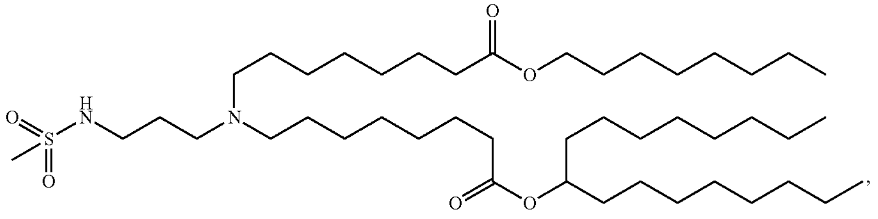
(Compound 39)
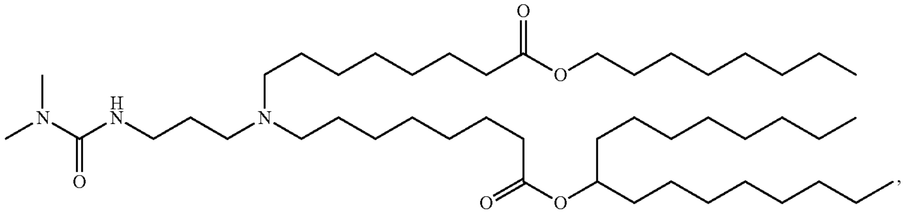

-continued
(Compound 40)
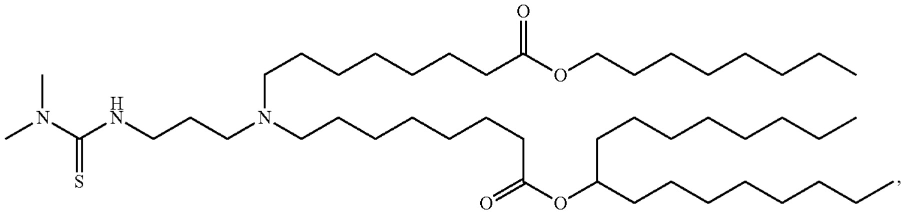
(Compound 41)
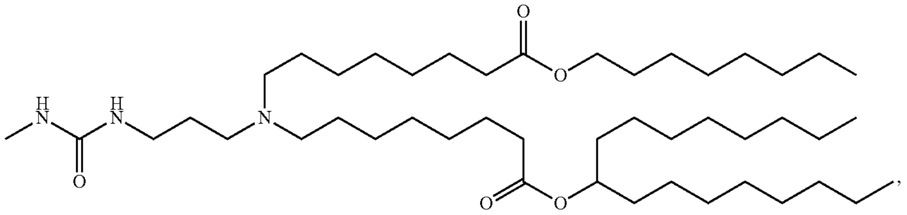
(Compound 42)
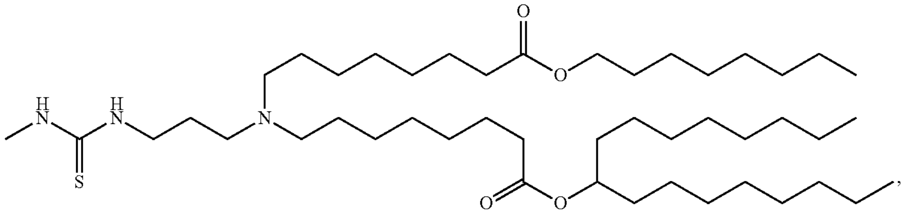
(Compound 43)
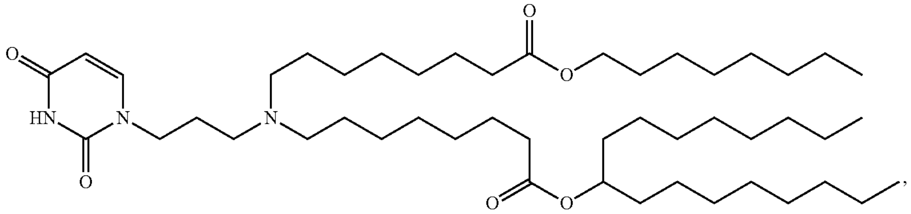
(Compound 44)
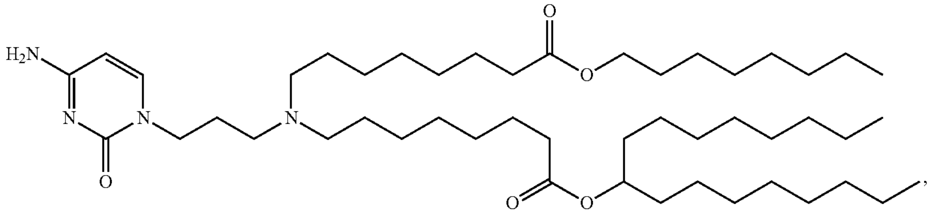
(Compound 45)
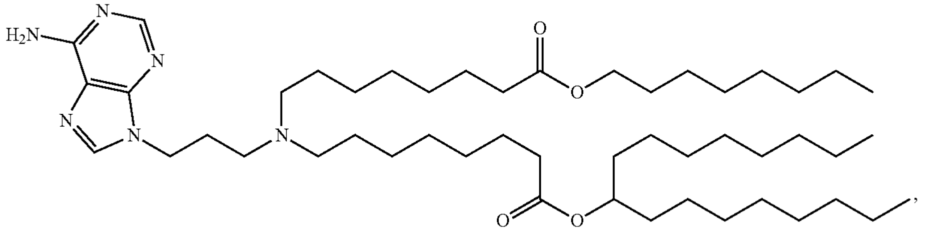
(Compound 46)
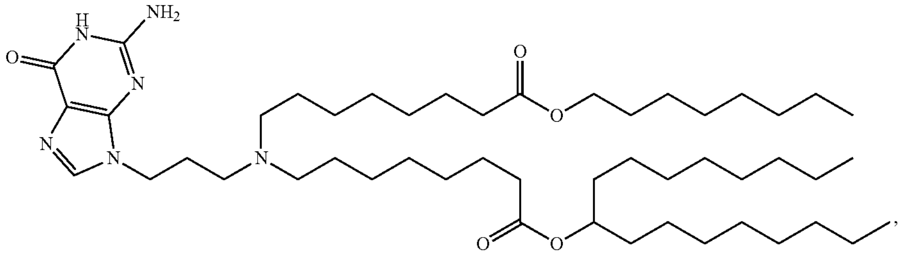

-continued
(Compound 47)
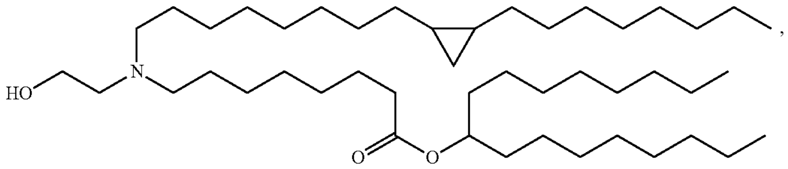
(Compound 48)
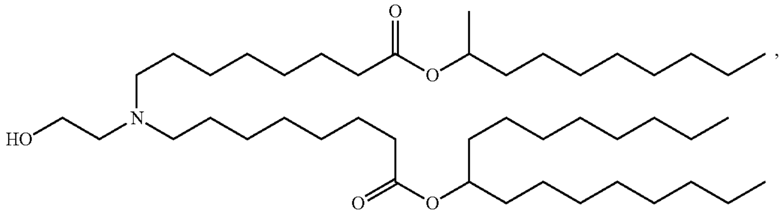
(Compound 49)
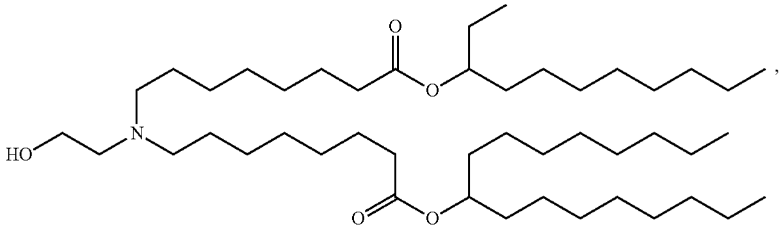
(Compound 50)
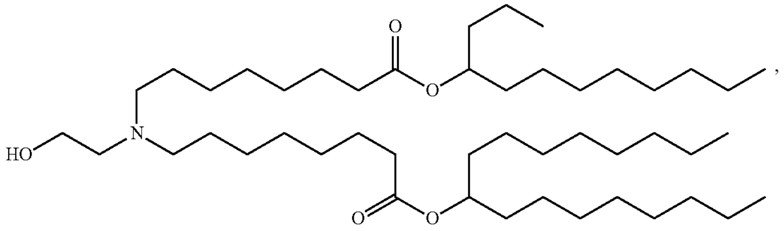
(Compound 51)
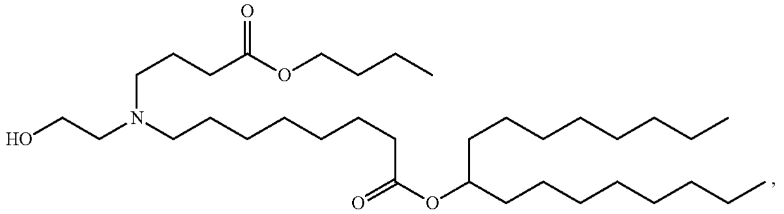
(Compound 52)
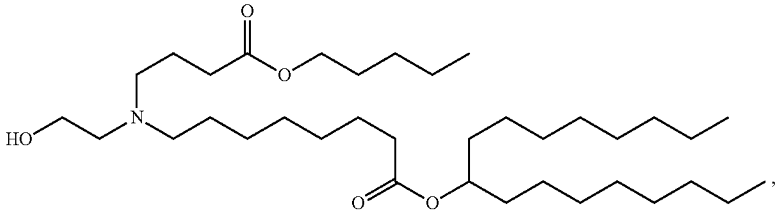
(Compound 53)
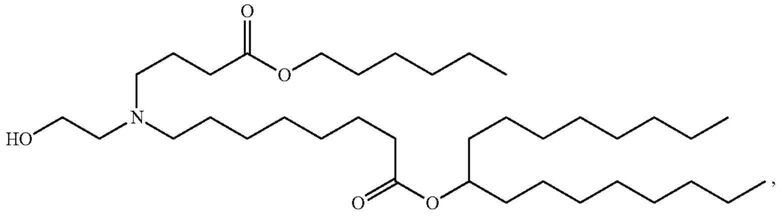

-continued
(Compound 54)
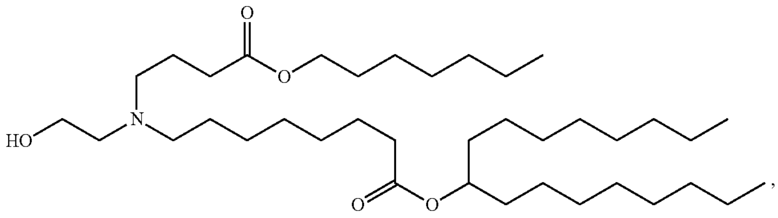
(Compound 55)
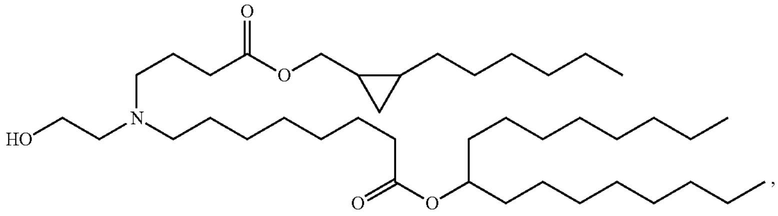
(Compound 56)
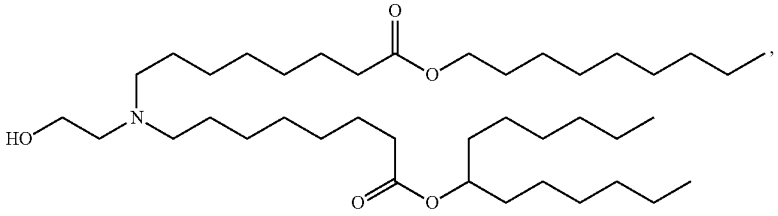
(Compound 57)
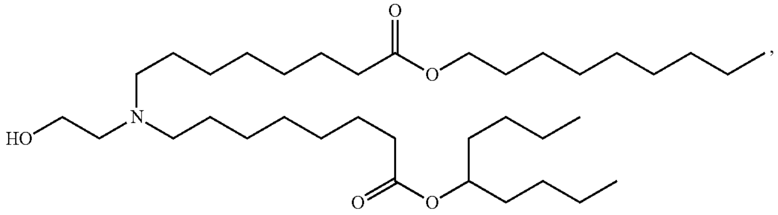
(Compound 58)
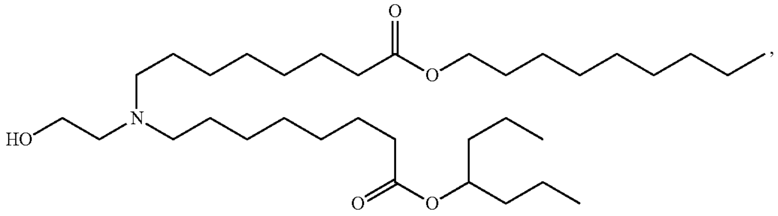
(Compound 59)
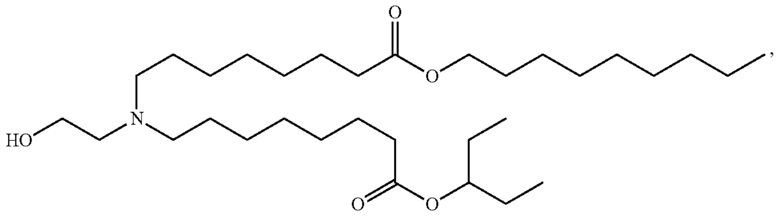
(Compound 60)
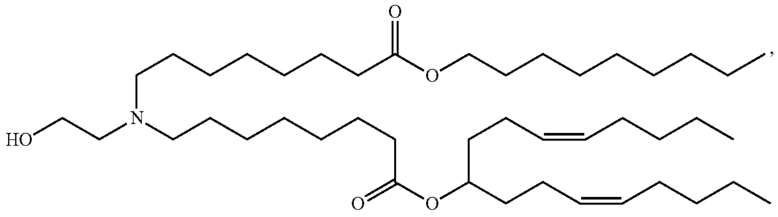

-continued
(Compound 61)
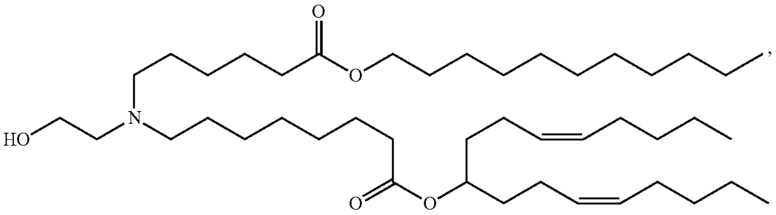
(Compound 62)
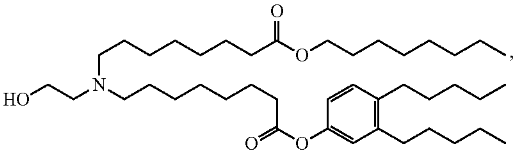
(Compound 63)
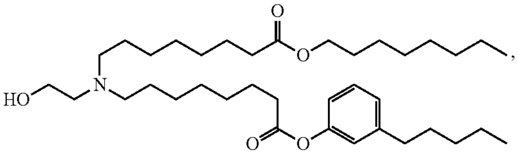
(Compound 64)
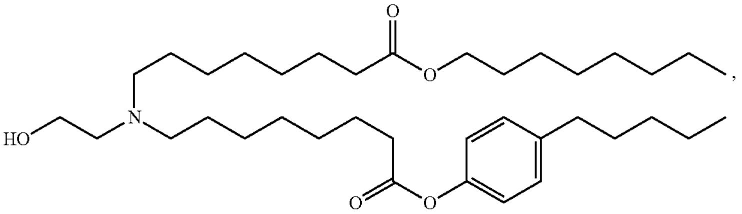
(Compound 65)
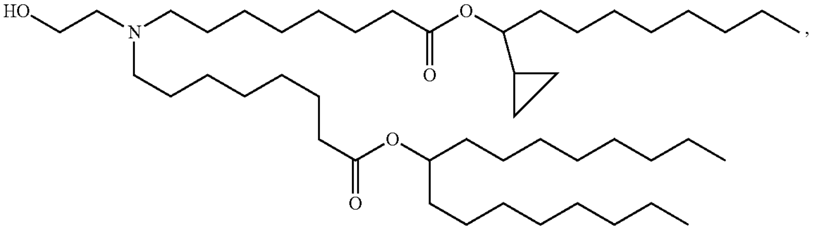
(Compound 66)
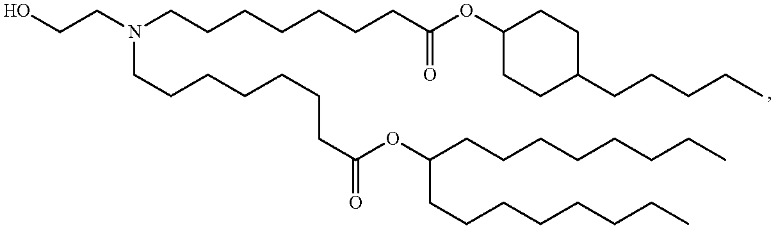
(Compound 67)
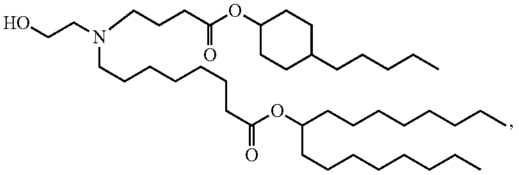
(Compound 68)
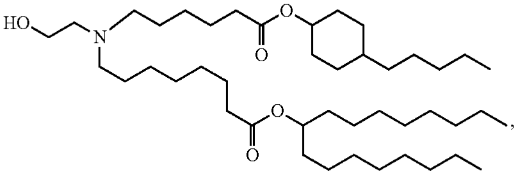
(Compound 69)
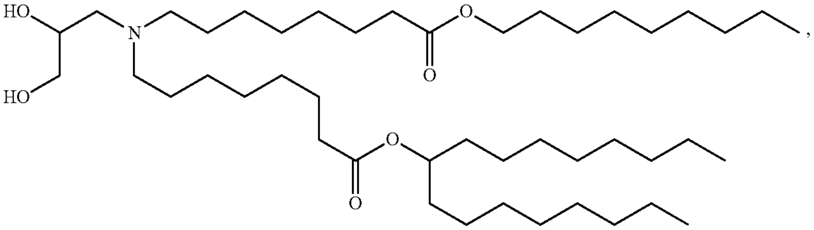

-continued
(Compound 70)
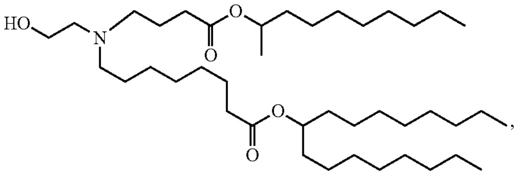
(Compound 71)
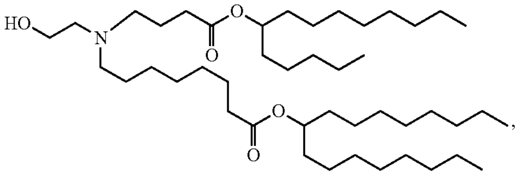
(Compound 72)
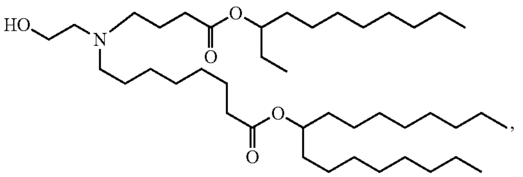
(Compound 73)
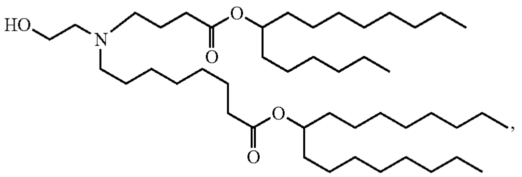
(Compound 74)
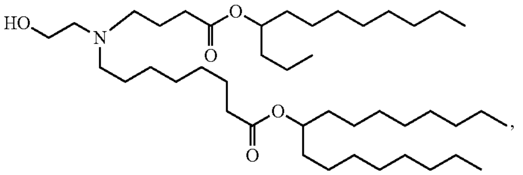
(Compound 75)
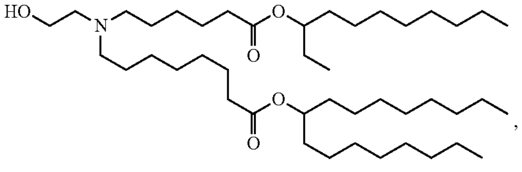
(Compound 76)
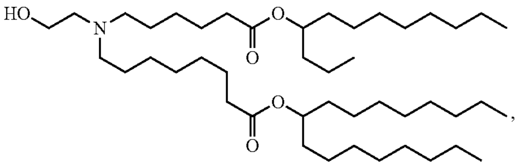
(Compound 77)
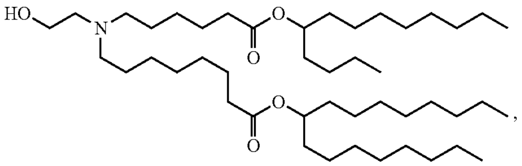
(Compound 78)
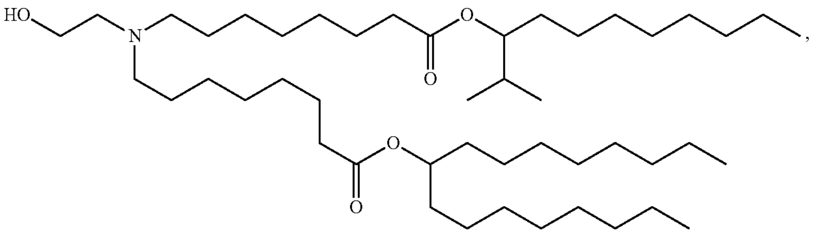
(Compound 79)
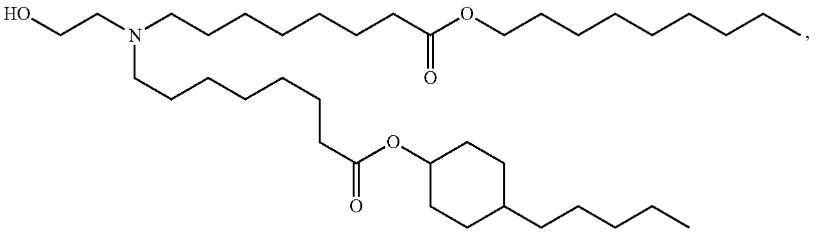
(Compound 80)
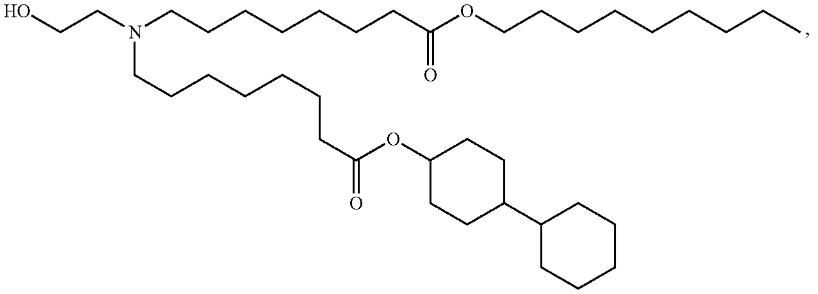

-continued
(Compound 81)
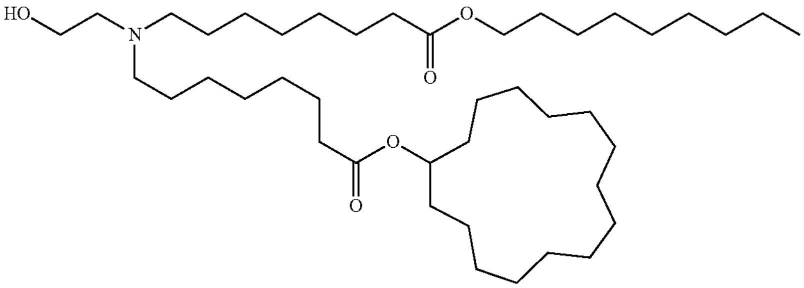
,
(Compound 82)
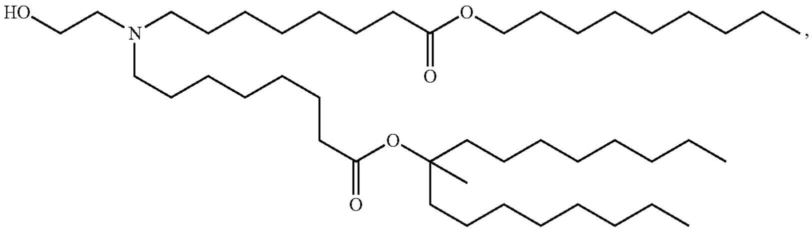
,
(Compound 83)
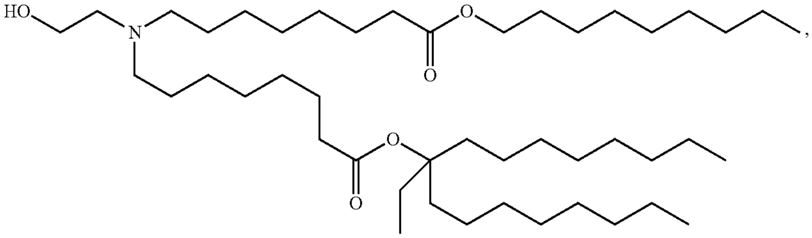
,
(Compound 84)
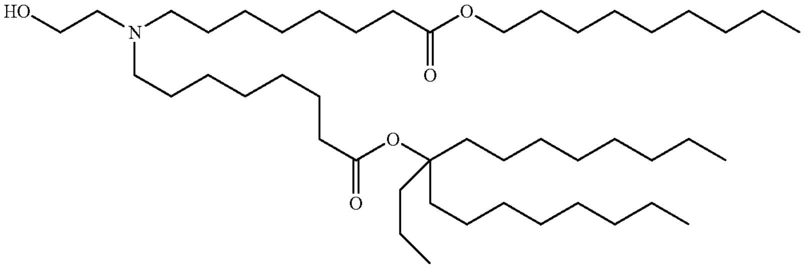
,
(Compound 85)
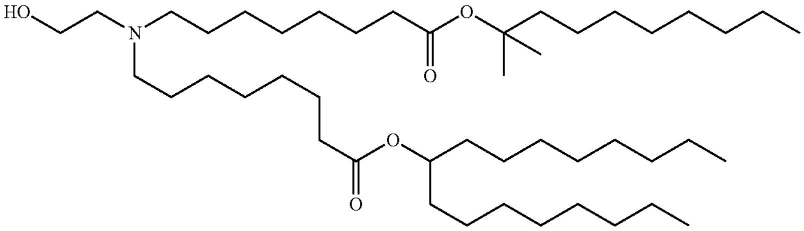
,
(Compound 86)
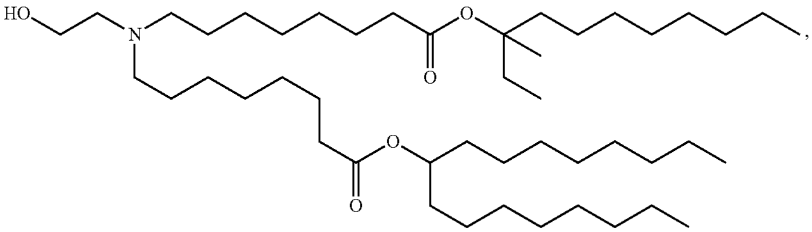
, -continued
(Compound 87)
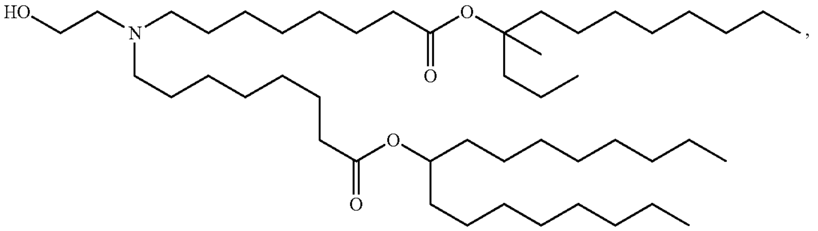
(Compound 88)
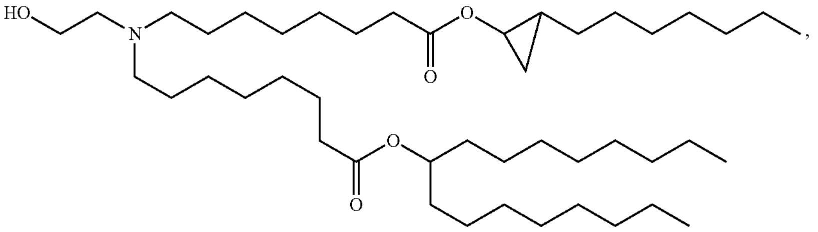
(Compound 89)
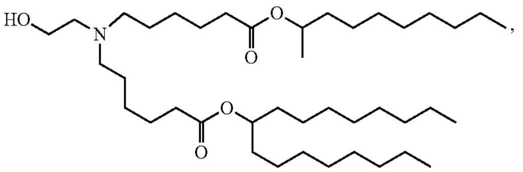
(Compound 90)
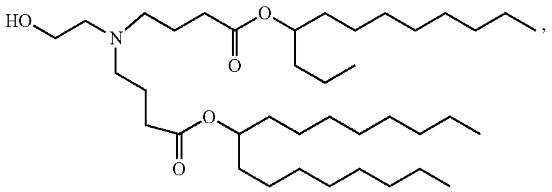
(Compound 91)
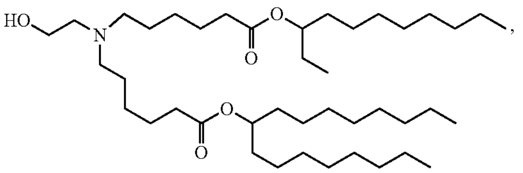
(Compound 92)
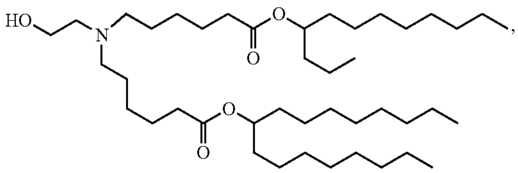
(Compound 93)
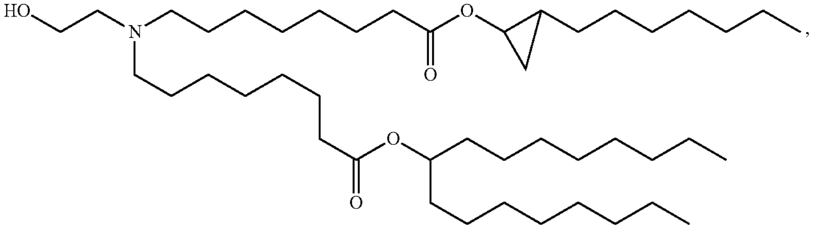
(Compound 94)
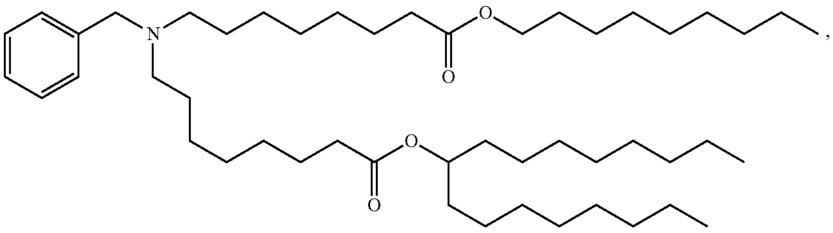
(Compound 95)
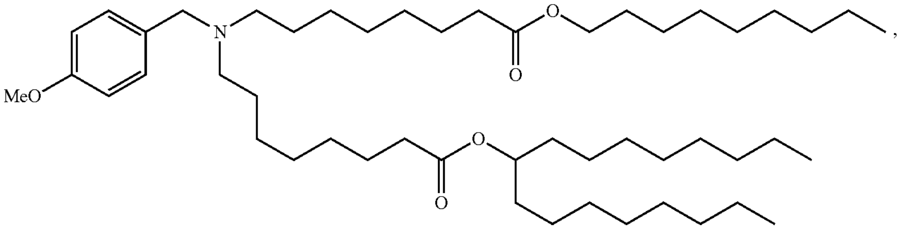

-continued
(Compound 96)
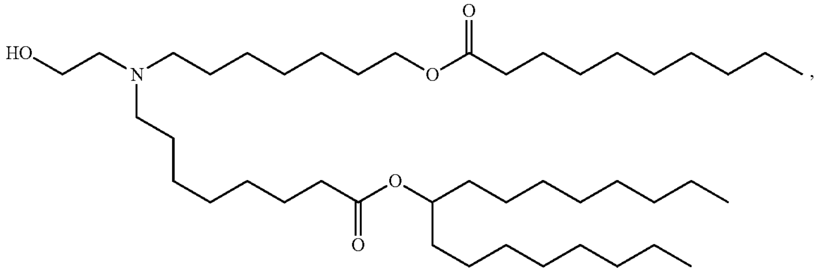
(Compound 97)
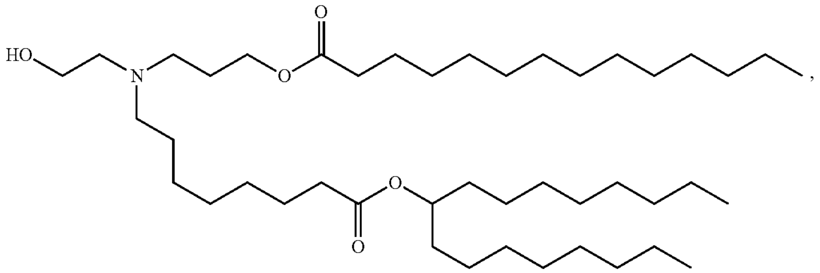
(Compound 98)
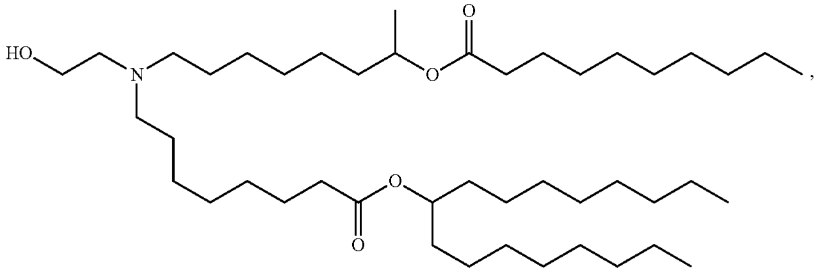
(Compound 99)
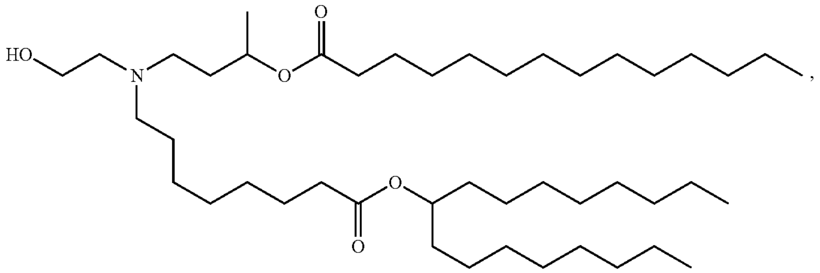
(Compound 100)
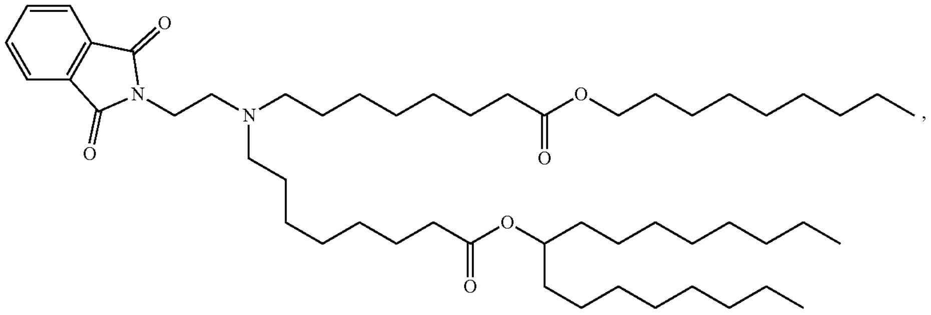

-continued
(Compound 101)
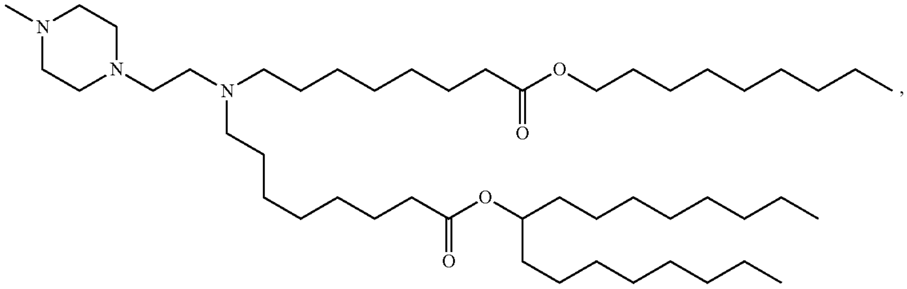
,
(Compound 102)
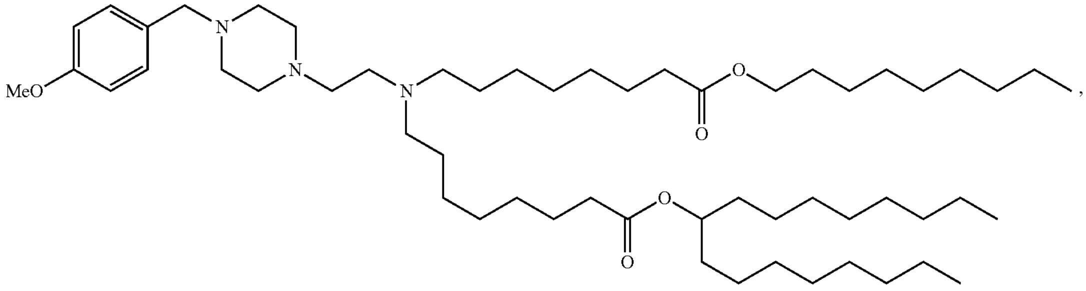
,
(Compound 103)
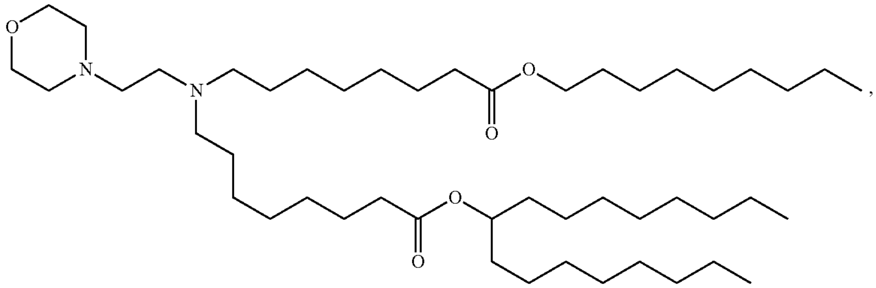
,
(Compound 104)
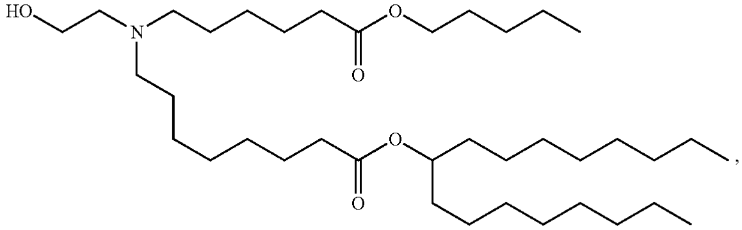
,
(Compound 105)
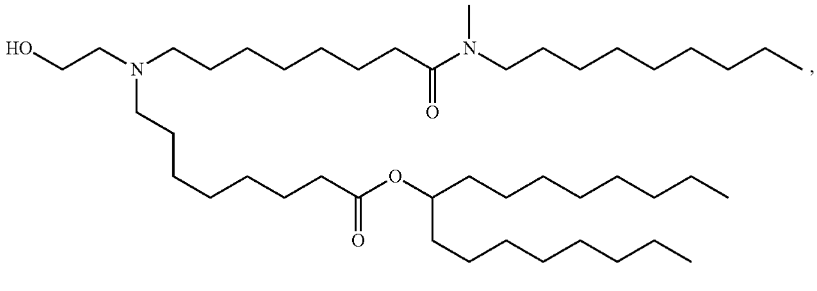
, -continued
(Compound 106)
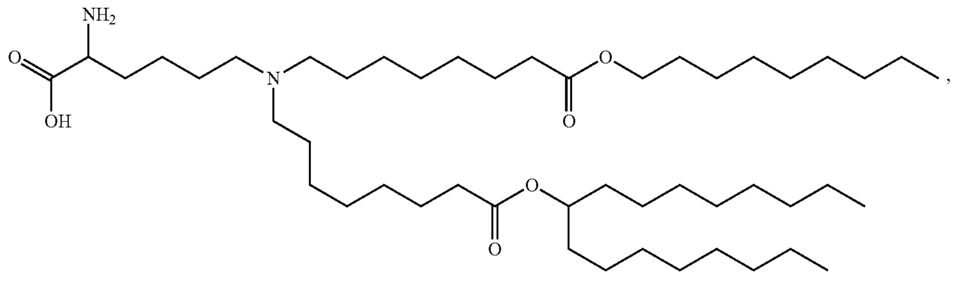
(Compound 107)
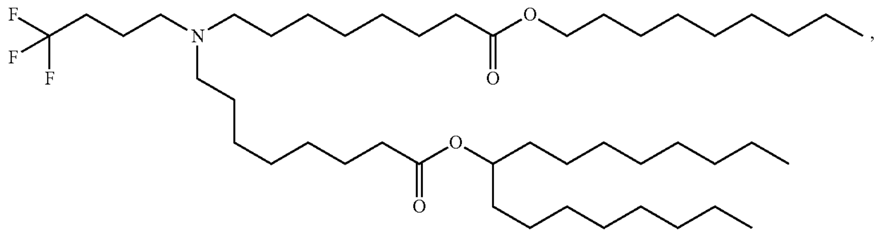
(Compound 108)
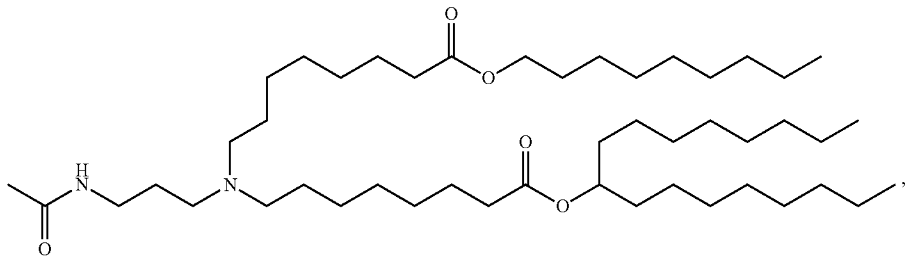
(Compound 109)
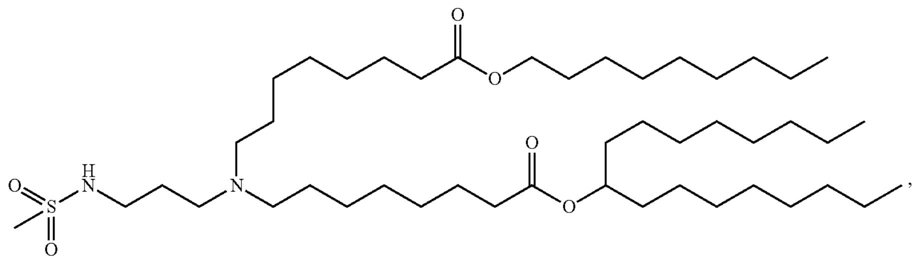
(Compound 110)
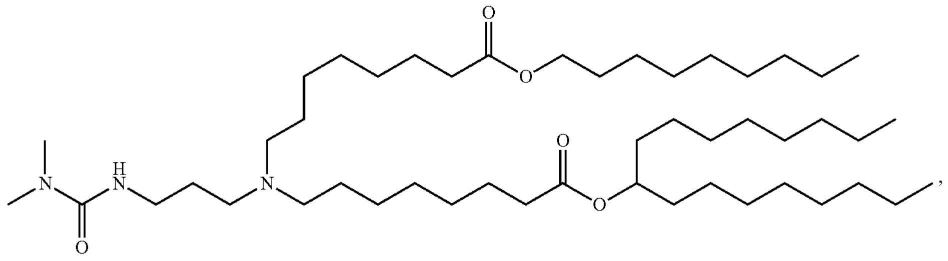
(Compound 111)
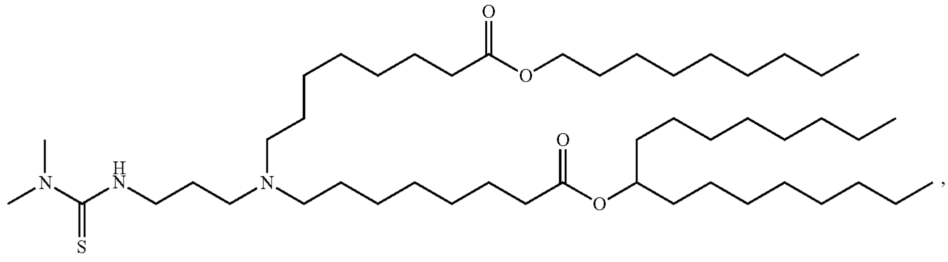

-continued
(Compound 112)
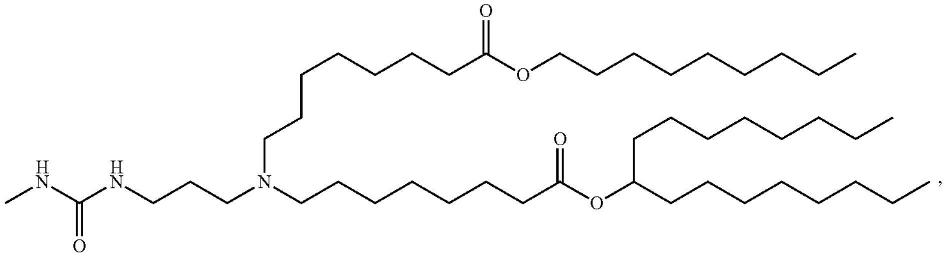
(Compound 113)
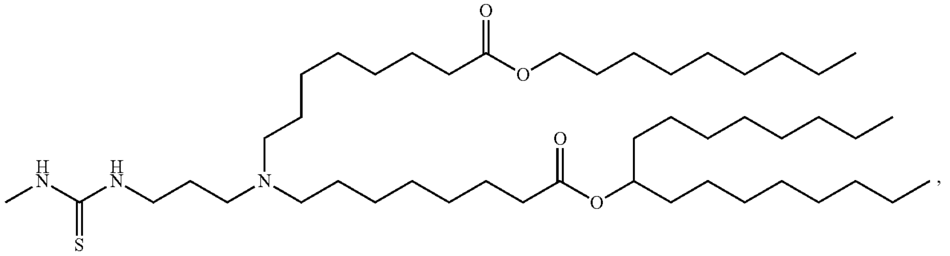
(Compound 114)
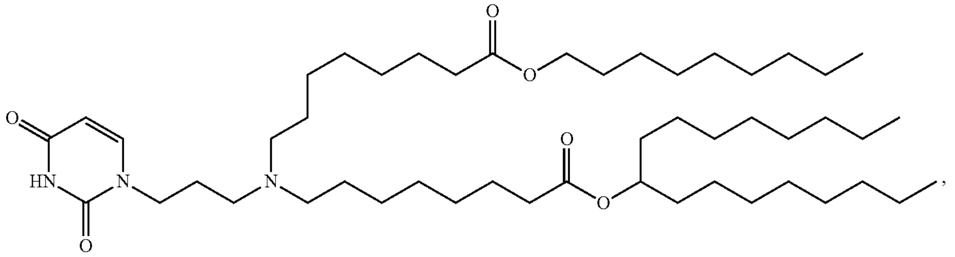
(Compound 115)
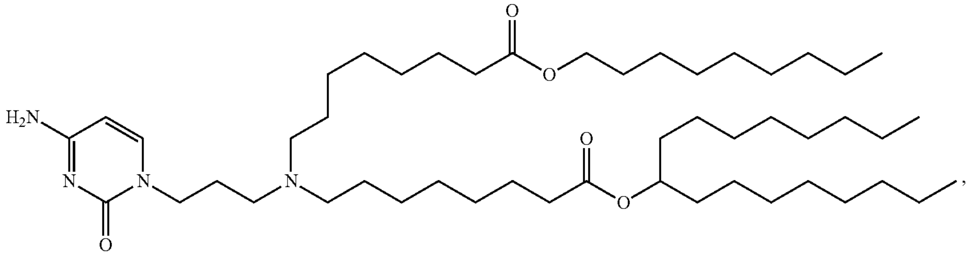
(Compound 116)
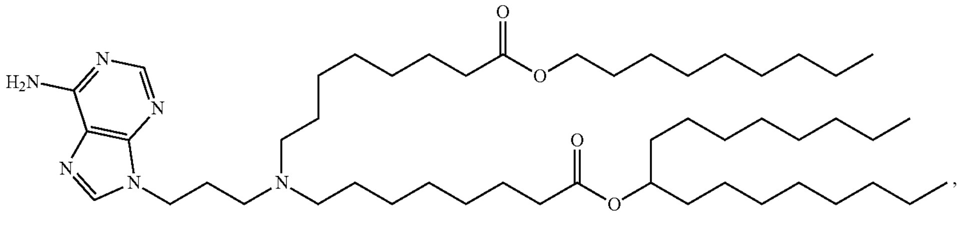
(Compound 117)
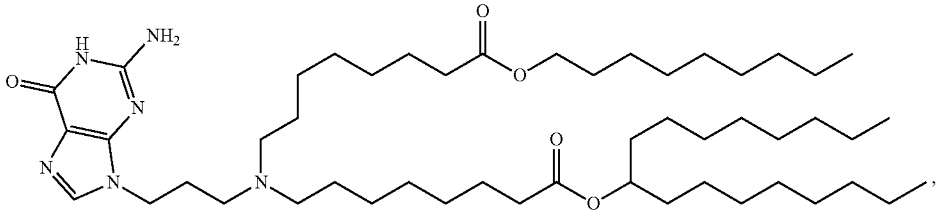

-continued
(Compound 118)
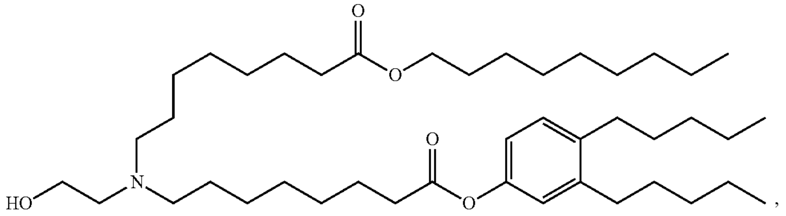
(Compound 119)
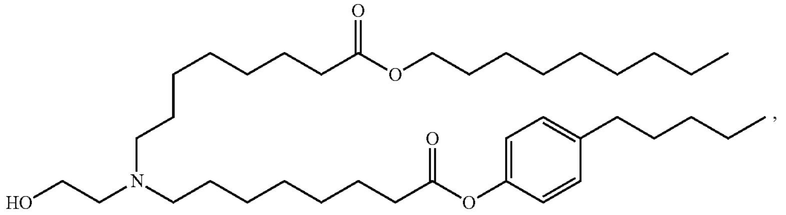
(Compound 120)
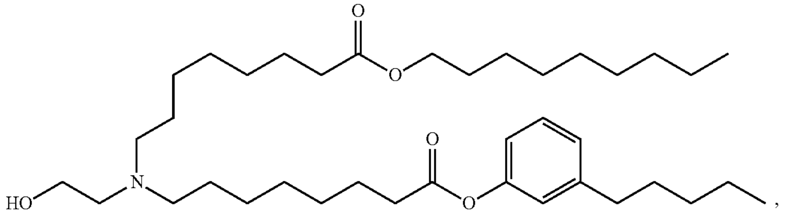
(Compound 121)
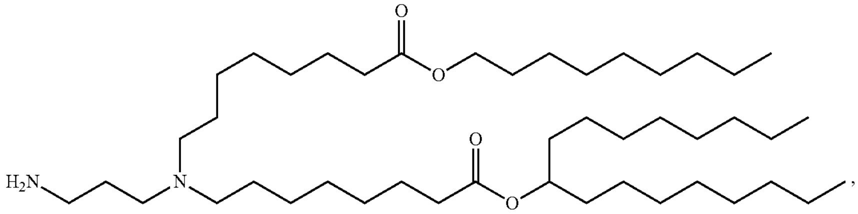
(Compound 122)
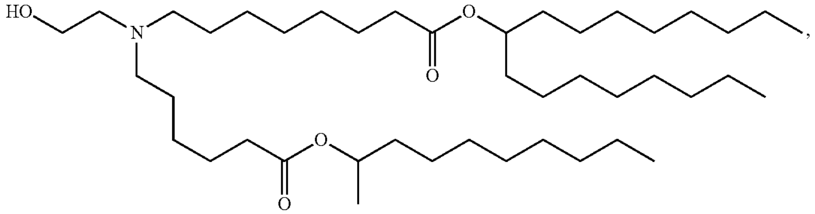
(Compound 123)
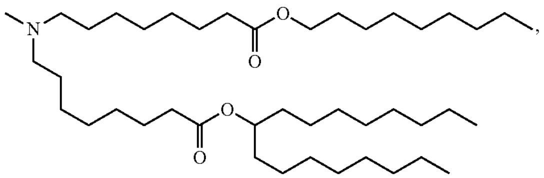
(Compound 124)
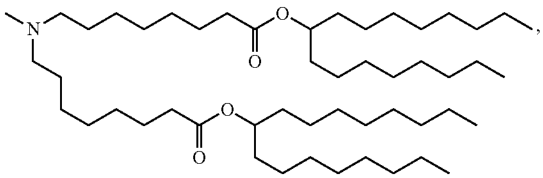
(Compound 125)
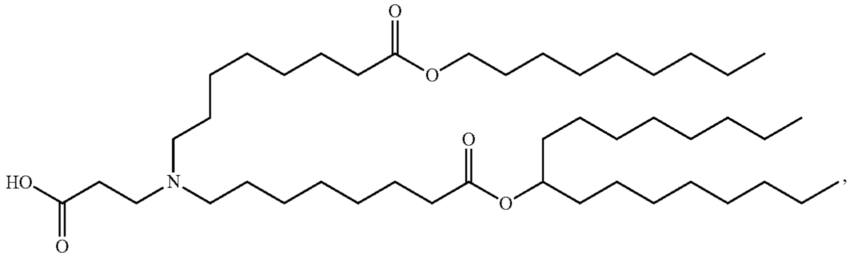

-continued
(Compound 126)
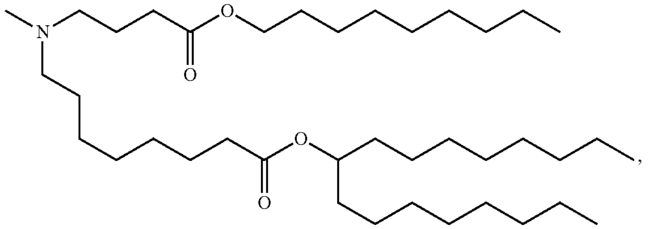
(Compound 127)
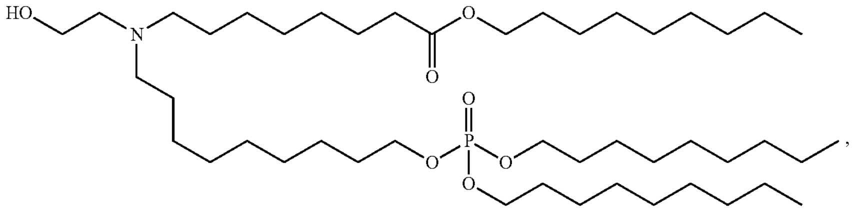
(Compound 128)
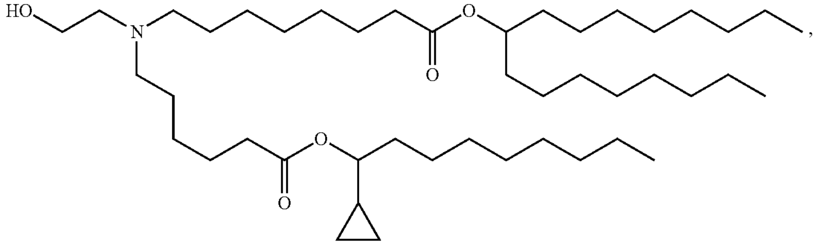
(Compound 129)
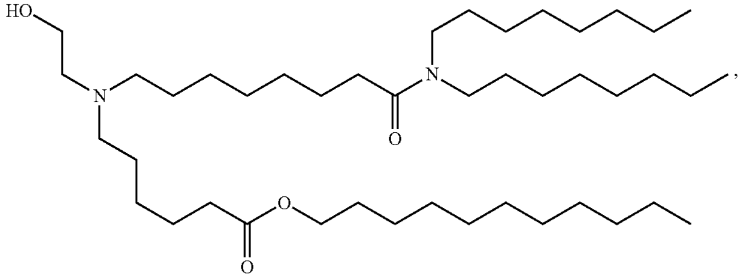
(Compound 130)
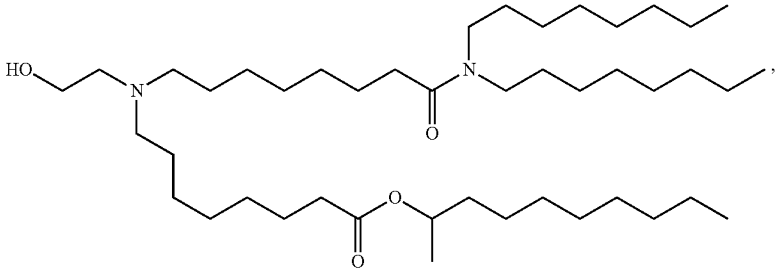
(Compound 131)
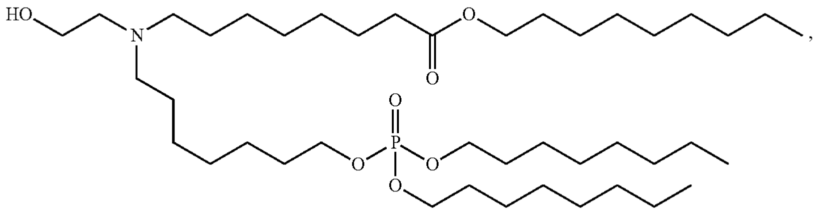

-continued
(Compound 132)
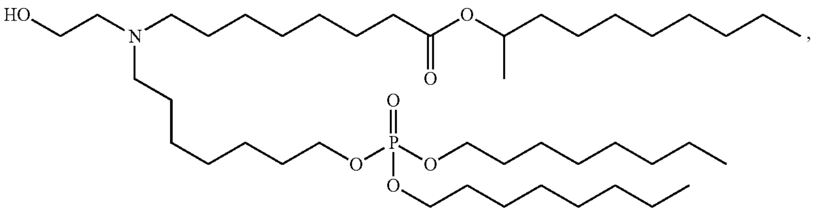
,
(Compound 133)
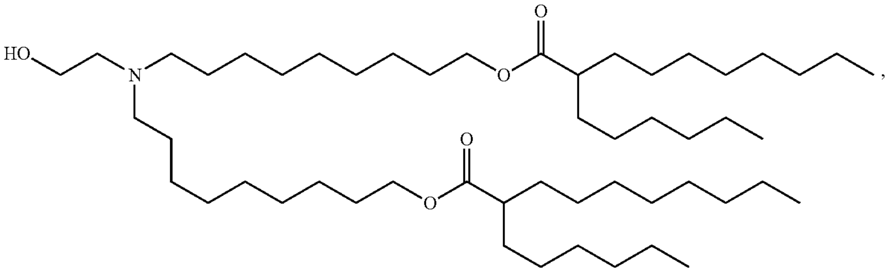
,
(Compound 134)
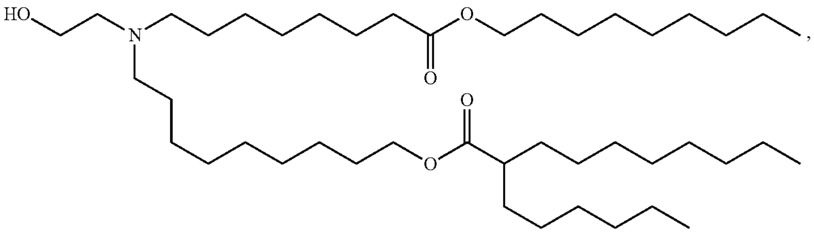
,
(Compound 135)
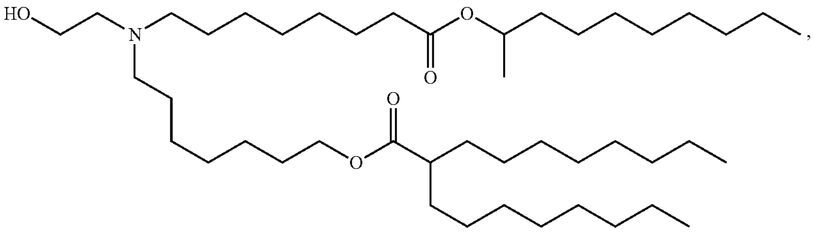
,
(Compound 136)
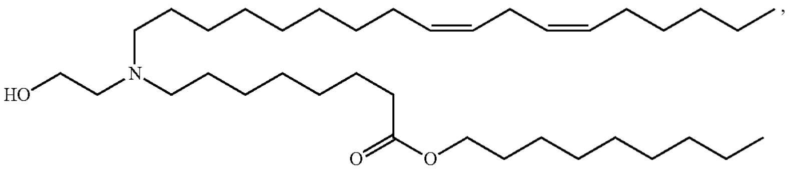
,
(Compound 137)
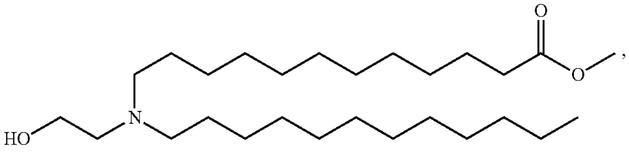
,
(Compound 138)
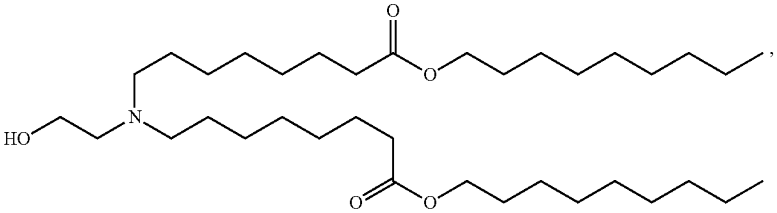
, -continued
(Compound 139)
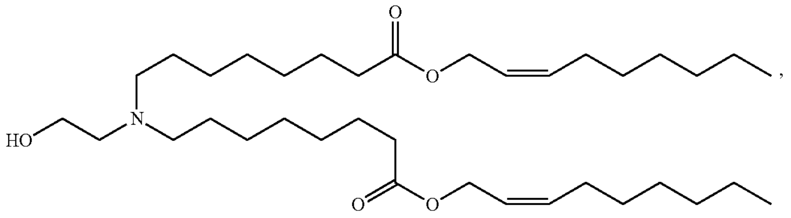
(Compound 140)
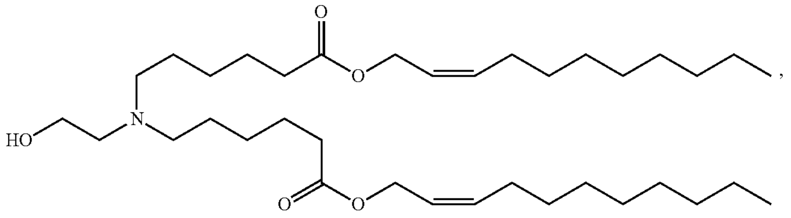
(Compound 141)
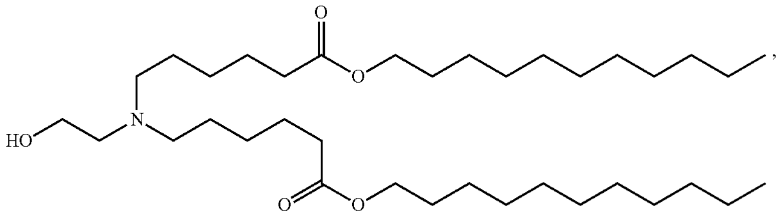
(Compound 142)
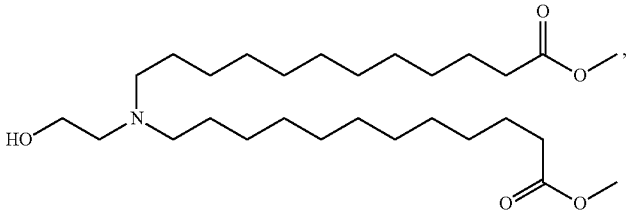
(Compound 143)
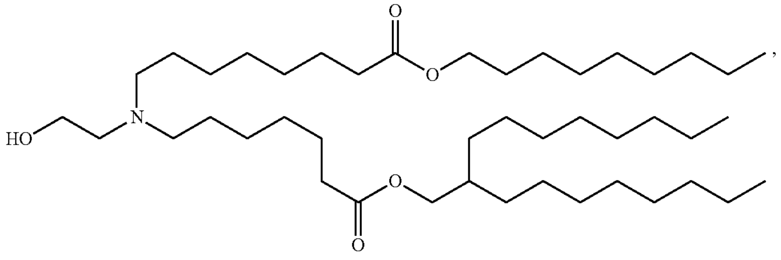
(Compound 144)
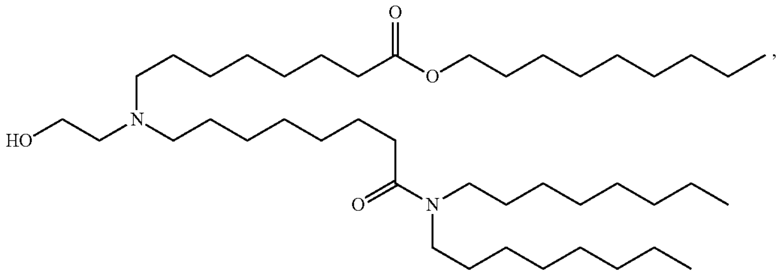

-continued
(Compound 145)
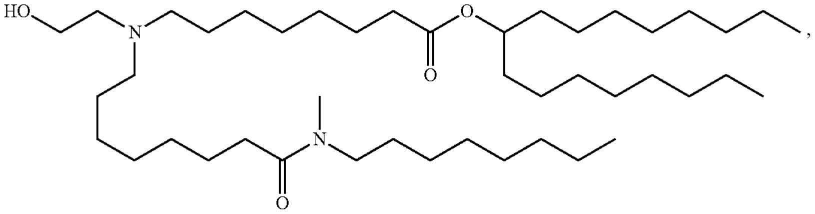
(Compound 146)
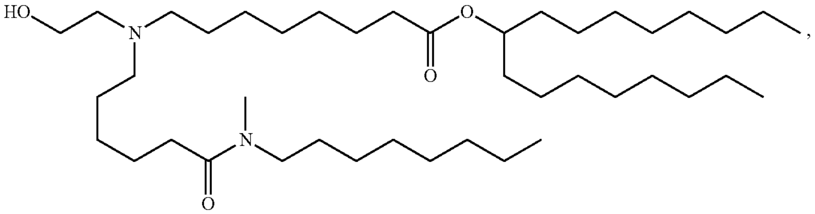
(Compound 147)
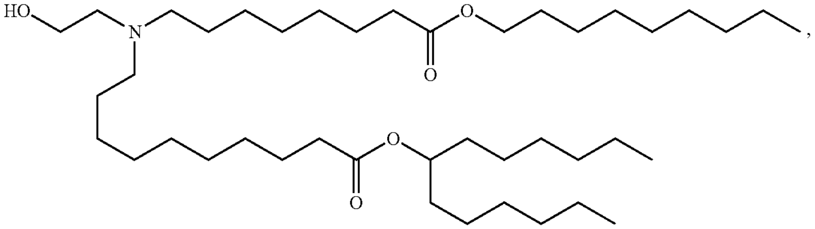
(Compound 148)
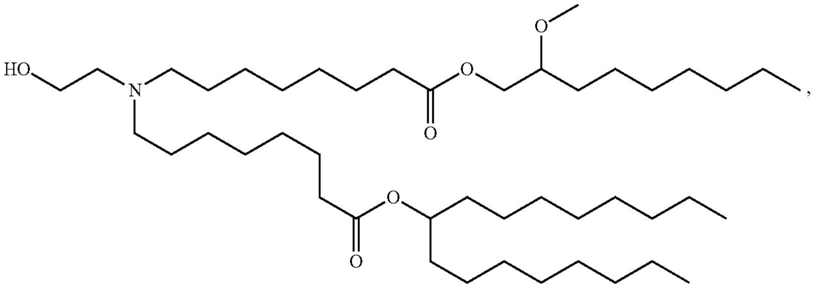
(Compound 149)
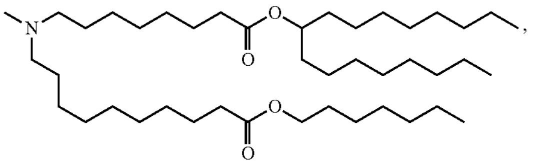
(Compound 150)
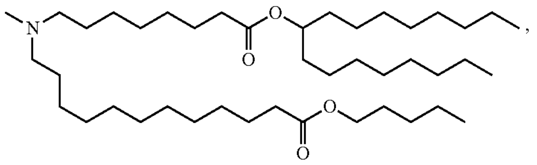
(Compound 151)
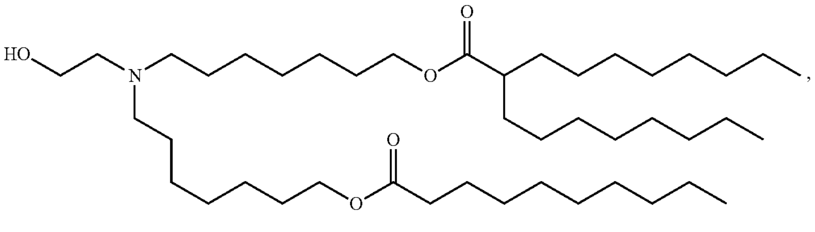
(Compound 152)
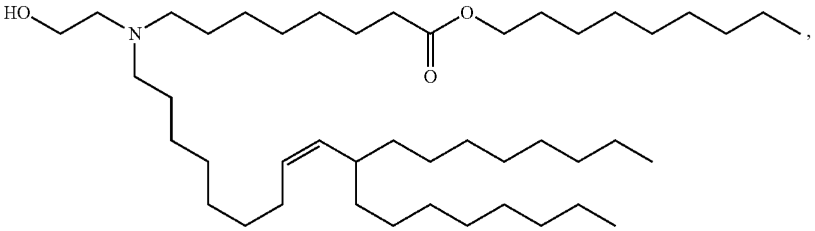

-continued
(Compound 153)
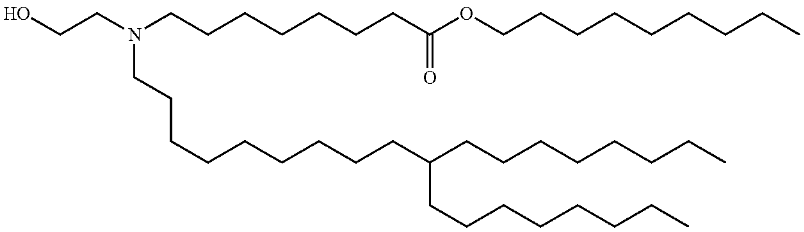
,
(Compound 154)
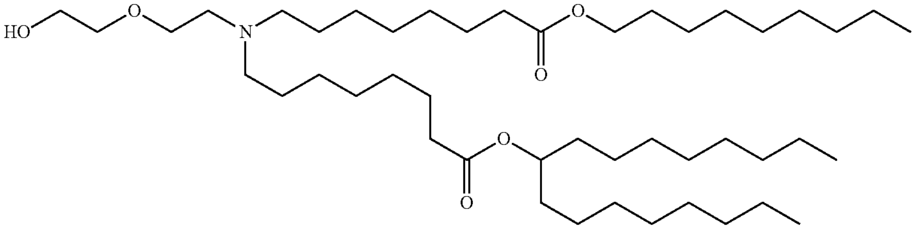
,
(Compound 155)
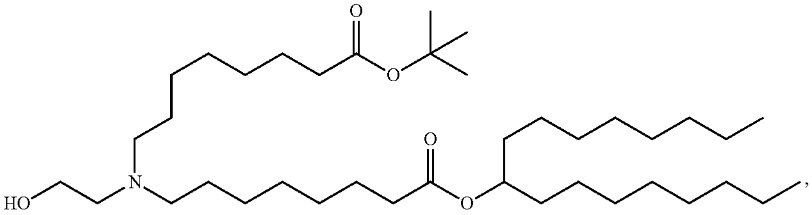
,
(Compound 156)
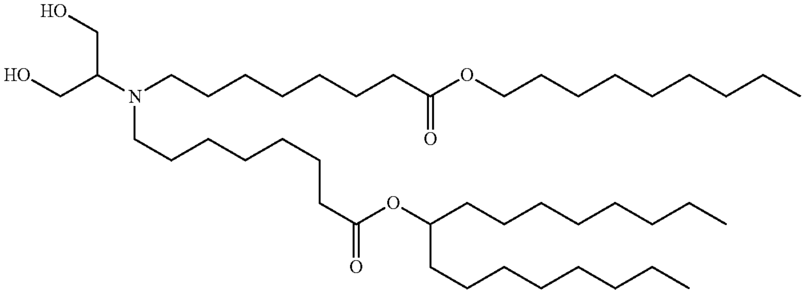
,
(Compound 157)
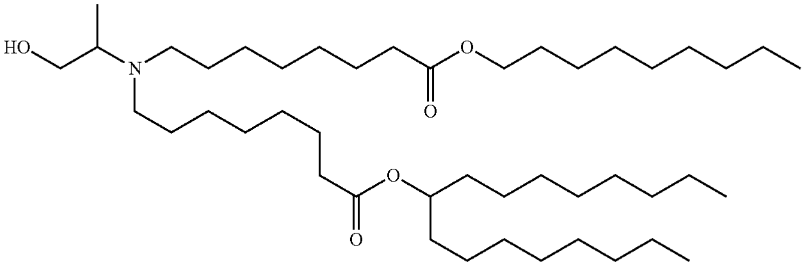
,
(Compound 158)
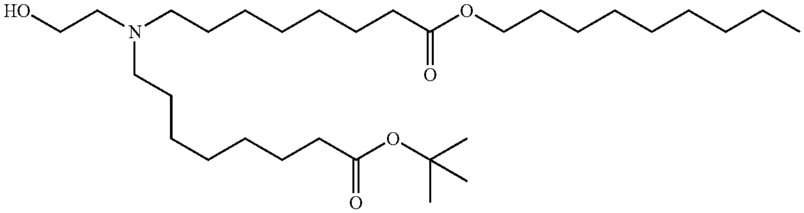
, -continued
(Compound 159)
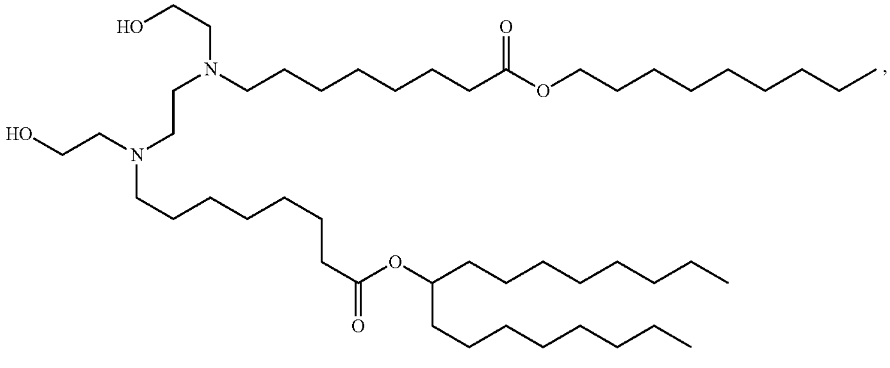
,
(Compound 160)
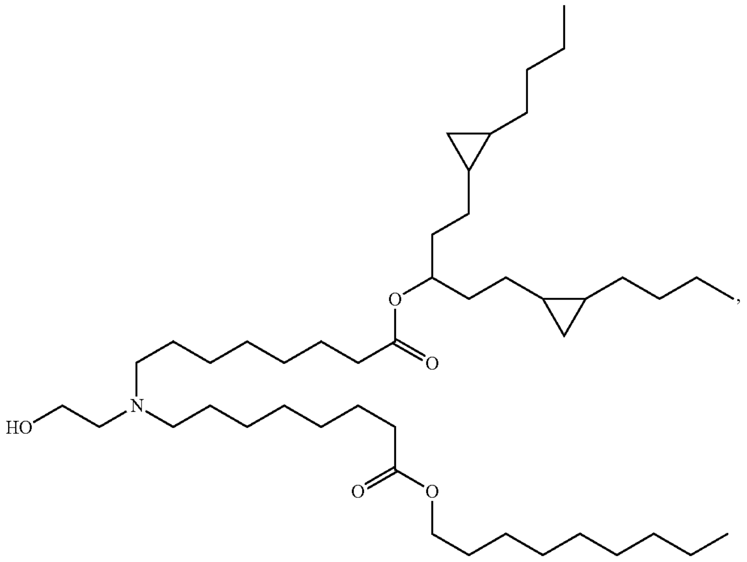
,
(Compound 161)
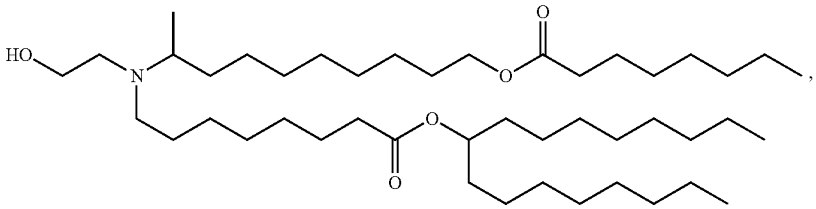
,
(Compound 162)
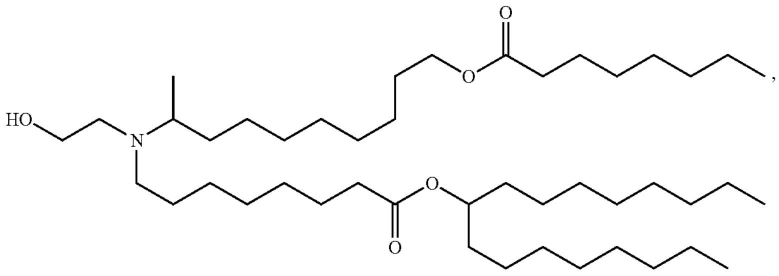
, -continued
(Compound 163)
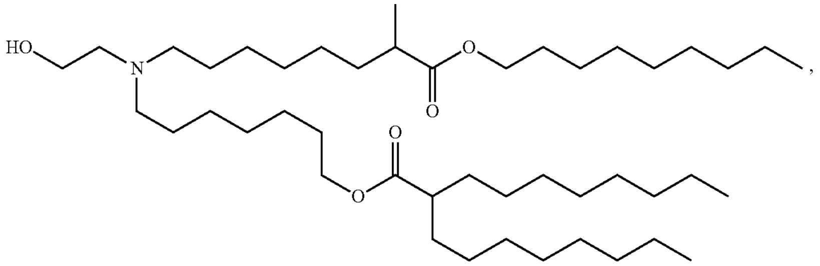
(Compound 164)
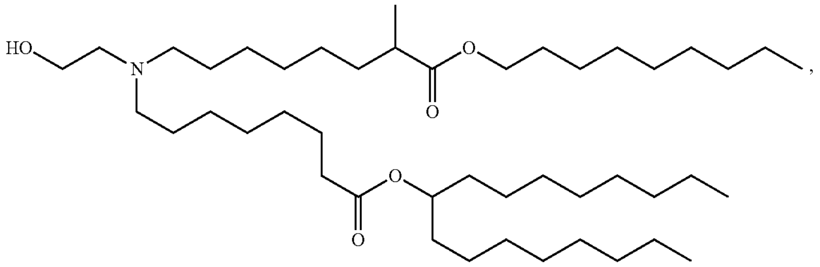
(Compound 165)
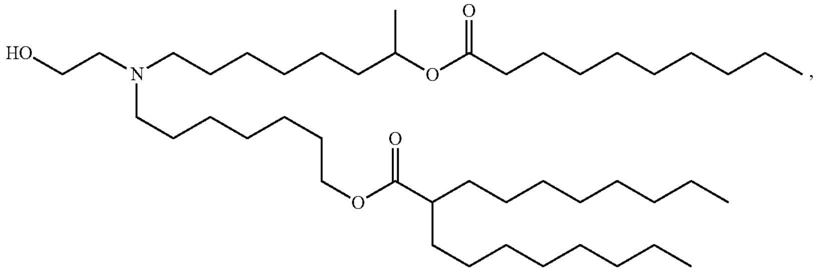
(Compound 166)
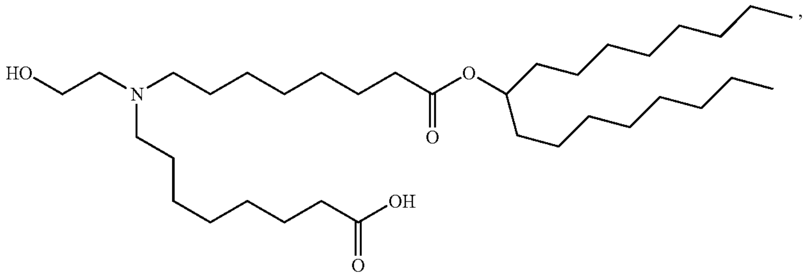
(Compound 167)
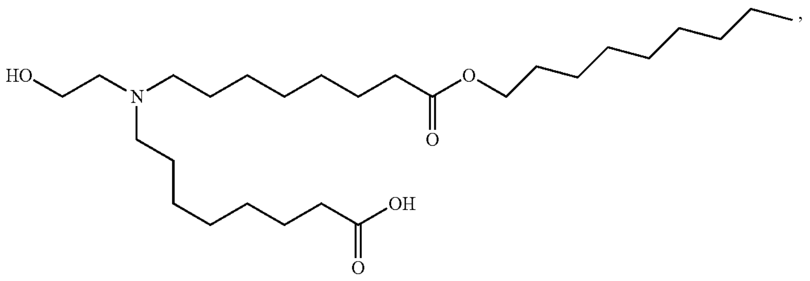

-continued
(Compound 168)
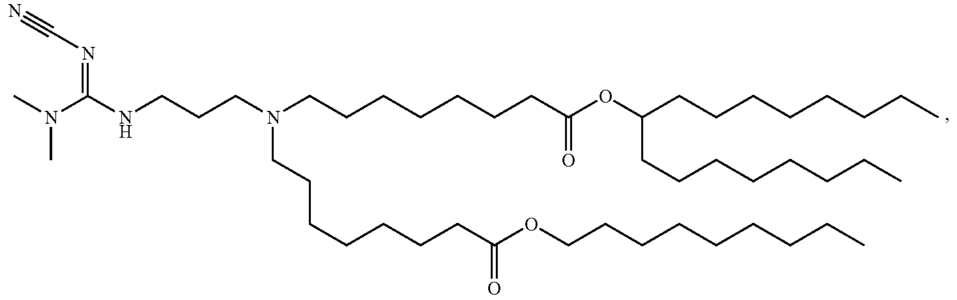
(Compound 169)
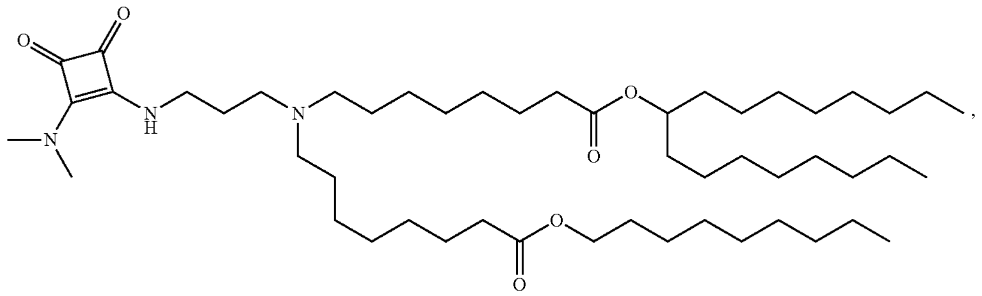
(Compound 170)
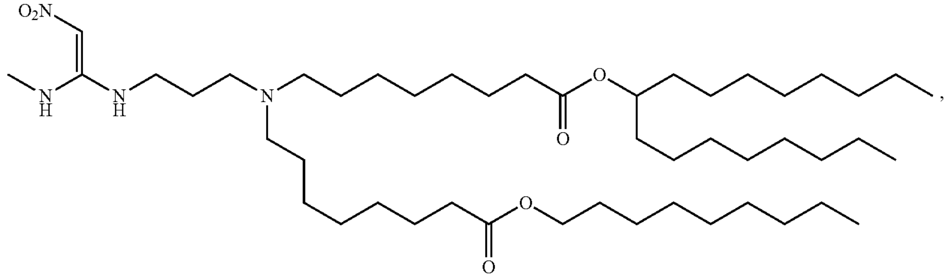
(Compound 171)
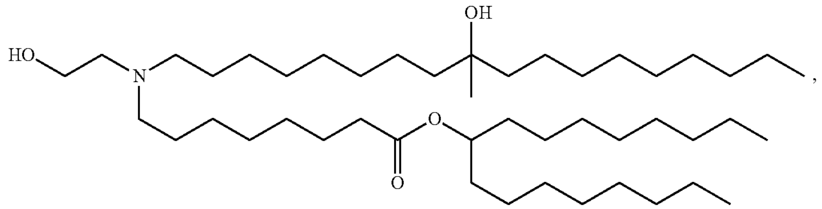
(Compound 172)
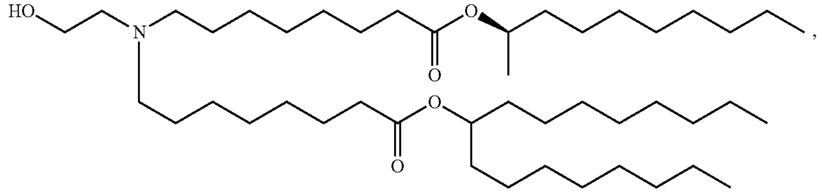
(Compound 173)
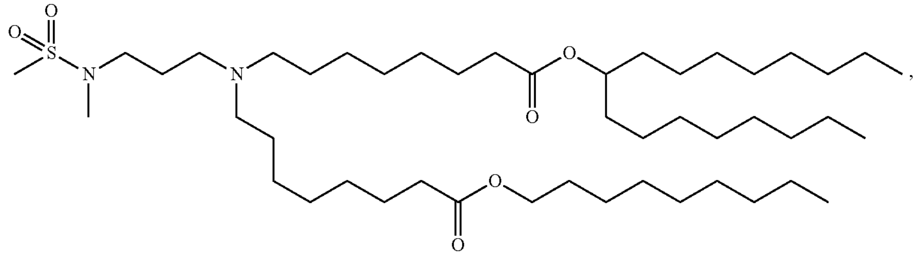

-continued
(Compound 174)
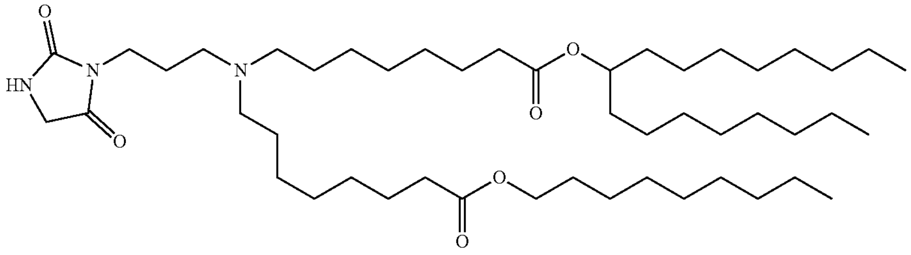
,
(Compound 175)
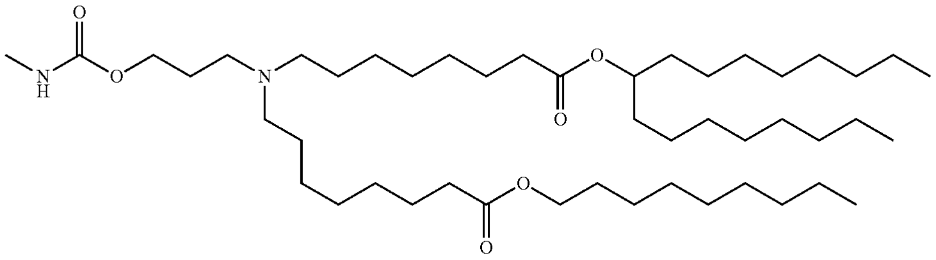
,
(Compound 176)
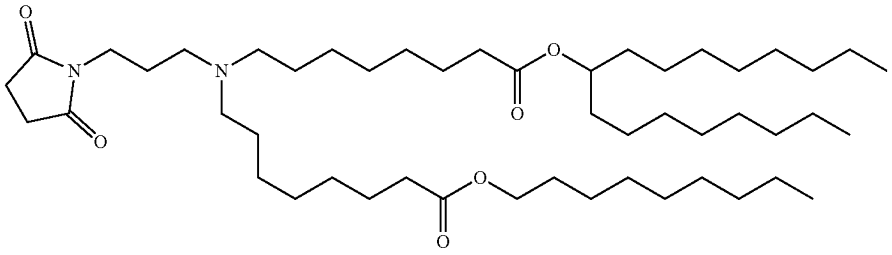
,
(Compound 177)
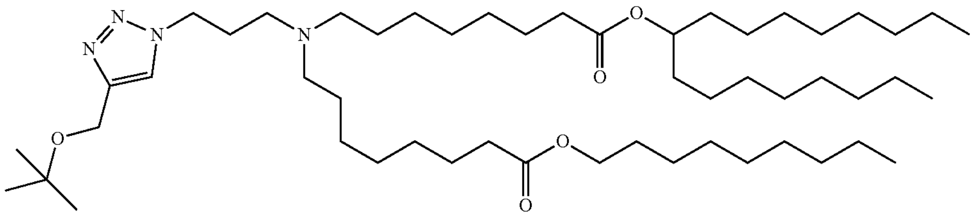
,
(Compound 178)
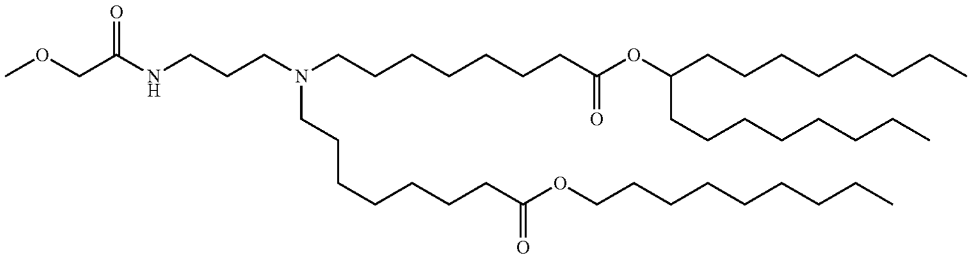
,
(Compound 179)
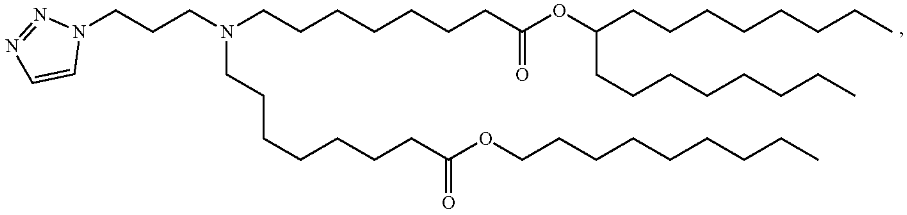
, -continued
(Compound 180)
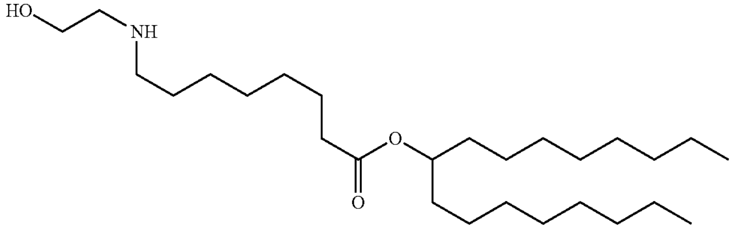
,
(Compound 181)
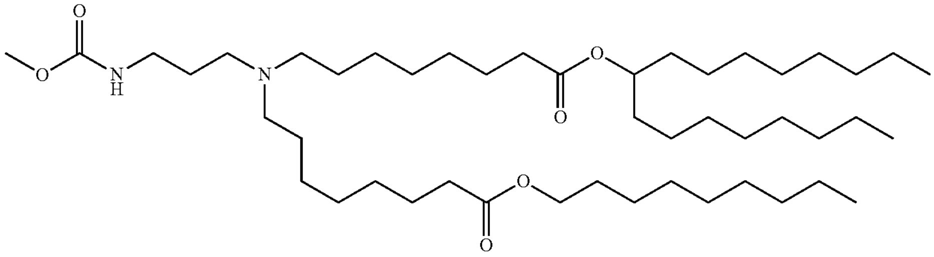
,
(Compound 182)
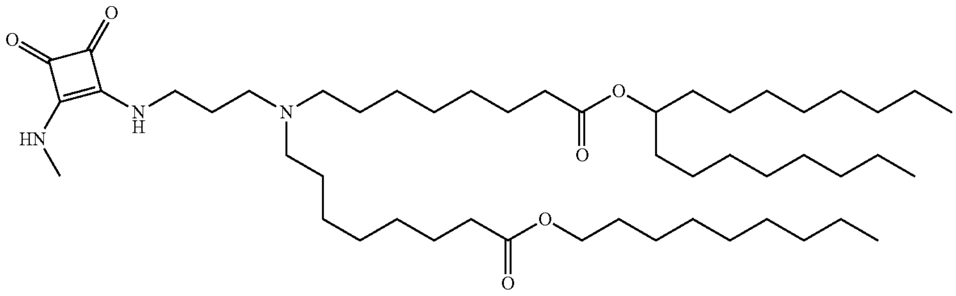
,
(Compound 183)
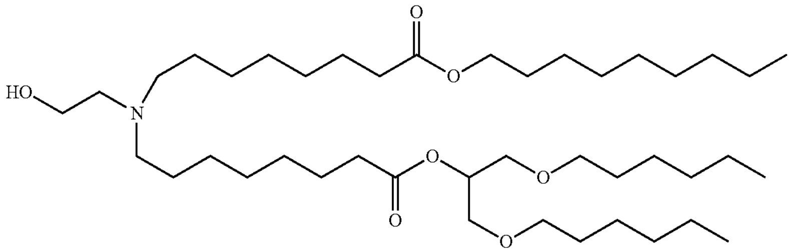
,
(Compound 184)
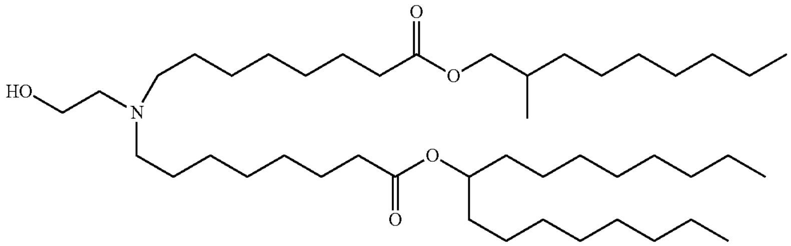
,
(Compound 185)
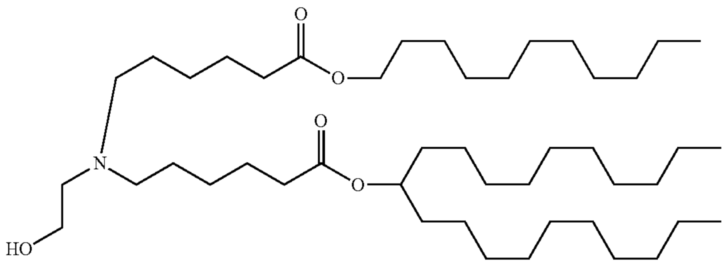
, -continued
(Compound 186)
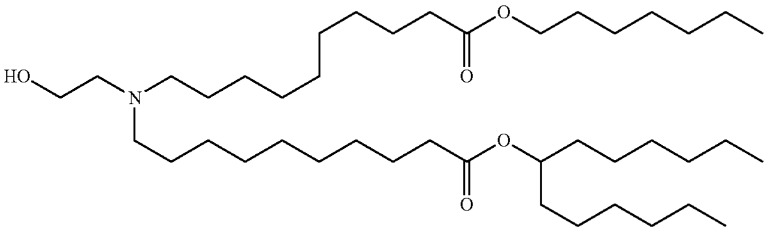,
(Compound 187)
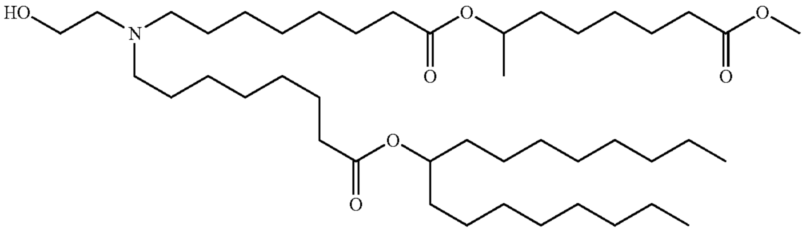,
(Compound 188)
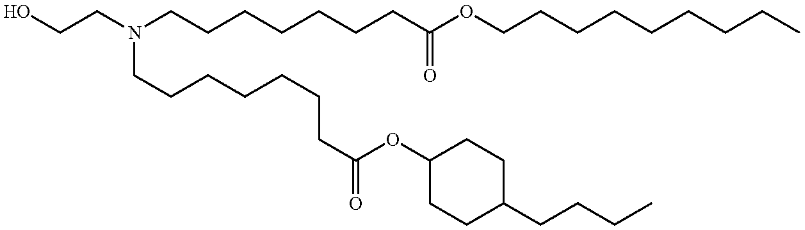,
(Compound 189)
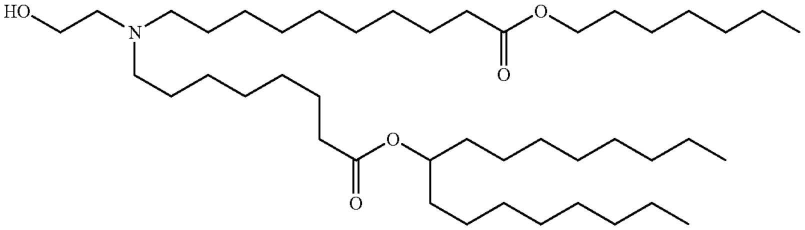,
(Compound 190)
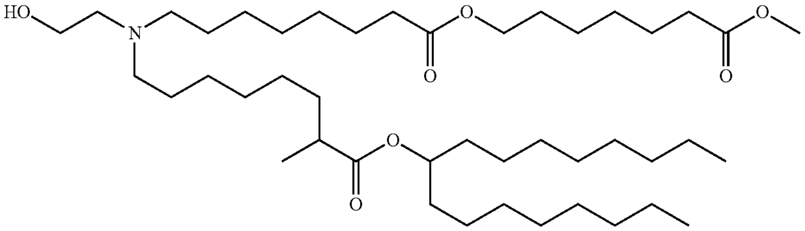,
(Compound 191)
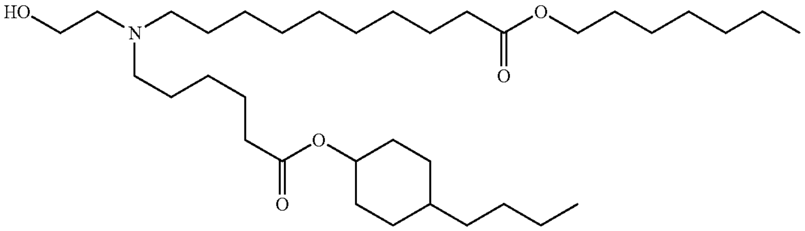, -continued
(Compound 192)
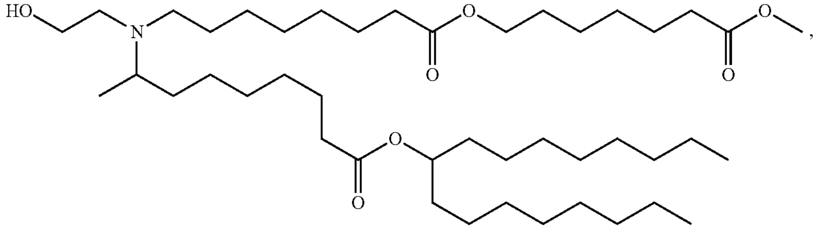
(Compound 193)
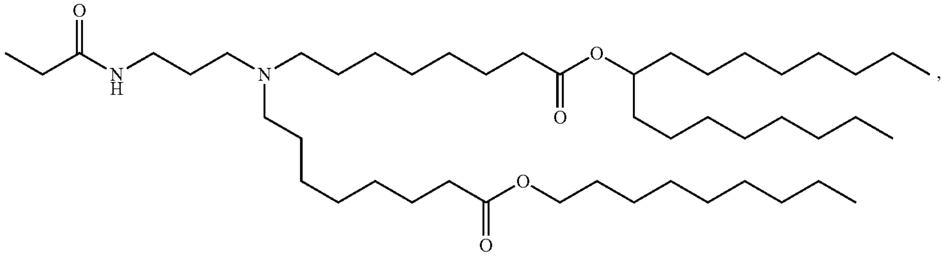
(Compound 194)
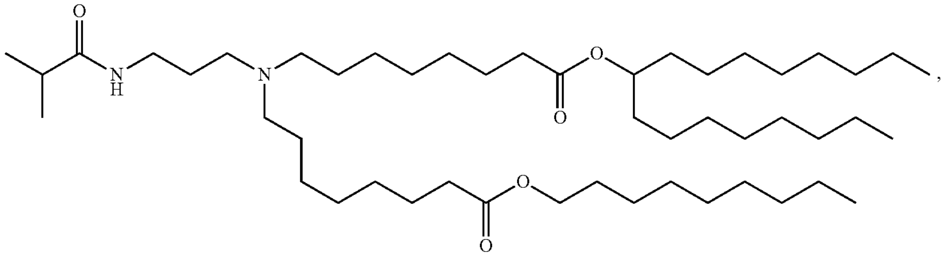
(Compound 195)
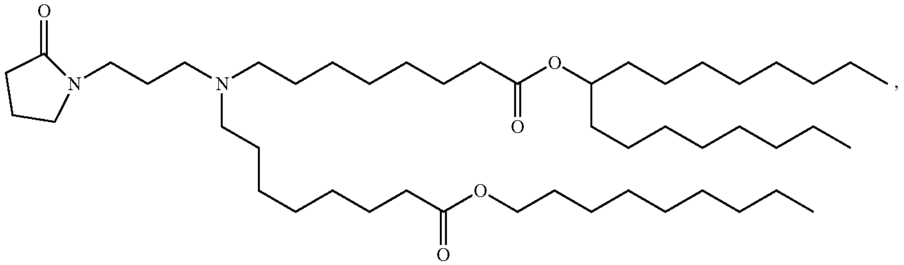
(Compound 196)
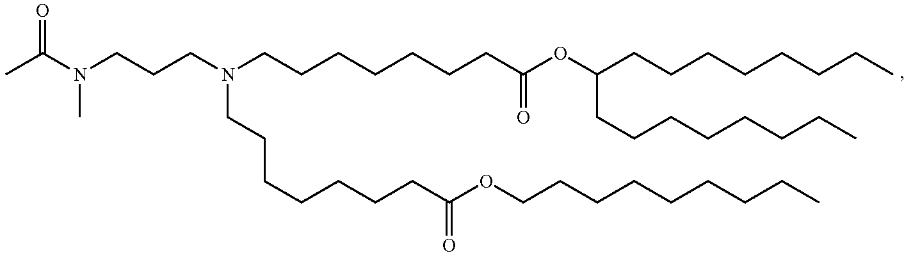
(Compound 197)
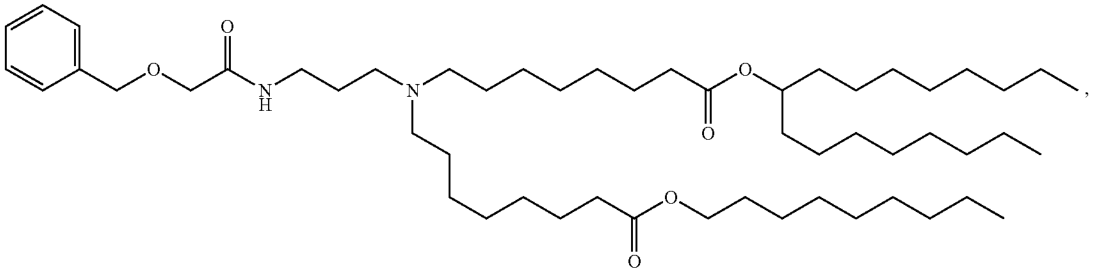

-continued
(Compound 198)
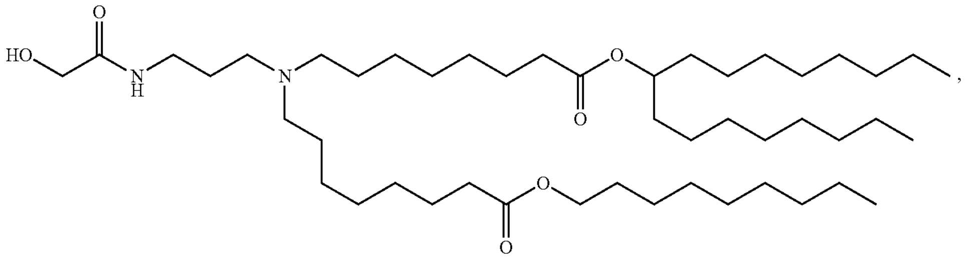
(Compound 199)
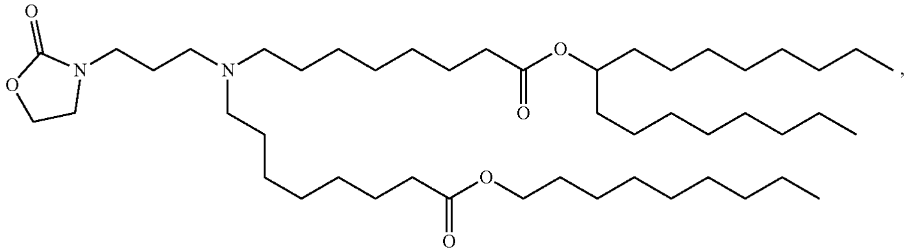
(Compound 200)
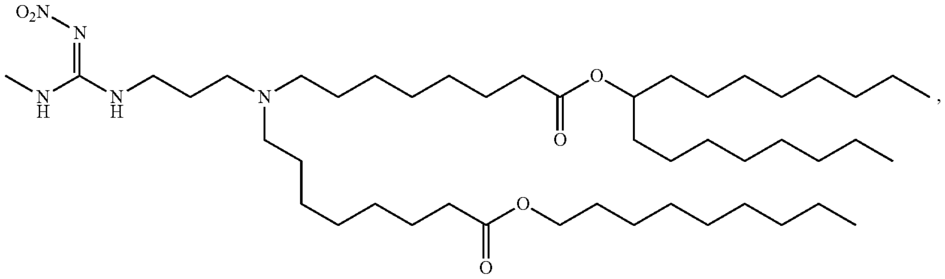
(Compound 201)
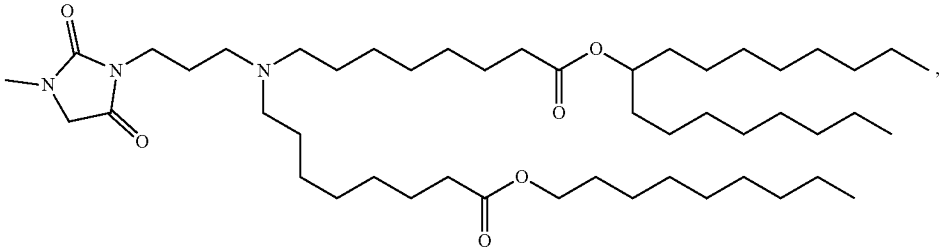
(Compound 202)
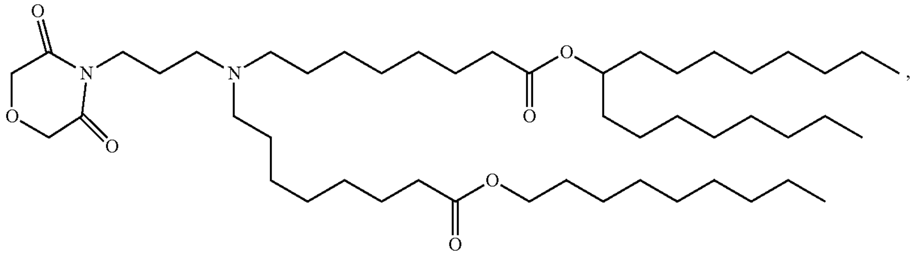
(Compound 203)
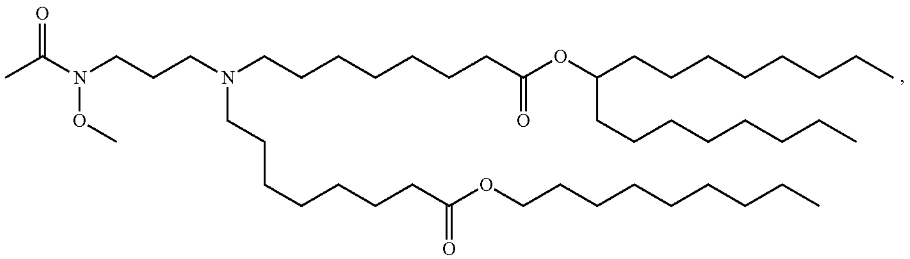

-continued
(Compound 204)
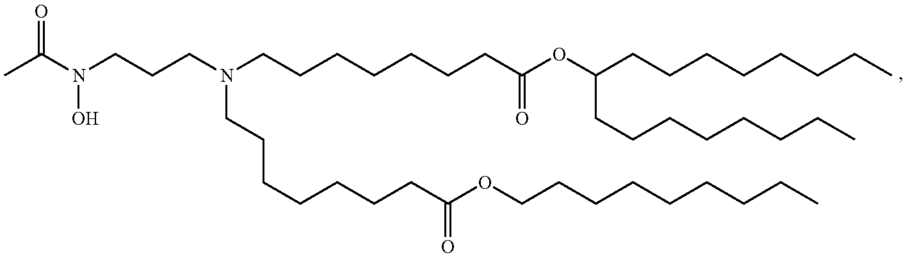
(Compound 205)
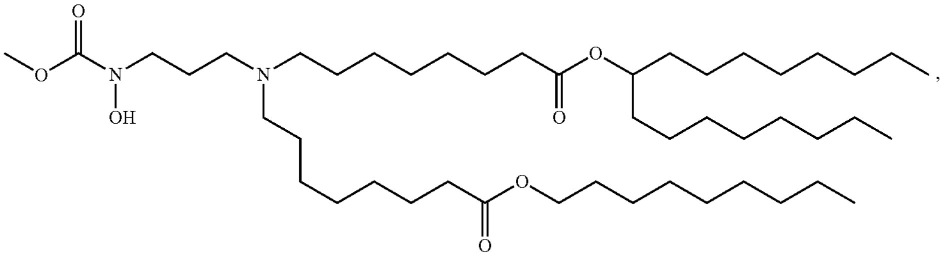
(Compound 206)
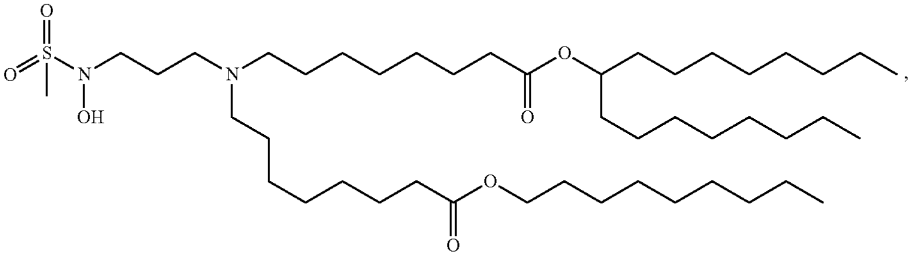
(Compound 207)
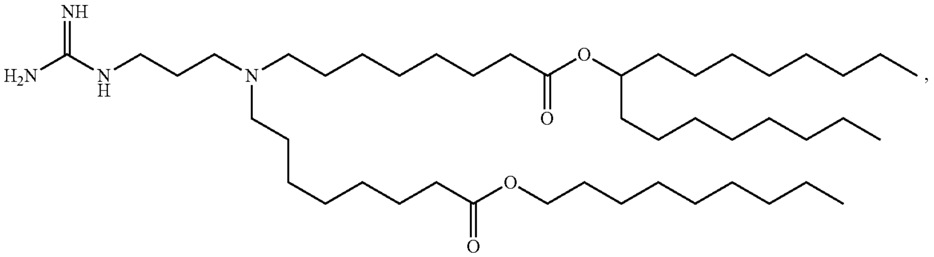
(Compound 208)
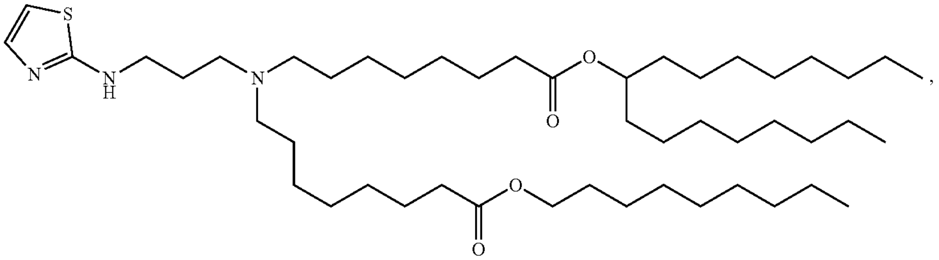
(Compound 209)
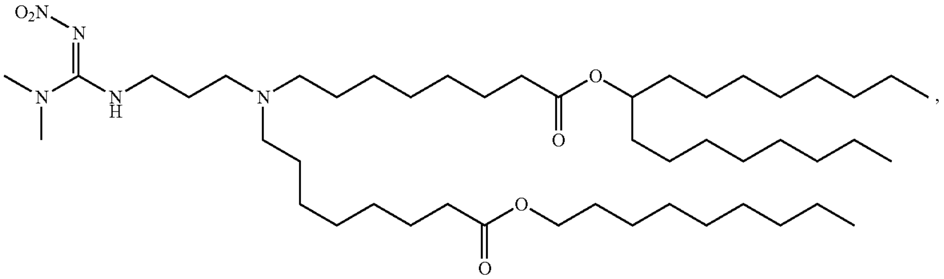

-continued
(Compound 210)
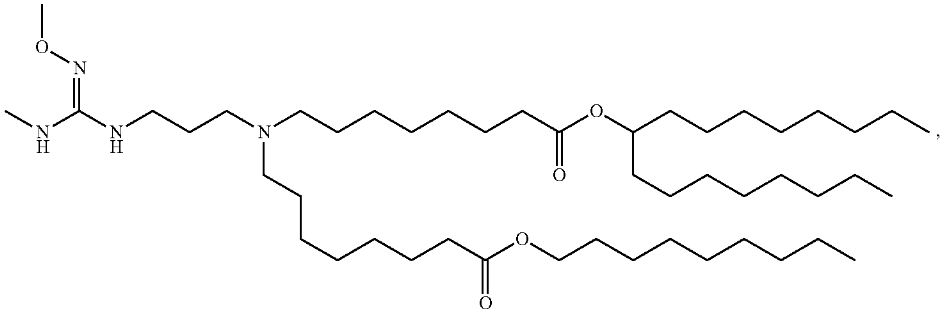
(Compound 211)
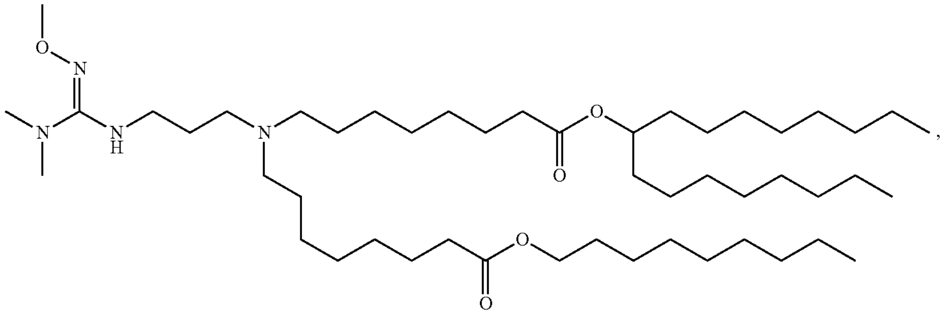
(Compound 212)
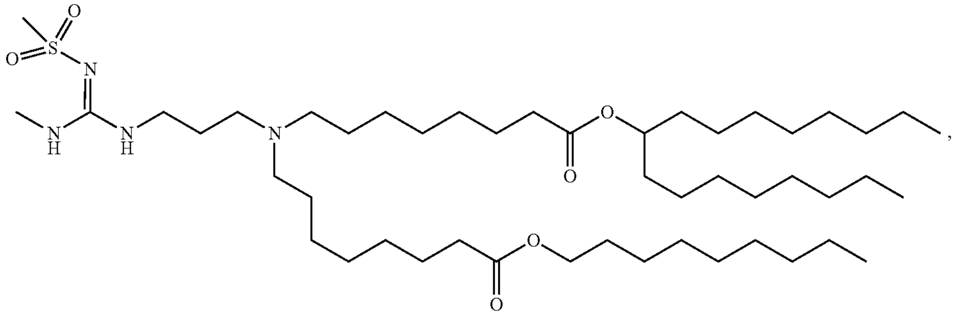
(Compound 213)
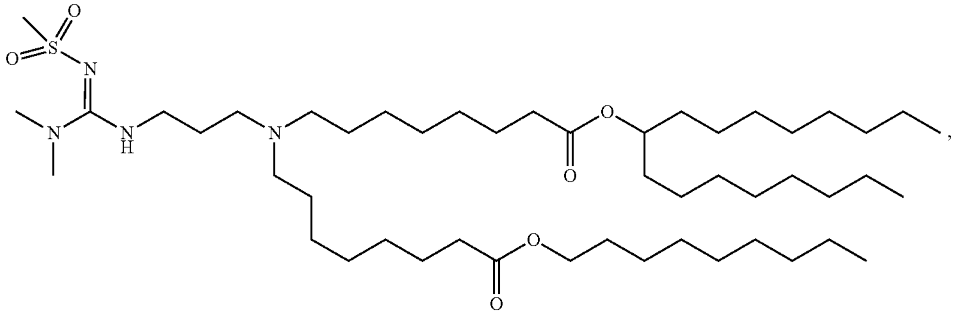
(Compound 214)
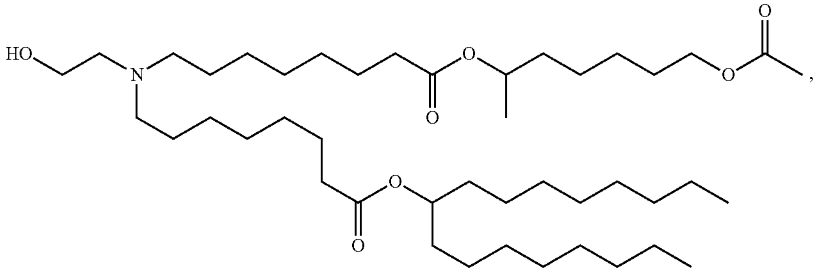

-continued
(Compound 215)
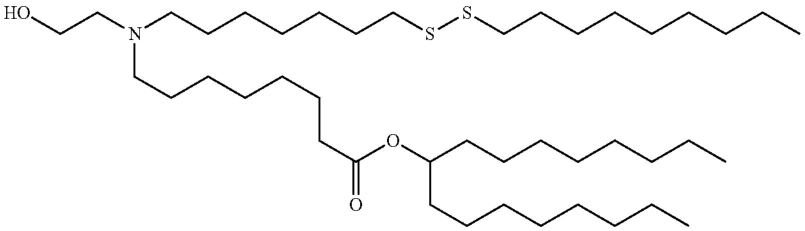,
(Compound 216)
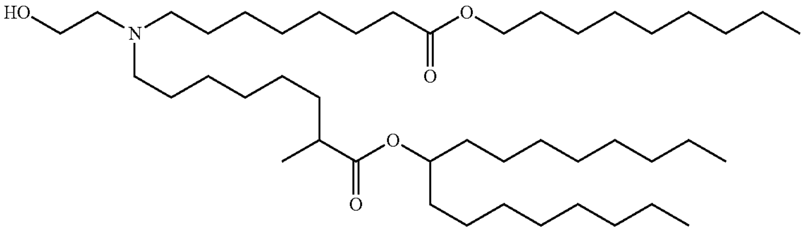,
(Compound 217)
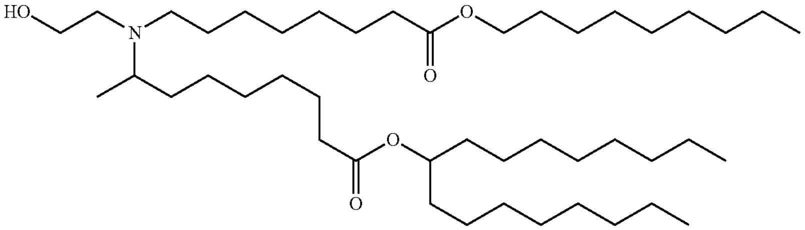,
(Compound 218)
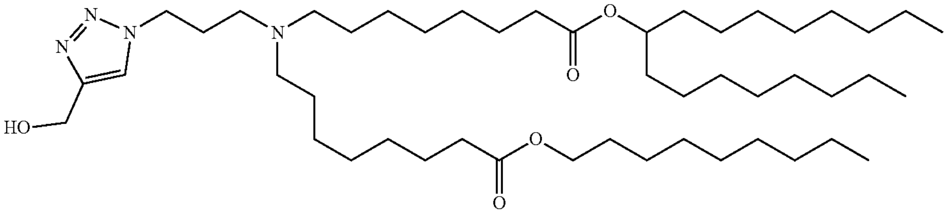,
(Compound 219)
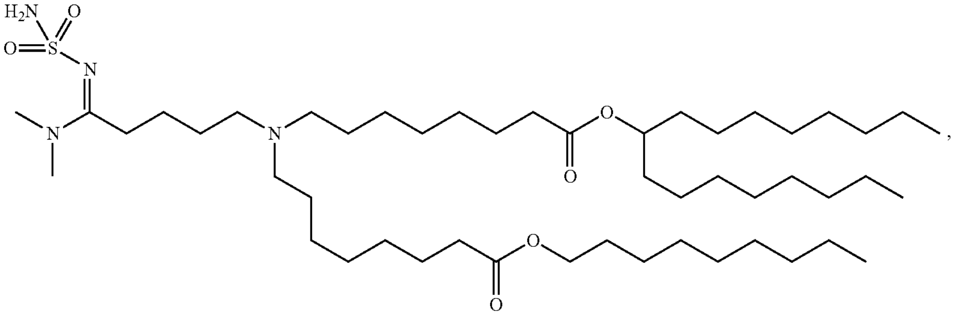,
(Compound 220)
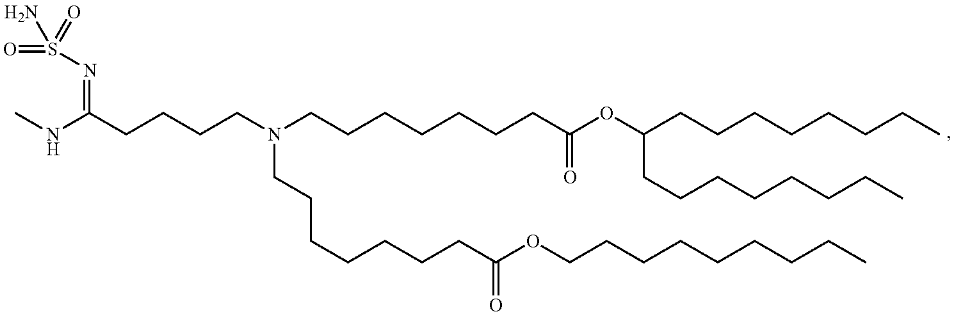, -continued
(Compound 221)
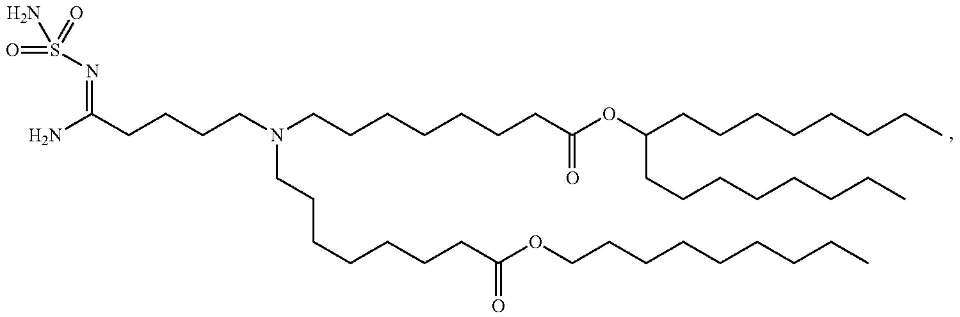
(Compound 222)
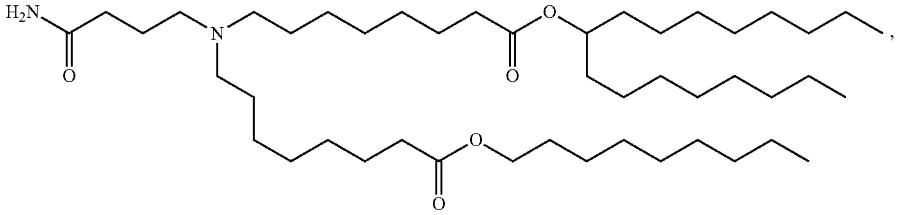
(Compound 223)
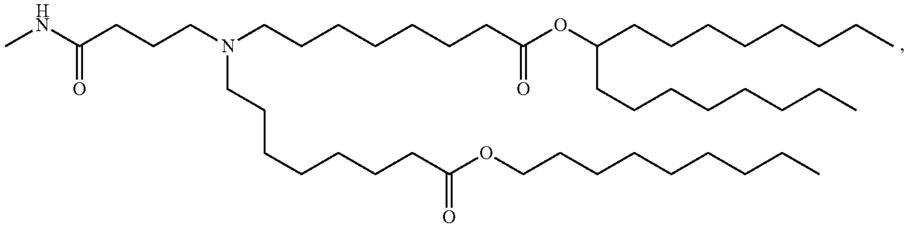
(Compound 224)
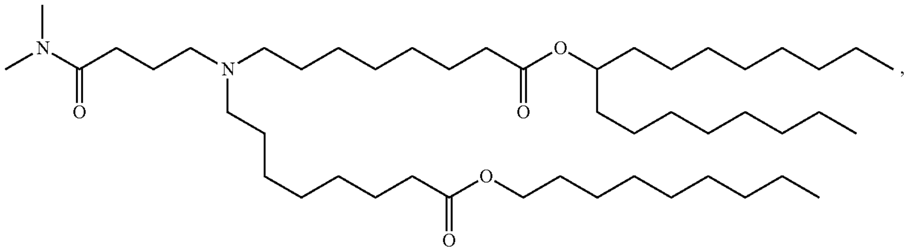
(Compound 225)
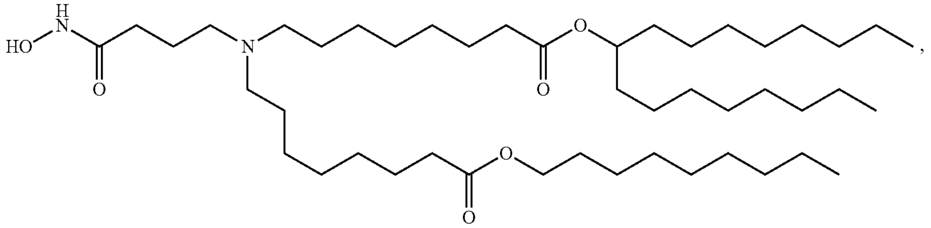
(Compound 226)
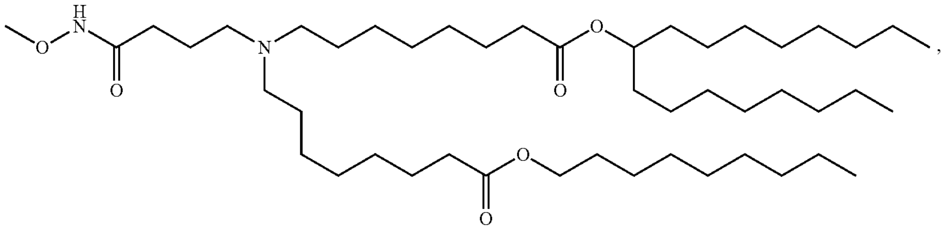

-continued (Compound 227)

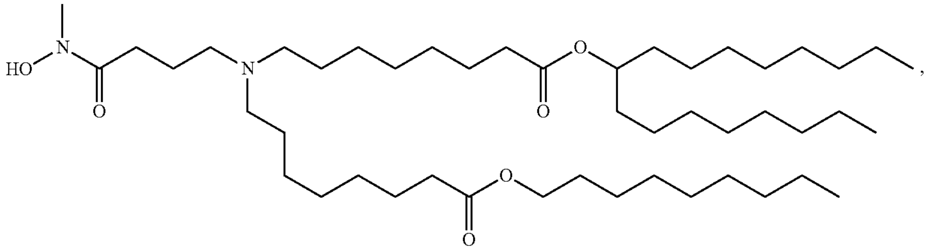

(Compound 228)

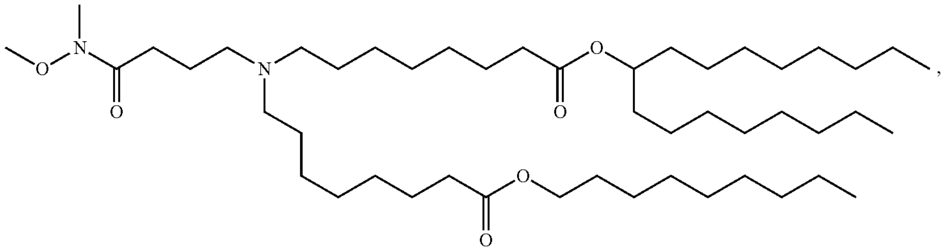

(Compound 229)

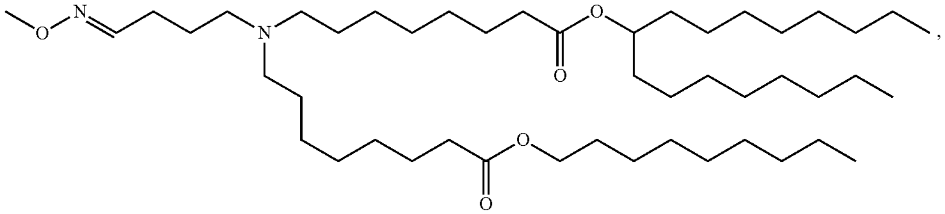

(Compound 230)

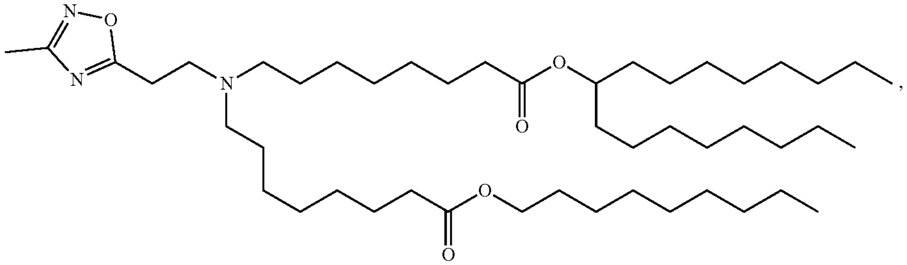

(Compound 231)

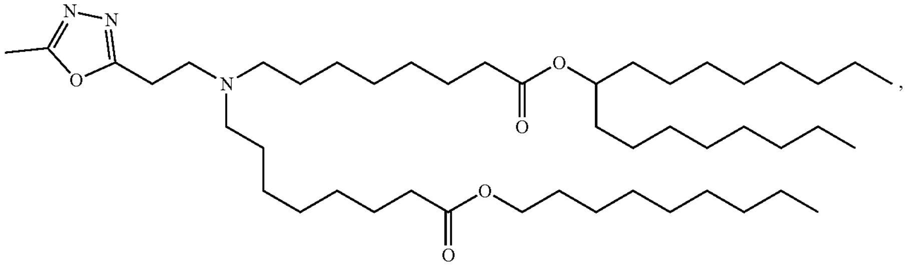

(Compound 232)

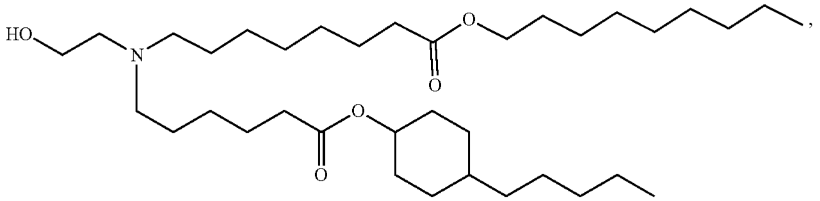

and salts or stereoisomers thereof.

In other embodiments, the compound of Formula (I) is selected from the group consisting of Compound 1-Compound 147, or salt or stereoisomers thereof.

Amine moieties of the lipid compounds disclosed herein can be protonated under certain conditions. For example, the central amine moiety of a lipid according to formula (I) is typically protonated (i.e., positively charged) at a pH below the pKa of the amino moiety and is substantially not charged at a pH above the pKa. Such lipids may be referred to ionizable amino lipids. In some embodiments, the ionizable lipid is an ionizable amino lipid, sometimes referred to in the art as an "ionizable cationic lipid".

In some embodiments, the amount the ionizable amino lipid, e.g., the compound of formula (I), ranges from about 1 mol % to 99 mol % in the lipid composition.

In one embodiment, the amount of the ionizable amino lipid, e.g., the compound of formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of formula (I), ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., the compound of formula (I), is about 50 mol % in the lipid composition.

In addition to the ionizable amino lipid, e.g., the compound of formula I, the lipid composition of the pharmaceutical compositions disclosed herein can comprise additional components such as phospholipids, structural lipids, quaternary amine compounds, PEG-lipids, and any combination thereof.

Additional Components in the Lipid Composition

A. Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties. For example, a phospholipid can be a lipid according to formula (VII):

(III)

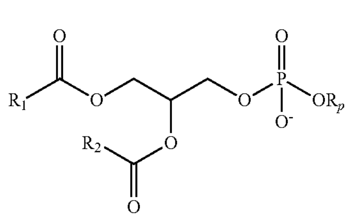

in which $R_p$ represents a phospholipid moiety and $R_1$ and $R_2$ represent fatty acid moieties with or without unsaturation that may be the same or different.

A phospholipid moiety may be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety may be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements (e.g., a therapeutic agent) of a lipid-containing composition (e.g., LNPs) to pass through the membrane permitting, e.g., delivery of the one or more elements to a target tissue (e.g., tumoral tissue).

Non-natural phospholipid species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidyl glycerols, and phosphatidic acids. Phospholipids also include phosphosphingolipid, such as sphingomyelin. In some embodiments, a pharmaceutical composition for intratumoral delivery disclosed herein can comprise more than one phospholipid. When more than one phospholipid is used, such phospholipids can belong to the same phospholipid class (e.g., MSPC and DSPC) or different classes (e.g., MSPC and MSPE).

Phospholipids may be of a symmetric or an asymmetric type. As used herein, the term "symmetric phospholipid" includes glycerophospholipids having matching fatty acid moieties and sphingolipids in which the variable fatty acid moiety and the hydrocarbon chain of the sphingosine backbone include a comparable number of carbon atoms. As used herein, the term "asymmetric phospholipid" includes lysolipids, glycerophospholipids having different fatty acid moieties (e.g., fatty acid moieties with different numbers of carbon atoms and/or unsaturations (e.g., double bonds)), and sphingolipids in which the variable fatty acid moiety and the hydrocarbon chain of the sphingosine backbone include a dissimilar number of carbon atoms (e.g., the variable fatty acid moiety include at least two more carbon atoms than the hydrocarbon chain or at least two fewer carbon atoms than the hydrocarbon chain).

In some embodiments, the lipid composition of a pharmaceutical composition disclosed herein comprises at least one symmetric phospholipid. Symmetric phospholipids may be selected from the non-limiting group consisting of 1,2-dipropionyl-sn-glycero-3-phosphocholine (03:0 PC),
1,2-dibutyryl-sn-glycero-3-phosphocholine (04:0 PC),
1,2-dipentanoyl-sn-glycero-3-phosphocholine (05:0 PC),
1,2-dihexanoyl-sn-glycero-3-phosphocholine (06:0 PC),
1,2-diheptanoyl-sn-glycero-3-phosphocholine (07:0 PC),
1,2-dioctanoyl-sn-glycero-3-phosphocholine (08:0 PC),
1,2-dinonanoyl-sn-glycero-3-phosphocholine (09:0 PC),
1,2-didecanoyl-sn-glycero-3-phosphocholine (10:0 PC),
1,2-diundecanoyl-sn-glycero-3-phosphocholine (11:0 PC, DUPC),
1,2-dilauroyl-sn-glycero-3-phosphocholine (12:0 PC), 1,2-ditridecanoyl-sn-glycero-3-phosphocholine (13:0 PC),
1,2-dimyristoyl-sn-glycero-3-phosphocholine (14:0 PC, DMPC),
1,2-dipentadecanoyl-sn-glycero-3-phosphocholine (15:0 PC),
1,2-dipalmitoyl-sn-glycero-3-phosphocholine (16:0 PC, DPPC),
1,2-diphytanoyl-sn-glycero-3-phosphocholine (4ME 16:0 PC),
1,2-diheptadecanoyl-sn-glycero-3-phosphocholine (17:0 PC),
1,2-distearoyl-sn-glycero-3-phosphocholine (18:0 PC, DSPC),
1,2-dinonadecanoyl-sn-glycero-3-phosphocholine (19:0 PC),
1,2-diarachidoyl-sn-glycero-3-phosphocholine (20:0 PC),
1,2-dihenarachidoyl-sn-glycero-3-phosphocholine (21:0 PC),
1,2-dibehenoyl-sn-glycero-3-phosphocholine (22:0 PC),
1,2-ditricosanoyl-sn-glycero-3-phosphocholine (23:0 PC),
1,2-dilignoceroyl-sn-glycero-3-phosphocholine (24:0 PC),
1,2-dimyristoleoyl-sn-glycero-3-phosphocholine (14:1 (Δ9-Cis) PC),
1,2-dimyristelaidoyl-sn-glycero-3-phosphocholine (14:1 (Δ9-Trans) PC),
1,2-dipalmitoleoyl-sn-glycero-3-phosphocholine (16:1 (Δ9-Cis) PC),
1,2-dipalmitelaidoyl-sn-glycero-3-phosphocholine (16:1 (Δ9-Trans) PC),
1,2-dipetroselenoyl-sn-glycero-3-phosphocholine (18:1 (Δ6-Cis) PC),
1,2-dioleoyl-sn-glycero-3-phosphocholine (18:1 (Δ9-Cis) PC, DOPC),
1,2-dielaidoyl-sn-glycero-3-phosphocholine (18:1 (Δ9-Trans) PC),
1,2-dilinoleoyl-sn-glycero-3-phosphocholine (18:2 (Cis) PC, DLPC),
1,2-dilinolenoyl-sn-glycero-3-phosphocholine (18:3 (Cis) PC, DLnPC),
1,2-dieicosenoyl-sn-glycero-3-phosphocholine (20:1 (Cis) PC),
1,2-diarachidonoyl-sn-glycero-3-phosphocholine (20:4 (Cis) PC, DAPC),
1,2-dierucoyl-sn-glycero-3-phosphocholine (22:1 (Cis) PC),
1,2-didocosahexaenoyl-sn-glycero-3-phosphocholine (22:6 (Cis) PC, DHAPC),
1,2-dinervonoyl-sn-glycero-3-phosphocholine (24:1 (Cis) PC),
1,2-dihexanoyl-sn-glycero-3-phosphoethanolamine (06:0 PE),
1,2-dioctanoyl-sn-glycero-3-phosphoethanolamine (08:0 PE),
1,2-didecanoyl-sn-glycero-3-phosphoethanolamine (10:0 PE),
1,2-dilauroyl-sn-glycero-3-phosphoethanolamine (12:0 PE),
1,2-dimyristoyl-sn-glycero-3-phosphoethanolamine (14:0 PE),
1,2-dipentadecanoyl-sn-glycero-3-phosphoethanolamine (15:0 PE),
1,2-dipalmitoyl-sn-glycero-3-phosphoethanolamine (16:0 PE),
1,2-diphytanoyl-sn-glycero-3-phosphoethanolamine (4ME 16:0 PE),
1,2-diheptadecanoyl-sn-glycero-3-phosphoethanolamine (17:0 PE),
1,2-distearoyl-sn-glycero-3-phosphoethanolamine (18:0 PE, DSPE),
1,2-dipalmitoleoyl-sn-glycero-3-phosphoethanolamine (16:1 PE),
1,2-dioleoyl-sn-glycero-3-phosphoethanolamine (18:1 (Δ9-Cis) PE, DOPE),
1,2-dielaidoyl-sn-glycero-3-phosphoethanolamine (18:1 (Δ9-Trans) PE),
1,2-dilinoleoyl-sn-glycero-3-phosphoethanolamine (18:2 PE, DLPE),
1,2-dilinolenoyl-sn-glycero-3-phosphoethanolamine (18:3 PE, DLnPE),
1,2-diarachidonoyl-sn-glycero-3-phosphoethanolamine (20:4 PE, DAPE),
1,2-didocosahexaenoyl-sn-glycero-3-phosphoethanolamine (22:6 PE, DHAPE),
1,2-di-O-octadecenyl-sn-glycero-3-phosphocholine (18:0 Diether PC),
1,2-dioleoyl-sn-glycero-3-phospho-rac-(1-glycerol) sodium salt (DOPG), and
any combination thereof.

In some embodiments, the lipid composition of a pharmaceutical composition disclosed herein comprises at least one symmetric phospholipid selected from the non-limiting group consisting of DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof.

In some embodiments, the lipid composition of a pharmaceutical composition disclosed herein comprises at least one asymmetric phospholipid. Asymmetric phospholipids may be selected from the non-limiting group consisting of
1-myristoyl-2-palmitoyl-sn-glycero-3-phosphocholine (14:0-16:0 PC, MPPC),
1-myristoyl-2-stearoyl-sn-glycero-3-phosphocholine (14:0-18:0 PC, MSPC),
1-palmitoyl-2-acetyl-sn-glycero-3-phosphocholine (16:0-02:0 PC),
1-palmitoyl-2-myristoyl-sn-glycero-3-phosphocholine (16:0-14:0 PC, PMPC),
1-palmitoyl-2-stearoyl-sn-glycero-3-phosphocholine (16:0-18:0 PC, PSPC),
1-palmitoyl-2-oleoyl-sn-glycero-3-phosphocholine (16:0-18:1 PC, POPC),
1-palmitoyl-2-linoleoyl-sn-glycero-3-phosphocholine (16:0-18:2 PC, PLPC),
1-palmitoyl-2-arachidonoyl-sn-glycero-3-phosphocholine (16:0-20:4 PC),
1-palmitoyl-2-docosahexaenoyl-sn-glycero-3-phosphocholine (14:0-22:6 PC),
1-stearoyl-2-myristoyl-sn-glycero-3-phosphocholine (18:0-14:0 PC, SMPC),
1-stearoyl-2-palmitoyl-sn-glycero-3-phosphocholine (18:0-16:0 PC, SPPC),
1-stearoyl-2-oleoyl-sn-glycero-3-phosphocholine (18:0-18:1 PC, SOPC),
1-stearoyl-2-linoleoyl-sn-glycero-3-phosphocholine (18:0-18:2 PC),
1-stearoyl-2-arachidonoyl-sn-glycero-3-phosphocholine (18:0-20:4 PC),
1-stearoyl-2-docosahexaenoyl-sn-glycero-3-phosphocholine (18:0-22:6 PC),
1-oleoyl-2-myristoyl-sn-glycero-3-phosphocholine (18:1-14:0 PC, OMPC),
1-oleoyl-2-palmitoyl-sn-glycero-3-phosphocholine (18:1-16:0 PC, OPPC),
1-oleoyl-2-stearoyl-sn-glycero-3-phosphocholine (18:1-18:0 PC, OSPC), 1-palmitoyl-2-oleoyl-sn-glycero-3-phosphoethanolamine (16:0-18:1 PE, POPE),
1-palmitoyl-2-linoleoyl-sn-glycero-3-phosphoethanolamine (16:0-18:2 PE),
1-palmitoyl-2-arachidonoyl-sn-glycero-3-phosphoethanolamine (16:0-20:4 PE),
1-palmitoyl-2-docosahexaenoyl-sn-glycero-3-phosphoethanolamine (16:0-22:6 PE),
1-stearoyl-2-oleoyl-sn-glycero-3-phosphoethanolamine (18:0-18:1 PE),
1-stearoyl-2-linoleoyl-sn-glycero-3-phosphoethanolamine (18:0-18:2 PE),
1-stearoyl-2-arachidonoyl-sn-glycero-3-phosphoethanolamine (18:0-20:4 PE),
1-stearoyl-2-docosahexaenoyl-sn-glycero-3-phosphoethanolamine (18:0-22:6 PE),
1-oleoyl-2-cholesterylhemisuccinoyl-sn-glycero-3-phosphocholine (OChemsPC), and
any combination thereof.

Asymmetric lipids useful in the lipid composition may also be lysolipids. Lysolipids may be selected from the non-limiting group consisting of
1-hexanoyl-2-hydroxy-sn-glycero-3-phosphocholine (06:0 Lyso PC),
1-heptanoyl-2-hydroxy-sn-glycero-3-phosphocholine (07:0 Lyso PC),
1-octanoyl-2-hydroxy-sn-glycero-3-phosphocholine (08:0 Lyso PC),
1-nonanoyl-2-hydroxy-sn-glycero-3-phosphocholine (09:0 Lyso PC),
1-decanoyl-2-hydroxy-sn-glycero-3-phosphocholine (10:0 Lyso PC),
1-undecanoyl-2-hydroxy-sn-glycero-3-phosphocholine (11:0 Lyso PC),
1-lauroyl-2-hydroxy-sn-glycero-3-phosphocholine (12:0 Lyso PC),
1-tridecanoyl-2-hydroxy-sn-glycero-3-phosphocholine (13:0 Lyso PC),
1-myristoyl-2-hydroxy-sn-glycero-3-phosphocholine (14:0 Lyso PC),
1-pentadecanoyl-2-hydroxy-sn-glycero-3-phosphocholine (15:0 Lyso PC),
1-palmitoyl-2-hydroxy-sn-glycero-3-phosphocholine (16:0 Lyso PC),
1-heptadecanoyl-2-hydroxy-sn-glycero-3-phosphocholine (17:0 Lyso PC),
1-stearoyl-2-hydroxy-sn-glycero-3-phosphocholine (18:0 Lyso PC),
1-oleoyl-2-hydroxy-sn-glycero-3-phosphocholine (18:1 Lyso PC),
1-nonadecanoyl-2-hydroxy-sn-glycero-3-phosphocholine (19:0 Lyso PC),
1-arachidoyl-2-hydroxy-sn-glycero-3-phosphocholine (20:0 Lyso PC),
1-behenoyl-2-hydroxy-sn-glycero-3-phosphocholine (22:0 Lyso PC),
1-lignoceroyl-2-hydroxy-sn-glycero-3-phosphocholine (24:0 Lyso PC),
1-hexacosanoyl-2-hydroxy-sn-glycero-3-phosphocholine (26:0 Lyso PC),
1-myristoyl-2-hydroxy-sn-glycero-3-phosphoethanolamine (14:0 Lyso PE),
1-palmitoyl-2-hydroxy-sn-glycero-3-phosphoethanolamine (16:0 Lyso PE),
1-stearoyl-2-hydroxy-sn-glycero-3-phosphoethanolamine (18:0 Lyso PE),
1-oleoyl-2-hydroxy-sn-glycero-3-phosphoethanolamine (18:1 Lyso PE),
1-hexadecyl-sn-glycero-3-phosphocholine (C16 Lyso PC), and
any combination thereof.

In some embodiment, the lipid composition of a pharmaceutical composition disclosed herein comprises at least one asymmetric phospholipid selected from the group consisting of MPPC, MSPC, PMPC, PSPC, SMPC, SPPC, and any combination thereof. In some embodiments, the asymmetric phospholipid is 1-myristoyl-2-stearoyl-sn-glycero-3-phosphocholine (MSPC).

In some embodiments, the lipid compositions disclosed herein may contain one or more symmetric phospholipids, one or more asymmetric phospholipids, or a combination thereof. When multiple phospholipids are present, they can be present in equimolar ratios, or non-equimolar ratios.

In one embodiment, the lipid composition of a pharmaceutical composition disclosed herein comprises a total amount of phospholipid (e.g., MSPC) which ranges from about 1 mol % to about 20 mol %, from about 5 mol % to about 20 mol %, from about 10 mol % to about 20 mol %, from about 15 mol % to about 20 mol %, from about 1 mol % to about 15 mol %, from about 5 mol % to about 15 mol %, from about 10 mol % to about 15 mol %, from about 5 mol % to about 10 mol % in the lipid composition. In one embodiment, the amount of the phospholipid is from about 8 mol % to about 15 mol % in the lipid composition. In one embodiment, the amount of the phospholipid (e.g., MSPC) is about 10 mol % in the lipid composition.

In some aspects, the amount of a specific phospholipid (e.g., MSPC) is at least about 1, 2, 3, 4, 5, 6, 7, 8, 9, 10, 11, 12, 13, 14, 15, 16, 17, 18, 19 or 20 mol % in the lipid composition.

B. Quaternary Amine Compounds

The lipid composition of a pharmaceutical composition disclosed herein can comprise one or more quaternary amine compounds (e.g., DOTAP). The term “quaternary amine compound” is used to include those compounds having one or more quaternary amine groups (e.g., trialkylamino groups) and permanently carrying a positive charge and existing in a form of a salt. For example, the one or more quaternary amine groups can be present in a lipid or a polymer (e.g., PEG). In some embodiments, the quaternary amine compound comprises (1) a quaternary amine group and (2) at least one hydrophobic tail group comprising (i) a hydrocarbon chain, linear or branched, and saturated or unsaturated, and (ii) optionally an ether, ester, carbonyl, or ketal linkage between the quaternary amine group and the hydrocarbon chain. In some embodiments, the quaternary amine group can be a trimethylammonium group. In some embodiments, the quaternary amine compound comprises two identical hydrocarbon chains. In some embodiments, the quaternary amine compound comprises two different hydrocarbon chains.

In some embodiments, the lipid composition of a pharmaceutical composition disclosed herein comprises at least one quaternary amine compound. Quaternary amine compound may be selected from the non-limiting group consisting of
1,2-dioleoyl-3-trimethylammonium-propane (DOTAP),
N-[1-(2,3-dioleoyloxy)propyl]-N,N,N-trimethylammonium chloride (DOTMA),
1-[2-(oleoyloxy)ethyl]-2-oleyl-3-(2-hydroxyethyl)imidazolinium chloride (DOTIM),
2,3-dioleyloxy-N-[2(sperminecarboxamido)ethyl]-N,N-dimethyl-1-propanaminium trifluoroacetate (DOSPA), N,N-distearyl-N,N-dimethylammonium bromide (DDAB),
N-(1,2-dimyristyloxyprop-3-yl)-N,N-dimethyl-N-hydroxyethyl ammonium bromide (DMRIE),
N-(1,2-dioleoyloxyprop-3-yl)-N,N-dimethyl-N-hydroxyethyl ammonium bromide (DORIE),
N,N-dioleyl-N,N-dimethylammonium chloride (DODAC),
1,2-dilauroyl-sn-glycero-3-ethylphosphocholine (DLePC),
1,2-distearoyl-3-trimethylammonium-propane (DSTAP),
1,2-dipalmitoyl-3-trimethylammonium-propane (DPTAP),
1,2-dilinoleoyl-3-trimethylammonium-propane (DLTAP),
1,2-dimyristoyl-3-trimethylammonium-propane (DMTAP)
1,2-distearoyl-sn-glycero-3-ethylphosphocholine (DSePC)
1,2-dipalmitoyl-sn-glycero-3-ethylphosphocholine (DPePC),
1,2-dimyristoyl-sn-glycero-3-ethylphosphocholine (DMePC),
1,2-dioleoyl-sn-glycero-3-ethylphosphocholine (DOePC),
1,2-di-(9Z-tetradecenoyl)-sn-glycero-3-ethylphosphocholine (14:1 EPC),
1-palmitoyl-2-oleoyl-sn-glycero-3-ethylphosphocholine (16:0-18:1 EPC),
and any combination thereof.

In one embodiment, the quaternary amine compound is 1,2-dioleoyl-3-trimethylammonium-propane (DOTAP).

Quaternary amine compounds are known in the art, such as those described in U.S. Patent Appl. Publ. Nos. US2013/0245107 and US2014/0363493, U.S. Pat. No. 8,158,601, and Int'l. Publ. Nos. WO2015/123264 and WO2015/148247, which are incorporated herein by reference in their entireties.

In one embodiment, the amount of the quaternary amine compound (e.g., DOTAP) in the lipid composition disclosed herein ranges from about 0.01 mol % to about 20 mol %.

In one embodiment, the amount of the quaternary amine compound (e.g., DOTAP) in the lipid composition disclosed herein ranges from about 0.5 mol % to about 20 mol %, from about 0.5 mol % to about 15 mol %, from about 0.5 mol % to about 10 mol %, from about 1 mol % to about 20 mol %, from about 1 mol % to about 15 mol %, from about 1 mol % to about 10 mol %, from about 2 mol % to about 20 mol %, from about 2 mol % to about 15 mol %, from about 2 mol % to about 10 mol %, from about 3 mol % to about 20 mol %, from about 3 mol % to about 15 mol %, from about 3 mol % to about 10 mol %, from about 4 mol % to about 20 mol %, from about 4 mol % to about 15 mol %, from about 4 mol % to about 10 mol %, from about 5 mol % to about 20 mol %, from about 5 mol % to about 15 mol %, from about 5 mol % to about 10 mol %, from about 6 mol % to about 20 mol %, from about 6 mol % to about 15 mol %, from about 6 mol % to about 10 mol %, from about 7 mol % to about 20 mol %, from about 7 mol % to about 15 mol %, from about 7 mol % to about 10 mol %, from about 8 mol % to about 20 mol %, from about 8 mol % to about 15 mol %, from about 8 mol % to about 10 mol %, from about 9 mol % to about 20 mol %, from about 9 mol % to about 15 mol %, from about 9 mol % to about 10 mol %.

In one embodiment, the amount of the quaternary amine compound (e.g., DOTAP) in the lipid composition disclosed herein ranges from about 5 mol % to about 10 mol %.

In one embodiment, the amount of the quaternary amine compound (e.g., DOTAP) in the lipid composition disclosed herein is about 5 mol %. In one embodiment, the amount of the quaternary amine compound (e.g., DOTAP) in the lipid composition disclosed herein is about 10 mol %.

In some embodiments, the amount of the quaternary amine compound (e.g., DOTAP) is at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 mol % in the lipid composition disclosed herein.

In some embodiments, the lipid composition of the pharmaceutical compositions disclosed herein comprises a compound of formula (I). In one embodiment, the mole ratio of the compound of formula (I) (e.g., Compounds 18, 25, 26 or 48) to the quaternary amine compound (e.g., DOTA) is about 100:1 to about 2.5:1. In one embodiment, the mole ratio of the compound of formula (I) (e.g., Compounds 18, 25, 26 or 48) to the quaternary amine compound (e.g., DOTAP) is about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, or about 2.5:1. In one embodiment, the mole ratio of the compound of formula (I) (e.g., Compounds 18, 25, 26 or 48) to the quaternary amine compound (e.g., DOTAP) in the lipid composition disclosed herein is about 10:1.

In some aspects, the lipid composition of the pharmaceutical compositions disclosed herein does not comprise a quaternary amine compound. In some aspects, the lipid composition of the pharmaceutical compositions disclosed herein does not comprise DOTAP.

C. Structural Lipids

The lipid composition of a pharmaceutical composition disclosed herein can comprise one or more structural lipids. As used herein, the term "structural lipid" refers to sterols and also to lipids containing sterol moieties. In some embodiments, the structural lipid is selected from the group consisting of cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol.

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 23.5 mol %, about 28.5 mol %, about 33.5 mol %, or about 38.5 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

In some aspects, the lipid composition component of the pharmaceutical compositions for intratumoral delivery disclosed does not comprise cholesterol.

D. Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid may be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about C14 to about $C_{16}$. In some embodiments, a PEG moiety, for example an mPEG-$NH_2$, has a size of about 1000, 2000, 5000, 10,000, 15,000 or 20,000 daltons. In one embodiment, the PEG-lipid is $PEG_{2k}$-DMG.

In one embodiment, the lipid nanoparticles described herein may comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO2015/130584, which are incorporated herein by reference in their entirety.

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

In some embodiments, the lipid composition disclosed herein comprises an ionizable amino lipid, e.g., a compound of formula (I), and an asymmetric phospholipid. In some embodiments, the lipid composition comprises Compound 18 and MSPC.

In some embodiments, the lipid composition disclosed herein comprises an ionizable amino lipid, e.g., a compound of formula (I), and a quaternary amine compound. In some embodiments, the lipid composition comprises Compound 18 and DOTAP.

In some embodiments, the lipid composition disclosed herein comprises an ionizable amino lipid, e.g., a compound of formula (I), an asymmetric phospholipid, and a quaternary amine compound. In some embodiments, the lipid composition comprises Compound 18, MSPC and DOTAP.

In one embodiment, the lipid composition comprises about 50 mol % of a compound of formula (I) (e.g. Compounds 18, 25, 26 or 48), about 10 mol % of DSPC or MSPC, about 33.5 mol % of cholesterol, about 1.5 mol % of PEG-DMG, and about 5 mol % of DOTAP. In one embodiment, the lipid composition comprises about 50 mol % of a compound of formula (I) (e.g. Compounds 18, 25, 26 or 48), about 10 mol % of DSPC or MSPC, about 28.5 mol % of cholesterol, about 1.5 mol % of PEG-DMG, and about 10 mol % of DOTAP.

The components of the lipid nanoparticle may be tailored for optimal delivery of the polynucleotides based on the desired outcome. As a non-limiting example, the lipid nanoparticle may comprise 40-60 mol % an ionizable amino lipid (e.g., a compound of formula (I)), 8-16 mol % phospholipid, 30-45 mol % cholesterol, 1-5 mol % PEG lipid, and optionally 1-15 mol % quaternary amine compound.

In some embodiments, the lipid nanoparticle may comprise 45-65 mol % of an ionizable amino lipid (e.g., a compound of formula (I)), 5-10 mol % phospholipid, 25-40 mol % cholesterol, 0.5-5 mol % PEG lipid, and optionally 1-15 mol % quaternary amine compound.

Non-limiting examples of nucleic acid lipid particles are disclosed in U.S. Patent Publication No. 20140121263, herein incorporated by reference in its entirety.

E. Other Ionizable Amino Lipids

The lipid composition of the pharmaceutical composition disclosed herein can comprise one or more ionizable amino lipids in addition to a lipid according to formula (I).

Ionizable lipids may be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid may also be a lipid including a cyclic amine group.

Ionizable lipids can also be the compounds disclosed in International Publication No. WO2015/199952 (see also US20150376115), hereby incorporated by reference in their entirety. For example, the ionizable amino lipids include, but not limited to:

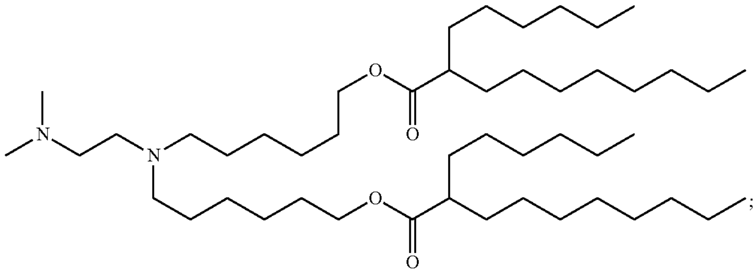
;
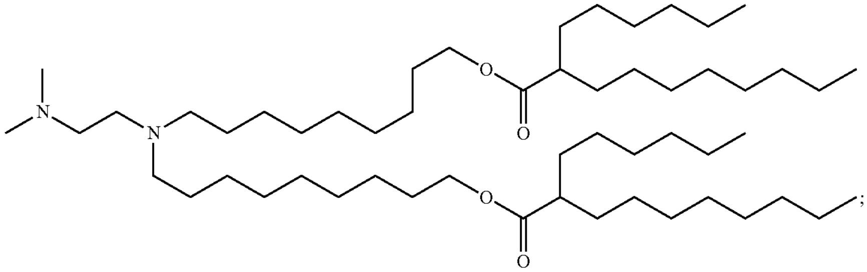
;
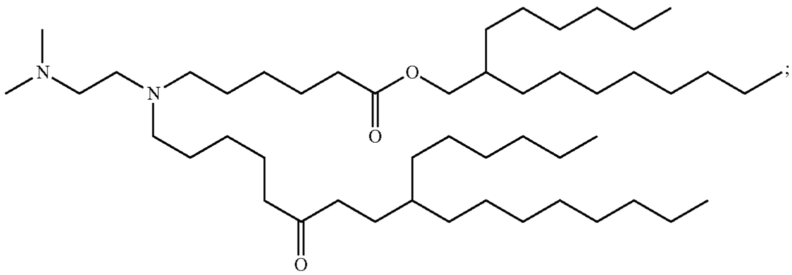
;
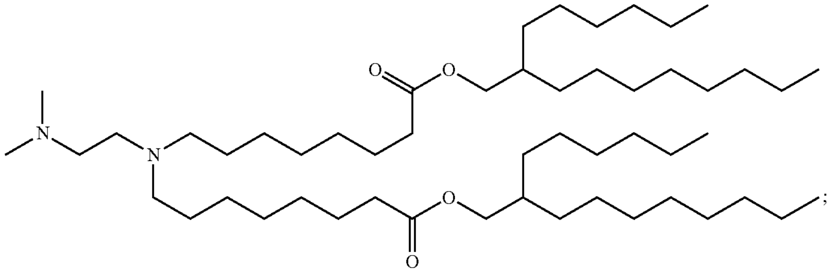
;
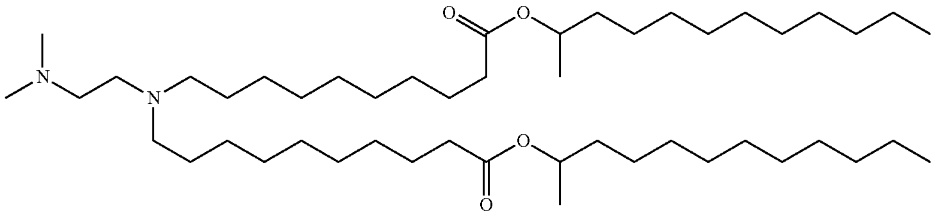
;
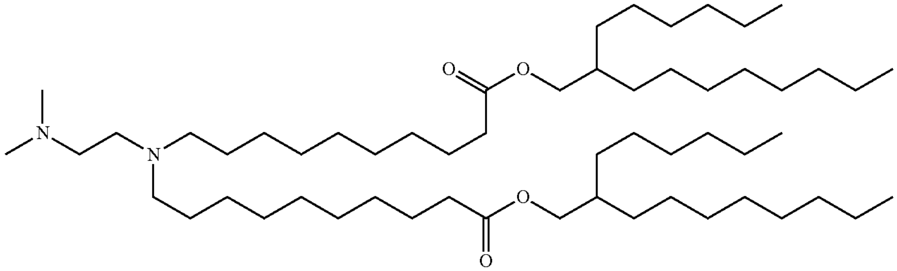
;

-continued

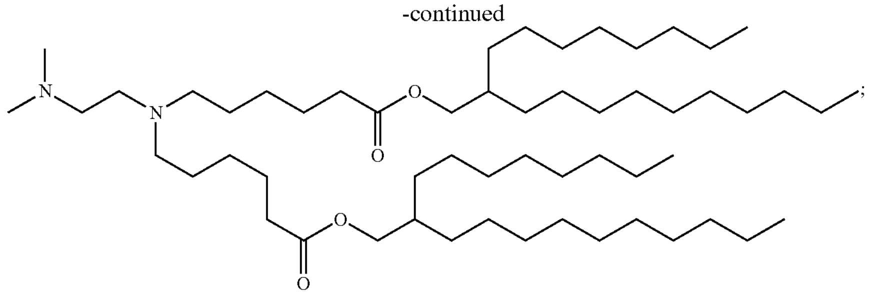

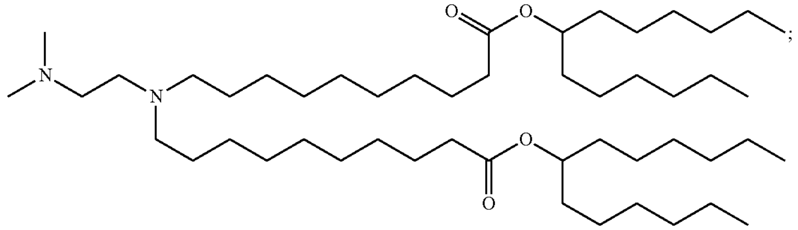

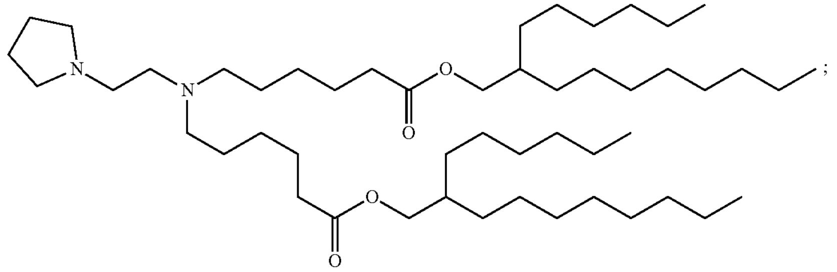

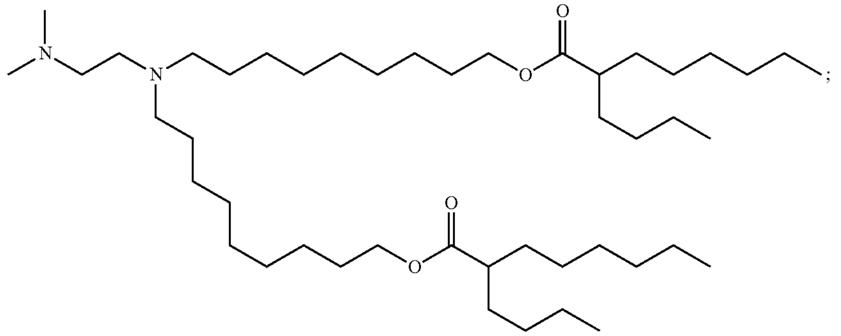

and any combination thereof.

F. Other Lipid Composition Components

The lipid composition of a pharmaceutical composition disclosed herein may include one or more components in addition to those described above. For example, the lipid composition may include one or more permeability enhancer molecules, carbohydrates, polymers, surface altering agents (e.g., surfactants), or other components. For example, a permeability enhancer molecule may be a molecule described by U.S. Patent Application Publication No. 2005/0222064. Carbohydrates may include simple sugars (e.g., glucose) and polysaccharides (e.g., glycogen and derivatives and analogs thereof). The lipid composition may include a buffer such as, but not limited to, citrate or phosphate at a pH of 7, salt and/or sugar. Salt and/or sugar may be included in the formulations described herein for isotonicity.

A polymer may be included in and/or used to encapsulate or partially encapsulate a pharmaceutical composition disclosed herein (e.g., a pharmaceutical composition in lipid nanoparticle form). A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide comprising an mRNA encoding an IL-23 polypeptide, the polynucleotide comprising an mRNA encoding an IL-36-gamma polypeptide, or the polynucleotide comprising an mRNA encoding an OX40L polypeptide, is about 20:1 or about 15:1.

In some embodiments, the pharmaceutical composition disclosed herein can contain more than one polypeptides, e.g., two, three or more polypeptides. For example, a pharmaceutical composition disclosed herein can contain two, three, or more polynucleotides (e.g., mRNA).

In one embodiment, the lipid nanoparticles described herein may comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein may comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In one embodiment, formulations comprising the polynucleotides and lipid nanoparticles described herein may comprise 0.15 mg/ml to 2 mg/ml of the polynucleotide described herein (e.g., mRNA). In some embodiments, the formulation may further comprise 10 mM of citrate buffer and the formulation may additionally comprise up to 10% w/w of sucrose (e.g., at least 1% w/w, at least 2% w/w/, at least 3% w/w, at least 4% w/w, at least 5% w/w, at least 6% w/w, at least 7% w/w, at least 8% w/w, at least 9% w/w or 10% w/w).

Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of formula (I) as described herein, and (ii) a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof. In such nanoparticle composition, the lipid composition disclosed herein can encapsulate the polynucleotide comprising an mRNA encoding an IL-23 polypeptide, the polynucleotide comprising an mRNA encoding an IL-36-gamma polypeptide, a polynucleotide comprising an mRNA encoding an IL-18 polypeptide, the polynucleotide comprising an mRNA encoding an OX40L polypeptide, or any combination thereof.

In one particular embodiment, (i) the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and the polynucleotide comprising an mRNA encoding an OX40L polypeptide are encapsulated separately (i.e., in two populations of nanoparticles). In another particular embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and the polynucleotide comprising an mRNA encoding an OX40L polypeptide are encapsulated separately (i.e., in three populations of nanoparticles). In one particular embodiment, (i) the polynucleotide comprising an mRNA encoding an IL-23 polypeptide and the polynucleotide comprising an mRNA encoding an IL-36-gamma polypeptide, or the polynucleotide comprising an mRNA encoding an IL-18 polypeptide, (ii) the polynucleotide comprising an mRNA encoding an IL-23 polypeptide and the polynucleotide comprising an mRNA encoding an OX40L polypeptide, or (iii) the polynucleotide comprising an mRNA encoding an IL-23 polypeptide and the polynucleotide comprising an mRNA encoding an OX40L polypeptide are encapsulated together (i.e., in a single population of nanoparticles). In another particular embodiment, the polynucleotide comprising an mRNA encoding an IL-23 polypeptide, the polynucleotide comprising an mRNA encoding an IL-36-gamma polypeptide or the polynucleotide comprising an mRNA encoding an IL-18 polypeptide, and the polynucleotide comprising an mRNA encoding an OX40L polypeptide are encapsulated together (i.e., in a single population of nanoparticles).

Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

Nanoparticle compositions of the present disclosure comprise at least one compound according to formula (I). For example, the nanoparticle composition can include one or more of Compounds 1-147, or one or more of Compounds 1-232. Nanoparticle compositions can also include a variety of other components. For example, the nanoparticle composition may include one or more other lipids in addition to a lipid according to formula (I), (II), or (IIa)-(IId), such as (i) at least one phospholipid, (ii) at least one quaternary amine compound, (iii) at least one structural lipid, (iv) at least one PEG-lipid, or (v) any combination thereof.

In some embodiments, the nanoparticle composition comprises a compound of formula (I) (e.g., Compounds 18, 25, 26 or 48). In some embodiments, the nanoparticle composition comprises a compound of formula (I) (e.g., Compounds 18, 25, 26 or 48) and a phospholipid (e.g., DSPC or MSPC). In some embodiments, the nanoparticle composition comprises a compound of formula (I) (e.g., Compounds 18, 25, 26 or 48), a phospholipid (e.g., DSPC or MSPC), and a quaternary amine compound (e.g., DOTAP). In some embodiments, the nanoparticle composition comprises a compound of formula (I) (e.g., Compounds 18, 25, 26 or 48), and a quaternary amine compound (e.g., DOTAP).

In some embodiments, the nanoparticle composition comprises a lipid composition consisting or consisting essentially of compound of formula (I) (e.g., Compounds 18, 25, 26 or 48). In some embodiments, the nanoparticle composition comprises a lipid composition consisting or consisting essentially of a compound of formula (I) (e.g., Compounds 18, 25, 26 or 48) and a phospholipid (e.g., DSPC or MSPC). In some embodiments, the nanoparticle composition comprises a lipid composition consisting or consisting essentially of a compound of formula (I) (e.g., Compounds 18, 25, 26 or 48), a phospholipid (e.g., DSPC or MSPC), and a quaternary amine compound (e.g., DOTAP). In some embodiments, the nanoparticle composition comprises a lipid composition consisting or consisting essentially of a compound of formula (I) (e.g., Compounds 18, 25, 26 or 48), and a quaternary amine compound (e.g., DOTAP).

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 33.5 mole % of cholesterol; about 1.5 mole % of PEG-DMG (e.g., $PEG_{2k}$-DMG); about 5 mole % of DOTAP; and (2) a polynucleotide.

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 28.5 mole % of cholesterol; about 1.5 mole % of PEG-DMG (e.g., $PEG_{2k}$-DMG); about 10 mole % of DOTAP; and (2) a polynucleotide.

In one embodiment, the nanoparticle composition comprises (1) a lipid composition comprising about 50 mole % of a compound of formula (I) (e.g., Compounds 18, 25, 26 or 48); about 10 mole % of DSPC or MSPC; about 23.5 mole % of cholesterol; about 1.5 mole % of PEG-DMG (e.g., $PEG_2$k-DMG); about 15 mole % of DOTAP; and (2) a polynucleotide.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". For example, an ionizable molecule may comprise an amine group, referred to as ionizable amino lipids. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide comprising an mRNA encoding an IL-23 polypeptide, the polynucleotide comprising an mRNA encoding an IL-36-gamma polypeptide, and the polynucleotide comprising an mRNA encoding an OX40L polypeptide are formulated in lipid nanoparticles. In some aspects, the lipid nanoparticles have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 m or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition may be relatively homogenous. A polydispersity index may be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition disclosed herein may be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles may be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles may be from about 10 mV to about 50 mV, from about 15 mV to about 45 mV, from about 20 mV to about 40 mV, and from about 25 mV to about 35 mV. In some embodiments, the zeta potential of the lipid nanoparticles may be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" may refer to complete, substantial, or partial enclosure, confinement, surrounding, or encasement.

Encapsulation efficiency is desirably high (e.g., close to 100%). The encapsulation efficiency may be measured, for example, by comparing the amount of the polynucleotide in a solution containing the nanoparticle composition before and after breaking up the nanoparticle composition with one or more organic solvents or detergents.

Fluorescence may be used to measure the amount of free polynucleotide in a solution. For the nanoparticle compositions described herein, the encapsulation efficiency of a polynucleotide may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition may depend on the size (expressed as length, or molecular mass), sequence, and other characteristics of the mRNA. The relative amounts of a polynucleotide in a nanoparticle composition may also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang (et al. 2015) Adv. Drug Deliv. Rev. 87:68-80; Silva et al. (2015) Curr. Pharm. Technol. 16: 940-954; Naseri et al. (2015) Adv. Pharm. Bull. 5:305-13; Silva et al. (2015) Curr. Pharm. Biotechnol. 16:291-302, and references cited therein.

In some embodiments, the polynucleotide of the disclosure is formulated in a lipid nanoparticle, wherein the polynucleotide comprises an mRNA disclosed in Table 1. In some embodiments, the polynucleotide of the disclosure is formulated in a lipid nanoparticle, wherein the polynucleotide comprises a sequence set forth in Table 1.

Lipid nanoparticle formulations typically comprise a lipid, in particular, an ionizable amino lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% ionizable amino lipid: 5-25% neutral lipid: 25-55% sterol; 0.5-15% PEG-lipid.

In one embodiment, the formulation includes from about 25% to about 75% on a molar basis of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid, e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. (2005) J. Controlled Release 107:276-287).

In one embodiment, the formulations of the disclosure include 25-75% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the disclosure include 35-65% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the disclosure include 45-65% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the disclosure include about 60% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the disclosure include about 50% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the disclosure include about 50% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the disclosure include about 40% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations of the disclosure include about 57.2% of a ionizable amino lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the disclosure include about 57.5% of a ionizable amino lipid selected from the PEG lipid is PEG-cDMA (PEG-cDMA is further discussed in Reyes et al. (2005) J. Controlled Release 107:276-287, about 7.5% of the neutral lipid, about 31.5% of the sterol, and about 3.5% of the PEG or PEG-modified lipid on a molar basis.

In some embodiments, lipid nanoparticle formulation consists essentially of a lipid mixture in molar ratios of about 20-70% ionizable amino lipid: 5-45% neutral lipid: 20-55% cholesterol: 0.5-15% PEG-modified lipid; e.g., in a molar ratio of about 20-60% ionizable amino lipid: 5-25% neutral lipid: 25-55% cholesterol: 0.5-15% PEG-modified lipid.

In particular embodiments, the molar lipid ratio is approximately 50/10/38.5/1.5 (mol % ionizable amino lipid/neutral lipid, e.g., DSPC/Chol/PEG-modified lipid, e.g., PEG-DMG, PEG-DSG or PEG-DPG), 57.2/7.1134.3/1.4 (mol % ionizable amino lipid/neutral lipid, e.g., DPPC/Chol/PEG-modified lipid, e.g., PEG-cDMA), 40/15/40/5 (mol % ionizable amino lipid/neutral lipid, e.g., DSPC/Chol/PEG-modified lipid, e.g., PEG-DMG), 50/10/35/4.5/0.5 (mol % ionizable amino lipid/neutral lipid, e.g., DSPC/Chol/PEG-modified lipid, e.g., PEG-DSG), 50/10/35/5 (ionizable amino lipid/neutral lipid, e.g., DSPC/Chol/PEG-modified lipid, e.g., PEG-DMG), 40/10/40/10 (mol % ionizable amino lipid/neutral lipid, e.g., DSPC/Chol/PEG-modified lipid, e.g., PEG-DMG or PEG-cDMA), 35/15/40/10 (mol % ionizable amino lipid/neutral lipid, e.g., DSPC/Chol/PEG-modified lipid, e.g., PEG-DMG or PEG-cDMA) or 52/13/30/5 (mol % ionizable amino lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012) Angew. Chem. Int. Ed. 51:8529-8533; and Maier et al. (2013) Molecular Therapy 21:570-1578.

In one embodiment, the lipid nanoparticle formulations described herein comprise a ionizable amino lipid, a PEG lipid and a structural lipid and optionally comprise a non-cationic lipid. As a non-limiting example, the lipid nanoparticle comprises about 40-60% of ionizable amino lipid, about 5-15% of a non-cationic lipid, about 1-2% of a PEG lipid and about 30-50% of a structural lipid. As another non-limiting example, the lipid nanoparticle comprises about 50% ionizable amino lipid, about 10% non-cationic lipid, about 1.5% PEG lipid and about 38.5% structural lipid. As yet another non-limiting example, the lipid nanoparticle comprises about 55% ionizable amino lipid, about 10% non-cationic lipid, about 2.5% PEG lipid and about 32.5% structural lipid. In one embodiment, the ionizable amino lipid is any ionizable amino lipid described herein such as, but not limited to, DLin-KC2-DMA, DLin-MC3-DMA and L319.

In one embodiment, the lipid nanoparticle formulations described herein are 4 component lipid nanoparticles. The lipid nanoparticle can comprise a ionizable amino lipid, a non-cationic lipid, a PEG lipid and a structural lipid. As a non-limiting example, the lipid nanoparticle can comprise about 40-60% of ionizable amino lipid, about 5-15% of a non-cationic lipid, about 1-2% of a PEG lipid and about 30-50% of a structural lipid. As another non-limiting example, the lipid nanoparticle can comprise about 50% ionizable amino lipid, about 10% non-cationic lipid, about 1.5% PEG lipid and about 38.5% structural lipid. As yet another non-limiting example, the lipid nanoparticle can comprise about 55% ionizable amino lipid, about 10% non-cationic lipid, about 2.5% PEG lipid and about 32.5% structural lipid. In one embodiment, the ionizable amino lipid can be any ionizable amino lipid described herein such as, but not limited to, DLin-KC2-DMA, DLin-MC3-DMA and L319.

In one embodiment, the lipid nanoparticle formulations described herein comprise a ionizable amino lipid, a non-cationic lipid, a PEG lipid and a structural lipid. As a non-limiting example, the lipid nanoparticle comprise about 50% of the ionizable amino lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the ionizable amino lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the ionizable amino lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the ionizable amino lipid L319, about 10% of the non-cationic lipid DSPC, about 2.5% of the PEG lipid PEG-DMG and about 32.5% of the structural lipid cholesterol.

In one embodiment, the lipid is a cleavable lipid such as those described in International Publication No. WO2012170889. In another embodiment, the lipid is a cationic lipid such as, but not limited to, Formula (I) of U.S. Patent Application No. US20130064894.

In one embodiment, the lipid is synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354.

In another embodiment, the cationic lipid is a trialkyl cationic lipid. Non-limiting examples of trialkyl cationic lipids and methods of making and using the trialkyl cationic lipids are described in International Patent Publication No. WO2013126803.

In one embodiment, the LNP formulations of the polynucleotides contain PEG-c-DOMG at 3% lipid molar ratio. In another embodiment, the LNP formulations of the polynucleotides contains PEG-c-DOMG at 1.5% lipid molar ratio.

In one embodiment, the pharmaceutical compositions of the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide include at least one of the PEGylated lipids described in International Publication No. WO2012099755.

In one embodiment, the LNP formulation contains PEG-DMG 2000 (1,2-dimyristoyl-sn-glycero-3-phophoethanolamine-N-[methoxy(polyethylene glycol)-2000). In one embodiment, the LNP formulation can contain PEG-DMG 2000, a ionizable amino lipid known in the art and at least one other component. In another embodiment, the LNP formulation contains PEG-DMG 2000, a ionizable amino lipid known in the art, DSPC and cholesterol. As a non-limiting example, the LNP formulation contains PEG-DMG 2000, DLin-DMA, DSPC and cholesterol. As another non-limiting example the LNP formulation contains PEG-DMG 2000, DLin-DMA, DSPC and cholesterol in a molar ratio of 2:40:10:48 (see, e.g., Geall et al. (2012) Proc. Nat'l. Acad. Sci. USA 109:14604-9).

In one embodiment, the LNP formulation is formulated by the methods described in International Publication Nos. WO2011127255 or WO2008103276. As a non-limiting example, the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide described herein are encapsulated in LNP formulations as described in WO2011127255 and/or WO2008103276; see also, U.S. Pat. Appl. Publ. Nos. US20130037977 and US20100015218, which are herein incorporated by reference in their entireties.

In one embodiment, the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide described herein are formulated in a nanoparticle to be delivered by a parenteral route as described in U.S. Patent Application Publication No. US20120207845.

In one embodiment, the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide are formulated in a lipid nanoparticle made by the methods described in U.S. Patent Application Publication No. US20130156845 or International Publication No. WO2013093648 or WO2012024526.

The lipid nanoparticles described herein can be made in a sterile environment by the system and/or methods described in U.S. Patent Application Publication No. US20130164400.

In one embodiment, the LNP formulation is formulated in a nanoparticle such as a nucleic acid-lipid particle described in U.S. Pat. No. 8,492,359. As a non-limiting example, the lipid particle comprises one or more active agents or therapeutic agents; one or more ionizable amino lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle can be the polynucleotides described herein and/or are known in the art.

In one embodiment, the LNP formulation is formulated by the methods described in International Publication Nos. WO2011127255 or WO2008103276. As a non-limiting example, modified RNA described herein is encapsulated in LNP formulations as described in WO2011127255 and/or WO2008103276.

In one embodiment, LNP formulations described herein comprise a polycationic composition. As a non-limiting example, the polycationic composition is selected from formula 1-60 of U.S. Patent Publication No. US20050222064. In another embodiment, the LNP formulations comprising a polycationic composition are used for the delivery of the modified RNA described herein in vivo and/or in vitro.

In one embodiment, the LNP formulations described herein additionally comprise a permeability enhancer molecule. Non-limiting permeability enhancer molecules are described in U.S. Patent Application Publication No. US20050222064.

In one embodiment, the polynucleotide pharmaceutical compositions are formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. (2006) Cancer Biology & Therapy 5:1708-1713) and hyaluronan-coated liposomes (Quiet Therapeutics, Israel).

In one embodiment, the polynucleotide comprising an mRNA encoding an IL-23 polypeptide, the polynucleotide comprising an mRNA encoding an IL-36-gamma polypeptide, and the polynucleotide comprising an mRNA encoding an OX40L polypeptide are formulated in a lyophilized gel-phase liposomal composition as described in U.S. Patent Application Publication No. US2012060293.

The nanoparticle formulations can comprise a phosphate conjugate. The phosphate conjugate can increase in vivo circulation times and/or increase the targeted delivery of the nanoparticle. Phosphate conjugates for use with the present disclosure can be made by the methods described in International Application No. WO2013033438 or U.S. Patent Application Publication No. US20130196948. As a non-limiting example, the phosphate conjugates can include a compound of any one of the formulas described in International Application No. WO2013033438; see also, U.S. Pat. Appl. Publ. No. US20130066086.

The nanoparticle formulation can comprise a polymer conjugate. The polymer conjugate can be a water soluble conjugate. The polymer conjugate can have a structure as described in U.S. Patent Application Publication No. 20130059360. In one embodiment, polymer conjugates with the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure can be made using the methods and/or segmented polymeric reagents described in U.S. Patent Application Publication No. US20130072709. In another embodiment, the polymer conjugate can have pendant side groups comprising ring moieties such as, but not limited to, the polymer conjugates described in U.S. Patent Application Publication No. US20130196948.

The nanoparticle formulations can comprise a conjugate to enhance the delivery of nanoparticles of the present disclosure in a subject. Further, the conjugate can inhibit phagocytic clearance of the nanoparticles in a subject. In one embodiment, the conjugate is a "self" peptide designed from the human membrane protein CD47, e.g., the "self" particles described by Rodriguez et al. (2013) Science 339:971-975. As shown by Rodriguez et al. the self peptides delayed macrophage-mediated clearance of nanoparticles which enhanced delivery of the nanoparticles. In another embodiment, the conjugate is the membrane protein CD47. See, e.g., Rodriguez et al. (2013) Science 339:971-975. Rodriguez et al. showed that, similarly to "self" peptides, CD47 can increase the circulating particle ratio in a subject as compared to scrambled peptides and PEG coated nanoparticles.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure are formulated in nanoparticles which comprise a conjugate to enhance the delivery of the nanoparticles of the present disclosure in a subject. The conjugate can be the CD47 membrane or the conjugate can be derived from the CD47 membrane protein, such as the "self" peptide described previously. In another aspect the nanoparticle can comprise PEG and a conjugate of CD47 or a derivative thereof. In yet another aspect, the nanoparticle comprises both the "self" peptide described above and the membrane protein CD47.

In another aspect, a "self" peptide and/or CD47 protein is conjugated to a virus-like particle or pseudovirion, as described herein for delivery of the polynucleotides of the present disclosure.

In another embodiment, pharmaceutical compositions comprising the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide of the present disclosure, can comprise a conjugate with a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Patent Application Publication No. US20130184443.

The nanoparticle formulations can be a carbohydrate nanoparticle comprising a carbohydrate carrier and a polynucleotide. As a non-limiting example, the carbohydrate carrier includes, but is not limited to, an anhydride-modified phytoglycogen or glycogen-type material, phtoglycogen octenyl succinate, phytoglycogen beta-dextrin, anhydride-modified phytoglycogen beta-dextrin. See, e.g., International Publication No. WO2012109121; see also U.S. Pat. Appl. Publ. No. US20140066363.

Nanoparticle formulations of the present disclosure can be coated with a surfactant or polymer in order to improve the delivery of the particle. In one embodiment, the nanoparticle is coated with a hydrophilic coating such as, but not limited to, PEG coatings and/or coatings that have a neutral surface charge. The hydrophilic coatings can help to deliver nanoparticles with larger payloads such as, but not limited to, polynucleotides within the central nervous system. As a non-limiting example nanoparticles comprising a hydrophilic coating and methods of making such nanoparticles are described in U.S. Patent Application Publication No. US20130183244.

In one embodiment, the lipid nanoparticles of the present disclosure are hydrophilic polymer particles. Non-limiting examples of hydrophilic polymer particles and methods of making hydrophilic polymer particles are described in U.S. Patent Application Publication No. US20130210991.

In another embodiment, the lipid nanoparticles of the present disclosure are hydrophobic polymer particles. Lipid nanoparticle formulations can be improved by replacing the ionizable cationic lipid with a biodegradable ionizable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and can be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain.

In one embodiment, the internal ester linkage is located on either side of the saturated carbon.

In one embodiment, an immune response is elicited by delivering a lipid nanoparticle which can include a nanospecies, a polymer and an immunogen. See, e.g., U.S. Patent Application Publication No. US20120189700 and International Publication No. WO2012099805. The polymer can encapsulate the nanospecies or partially encapsulate the nanospecies. The immunogen can be a recombinant protein, a modified RNA and/or a polynucleotide comprising an mRNA encoding an IL-23 polypeptide described herein, a polynucleotide comprising an mRNA encoding an IL-36-gamma polypeptide or a polynucleotide comprising an mRNA encoding an IL-18 polypeptide described herein, and/or a polynucleotide comprising an mRNA encoding an OX40L polypeptide described herein.

Lipid nanoparticles can be engineered to alter the surface properties of particles so the lipid nanoparticles can penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles can be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. (2007) Proc. Nat'l. Acad. Sci. USA 104:1482-487; Lai et al. (2009) Adv. Drug Deliv. Rev. 61:158-171). The transport of nanoparticles can be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier can be made as described in U.S. Pat. No. 8,241,670 or International Patent Publication No. WO2013110028 (see, also U.S. Pat. Appl. Publ. No. US20150297531).

The lipid nanoparticle engineered to penetrate mucus can comprise a polymeric material (i.e. a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material can be biodegradable and/or biocompatible. Non-limiting examples of biocompatible polymers are described in International Patent Publication No. WO2013116804; see also, U.S. Pat. Appl. Publ. No. US20130203713, which is herein incorporated by reference in its entirety. The polymeric material can additionally be irradiated. As a non-limiting example, the polymeric material can be gamma irradiated. See, e.g., International App. No. WO2012082165; see also, U.S. Pat. Appl. Publ. No. US20130101609, which is herein incorporated by reference in its entirety.

Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropyl cellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle can be coated or associated with a co-polymer such as, but not limited to, a block co-polymer (such as a branched polyether-polyamide block copolymer described in International Publication No. WO2013012476), and (poly(ethylene glycol))-(poly(propylene oxide))-(poly(ethylene glycol)) triblock copolymer. See, e.g., U.S. Patent Application Publication Nos. US20120121718 and US20100003337, and U.S. Pat. No. 8,263,665.

The co-polymer can be a polymer that is generally regarded as safe (GRAS) and the formation of the lipid nanoparticle can be in such a way that no new chemical entities are created. For example, the lipid nanoparticle can comprise poloxamers coating PLGA nanoparticles without forming new chemical entities which are still able to rapidly penetrate human mucus. Yang et al. (2011) Angew. Chem. Int. Ed. 50:2597-2600. A non-limiting scalable method to produce nanoparticles which can penetrate human mucus is described by Xu et al. (2013) J. Control Release 170:279-86.

The vitamin of the polymer-vitamin conjugate can be vitamin E. The vitamin portion of the conjugate can be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus can include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocysteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent can be embedded or enmeshed in the particle's surface or disposed (e.g., by coating, adsorption, covalent linkage, or other process) on the surface of the lipid nanoparticle. See, e.g., U.S. Patent Application Publication Nos. US20100215580, US20080166414, and US20130164343.

In one embodiment, the mucus penetrating lipid nanoparticles comprises at least one polynucleotide described herein. The polynucleotide can be encapsulated in the lipid nanoparticle and/or disposed on the surface of the particle. The polynucleotide can be covalently coupled to the lipid nanoparticle. Formulations of mucus penetrating lipid nanoparticles can comprise a plurality of nanoparticles. Further, the formulations can contain particles which can interact with the mucus and alter the structural and/or adhesive properties of the surrounding mucus to decrease mucoadhesion which can increase the delivery of the mucus penetrating lipid nanoparticles to the mucosal tissue.

In another embodiment, the mucus penetrating lipid nanoparticles are a hypotonic formulation comprising a mucosal penetration enhancing coating. The formulation can be hypotonic for the epithelium to which it is being delivered. Non-limiting examples of hypotonic formulations can be found in International Patent Publication No. WO2013110028; see also U.S. Pat. Appl. Publ. No. US20150297531, which is herein incorporated by reference in its entirety.

In one embodiment, in order to enhance the delivery through the mucosal barrier the polynucleotide formulation comprises or is a hypotonic solution. Hypotonic solutions were found to increase the rate at which mucoinert particles such as, but not limited to, mucus-penetrating particles, were able to reach the vaginal epithelial surface. See, e.g., Ensign et al. (2013) Biomaterials 34:6922-9.

In one embodiment, the polynucleotide is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids. See Aleku et al. (2008) Cancer Res. 68:9788-9798; Strumberg et al. (2012) Int. J. Clin. Pharmacol. Ther. 50:76-78; Santel et al. (2006) Gene Ther. 13:1222-1234; Santel et al. (2006) Gene Ther. 13:1360-1370; Gutbier et al. (2010) Pulm. Pharmacol. Ther. 23:334-344; Kaufmann et al. (2010) Microvasc. Res. 80:286-293; Weide et al. (2009) J. Immunother. 32:498-507; Weide et al. (2008) J. Immunother. 31:180-188; Pascolo (2004) Expert Opin. Biol. Ther. 4:1285-1294; Fotin-Mleczek et al. (2011) J. Immunother. 34:1-15; Song et al. (2005) Nature Biotechnol. 23:709-717; Peer et al. (2007) Proc. Natl. Acad. Sci. USA 6:104:4095-4100; deFougerolles (2008) Hum. Gene Ther. 19:125-132).

In one embodiment, such formulations are also constructed or compositions altered such that they passively or actively are directed to different cell types in vivo, including but not limited to hepatocytes, immune cells, tumor cells, endothelial cells, antigen presenting cells, and leukocytes (Akinc et al. (2010) Mol. Ther. 18:1357-1364; Song et al. (2005) Nat. Biotechnol. 23:709-717; Judge et al. (2009) J. Clin. Invest. 119:661-673; Kaufmann et al. (2010) Microvasc. Res. 80:286-293; Santel et al. (2006) Gene Ther. 13:1222-1234; Santel et al. (2006) Gene Ther. 13:1360-1370; Gutbier et al. (2010) Pulm. Pharmacol. Ther. 23:334-344; Basha et al. (2011) Mol. Ther. 19:2186-2200; Fenske and Cullis (2008) Expert Opin. Drug Deliv. 5:25-44; Peer et al. (2008) Science 319:627-630; Peer and Lieberman (2011) Gene Ther. 18:1127-1133). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. (2010) Mol. Ther. 18:1357-1364).

Formulations can also be selectively targeted through expression of different ligands on their surface as exemplified by, but not limited by, folate, transferrin, N-acetylgalactosamine (GalNAc), and antibody targeted approaches. See, e.g., Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721: 339-353; Subramanya et al., Mol Ther. 2010 18:2028-2037; Song et al., Nat Biotechnol. 2005 23:709-717; Peer et al., Science. 2008 319:627-630; and, Peer and Lieberman, Gene Ther. 2011 18:1127-1133; all of which are herein incorporated by reference in their entireties.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and the polynucleotide comprising an mRNA encoding an OX40L polypeptide of the disclosure are formulated as a solid lipid nanoparticle.

A solid lipid nanoparticle (SLN) can be spherical with an average diameter between 10 to 1,000 nm. SLN possess a solid lipid core matrix that can solubilize lipophilic molecules and can be stabilized with surfactants and/or emulsifiers. In a further embodiment, the lipid nanoparticle can be a self-assembly lipid-polymer nanoparticle. See Zhang et al. (2008) ACS Nano 2:1696-1702. As a non-limiting example, the SLN can be the SLN described in International Patent Publication No. WO2013105101. As another non-limiting example, the SLN can be made by the methods or processes described in International Patent Publication No. WO2013105101.

Liposomes, lipoplexes, or lipid nanoparticles can be used to improve the efficacy of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, and any combination thereof as these formulations can be able to increase cell transfection by the polynucleotides; and/or increase the translation of encoded IL-23, IL-36, IL-18, and OX40L. One such example involves the use of lipid encapsulation to enable the effective systemic delivery of polyplex plasmid DNA. See Heyes et al. (2007) Mol. Ther. 15:713-720. The liposomes, lipoplexes, or lipid nanoparticles can also be used to increase the stability of the polynucleotide.

In one embodiment, the polynucleotide comprising an mRNA encoding an IL-23 polypeptide, the polynucleotide comprising an mRNA encoding an IL-36-gamma polypeptide, a polynucleotide comprising an mRNA encoding an IL-18 polypeptide, and/or the polynucleotide comprising an mRNA encoding an OX40L polypeptide of the present disclosure are formulated for controlled release and/or targeted delivery.

As used herein, "controlled release" refers to a pharmaceutical composition or compound release profile that conforms to a particular pattern of release to effect a therapeutic outcome. In one embodiment, the polynucleotides are encapsulated into a delivery agent described herein and/or known in the art for controlled release and/or targeted delivery. As used herein, the term "encapsulate" means to enclose, surround or encase. As it relates to the formulation of the compounds of the disclosure, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure can be enclosed, surrounded or encased within the delivery agent. "Partially encapsulation" means that less than 10, 10, 20, 30, 40 50 or less of the pharmaceutical composition or compound of the disclosure can be enclosed, surrounded or encased within the delivery agent. Advantageously, encapsulation can be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

In one embodiment, the controlled release formulation includes, but is not limited to, tri-block co-polymers. As a non-limiting example, the formulation includes two different types of tri-block co-polymers. See International Publ. Nos. WO2012131104 and WO2012131106; see also U.S. Pat. Appl. Publ. Nos. US20140219923 and US20150165042, which are herein incorporated by reference in their entireties.

In another embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding OX40L polypeptide are encapsulated into a lipid nanoparticle or a rapidly eliminated lipid nanoparticle and the lipid nanoparticles or a rapidly eliminated lipid nanoparticle can then be encapsulated into a polymer, hydrogel and/or surgical sealant described herein and/or known in the art. As a non-limiting example, the polymer, hydrogel or surgical sealant is PLGA, ethylene vinyl acetate (EVAc), poloxamer, GELSITE® (Nanotherapeutics, Inc. Alachua, Flo.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, or COSEAL® (Baxter International, Inc Deerfield, Ill.).

In another embodiment, the lipid nanoparticle is encapsulated into any polymer known in the art which can form a gel when injected into a subject. As another non-limiting example, the lipid nanoparticle is encapsulated into a polymer matrix which can be biodegradable.

In one embodiment, the formulation for controlled release and/or targeted delivery comprises a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding OX40L polypeptide also includes at least one controlled release coating.

Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the polynucleotide controlled release and/or targeted delivery formulation comprises at least one degradable polyester which can contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

In one embodiment, the polynucleotide controlled release and/or targeted delivery formulation comprising at least one polynucleotide comprises at least one PEG and/or PEG related polymer derivatives as described in U.S. Pat. No. 8,404,222.

In another embodiment, the polynucleotide controlled release delivery formulation comprising at least one polynucleotide is the controlled release polymer system described in U.S. Pat. Appl. Publ. No. US20130130348.

In one embodiment, the polynucleotide comprising an mRNA encoding an IL-23 polypeptide and the polynucleotide comprising an mRNA encoding an IL-36-gamma polypeptide or the polynucleotide comprising an mRNA encoding an IL-18 polypeptide, of the present disclosure is encapsulated in a therapeutic nanoparticle Therapeutic nanoparticles can be formulated by methods described herein and known in the art such as, but not limited to, International Publ. Nos. WO2010005740, WO2010030763, WO2010005721, WO2010005723, WO2012054923, U.S. Pat. Appl. Publ. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211. In another embodiment, therapeutic polymer nanoparticles can be identified by the methods described in U.S. Pat. Appl. Publ. No. US20120140790.

In one embodiment, the polynucleotide comprising an mRNA encoding an IL-23 polypeptide, the polynucleotide comprising an mRNA encoding an IL-36-gamma polypeptide or the polynucleotide comprising an mRNA encoding an IL-18 polypeptide, and/or the polynucleotide comprising an mRNA encoding an OX40L polypeptide are formulated for sustained release.

As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle comprises a polymer and a therapeutic agent such as, but not limited to, the polynucleotide comprising an mRNA encoding an IL-23 polypeptide and the polynucleotide comprising an mRNA encoding an IL-36-gamma polypeptide or the polynucleotide comprising an mRNA encoding an IL-18 polypeptide of the present disclosure. See International Publ. No. WO2010075072 and U.S. Pat. Appl. Publ. Nos. US20100216804, US20110217377 and US20120201859. In another non-limiting example, the sustained release formulation comprises agents which permit persistent bioavailability such as, but not limited to, crystals, macromolecular gels and/or particulate suspensions. See U.S. Pat. Appl. Publ. No. US20130150295.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and/or the polynucleotide comprising an mRNA encoding an OX40L polypeptide can be formulated to be target specific.

As a non-limiting example, the therapeutic nanoparticles include a corticosteroid. See International Pub. No. WO2011084518. As a non-limiting example, the therapeutic nanoparticles are formulated in nanoparticles described in International Publ. Nos. WO2008121949, WO2010005726, WO2010005725, WO2011084521 and U.S. Pat. Appl. Publ. Nos. US20100069426, US20120004293 and US20100104655.

In one embodiment, the nanoparticles of the present disclosure comprise a polymeric matrix. As a non-limiting example, the nanoparticle comprises two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly (serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer includes PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly (serine ester), poly(L-lactide-co-L-lysine), poly(4-hydroxy-L-proline ester) or combinations thereof. In yet another embodiment, the diblock copolymer is a high-X diblock copolymer such as those described in International Patent Publication No. WO2013120052; see also U.S. Pat. Appl. Publ. No. US20150337068, which is herein incorporated by reference in its entirety.

As a non-limiting example the therapeutic nanoparticle comprises a PLGA-PEG block copolymer. See U.S. Pat. Appl. Publ. No. US20120004293 and U.S. Pat. No. 8,236,330. In another non-limiting example, the therapeutic nanoparticle is a stealth nanoparticle comprising a diblock copolymer of PEG and PLA or PEG and PLGA. See U.S. Pat. No. 8,246,968 and International Publication No. WO2012166923. In yet another non-limiting example, the therapeutic nanoparticle is a stealth nanoparticle or a target-specific stealth nanoparticle as described in U.S. Pat. Appl. Publ. No. US20130172406.

In one embodiment, the therapeutic nanoparticle comprises a multiblock copolymer. See, e.g., U.S. Pat. Nos. 8,263,665 and 8,287,910 and U.S. Pat. Appl. Publ. No. US20130195987. In yet another non-limiting example, the lipid nanoparticle comprises the block copolymer PEG-PLGA-PEG. See, e.g., Lee et al. (2003) Pharmaceutical Research 20:1995-2000; Li et al. (2003) Pharmaceutical Research 20:884-888; and Chang et al. (2007) J. Controlled Release. 118:245-253.

The polynucleotides comprising an mRNA encoding an IL-23, IL-36-gamma and/or OX40L polypeptide of the present disclosure can be formulated in lipid nanoparticles comprising the PEG-PLGA-PEG block copolymer.

In one embodiment, the therapeutic nanoparticle comprises a multiblock copolymer. See, e.g., U.S. Pat. Nos. 8,263,665 and 8,287,910 and U.S. Patent Appl. Publ. No. US20130195987.

In one embodiment, the block copolymers described herein are included in a polyion complex comprising a non-polymeric micelle and the block copolymer. See, e.g., U.S. Pat. App. Publ. No. US20120076836.

In one embodiment, the therapeutic nanoparticle comprises at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the therapeutic nanoparticles comprises at least one poly(vinyl ester) polymer. The poly(vinyl ester) polymer can be a copolymer such as a random copolymer. As a non-limiting example, the random copolymer has a structure such as those described in International Application No. WO2013032829 or U.S. Pat. Appl. Publ. No. US20130121954. In one aspect, the poly(vinyl ester) polymers can be conjugated to the polynucleotides described herein.

In one embodiment, the therapeutic nanoparticle comprises at least one diblock copolymer. The diblock copolymer can be, but it not limited to, a poly(lactic) acid-poly (ethylene)glycol copolymer. See, e.g., International Patent Publication No. WO2013044219.

As a non-limiting example, the therapeutic nanoparticle are used to treat cancer. See International Publication No. WO2013044219; see also, U.S. Pat. Appl. Publ. No. US20150017245, which is herein incorporated by reference in its entirety.

In one embodiment, the therapeutic nanoparticles comprise at least one cationic polymer described herein and/or known in the art.

In one embodiment, the therapeutic nanoparticles comprise at least one amine-containing polymer such as, but not limited to polylysine, polyethylene imine, poly(amidoamine) dendrimers, poly(beta-amino esters) and combinations thereof. See, e.g., U.S. Pat. No. 8,287,849.

In another embodiment, the nanoparticles described herein comprise an amine cationic lipid such as those described in International Patent Application No. WO2013059496. In one aspect the cationic lipids have an amino-amine or an amino-amide moiety.

In one embodiment, the therapeutic nanoparticles comprise at least one degradable polyester which can contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

In another embodiment, the therapeutic nanoparticle include a conjugation of at least one targeting ligand. The targeting ligand can be any ligand known in the art such as, but not limited to, a monoclonal antibody. See Kirpotin et al (2006) Cancer Res. 66:6732-6740.

In one embodiment, the therapeutic nanoparticle is formulated in an aqueous solution which can be used to target cancer (see International Pub No. WO2011084513 and U.S. Pat. Appl. Publ. No. US20110294717).

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, are formulated using the methods described in U.S. Pat. No. 8,404,799.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, are encapsulated in, linked to and/or associated with synthetic nanocarriers.

Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and U.S. Pat. Appl. Publ. Nos. US20110262491, US20100104645, US20100087337 and US20120244222. The synthetic nanocarriers can be formulated using methods known in the art and/or described herein. As a non-limiting example, the synthetic nanocarriers can be formulated by the methods described in International Pub Nos. WO2010005740, WO2010030763 and WO201213501 and U.S. Pat. Appl. Publ. Nos. US20110262491, US20100104645, US20100087337 and US2012024422. In another embodiment, the synthetic nanocarrier formulations can be lyophilized by methods described in International Pub. No. WO2011072218 and U.S. Pat. No. 8,211,473. In yet another embodiment, formulations of the present disclosure, including, but not limited to, synthetic nanocarriers, can be lyophilized or reconstituted by the methods described in US Pat. Appl. Publ. No. US20130230568.

In one embodiment, the synthetic nanocarriers contain reactive groups to release the polynucleotides described herein (see International Publ. No. WO20120952552 and U.S. Pat. Appl. Publ. No. US20120171229).

In one embodiment, the synthetic nanocarriers contain an immunostimulatory agent to enhance the immune response from delivery of the synthetic nanocarrier. As a non-limiting example, the synthetic nanocarrier can comprise a Th1 immunostimulatory agent which can enhance a Th1-based response of the immune system (see International Publ. No. WO2010123569 and U. S. Pat. Appl. Publ. No. US20110223201).

In one embodiment, the synthetic nanocarriers are formulated for targeted release. In one embodiment, the synthetic nanocarrier is formulated to release the polynucleotides at a specified pH and/or after a desired time interval. As a non-limiting example, the synthetic nanoparticle are formulated to release the polynucleotides after 24 hours and/or at a pH of 4.5 (see International Publ. Nos. WO2010138193 and WO2010138194 and U.S. Pat. Appl. Publ. Nos. US20110020388 and US20110027217).

In one embodiment, the synthetic nanocarriers are formulated for controlled and/or sustained release of the polynucleotides described herein. As a non-limiting example, the synthetic nanocarriers for sustained release are formulated by methods known in the art, described herein and/or as described in International Pub No. WO2010138192 and U.S. Pat. Appl. Publ. No. 20100303850, both of which are herein incorporated by reference in their entireties.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, are formulated for controlled and/or sustained release wherein the formulation comprises at least one polymer that is a crystalline side chain (CYSC) polymer. CYSC polymers are described in U.S. Pat. No. 8,399,007.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, are encapsulated in, linked to and/or associated with zwitterionic lipids. Non-limiting examples of zwitterionic lipids and methods of using zwitterionic lipids are described in U.S. Pat. Appl. Publ. No. US20130216607. In one aspect, the zwitterionic lipids can be used in the liposomes and lipid nanoparticles described herein.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, are formulated in colloid nanocarriers as described in U.S. Pat. Appl. Publ. No. US20130197100.

In one embodiment, the nanoparticle is optimized for oral administration. The nanoparticle can comprise at least one cationic biopolymer such as, but not limited to, chitosan or a derivative thereof. As a non-limiting example, the nanoparticle can be formulated by the methods described in U.S. Pat. Appl. Publ. No. US20120282343.

In some embodiments, LNPs comprise the lipid KL52 (an amino-lipid disclosed in U.S. Pat. Appl. Publ. No. US2012/0295832). Activity and/or safety (as measured by examining one or more of ALT/AST, white blood cell count and cytokine induction) of LNP administration can be improved by incorporation of such lipids. LNPs comprising KL52 can be administered intravenously and/or in one or more doses. In some embodiments, administration of LNPs comprising KL52 results in equal or improved mRNA and/or protein expression as compared to LNPs comprising MC3.

In some embodiments, a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, are delivered using smaller LNPs. Such particles can comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

In another embodiment, polynucleotides comprising an mRNA encoding an IL-23 polypeptide, polynucleotides comprising an mRNA encoding an IL-36-gamma polypeptide, polynucleotides comprising an mRNA encoding an IL-18 polypeptide, polynucleotides comprising an mRNA encoding an OX40L polypeptide, or any combination thereof, are delivered using smaller LNPs which can comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers can include, but are not limited to a slit interdigitial micromixer including, but not limited to those manufactured by Microinnova (Allerheiligen bei Wildon, Austria) and/or a staggered herringbone micromixer (SHM). See Zhigaltsev et al. (2012) Langmuir 28:3633-40; Belliveau et al. (2012) Molecular Therapy-Nucleic Acids 1:e37; Chen et al. (2012) J. Am. Chem. Soc. 134:6948-51.

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pat. Appl. Publ. Nos. US2004/0262223 and US2012/0276209.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, of the present disclosure are formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut fir Mikrotechnik Mainz GmbH, Mainz Germany).

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an OX40L polypeptide, or a combination thereof, of the present disclosure are formulated in lipid nanoparticles created using microfluidic technology. See Whitesides (2006) Nature 442: 368-373; and Abraham et al. (2002) Science 295:647-651. As a non-limiting example, controlled microfluidic formulation includes a passive method for mixing streams of steady pressure-driven flows in micro channels at a low Reynolds number. See, e.g., Abraham et al. (2002) Science 295: 647-651.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof, can be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated for delivery using the drug encapsulating microspheres described in International Patent Publication No. WO2013063468 or U.S. Pat. No. 8,440,614. The microspheres can comprise a compound of the formula (I), (II), (III), (IV), (V) or (VI) as described in International Patent Publication No. WO2013063468. In another aspect, the amino acid, peptide, polypeptide, lipids (APPL) are useful in delivering the polynucleotides of the disclosure to cells. See International Patent Publication No. WO2013063468; see also, U.S. Pat. Appl. Publ. No. US20130158021, which is herein incorporated by reference in its entirety.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles have a diameter from about 10 to 500 nm. In one embodiment, the lipid nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle is a limit size lipid nanoparticle described in International Patent Publication No. WO2013059922 (see also U.S. Pat. Appl. Publ. No. US20140328759, which is herein incorporated by reference in its entirety). The limit size lipid nanoparticle can comprise a lipid bilayer surrounding an aqueous core or a hydrophobic core; where the lipid bilayer can comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle can comprise a polyethylene glycol-lipid such as, but not limited to, DLPE-PEG, DMPE-PEG, DPPC-PEG and DSPE-PEG.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are delivered, localized and/or concentrated in a specific location using the delivery methods described in International Patent Publication No. WO2013063530. See also, U.S. Pat. Appl. Publ. No. US20140323907, which is herein incorporated by reference in its entirety. As a non-limiting example, a subject can be administered an empty polymeric particle prior to, simultaneously with or after delivering the polynucleotides to the subject. The empty polymeric particle undergoes a change in volume once in contact with the subject and becomes lodged, embedded, immobilized or entrapped at a specific location in the subject.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in an active substance release system (see, e.g., U.S. Patent Appl. Publ. No. US20130102545). The active substance release system can comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in a nanoparticle comprising an inner core comprising a non-cellular material and an outer surface comprising a cellular membrane. The cellular membrane can be derived from a cell or a membrane derived from a virus. As a non-limiting example, the nanoparticle is made by the methods described in International Patent Publication No. WO2013052167. As another non-limiting example, the nanoparticle described in International Patent Publication No. WO2013052167, is used to deliver the polynucleotides described herein. See also, U.S. Pat. Appl. Publ. No. US20130337066, which is herein incorporated by reference in its entirety.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in porous nanoparticle-supported lipid bilayers (protocells). Protocells are described in International Patent Publication No. WO2013056132 (see also U.S. Pat. Appl. Publ. No. US20150272885, which is herein incorporated by reference in its entirety).

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, described herein are formulated in polymeric nanoparticles as described in or made by the methods described in U.S. Pat. Nos. 8,420,123 and 8,518,963 and European Patent No. EP2073848B1 As a non-limiting example, the polymeric nanoparticle has a high glass transition temperature such as the nanoparticles described in or nanoparticles made by the methods described in U.S. Pat. No. 8,518,963. As another non-limiting example, the polymer nanoparticle for oral and parenteral formulations is made by the methods described in European Patent No. EP2073848B1.

In another embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, described herein are formulated in nanoparticles used in imaging. The nanoparticles can be liposome nanoparticles such as those described in U.S. Pat. Appl. Publ. No. US20130129636. As a non-limiting example, the liposome can comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see, e.g., U.S. Pat. Appl. Publ. No. US20130129636).

In one embodiment, the nanoparticles which can be used in the present disclosure are formed by the methods described in U.S. Pat. Appl. Publ. No. US20130130348.

The nanoparticles of the present disclosure can further include nutrients such as, but not limited to, those which deficiencies can lead to health hazards from anemia to neural tube defects. See, e.g, the nanoparticles described in International Patent Publication No WO2013072929; see also, U.S. Pat. Appl. Publ. No. US20150224035, which is herein incorporated by reference in its entirety. As a non-limiting example, the nutrient is iron in the form of ferrous, ferric salts or elemental iron, iodine, folic acid, vitamins or micronutrients.

In one embodiment, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in a swellable nanoparticle. The swellable nanoparticle can be, but is not limited to, those described in U.S. Pat. No. 8,440,231. As a non-limiting embodiment, the swellable nanoparticle is used for delivery of the polynucleotides of the present disclosure to the pulmonary system (see, e.g., U.S. Pat. No. 8,440,231).

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in polyanhydride nanoparticles such as, but not limited to, those described in U.S. Pat. No. 8,449,916.

The nanoparticles and microparticles of the present disclosure can be geometrically engineered to modulate macrophage and/or the immune response. In one aspect, the geometrically engineered particles can have varied shapes, sizes and/or surface charges in order to incorporated the polynucleotides of the present disclosure for targeted delivery such as, but not limited to, pulmonary delivery (see, e.g., International Publication No WO2013082111). Other physical features the geometrically engineering particles can have include, but are not limited to, fenestrations, angled arms, asymmetry and surface roughness, charge which can alter the interactions with cells and tissues. As a non-limiting example, nanoparticles of the present disclosure are made by the methods described in International Publication No WO2013082111 (see also U.S. Pat. Appl. Publ. No. US20150037428).

In one embodiment, the nanoparticles of the present disclosure are water soluble nanoparticles such as, but not limited to, those described in International Publication No. WO2013090601 (see also, U.S. Pat. Appl. Publ. No. US20130184444). The nanoparticles can be inorganic nanoparticles which have a compact and zwitterionic ligand in order to exhibit good water solubility. The nanoparticles can also have small hydrodynamic diameters (HD), stability with respect to time, pH, and salinity and a low level of non-specific protein binding.

In one embodiment the nanoparticles of the present disclosure are developed by the methods described in U.S. Patent Appl. Publ. No. US20130172406.

In one embodiment, the nanoparticles of the present disclosure are stealth nanoparticles or target-specific stealth nanoparticles such as, but not limited to, those described in U.S. Patent Appl. Publ. No. US20130172406. The nanoparticles of the present disclosure can be made by the methods described in U.S. Patent Appl. Publ. No. US20130172406.

In another embodiment, the stealth or target-specific stealth nanoparticles comprise a polymeric matrix. The polymeric matrix can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle is a nanoparticle-nucleic acid hybrid structure having a high density nucleic acid layer. As a non-limiting example, the nanoparticle-nucleic acid hybrid structure is made by the methods described in US Patent Appl. Publ. No. US20130171646. The nanoparticle can comprise a nucleic acid such as, but not limited to, polynucleotides described herein and/or known in the art.

At least one of the nanoparticles of the present disclosure can be embedded in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523. See also U.S. Patent Appl. Publ. No. US20150037249, which is herein incorporated by reference in its entirety.

Hyaluronidase

The intramuscular, intratumoral, or subcutaneous localized injection of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, can include hyaluronidase, which catalyzes the hydrolysis of hyaluronan.

By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440). It is useful to speed their dispersion and systemic distribution of encoded proteins produced by transfected cells. Alternatively, the hyaluronidase can be used to increase the number of cells exposed to a polynucleotide of the disclosure administered intramuscularly, intratumorally, or subcutaneously.

Nanoparticle Mimics

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the polynucleotides of the disclosure can be encapsulated in a non-virion particle which can mimic the delivery function of a virus (see International Pub. No. WO2012006376 and U.S. Patent Appl. Publ. Nos. US20130171241 and US20130195968).

Nanotubes

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be attached or otherwise bound to at least one nanotube such as, but not limited to, rosette nanotubes, rosette nanotubes having twin bases with a linker, carbon nanotubes and/or single-walled carbon nanotubes. The polynucleotides can be bound to the nanotubes through forces such as, but not limited to, steric, ionic, covalent and/or other forces. Nanotubes and nanotube formulations comprising polynucleotides are described in International Patent Application No. PCT/US2014/027077 (published as WO2014152211).

Self-Assembled Nanoparticles

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in self-assembled nanoparticles. Nucleic acid self-assembled nanoparticles are described in International Patent Application No. PCT/US2014/027077 (published as WO2014152211), such as in paragraphs [000740]-[000743]. Polymer-based self-assembled nanoparticles are described in International Patent Application No. PCT/US2014/027077. See also U.S. Patent Appl. Publ. No. US20160038612, which is herein incorporated by reference in its entirety.

Self-Assembled Macromolecules

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in amphiphilic macromolecules (AMs) for delivery. AMs comprise biocompatible amphiphilic polymers which have an alkylated sugar backbone covalently linked to poly (ethylene glycol). In aqueous solution, the AMs self-assemble to form micelles. Non-limiting examples of methods of forming AMs and AMs are described in U.S. Patent Appl. Publ. No. US20130217753.

Inorganic Nanoparticles

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in inorganic nanoparticles (U.S. Pat. No. 8,257,745). The inorganic nanoparticles can include, but are not limited to, clay substances that are water swellable. As a non-limiting example, the inorganic nanoparticle include synthetic smectite clays which are made from simple silicates (See e.g., U.S. Pat. Nos. 5,585,108 and 8,257,745).

In some embodiments, the inorganic nanoparticles comprises a core of the polynucleotides disclosed herein and a polymer shell. The polymer shell can be any of the polymers described herein and are known in the art. In an additional embodiment, the polymer shell can be used to protect the polynucleotides in the core.

Semi-Conductive and Metallic Nanoparticles

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in water-dispersible nanoparticle comprising a semiconductive or metallic material (U.S. Patent Appl. Publ. No. US20120228565) or formed in a magnetic nanoparticle (U.S. Patent Appl. Publ. No. US20120265001 and US20120283503). The water-dispersible nanoparticles can be hydrophobic nanoparticles or hydrophilic nanoparticles.

In some embodiments, the semi-conductive and/or metallic nanoparticles can comprise a core of the polynucleotides disclosed herein and a polymer shell. The polymer shell can be any of the polymers described herein and are known in the art. In an additional embodiment, the polymer shell can be used to protect the polynucleotides in the core.

Surgical Sealants: Gels and Hydrogels

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding, an OX40L polypeptide, or any combination thereof, are encapsulated into any hydrogel known in the art which forms a gel when injected into a subject. Surgical sealants such as gels and hydrogels are described in International Patent Application No. PCT/US2014/027077.

Suspension Formulations

In some embodiments, suspension formulations are provided comprising polynucleotides, water immiscible oil depots, surfactants and/or co-surfactants and/or co-solvents. Combinations of oils and surfactants can enable suspension formulation with polynucleotides. Delivery of polynucleotides in a water immiscible depot can be used to improve bioavailability through sustained release of mRNA from the depot to the surrounding physiologic environment and prevent polynucleotides degradation by nucleases.

In some embodiments, suspension formulations of mRNA are prepared using combinations of polynucleotides, oil-based solutions and surfactants. Such formulations can be prepared as a two-part system comprising an aqueous phase comprising polynucleotides and an oil-based phase comprising oil and surfactants. Exemplary oils for suspension formulations can include, but are not limited to sesame oil and Miglyol (comprising esters of saturated coconut and palm kernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, CAPMUL®, labrasol, isopropyl myristate, and/or Span 80. In some embodiments, suspensions can comprise co-solvents including, but not limited to ethanol, glycerol and/or propylene glycol.

Suspensions can be formed by first preparing polynucleotides formulation comprising an aqueous solution of polynucleotide and an oil-based phase comprising one or more surfactants. Suspension formation occurs as a result of mixing the two phases (aqueous and oil-based). In some embodiments, such a suspension can be delivered to an aqueous phase to form an oil-in-water emulsion. In some embodiments, delivery of a suspension to an aqueous phase results in the formation of an oil-in-water emulsion in which the oil-based phase comprising polynucleotides forms droplets that can range in size from nanometer-sized droplets to micrometer-sized droplets. In some embodiments, specific combinations of oils, surfactants, cosurfactants and/or co-solvents can be utilized to suspend polynucleotides in the oil phase and/or to form oil-in-water emulsions upon delivery into an aqueous environment.

In some embodiments, suspensions provide modulation of the release of polynucleotides into the surrounding environment. In such embodiments, polynucleotides release can be modulated by diffusion from a water immiscible depot followed by resolubilization into a surrounding environment (e.g. an aqueous environment).

In some embodiments, polynucleotides within a water immiscible depot (e.g. suspended within an oil phase) result in altered polynucleotides stability (e.g. altered degradation by nucleases).

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated such that upon injection, an emulsion forms spontaneously (e.g. when delivered to an aqueous phase). Such particle formation can provide a high surface area to volume ratio for release of polynucleotides from an oil phase to an aqueous phase.

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in a nanoemulsion such as, but not limited to, the nanoemulsions described in U.S. Pat. No. 8,496,945. The nanoemulsions can comprise nanoparticles described herein. As a non-limiting example, the nanoparticles can comprise a liquid hydrophobic core which can be surrounded or coated with a lipid or surfactant layer. The lipid or surfactant layer can comprise at least one membrane-integrating peptide and can also comprise a targeting ligand (see, e.g., U.S. Pat. No. 8,496,945).

Cations and Anions

Formulations of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, can include cations or anions. In some embodiments, the formulations include metal cations such as, but not limited to, $Zn^{2+}$, $Ca^{2+}$, $Cu^{2+}$, $Mg^{2+}$ and combinations thereof. As a non-limiting example, formulations include polymers and a polynucleotides complexed with a metal cation (see, e.g., U.S. Pat. Nos. 6,265,389 and 6,555,525).

In some embodiments, cationic nanoparticles comprising combinations of divalent and monovalent cations are formulated with polynucleotides. Such nanoparticles can form spontaneously in solution over a given period (e.g. hours, days, etc). Such nanoparticles do not form in the presence of divalent cations alone or in the presence of monovalent cations alone. The delivery of polynucleotides in cationic nanoparticles or in one or more depot comprising cationic nanoparticles can improve polynucleotide bioavailability by acting as a long-acting depot and/or reducing the rate of degradation by nucleases.

Molded Nanoparticles and Microparticles

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in nanoparticles and/or microparticles. As an example, the nanoparticles and/or microparticles can be made using the PRINT® technology by LIQUIDA TECHNOLOGIES® (Morrisville, N.C.) (see, e.g., International Pub. No. WO2007024323).

In some embodiments, the nanoparticles comprise a core of the polynucleotides disclosed herein and a polymer shell. The polymer shell can be any of the polymers described herein and are known in the art. In an additional embodiment, the polymer shell can be used to protect the polynucleotides in the core.

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in microparticles. The microparticles can contain a core of the polynucleotides and a cortex of a biocompatible and/or biodegradable polymer. As a non-limiting example, the microparticles which can be used with the present disclosure can be those described in U.S. Pat. No. 8,460,709, U.S. Patent Appl. Publ. No. US20130129830 and International Patent Publication No WO2013075068. As another non-limiting example, the microparticles can be designed to extend the release of the polynucleotides of the present disclosure over a desired period of time (see e.g, extended release of a therapeutic protein in U.S. Patent Appl. Publ. No. US20130129830).

NanoJackets and NanoLiposomes

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in NanoJackets and NanoLiposomes by Keystone Nano (State College, Pa.). NanoJackets are made of compounds that are naturally found in the body including calcium, phosphate and can also include a small amount of silicates. Nanojackets can range in size from 5 to 50 nm and can be used to deliver hydrophilic and hydrophobic compounds such as, but not limited to, polynucleotides.

NanoLiposomes are made of lipids such as, but not limited to, lipids which naturally occur in the body. NanoLiposomes can range in size from 60-80 nm and can be used to deliver hydrophilic and hydrophobic compounds such as, but not limited to, polynucleotides. In one aspect, the polynucleotide comprising an mRNA encoding an IL-23 polypeptide, the polynucleotide comprising an mRNA encoding an IL-36-gamma polypeptide, and/or the polynucleotide comprising an mRNA encoding an OX40L polypeptide are formulated in a NanoLiposome such as, but not limited to, Ceramide NanoLiposomes.

Minicells

In one aspect, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be formulated in bacterial minicells. As a non-limiting example, bacterial minicells are those described in International Publication No. WO2013088250 or U.S. Patent Publication No. US20130177499. The bacterial minicells comprising therapeutic agents such as polynucleotides described herein can be used to deliver the therapeutic agents to brain tumors.

Semi-Solid Compositions

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated with a hydrophobic matrix to form a semi-solid composition. As a non-limiting example, the semi-solid composition or paste-like composition is made by the methods described in International Patent Publication No. WO201307604. The semi-solid composition can be a sustained release formulation as described in International Patent Publication No. WO201307604.

In another embodiment, the semi-solid composition further has a micro-porous membrane or a biodegradable polymer formed around the composition (see e.g., International Patent Publication No. WO201307604).

The semi-solid composition using the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can have the characteristics of the semi-solid mixture as described in International Patent Publication No WO201307604 (e.g., a modulus of elasticity of at least $10^{-4}$ $N \cdot mm^{-2}$, and/or a viscosity of at least 100 mPa·s).

Exosomes

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in exosomes. The exosomes can be loaded with at least one polynucleotide and delivered to cells, tissues and/or organisms. As a non-limiting example, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, can be loaded in the exosomes described in International Publication No. WO2013084000.

Silk-Based Delivery

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in a sustained release silk-based delivery system. The silk-based delivery system can be formed by contacting a silk fibroin solution with a therapeutic agent such as, but not limited to, the polynucleotide comprising an mRNA encoding an IL-23 polypeptide, the polynucleotide comprising an mRNA encoding an IL-36-gamma polypeptide, the polynucleotide comprising an mRNA encoding an OX40L polypeptide, or any combination thereof. As a non-limiting example, the sustained release silk-based delivery system which can be used in the present disclosure and methods of making such system are described in U.S. Patent Publication No. 20130177611.

Microparticles

In some embodiments, formulations comprising a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, comprise microparticles. The microparticles can comprise a polymer described herein and/or known in the art such as, but not limited to, poly(α-hydroxy acid), a polyhydroxy butyric acid, a polycaprolactone, a polyorthoester and a polyanhydride. The microparticle can have adsorbent surfaces to adsorb biologically active molecules such as polynucleotides. As a non-limiting example microparticles for use with the present disclosure and methods of making microparticles are described in U.S. Patent Publication No. US2013195923 and US20130195898 and U.S. Pat. Nos. 8,309,139 and 8,206,749.

In another embodiment, the formulation is a microemulsion comprising microparticles and polynucleotides. As a non-limiting example, microemulsions comprising microparticles are described in U.S. Patent Publication Nos. 2013195923 and 20130195898 and U.S. Pat. Nos. 8,309,139 and 8,206,749.

Amino Acid Lipids

In some embodiments, the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or any combination thereof, are formulated in amino acid lipids. Amino acid lipids are lipophilic compounds comprising an amino acid residue and one or more lipophilic tails. Non-limiting examples of amino acid lipids and methods of making amino acid lipids are described in U.S. Pat. No. 8,501,824.

In some embodiments, the amino acid lipids have a hydrophilic portion and a lipophilic portion. The hydrophilic portion can be an amino acid residue and a lipophilic portion can comprise at least one lipophilic tail.

In some embodiments, the amino acid lipid formulations are used to deliver the polynucleotides to a subject.

In another embodiment, the amino acid lipid formulations deliver a polynucleotide in releasable form which comprises an amino acid lipid that binds and releases the polynucleotides. As a non-limiting example, the release of the polynucleotides can be provided by an acid-labile linker such as, but not limited to, those described in U.S. Pat. Nos. 7,098,032, 6,897,196, 6,426,086, 7,138,382, 5,563,250, and 5,505,931.

Microvesicles

In some embodiments, the polynucleotides comprising an mRNA encoding an IL-23, IL-36-gamma, IL-18 and/or OX40L polypeptide, are formulated in microvesicles. Non-limiting examples of microvesicles include those described in US20130209544.

In some embodiments, the microvesicle is an ARRDC1-mediated microvesicles (ARMMs). Non-limiting examples of ARMMs and methods of making ARMMs are described in International Patent Publication No. WO2013119602.

Interpolyelectrolyte Complexes

In some embodiments, the polynucleotides comprising an mRNA encoding an IL-23, IL-36-gamma, IL-18 and/or OX40L polypeptide are formulated in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368.

Crystalline Polymeric Systems

In some embodiments, the polynucleotides comprising an mRNA encoding an IL-23, IL-36-gamma, 11-18 and/or OX40L polypeptide are formulated in crystalline polymeric systems. Crystalline polymeric systems are polymers with crystalline moieties and/or terminal units comprising crystalline moieties. Non-limiting examples of polymers with crystalline moieties and/or terminal units comprising crystalline moieties termed "CYC polymers," crystalline polymer systems and methods of making such polymers and systems are described in U.S. Pat. No. 8,524,259.

Excipients

Pharmaceutical formulations can additionally comprise a pharmaceutically acceptable excipient, which, as used herein, includes, but are not limited to, any and all solvents, dispersion media, diluents, or other liquid vehicles, dispersion or suspension aids, surface active agents, isotonic agents, thickening or emulsifying agents, preservatives, solid binders, lubricants, flavoring agents, stabilizers, antioxidants, osmolality adjusting agents, pH adjusting agents and the like, as suited to the particular dosage form desired. Various excipients for formulating pharmaceutical compositions and techniques for preparing the composition are known in the art (see *Remington: The Science and Practice of Pharmacy,* 21$^{st}$ Edition, A. R. Gennaro (Lippincott, Williams & Wilkins, Baltimore, Md., 2006). The use of a conventional excipient medium can be contemplated within the scope of the present disclosure, except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use for humans and for veterinary use. In some embodiments, an excipient can be approved by United States Food and Drug Administration. In some embodiments, an excipient can be of pharmaceutical grade. In some embodiments, an excipient can meet the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients can optionally be included in pharmaceutical compositions. The composition can also include excipients such as cocoa butter and suppository waxes, coloring agents, coating agents, sweetening, flavoring, and/or perfuming agents.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); amino acids (e.g., glycine); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives can include, but are not limited to, antioxidants, chelating agents, antimicrobial preservatives, antifungal preservatives, alcohol preservatives, acidic preservatives, and/or other preservatives. Oxidation is a potential degradation pathway for mRNA, especially for liquid mRNA formulations. In order to prevent oxidation, antioxidants can be added to the formulation. Exemplary antioxidants include, but are not limited to, alpha tocopherol, ascorbic acid, acorbyl palmitate, benzyl alcohol, butylated hydroxyanisole, EDTA, m-cresol, methionine, butylated hydroxytoluene, monothioglycerol, potassium metabisulfite, propionic acid, propyl gallate, sodium ascorbate, sodium bisulfite, sodium metabisulfite, thioglycerol and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

In some embodiments, the pH of polynucleotide solutions is maintained between pH 5 and pH 8 to improve stability.

Exemplary buffers to control pH can include, but are not limited to sodium phosphate, sodium citrate, sodium succinate, histidine (or histidine-HCl), sodium carbonate, and/or sodium malate. In another embodiment, the exemplary buffers listed above can be used with additional monovalent counterions (including, but not limited to potassium). Divalent cations can also be used as buffer counterions; however, these are not preferred due to complex formation and/or mRNA degradation.

Exemplary buffering agents can also include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Exemplary additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Cryoprotectants for mRNA

In some embodiments, the polynucleotide formulations comprise cryoprotectants. As used herein, the term "cryoprotectant" refers to one or more agent that when combined with a given substance, helps to reduce or eliminate damage to that substance that occurs upon freezing. In some embodiments, cryoprotectants are combined with polynucleotides in order to stabilize them during freezing. Frozen storage of mRNA between −20° C. and −80° C. can be advantageous for long term (e.g. 36 months) stability of polynucleotide. In some embodiments, cryoprotectants are included in polynucleotide formulations to stabilize polynucleotide through freeze/thaw cycles and under frozen storage conditions. Cryoprotectants of the present disclosure can include, but are not limited to sucrose, trehalose, lactose, glycerol, dextrose, raffinose and/or mannitol. Trehalose is listed by the Food and Drug Administration as being generally regarded as safe (GRAS) and is commonly used in commercial pharmaceutical formulations.

Bulking Agents

In some embodiments, the polynucleotide formulations comprise bulking agents. As used herein, the term "bulking agent" refers to one or more agents included in formulations to impart a desired consistency to the formulation and/or stabilization of formulation components. In some embodiments, bulking agents are included in lyophilized polynucleotide formulations to yield a "pharmaceutically elegant" cake, stabilizing the lyophilized polynucleotides during long term (e.g. 36 month) storage. Bulking agents of the present disclosure can include, but are not limited to sucrose, trehalose, mannitol, glycine, lactose and/or raffinose. In some embodiments, combinations of cryoprotectants and bulking agents (for example, sucrose/glycine or trehalose/mannitol) can be included to both stabilize polynucleotides during freezing and provide a bulking agent for lyophilization.

Non-limiting examples of formulations and methods for formulating the polynucleotides of the present disclosure are also provided in International Publication No WO2013090648 filed Dec. 14, 2012.

Naked Delivery

The polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, the polynucleotide comprising an mRNA encoding an OX40L polypeptide, or a combination thereof can be delivered to a cell (e.g., to a tumor cell) naked. As used herein in, "naked" refers to delivering polynucleotides free from agents which promote transfection. For example, the polynucleotides delivered to the cell, e.g., tumor cell, can contain no modifications. The naked polynucleotides comprising an mRNA encoding an IL-23, IL-36-gamma, IL-18, and/or OX40L polypeptide can be delivered to the tumor cell using routes of administration known in the art, e.g., intratumoral administration, and described herein.

Parenteral and Injectable Administration

Liquid dosage forms for parenteral administration, e.g. intratumoral, include, but are not limited to, pharmaceutically acceptable emulsions, microemulsions, solutions, suspensions, syrups, and/or elixirs. In addition to active ingredients, liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

A pharmaceutical composition for parenteral administration, e.g., intratumoral administration, can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations, e.g., intratumoral, can be sterilized, for example, by filtration through a bacterial-retaining filter, and/or by incorporating sterilizing agents in the form of sterile solid compositions which can be dissolved or dispersed in sterile water or other sterile injectable medium prior to use.

Injectable formulations, e.g., intratumoral, can be for direct injection into a region of a tissue, organ and/or subject, e.g., tumor.

In order to prolong the effect of an active ingredient, it is often desirable to slow the absorption of the active ingredient from intratumoral injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Dosage Forms

A pharmaceutical composition described herein can be formulated into a dosage form described herein, such as a topical, intranasal, intratracheal, or injectable (e.g., intravenous, intratumoral, intraocular, intravitreal, intramuscular, intracardiac, intraperitoneal, subcutaneous).

Liquid Dosage Forms

Liquid dosage forms for parenteral administration (e.g., intratumoral) include, but are not limited to, pharmaceutically acceptable emulsions, microemulsions, solutions, suspensions, syrups, and/or elixirs. In addition to active ingredients, liquid dosage forms can comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions can be mixed with solubilizing agents such as CREMOPHOR®, alcohols, oils, modified oils, glycols, polysorbates, cyclodextrins, polymers, and/or combinations thereof.

Injectable

Injectable preparations (e.g., intratumoral), for example, sterile injectable aqueous or oleaginous suspensions can be formulated according to the known art and can include suitable dispersing agents, wetting agents, and/or suspending agents. Sterile injectable preparations can be sterile injectable solutions, suspensions, and/or emulsions in nontoxic parenterally acceptable diluents and/or solvents, for example, a solution in 1,3-butanediol. Among the acceptable vehicles and solvents that can be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it can be desirable to slow the absorption of the active ingredient from subcutaneous or intramuscular injection. This can be accomplished by the use of a liquid suspension of crystalline or amorphous material with poor water solubility. The rate of absorption of the polynucleotides then depends upon its rate of dissolution which, in turn, can depend upon crystal size and crystalline form. Alternatively, delayed absorption of a parenterally administered polynucleotides can be accomplished by dissolving or suspending the polynucleotides in an oil vehicle. Injectable depot forms are made by forming microencapsule matrices of the polynucleotides in biodegradable polymers such as polylactide-polyglycolide. Depending upon the ratio of polynucleotides to polymer and the nature of the particular polymer employed, the rate of polynucleotides release can be controlled. Examples of other biodegradable polymers include, but are not limited to, poly(orthoesters) and poly(anhydrides). Depot injectable formulations can be prepared by entrapping the polynucleotides in liposomes or microemulsions which are compatible with body tissues.

Methods of Intratumoral Delivery

The pharmaceutical compositions disclosed herein are suitable for administration to tumors. The term "tumor" is used herein in a broad sense and refers to any abnormal new growth of tissue that possesses no physiological function and arises from uncontrolled usually rapid cellular proliferation. The term "tumor" as used herein relates to both benign tumors and to malignant tumors.

In certain embodiments, the disclosure provides a method of delivering a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or a combination thereof, to a tumor comprising formulating the polynucleotide in the pharmaceutical composition described herein, e.g., in lipid nanoparticle form, and administering the pharmaceutical composition to a tumor. The administration of the pharmaceutical composition to the tumor can be performed using any method known in the art (e.g., bolus injection, perfusion, surgical implantation, etc.).

The delivery of the polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, or a polynucleotide comprising an mRNA encoding an OX40L polypeptide, alone or in combination, to a tumor using a pharmaceutical compositions for intratumoral administration disclosed herein can:

(i) increase the retention of the polynucleotide in the tumor;

(ii) increase the levels of expressed polypeptide in the tumor compared to the levels of expressed polypeptide in peritumoral tissue;

(iii) decrease leakage of the polynucleotide or expressed product to off-target tissue (e.g., peritumoral tissue, or to distant locations, e.g., liver tissue); or, (iv) any combination thereof, wherein the increase or decrease observed for a certain property is relative to a corresponding reference composition (e.g., composition in which compounds of formula (I) are not present or have been substituted by another ionizable amino lipid, e.g., MC3).

In one embodiment, a decrease in leakage can be quantified as increase in the ratio of polypeptide expression in the tumor to polypeptide expression in non-tumor tissues, such as peritumoral tissue or to another tissue or organ, e.g., liver tissue.

Delivery of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or a combination thereof to a tumor involves administering a pharmaceutical composition disclosed herein, e.g., in nanoparticle form, including the polynucleotide encoding an IL-23, IL-36-gamma, IL-18 and/or an OX40L polypeptide to a subject, where administration of the pharmaceutical composition involves contacting the tumor with the composition.

In the instance that the polynucleotide comprising an mRNA encoding an IL-23 polypeptide, the polynucleotide comprising an mRNA encoding an IL-36-gamma polypeptide, the polynucleotide comprising an mRNA encoding an IL-18 polypeptide, and the polynucleotide comprising an mRNA encoding an OX40L polypeptide, is an mRNA, upon contacting a cell in the tumor with the pharmaceutical composition, a translatable mRNA may be translated in the cell to produce a polypeptide of interest. However, mRNAs that are substantially not translatable may also be delivered to tumors. Substantially non-translatable mRNAs may be useful as vaccines and/or may sequester translational components of a cell to reduce expression of other species in the cell.

The pharmaceutical compositions disclosed herein can increase specific delivery. As used herein, the term "specific delivery," means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, or a polynucleotide comprising an mRNA encoding an OX40L polypeptide, by pharmaceutical composition disclosed herein (e.g., in nanoparticle form) to a target tissue of interest (e.g., a tumor) compared to an off-target tissue (e.g., mammalian liver).

The level of delivery of a nanoparticle to a particular tissue may be measured, for example, by comparing (i) the amount of protein expressed from a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, or a polynucleotide comprising an mRNA encoding an OX40L polypeptide, in a tissue to the weight of said tissue;

(ii) comparing the amount of the polynucleotide in a tissue to the weight of said tissue; or (iii) comparing the amount of protein expressed from a polynucleotide comprising an mRNA encoding an IL-23 polypeptide, a polynucleotide comprising an mRNA encoding an IL-36-gamma polypeptide, or a polynucleotide comprising an mRNA encoding an IL-18 polypeptide, or a polynucleotide comprising an mRNA encoding an OX40L polypeptide, in a tissue to the amount of total protein in said tissue.

Specific delivery to a tumor or a particular class of cells in the tumor implies that a higher proportion of pharmaceutical composition including a polynucleotide encoding an IL-23, IL-36-gamma, and/or OX40L polypeptide, is delivered to the target destination (e.g., target tissue) relative to other off-target destinations upon administration of a pharmaceutical composition to a subject.

Methods for Improved Intratumoral Delivery

The present disclosure also provides methods to achieve improved intratumoral delivery of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding an OX40L polypeptide, when a pharmaceutical composition disclosed herein (e.g., in nanoparticle form) is administered to a tumor. The improvement in delivery can be due, for example, to (i) increased retention of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding an OX40L polypeptide, in the tumor;

(ii) increased levels of expressed polypeptide in the tumor compared to the levels of expressed polypeptide in peritumoral tissue;

(iii) decreased leakage of the polynucleotide or expressed product to off-target tissue (e.g., peritumoral tissue, or to distant locations, e.g., liver tissue); or, (iv) any combination thereof, wherein the increase or decrease observed for a certain property is relative to a corresponding reference composition (e.g., composition in which compounds of formula (I) are not present or have been substituted by another ionizable amino lipid, e.g., MC3).

In one embodiment, a decrease in leakage can be quantified as increase in the ratio of polypeptide expression in the tumor to polypeptide expression in non-tumor tissues, such as peritumoral tissue or to another tissue or organ, e.g., liver tissue.

Another improvement in delivery caused as a result of using the pharmaceutical compositions disclosed herein is a reduction in immune response with respect to the immune response observed when other lipid components are used to deliver the same a therapeutic agent or polynucleotide encoding a therapeutic agent.

Accordingly, the present disclosure provides a method of increasing retention of a therapeutic agent (e.g., a polypeptide administered as part of the pharmaceutical composition) in a tumor tissue in a subject, comprising administering intratumorally to the tumor tissue a pharmaceutical composition disclosed herein, wherein the retention of the therapeutic agent in the tumor tissue is increased compared to the retention of the therapeutic agent in the tumor tissue after administering a corresponding reference composition.

Also provided is a method of increasing retention of a polynucleotide in a tumor tissue in a subject, comprising administering intratumorally to the tumor tissue a pharmaceutical composition disclosed herein, wherein the retention of the polynucleotide in the tumor tissue is increased compared to the retention of the polynucleotide in the tumor tissue after administering a corresponding reference composition.

Also provided is a method of increasing retention of an expressed polypeptide in a tumor tissue in a subject, comprising administering to the tumor tissue a pharmaceutical composition disclosed herein, wherein the pharmaceutical composition comprises a polynucleotide encoding the expressed polypeptide, and wherein the retention of the expressed polypeptide in the tumor tissue is increased compared to the retention of the polypeptide in the tumor tissue after administering a corresponding reference composition.

The present disclosure also provides a method of decreasing expression leakage of a polynucleotide administered intratumorally to a subject in need thereof, comprising administering said polynucleotide intratumorally to the tumor tissue as a pharmaceutical composition disclosed herein, wherein the expression level of the polypeptide in non-tumor tissue is decreased compared to the expression level of the polypeptide in non-tumor tissue after administering a corresponding reference composition.

Also provided is a method of decreasing expression leakage of a therapeutic agent (e.g., a polypeptide administered as part of the pharmaceutical composition) administered intratumorally to a subject in need thereof, comprising administering said therapeutic agent intratumorally to the tumor tissue as a pharmaceutical composition disclosed herein, wherein the amount of therapeutic agent in non-tumor tissue is decreased compared to the amount of therapeutic in non-tumor tissue after administering a corresponding reference composition.

Also provided is a method of decreasing expression leakage of an expressed polypeptide in a tumor in a subject, comprising administering to the tumor tissue a pharmaceutical composition disclosed herein, wherein the pharmaceutical composition comprises a polynucleotide encoding the expressed polypeptide, and wherein the amount of expressed polypeptide in non-tumor tissue is decreased compared to the amount of expressed polypeptide in non-tumor tissue after administering a corresponding reference composition.

In some embodiments, the non-tumoral tissue is peritumoral tissue. In other embodiments, the non-tumoral tissue is liver tissue.

The present disclosure also provided a method to reduce or prevent the immune response caused by the intratumoral administration of a pharmaceutical composition, e.g., a pharmaceutical composition comprising lipids known in the art, by replacing one or all the lipids in such composition with a compound of Formula (I). For example, the immune response caused by the administration of a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding an OX40L polypeptide in a pharmaceutical composition comprising MC3 (or other lipids known in the art) can be prevented (avoided) or ameliorated by replacing MC3 with a compound of Formula (I), e.g., Compound 18.

In some embodiments, the immune response observed after a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, is administered in a pharmaceutical composition disclosed herein is not elevated compared to the immune response observed when the therapeutic agent or a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, is administered in phosphate buffered saline (PBS) or another physiological buffer solution (e.g., Ringer's solution, Tyrode's solution, Hank's balanced salt solution, etc.).

In some embodiments, the immune response observed after a therapeutic agent or a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof, is administered in a pharmaceutical composition disclosed herein is not elevated compared to the immune response observed when PBS or another physiological buffer solution is administered alone.

In some embodiments, no immune response is observed when a pharmaceutical composition disclosed herein is administered intratumorally to a subject.

Accordingly, the present disclosure also provides a method of delivering a therapeutic agent or a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding an OX40L polypeptide to a subject in need thereof, comprising administering intratumorally to the subject a pharmaceutical composition disclosed herein, wherein the immune response caused by the administration of the pharmaceutical composition is not elevated compared to the immune response caused by the intratumoral administration of (i) PBS alone, or another physiological buffer solution (e.g., Ringer's solution, Tyrode's solution, Hank's balanced salt solution, etc.);

(ii) the therapeutic agent or a polynucleotide comprising an mRNA encoding an IL-23 polypeptide and a polynucleotide comprising an mRNA encoding an IL-36-gamma polypeptide a polynucleotide comprising an mRNA encoding an IL-18 polypeptide, in PBS or another physiological buffer solution; or the therapeutic agent or a polynucleotide comprising an mRNA encoding an IL-23 polynucleotide, a polynucleotide comprising an mRNA encoding an IL-36-gamma polypeptide, a polynucleotide comprising an mRNA encoding an IL-18 polypeptide, and a polynucleotide comprising an mRNA encoding an OX40L polypeptide in PBS or another physiological buffer solution; or, (iii) a corresponding reference composition, i.e., the same pharmaceutical composition in which the compound of Formula (I) is substituted by another ionizable amino lipid, e.g., MC3.

XIII. Kits and Devices

Kits

The disclosure provides a variety of kits for conveniently and/or effectively carrying out methods or compositions of the present disclosure. Typically kits will comprise sufficient amounts and/or numbers of components to allow a user to perform multiple treatments of a subject(s) and/or to perform multiple experiments.

In one aspect, the present disclosure provides kits comprising the polynucleotides of the disclosure. In some embodiments, the kit comprises one or more polynucleotides.

The kits can be for protein production, comprising a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or a polynucleotide comprising an mRNA encoding an OX40L polypeptide. The kit can further comprise packaging and instructions and/or a delivery agent to form a formulation composition. The delivery agent can comprise a saline, a buffered solution, a lipidoid or any delivery agent disclosed herein.

In some aspects, the disclosure provides a kit comprising a container comprising a polynucleotide (e.g., an mRNA) composition or a lipid nanoparticle comprising polynucleotides as (e.g., mRNAs) as disclosed herein, and an optional pharmaceutically acceptable carrier, and a package insert comprising instructions for administration of the lipid nanoparticle or pharmaceutical composition for treating or delaying progression of cancer in an individual. In some aspects, the package insert further comprises instructions for administration of the pharmaceutical composition in combination with a composition comprising a checkpoint inhibitor polypeptide and an optional pharmaceutically acceptable carrier for treating or delaying progression of cancer in an individual.

In other aspects, the disclosure provides a kit comprising a medicament comprising a lipid nanoparticle comprising polynucleotides (e.g., mRNAs) as disclosed herein, and an optional pharmaceutically acceptable carrier, and a package insert comprising instructions for administration of the medicament alone or in combination with a composition comprising a checkpoint inhibitor polypeptide and an optional pharmaceutically acceptable carrier for treating or delaying progression of cancer in an individual. In some aspects, the kit further comprises a package insert comprising instructions for administration of the first medicament and the second medicament for treating or delaying progression of cancer in an individual.

In related aspects, the checkpoint inhibitor polypeptide inhibits PD1, PD-L1, CTLA4, or a combination thereof. In some aspects, the checkpoint inhibitor polypeptide is an antibody, such as an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab.

In some embodiments, the kit comprises a buffer solution including, for example, sodium chloride, calcium chloride, phosphate and/or EDTA. In another embodiment, the buffer solution includes, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046). In a further embodiment, the buffer solutions is precipitated or it is lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present disclosure provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present disclosure provides kits for protein production, comprising a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, and/or the polynucleotide comprising an mRNA encoding an OX40L polypeptide, wherein the polynucleotides exhibits reduced degradation by a cellular nuclease, and packaging and instructions.

In some embodiments, a single polynucleotide comprises (i) the mRNA encoding an IL-23 polypeptide and the mRNA encoding an IL-36-gamma polypeptide or a polynucleotide comprising an mRNA encoding an IL-18 polypeptide, (ii) the mRNA encoding an IL-23 polypeptide and the mRNA encoding an OX40L polypeptide, or (iii) the mRNA encoding an IL-36-gamma polypeptide or a polynucleotide comprising an mRNA encoding an IL-18 polypeptide, and the mRNA encoding an OX40L polypeptide. In some embodiments, a single polynucleotide comprises the mRNA encoding an IL-23 polypeptide, the mRNA encoding an IL-36-gamma polypeptide, or the polynucleotide comprising an mRNA encoding an IL-18 polypeptide, the mRNA encoding a third protein (e.g., an OX40L polypeptide), or any combination thereof.

Devices

The present disclosure provides for devices which can incorporate a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding a IL-36-gamma polypeptide. For example, the device can incorporate a polynucleotide comprising an mRNA encoding an IL-23 polypeptide, a polynucleotide comprising an mRNA encoding an IL-36-gamma polypeptide, a polynucleotide comprising an mRNA encoding an IL-18 polypeptide, a polynucleotide comprising an mRNA encoding an OX40L polypeptide, or any combination thereof. These devices contain in a stable formulation the reagents to synthesize a polynucleotide in a formulation available to be immediately delivered to a subject in need thereof, such as a human patient. In some embodiments, a single polynucleotide comprises the mRNA encoding an IL-23 polypeptide and the mRNA encoding an IL-36-gamma polypeptide or a polynucleotide comprising an mRNA encoding an IL-18 polypeptide. In some embodiments, a single polynucleotide comprises the mRNA encoding an IL-23 polypeptide, the mRNA encoding an IL-36-gamma polypeptide, or the polynucleotide comprising an mRNA encoding an IL-18 polypeptide, the mRNA encoding an OX40L polypeptide, or any combination thereof.

Devices for administration can be employed to deliver a polynucleotide comprising an mRNA encoding an IL-23 polypeptide and a polynucleotide comprising an mRNA encoding an IL-36-gamma polypeptide, a polynucleotide comprising an mRNA encoding an IL-18 polypeptide, and a polynucleotide comprising an mRNA encoding an OX40L polypeptide according to single, multi- or split-dosing regimens taught herein. Such devices are taught in, for example, International Publication No. WO 2013151666 A2.

Method and devices known in the art for multi-administration to cells, organs and tissues are contemplated for use in conjunction with the methods and compositions disclosed herein as embodiments of the present disclosure. These include, for example, those methods and devices having multiple needles, hybrid devices employing for example lumens or catheters as well as devices utilizing heat, electric current or radiation driven mechanisms.

According to the present disclosure, these multi-administration devices can be utilized to deliver the single, multi- or split doses contemplated herein. Such devices are taught for example in, International Publication No. WO 2013151666 A2.

Other Embodiments of the Disclosure

E1. A method of reducing or decreasing a size of a tumor or inhibiting a tumor growth in a subject in need thereof comprising administering to the subject at least two polynucleotides in combination, wherein the at least two polynucleotides are selected from a first polynucleotide encoding a first protein comprising an Interleukin-23 (IL-23) polypeptide, a second polynucleotide encoding a second protein comprising an Interleukin-36-gamma (IL-36-gamma) polypeptide, and a third polynucleotide encoding a third protein comprising an OX40L polypeptide.

E2. The method of embodiment 1, the at least two polynucleotides comprise (i) the first polynucleotide and the second polynucleotide; (ii) the first polynucleotide and the third polynucleotide; (iii) the second polynucleotide and the third polynucleotide; or (iv) the first polynucleotide, the second polynucleotide, and the third polynucleotide.

E3. The method of embodiment 1, the at least two polynucleotides comprise the first polynucleotide, the second polynucleotide, and the third polynucleotide.

E4. The method of embodiment 1, wherein the administration reduces or decreases a size of a tumor or inhibits a tumor growth at least 1.5 fold, at least 2 fold, at least 2.5 fold, at least 3 fold, at least 3.5 fold, at least 4 fold, at least 4.5 fold, or at least 5 fold better than (i) an administration of the first polynucleotide encoding the first protein; (ii) an administration of the second polynucleotide encoding the second protein; or (iii) an administration of the third polynucleotide encoding the third protein.

E5. The method of embodiment 1 or 4, wherein the first polynucleotide comprises an mRNA encoding the first protein.

E6. The method of any one of embodiments 1 to 5, wherein the second polynucleotide comprises an mRNA encoding the second protein.

E7. The method of any one of embodiments 1 to 6, wherein the third polynucleotide comprises an mRNA encoding the third protein.

E8. The method of any one of embodiments 1 to 7, wherein the first polynucleotide, the second polynucleotide and/or the third polynucleotide comprise at least one chemically modified nucleoside.

E9. The method of embodiment 8, wherein the at least one chemically modified nucleoside is selected from the group consisting of any of those listed in Section XI and a combination thereof.

E10. The method of embodiment 8 or 9, wherein the at least one chemically modified nucleoside is selected from the group consisting of pseudouridine, N1-methylpseudouridine, 5-methylcytosine, 5-methoxyuridine, and a combination thereof.

E11. The method of any one of embodiments 1 to 10, wherein the nucleosides in the first polynucleotide, the second polynucleotide and/or the third polynucleotide are chemically modified by at least 10%, at least 20%, at least 30%, at least 40%, at least 50%, at least 60%, at least 70%, at least 80%, at least 90%, at least 95%, at least 99%, or 100%.

E12. The method of any one of embodiments 8 to 11, wherein the chemically modified nucleosides in the first polynucleotide, the second polynucleotide and/or the third polynucleotide are selected from the group consisting of uridine, adenine, cytosine, guanine, and any combination thereof.

E13. The method of any one of embodiments 1 to 12, wherein the uridine nucleosides in the first polynucleotide, the second polynucleotide and/or the third polynucleotide are chemically modified by at least 10%, at least 20%, at least 30%, at least 40%, at least 50%, at least 60%, at least 70%, at least 80%, at least 90%, at least 95%, at least 99%, or 100%.

E14. The method of any one of embodiments 1 to 13, wherein the adenosine nucleosides in the first polynucleotide, the second polynucleotide and/or the third polynucleotide are chemically modified by at least 10%, at least 20%, at least 30%, at least 40%, at least 50%, at least 60%, at least 70%, at least 80%, at least 90%, at least 95%, at least 99%, or 100%.

E15. The method of any one of embodiments 1 to 14, wherein the cytidine nucleosides in the first polynucleotide, the second polynucleotide and/or the third polynucleotide are chemically modified by at least 10%, at least 20%, at least 30%, at least 40%, at least 50%, at least 60%, at least 70%, at least 80%, at least 90%, at least 95%, at least 99%, or 100%.

E16. The method of any one of embodiments 1 to 15, wherein the guanosine nucleosides in the first polynucleotide, the second polynucleotide and/or the third polynucleotide are chemically modified by at least 10%, at least 20%, at least 30%, at least 40%, at least 50%, at least 60%, at least 70%, at least 80%, at least 90%, at least 95%, at least 99%, or 100%.

E17. The method of any one of embodiments 5 to 16, wherein each of the mRNA encoding the first protein, the mRNA encoding the second protein, and the mRNA encoding the third protein comprises an open reading frame.

E18. The method of any one of embodiments 1 to 17, wherein the IL-23 polypeptide comprises an IL-12p40 subunit comprising an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of binding to an IL-23p19 subunit and forming IL-23, which has an IL-23 activity.

E19. The method of embodiment 18, wherein the IL-12p40 subunit is encoded by a nucleic acid sequence at least 70%, at least 80%, at least 85%, at least 90%, at least 95%, at least 99%, or 100% identical to a sequence listed in Table 1.

E20. The method of any one of embodiments 1 to 19, wherein the IL-23 polypeptide comprises an IL-23p19 subunit comprising an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of binding to an IL-12p40 subunit and forming IL-23, which has an IL-23 activity.

E21. The method of embodiment 20, wherein the IL-23p19 subunit is encoded by a nucleic acid sequence at least 70%, at least 80%, at least 85%, at least 90%, at least 95%, at least 99%, or 100% identical to a sequence listed in Table 1.

E22. The method of embodiment 20 or 21, wherein the IL-12p40 subunit and the IL-23P19 subunit are on a single polypeptide chain or two different chains.

E23. The method of embodiment 20 or 21, wherein the IL-12p40 subunit and the IL-23P19 subunit are fused by a linker.

E24. The method of embodiment 23, wherein the linker comprises (GS) linker.

E25. The method of embodiment 24, wherein the (GS) linker comprises (GnS)m, wherein n is 1-10 and m is 1-100.

E26. The method of embodiment 24, wherein the (GS) linker comprises GGS, GGGS (SEQ ID NO: 194), GGGGS (SEQ ID NO:136), GGGGGS (SEQ ID NO: 137), GGGGGGS (SEQ ID NO: 138), or GGGGGGGS (SEQ ID NO: 139).

E27. The method of any one of embodiments 1 to 26, wherein the IL-23 polypeptide comprises an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of having at least one IL-23 activity.

E28. The method of embodiment 27, wherein the IL-23 polypeptide is encoded by a nucleic acid sequence at least 70%, at least 80%, at least 85%, at least 90%, at least 95%, at least 99%, or 100% identical to a sequence listed in Table 1.

E29. The method of any one of embodiments 1 to 28, wherein the IL-36-gamma polypeptide comprises an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of having an IL-36 gamma activity.

E30. The method of embodiment 29, wherein the IL-36-gamma polypeptide is encoded by a nucleic acid sequence at least 70%, at least 80%, at least 85%, at least 90%, at least 95%, at least 99%, or 100% identical to a sequence listed in Table 1.

E31. The method of any one of embodiments 1 to 30, wherein the OX40L polypeptide comprises an amino acid sequence at least 50%, at least 60%, at least 70%, at least 80%, at least 85%, at least 90%, at least 95%, at least 99%, or 100% identical to a sequence listed in Table 1A, wherein the amino acid sequence is capable of having OX40L activity.

E32. The method of embodiment 31, wherein the OX40L polypeptide is encoded by a nucleic acid sequence at least 70%, at least 80%, at least 85%, at least 90%, at least 95%, at least 99%, or 100% identical to a sequence listed in Table 1A.

E33. The method of any one of embodiments 1 to 32, wherein the first polynucleotide, the second polynucleotide and/or the third polynucleotide further comprise a nucleic acid sequence comprising a miRNA binding site.

E34. The method of embodiment 33, wherein the miRNA binding site binds to miR-122.

E35. The method of embodiment 33 or 34, wherein the miRNA binding site binds to miR-122-3p or miR-122-5p.

E36. The method of embodiment 34, wherein the miRNA binding site comprises a nucleotide sequence at least 80%, at least 85%, at least 90%, at least 95%, or 100% identical to aacgccauua ucacacuaaa ua (SEQ ID NO: 23, wherein the miRNA binding site binds to miR-122.

E37. The method of embodiment 34, wherein the miRNA binding site comprises a nucleotide sequence at least 80%, at least 85%, at least 90%, at least 95%, or 100% identical to uggaguguga caaugguguu ug (SEQ ID NO: 25), wherein the miRNA binding site binds to miR-122.

E38. The method of any one of embodiments 33 to, wherein the first polynucleotide, the second polynucleotide, and the third polynucleotide comprise different miRNA binding sites or the same miRNA binding site.

E39. The method of any one of embodiments 17 to 38, wherein the first polynucleotide, the second polynucleotide and/or the third polynucleotide further comprise a 5' untranslated region (UTR).

E40. The method of embodiment 39, wherein the 5' UTR comprises a nucleic acid sequence at least 90%, 95%, 96%, 97%, 98%, 99%, or 100% identical to a sequence listed in Table 3.

E41. The method of any one of embodiments 17 to 40, wherein the first polynucleotide and/or the second polynucleotide and/or the third polynucleotide comprise a 3' untranslated region (UTR).

E42. The method of embodiment 41, wherein the 3' UTR comprises a nucleic acid sequence at least 90%, 95%, 96%, 97%, 98%, 99%, or 100% identical to a sequence listed in Table 4A or 4B.

E43. The method of embodiment 40 or 41, wherein the miRNA binding site is inserted within the 3' UTR.

E44. The method of embodiment 43, wherein the first polynucleotide and/or the second polynucleotide and/or the third polynucleotide further comprise a spacer sequence fused to the miRNA binding site.

E45. The method of embodiment 44, wherein the spacer sequence comprises at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, or at least about 100 nucleotides.

E46. The method of any one of embodiments 17 to 45, wherein the first polynucleotide and/or the second polynucleotide and/or the third polynucleotide further comprise a 5' terminal cap.

E47. The method of embodiment 46, wherein the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

E48. The method of any one of embodiments 17 to 47, wherein the first polynucleotide and/or the second polynucleotide and/or the third polynucleotide comprise a 3' polyA tail.

E49. The method of any one of embodiments 33 to 48, wherein the first polynucleotide and/or the second polynucleotide and/or the third polynucleotide comprise at least two, at least three, at least four, at least five, at least six, at least seven, at least eight, at least nine, or at least ten miRNA binding sites.

E50. The methods of any one of embodiments 1 to 49, wherein the first polynucleotide and/or the second polynucleotide and/or the third polynucleotide are codon optimized.

E51. The method of any one of embodiments 1 to 50, wherein the first polynucleotide and/or the second polynucleotide and/or the third polynucleotide is in vitro transcribed (IVT).

E52. The method of any one of embodiments 1 to 51, wherein the first polynucleotide and/or the second polynucleotide and/or the third polynucleotide is chimeric.

E53. The method of any one of embodiments 1 to 51, wherein the first polynucleotide and/or the second polynucleotide and/or the third polynucleotide is circular.

E54. The method of any one of embodiments 18 to 53, wherein the IL-12p40 subunit, the IL-23p19 subunit, the IL-36-gamma polypeptide, and/or the OX40L polypeptide are fused to a heterologous polypeptide.

E55. The method of any one of embodiments 1 to 54, wherein the first polynucleotide comprises a nucleotide sequence at least 50%, at least 60%, at least 70%, at least 80%, at least 85%, at least 90%, at least 95%, at least 99%, or 100% identical to an IL-23-encoding sequence or hIL-23_miR-122 construct of Table 1 (SEQ ID NO: 19 or SEQ ID NO: 71).

E56. The method of any one of embodiments 1 to 55, wherein the second polynucleotide comprises a nucleotide sequence at least 50%, at least 60%, at least 70%, at least 80%, at least 85%, at least 90%, at least 95%, at least 99%, or 100% identical to an IL-36-encoding sequence or hIL-36_miR-122 construct of Table 1 (SEQ ID NO: 17 or SEQ ID NO: 94).

E57. The method of any one of embodiments 1 to 56, wherein the third polynucleotide comprises a nucleotide sequence at least 50%, at least 60%, at least 70%, at least 80%, at least 85%, at least 90%, at least 95%, at least 99%, or 100% identical to an OX40L-encoding sequence or OX40L_miR-122 construct of Table 1 (SEQ ID NO: 116).

E58. The method of any one of embodiments 1 to 57, further comprising administering a fourth protein or a fourth polynucleotide encoding the fourth protein.

E59. The method of embodiment 58, wherein the fourth polynucleotide comprises an mRNA encoding the fourth protein.

E60. The method of any one of embodiments 1 to 59, wherein the first polynucleotide, the second polynucleotide, the third polynucleotide, and/or the fourth polynucleotide is formulated with a delivery agent.

E61. The method of embodiment 60, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E62. The method of embodiment 60, wherein the delivery agent is a lipid nanoparticle.

E63. The method of embodiment 62, wherein the lipid nanoparticle comprises the lipid selected from the group consisting of DLin-DMA, DLin-K-DMA, 98N12-5, C12-200, DLin-MC3-DMA, DLin-KC2-DMA, DODMA, PLGA, PEG, PEG-DMG, PEGylated lipids, amino alcohol lipids, KL22, and combinations thereof.

E64. The method of any one of embodiments 60 to 63 or 80, wherein the delivery agent comprises a compound having formula (I)

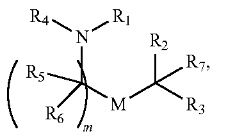

(I)

or a salt or stereoisomer thereof, wherein

R1 is selected from the group consisting of C5-20 alkyl, C5-20 alkenyl, —R*YR", —YR", and —R"M'R';

R2 and R3 are independently selected from the group consisting of H, C1-14 alkyl, C2-14 alkenyl, —R*YR", —YR", and —R*OR", or R2 and R3, together with the atom to which they are attached, form a heterocycle or carbocycle;

R4 is selected from the group consisting of a C3-6 carbocycle, —(CH2)nQ, —(CH2)nCHQR, —CHQR, —CQ(R)2, and unsubstituted C1-6 alkyl, where Q is selected from a carbocycle, heterocycle, —OR, —O(CH2)nN(R)2, —C(O)OR, —OC(O)R, —CX3, —CX2H, —CXH2, —CN, —N(R)2, —C(O)N(R)2, —N(R)C(O)R, —N(R)S(O)2R, —N(R)C(O)N(R)2, —N(R)C(S)N(R)2, and —C(R)N(R)2C(O)OR, and each n is independently selected from 1, 2, 3, 4, and 5;

each R5 is independently selected from the group consisting of C1-3 alkyl, C2-3 alkenyl, and H;

each R6 is independently selected from the group consisting of C1-3 alkyl, C2-3 alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, an aryl group, and a heteroaryl group;

R7 is selected from the group consisting of C1-3 alkyl, C2-3 alkenyl, and H;

each R is independently selected from the group consisting of C1-3 alkyl, C2-3 alkenyl, and H;

each R' is independently selected from the group consisting of C1-18 alkyl, C2-18 alkenyl, —R*YR", —YR", and H;

each R" is independently selected from the group consisting of C3-14 alkyl and C3-14 alkenyl;

each R* is independently selected from the group consisting of C1-12 alkyl and C2-12 alkenyl;

each Y is independently a C3-6 carbocycle;

each X is independently selected from the group consisting of F, Cl, Br, and I; and m is selected from 5, 6, 7, 8, 9, 10, 11, 12, and 13; and provided when R4 is —(CH2)nQ, —(CH2)nCHQR, —CHQR, or —CQ(R)2, then (i) Q is not —N(R)2 when n is 1, 2, 3, 4 or 5, or (ii) Q is not 5, 6, or 7-membered heterocycloalkyl when n is 1 or 2.

E65. The method of embodiment 64, wherein the compound is of Formula (IA):

(IA)

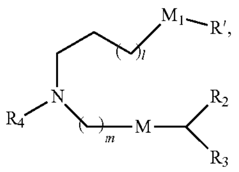

or a salt or stereoisomer thereof, wherein l is selected from 1, 2, 3, 4, and 5;

m is selected from 5, 6, 7, 8, and 9;

M1 is a bond or M';

R4 is unsubstituted C1-3 alkyl, or —(CH2)nQ, in which n is 1, 2, 3, 4, or 5 and Q is OH, —NHC(S)N(R)2, or —NHC(O)N(R)2;

M and M' are independently selected from —C(O)O—, —OC(O)—, —C(O)N(R')—, —P(O)(OR')O—, an aryl group, and a heteroaryl group; and R2 and R3 are independently selected from the group consisting of H, C1-14 alkyl, and C2-14 alkenyl.

E66. The method of any one of embodiments 64 to 66, wherein m is 5, 7, or 9.

E67. The method of embodiment 64, wherein the compound is of Formula (II):

(II)

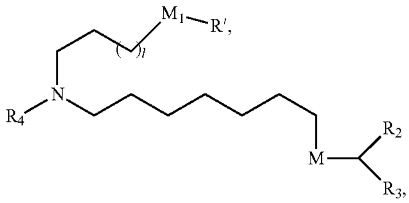

or a salt or stereoisomer thereof, wherein l is selected from 1, 2, 3, 4, and 5;

M1 is a bond or M';

R4 is unsubstituted C1-3 alkyl, or —(CH2)nQ, in which n is 2, 3, or 4 and Q is OH, —NHC(S)N(R)2, or —NHC(O)N(R)2;

M and M' are independently selected from —C(O)O—, —OC(O)—, —C(O)N(R')—, —P(O)(OR')O—, an aryl group, and a heteroaryl group; and R2 and R3 are independently selected from the group consisting of H, C1-14 alkyl, and C2-14 alkenyl.

E68. The method of any one of embodiments 64 to 67, wherein the compound is selected from Compound 1 to Compound 147, and salts and stereoisomers thereof.

E69. The method of embodiment 64, wherein the compound is of the Formula (IIa), (IIa)

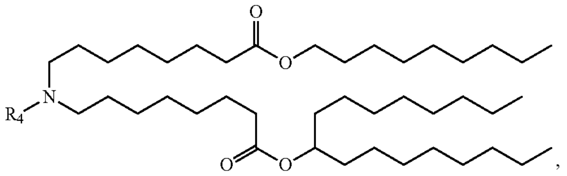

or a salt or stereoisomer thereof.

E70. The method of embodiment 64, wherein the compound is of the Formula (IIb), (IIb)

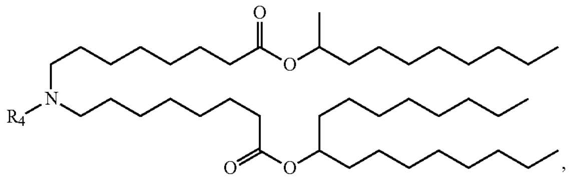

or a salt or stereoisomer thereof.

E71. The method of embodiment 64 or 65, wherein the compound is of the Formula (IIc) or (IIe), (IIc)

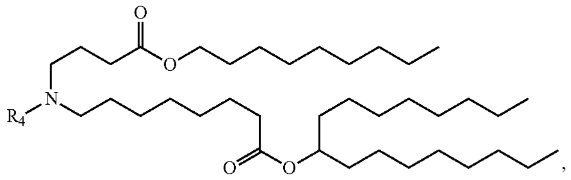

(IIe)

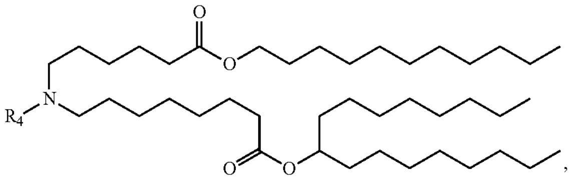

or a salt or stereoisomer thereof.

E72. The method of embodiment 64, wherein R4 is selected from —(CH2)nQ and —(CH2)nCHQR, wherein Q, R and n are as defined above in embodiment 64.

E73. The method of embodiment 64, wherein the compound is of the Formula (IId), (IId)

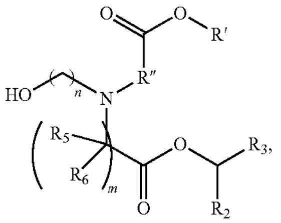

or a salt or stereoisomer thereof, wherein R2 and R3 are independently selected from the group consisting of C5-14 alkyl and C5-14 alkenyl, n is selected from 2, 3, and 4, and R', R", R5, R6 and m are as defined in embodiment 64.

E74. The method of embodiment 73, wherein R2 is C8 alkyl.

E75. The method of embodiment 73 or 74, wherein R3 is C5 alkyl, C6 alkyl, C7 alkyl, C8 alkyl, or C9 alkyl.

E76. The method of any one of embodiments 73 to 75, wherein m is 5, 7, or 9.

E77. The method of any one of embodiments 73 to 76, wherein each R5 is H.

E78. The method of embodiment 77, wherein each R6 is H.

E79. The method of any one of embodiments 60 to 63, wherein the delivery agent comprises a compound having the formula (I)

(I)

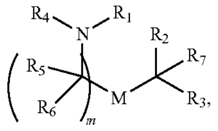

or a salt or stereoisomer thereof, wherein

R1 is selected from the group consisting of C530 alkyl, C520 alkenyl, R*YR", YR", and R"M'R';

R2 and R3 are independently selected from the group consisting of H, C114 alkyl, C214 alkenyl, —R*YR", YR", and R*OR", or R2 and R3, together with the atom to which they are attached, form a heterocycle or carbocycle;

R4 is selected from the group consisting of a C36 carbocycle, (CH2)nQ, (CH2)nCHQR, CHQR, —CQ(R)2, and unsubstituted C16 alkyl, where Q is selected from a carbocycle, heterocycle, OR, —O(CH2)nN(R)2, C(O)OR, OC(O)R, CX3, CX2H, CXH2, CN, N(R)2, C(O)N(R)2, N(R)C(O)R, —N(R)S(O)2R, N(R)C(O)N(R)2, N(R)C(S)N(R)2, —N(R)R8, —O(CH2)nOR, —N(R)C(═NR9)N(R)2, —N(R)C(═CHR9)N(R)2, —OC(O)N(R)2, —N(R)C(O)OR, —N(OR)C(O)R, —N(OR)S(O)2R, —N(OR)C(O)OR, —N(OR)C(O)N(R)2, —N(OR)C(S)N(R)2, —N(OR)C(═NR9)N(R)2, —N(OR)C(═CHR9)N(R)2, —C(═NR9)N(R)2, —C(═NR9)R, —C(O)N(R)OR, and C(R)N(R)2C(O)OR, and each n is independently selected from 1, 2, 3, 4, and 5;

each R5 is independently selected from the group consisting of C13 alkyl, C23 alkenyl, and H;

each R6 is independently selected from the group consisting of C13 alkyl, C23 alkenyl, and H;

M and M' are independently selected from C(O)O, OC(O), C(O)N(R'), N(R')C(O), C(O), C(S), —C(S)S, SC(S), CH(OH), P(O)(OR')O, S(O)2, —S—S—, an aryl group, and a heteroaryl group;

R7 is selected from the group consisting of C13 alkyl, C23 alkenyl, and H;

R8 is selected from the group consisting of C3-6 carbocycle and heterocycle;

R9 is selected from the group consisting of H, CN, NO2, C1-6 alkyl, —OR, —S(O)2R, —S(O)2N(R)2, C2-6 alkenyl, C3-6 carbocycle and heterocycle;

each R is independently selected from the group consisting of C13 alkyl, C23 alkenyl, and H;

each R' is independently selected from the group consisting of C118 alkyl, C218 alkenyl, R*YR", YR", and H;

each R" is independently selected from the group consisting of C314 alkyl and C314 alkenyl;

each R* is independently selected from the group consisting of C112 alkyl and C212 alkenyl;

each Y is independently a C36 carbocycle;

each X is independently selected from the group consisting of F, Cl, Br, and I; and m is selected from 5, 6, 7, 8, 9, 10, 11, 12, and 13; and provided that when R4 is —(CH2)nQ, —(CH2)nCHQR, —CHQR, or —CQ(R)2, then (i) Q is not —N(R)2 when n is 1, 2, 3, 4 or 5, or (ii) Q is not 5, 6, or 7-membered heterocycloalkyl when n is 1 or 2.

E80. The composition of embodiment 79, wherein the delivery agent comprises the compound is of Formula (IA):

(IA)

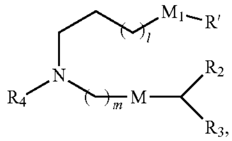

or a salt or stereoisomer thereof, wherein l is selected from 1, 2, 3, 4, and 5;

m is selected from 5, 6, 7, 8, and 9;

M1 is a bond or M';

R4 is unsubstituted C13 alkyl, or (CH2)nQ, in which Q is OH, NHC(S)N(R)2, or —NHC(O)N(R)2, —NHC(O)N(R)2, —N(R)C(O)R, —N(R)S(O)2R, —N(R)R8, —NHC(═NR9)N(R)2, —NHC(═CHR9)N(R)2, —OC(O)N(R)2, —N(R)C(O)OR, heteroaryl or heterocycloalkyl;

M and M' are independently selected from C(O)O, OC(O), C(O)N(R'), P(O)(OR')O, —S—S—, an aryl group, and a heteroaryl group; and R2 and R3 are independently selected from the group consisting of H, C114 alkyl, and C214 alkenyl.

E81. The composition of embodiment 79 or 80, wherein m is 5, 7, or 9.

E82. The composition of any one of embodiments 79 to 81, wherein the compound is of Formula (II)

(II)

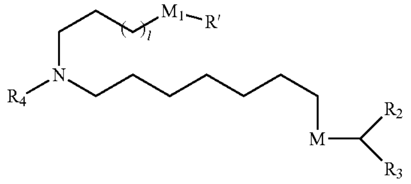

or a salt or stereoisomer thereof, wherein l is selected from 1, 2, 3, 4, and 5;

M1 is a bond or M';

R4 is unsubstituted C13 alkyl, or (CH2)nQ, in which n is 2, 3, or 4, and Q is OH, NHC(S)N(R)2, or NHC(O)N(R)2, —N(R)C(O)R, —N(R)S(O)2R, —N(R)R8, —NHC(═NR9)N(R)2, —NHC(═CHR9)N(R)2, —OC(O)N(R)2, —N(R)C(O)OR, heteroaryl or heterocycloalkyl;

M and M' are independently selected from C(O)O, OC(O), C(O)N(R'), P(O)(OR')O, —S—S—, an aryl group, and a heteroaryl group; and R2 and R3 are independently selected from the group consisting of H, C114 alkyl, and C214 alkenyl.

E83. The composition of any one of embodiments 80 to 82, wherein $M_1$ is M'.

E84. The composition of embodiment 83, wherein M and M' are independently —C(O)O— or —OC(O)—.

E85. The composition of any one of embodiments 80 to 84, wherein 1 is 1, 3, or 5.

E86. The composition of embodiment 79, wherein the compound is selected from the group consisting of Compound 1 to Compound 232, salts and stereoisomers thereof, and any combination thereof.

E87. The method of any one of embodiments 60 to 86, wherein the delivery agent further comprises a phospholipid.

E88. The method of embodiment 87, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

E89. The method of embodiment 87, wherein the phospholipid is selected from the group consisting of 1-myristoyl-2-palmitoyl-sn-glycero-3-phosphocholine (14:0-16:0 PC, MPPC), 1-myristoyl-2-stearoyl-sn-glycero-3-phosphocholine (14:0-18:0 PC, MSPC), 1-palmitoyl-2-acetyl-sn-glycero-3-phosphocholine (16:0-02:0 PC), 1-palmitoyl-2-myristoyl-sn-glycero-3-phosphocholine (16:0-14:0 PC, PMPC), 1-palmitoyl-2-stearoyl-sn-glycero-3-phosphocholine (16:0-18:0 PC, PSPC), 1-palmitoyl-2-oleoyl-sn-glycero-3-phosphocholine (16:0-18:1 PC, POPC), 1-palmitoyl-2-linoleoyl-sn-glycero-3-phosphocholine (16:0-18:2 PC, PLPC), 1-palmitoyl-2-arachidonoyl-sn-glycero-3-phosphocholine (16:0-20:4 PC), 1-palmitoyl-2-docosahexaenoyl-sn-glycero-3-phosphocholine (14:0-22:6 PC), 1-stearoyl-2-myristoyl-sn-glycero-3-phosphocholine (18:0-14:0 PC, SMPC), 1-stearoyl-2-palmitoyl-sn-glycero-3-phosphocholine (18:0-16:0 PC, SPPC), 1-stearoyl-2-oleoyl-sn-glycero-3-phosphocholine (18:0-18:1 PC, SOPC), 1-stearoyl-2-linoleoyl-sn-glycero-3-phosphocholine (18:0-18:2 PC), 1-stearoyl-2-arachidonoyl-sn-glycero-3-phosphocholine (18:0-20:4 PC), 1-stearoyl-2-docosahexaenoyl-sn-glycero-3-phosphocholine (18:0-22:6 PC), 1-oleoyl-2-myristoyl-sn-glycero-3-phosphocholine (18:1-14:0 PC, OMPC), 1-oleoyl-2-palmitoyl-sn-glycero-3-phosphocholine (18:1-16:0 PC, OPPC), 1-oleoyl-2-stearoyl-sn-glycero-3-phosphocholine (18:1-18:0 PC, OSPC), 1-palmitoyl-2-oleoyl-sn-glycero-3-phosphoethanolamine (16:0-18:1 PE, POPE), 1-palmitoyl-2-linoleoyl-sn-glycero-3-phosphoethanolamine (16:0-18:2 PE), 1-palmitoyl-2-arachidonoyl-sn-glycero-3-phosphoethanolamine (16:0-20:4 PE), 1-palmitoyl-2-docosahexaenoyl-sn-glycero-3-phosphoethanolamine (16:0-22:6 PE), 1-stearoyl-2-oleoyl-sn-glycero-3-phosphoethanolamine (18:0-18:1 PE), 1-stearoyl-2-linoleoyl-sn-glycero-3-phosphoethanolamine (18:0-18:2 PE), 1-stearoyl-2-arachidonoyl-sn-glycero-3-phosphoethanolamine (18:0-20:4 PE), 1-stearoyl-2-docosahexaenoyl-sn-glycero-3-phosphoethanolamine (18:0-22:6 PE), 1-oleoyl-2-cholesterylhemisuccinoyl-sn-glycero-3-phosphocholine (OChemsPC), and any combination thereof.

E90. The method of any one of embodiments 60 to 89, wherein the delivery agent further comprises a structural lipid.

E91. The method of embodiment 90, wherein the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof.

E92. The method of any one of embodiments 60 to 91, wherein the delivery agent further comprises a PEG lipid.

E93. The method of embodiment 92, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

E94. The method of any one of embodiments 60 to 93, wherein the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethyl aminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

E95. The method of any one of embodiments 60 to 94, wherein the delivery agent further comprises a quaternary amine compound.

E96. The method of embodiment 95, wherein the quaternary amine compound is selected from the group consisting of 1,2-dioleoyl-3-trimethylammonium-propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), N,N-distearyl-N,N-dimethylammonium bromide (DDAB), N-(1,2-dimyristyloxyprop-3-yl)-N,N-dimethyl-N-hydroxyethyl ammonium bromide (DMRIE), N-(1,2-dioleoyloxyprop-3-yl)-N,N-dimethyl-N-hydroxyethyl ammonium bromide (DORIE), N,N-dioleyl-N,N-dimethylammonium chloride (DODAC), 1,2-dilauroyl-sn-glycero-3-ethylphosphocholine (DLePC),
1,2-distearoyl-3-trimethylammonium-propane (DSTAP),
1,2-dipalmitoyl-3-trimethylammonium-propane (DPTAP),
1,2-dilinoleoyl-3-trimethylammonium-propane (DLTAP),
1,2-dimyristoyl-3-trimethylammonium-propane (DMTAP),
1,2-distearoyl-sn-glycero-3-ethylphosphocholine (DSePC),
1,2-dipalmitoyl-sn-glycero-3-ethylphosphocholine (DPePC),
1,2-dimyristoyl-sn-glycero-3-ethylphosphocholine (DMePC),
1,2-dioleoyl-sn-glycero-3-ethylphosphocholine (DOePC),
1,2-di-(9Z-tetradecenoyl)-sn-glycero-3-ethylphosphocholine (14:1 EPC),
1-palmitoyl-2-oleoyl-sn-glycero-3-ethylphosphocholine (16:0-18:1 EPC),
and any combination thereof.

E97. A composition comprising the first polynucleotide according to any one of embodiments 1 to 57 or the first polynucleotide according to any one of embodiments 1 to 57 formulated in the delivery agent according to any one of embodiments 60 to 96.

E98. A composition comprising the second polynucleotide according to any one of embodiments 1 to 59 or the second polynucleotide according to any one of embodiments 1 to 57 formulated in the delivery agent according to any one of embodiments 60 to 96.

E99. A composition comprising the third polynucleotide according to any one of embodiments 1 to 57 and the third polynucleotide according to any one of embodiments 1 to 57 formulated in the delivery agent according to any one of embodiments 60 to 96.

E100. A composition comprising (i) the first polynucleotide according to any one of embodiments 1 to 59 and the second polynucleotide according to any one of embodiments 1 to 57, (ii) the first polynucleotide according to any one of embodiments 1 to 57 and the third polynucleotide according to any one of embodiments 1 to 57, (iii) the second polynucleotide according to any one of embodiments 1 to 57 and the third polynucleotide according to any one of embodiments 1 to 57, or (iv) the first polynucleotide according to any one of embodiments 1 to 57, the second polynucleotide according to any one of embodiments 1 to 57, and the third polynucleotide according to any one of embodiments 1 to 59.

E101. The composition of embodiment 93, comprising the first polynucleotide according to any one of embodiments 1 to 57, the second polynucleotide according to any one of embodiments 1 to 57, and the third polynucleotide according to any one of embodiments 1 to 57.

E102. The composition of embodiment 101, which further comprises a delivery agent.

E103. The composition of embodiment 102, wherein the delivery agent comprises a lipidoid, a liposome, a lipoplex, a lipid nanoparticle, a polymeric compound, a peptide, a protein, a cell, a nanoparticle mimic, a nanotube, or a conjugate E104. The composition of embodiment 102, wherein the delivery agent comprises a delivery agent according to any one of embodiments 64 to 104.

E105. The composition of any one of embodiments 87 to 104, for use in reducing or decreasing a size of a tumor or inhibiting a tumor growth in a subject in need thereof.

E106. The composition of embodiment 97 in combination with the composition of embodiment 98, for use in reducing or decreasing a size of a tumor or inhibiting a tumor growth in a subject in need thereof.

E107. The method of any one of embodiments 1 to 96 or the composition of any one of embodiments 97 to 106, wherein the first polynucleotide, the second polynucleotide and/or the third polynucleotide is formulated for in vivo delivery.

E108. The method or the composition of embodiment 107, wherein the first polynucleotide and/or the second polynucleotide, and/or the third polynucleotide is formulated for intramuscular, subcutaneous, intratumoral, or intradermal delivery.

E109. The method of any one of embodiments 1 to 96, 107 and 108 or the composition of any one of embodiments 97 to 108, wherein the first polynucleotide and/or the second polynucleotide is administered subcutaneously, intravenously, intramuscularly, intra-articularly, intra-synovially, intrasternally, intrathecally, intrahepatically, intralesionally, intracranially, intraventricularly, orally, by inhalation spray, topically, rectally, nasally, buccally, vaginally or via an implanted reservoir.

E110. The method of any one of embodiments 1 to 96, 107 and 108 or composition of any one of embodiments 97 to 109, wherein the administration treats a cancer.

E111. The method of embodiment 110, wherein the cancer is selected from the group consisting of adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

E112. The method of any one of embodiments 1 to 96 and 107 to 111 or the composition of any one of embodiment 97, wherein the first polynucleotide, the second polynucleotide, and/or the third polynucleotide is delivered by a device comprising a pump, patch, drug reservoir, short needle device, single needle device, multiple needle device, microneedle device, jet injection device, ballistic powder/particle delivery device, catheter, lumen, cryoprobe, cannula, microcanular, or devices utilizing heat, RF energy, electric current, or any combination thereof.

E113. The method of any one of embodiments 1 to 96 and 107 to 112 or the composition of any one of embodiments 97 to 112, wherein the effective amount is between about 0.10 mg/kg to about 1,000 mg/kg.

E114. The method of any one of embodiments 1 to 96 and 107 to 113 or the composition of any one of embodiments 97 to 113, wherein the subject is a human.

E115. A kit comprising the composition of any one of embodiments 107 to 113 and instructions to use according to the method of any one of embodiments 1 to 97 and 107 to 115.

E116. The method of any one of embodiments 1 to 96 or 107 to 113, the composition of embodiments 97 to 115, or the kit of embodiment 123, wherein the administration of the polynucleotides to the subject results in:

increase in granulocyte level in one or more samples obtained from the subject after administration of doublet or triplet relative to a threshold level or relative to the level after administration of a single polynucleotide encoding an IL-23, an IL-36-gamma, or an OX40L polypeptide;

increase in cross-presenting dendritic cell level in one or more samples obtained from the subject after administration of doublet or triplet relative to a threshold level or relative to the level after administration of a single polynucleotide encoding an IL-23, an IL-36-gamma, or an OX40L polypeptide;

increase in effector to suppressor T cell ratio in one or more samples obtained from the subject after administration of doublet or triplet relative to a threshold level or relative to the ratio after administration of a single polynucleotide encoding an OX40L polypeptide;

increase in effector memory T cell level in one or more samples obtained from the subject after administration of doublet or triplet relative to a threshold level or relative to the level after administration of a single polynucleotide encoding an OX40L polypeptide;

increase in PDL1 expression level in one or more samples obtained from the subject after administration of doublet or triplet relative to a threshold level or relative to the level after administration of a single polynucleotide encoding an IL-23, an IL-36-gamma, or an OX40L polypeptide; or a combination thereof.

E117. A method of reducing or decreasing a size of a tumor or inhibiting a tumor growth in a subject in need thereof comprising administering to the subject a composition comprising:

two polynucleotides in combination (doublet), wherein the first polynucleotide encodes a first protein comprising an interleukin-23 polypeptide (IL-23), and the second polynucleotide encodes a second protein comprising an interleukin-36-gamma polypeptide (IL-36-gamma); or, three polynucleotides in combination (triplet), where the first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide (OX40L), wherein the administration of the doublet or triplet to the subject results in:

increase in granulocyte level in one or more samples obtained from the subject after administration of doublet or triplet relative to a threshold level or relative to the level after administration of a single polynucleotide encoding an IL-23, an IL-36-gamma, or an OX40L polypeptide;

increase in cross-presenting dendritic cell level in one or more samples obtained from the subject after administration of doublet or triplet relative to a threshold level or relative to the level after administration of a single polynucleotide encoding an IL-23, an IL-36-gamma, or an OX40L polypeptide;

increase in effector to suppressor T cell ratio in one or more samples obtained from the subject after administration of doublet or triplet relative to a threshold level or relative to the ratio after administration of a single polynucleotide encoding an OX40L polypeptide;

increase in effector memory T cell level in one or more samples obtained from the subject after administration of doublet or triplet relative to a threshold level or relative to the level after administration of a single polynucleotide encoding an OX40L polypeptide;

increase in PDL1 expression level in one or more samples obtained from the subject after administration of doublet or triplet relative to a threshold level or relative to the level after administration of a single polynucleotide encoding an IL-23, an IL-36-gamma, or an OX40L polypeptide; or a combination thereof.

E118. The method of embodiment 117, wherein the increase in granulocyte level is quantitated as (i) granulocytes as percent of CD45+ cells, or (ii) granulocytes per mg of tumor.

E119. The method of embodiment 117, wherein the cross-presenting dendritic cells are CD103+ cells.

E120. The method of embodiment 117, wherein the increase in cross-presenting dendritic cell level is quantitated as (i) cross-presenting dendritic cells per mg of tumor, (ii) cross-presenting CD103+ dendritic cells in tumor draining lymph node (TdLN), or (iii) cross-presenting CD103+ dendritic cells as percentage of CD45+ cells.

E121. The method of embodiment 117, wherein the effector to suppressor T cell ratio is quantitated as CD8:Treg ratio.

E122. The method of embodiment 117, wherein the effector memory T cells are CD4+ and/or CD8+ cells.

E123. The method of embodiment 117, wherein PDL1 expression level is quantitated as (i) number of positive CD11b+ cells, or (ii) PDL1 expression in CD11b+ cells.

E124. A method to increase granulocyte levels in a subject in need thereof comprising administering to the subject a composition comprising:

two polynucleotides in combination (doublet), wherein first polynucleotide encodes a first protein comprising an IL-23 polypeptide, and the second polynucleotide encodes a second protein comprising an IL-36-gamma polypeptide; or, three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein granulocyte levels are measured in one or more samples obtained from the subject.

E125. The method of embodiment 124, wherein the increase in granulocyte level is measured as (i) granulocytes as percent of CD45+ cells, and/or (ii) granulocytes per mg of tumor, relative to a threshold level or relative to the level after administration of a single polynucleotide encoding IL-23 or a single polynucleotide encoding IL-36-gamma.

E126. A method to increase cross-presenting dendritic cell levels in a subject in need thereof comprising administering to the subject a composition comprising:

two polynucleotides in combination (doublet), wherein first polynucleotide encodes a first protein comprising an IL-23 polypeptide, and the second polynucleotide encodes a second protein comprising an IL-36-gamma polypeptide; or, three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein cross-presenting dendritic cell levels are measured in one or more samples obtained from the subject.

E127. The method of embodiment 126, wherein the cross-presenting dendritic cells are CD103+ cells.

E128. The method of embodiment 127, wherein the increase in cross-presenting CD103+ dendritic cell level is measured as (i) cross-presenting CD103+ dendritic cells per mg of tumor, (ii) cross-presenting CD103+ dendritic cells in TdLN, (iii) cross-presenting CD103+ dendritic cells as percentage of CD45+ cells, or (iv) a combination thereof, relative to a threshold level or relative to the level after administration of a single polynucleotide encoding IL-23, a single polynucleotide encoding IL-36-gamma, or a single polynucleotide encoding OX40L.

E129. A method to increase the effector to suppressor T cell ratio in a subject in need thereof comprising administering to the subject a composition comprising:

two polynucleotides in combination (doublet), wherein first polynucleotide encodes a first protein comprising an IL-23 polypeptide, and the second polynucleotide encodes a second protein comprising an IL-36-gamma polypeptide; or, three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the effector to suppressor T cell ratio is measured in one or more samples obtained from the subject.

E130. The method of embodiment 129, wherein the effector to suppressor T cell ratio is measured as CD8:Treg ratio.

E131. A method to increase effector memory T cells levels in a subject in need thereof comprising administering to the subject a composition comprising:

two polynucleotides in combination (doublet), wherein first polynucleotide encodes a first protein comprising an IL-23 polypeptide, and the second polynucleotide encodes a second protein comprising an IL-36-gamma polypeptide; or, three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the effector memory T cells levels are measured in one or more samples obtained from the subject.

E132. The method of embodiment 131, wherein the effector memory T cells are CD4+ and/or CD8+ cells.

E133. The method of embodiment 132, wherein the increase in effector memory T cells levels is measured as effector memory T cells within the tumor relative to a threshold level or relative to the level after administration of a single polynucleotide encoding OX40L.

E134. A method to increase PDL1 positive cells levels in a subject in need thereof comprising administering to the subject a composition comprising:

two polynucleotides in combination (doublet), wherein first polynucleotide encodes a first protein comprising an IL-23 polypeptide, and the second polynucleotide encodes a second protein comprising an IL-36-gamma polypeptide; or, three polynucleotides in combination (triplet), where first polynucleotide encodes a first protein comprising an IL-23 polypeptide, the second polynucleotide encodes a second protein comprising an IL-36-gamma polypeptide, and the third polynucleotide encodes a third protein comprising an OX40L polypeptide, wherein the PDL1 positive cells levels are measured in one or more samples obtained from the subject.

E135. The method of embodiment 134, wherein the PDL1 positive cells are CD11b+ cells.

E136. The method of any one of embodiments 117-135, wherein the sample obtained from the subject is selected from the group consisting of tumoral tissue, tumor infiltrate, blood, plasma, and a combination thereof.

E137. The method of any one of embodiments 117-136, wherein the one or more control samples is a sample or samples obtained from a healthy subject or a subject with a tumor.

E138. The method of any one of embodiments 117-137, wherein the threshold level is a predetermined value or a value obtained from one or more samples.

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Synthesis of Compounds According to Formula I

A. General Considerations

All solvents and reagents used were obtained commercially and used as such unless noted otherwise. $^1$H NMR spectra were recorded in $CDCl_3$, at 300 K using a Bruker Ultrashield 300 MHz instrument. Chemical shifts are reported as parts per million (ppm) relative to TMS (0.00) for $^1$H. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 µm, and a gradient of 65 to 100% acetonitrile in water with 0.1% TFA over 5 minutes at 1.2 mL/min. Injection volume was 5 µL and the column temperature was 80° C. Detection was based on electrospray ionization (ESI) in positive mode using Waters SQD mass spectrometer (Milford, Mass., USA) and evaporative light scattering detector.

The representative procedures described below are useful in the synthesis of Compounds 1-232.

The following abbreviations are employed herein:

THF: Tetrahydrofuran

DMAP: 4-Dimethylaminopyridine

LDA: Lithium Diisopropylamide rt: Room Temperature

DME: 1,2-Dimethoxyethane n-BuLi: n-Butyllithium

B. Compound 2: Heptadecan-9-yl 8-((2-hydroxyethyl)(tetradecyl)amino) octanoate Representative Procedure 1:

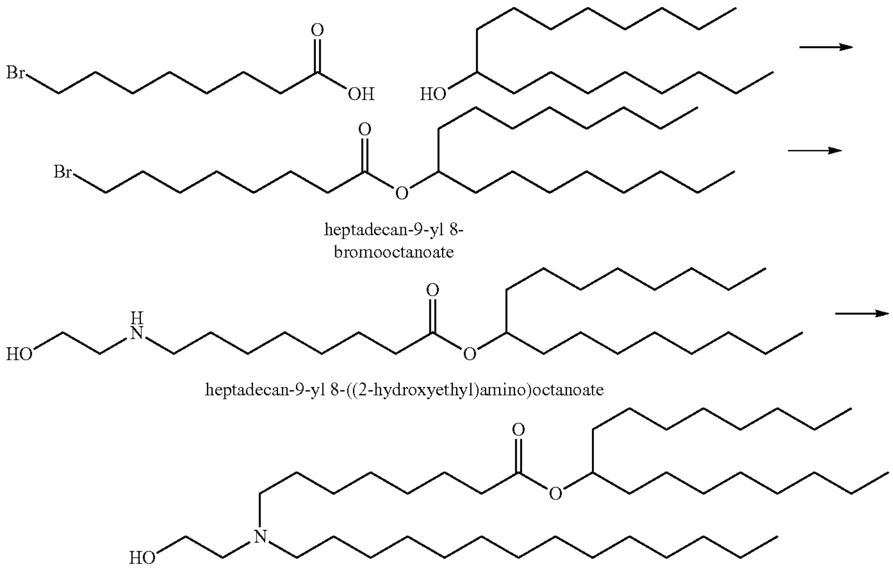

heptadecan-9-yl 8-bromooctanoate heptadecan-9-yl 8-((2-hydroxyethyl)amino)octanoate heptadecan-9-yl 8-((2-hydroxyethyl)(tetradecyl)amino)octanoate

Heptadecan-9-yl 8-bromooctanoate (Method A)

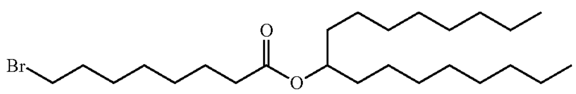 [SMILES: CCCCCCCCC(CCCCCCCC)OC(=O)CCCCCCCBr]

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at rt for 18 h. The reaction was diluted with dichloromethane and washed with saturated sodium bicarbonate. The organic layer was separated and washed with brine, and dried over $MgSO_4$. The organic layer was filtered and evaporated in vacuo. The residue was purified by silica gel chromatography (0-10% ethyl acetate in hexanes) to obtain heptadecan-9-yl 8-bromooctanoate (875 mg, 1.9 mmol, 41%).

$^1$H NMR (300 MHz, $CDCl_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Heptadecan-9-yl 8-((2-hydroxyethyl)amino)octanoate (Method B)

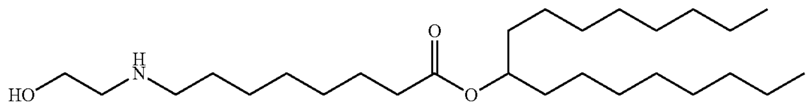 [SMILES: CCCCCCCCC(CCCCCCCC)OC(=O)CCCCCCCNCCO]

A solution of heptadecan-9-yl 8-bromooctanoate (3.8 g, 8.2 mmol) and 2-aminoethan-1-ol (15 mL, 248 mmol) in ethanol (3 mL) was allowed to stir at 62° C. for 18 h. The reaction mixture was concentrated in vacuo and the residue was taken-up in ethyl acetate and water. The organic layer was separated and washed with water, brine and dried over $Na_2SO_4$. The mixture was filtered and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)amino)octanoate (3.1 g, 7 mmol, 85%). UPLC/ELSD: RT=2.67 min. MS (ES): m/z ($MH^+$) 442.68 for $C_{27}H_{55}NO_3$ $^1H$ NMR (300 MHz, $CDCl_3$) δ: ppm 4.89 (p, 1H); 3.67 (t, 2H); 2.81 (t, 2H); 2.65 (t, 2H); 2.30 (t, 2H); 2.05 (br. m, 2H); 1.72-1.41 (br. m, 8H); 1.40-1.20 (br. m, 30H); 0.88 (m, 6H).

Heptadecan-9-yl 8-((2-hydroxyethyl)(tetradecyl)amino)octanoate (Method C)

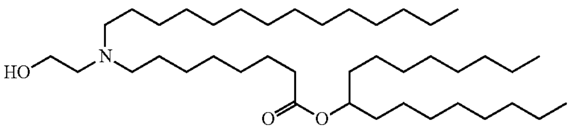 [SMILES: CCCCCCCCCCCCCCN(CCO)CCCCCCCC(=O)OC(CCCCCCCC)CCCCCCCC]

Chemical Formula: $C_{41}H_{83}NO_3$
Molecular Weight: 638.12

A solution of heptadecan-9-yl 8-((2-hydroxyethyl)amino)octanoate (125 mg, 0.28 mmol), 1-bromotetradecane (94 mg, 0.34 mmol) and N,N-diisopropylethylamine (44 mg, 0.34 mmol) in ethanol was allowed to stir at 65° C. for 18 h. The reaction was cooled to room temperature and solvents were evaporated in vacuo. The residue was taken-up in ethyl acetate and saturated sodium bicarbonate. The organic layer was separated, dried over $Na_2SO_4$ and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)(tetradecyl)amino)octanoate (89 mg, 0.14 mmol, 50%). UPLC/ELSD: RT=3.61 min. MS (ES): m/z ($MH^+$) 638.91 for $C_{41}H_{83}NO_3$. $^1H$ NMR (300 MHz, $CDCl_3$) δ: ppm 4.86 (p, 1H); 3.72-3.47 (br. m, 2H); 2.78-2.40 (br. m, 5H); 2.28 (t, 2H); 1.70-1.40 (m, 10H); 1.38-1.17 (br. m, 54H); 0.88 (m, 9H).

Synthesis of Intermediates

Intermediate A: 2-Octyldecanoic Acid

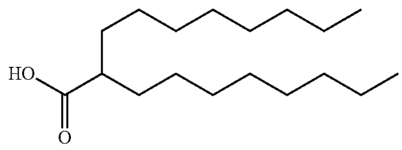 [SMILES: CCCCCCCCC(CCCCCCCC)C(=O)O]

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at rt for 30 min. After this time 1-iodooctane (5 g, 20.8 mmol) was added and the reaction mixture was heated at 45° C. for 6 h. The reaction was quenched with 1N HCl (10 mL). The organic layer was dried over $MgSO_4$, filtered and evaporated in vacuo. The residue was purified by silica gel chromatography (0-20% ethyl acetate in hexanes) to yield 2-octyldecanoic acid (1.9 g, 6.6 mmol, 38%). $^1H$ NMR (300 MHz, $CDCl_3$) δ: ppm 2.38 (br. m, 1H); 1.74-1.03 (br. m, 28H); 0.91 (m, 6H).

Intermediate B: 7-Bromoheptyl 2-octyldecanoate

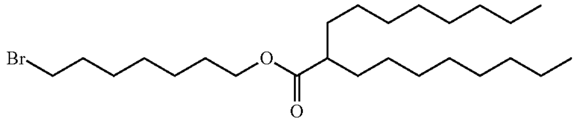 [SMILES: CCCCCCCCC(CCCCCCCC)C(=O)OCCCCCCCBr]

7-bromoheptyl 2-octyldecanoate was synthesized using Method A from 2-octyldecanoic acid and 7-bromoheptan-1-ol. $^1H$ NMR (300 MHz, $CDCl_3$) δ: ppm 4.09 (br. m, 2H); 3.43 (br. m, 2H); 2.48-2.25 (br. m, 1H); 1.89 (br. m, 2H); 1.74-1.16 (br. m, 36H); 0.90 (m, 6H).

Intermediate C: (2-Hexylcyclopropyl)methanol

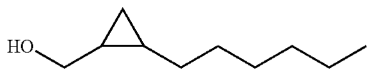

A solution of diethyl zinc (20 mL, 20 mmol, 1 M in hexanes), in dichloromethane (20 mL) was allowed to cool to −40° C. for 5 min. Then a solution of diiodomethane (3.22 mL, 40 mmol) in dichloromethane (10 mL) was added dropwise. After the reaction was allowed to stir for 1 h at −40° C., a solution of trichloro-acetic acid (327 mg, 2 mmol) and DME (1 mL, 9.6 mmol) in dichloromethane (10 mL) was added. The reaction was allowed to warm to −15° C. and stir at this temperature for 1 h. A solution of (Z)-non-2-en-1-ol (1.42 g, 10 mmol) in dichloromethane (10 mL) was then added to the −15° C. solution. The reaction was then slowly allowed to warm to rt and stir for 18 h. After this time saturated $NH_4Cl$ (200 mL) was added and the reaction was extracted with dichloromethane (3×), washed with brine, and dried over $Na_2SO_4$. The organic layer was filtered, evaporated in vacuo and the residue was purified by silica gel chromatography (0-50% ethyl acetate in hexanes) to yield (2-hexylcyclopropyl)methanol (1.43 g, 9.2 mmol, 92%). $^1$H NMR (300 MHz, $CDCl_3$) δ: ppm 3.64 (m, 2H); 1.57-1.02 (m, 12H); 0.99-0.80 (m, 4H); 0.72 (m, 1H), 0.00 (m, 1H).

C. Compound 18: Heptadecan-9-yl 8-((2-hydroxyethyl)(8-(nonyloxy)-8-oxooctyl)amino) octanoate

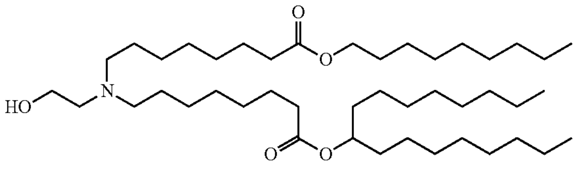 [SMILES: CCCCCCCCCOC(=O)CCCCCCCN(CCO)CCCCCCCC(=O)OC(CCCCCCCC)CCCCCCCC]

Chemical Formula: $C_{44}H_{87}NO_5$

Molecular Weight: 710.18

Compound 18 was synthesized according to the general procedure and Representative Procedure 1 described above.

UPLC/ELSD: RT=3.59 min. MS (ES): m/z ($MH^+$) 710.89 for $C_{44}H8_7NO_5$. $^1$H NMR (300 MHz, $CDCl_3$) δ: ppm 4.86 (m, 1H); 4.05 (t, 2H); 3.53 (br. m, 2H); 2.83-2.36 (br. m, 5H); 2.29 (m, 4H); 0.96-1.71 (m, 64H); 0.88 (m, 9H).

D. Compound 136: Nonyl 8-((2-hydroxyethyl)((9Z, 12Z)-octadeca-9,12-dien-1-yl)amino)octanoate Representative Procedure 2

Nonyl 8-bromooctanoate (Method A)

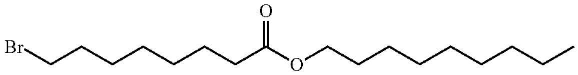 [SMILES: CCCCCCCCCOC(=O)CCCCCCCBr]

To a solution of 8-bromooctanoic acid (5 g, 22 mmol) and nonan-1-ol (6.46 g, 45 mmol) in dichloromethane (100 mL) were added N-(3-Dimethylaminopropyl)-N'-ethylcarbodiimide hydrochloride (4.3 g, 22 mmol) and DMAP (547 mg, 4.5 mmol). The reaction was allowed to stir at rt for 18 h. The reaction was diluted with dichloromethane and washed with saturated sodium bicarbonate. The organic layer was separated and washed with brine, dried over $MgSO_4$. The organic layer was filtered and evaporated under vacuum. The residue was purified by silica gel chromatography (0-10% ethyl acetate in hexanes) to obtain nonyl 8-bromooctanoate (6.1 g, 17 mmol, 77%).

$^1$H NMR (300 MHz, $CDCl_3$) δ: ppm 4.06 (t, 2H); 3.40 (t, 2H); 2.29 (t, 2H); 1.85 (m, 2H); 1.72-0.97 (m, 22H); 0.88 (m, 3H).

Nonyl 8-((2-hydroxyethyl)amino)octanoate

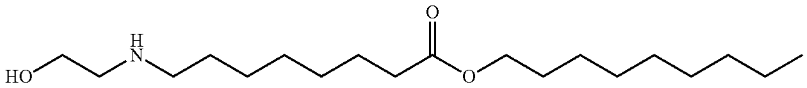 [SMILES: CCCCCCCCCOC(=O)CCCCCCCNCCO]

A solution of nonyl 8-bromooctanoate (1.2 g, 3.4 mmol) and 2-aminoethan-1-ol (5 mL, 83 mmol) in ethanol (2 mL) was allowed to stir at 62° C. for 18 h. The reaction mixture was concentrated in vacuum and the residue was extracted with ethyl acetate and water. The organic layer was separated and washed with water, brine and dried over $Na_2SO_4$. The organic layer was filtered and evaporated in vacuo. The residue was purified by silica gel chromatography (0-100% (mixture of 1% $NH_4OH$, 20% MeOH in dichloromethane) in dichloromethane) to obtain nonyl 8-((2-hydroxyethyl) amino)octanoate (295 mg, 0.9 mmol, 26%).

UPLC/ELSD: RT=1.29 min. MS (ES): m/z ($MH^+$) 330.42 for $C_{19}H_{39}NO_3$ $^1$H NMR (300 MHz, $CDCl_3$) δ: ppm 4.07 (t, 2H); 3.65 (t, 2H); 2.78 (t, 2H); 2.63 (t, 2H); 2.32-2.19 (m, 4H); 1.73-1.20 (m, 24H); 0.89 (m, 3H)

Nonyl 8-((2-hydroxyethyl)((9Z,12Z)-octadeca-9,12-dien-1-yl)amino)octanoate

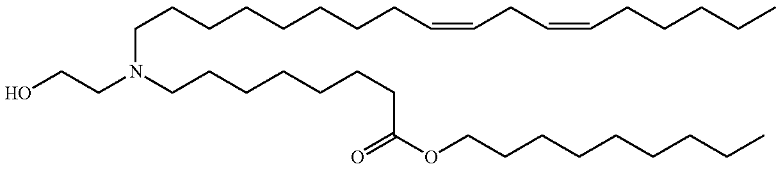 [SMILES: CCCCC/C=C\C/C=C\CCCCCCCCN(CCO)CCCCCCCC(=O)OCCCCCCCCC]

Chemical Formula: $C_{37}H_{71}NO_3$
Molecular Weight: 577.98

A solution of nonyl 8-((2-hydroxyethyl)amino)octanoate (150 mg, 0.46 mmol), (6Z,9Z)-18-bromooctadeca-6,9-diene (165 mg, 0.5 mmol) and N,N-diisopropylethylamine (65 mg, 0.5 mmol) in ethanol (2 mL) was allowed to stir at reflux for 48 h. The reaction was allowed to cool to rt and solvents were evaporated under vacuum. The residue was purified by silica gel chromatography (0-10% MeOH in dichloromethane) to obtain nonyl 8-((2-hydroxyethyl)((9Z,12Z)-octadeca-9,12-dien-1-yl)amino)octanoate (81 mg, 0.14 mmol, 30%) as a HBr salt.

UPLC/ELSD: RT=3.24 min. MS (ES): m/z ($MH^+$) 578.64 for $C_{37}H7_1NO3$ $^1H$ NMR (300 MHz, $CDCl_3$) δ: ppm 10.71 (br., 1H); 5.36 (br. m, 4H); 4.04 (m, 4H); 3.22-2.96 (br. m, 5H); 2.77 (m, 2H); 2.29 (m, 2H); 2.04 (br. m, 4H); 1.86 (br. m, 4H); 1.66-1.17 (br. m, 40H); 0.89 (m, 6H)

E. Compound 138: Dinonyl 8,8'-((2-hydroxyethyl)azanediyl)dioctanoate

Representative Procedure 3

Dinonyl 8,8'-((2-hydroxyethyl)azanediyl)dioctanoate

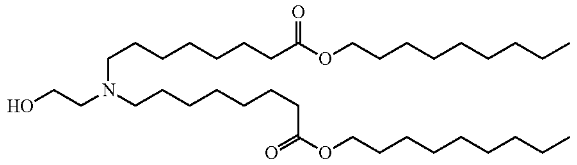 [SMILES: CCCCCCCCCOC(=O)CCCCCCCN(CCO)CCCCCCCC(=O)OCCCCCCCCC]

Chemical Formula: $C_{36}H_{71}NO_5$
Molecular Weight: 597.97

A solution of nonyl 8-bromooctanoate (200 mg, 0.6 mmol) and 2-aminoethan-1-ol (16 mg, 0.3 mmol) and N,N-diisopropylethylamine (74 mg, 0.6 mmol) in THF/$CH_3CN$ (1:1) (3 mL) was allowed to stir at 63° C. for 72 h. The reaction was cooled to rt and solvents were evaporated under vacuum. The residue was extracted with ethyl acetate and saturated sodium bicarbonate. The organic layer was separated, dried over $Na_2SO_4$ and evaporated under vacuum. The residue was purified by silica gel chromatography (0-10% MeOH in dichloromethane) to obtain dinonyl 8,8'-((2-hydroxyethyl)azanediyl)dioctanoate (80 mg, 0.13 mmol, 43%).

UPLC/ELSD: RT=3.09 min. MS (ES): m/z ($MH^+$) 598.85 for $C_{36}H_{71}NO_5$

1H NMR (300 MHz, $CDCl_3$) δ: ppm 4.05 (m, 4H); 3.57 (br. m, 2H); 2.71-2.38 (br. m, 6H); 2.29 (m, 4H), 1.71-1.01 (br. m, 49H), 0.88 (m, 6H).

All other lipid compounds disclosed herein can be obtained by a method analogous to Representative Procedures 1-3 as described above and/or a method known in the art.

Example 2

Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I), a phospholipid (such as DOPE or DSPC, obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kD. The first dialysis is carried out at room temperature for 3 hours. The formulations are then dialyzed overnight at 40° C. The resulting nanoparticle suspension is filtered through 0.2 m sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, may be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, Calif.) can be used to evaluate the encapsulation of an RNA by the nanoparticle composition. The samples are diluted to a concentration of approximately g/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in Table 9 below.

TABLE 9

Exemplary formulations of nanopoarticle compositions

| Composition (mol %) | Components |
|---|---|
| 40:20:38.5:1.5 | Compound:Phospholipid:Chol:PEG-DMG |
| 45:15:38.5:1.5 | Compound:Phospholipid:Chol:PEG-DMG |
| 50:10:38.5:1.5 | Compound:Phospholipid:Chol:PEG-DMG |
| 55:5:38.5:1.5 | Compound:Phospholipid:Chol:PEG-DMG |
| 60:5:33.5:1.5 | Compound:Phospholipid:Chol:PEG-DMG |
| 45:20:33.5:1.5 | Compound:Phospholipid:Chol:PEG-DMG |
| 50:20:28.5:1.5 | Compound:Phospholipid:Chol:PEG-DMG |
| 55:20:23.5:1.5 | Compound:Phospholipid:Chol:PEG-DMG |
| 60:20:18.5:1.5 | Compound:Phospholipid:Chol:PEG-DMG |
| 40:15:43.5:1.5 | Compound:Phospholipid:Chol:PEG-DMG |
| 50:15:33.5:1.5 | Compound:Phospholipid:Chol:PEG-DMG |
| 55:15:28.5:1.5 | Compound:Phospholipid:Chol:PEG-DMG |
| 60:15:23.5:1.5 | Compound:Phospholipid:Chol:PEG-DMG |
| 40:10:48.5:1.5 | Compound:Phospholipid:Chol:PEG-DMG |
| 45:10:43.5:1.5 | Compound:Phospholipid:Chol:PEG-DMG |
| 55:10:33.5:1.5 | Compound:Phospholipid:Chol:PEG-DMG |
| 60:10:28.5:1.5 | Compound:Phospholipid:Chol:PEG-DMG |
| 40:5:53.5:1.5 | Compound:Phospholipid:Chol:PEG-DMG |
| 45:5:48.5:1.5 | Compound:Phospholipid:Chol:PEG-DMG |
| 50:5:43.5:1.5 | Compound:Phospholipid:Chol:PEG-DMG |
| 40:20:40:0 | Compound:Phospholipid:Chol:PEG-DMG |
| 45:20:35:0 | Compound:Phospholipid:Chol:PEG-DMG |
| 50:20:30:0 | Compound:Phospholipid:Chol:PEG-DMG |
| 55:20:25:0 | Compound:Phospholipid:Chol:PEG-DMG |
| 60:20:20:0 | Compound:Phospholipid:Chol:PEG-DMG |
| 40:15:45:0 | Compound:Phospholipid:Chol:PEG-DMG |
| 45:15:40:0 | Compound:Phospholipid:Chol:PEG-DMG |
| 50:15:35:0 | Compound:Phospholipid:Chol:PEG-DMG |
| 55:15:30:0 | Compound:Phospholipid:Chol:PEG-DMG |
| 60:15:25:0 | Compound:Phospholipid:Chol:PEG-DMG |
| 40:10:50:0 | Compound:Phospholipid:Chol:PEG-DMG |
| 45:10:45:0 | Compound:Phospholipid:Chol:PEG-DMG |
| 50:10:40:0 | Compound:Phospholipid:Chol:PEG-DMG |
| 55:10:35:0 | Compound:Phospholipid:Chol:PEG-DMG |
| 60:10:30:0 | Compound:Phospholipid:Chol:PEG-DMG |

Example 3

IL-23 mRNA Monotherapy Efficacy in A20 (Lymphoma) and MC38-C (Colon Cancer) Models Monotherapy efficacy using IL-23 mRNA monotherapy was assessed in a A20 lymphoma model and in a MC38-C colon cancer model. MC-38 colon adenocarcinoma tumors were established subcutaneously in C57BL/6 mice. See Rosenberg et al., Science 233(4770):1318-21 (1986). A20 mouse B-cell lymphoma cells (A20, ATCC No. TIB-208; ATCC, Manassas, Va.) were cultured according to the vendor's instructions. A20 cells were inoculated subcutaneously in BALB/c mice to generate subcutaneous tumors. Tumor were monitored for size and palpability. See Kim et al., Journal of Immunology 122(2):549-554 (1979); Donnou et al., Advances in Hematology 2012:701704 (2012)

Polynucleotides corresponding to mRNAs encoding IL-23 (mRNA without a miR-122 binding site) and NST-FIX control mRNA were prepared as described in the present specification. The mRNAs were formulated in Compound 18 LNPs.

Once the MC-38 or A20 tumors reached a mean size of approximately 100 mm3, animals were treated with single intratumoral doses of mRNAs (2.5 μg/dose).

Control animals were treated with an equivalent dose of negative control mRNA. "NST" controls are non-translatable versions of an mRNA encoding a control protein, wherein the mRNA comprises multiple stop codons.

Tumor volume was measured at the indicated time points using manual calipers. Tumor volume was recorded in cubic millimeters.

Figure 1B:
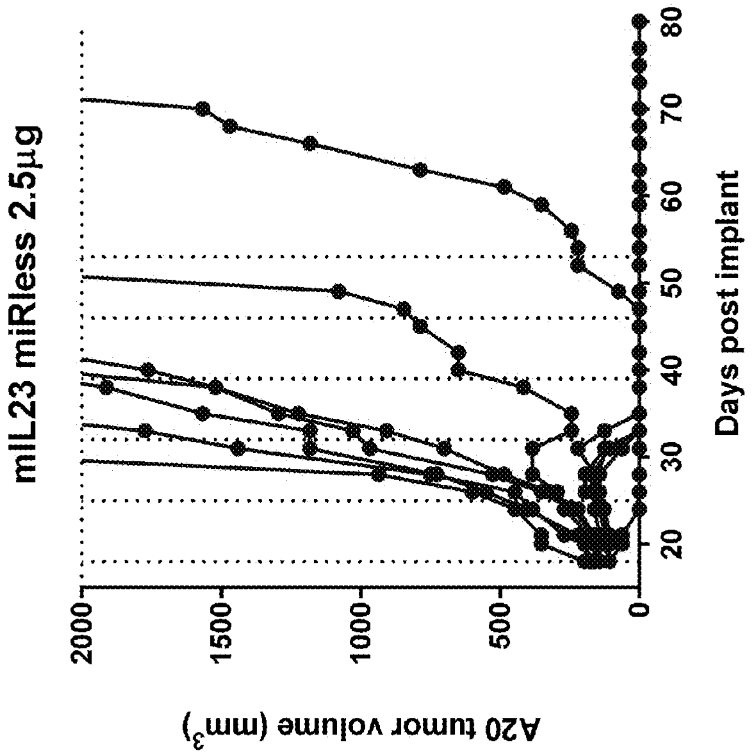
Figure 1A:
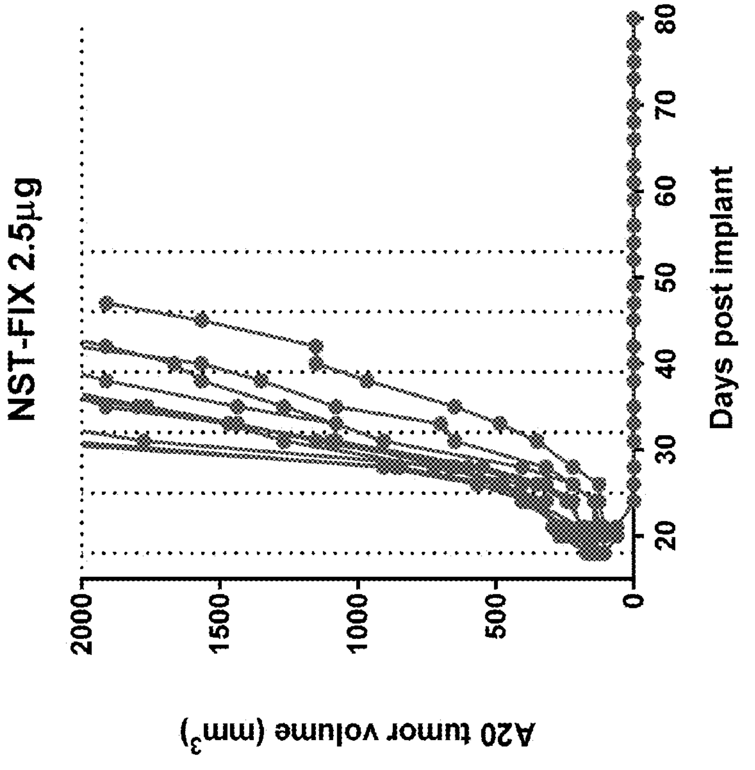
Figure 2B:
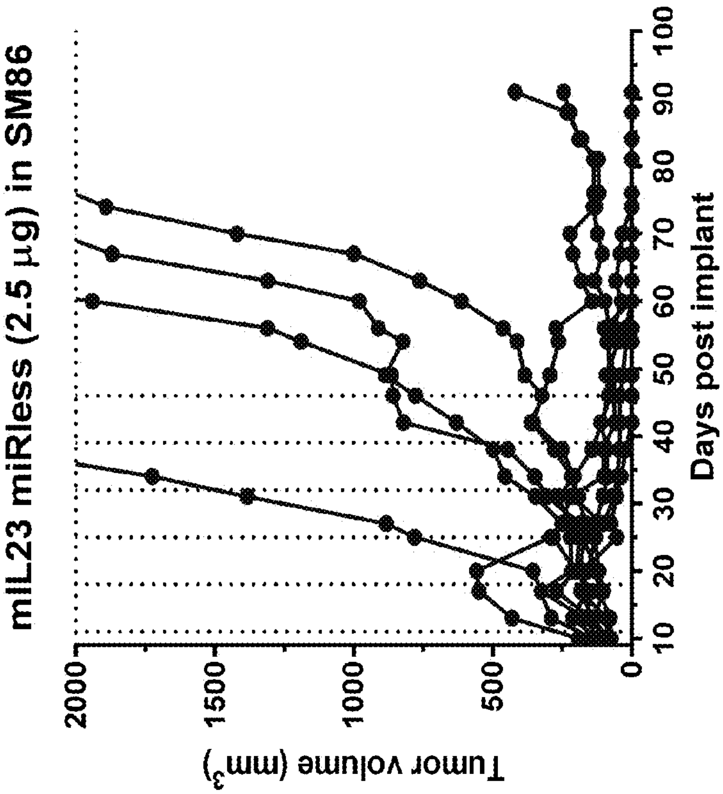
Figure 2A:
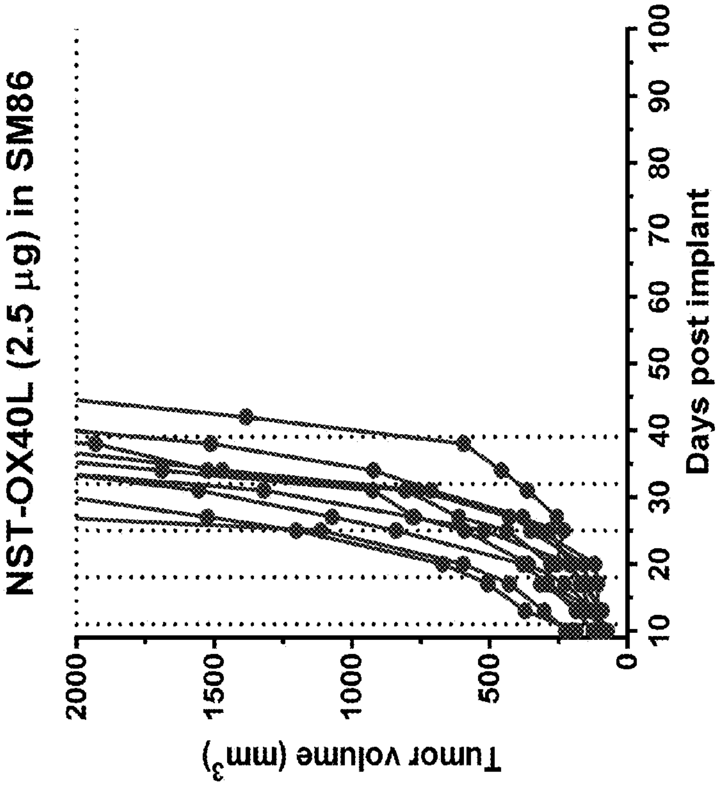

IL-23 mRNA monotherapy efficacy in the A20 lymphoma model is shown in FIGS. 1A and 1B. FIG. 1A shows treatment with NST-FIX mRNA control (2.5 μg mRNA). A complete response ("CR") was observed in 1 of 12 subjects (8.3%). FIG. 1B shows treatment with mRNA encoding mIL-23 without miRNA binding site "miRless" (2.5 μg mRNA). Treatment with the IL-23 mRNA elicited complete responses in 5 of 12 subjects (41.6%). IL-23 mRNA monotherapy efficacy in the MC38-C colon cancer model is shown in FIGS. 2A and 2B. FIG. 2A shows treatment with NST-OXL40 mRNA control (2.5 μg mRNA). FIG. 2B shows treatment with mRNA encoding mIL-23 without miRNA binding site "miRless" (2.5 μg mRNA). Administration of the IL-23 mRNA elicited complete responses in 4 of 10 subjects (40%). Partial response was observed in 2 of 10 subjects (20%).

Example 4

Addition of mRNA Encoding IL-36 Gamma or IL-18 to mRNA Encoding IL-23 Increases Efficacy in the MC38-C Model The effect of the addition of mRNAs encoding interleukin 36-gamma or interleukin 18 to IL-23 mRNA treatment was also assessed in the MC38-C colon cancer model. As in example 3, MC-38 colon adenocarcinoma tumors were established subcutaneously in C57BL/6 mice to generate subcutaneous tumors.

Polynucleotides corresponding to mRNAs encoding IL-23, IL-36-gamma and IL-18 mRNA were prepared as described in the present specification. The mRNAs were formulated in Compound 18 LNPs. Once the MC38 tumors reached a mean size of approximately 100 mm3, animals were treated with single intratumoral doses of mRNAs. Control animals were treated with an equivalent dose of negative control mRNA.

Tumor volume was measured at the indicated time points using manual calipers. Tumor volume was recorded in cubic millimeters. The in vivo efficacy study was carried out through Day 50 post-dosing.

Figure 3A:
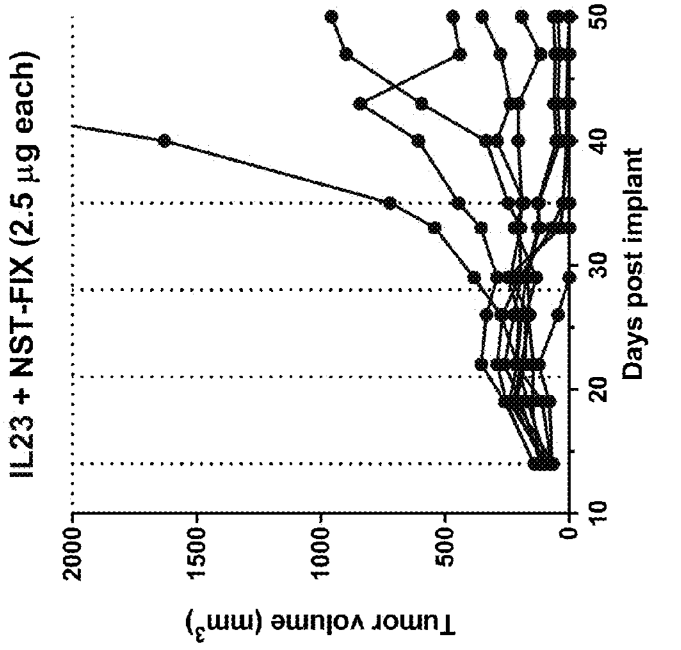

The data showed that the addition of IL-36-gamma or IL-18 to a treatment comprising IL-23-encoding mRNA increased the efficacy of the treatment in the MC38-C colon cancer model. FIG. 3A shows treatment with mRNA encoding IL-23 and NST-FIX mRNA control (2.5 μg each mRNA). Complete response was observed in 3 of 10 subjects (30%). Partial response was observed in 6 of 10 subjects (60%). Extended data up to day 90 is shown in FIG. 3E.

Figure 3B:
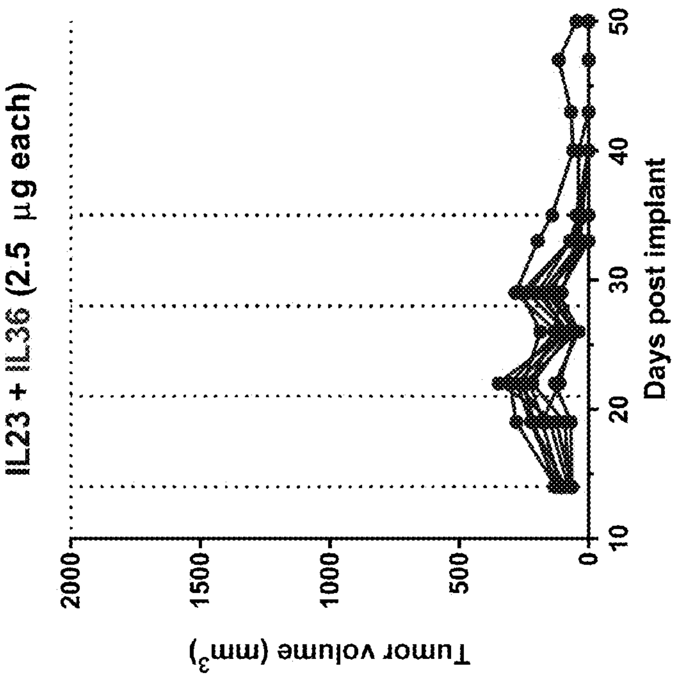
Figure 3D:
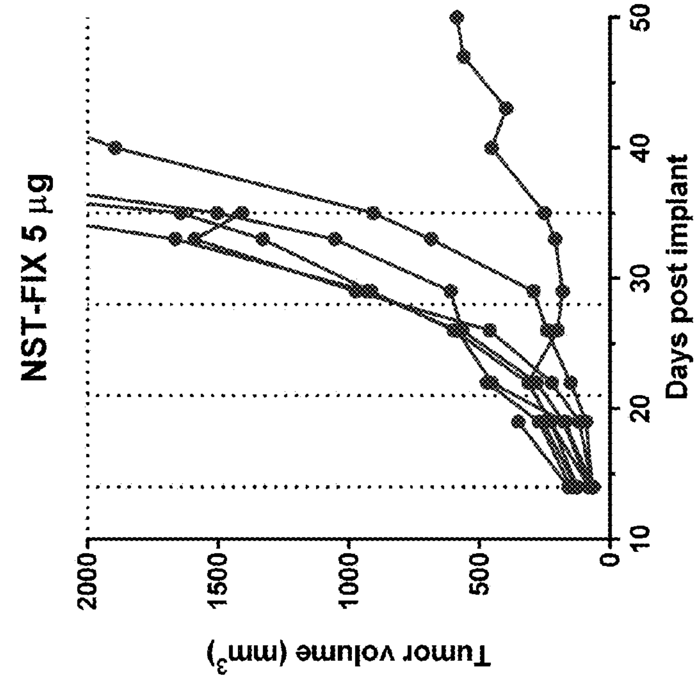

FIG. 3B shows treatment with mRNAs encoding IL-23 and IL-36-gamma (2.5 μg each mRNA). Complete response was observed in 9 of 10 subjects (90%). Partial response was observed in 1 of 10 subjects (10%). Extended data up to day 90 is shown in FIG. 3F.

Figure 3C:
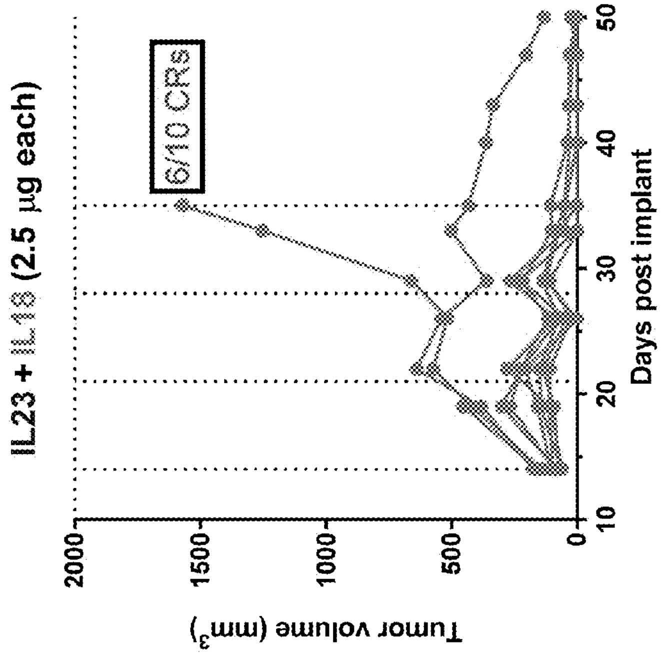
Figure 3E:
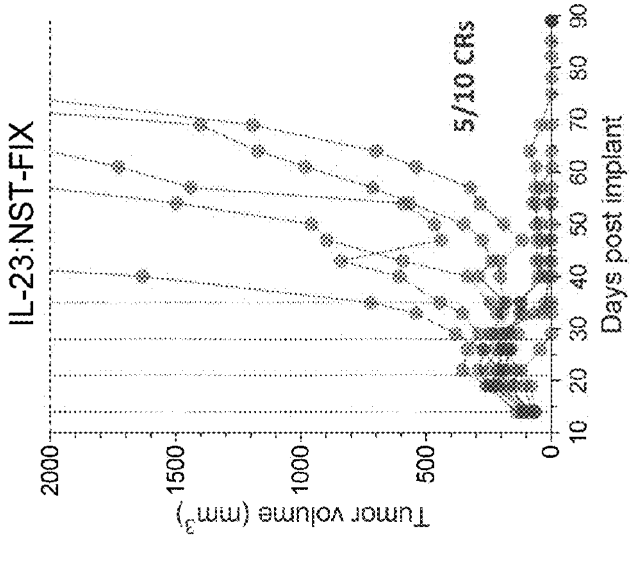
Figure 3F:
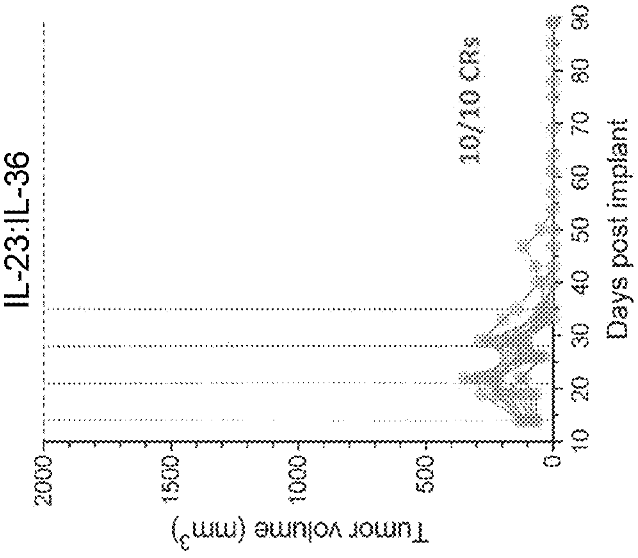

FIG. 3C shows treatment with an mRNA encoding IL-23 and a second mRNA encoding IL-18 (2.5 μg each mRNA). Complete response was observed in 6 of 10 subjects (60%). Partial response was observed in 3 of 10 subjects (30%).

Figure 3G:
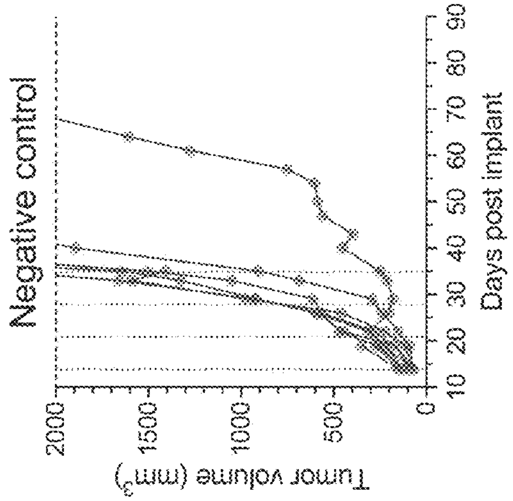

FIG. 3D shows treatment with NST-FIX mRNA control alone (5 μg mRNA). Extended data up to day 70 is shown in FIG. 3G.

The data indicates that the combination of IL-23-encoding mRNA with a second mRNA encoding IL-36-gamma was more effective than IL-23 mRNA monotherapy. Furthermore, the IL-23 and IL-36-gamma combination therapy was more effective than IL-36-gamma monotherapy plus negative control mRNA (not shown). The data also indicates that the combination of an mRNA encoding IL-23 mRNA with a second mRNA encoding IL-18 was more effective than monotherapy with an mRNA encoding IL-23. Furthermore, the combination of an mRNA encoding IL-23 with mRNA encoding IL-18 was more effective than an mRNA encoding IL-18 monotherapy plus negative control mRNA (not shown).

Example 5

Effect of Addition of miR-122 Binding Site to IL-36-Gamma and IL-18 Combination Therapy The efficacy of combining mRNA encoding IL-36-gamma with IL-23 mRNA therapy, as well as the effect of adding a miR-122 to an mRNA encoding IL-36-gamma used in a combination therapy with an mRNA encoding IL-23 was evaluated.

Efficacy using IL-23 mRNA combination therapies was assessed in the A20 lymphoma model as described above. A20 mouse B-cell lymphoma cells were cultured according to the vendor's instructions, inoculated subcutaneously in BALB/c mice to generate subcutaneous tumors, and once the A20 tumors reached a mean size of approximately 100 mm3, animals were treated with single intratumoral doses of mRNAs.

Polynucleotides corresponding to mRNAs encoding NST-FIX control, mRNA encoding IL-23 or IL-18 without miR-122 "miRless", and mRNA encoding IL-36-gamma or IL-18 with miR-122 were prepared as described in the present specification. The mRNAs were formulated in Compound 18 LNPs. Tumor volume was measured at the indicated time points using manual calipers. Tumor volume was recorded in cubic millimeters. The in vivo efficacy study was carried out through Day 80 post-dosing.

Figure 4A:
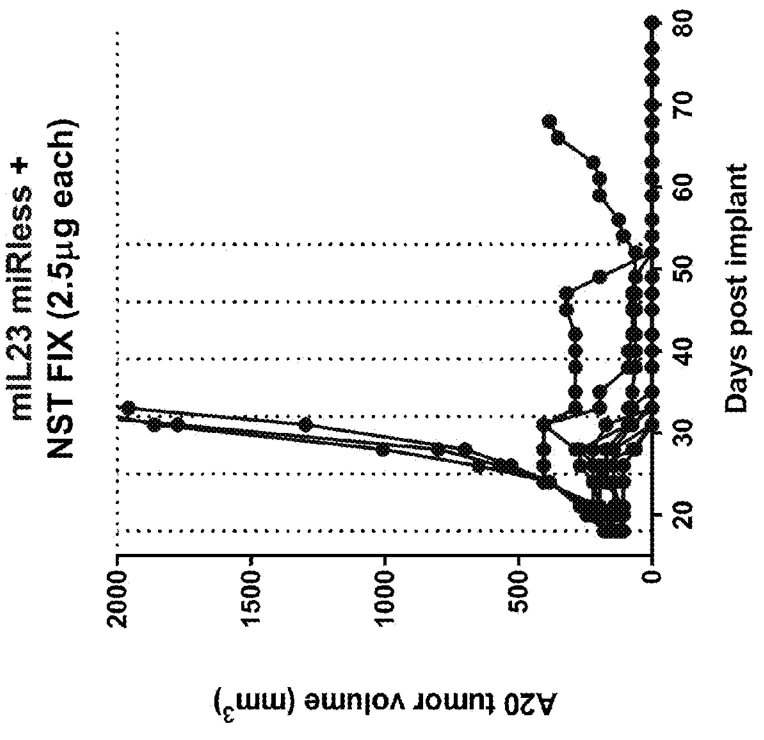
Figure 4B:
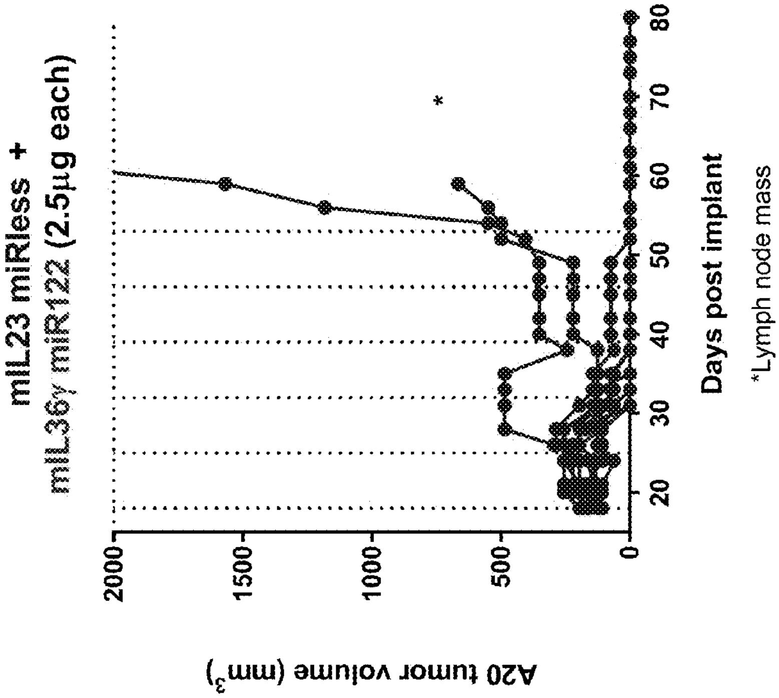
Figure 4C:
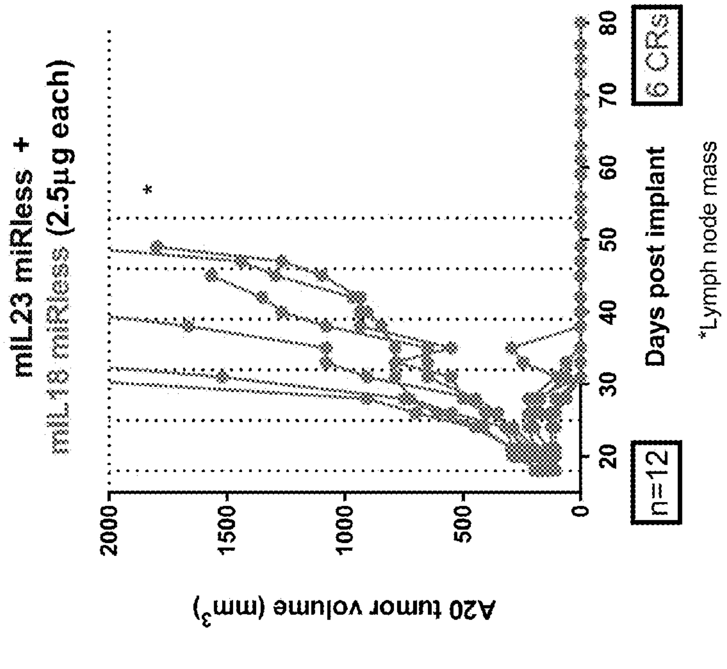
Figure 4D:
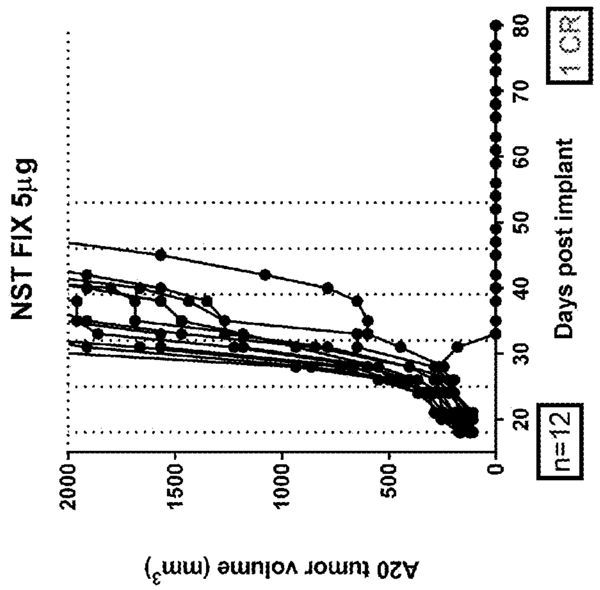

FIGS. 4A-4C show that addition of mRNA encoding IL-36-gamma to mRNA encoding IL-23 increases efficacy in the A20 lymphoma model. FIG. 4A shows treatment with a combination therapy comprising mRNA encoding IL-23 without miR-122 "miRless" and NST-FIX mRNA (2.5 μg each mRNA). Complete response was observed in 8 of 12 subjects (66.6%). Partial response was observed in 1 of 12 subjects (8.3%). FIG. 4B shows treatment with mRNA encoding IL-23 without miR-122 "miRless" and mRNA encoding IL-36-gamma with miR-122 (2.5 μg each mRNA). Complete response was observed in 10 of 12 subjects (83.3%). FIG. 4C shows treatment with an mRNA encoding IL-23 without miR122 binding site "miRless" and an mRNA encoding IL-18 without miR122 binding site "miRless" (2.5 μg each mRNA). Complete response was observed in 6 of 12 subjects (50%). FIG. 4D shows treatment with NST-FIX mRNA control (5 μg mRNA). mRNA encoding IL-23 plus mRNA encoding IL-36-gamma or IL-18 combinations were superior to mono constituents plus negative control mRNA (IL-1 monotherapies not shown). The efficacy of the combination of mRNA encoding IL-23 plus mRNA encoding IL-36-gamma comprising an mR122 binding site in the 5' UTR region of the mRNA was particularly high in comparison to a combination comprising miRless mRNA (i.e., mRNAs without a miR-122 binding site in the 5'-UTR region).

Example 6

Efficacy of mRNA Encoding IL-36-Gamma Plus mRNA Encoding IL-23 in the A20 Lymphoma Model The efficacy of mRNA encoding IL-36-gamma plus mRNA encoding IL-23 over mRNA encoding IL-23 alone with fixed 5 mg dose of mRNAs was assessed in the A20 lymphoma model. Experiments were conducted as detailed above.

Figure 5B:
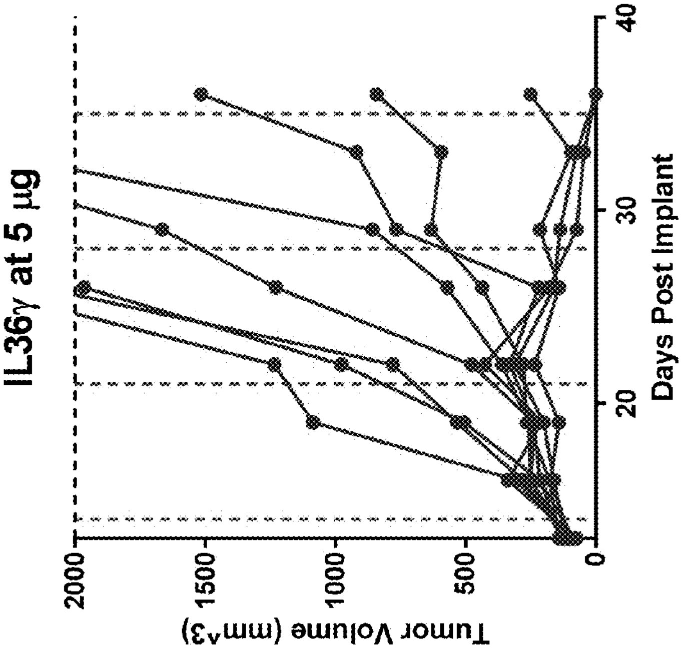
Figure 5A:
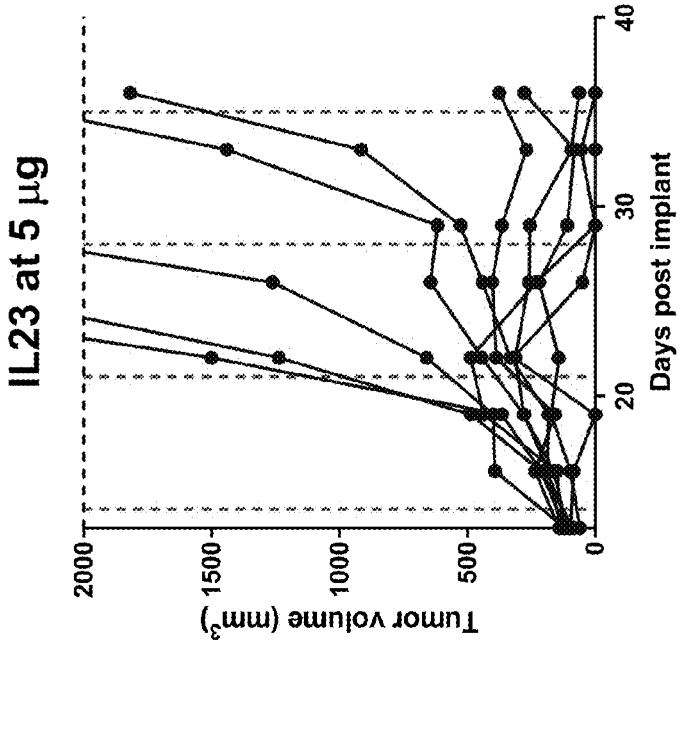
Figure 5D:
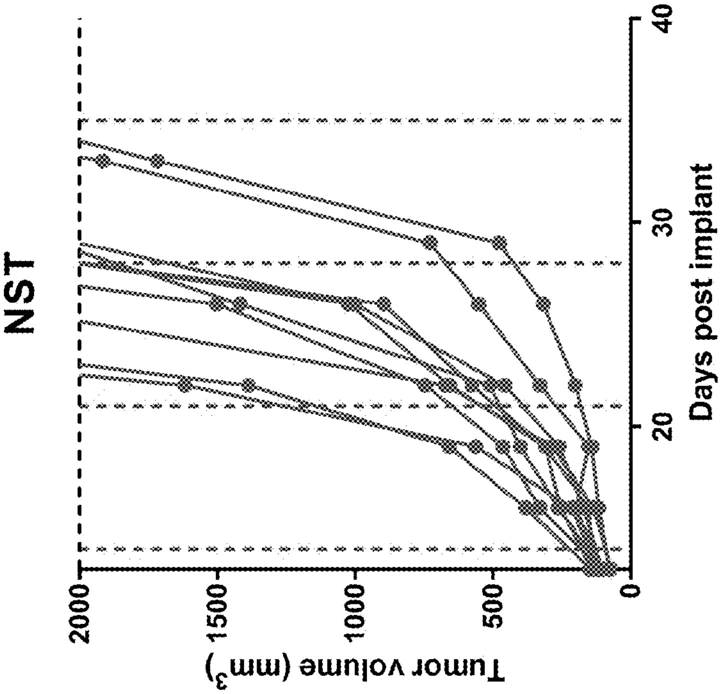
Figure 5C:
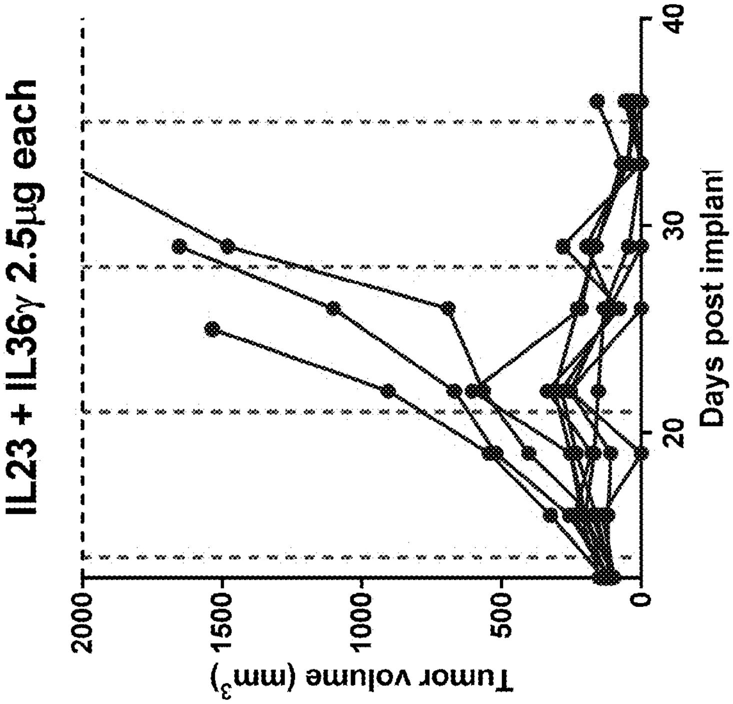

FIG. 5A shows treatment with mRNA encoding IL-23 (5 μg mRNA). Complete response was observed in 1 of 10 subjects (10%). Partial response was observed in 4 of 10 subjects (40%). FIG. 5B shows treatment with mRNA encoding IL-36-gamma (5 μg mRNA). Complete response was observed in 2 of 10 subjects (20%). Partial response was observed in 1 of 10 subjects (10/%). FIG. 5C shows treatment with mRNA encoding IL-23 and mRNA encoding IL-36-gamma (2.5 μg each mRNA). FIG. 5D shows treatment with NST-FIX mRNA control (5 μg mRNA). The data indicates that the IL-23/IL-36-gamma mRNA combination was superior to the administration of monoconstituent therapy at fixed 5 μg mRNA dose.

Example 7

Figure 6A:
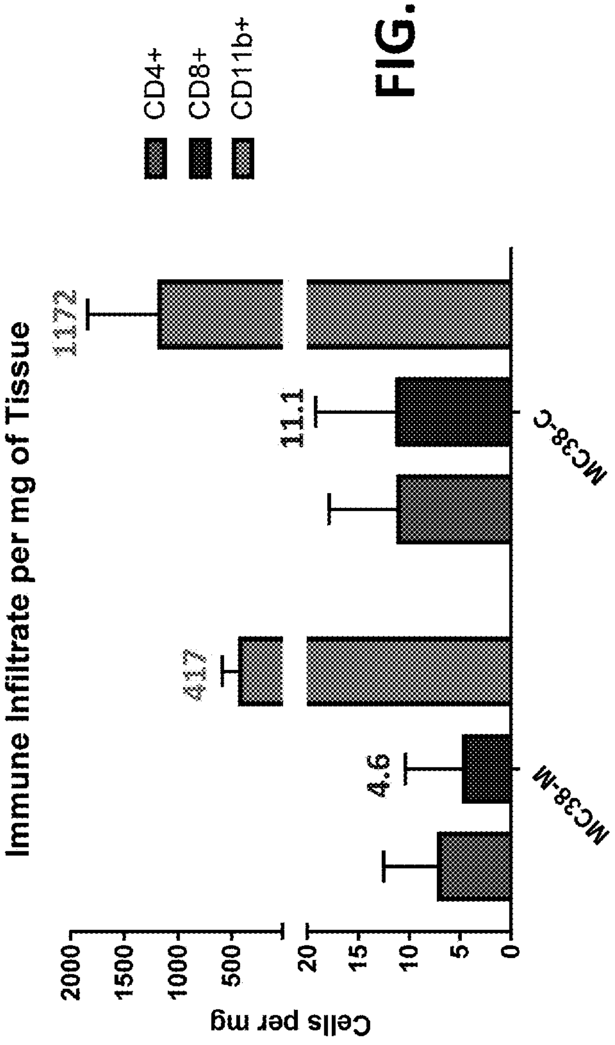
Figure 6B:
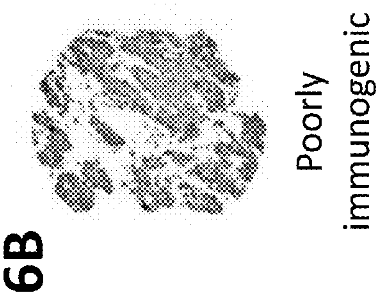
Figure 6C:
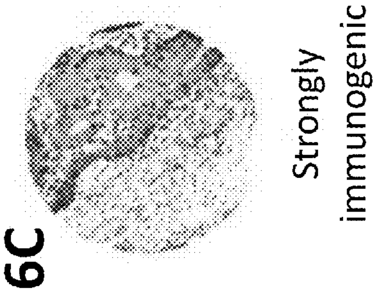

Efficacy of mRNA Encoding IL-23 Plus mRNA Encoding IL-36-Gamma or IL-18 in the MC38-M Colon Cancer Model The efficacy of combination therapy comprising mRNA encoding IL-23 plus mRNA encoding IL-36-gamma or IL-18 was assessed in the MC38 colon cancer model as described above. The experiments in previous examples were conducted using an MC38-C model (strongly immunogenic). In contrast, the experiments in the current example were conducted using an MC38-M model (poorly immunogenic). The differences in immune infiltrates and histological differences between both models are shown in FIGS. 6A and 6B.

Figure 7A:
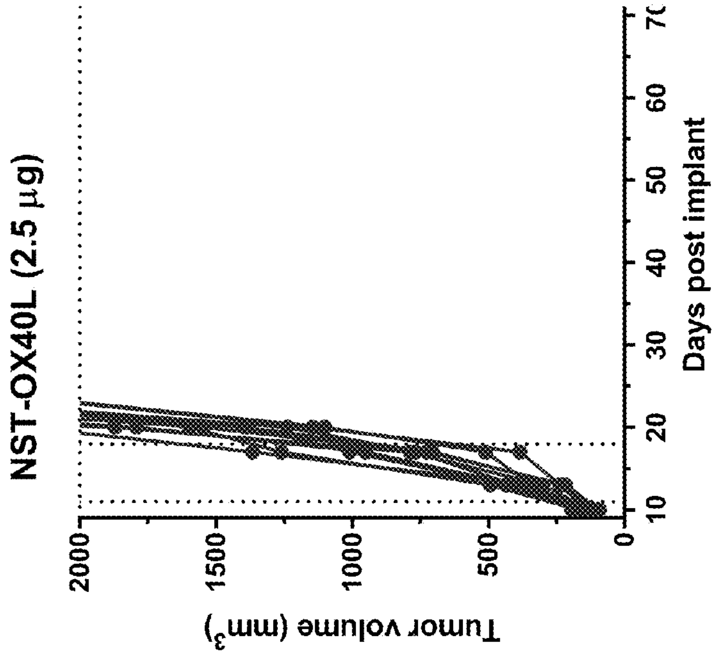
Figure 7B:
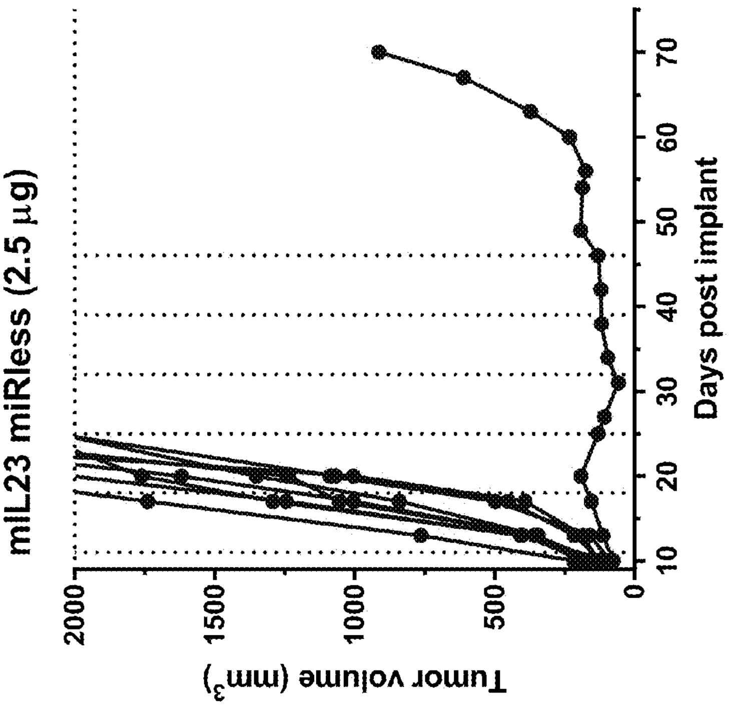

FIGS. 7A and 7B shows lack of compelling IL-23 mRNA monotherapy efficacy in the MC38-M colon cancer model. FIG. 7A shows treatment with NST-OX40L mRNA control (2.5 μg mRNA) in Compound 18-based LNPs. No response was observed. FIG. 7B shows treatment with mRNA encoding IL-23 without miR-122 "miRless" (2.5 μg mRNA) in Compound 18-based LNPs. Only one partial response was observed (1 of 10, 10%). MC38-M is a relatively insensitive model in which OX40L, anti-PD-1 antibody, and IL-23 monotherapies are ineffective.

Figure 7D:
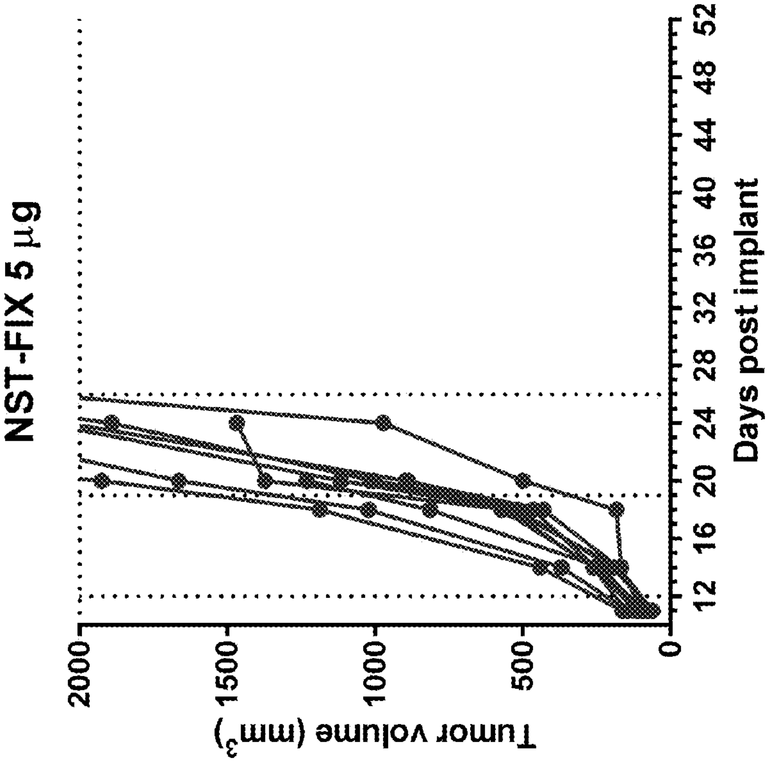
Figure 7C:
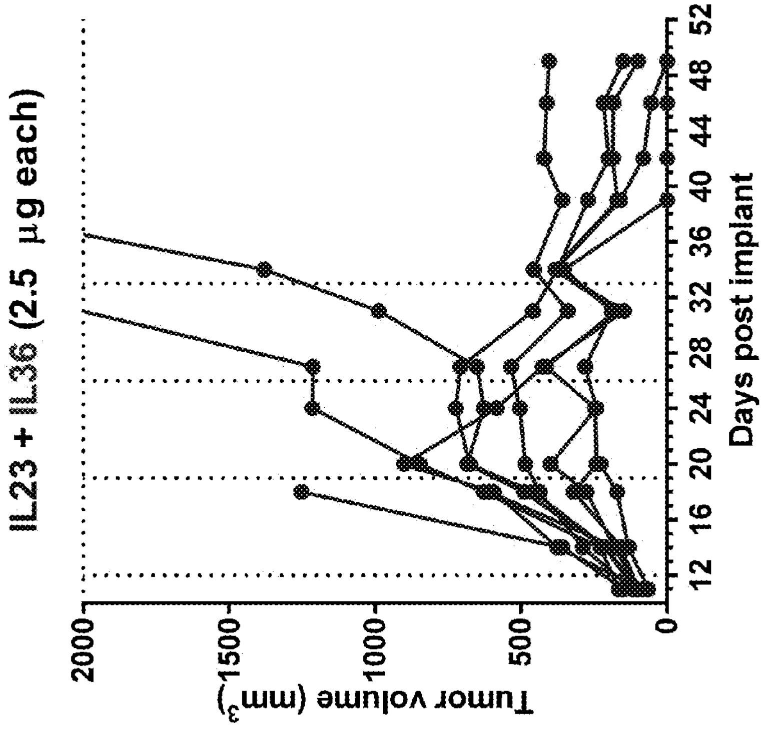

FIG. 7C shows that the combination of mRNA encoding IL-23 with mRNA encoding IL-36-gamma is efficacious in poorly immunogenic MC38-M colon cancer. The figure shows treatment with mRNA encoding IL-23 and mRNA encoding IL-36-gamma (2.5 μg each mRNA). The treatment with mRNA encoding IL-23 and mRNA encoding IL-36-gamma elicited complete responses in 2 of 10 subjects (20%) and partial responses were observed in 5 of 10 subjects (50%).

Figure 7E:
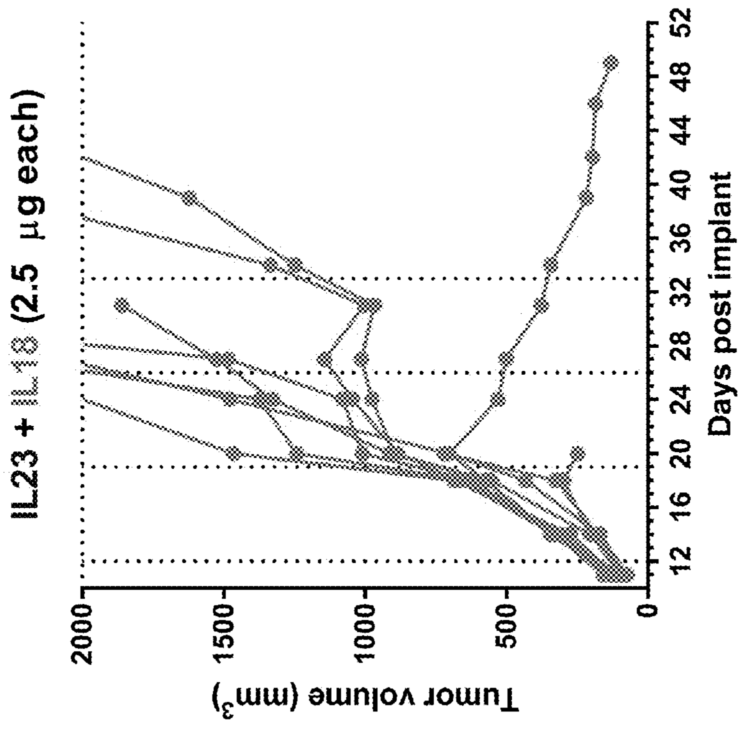

FIG. 7E shows that the combination of an mRNA encoding IL-23 with an mRNA encoding IL-18 is efficacious in poorly immunogenic MC38-M colon cancer. The figure shows treatment with an mRNA encoding IL-23 and an mRNA encoding IL-18 (2.5 μg each mRNA). FIG. 7D shows treatment with NST-FIX mRNA control (5 μg mRNA).

Example 8

Efficacy of Triple Combination of mRNAs Encoding IL-23, IL-36-Gamma, and OX40L in the MC38-M Colon Cancer Model The efficacy of triple combination therapy comprising mRNA encoding IL-23, mRNA encoding IL-36-gamma, and mRNA encoding OX40L was assessed in the MC38 colon cancer model as described above. The experiments in the current example were conducted using an MC38-M model (poorly immunogenic), see FIG. 9C.

Figure 8:
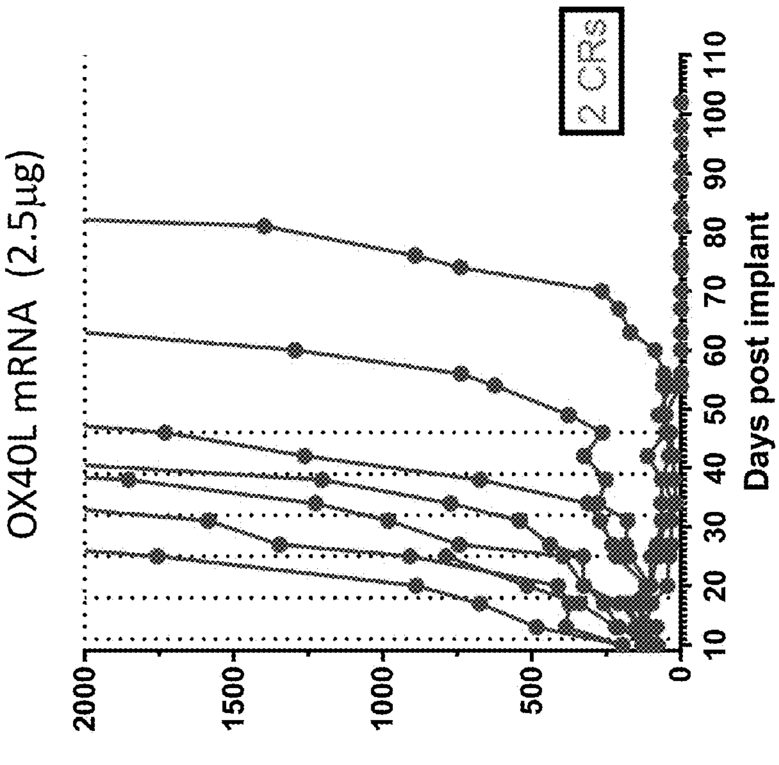

FIG. 8 shows that OX40L was efficacious in the A20 tumor model. In contrast, there was lack of compelling efficacy when OX40L was used in the MC38-M colon cancer model (FIG. 9A). The observed effect was similar to that observed when the same model was treated in an anti-PD-1 antibody (FIG. 9B).

Figure 10A:
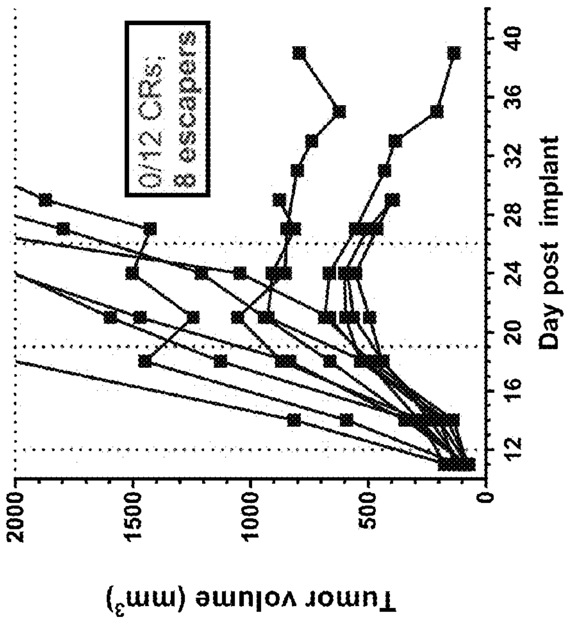
Figure 10B:
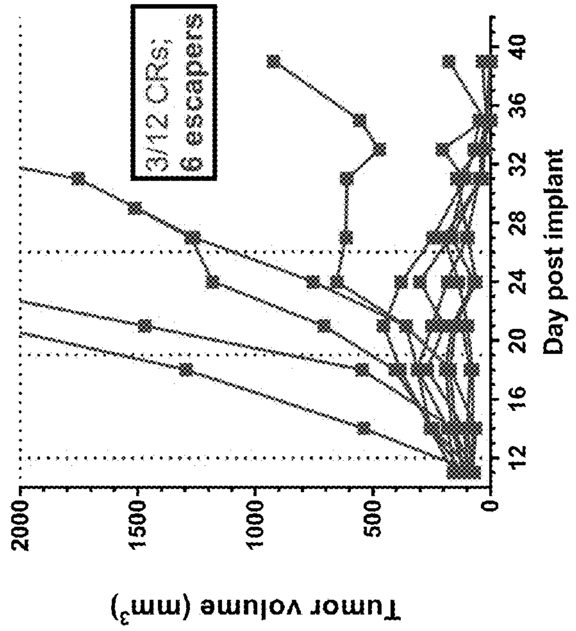
Figure 10C:
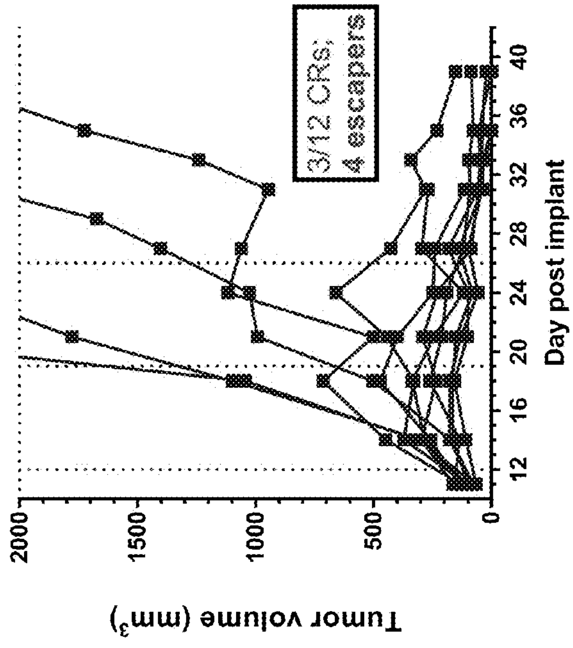
Figures 10D, 10E, 10F:
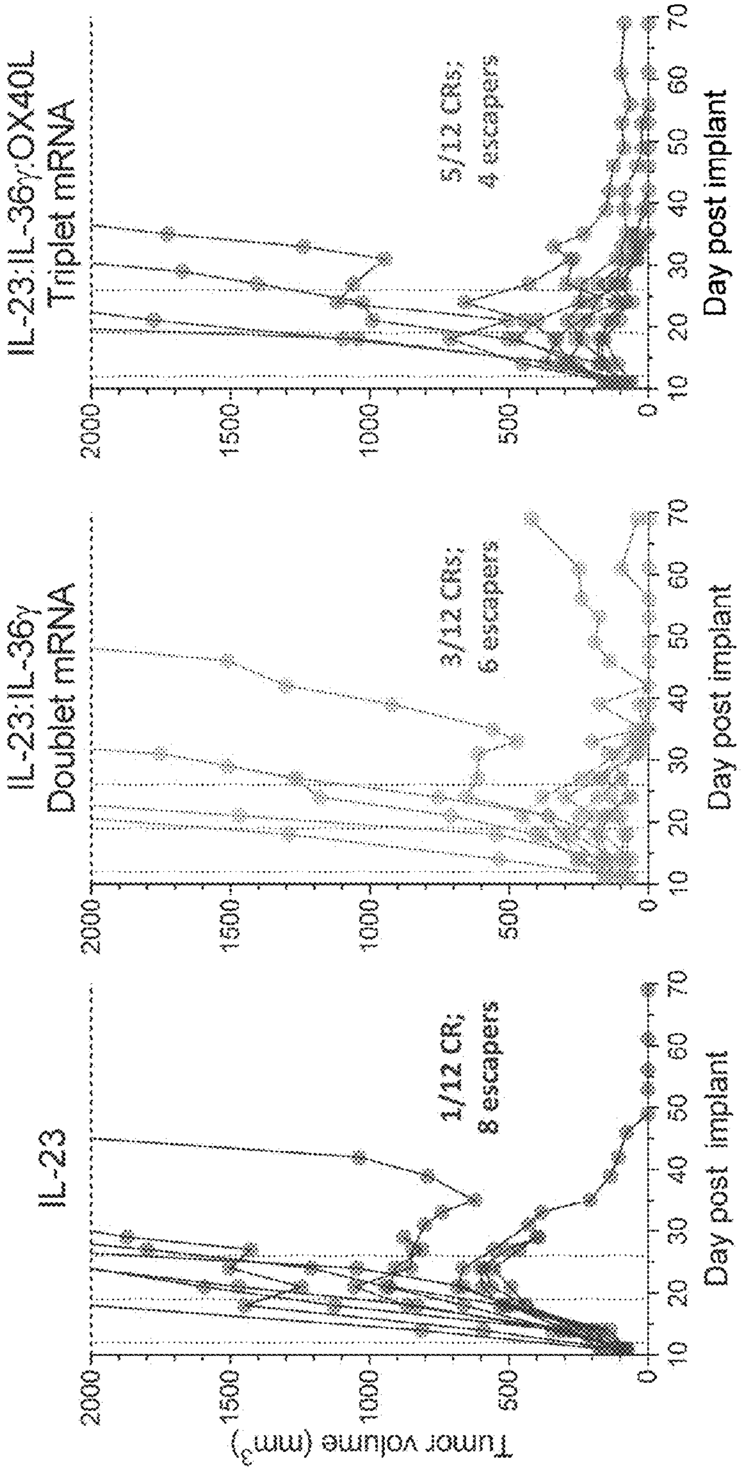

In contrast, efficacy in MC38-M colon cancer model was observed when mRNA encoding IL-23 comprising an miR-122 binding site (5 μg mRNA in Compound 18-based LNPs) (FIG. 10A). No complete response was observed, but 8 escapers were observed. Experimental data extended to day 70 is shown in FIG. 10D.

When mRNA encoding IL-23 comprising an miR-122 binding site (2.5 μg mRNA) was combined with mRNA encoding IL-36-gamma comprising an miR-122 binding site (2.5 μg mRNA) (FIG. 10B), three complete responders were observed (25%), and the number of escapers was reduced from eight to six. Experimental data extended to day 70 is shown in FIG. 10E.

When mRNA encoding IL-23 comprising an miR-122 binding site (1.7 μg mRNA) was combined with an mRNA encoding IL-36-gamma comprising an miR-122 binding site (1.7 μg mRNA) and with an mRNA encoding OX40L comprising an miR-122 binding site (1.7 μg mRNA) (FIG. 10C), three complete responders were observed (25%), and the number of escaper was further reduced from six to four. Experimental data extended to day 70 is shown in FIG. 10F.

Figure 10G:
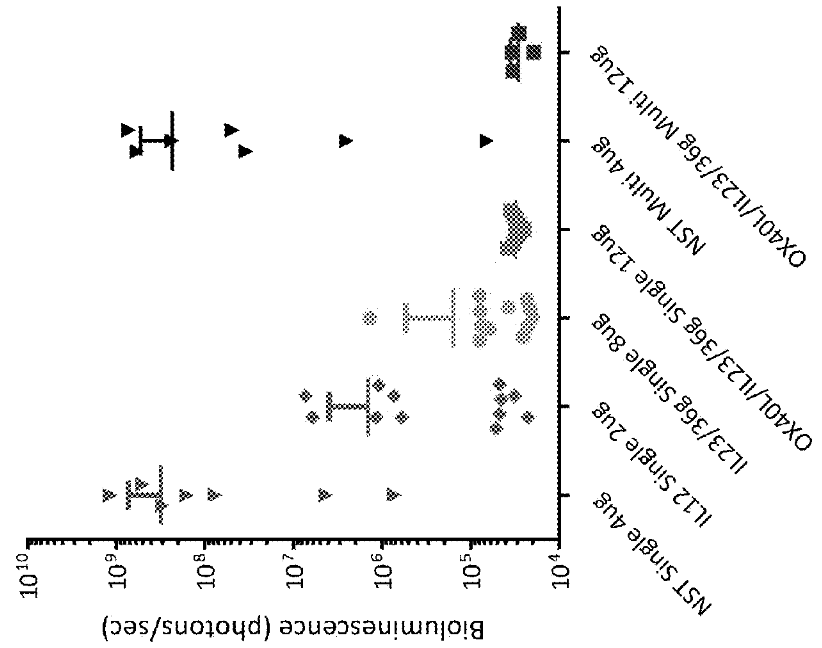
Figure 10H:
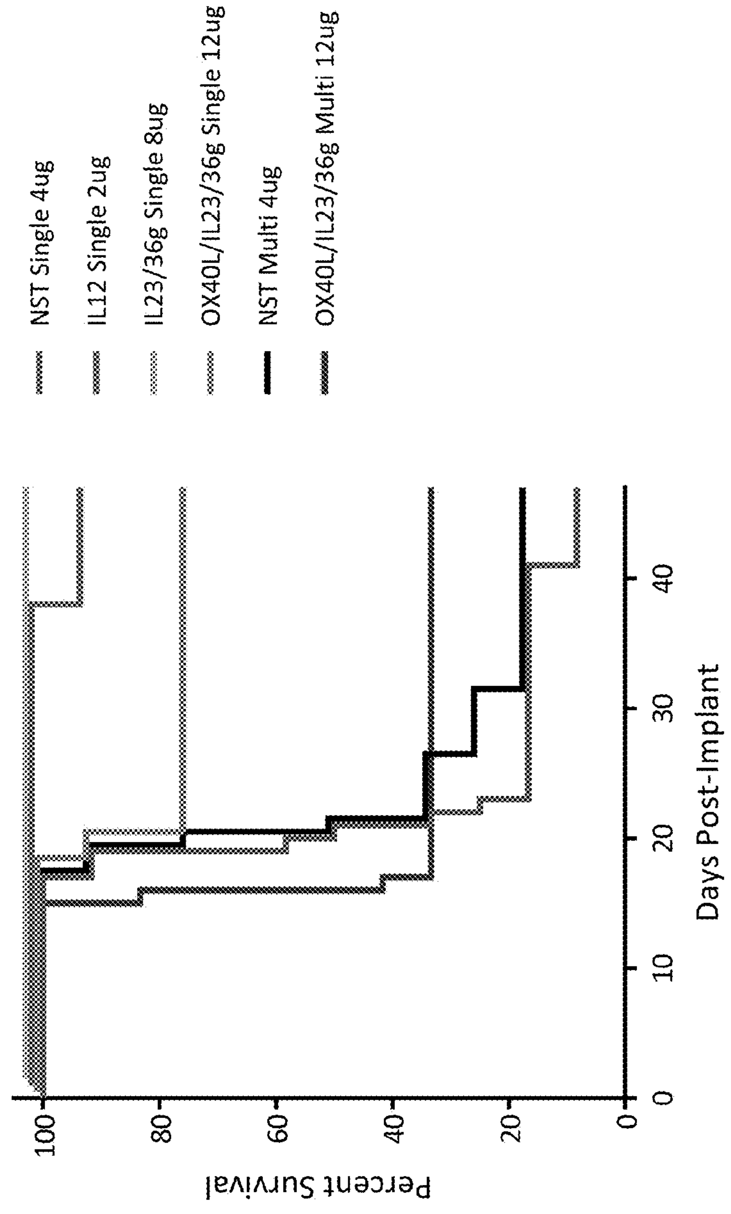

A further experiment assessed single dosing of the doublet and single or multiple dosing of the triplet in the MC38 model using MC38 luciferase cells. mRNA encoding IL-23 comprising an miR-122 binding site was combined with mRNA encoding IL-36-gamma comprising an miR-122 binding site and administered at a single dose (8 μg). mRNA encoding IL-23 comprising an miR-122 binding site, mRNA encoding IL-36-gamma comprising an miR-122 binding site, and mRNA encoding OX40L comprising an miR-122 binding site, was administered at a single dose or multiple doses of 12 μg. Relative to control, bioluminescence was reduced with the single dose of the double combination, and both single and multiple doses with the triple combination, with a more significant reduction seen in the triple combination (FIG. 10G). However, survival over 45 days was reduced in mice treated with multiple doses of the triple combination, corresponding to treatment-related deaths (FIG. 10H).

Example 9

Bioactivity of IL-23 Produced from mRNA

The activity of IL-23 protein produced from mRNA introduced into a cell was assessed in a bioassay and compared to the activity of recombinant IL-23 protein. Polynucleotides corresponding to mRNAs encoding murine IL-23 or human IL-23 were prepared as described in the present specification. HeLa cells were transfected with mRNA encoding murine IL-23 (mRNA mIL-23), mRNA encoding human IL-23 (mRNA hIL-23), or mock transfected, and the supernatant was harvested from the transfected cells. The amount of IL-23 protein in the collected supernatants was measured by ELISA, then varying levels (mock (0 ng/ml), 0.1 ng/ml, 1 ng/ml, 3.3 ng/ml, 10 ng/ml, or 100 ng/ml) of the mRNA-produced proteins, or recombinant murine IL-23 (rec mIL-23), or recombinant human IL-23 (mRNA hIL-23) was added to cultured mouse primary splenocytes. The splenocytes were cultured with the IL-23-containing supernatants, or recombinant proteins for 3 days, and the amount of IL-17 produced by the splenocytes was then measured. IL-17 production serves as an indicator of IL-23 bioactivity.

Figure 11:
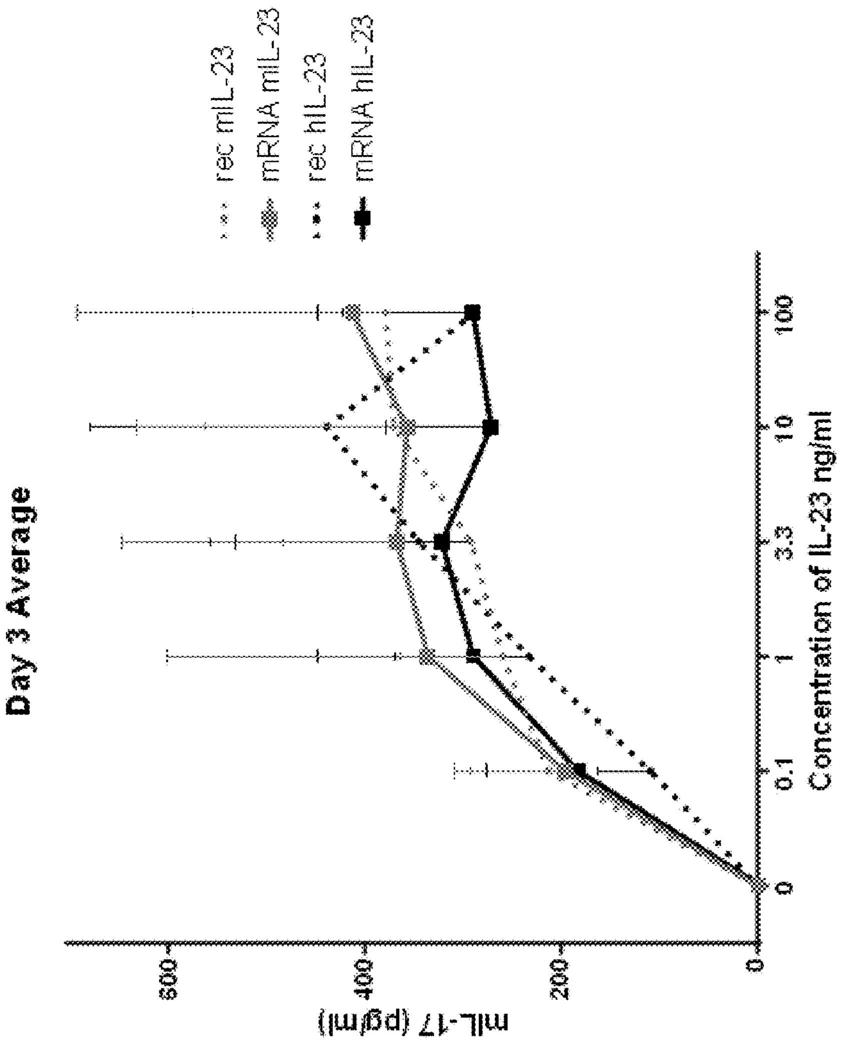

FIG. 11 shows that IL-23 produced from mRNA has equivalent bioactivity, i.e., induction of IL-17 expression from primary mouse splenocytes, to recombinant IL-23 proteins (e.g. protein form mRNA hIL-23 compared to rec hIL-23). Additionally, in vivo expression from human IL-23 mRNA was determined to be greater than expression from the mouse orthologue (data not shown).

Example 10

Bioactivity of IL-36-Gamma Produced from mRNA

The activity of IL-36-gamma protein produced from mRNA introduced into a cell was assessed in a bioassay and compared to the activity of recombinant IL-36-gamma protein. Polynucleotides corresponding to mRNAs encoding murine IL-36-gamma or human IL-36-gamma were prepared as described in the present specification.

Figure 12A:
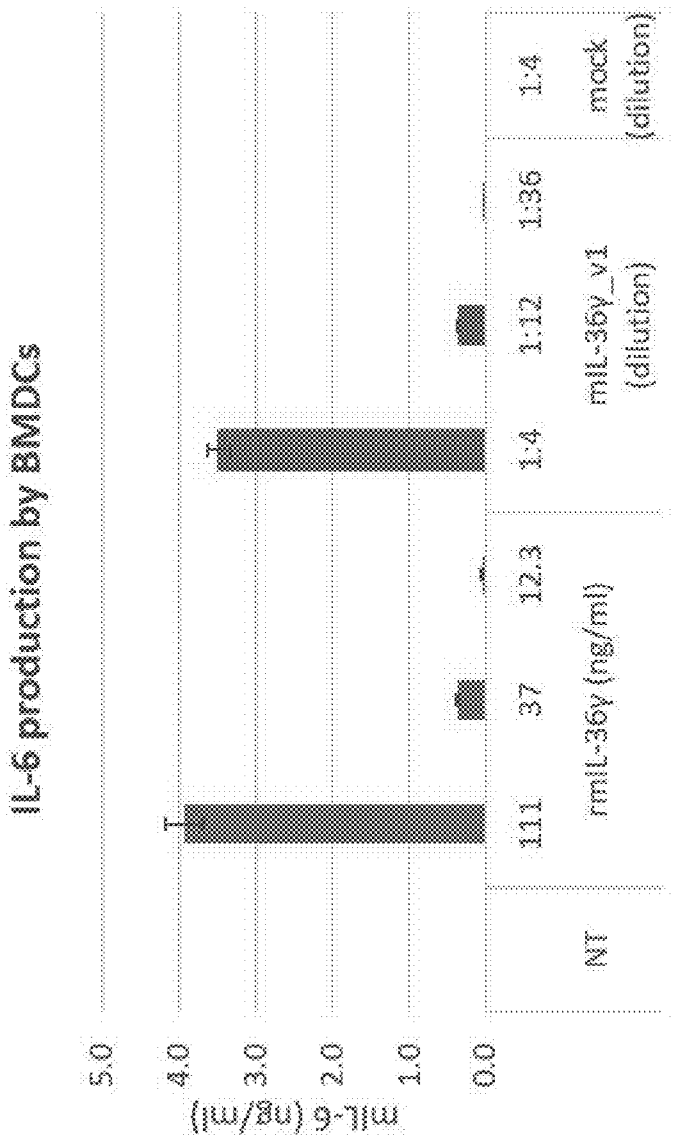

For murine IL-36-gamma experiments, HeLa cells were transfected with mRNA encoding murine IL-36-gamma protein (mIL-36γ mRNA_v1) or mock-transfected, and the supernatants from the transfected cells were collected. Bone-marrow derived dendritic cells (BMDCs) were exposed to the collected supernatants containing secreted mature murine IL-36-gamma or recombinant murine IL-36-gamma (rmIL-36γ) at varying concentrations, and IL6 production by the exposed BMDCs was assessed. IL6 production serves as an indicator of murine IL-36-gamma activity. FIG. 12A shows that mRNA encoding murine IL-36-gamma protein has equivalent bioactivity to recombinant human IL-36-gamma protein (rmIL-36γ compared to mIL-36γ).

Figure 12B:
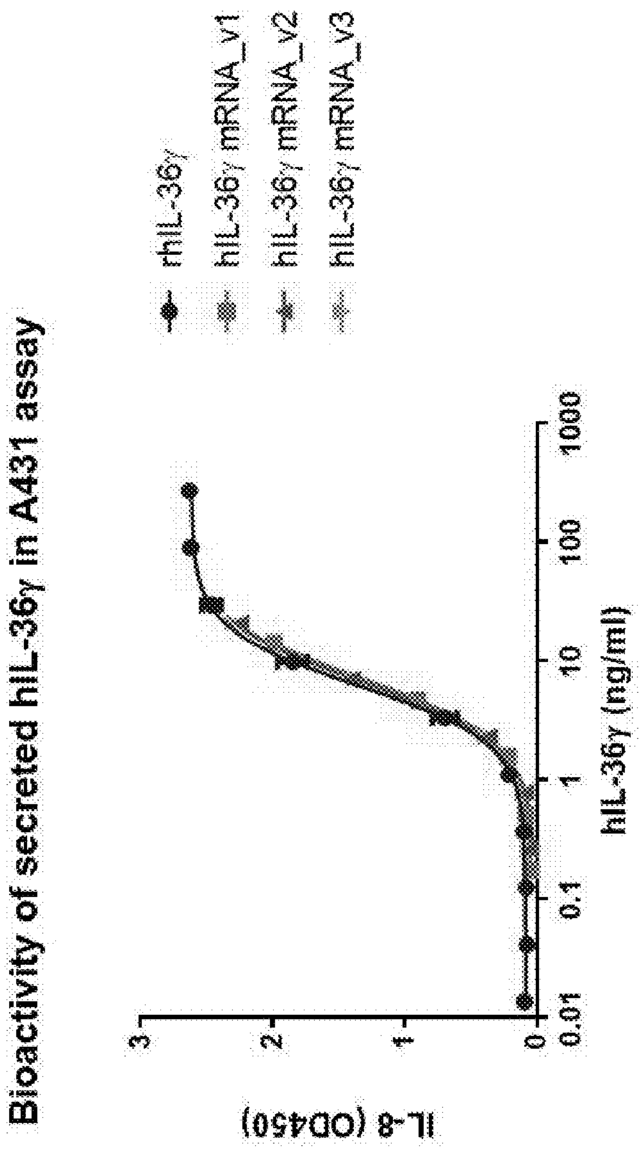

For human IL-36-gamma experiments, the bioactivity of IL-36-gamma was assessed using epidermoid carcinoma (e.g., A431) cells. B16F10 cells were transfected with mRNA encoding human IL-36-gamma with different signal peptides (hIL-36γ mRNA_v1; hIL-36γ mRNA_v2; or hIL-36γ mRNA_v3) and the supernatants from the transfected cells were collected. The concentrations of hIL-36g in the supernatants were determined by ELISA. A431 cells were exposed to hIL-36g-containing supernatants or recombinant human IL-36-gamma protein (rhIL-36γ) at varying levels and IL8 production in the supernatants of treated A431 cells was measured. IL8 production serves as an indicator of human IL-36-gamma activity. FIG. 12B shows that mRNAs-derived human IL-36-gamma protein have equivalent bioactivity to recombinant human IL-36-gamma protein (hIL-36γ mRNA_v1; hIL-36γ mRNA_v2; or hIL-36γ mRNA_v3 compared to rhIL-36γ).

Example 11

In Vitro Biological Activity of OX40L

T-cell activation involves two concurrent cell signaling events: a primary signal from the T-cell receptor complex (e.g., CD3 stimulation) and a second signal from a costimulatory ligand-receptor interaction (e.g., OX40L/OX40R interaction). Kober et al., European Journal of Immunology 38:2678-2688 (2008). In this example, the costimulatory biological activity of OX40L expressed on the surface of cells treated with mOX40L_miR-122 or hOX40L_miR-122 was assessed.

A. Preparation of OX40L-Expressing Cells

Mouse melanoma cells (B16F10, ATCC No. CRL-6475; ATCC, Manassas, Va.) were seeded in 6-well plates at a density of 300,000 cells per well. Human cervical carcinoma cells (HeLa) were seeded in 6-well plates as described above. A polynucleotide comprising an mRNA encoding an OX40L polypeptide and further comprising a miR-122 binding site (mouse OX40L, mOX40L_miR-122, SEQ ID NO: 66; human OX40L, hOX40L_miR-122, SEQ ID NO: 65) was formulated in L2K as described above in Example 2. 24 hours after seeding the cells, formulations containing 3 μg of mOX40L_miR-122 or hOX40L_miR-122 mRNA were added to each well. Control cells were either mock-treated or treated with negative control mRNA (non-translatable version of the same mRNA except with no initiating codons). The cells were incubated for 24 hours at 37° C.

B. Preparation of Naïve CD4+ T-Cells

Figure 13A:
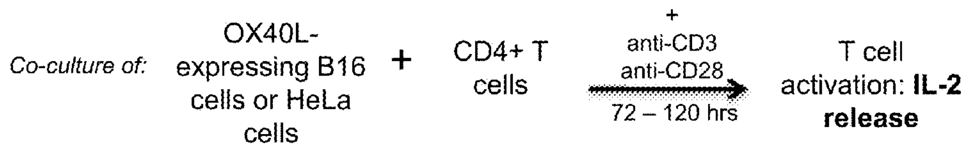

Spleens from Balb/c mice were removed and processed using standard techniques in the art to generate single cell suspensions of spleenocytes. Total $CD4^+$ T-cells were isolated from the splenocyte suspensions using a mouse CD4 T cell isolation kit (Miltenyi, San Diego, Calif.). Naïve human $CD4^+$ T-cells were isolated from human peripheral blood mononuclear cells (PBMCs) by depleting non-CD4 cells using a commercially available magnetic bead T cell isolation kit C. T-Cell Activation Assay 200,000 T-cells were added to each well of transfected B16F10 cells or HeLa cells in the presence of agonistic anti-mouse CD3 antibody (R&D Systems, Minneapolis, Minn.) or Dynabeads human T-activator; and the cells were co-cultured for 72 hours (mouse) or 120 hours (human). A schematic of the assays is shown in FIG. 13A.

Figure 13B:
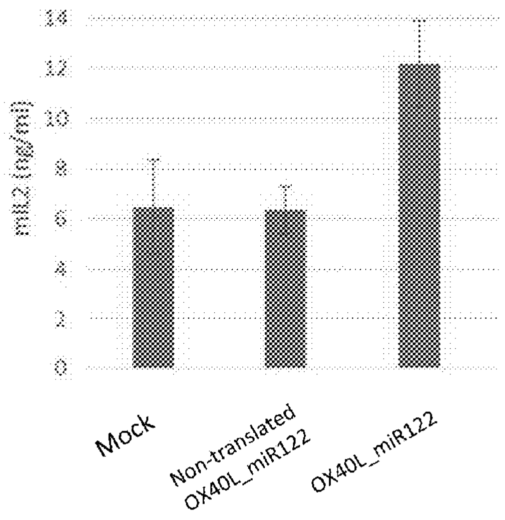

After co-culture with T-cells, mouse IL-2 production was measured using a mouse IL-2 ELISA. (mouse IL-2 DuoSet ELISA, R&D Systems, Minneapolis, Minn.). The amount of IL-2 produced by the $CD4^+$ T-cells serves as an indicator of T-cell activation. Results are shown in FIG. 13B. Human IL-2 production was measured using a human IL-2 ELISA (human IL-2 DuoSet ELISA, R&D Systems, Minneapolis, Minn.). Results are shown in FIGS. 13A, 13B, and 13C.

D. Results

FIG. 13B shows that OX40L expression on the surface of B16F10 cells treated with mOX40L_miR-122 elicits a T-cell IL-2 response in vitro. The mOX40L_miR-122 mRNA induced about 12 ng/ml of IL-2. B16F10 cells treated with non-translated negative control mRNA showed baseline levels of T-cell activation comparable to mock-treated cells (i.e., about 6 ng/ml of IL-2). Therefore, the mOX40L_miR-122 mRNA induced about two fold higher IL-2 expression compared to a control (mock treated or non-translated mRNA).

Figure 13C:
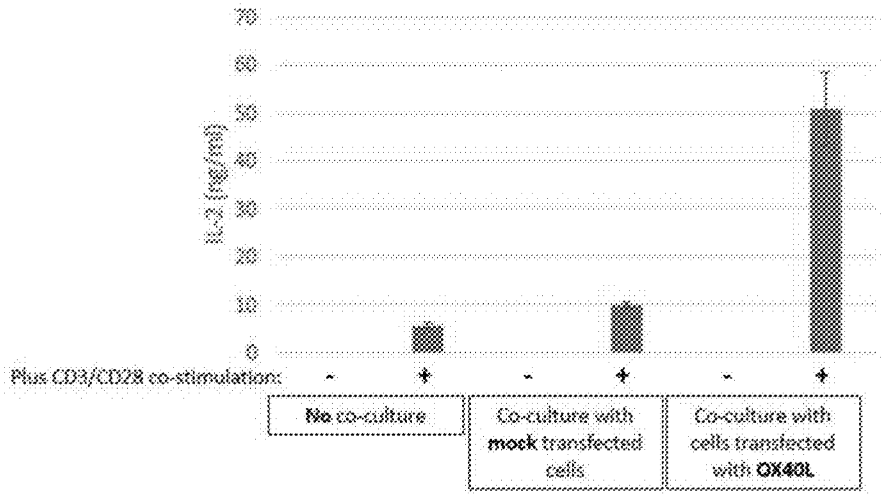
Figure 13D:
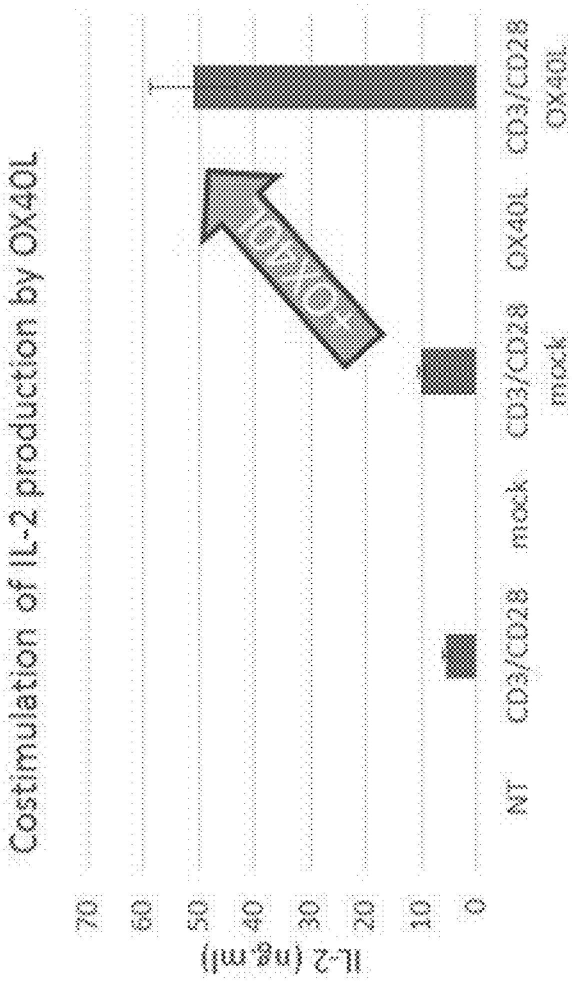
Figure 13E:
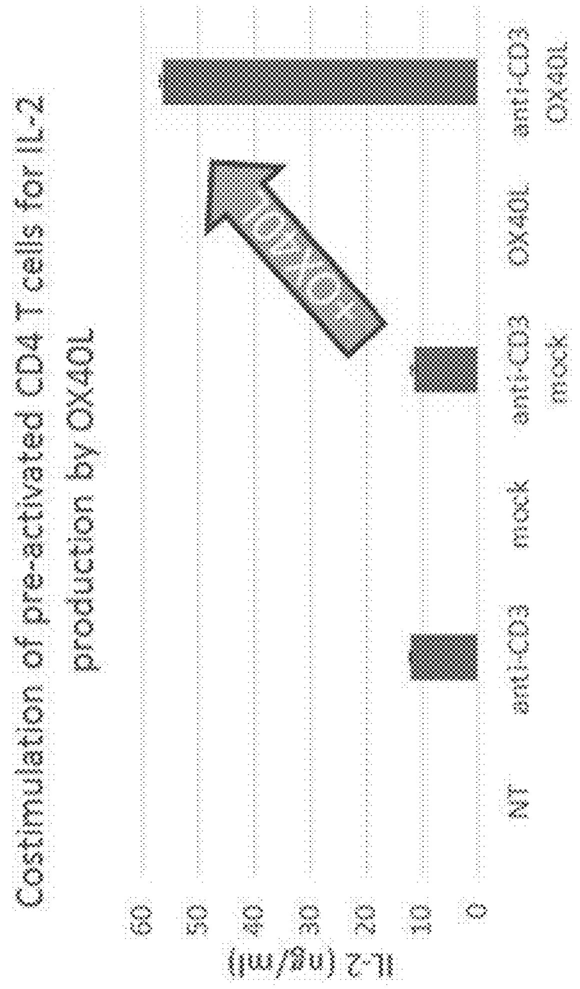

FIGS. 13C and 13D show that, in the presence of Dynabeads human T-activator as the primary T-cell activators, co-culture with the OX40L mRNA transfected HeLa cells greatly enhanced IL-2 production. Without OX40L expression, little to no IL-2 production was detected. FIG. 13E shows a similar level of increased human IL-2 production when the same experiment was performed with pre-stimulated (i.e., non-naïve) $CD4^+$ T-cells.

These results show that the OX40L polypeptide is biologically active as a costimulatory molecule.

Example 12

Modulation of Immune Cell Populations within Tumors Treated with OX40L mRNA

Given the demonstrated activity of OX40L on innate immune natural killer (NK) cells and adaptive CD4+/CD8+ T cells, the objective of the following studies was to evaluate the pharmacodynamic effects of OX40L intratumoral treatment on tumor-associated immune cell populations. Mouse A20 and MC38 tumor models were established as described above.

A. Cell Differentiation by Flow Cytometry

Figure 14A:
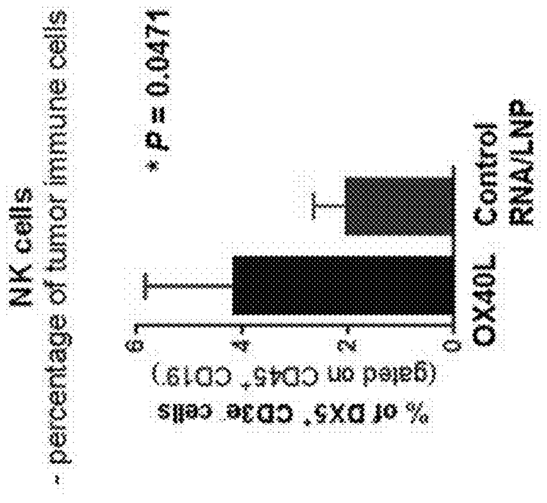
Figure 14B:
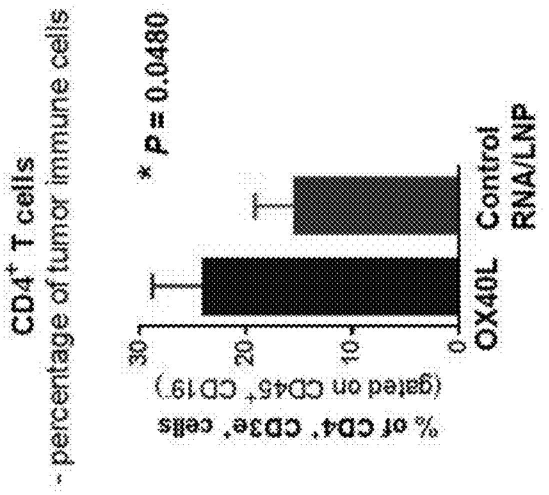
Figure 14C:
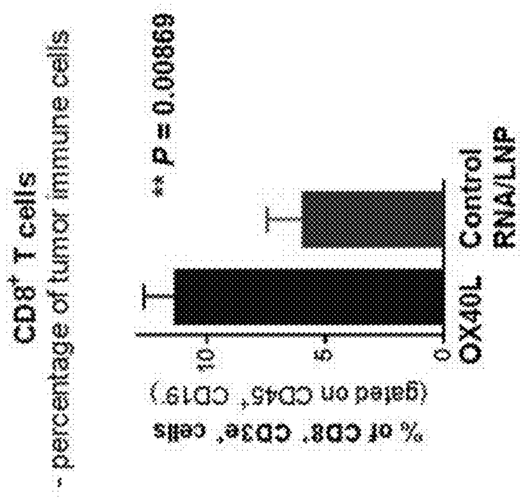

A20 tumors were treated with a single 12.5 μg dose of mOX40L_miR-122 or control mRNA (RNA/LNP) formulated in lipid nanoparticles. Tumor samples were initially analyzed 24 hours following treatment. NK cells were differentiated using an antibody against the mature NK cell surface marker, DX5. Results are shown in FIG. 14A. Other tumor samples were analyzed 14 days after treatment with mOX40L_miR-122. $CD4^+$ and $CD8^+$ T-cells were identified using anti-mouse CD4 and anti-mouse CD8 antibodies, respectively. Results are shown in FIG. 14B-14C.

A similar experiment was performed in the MC38 tumor model. Mice with MC38 tumors were administered a single intratumoral injection of mOX40L_miR-122 or NST-OX40L. In some animals a second dose of mRNA was administered 6 days after the first dose. Immune cell infiltrate was assessed for $CD8^+$ cells 24 hours and 72 hours after each dose of mRNA. Results are shown in FIG. 14D.

B. Results

FIG. 14A shows that 24 hours after administration of mOX40L_miR-122 to A20 tumors, NK cells infiltration significantly increased in OX40L-dosed animals compared to controls. FIG. 14B-14C show that 14 days after administration of mOX40L_miR-122 to A20 tumors, both $CD4^+$ (FIG. 14B) and $CD8^+$ (FIG. 14C) T-cell infiltration into the tumor microenvironment significantly increased compared to control tumor samples.

Figure 14D:
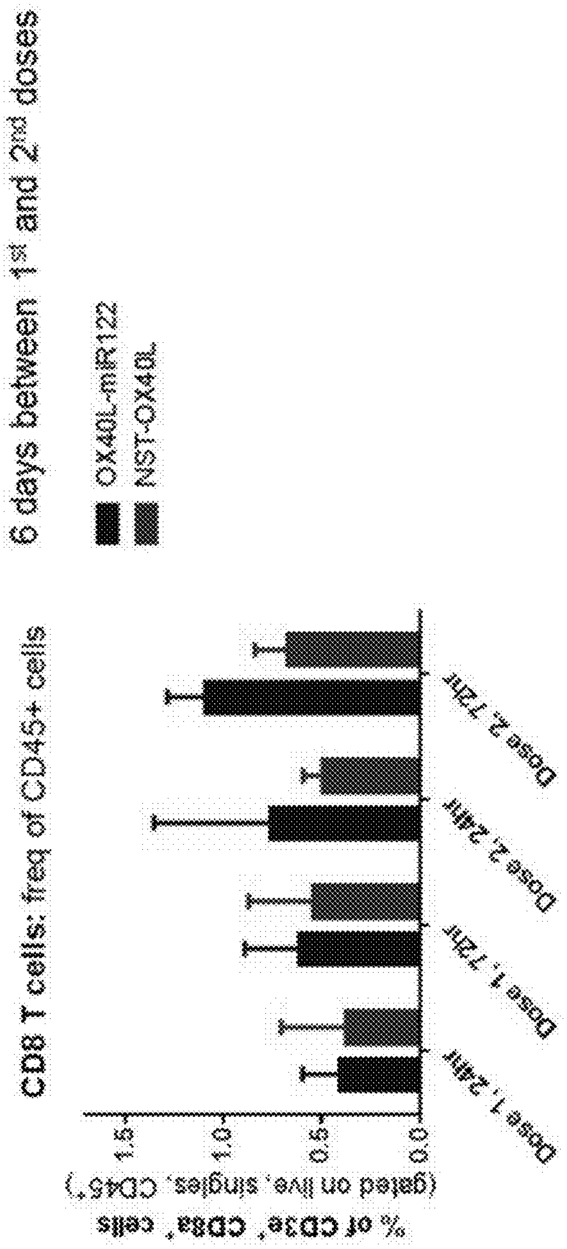

FIG. 14D shows a significant increase in infiltrating $CD8^+$ T-cells 72 hours after a second dose of mOX40L_miR-122 in MC38 tumors compared to control treated tumors.

These data from two tumor models demonstrate that administration of a polynucleotide comprising an mRNA encoding an OX40L polypeptide promotes increased numbers of both innate and adaptive immune cells within the tumor microenvironment.

Example 13

In Vivo Activity of an OX40L-Encoding Polynucleotide Following Intratumoral Administration A. Preparation of OX40L Modified mRNA A polynucleotide comprising an mRNA encoding an OX40L polypeptide (murine OX40L) and further comprising a miRNA binding site (miR-122) was prepared as described above (mOX40L_miR-122; SEQ ID NO: 66). A negative control mRNA was also prepared (non-translatable version of the same mRNA containing multiple stop codons: NST_OX40L_122).

B. Acute Myeloid Leukemia (AML) Tumor Model

Acute myeloid leukemia (AML) tumors were established subcutaneously in DBA/2 mice. Mouse AML cells P388D1, ATCC No. CCL-46; ATCC, Manassas, Va.) were cultured according to the vendor's instructions. Cells were inoculated subcutaneously in mice to generate subcutaneous tumors. Tumors were monitored for size and palpability.

Once the tumors were established, animals were separated into two groups, i.e., a mOX40L_miR-122 group and a control group. Intratumoral dosing for each group was every 7 days (Q7D), beginning 7 days after tumor implantation. Group I was treated with intratumoral doses of mOX40L_miR-122 at a dose of 12.5 ug (fixed dose) mRNA per kg body weight. Group II was treated with intratumoral doses of control NST_OX40L_122 mRNA at the same dosing regimen.

C. Results

Figure 15A:
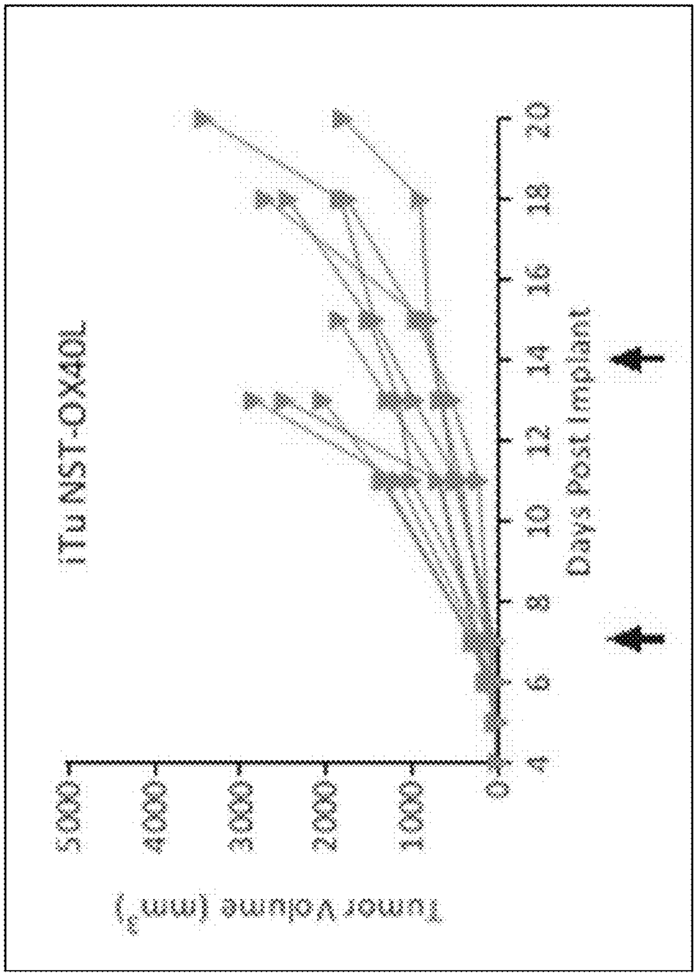
Figure 15B:
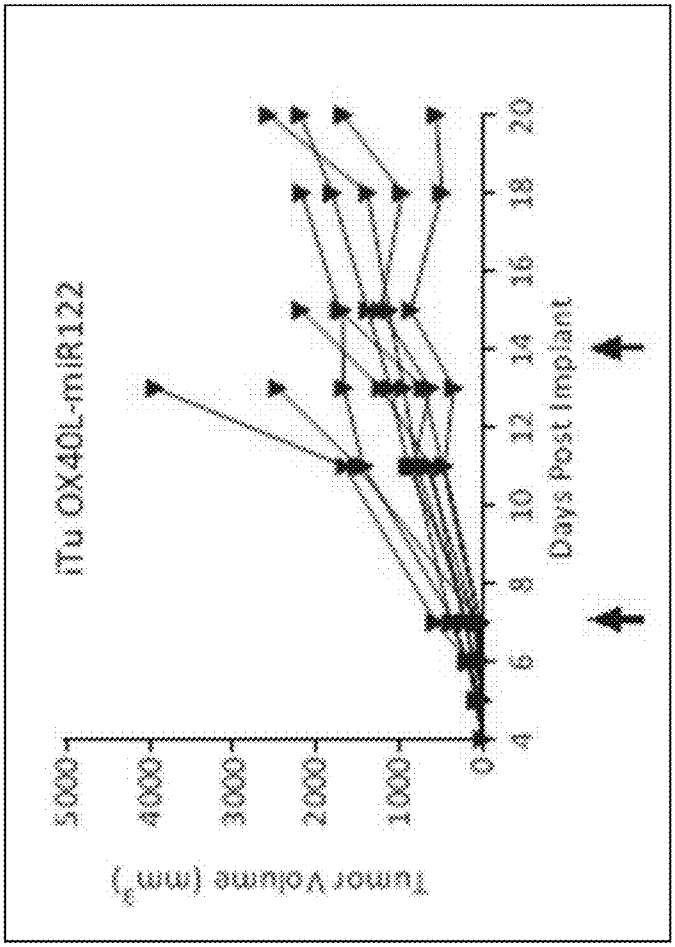

Results are shown in FIGS. 15A and 15B. FIG. 15A shows individual tumor growth in animals treated with intratumoral doses of control NST_OX40L_122 mRNA. FIG. 15B shows individual tumor growth in animals treated with intratumoral doses of mOX40L_miR-122 mRNA. These result show that intratumoral administration of a polynucleotide encoding an OX40L polypeptide comprising a miRNA binding site reduces or inhibits tumor growth compared to control mRNA or PBS treatment.

Example 14

In Vivo Efficacy of Combination of an mRNA Encoding an OX40L Polypeptide, and an Anti-PD-1 Antibody A. Preparation of OX40L Modified mRNA and Anti-PD-1

A polynucleotide comprising an mRNA encoding an OX40L polypeptide (murine OX40L) and further comprising a miRNA binding site (miR-122) was prepared as described above (mOX40L_miR-122; SEQ ID NO: 66). A negative control mRNA was also prepared (NST_OX40L_122).

Anti-PD-1 (BioXcell BE0146, anti-mPD-1, clone RMP1-14, Lot No. 5792-599016J1) dosing solutions were prepared by diluting an aliquot of the stock (6.37 mg/mL) to 0.5 mg/mL in sterile PBS. The 0.5 mg/mL dosing solution provided the 5 mg/kg dosage in a dosing volume of 10 mL/kg. The anti-PD-1 dosing solution was prepared fresh daily and stored protected from light at 4° C.

Rat IgG2a (BioXcell BE0089, Rat IgG2a, clone 2A3, Lot No. 601416M1) dosing solutions were prepared by diluting an aliquot of the stock (7.38 mg/mL) to 0.5 mg/mL in sterile PBS. The 0.5 mg/mL dosing solution provided the 5 mg/kg dosage in a dosing volume of 10 mL/kg. The anti-PD-1 dosing solution was prepared fresh daily and stored protected from light at 4° C.

B. MC38 Colon Adenocarcinoma Model

MC-38 colon adenocarcinoma tumors were established subcutaneously in C57BL/6 mice as described above.

Once the tumors were established, animals were divided into groups and received intratumoral doses of one of the following combination therapies shown in the table below:

TABLE 10

| Combination Dosing and Interval | | | |
|---|---|---|---|
| Group | Treatment | Dose | Interval |
| i | NST_OX40L_122 | 2.5 μg mRNA per dose | Q7D |
| | Rat IgG2a antibody | 5 mg per kg | BIWx2 |
| ii | mOX40L_miR-122 | 2.5 μg mRNA per dose | Q7D |
| | Rat IgG2a antibody | 5 mg per kg | BIWx2 |
| iii | NST_OX40L_122 | 2.5 μg mRNA per dose | Q7D |
| | Anti-PD-1 antibody | 5 mg per kg | BIWx2 |
| iv | mOX40L_miR-122 | 2.5 μg mRNA per dose | Q7D |
| | Anti-PD-1 antibody | 5 mg per kg | BIWx2 |
| v | PBS | NA | Q7D |
| | Anti-PD-1 antibody | 5 mg per kg | BIWx2 |
| vi | PBS | NA | Q7D |
| | Rat IgG2a antibody | 5 mg per kg | BIWx2 |

Mice received intratumoral doses of mRNA every 7 days (Q7D). Mice received intratumoral doses of antibody every two weeks (BIW×2).

C. Results

Figure 16B:
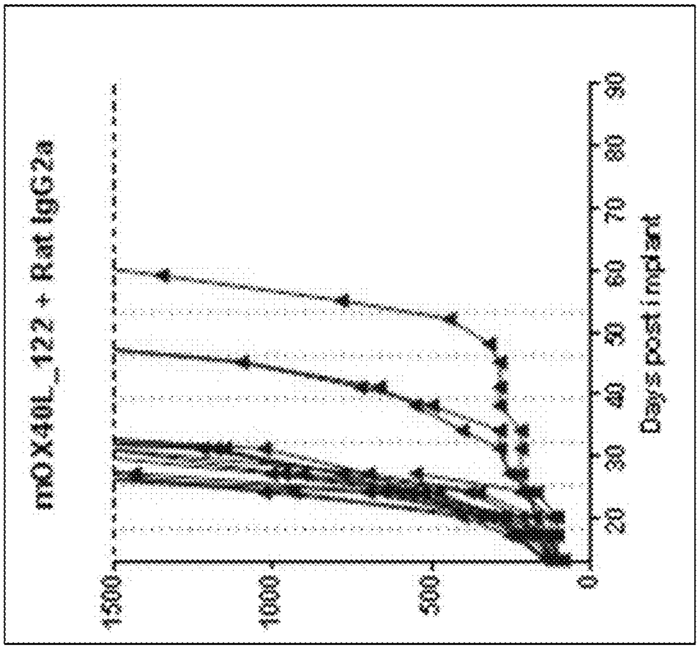
Figure 16A:
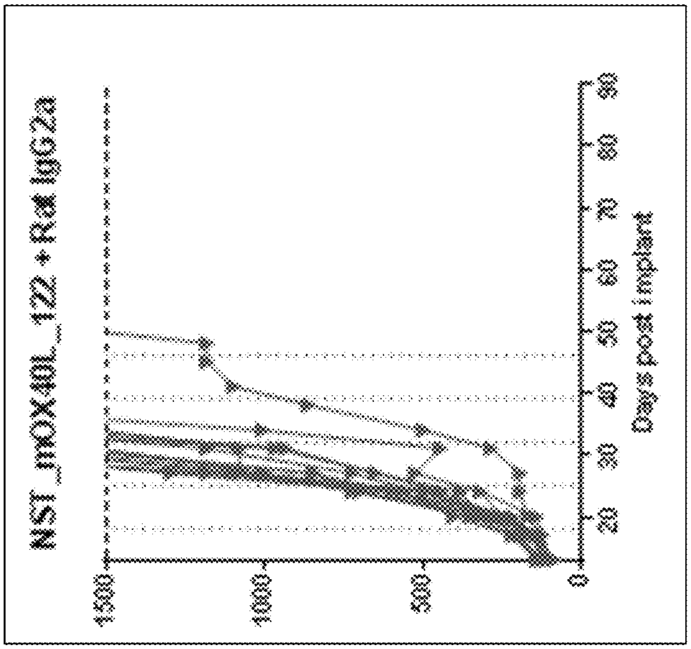
Figure 16D:
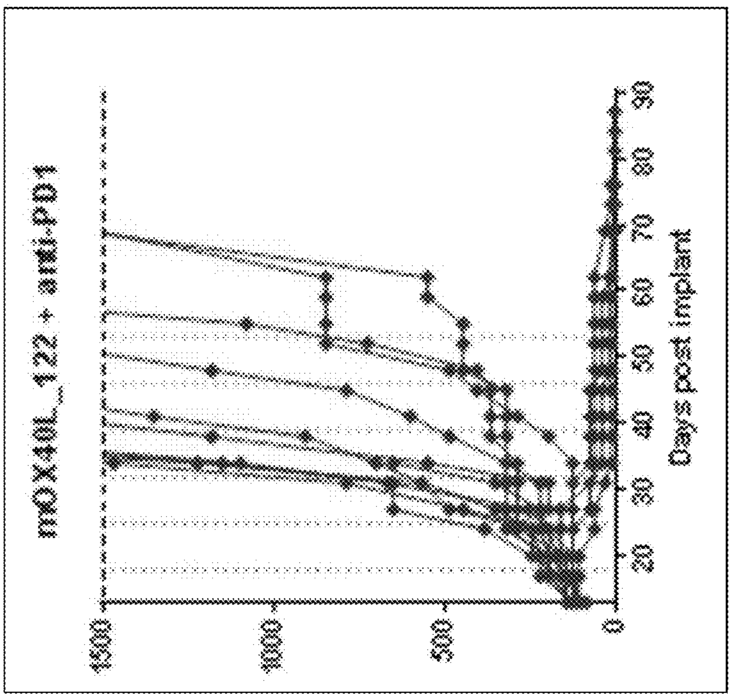
Figure 16C:
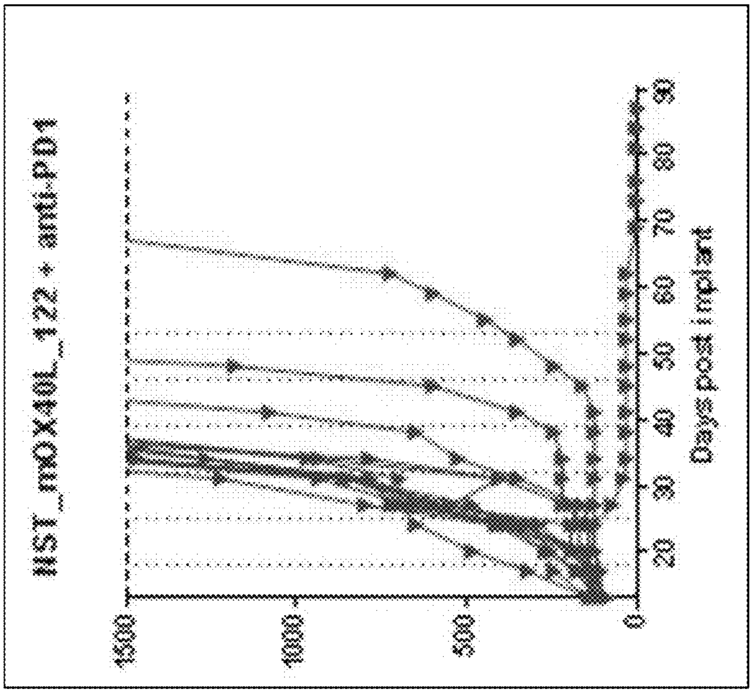
Figure 16E:
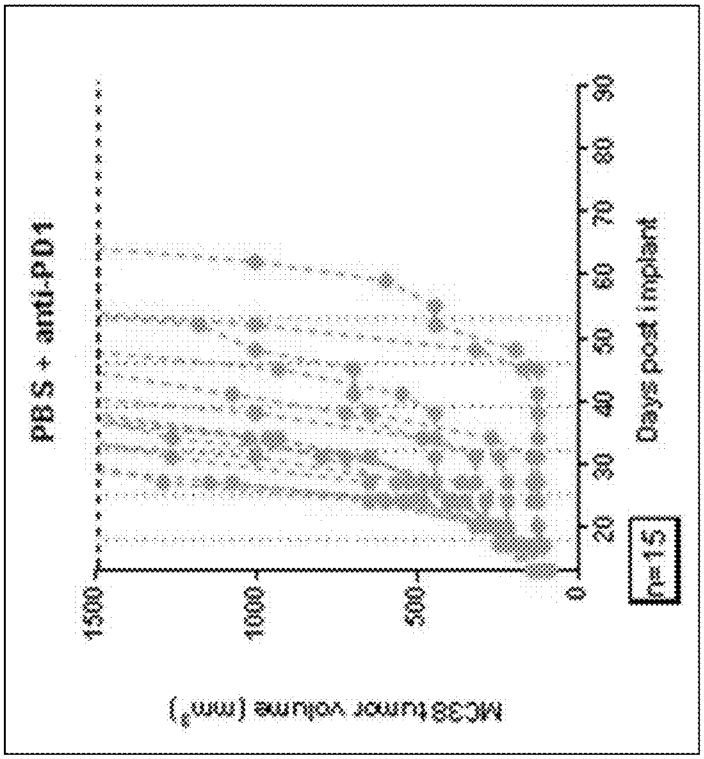
Figure 16F:
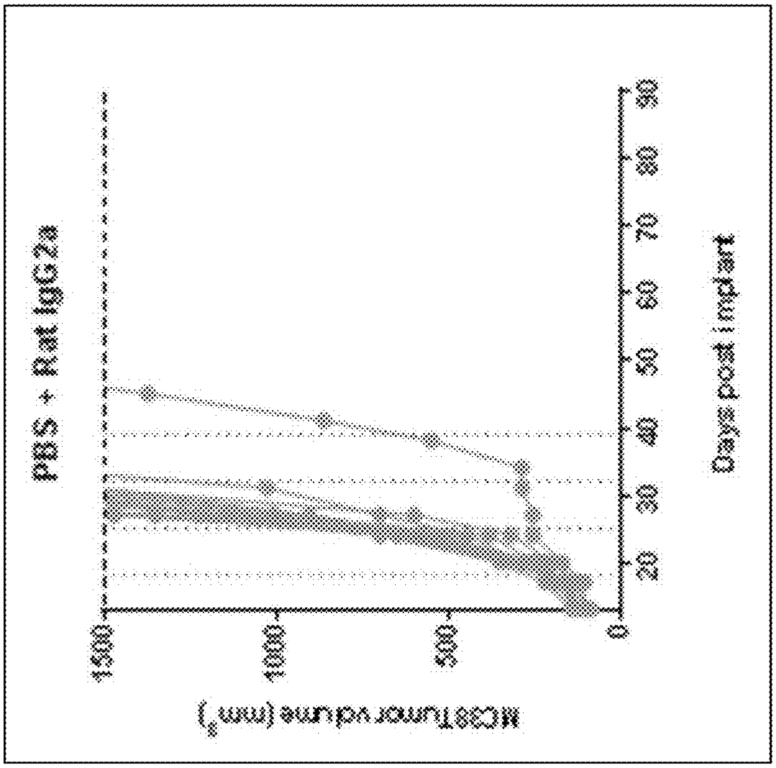

Results are shown in FIGS. 16A-16E and FIG. 17. FIG. 16A shows individual tumor growth in animals treated with intratumoral doses of control NST_OX40L_122 mRNA combined with intratumoral doses of control antibody. There were 0/15 complete responders (CR) in the control group. FIG. 16B shows individual tumor growth in animals treated with intratumoral doses of mOX40L_miR-122 mRNA combined with intratumoral doses of control antibody. By Day 90 post-implantation, the CR was 0/15 for this group. FIG. 16C shows individual tumor growth in animals treated with intratumoral control mRNA combined with intratumoral doses of anti-PD-1 antibody. By Day 90 post-implantation, the CR was 2/15 for this group. FIG. 16D shows individual tumor growth in animals treated with intratumoral doses of mOX40L_miR-122 mRNA combined with intratumoral doses of anti-PD-1 antibody. By Day 90 post-implantation, the CR was 6/15 for the dual combination group. FIG. 16E shows individual tumor growth in animals treated with intratumoral doses of PBS combined with intratumoral doses of anti-PD-1 antibody. By Day 90 post-implantation, the CR was 0/15 for this group. FIG. 16F shows individual tumor growth in animals treated with intratumoral doses of PBS combined with intratumoral doses of control antibody. By Day 90 post-implantation, the CR for this treatment group was 0/14.

These results show that combination therapy comprising a polynucleotide comprising an mRNA encoding an OX40L polypeptide and an immunotherapeutic agent, such as an anti-PD-1 antibody, is effective in vivo for inhibiting or reducing tumor growth in the MC38 mouse tumor model. The combination of mOX40L_miR-122 with anti-PD-1 showed synergistic in vivo anti-tumor efficacy. These results also show that lower doses of mRNA can be used in combination therapy.

Figure 17:
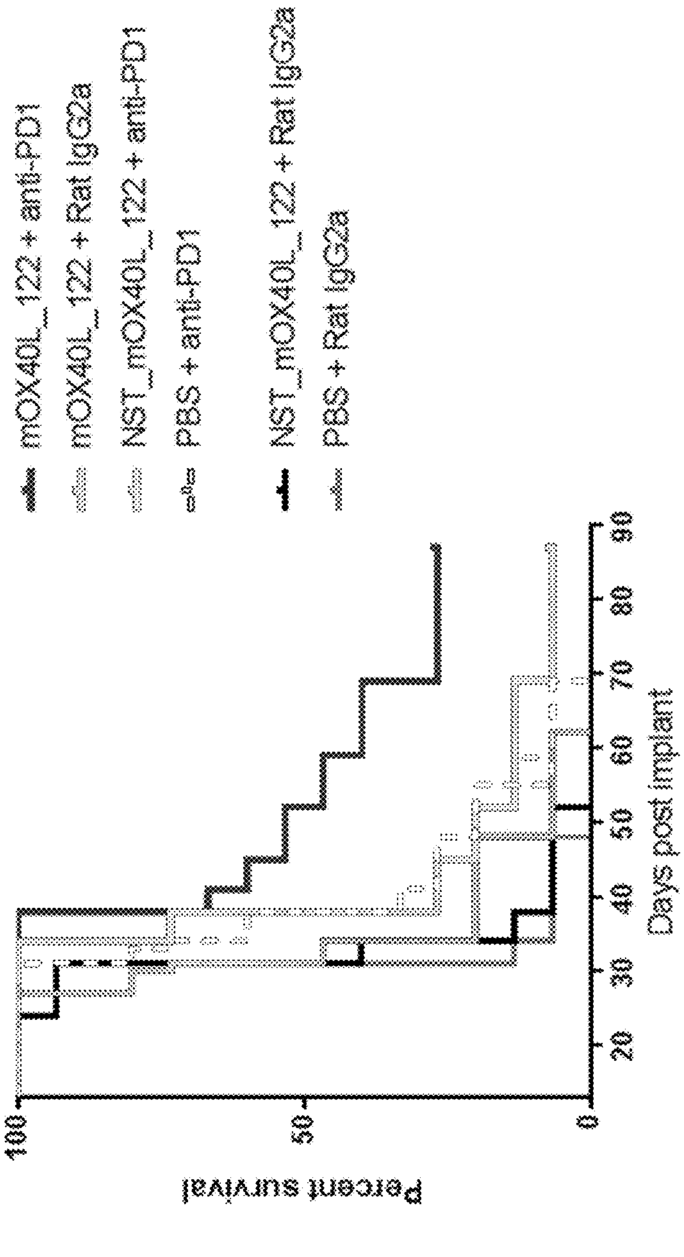

FIG. 17 shows the survival curves for animals in the same treatment groups. These results show that combining intratumoral dosing of a modified OX40L mRNA with intratumoral dosing of an anti-PD-1 antibody effectively increases survival in a mouse tumor model compared to control treatment groups.

Example 15

In Vivo Memory Immune Response Following Treatment with Combination Therapy

Figure 18B:
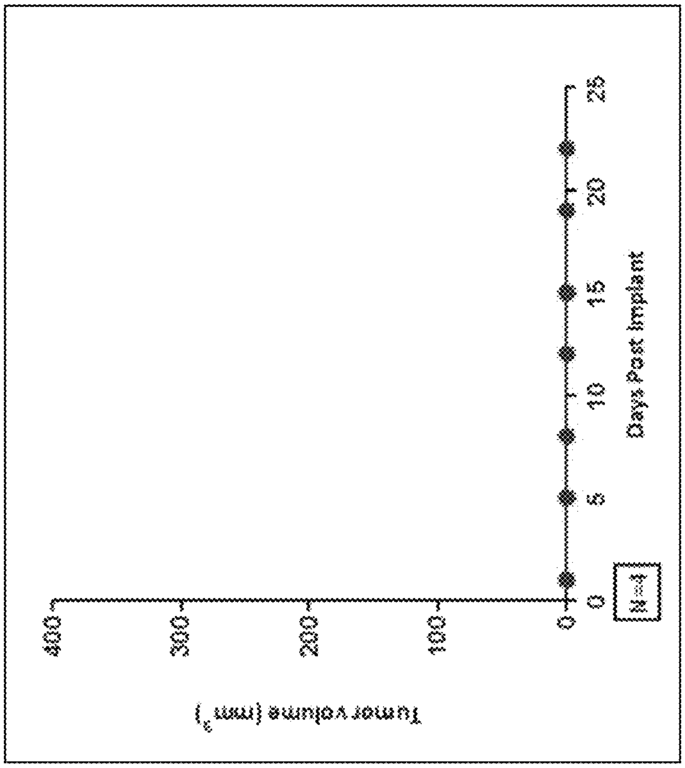

Mice were treated with mOX40L_miR-122 combined with anti-PD-1 antibody as described above in Example 14. At Day 90 post-tumor inoculation, four complete responder animals (CR) from the mOX40L_miR-122+anti-PD-1 combination therapy group were re-challenged with $5\times10^5$ MC38 tumor cells. As a control, 10 naïve animals were also inoculated with $5\times10^5$ MC38 cells. The results of the analysis are shown in FIGS. 18A and 18B.

Figure 18A:
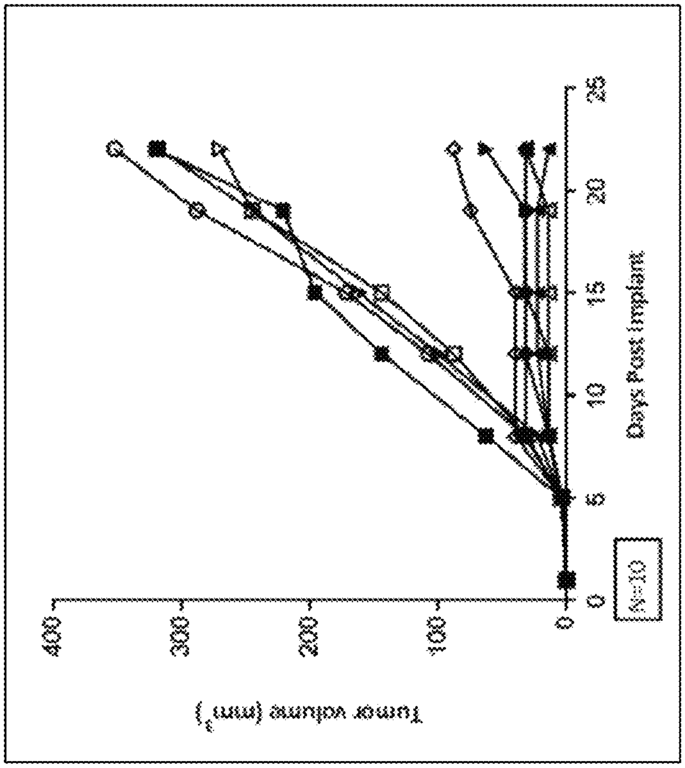

FIG. 18A shows individual tumor growth in naïve animals challenged with MC38 cells. Naïve mice began developing detectable tumors approximately 5 days after implantation, and tumors continued to grow during the study. FIG. 18B shows individual tumor growth in the complete responder animals previously given intratumoral doses of combination therapy of mOX40L_miR-122 and anti-PD-1 antibody. The complete responder animals showed no tumor growth (0/4 animals) for 23 days after re-challenge with tumor cells. In contrast, naïve animals showed a high percentage of tumor growth. These results show that intratumoral dosing of an mRNA encoding an OX40L polypeptide combined with an anti-PD-1 antibody induces a memory immune response with anti-tumor effects.

Example 16

Marked Efficacy in Both Primary Treated and Untreated Distal Tumors with Triplet mRNA Therapy Experiments were conducted using the MC38-S mice tumor model. A tumor was implanted in each flank of each animal. See FIG. 19A. A primary tumor on one flank was treated with control mRNA (non-translating mRNA encoding for OX40L), a combination of mRNAs encoding IL-23 and IL36-gamma, or a triple combination of mRNAs encoding IL-23, IL-36-gamma, and OX40L. Then, the effect of the treatment of the first tumor was measured on the second (untreated) tumor. FIG. 19A. The total dose of mRNA per treatment was 5 μg of mRNA. mRNAs were administered as single intratumoral doses.

Figure 19B:
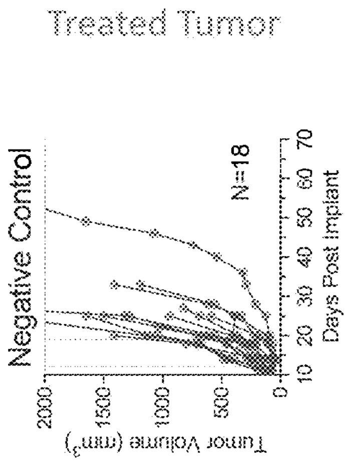
Figure 19C:
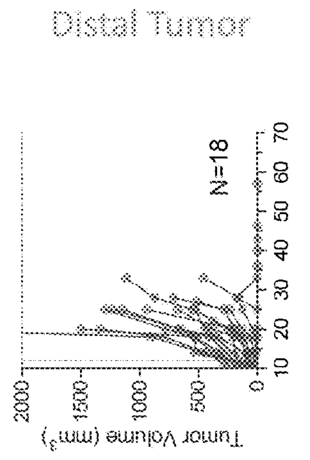
Figure 19A:
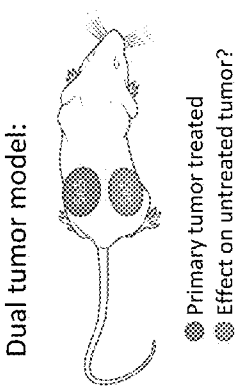
Figures 19D, 19E, 19F, 19G:
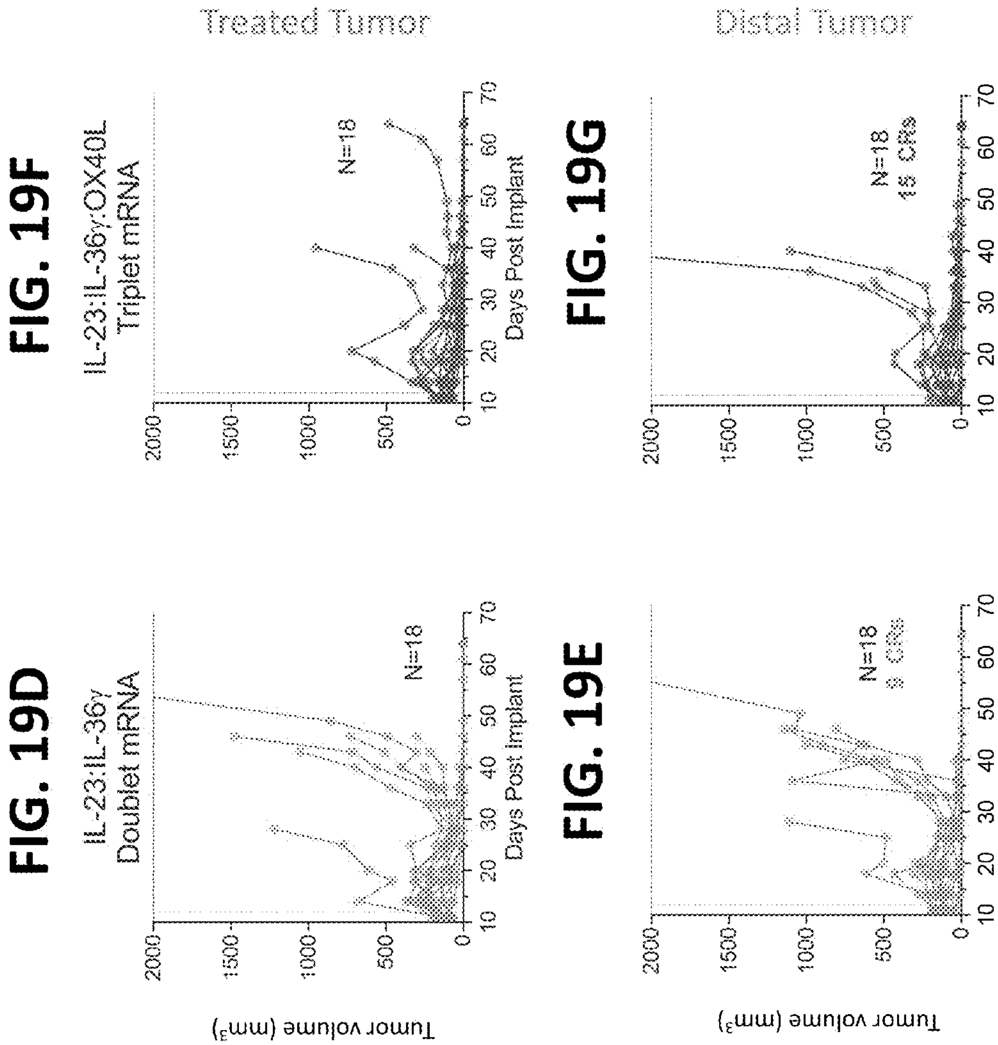

FIGS. 19B and 19C show large tumor volumes in both the treated tumors and distal tumors in mice treated with control mRNA. When doublet mRNA therapy was administered to the proximal tumor (FIG. 19D), 9 complete responses (50%) were observed in this distal tumor (FIG. 19E). When the triplet mRNA therapy was administered to the proximal tumor (FIG. 19F), 15 complete responses (83.3%) were observed in the distal tumor (FIG. 19G).

This data indicates that treatment of a tumor with an mRNA therapeutic composition can effectively treat tumor at other locations.

Example 17

Triplet mRNA Plus Anti-PD-L1 Ab Demonstrates Improved Efficacy in Difficult to Treat B16F10-AP3 Tumor Model To assess the improved efficacy of the triplet therapy (triple combination of mRNAs encoding IL-23, IL-36-gamma, and OX40L) in a difficult to treat model that is not responsive to checkpoint inhibitors, the B16F10-AP3 murine melanoma cell model was used. As in the previous example, total mRNA dosing was 5 ug of total mRNA, administered intratumorally as a single dose. The anti-PD-L1 antibody was dosed intraperitoneally twice per week at 10 mg/kg.

Figure 20B:
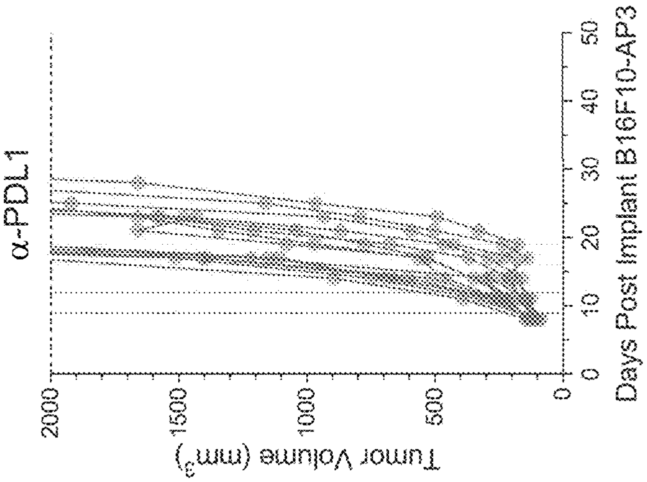
Figure 20A:
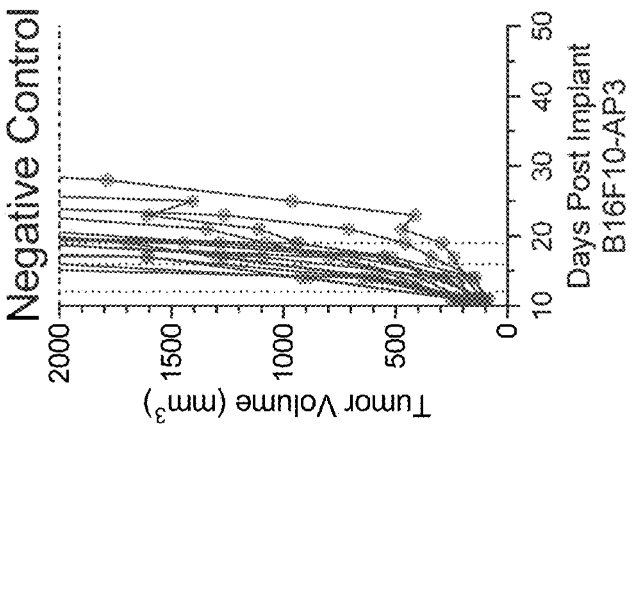
Figure 20C:
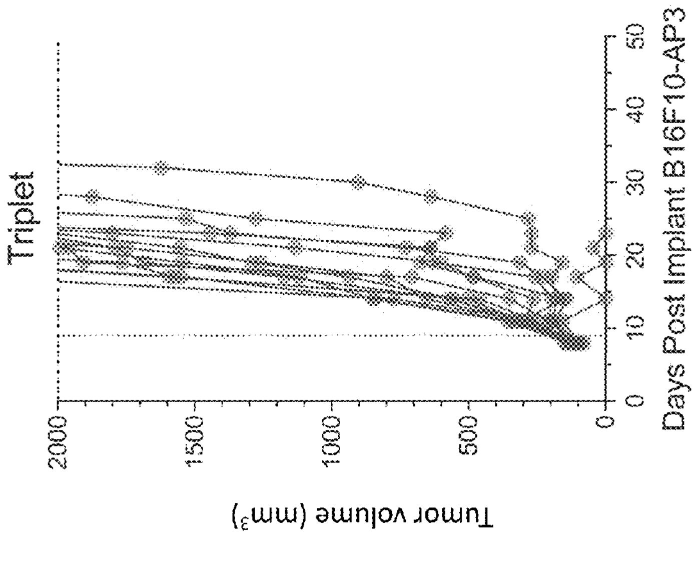
Figure 20D:
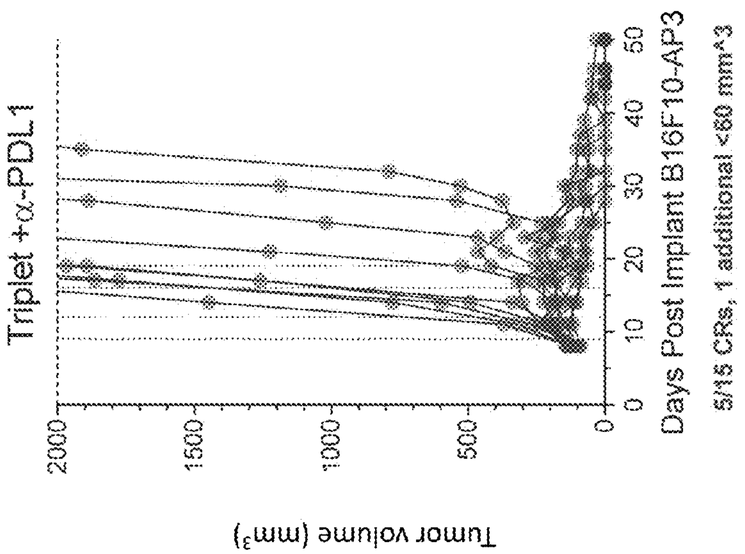

FIG. 20A shows tumor volume in mice treated with control mRNA. No responses were observed when the anti-PD-L1 antibody was administered alone (FIG. 20B). When the triplet mRNA therapy (mRNAs encoding IL23, IL36 gamma, and OX40L) was administered, no complete responses were observed either (FIG. 20C). On the other hand, when the triplet mRNA therapy was administered in combination with the anti-PD-L1 antibody, 5 complete responses out of 15 were observed (33%). In addition to the complete responses in one mouse the tumor reduced in size to less than 60 $mm^3$ (FIG. 20D).

This data indicates that tumors refractory to treatment with a conventional therapy, e.g., an anti-PD-L1 antibody, can be effectively treated by combining such therapy with several mRNAs disclosed herein (e.g., a triple therapy comprising mRNAs encoding IL-23, IL-36-gamma, and OX40L).

Example 18

Memory Immune Response after Treatment with IL-23:IL-36-Gamma Doublet Therapy and IL23:IL-36-Gamma:OX40L Triplet Therapy Memory immune response in animals treated with a doublet combination therapy was evaluated. Mice inoculated with MC38-S tumor cells were treated with a doublet combination therapy consisting of a polynucleotide comprising an mRNA encoding an IL-23 polypeptide and a second polynucleotide comprising an mRNA encoding an IL-36-gamma polypeptide. Five micrograms of total mRNA were injected intratumorally weekly for 4 weeks (Q7D).

Figure 21B:
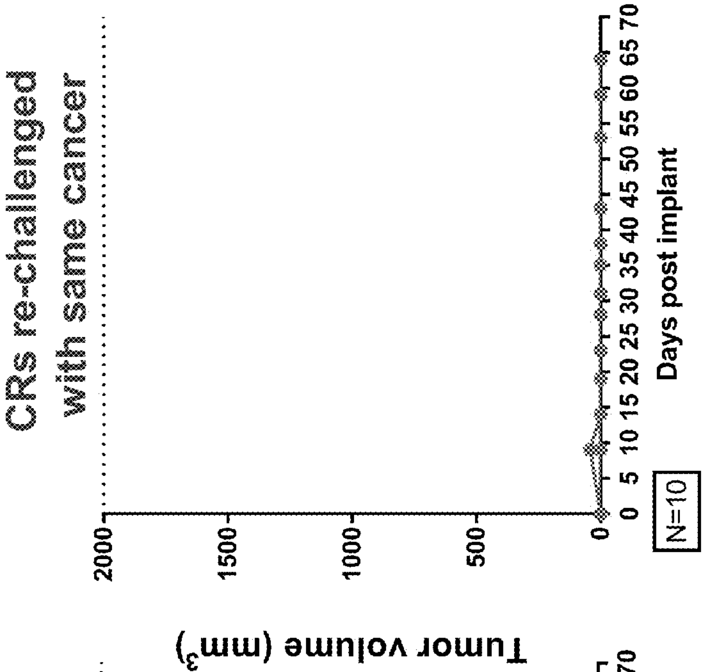
Figure 21A:
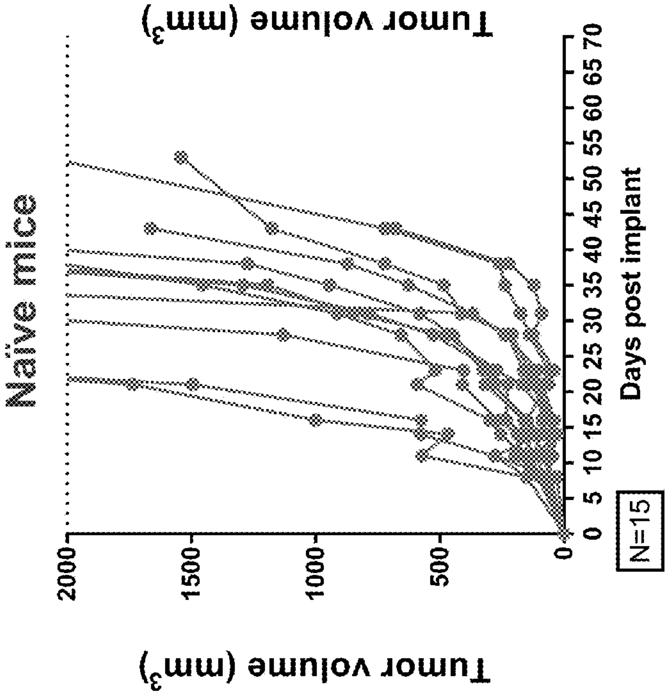

Ten out of ten mice were complete responders. When naïve animals were challenged with the same cancer all the mice (fifteen out of fifteen) were escapers (FIG. 21A). In contrast, when the mice that were complete responders were rechallenged with the same cancer, no tumoral growth was observed in any of the rechallenged mice (FIG. 21B).

The generation of anti-cancer memory post local therapy (i.e., tumor did not grown in re-challenged mice that were complete responders from initial treatment) was observed for mice treated with doublet mRNA therapy (IL-23:IL-36-gamma), as discussed above, and also for mice treated with triplet mRNA therapy (IL23:IL-36-gamma:OX40L) (tumors did not grow in 5 out of 5 re-challenged mice that were complete responders from initial treatment; not shown).

Example 19

Effect of Doublet and Triplet Therapy on Levels of Immune Cells

To assess the efficacy of the doublet therapy (double combination of mRNAs encoding IL-23 and IL-36-gamma, respectively) and triplet therapy (triple combination of mRNAs encoding IL-23, IL-36-gamma, and OX40L, respectively), immune cell levels were evaluated.

Figure 22A:
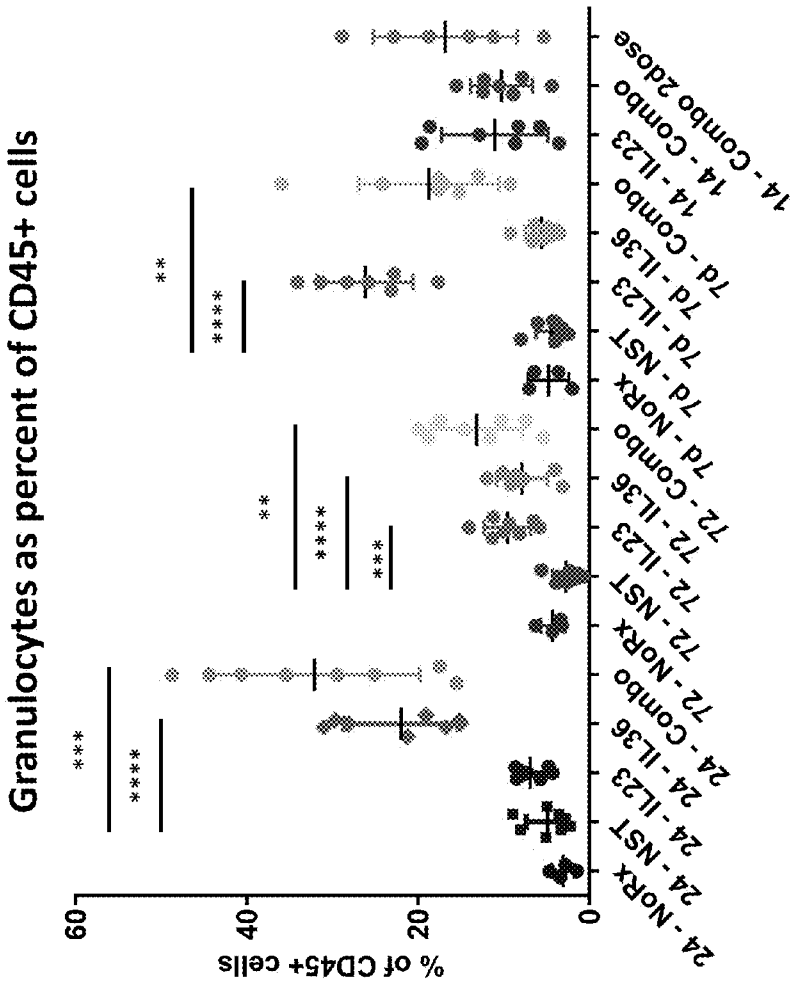
Figure 22B:
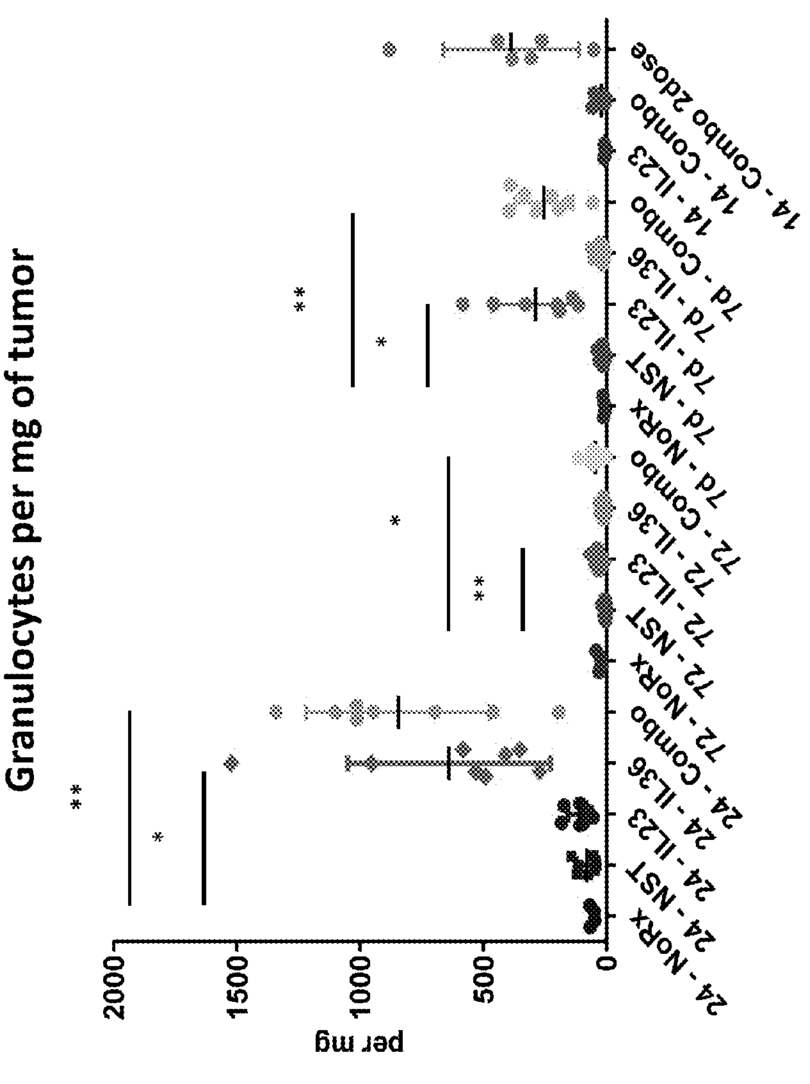
Figure 23:
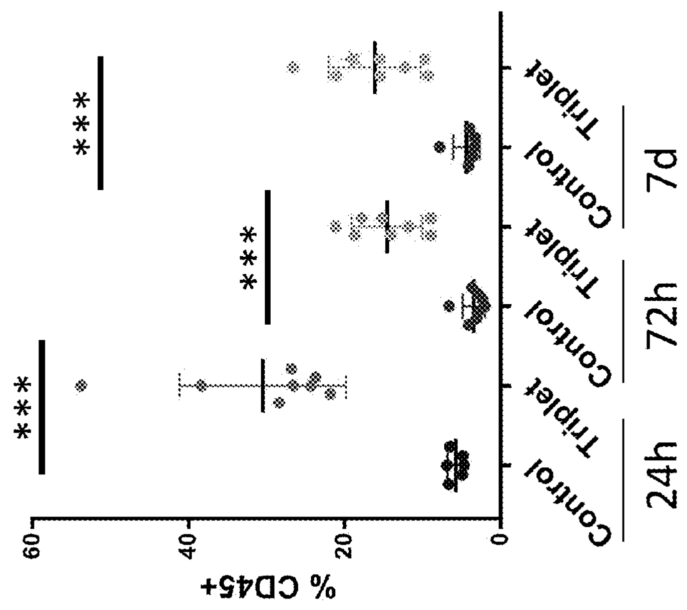

The treatment of mice inoculated with MC38-R tumor cells with the doublet therapy caused a marked increase in the level of Ly6G+ granulocytes in the MC38-R tumor, measured as granulocytes as percent of CD45+ cells (FIG. 22A) or as granulocytes per mg of tumor (FIG. 22B). A dramatic increase in granulocytes was also observed after treatment with triplet therapy (FIG. 23).

Figure 24B:
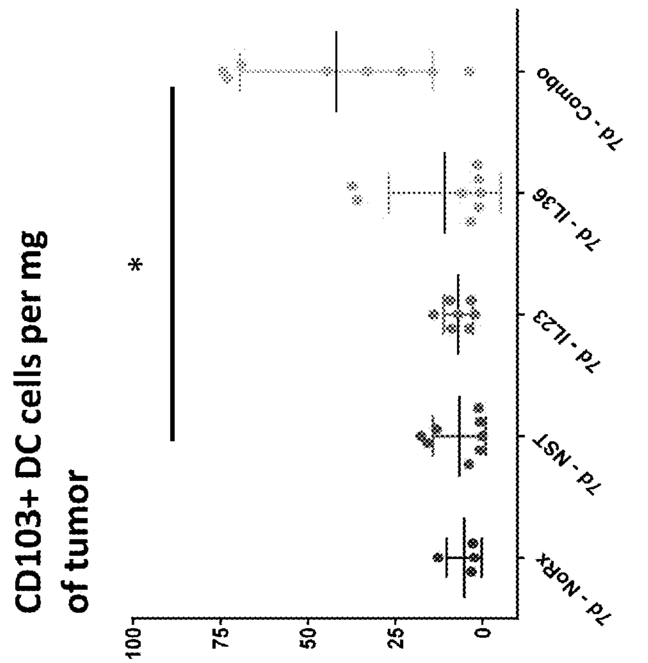
Figure 24A:
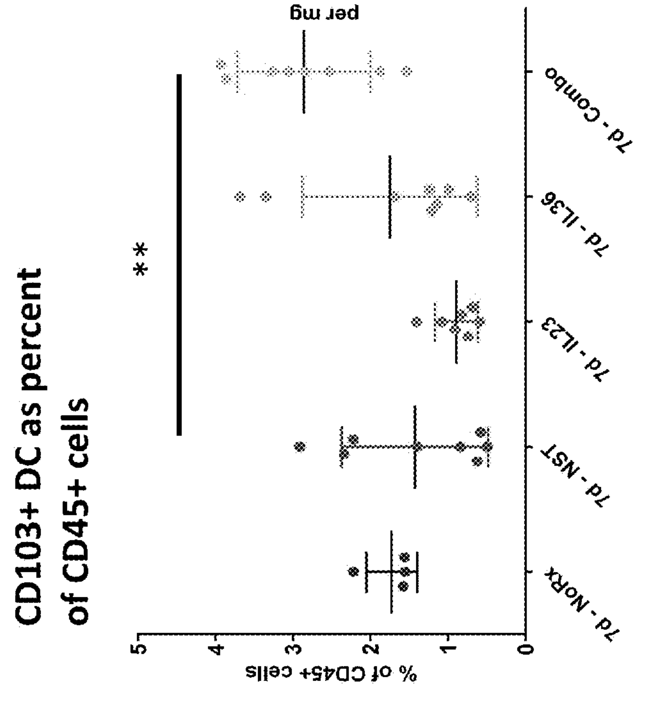

The treatment with doublet and triplet therapy increased levels of cross-presenting dendritic cells (see FIGS. 24A and 24B).

Figure 25A:
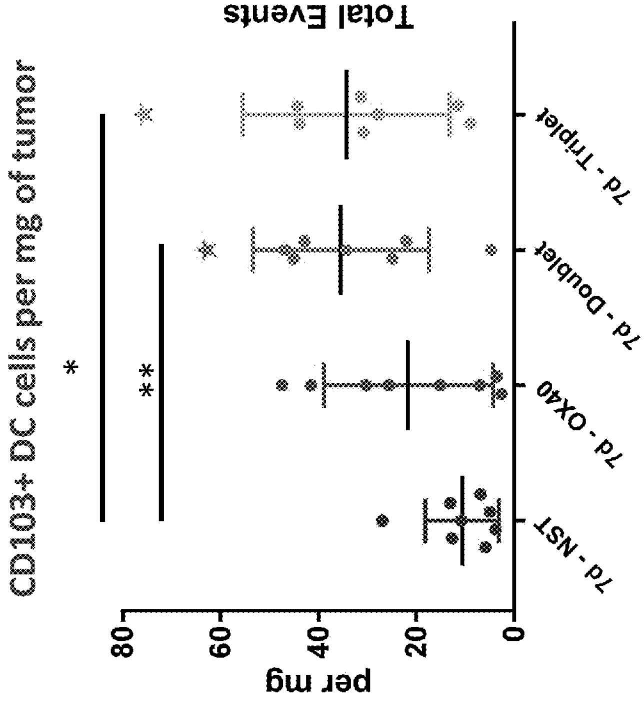
Figure 25B:
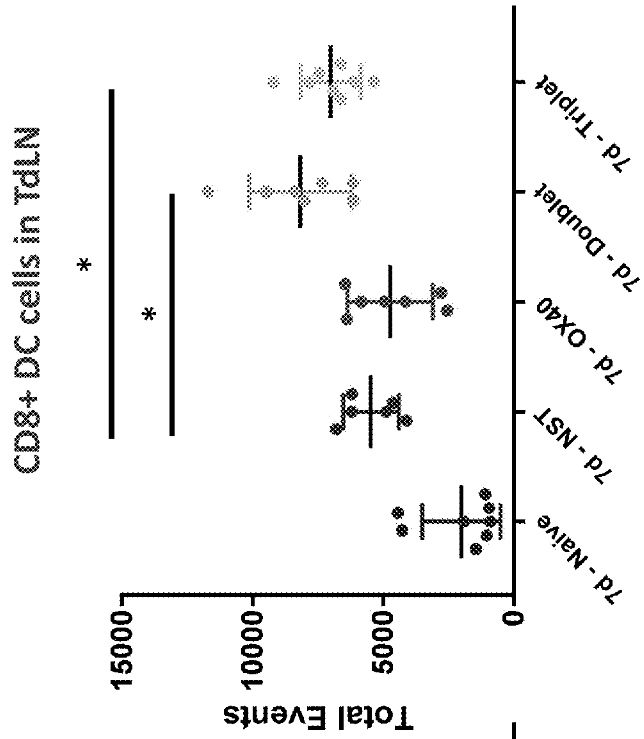

The treatment with doublet therapy increased levels of cross-presenting CD103+ dendritic cells in MC28-R tumors, measured as CD103+ dendritic cells as percent of CD45+ cells (FIG. 24A) or as CD103+ dendritic cells per mg of tumor (FIG. 24B). Treatment of mice inoculated with MC38-R tumor cells with triplet therapy showed similar increases in cross-presenting dendritic cells in both the tumor and in the draining lymph node (see FIG. 25A and FIG. 25B). These increases in dendritic cells were observed in analyses in which CD103+ dendritic cells per mg of tumor were quantified (FIG. 25A), and also in analyses in which CD8+ dendritic cells in the tumor draining lymph node (FIG. 25B) were quantified.

Figure 26B:
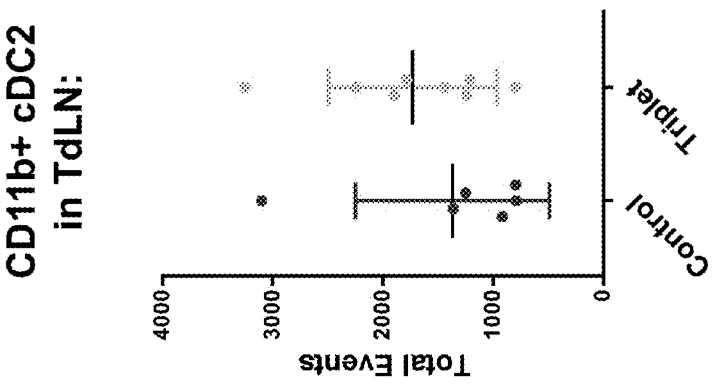
Figure 26A:
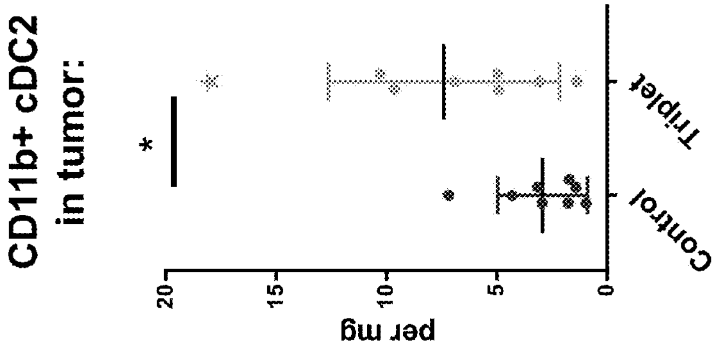
Figure 26C:
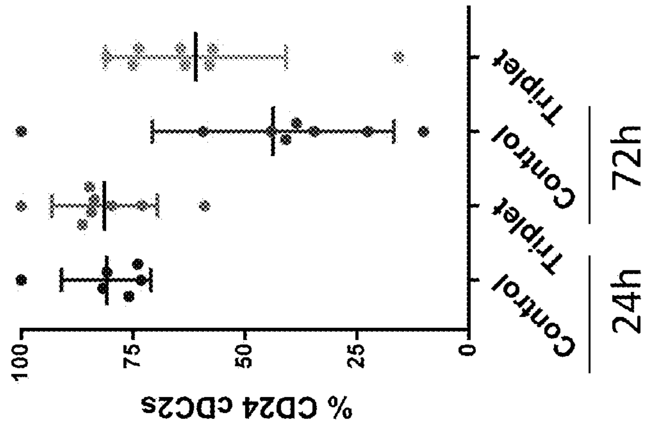
Figure 26D:
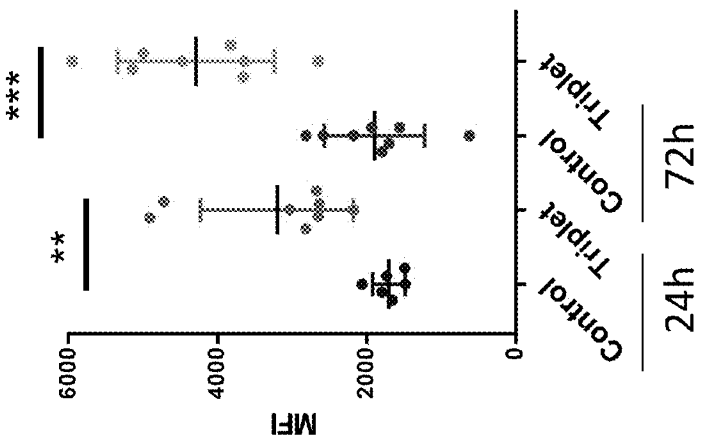

Treatment with triplet therapy increased levels of CD11b+ dendritic cells in the tumors, measured as CD11b+ dendritic cells per mg of tumor (FIG. 26A). Increases in CD11b+ dendritic cells were also observed in the draining lymph node (FIG. 26B). Administration of triplet therapy caused alteration of CD86 activation in CD11b+ dendritic cells in the draining lymph node (see FIG. 26C and FIG. 26D).

Figure 27A:
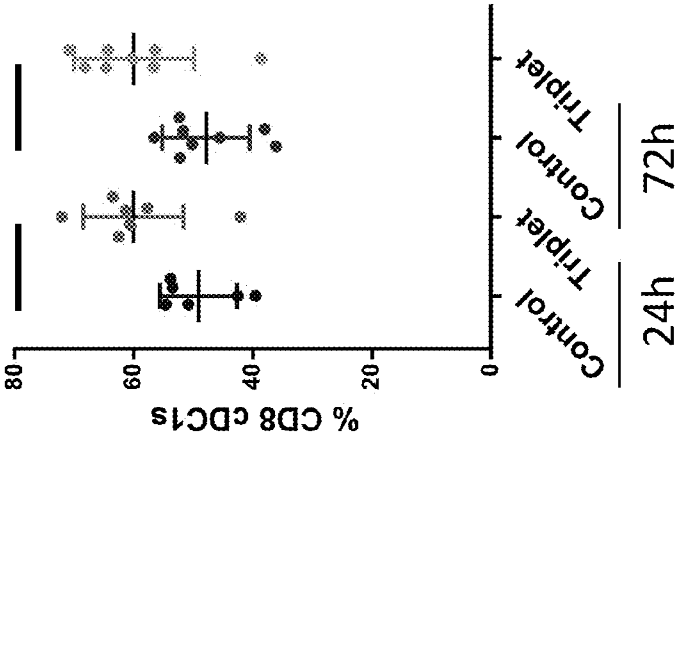
Figure 27B:
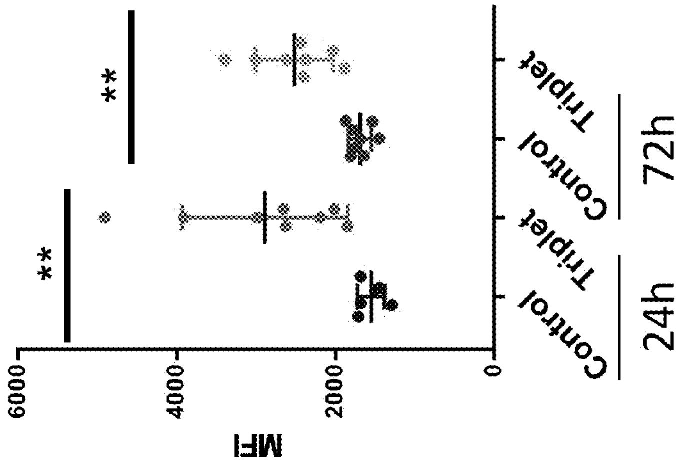

FIG. 27A and FIG. 27B show CD86 activation on CD8 cDC1 in the draining lymph node 24 h and 72 h post intratumoral administration of triplet mRNA therapy to MC38 tumors measured as percentage of CD8 cDC1 cells (FIG. 27A) or as mean fluorescence intensity (MFI) (FIG. 27B).

In addition, after the administration of doublet and triplet therapies, early increases in CD86 and MHCI were observed. CD86 and MHCI were higher on CD8+ dendritic cells post doublet treatment at 7 hours, yet MHCI was higher post triplet treatment at 7 days. In CD103+ dendritic cells there were early increases in CD86 and MHCI observed post administration. In CD8+ DC cells in draining lymph node there were also increased CD86 and MHCI post administration. CD 86 and MHCI were higher of CD8+ draining lymph node post doublet at 72 hours, yet MHCI was higher post triplet at 7 days (data not shown).

Figure 28A:
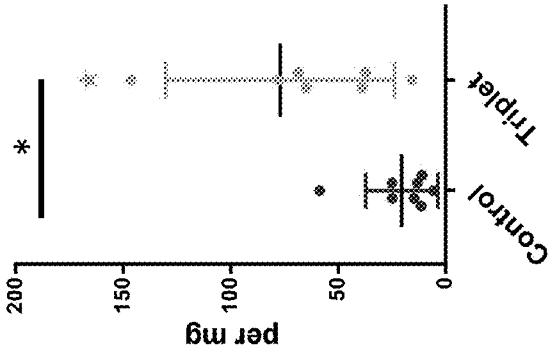
Figure 28B:
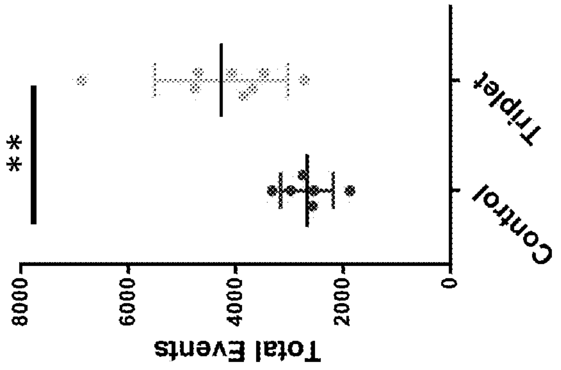
Figures 28C, 28D:
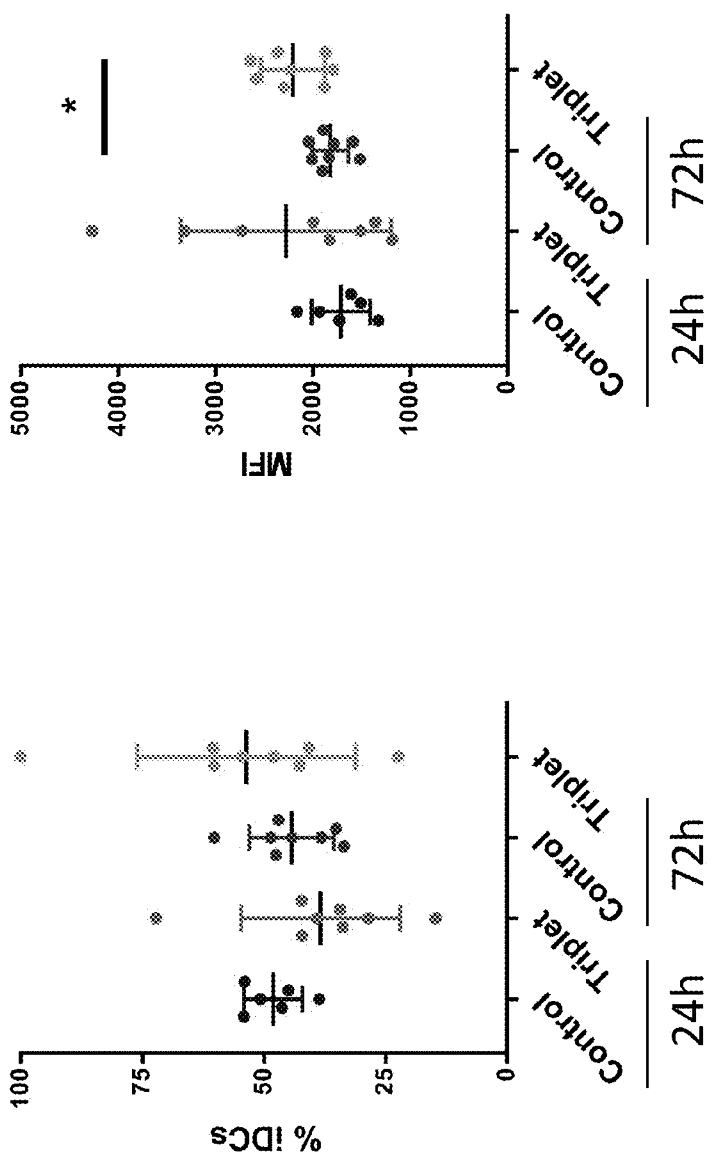

The administration of triplet therapy caused also increases in inflammatory dendritic cells (iDC) in both the tumor (FIG. 28A) and the draining lymph node (FIG. 28B). After the administration of triplet therapy, increases in CD86 were also observed on inflammatory dendritic cells (FIG. 28C and FIG. 28D).

Figure 29:
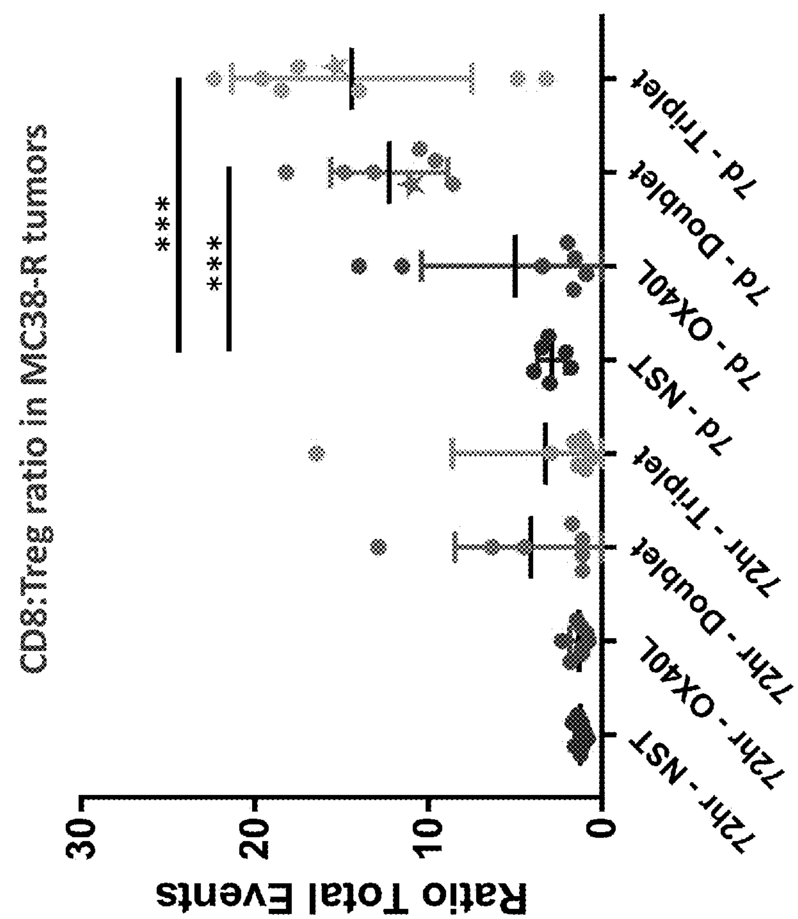

Treatment with doublet therapy or triplet therapy also increased the CD8:Treg ratio in MC38-R tumors, demonstrating an improved effector to suppressor T cell ratio (FIG. 29). This effect was more marked 7 days after administration of the doublet or triplet therapy.

Figure 30B:
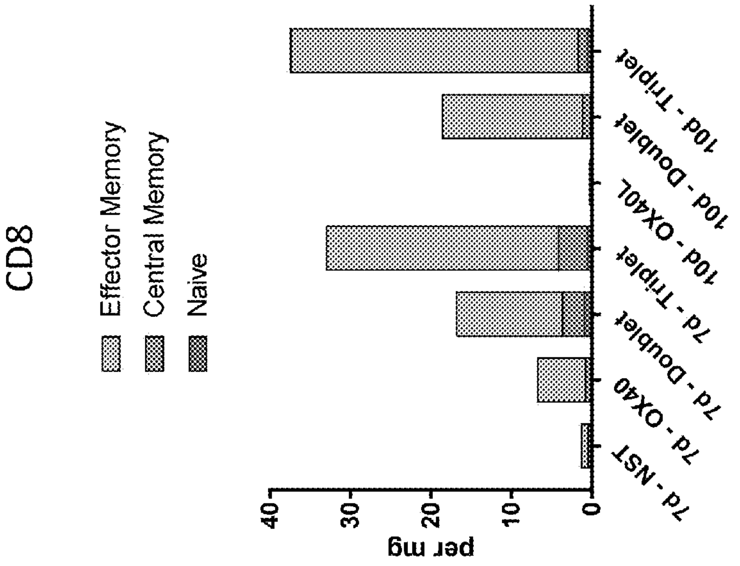
Figure 30A:
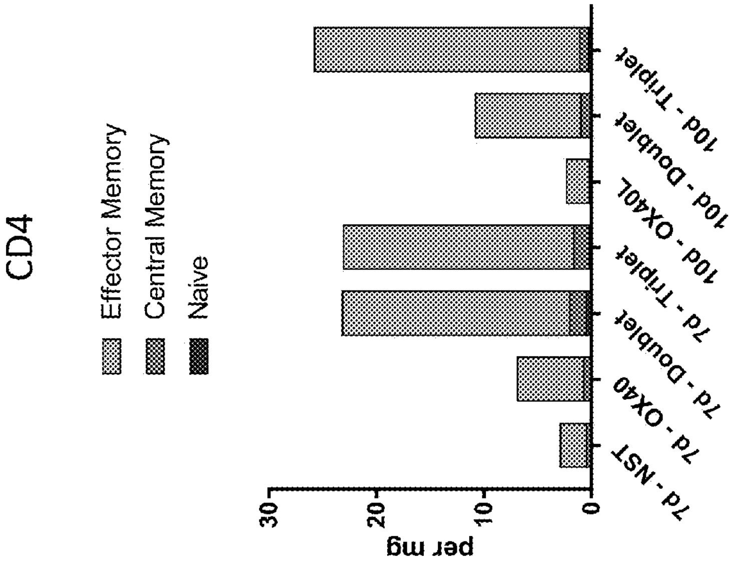

Upon activation, naive T cell subsets undergo proliferation and differentiation into effector cells, followed by the generation of a pool of memory T cells. Based upon migration pattern and functions, they are classified into central memory (predominantly homing to the lymph nodes) and effector memory (predominantly homing to extralymphoid sites) subsets. Treatment with doublet therapy or triplet therapy increased CD4+ (FIG. 30A) and CD8+ (FIG. 30B) central and effector memory T cells within the tumor. The OX40L:IL-23:IL-36-gamma triplet therapy caused greater increases of effector memory cells in tumors than the IL-23:IL-36-gamma doublet.

Figure 31:
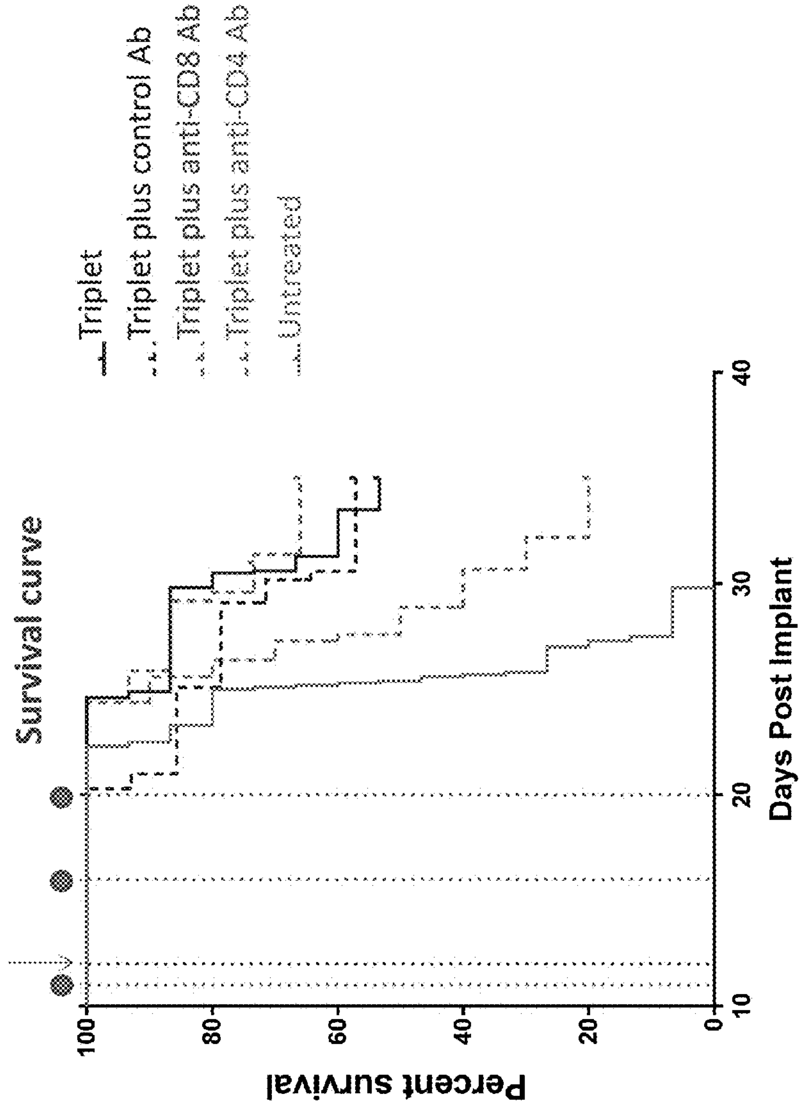

FIG. 31 shows the effect of cytotoxic T cell depletion on survival of mice inoculated with MC38-R tumoral cells. Mice were treated with 5 microgram doses of mRNA triplet administered intratumorally. The arrow in the drawing indicated the date of administration of the mRNA triplet therapy. Antibody depletion (circles) started 2 days prior to mRNA administration. The longest survival was observed in mice treated with the triplet alone, with the triplet plus a control antibody, or with the triplet plus anti-CD4 antibody. Co-administration of the triplet plus an anti-CD8 antibody resulted in a dramatic decrease in survival rate, demonstrating that cytotoxic T cells were essential to survival benefit from OX40L:IL-23:IL-36-gamma triplet therapy.

Example 20

Figures 32A, 32B:
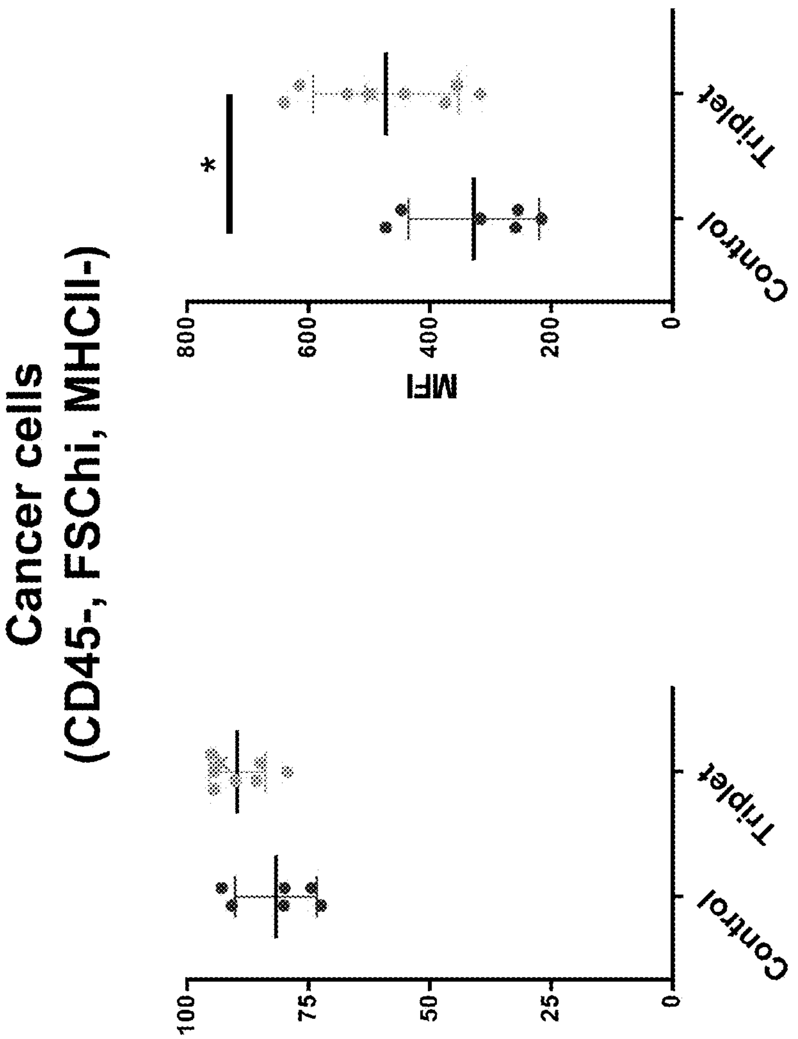

Efficacy of Combination Treatment Comprising Triplet mRNA Therapy and Anti-PDL1 Antibodies in MC38 Model The administration of doublet and triplet therapy increased levels of PD-L1. Slight increases in PD-L1 levels were observed in cancer cells, e.g., CD45-, FsChi and MHCII-, after the administration of triplet therapy (FIGS. 32A and 32B).

Figure 33B:
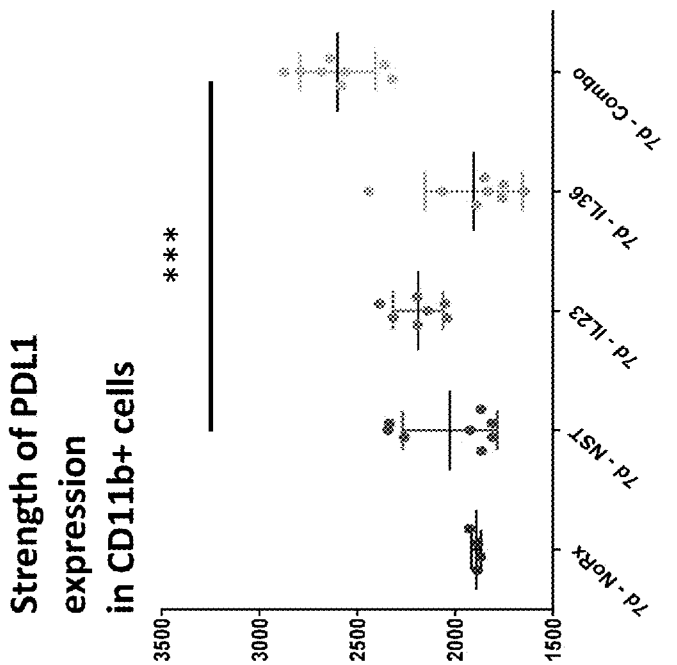
Figure 33A:
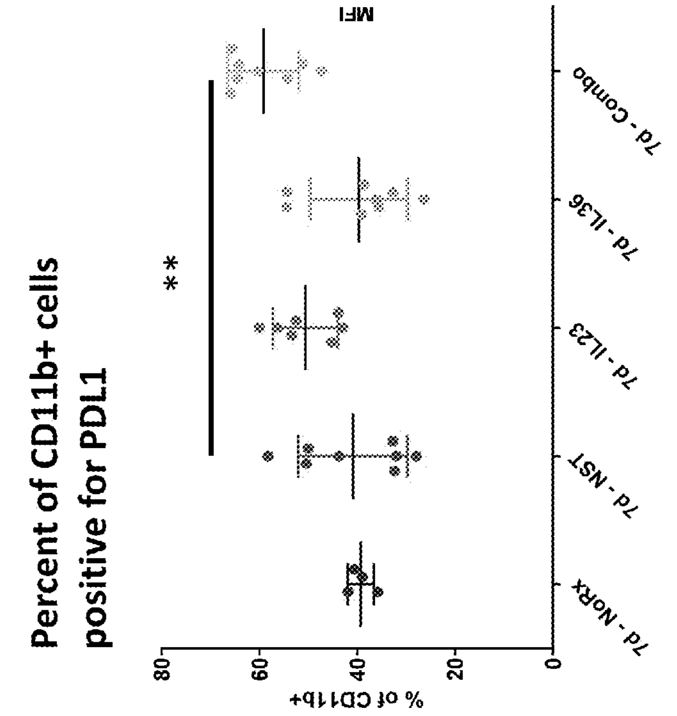
Figure 34B:
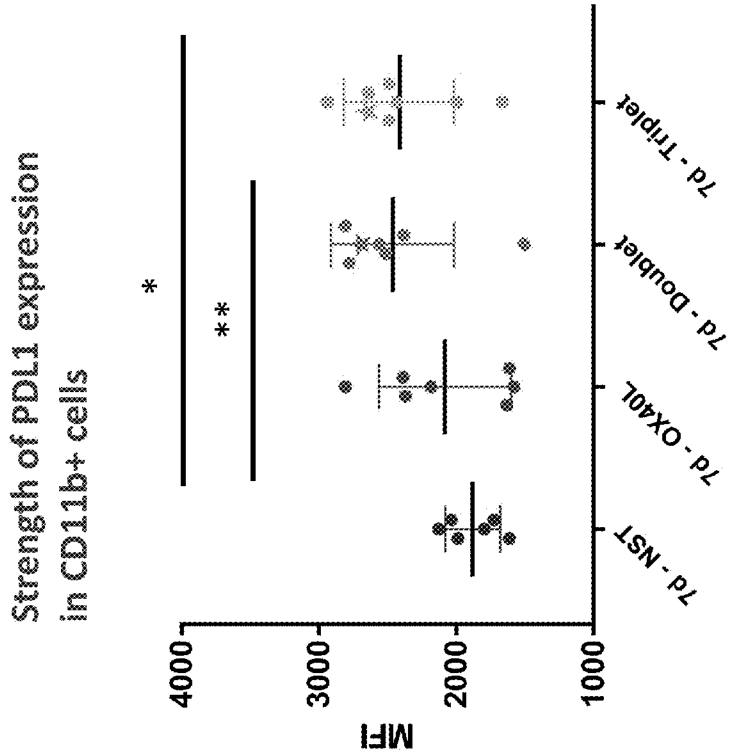
Figure 34A:
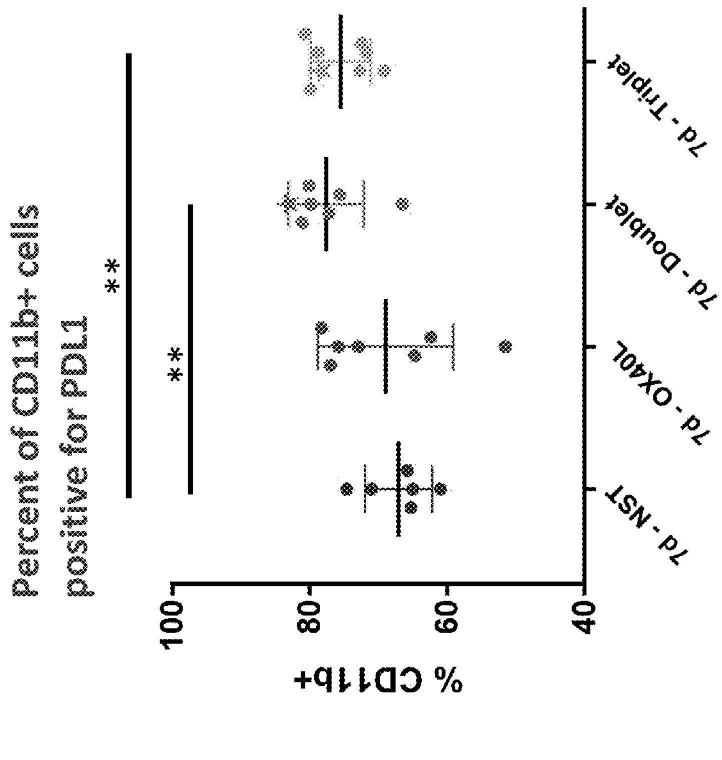

The administration of the doublet IL-23:IL-36-gamma also resulted in an increased percentage of CD11b+ cells positive for PD-L1 (FIG. 33A). This observation correlated with an increase in PD-L1 expression in CD11b+ cells (FIG. 33B). Administration of the triplet combination also resulted in an increased percentage of CD11b+ cells positive for PDL1 (FIG. 34A) and an increase in PDL1 expression in CD11b+ cells (FIG. 34B).

Figure 35A:
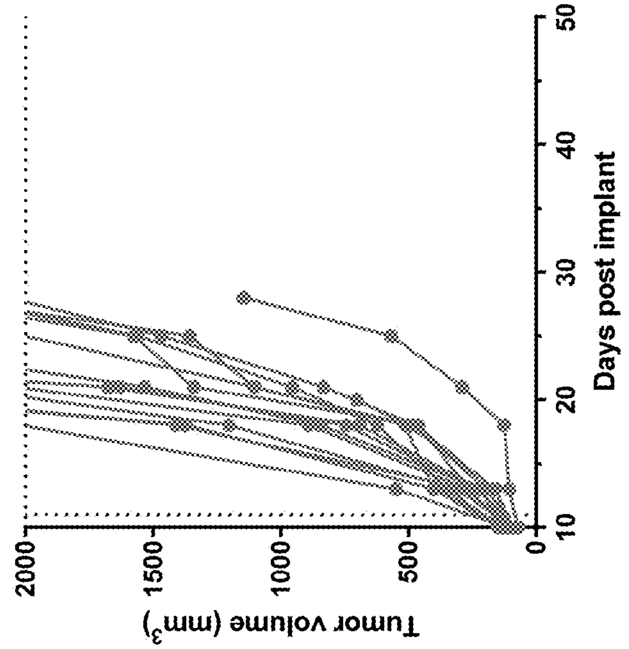
Figure 35B:
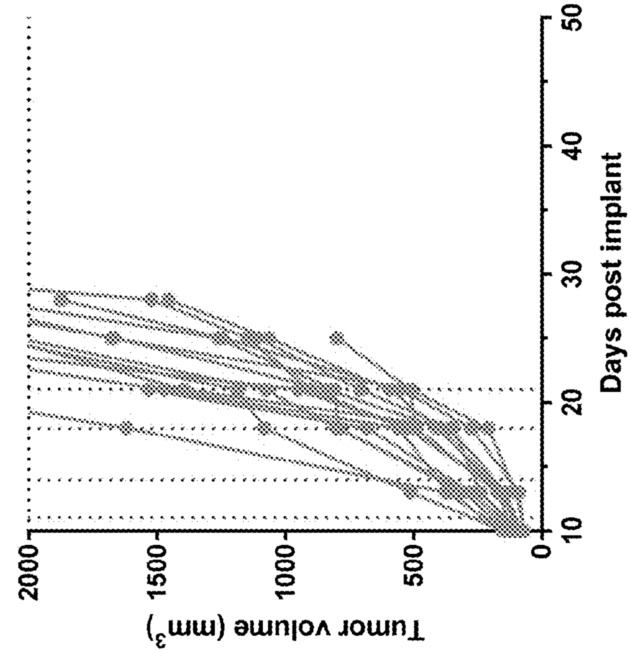
Figure 35D:
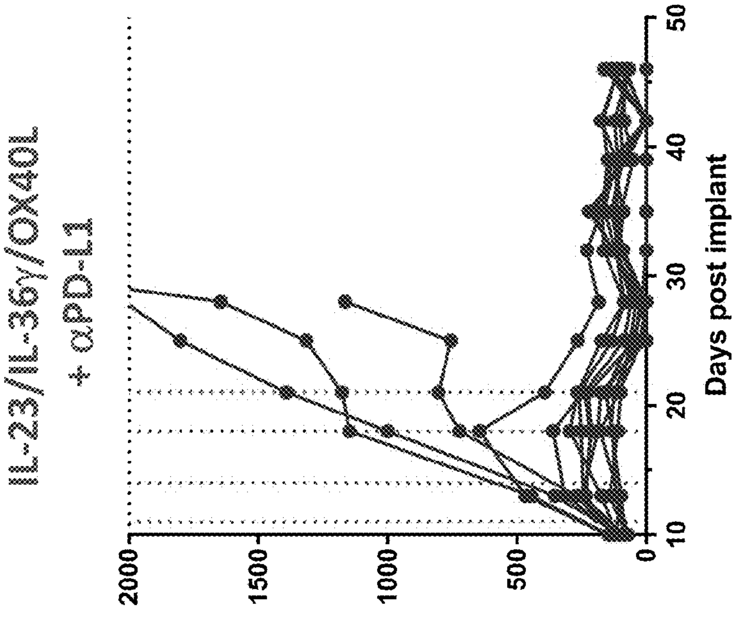
Figure 35C:
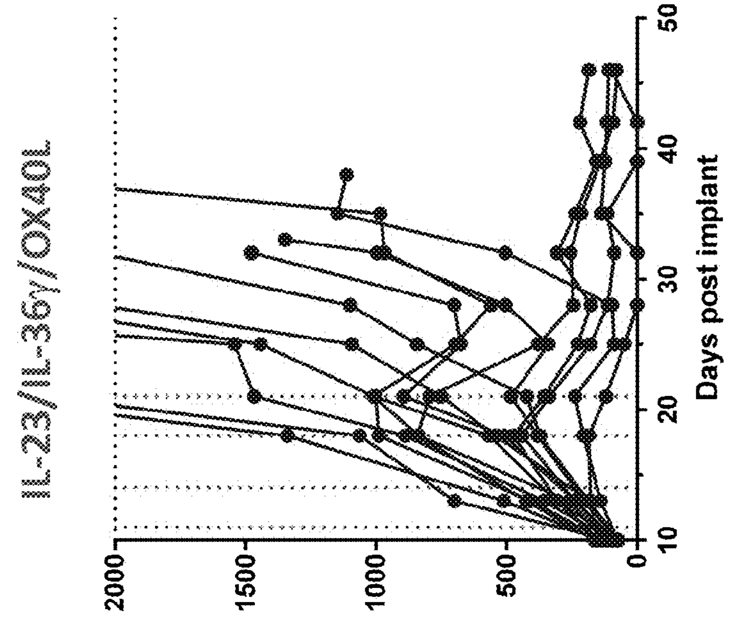

The increase in expression of PD-L1 in the MC38 model in response to treatment with triplet mRNA therapy provided a rational to combine the triplet therapy with anti-PD-L1 antibodies. Total mRNA dosing was 5 ug of total mRNA, administered intratumorally as a single dose. The antibody (anti-PD-L1 antibody 10F.9G2 or control) was dosed intraperitoneally twice per week at 10 mg/kg. No responses were observed when the negative control antibody (FIG. 35A) or the anti-PD-L1 antibody (FIG. 35B) were administered alone. When the triplet mRNA therapy (mRNAs encoding IL23, IL36 gamma, and OX40L) was administered, no complete responses were observed (FIG. 35C) but 4 out of 15 mice showed reduced size tumors. On the other hand, when the triplet mRNA therapy was administered in combination with the anti-PD-L1 antibody, 12 out of 15 mice experienced reduced tumor sizes or complete responses (FIG. 35D). This data indicates that tumors refractory to treatment with a conventional therapy, e.g., an anti-PD-L1 antibody, can be effectively treated by combining such therapy with several mRNAs disclosed herein (e.g., a triple therapy comprising mRNAs encoding IL-23, IL-36-gamma, and OX40L).

Example 21

Efficacy of Doublet and Triplet Therapies in HCC Syngeneic Model

Previous experiments shown above indicate that mRNA combination therapies, e.g., IL-23/IL-36-gamma (doublet) and IL-23/IL-36-gamma/OX40L (triplet) combination therapies, are efficacious in the MC38 colon adenocarcinoma, A20 mouse B-cell lymphoma, or B16F10-AP3 melanoma models. Each one of the cell lines used in the present disclosure, e.g., H22, MC38, and B16F10 cell lines, can be used to model distinct tumor microenvironments. MC38 cells model an immunosuppressive environment, whereas B16F10 cells model an immunologically barren environment. In the present experiment. the efficacy of doublet and triplet combination therapies was evaluated in the syngeneic H22 cell line, a hepatoma cell line that models an inflamed tumor microenvironment.

Figure 36B:
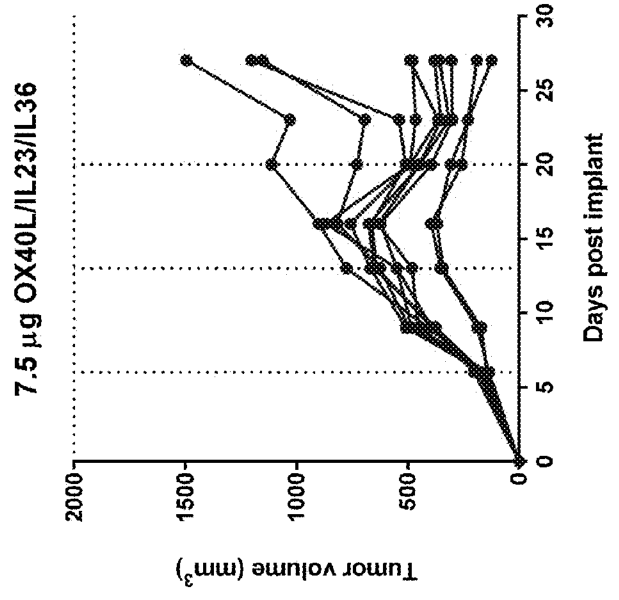
Figure 36A:
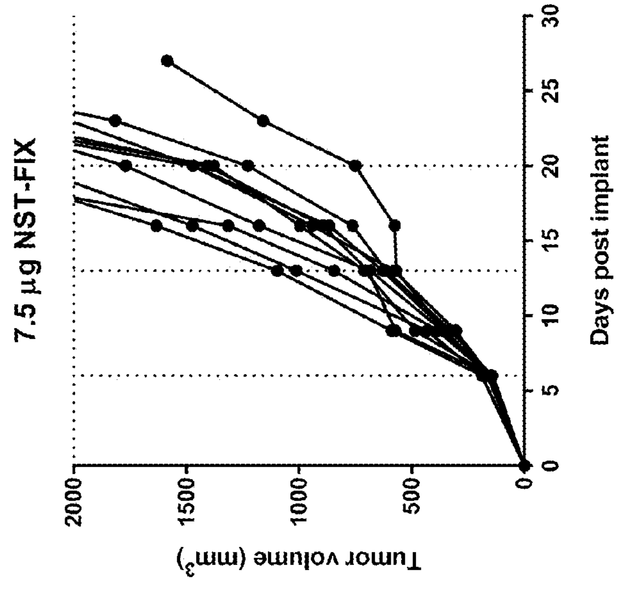

Mice were administered 2.5 ug of each mRNA in the triplet combination therapy (IL-23/IL-36-gamma/OX40L), i.e., a total of 7.5 ug formulated in Compound 18 lipid nanoparticles, or 7.5 ug of control mRNA (NST-FIX). mRNAs were dosed intratumorally Q7D×3 (N=10 mice/group). After 30 days, all the control mice had tumors with volumes above 1,500 $mm^3$ (FIG. 36A) In contrast, none of the mice treated with the triple therapy had tumors with volumes above 1,500 $mm^3$ (FIG. 36B), thus indicating that the triplet combination therapy was also efficacious in the HCC syngeneic model.

Example 22

Human IL-36 Versus Mouse IL-36 Efficacy as Part of OASIS in MC38-M(R)

To determine the efficacy of human IL-36 gamma versus mouse IL-36 in triplet mRNA therapy, a study was designed in which multiple combinations of mRNAs encoding OX40L, IL-23, and either mouse IL-36-gamma or human IL-36-gamma were tested. The design of the study is shown Table 11.

MC-38-M colon adenocarcinoma tumors were established subcutaneously in C57BL/6 mice as described above.

Once the tumors were established, animals were divided into groups and received intratumoral doses of one of the following combination therapies shown in the table below. Each group included 15 animals. Each animal was dosed qd×4 with a total mRNA dose of 5 ug/mouse in a total dose volume of 25 ul.

TABLE 11

| Group | mRNA/ treatment 1 | mRNA/ treatment 2 | mRNA/ treatment 3 | mRNA/ treatment 4 | mRNA dose (μg) | Final conc each treatment (mg/mL) |
|---|---|---|---|---|---|---|
| 1 | mOX40L_122 | mIL23_122 | mIL36_122 | | 1.67, 1.67, 1.67 | 0.067 |
| 2 | mOX40L_122 | mIL23_122 | mIL36_122 | NST-OX40L_122 | 1.67, 1.67, 0.83, 0.83 | 0.067, 0.067, 0.033, 0.033 |
| 3 | mOX40L_122 | mIL23_122 | mIL36_122 | NST-OX40L_122 | 1.67, 1.67, 0.42, 1.25 | 0.067, 0.067, 0.0165, 0.05 |
| 4 | mOX40L_122 | mIL23_122 | mIL36_122 | NST-OX40L_122 | 1.67, 1.67, 0.21, 1.46 | 0.067, 0.067, 0.008, 0.058 |
| 5 | mOX40L_122 | mIL23_122 | | NST-OX40L_122 | 1.67, 1.67, 1.67 | 0.067, 0.067, 0.067 |
| 6 | | mIL23_122 | mIL36_122 | NST-OX40L_122 | 1.67, 1.67, 1.67 | 0.067, 0.067, 0.067 |
| 7 | mOX40L_122 | | mIL36_122 | NST-OX40L_122 | 1.67, 1.67, 1.67 | 0.067, 0.067, 0.067 |
| 8 | mOX40L_122 | | | NST-OX40L_122 | 1.67, 3.34 | 0.067, 0.134 |
| 9 | | mIL23_122 | | NST-OX40L_122 | 1.67, 3.34 | 0.067, 0.134 |
| 10 | | | mIL36_122 | NST-OX40L_122 | 1.67, 3.34 | 0.067, 0.134 |
| 11 | | | | NST-OX40L_122 | 5 | 0.2 |
| 12 | mOX40L_122 | mIL23_122 | hIL36_122 | | 1.67, 1.67, 1.67 | 0.067, 0.067, 0.067 |
| 13 | mOX40L_122 | mIL23_122 | hIL36_122 | | 1.25, 1.25, 2.5 | 0.05, 0.05, 0.1 |
| 14 | mOX40L_122 | mIL23_122 | hIL36_122 | | 0.83, 0.83, 3.33 | 0.033, 0.033, 0.133 |
| 15 | mOX40L_122 | mIL23_122 | hIL36_122 | | 0.5, 0.5, 4 | 0.02, 0.02, 0.16 |

collect blood 6 h + 24 h post dose

Figure 37:
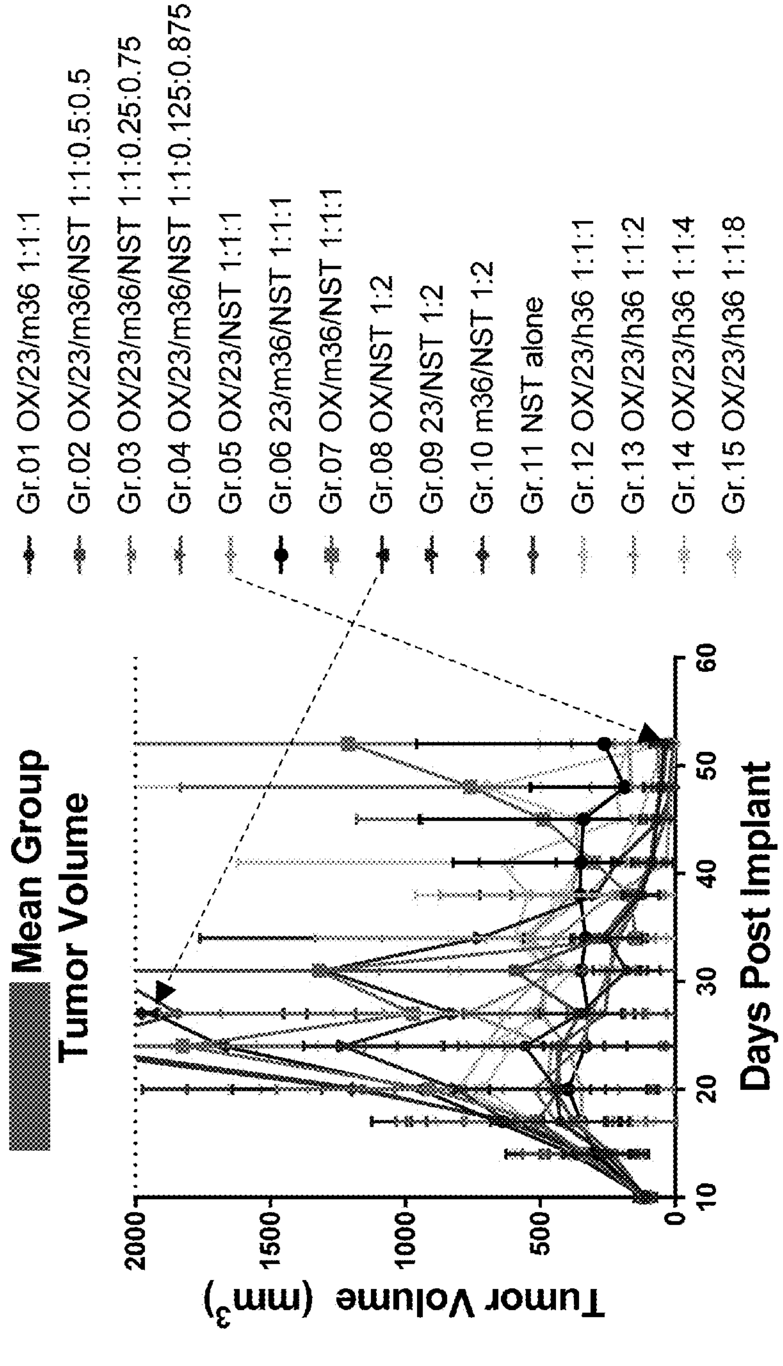
Figure 38A:
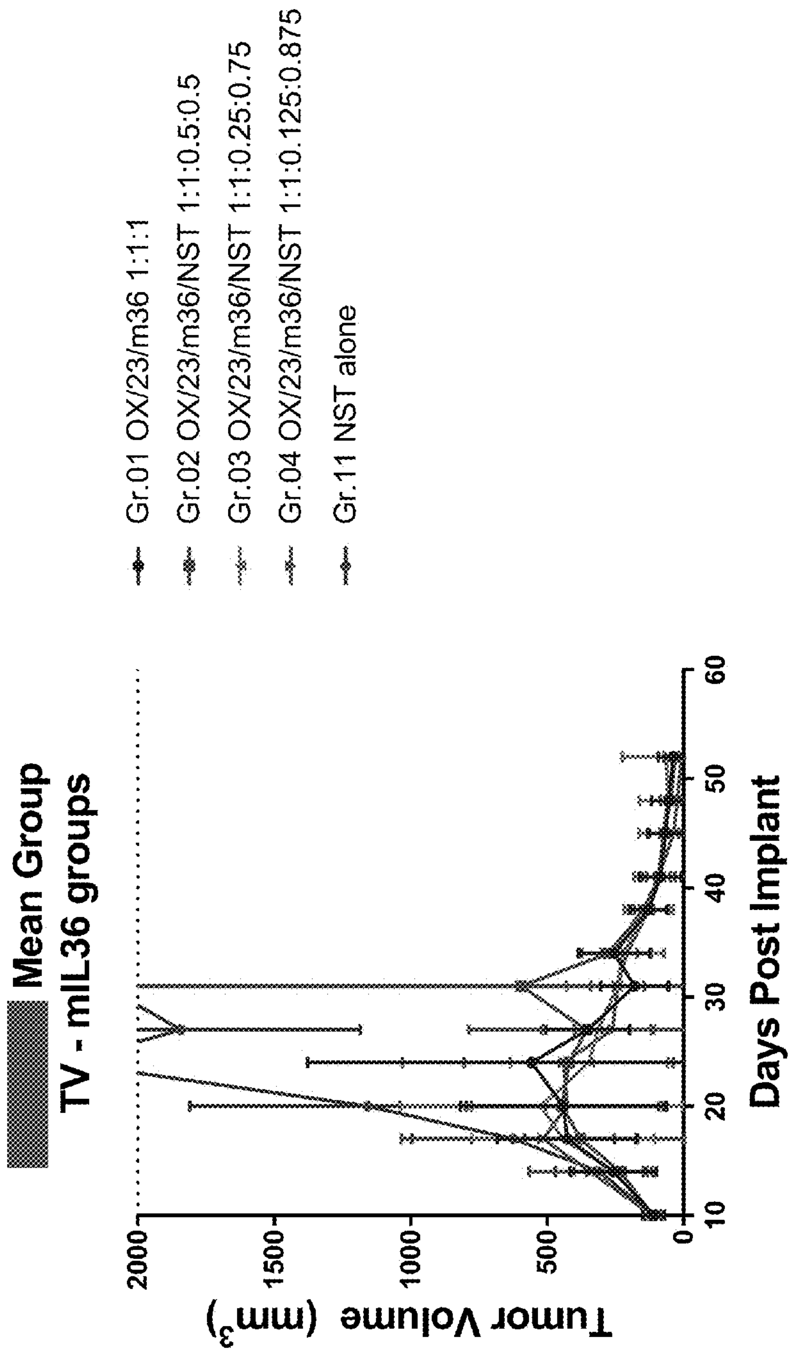
Figure 38B:
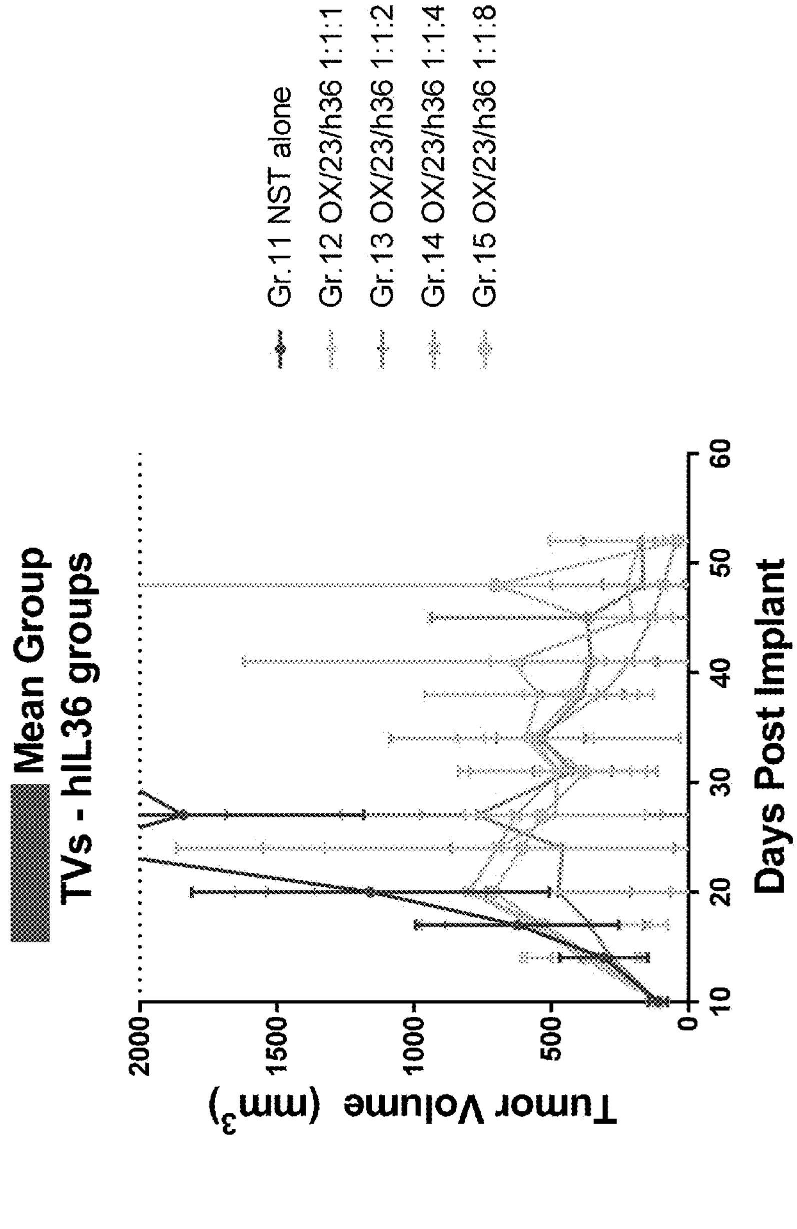
Figure 39C:
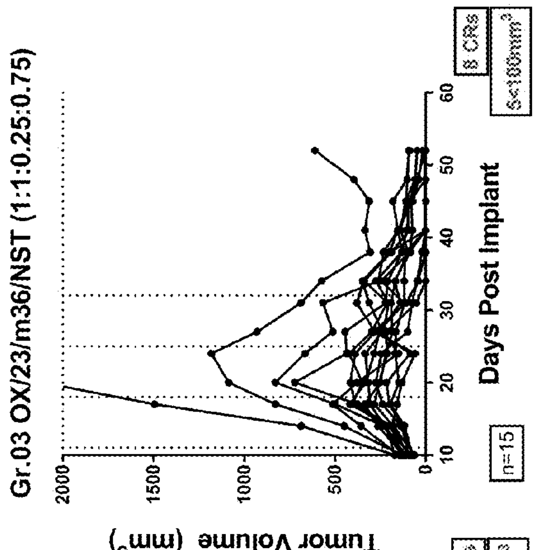
Figure 39B:
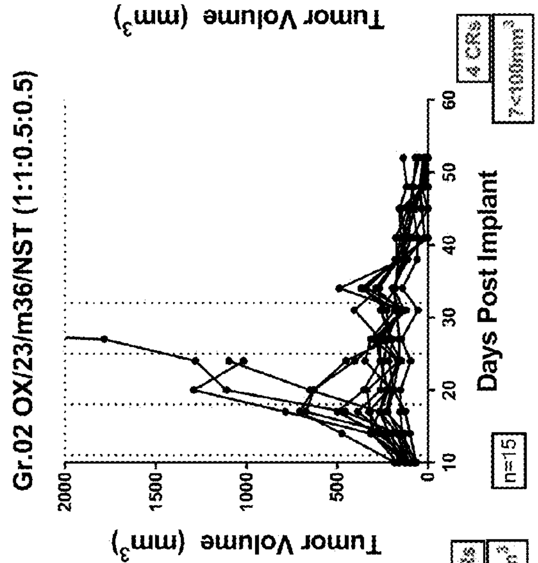
Figure 39A:
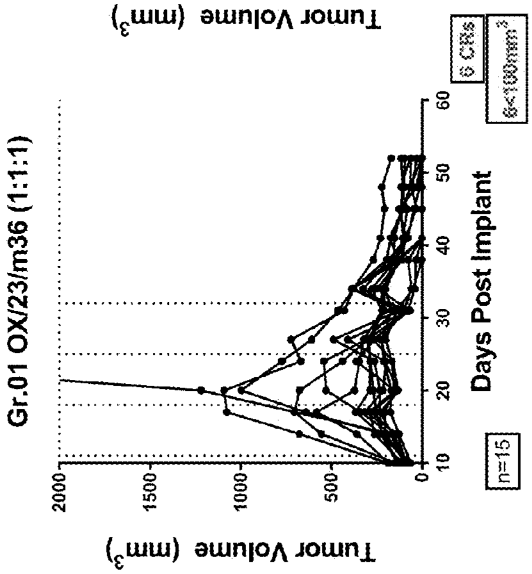
Figure 39D:
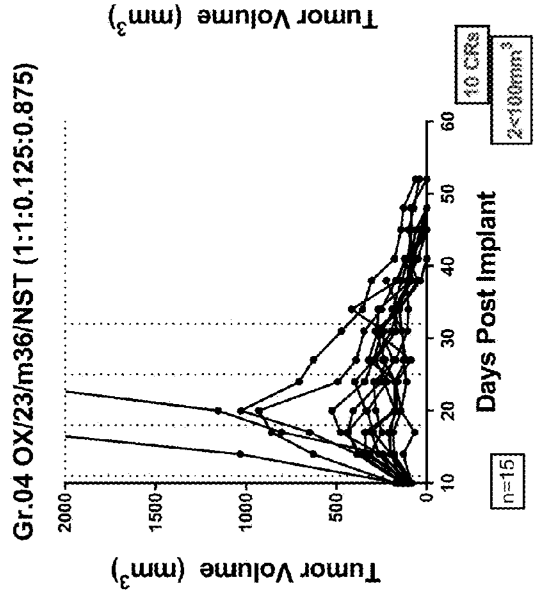
Figure 39E:
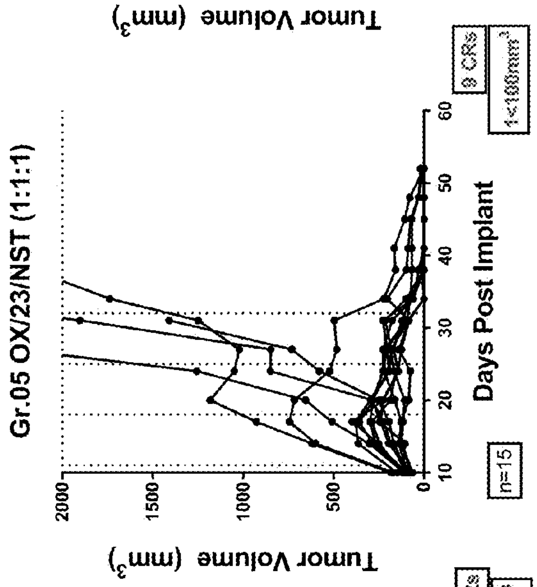
Figure 39F:
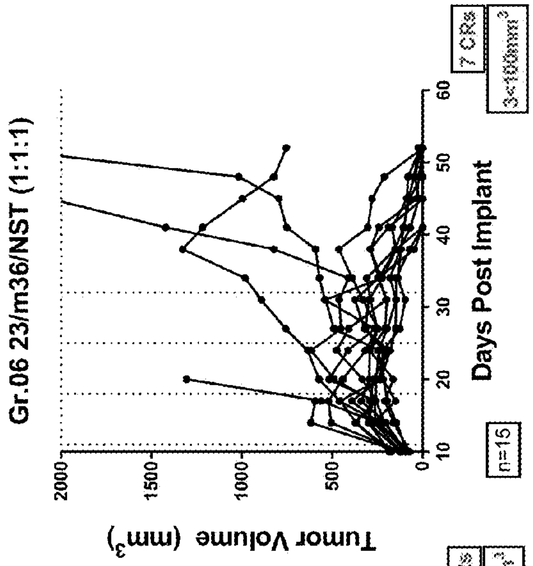
Figure 39I:
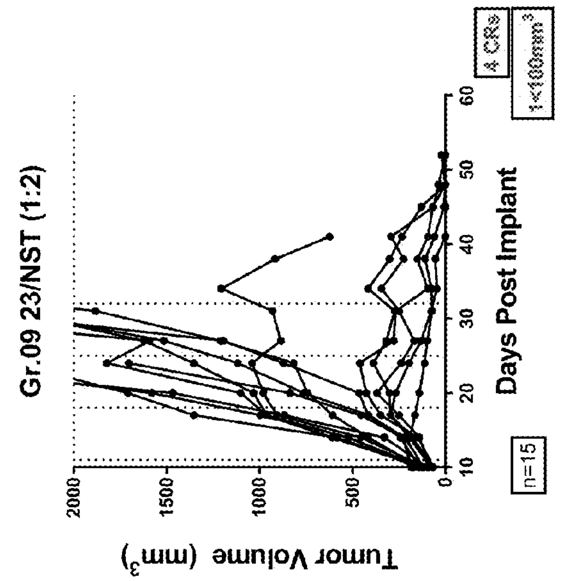
Figure 39H:
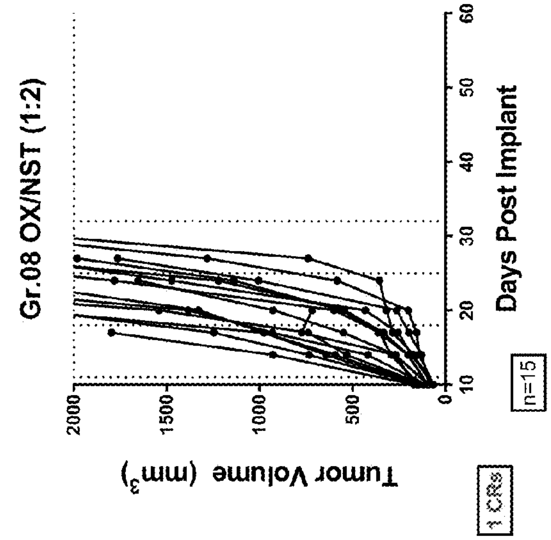
Figure 39G:
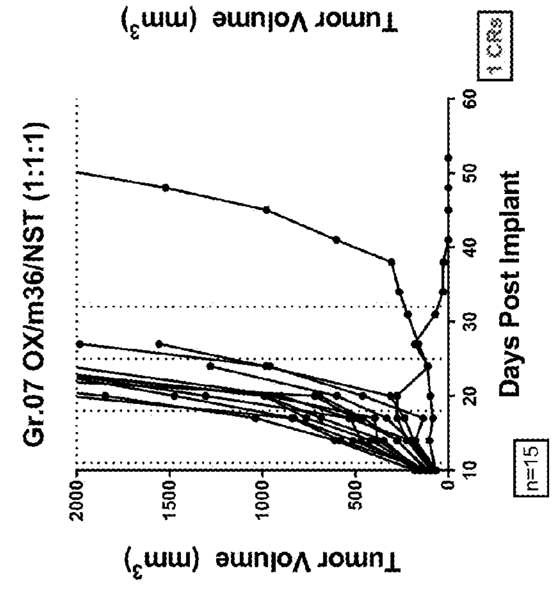
Figure 39J:
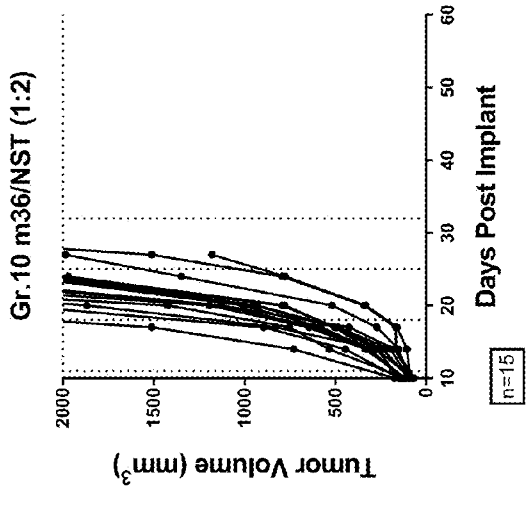
Figure 39K:
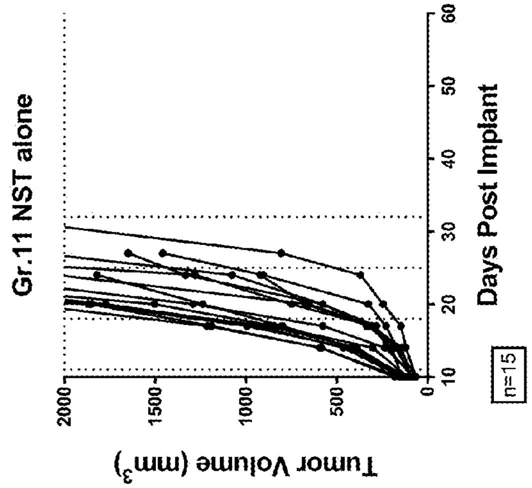
Figure 39L:
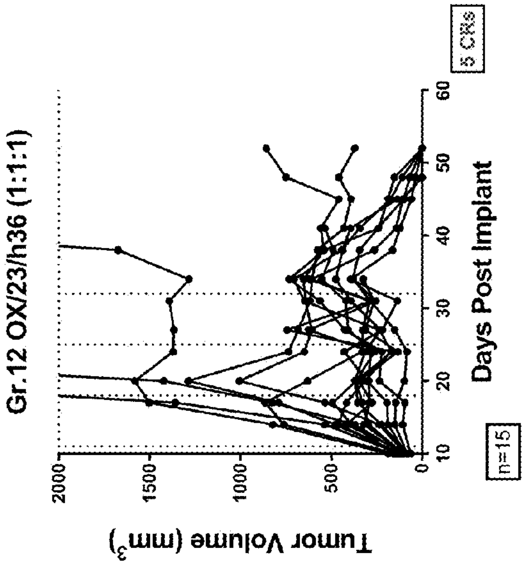
Figure 39O:
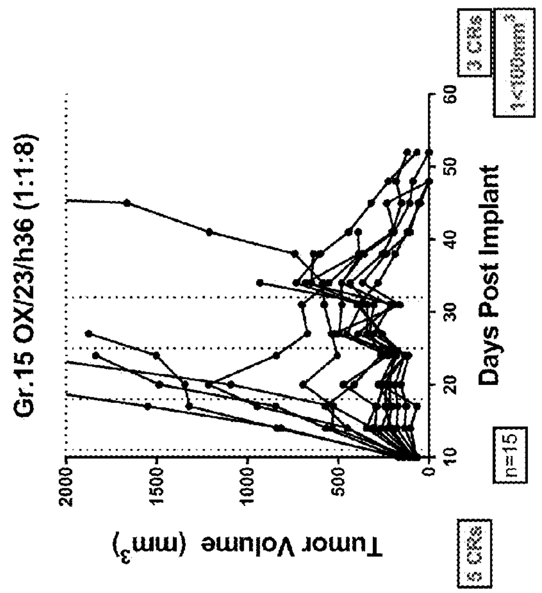
Figure 39N:
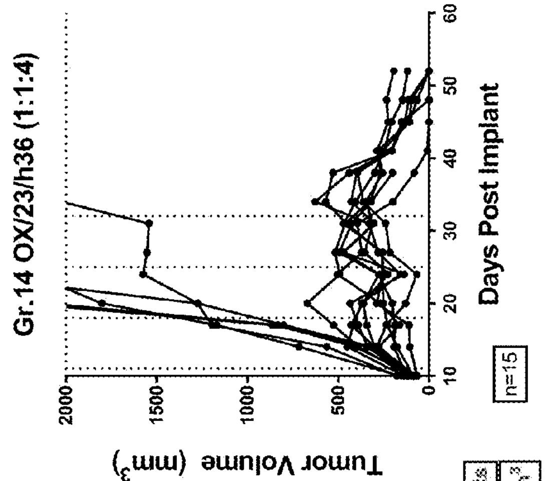
Figure 39M:
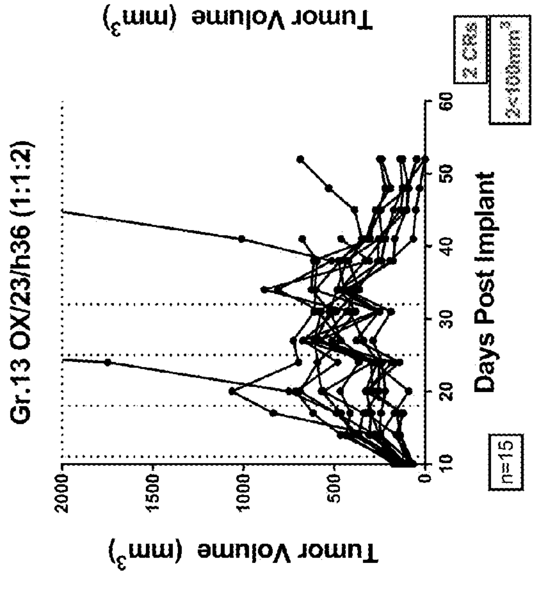
Figure 40:
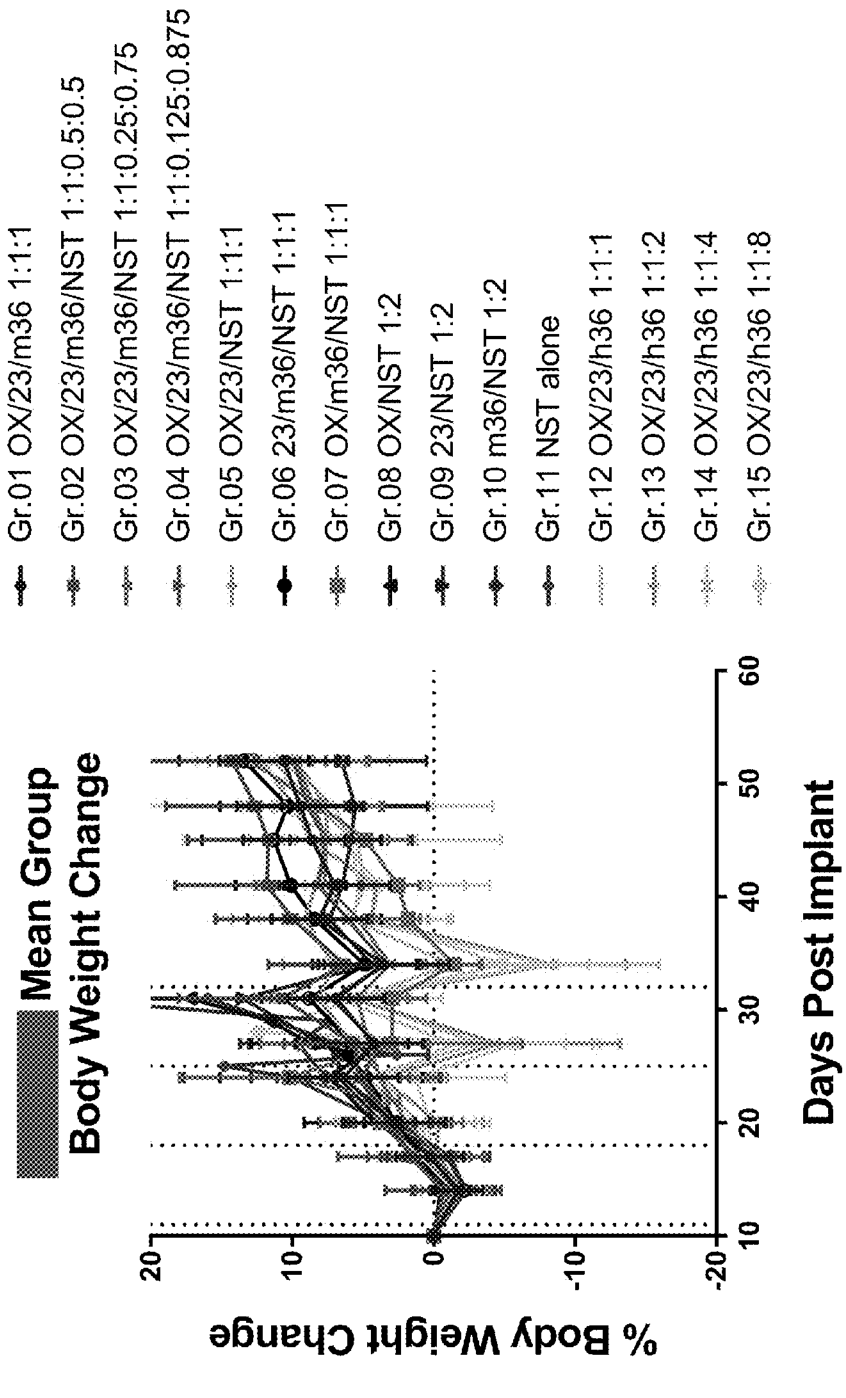
FIG. 40 shows changes in body weight (%) for each group of mice treated according to the study design outlined in Table 11. The drawing shows the mean body weight values for each group.
Figure 41A:
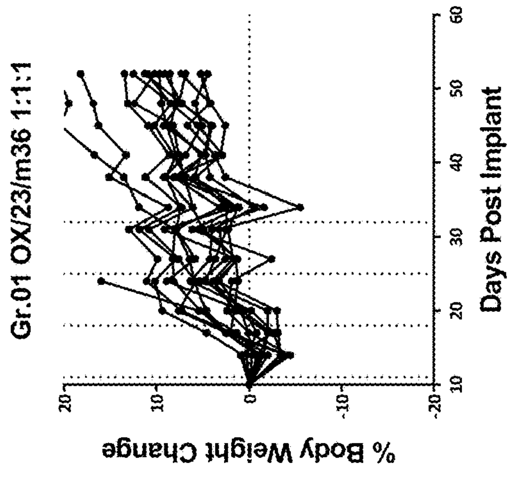
FIG. 41A-41O show changes in body weight (%) for each group of mice treated according to the study design outlined in Table 11. The drawing shows the individual changes in body weight values for each animal in each group.
Figure 41B:
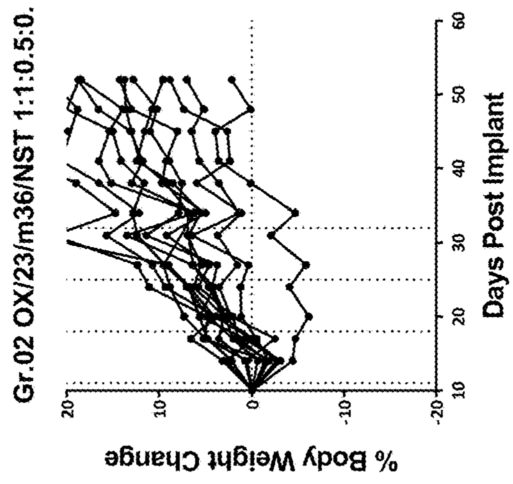
Figure 41C:
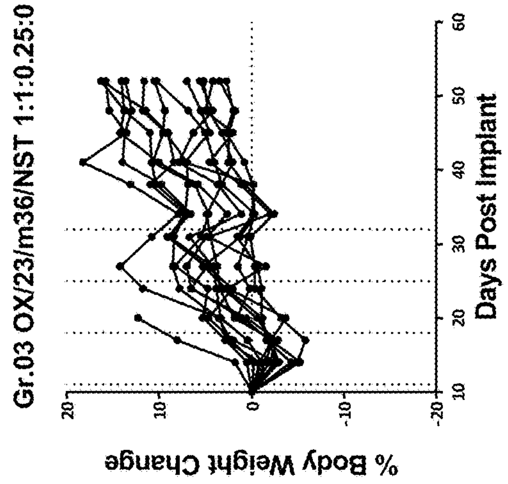
Figure 41D:
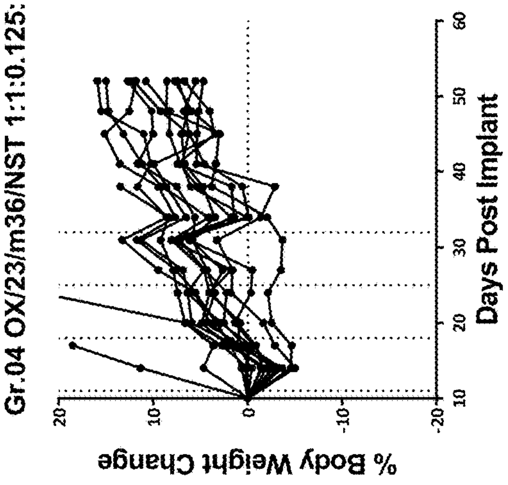
Figure 41E:
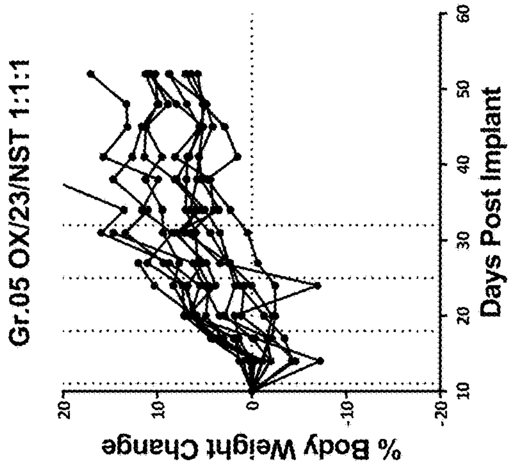
Figure 41F:
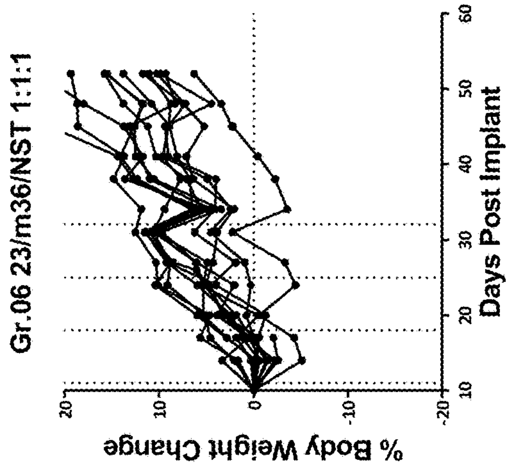
Figure 41G:
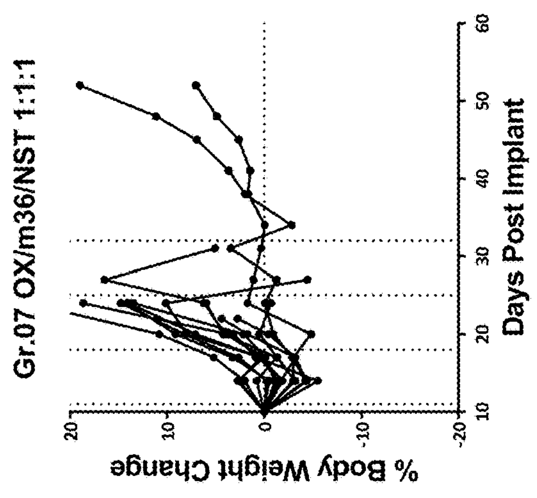
Figure 41H:
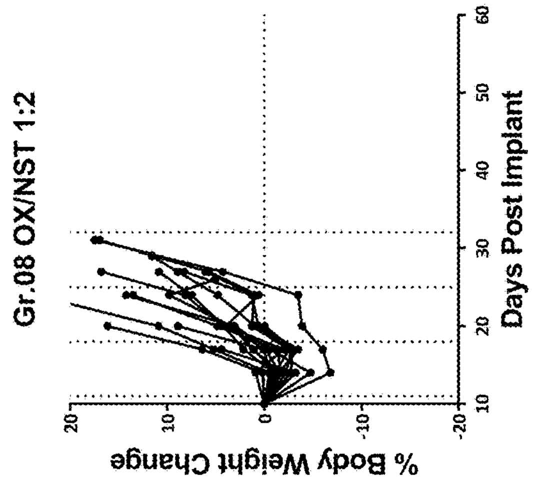
Figure 41I:
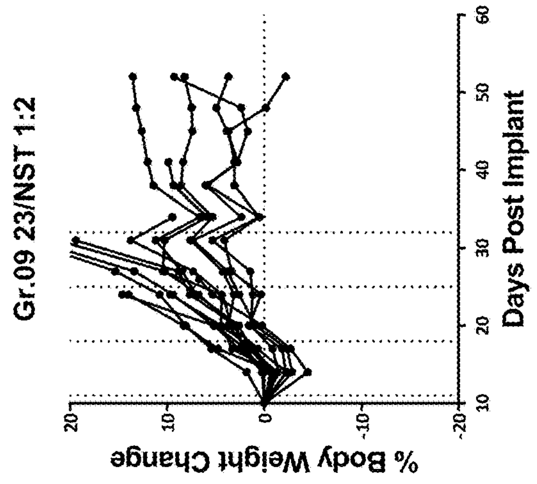
Figure 41J:
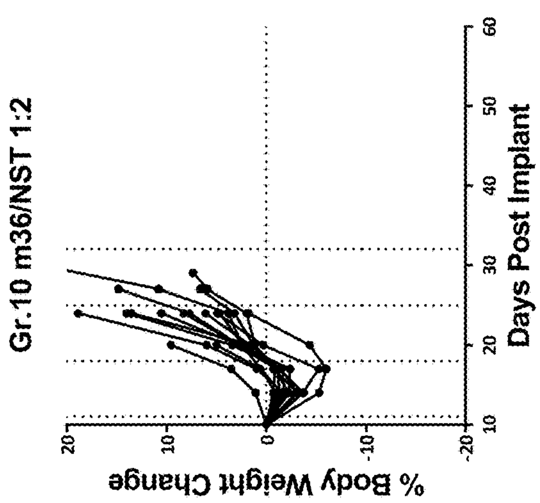
Figure 41K:
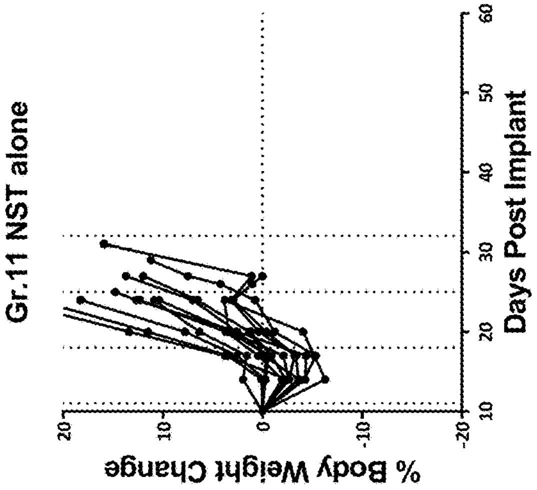
Figure 41L:
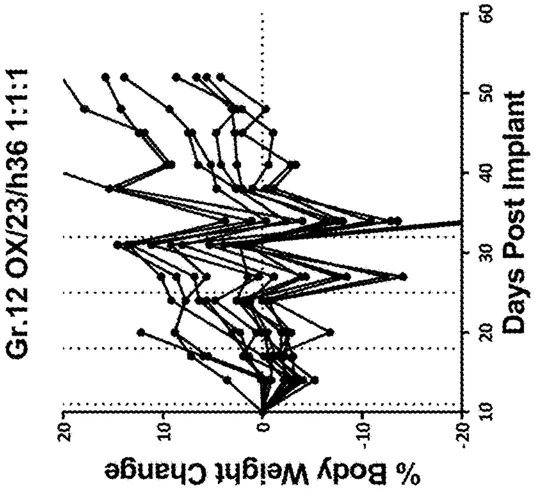
Figure 41M:
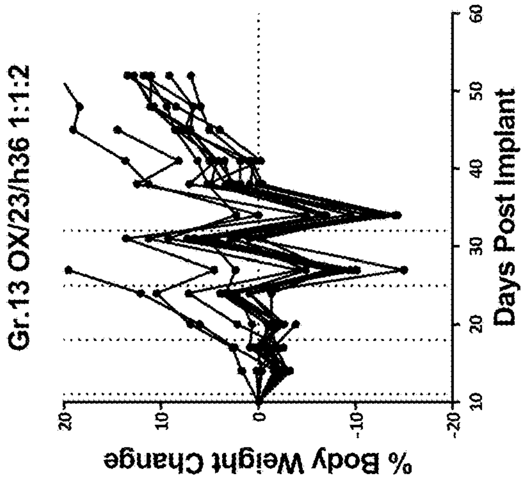
Figure 41N:
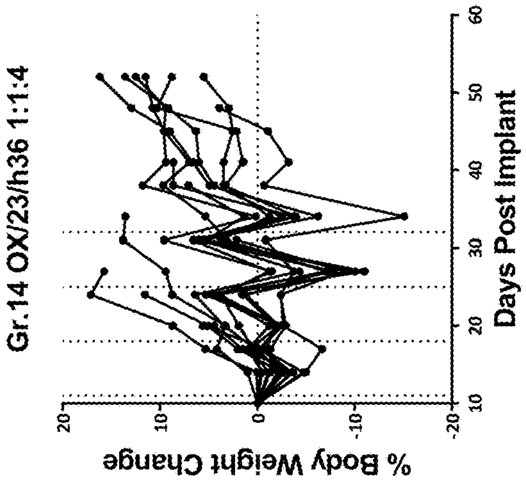
Figure 41O:
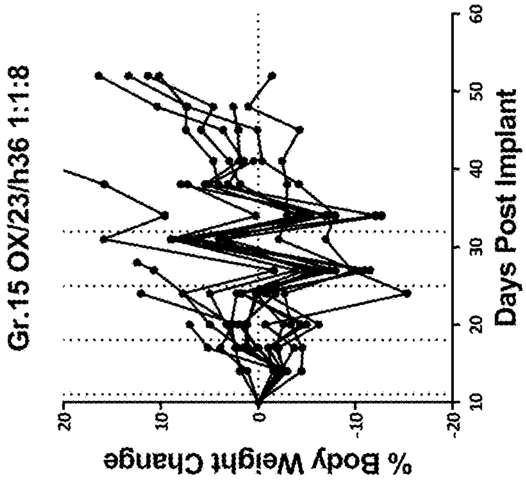

Reduction in tumor size was observed when using either human IL-36-gamma or mouse IL-36-gamma; however, the efficacy of triplet therapy using mouse IL-36 gamma was superior (FIG. 37). The data shows that OX40L monotherapy did not result in tumor size reduction. IL-23 monotherapy resulted in a reduction in tumor size. However, the response of the tumor to IL-23 was slower than the response to the synergistic combination of IL-23 and OX40L. Reductions in tumor size were observed at all the ratios of mIL-36-gamma to OX40 and IL-23 tested (FIG. 38A). A similar effect was observed regarding the triplet mRNA combination comprising hIL-36-gamma, although the effect of these compositions on mean tumor volume was less pronounced (FIG. 38B). Data corresponding to each group in the study and to each individual animal is presented in FIGS. 39A-390. All the animals in Group 8 (OX40L monotherapy) were escapers (FIG. 39H). Four animals in Group (IL-23 monotherapy) were complete responders (FIG. 39I). The combination the OX40L and IL-23 monotherapies resulted in 9 complete responders (FIG. 39E). Thus, the combination the OX40L and IL-23 monotherapies was not additive but synergic. The most effective combination therapy was a triple therapy comprising an mRNA encoding OX40L, an mRNA encoding IL-23, and a mouse mRNA encoding IL-36 gamma at 1:1:0.125 ratio (FIG. 39D). Such triplet therapy resulted in 10 complete responses plus two animals with tumor volumes below 100 $mm^3$. Out of the 15 animals in the group, one 2 were escapers. FIG. 40 and FIGS. 41A-41O show the effect the different therapies tested on body weight.

FIG. 42 shows the effect of the different therapies tested on survival rate. No animals treated with OX40L monotherapy survived past day 30 in the study. After day 50, the survival rate for animals treated with IL-23 monotherapy was slightly below 40%. However, the survival rate for animals treated with both OX40L and IL-23 was close to 70% after day 50, indicating again a synergistic action of the combination OX40L and IL-23. The highest survival rate corresponded to animals treated with triplet therapy mOX40L:mIL-23:mIL-36-gamma at a 1:1:1 ratio (survival ratio above 90%) or 1:1:0.5 (80% survival rate). The survival rates observed when using mouse IL-36-gamma were significantly higher than the survival rates observed when using human 11-36-gamma.

Example 23

Doublet mRNA Therapy as Effective as Triplet mRNA Therapy in Inflamed Tumor Microenvironment Model Experiments were conducted using the MC38-S mice tumor model as a model for an inflamed tumor microenvironment. Tumors were implanted and animals were treated with either doublet mRNA therapy, encoding IL-23 and OX40L (i.e., one immune response primer and one immune response co-stimulatory signal) or with triplet mRNA therapy, encoding IL-23, IL-36-gamma and OX40L (i.e., two immune response primers and one immune response co-stimulatory signal). The total dose of mRNA per treatment was 5 μg of mRNA. The total amount of mRNA in each dose was kept constant by adding the appropriate amount of NST control mRNA. The mRNAs were administered as single intratumoral doses. Tumor volume was measured over time post implant. The results are shown in FIG. 43A (triplet mRNA therapy) and FIG. 43B (doublet mRNA therapy). The results demonstrate that both the doublet and the triplet mRNA therapies were effective in inhibiting growth of the tumors in the animals.

This data indicates that effective treatment of a tumor having an inflamed tumor microenvironment can be achieved using mRNA(s) encoding a single immune response primer and a single immune response co-stimulatory signal (i.e., doublet mRNA therapy).

Other Embodiments

It is to be understood that the words which have been used are words of description rather than limitation, and that changes can be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A method for treating cancer in a subject by activating T cells in vivo, comprising administering to the subject (i) a first messenger RNA (mRNA) comprising an open reading frame (ORF) encoding a human IL-23 polypeptide;

(ii) a second mRNA comprising an ORF encoding a human IL-36gamma polypeptide; and (iii) a third mRNA comprising an ORF encoding a human OX40L polypeptide, thereby activating T cells in vivo to treat cancer in the subject.

2. The method of claim 1, wherein activating T cells results in one or more of: a reduction or a decrease in the size of a tumor, inhibition of growth of a tumor, and induction of a memory T cell response.

3. The method of claim 1, wherein the human IL-23 polypeptide comprises an IL-12p40 polypeptide operably linked, with or without a linker, to an IL-23p19 polypeptide.

4. The method of claim 3, wherein the human IL-23 polypeptide comprises an IL-12p40 polypeptide operably linked via a linker to an IL-23p19 polypeptide, and wherein the linker is a Gly/Ser linker.

5. The method of claim 1, wherein the human IL-23 polypeptide comprises the amino acid sequence set forth in SEQ ID NO: 140, wherein the human IL-36gamma polypeptide comprises the amino acid sequence set forth in SEQ ID NO: 16, and wherein the human OX40L polypeptide comprises the amino acid sequence set forth in SEQ ID NO: 21.

6. The method of claim 5, wherein (i) the first mRNA comprises an ORF comprising a nucleotide sequence at least 90% identical to the nucleotide sequence as set forth in SEQ ID NO: 141;

(ii) the second mRNA comprises an ORF comprising a nucleotide sequence at least 90% identical to the nucleotide sequence as set forth in SEQ ID NO: 143; and (iii) the third mRNA comprises an ORF comprising a nucleotide sequence at least 90% identical to the nucleotide sequence as set forth in SEQ ID NO: 145.

7. A method for treating cancer in a subject by activating T cells in vivo, comprising administering to the subject (i) a first mRNA encoding a human IL-23 polypeptide, wherein the first mRNA comprises an ORF comprising a nucleotide sequence at least 90% identical to the nucleotide sequence as set forth in SEQ ID NO: 141 or comprises the nucleotide sequence as set forth in SEQ ID NO: 141;

(ii) a second mRNA encoding a human IL-36gamma polypeptide, wherein the second mRNA comprises an ORF comprising a nucleotide sequence at least 90% identical to the nucleotide sequence as set forth in SEQ ID NO: 143 or comprises the nucleotide sequence as set forth in SEQ ID NO: 143; and (iii) a third mRNA encoding a human OX40L polypeptide, wherein the third mRNA comprises an ORF comprising a nucleotide sequence at least 90% identical to the nucleotide sequence as set forth in SEQ ID NO: 145, or comprises the nucleotide sequence as set forth in SEQ ID NO: 145, thereby activating T cells in vivo to treat cancer in the subject.

8. The method of claim 7, wherein (i) the first mRNA comprises an ORF comprising the nucleotide sequence as set forth in SEQ ID NO: 141;

(ii) the second mRNA comprises an ORF comprising the nucleotide sequence as set forth in SEQ ID NO: 143; and (iii) the third mRNA comprises an ORF comprising the nucleotide sequence as set forth in SEQ ID NO: 145.

9. The method of claim 8, wherein activating T cells results in one or more of: a reduction or a decrease in the size of a tumor, inhibition of growth of a tumor, and induction of a memory T cell response.

10. The method of claim 7, wherein the first mRNA, second mRNA and third mRNA each comprise a 5' untranslated region (UTR) comprising the nucleotide sequence as set forth in SEQ ID NO: 27, and a 3' UTR comprising the nucleotide sequence as set forth in SEQ ID NO: 120.

11. The method of claim 10, wherein the first, second and third mRNAs are each fully modified with chemically-modified uridines.

12. The method of claim 11, wherein the chemically modified uridines are N1-methylpseudouridines.

13. The method of claim 7, wherein the first, second and third mRNAs are formulated in the same lipid nanoparticle.

14. The method of claim 13, wherein the first, second and third mRNAs are formulated in the lipid nanoparticle at a mass ratio of OX40L:IL-23:IL-36gamma of 1:1:2.

15. A method for treating cancer in a subject by activating T cells in vivo, comprising administering to the subject (i) a first mRNA encoding a human IL-23 polypeptide, wherein the first mRNA comprises a nucleotide sequence at least 90% identical to the nucleotide sequence set forth in SEQ ID NO: 142 or comprises the nucleotide sequence set forth in SEQ ID NO: 142;

(ii) a second mRNA encoding a human IL-36gamma polypeptide, wherein the second mRNA comprises a nucleotide sequence at least 90% identical to the nucleotide sequence set forth in SEQ ID NO: 144 or comprises the nucleotide sequence set forth in SEQ ID NO: 144; and (iii) a third mRNA encoding a human OX40L polypeptide, wherein the third mRNA comprises a nucleotide sequence at least 90% identical to the nucleotide sequence set forth in SEQ ID NO: 146 or comprises the nucleotide sequence set forth in SEQ ID NO: 146, thereby activating T cells in vivo to treat cancer in the subject.

16. The method of claim 15, wherein (i) the first mRNA comprises the nucleotide sequence set forth in SEQ ID NO: 142;

(ii) the second mRNA comprises the nucleotide sequence set forth in SEQ ID NO: 144; and (iii) the third mRNA comprises the nucleotide sequence set forth in SEQ ID NO: 146.

17. The method of claim 16, wherein activating T cells results in one or more of: reduction or decrease in the size of a tumor, inhibition of growth of a tumor, and induction of a memory T cell response.

18. The method of claim 15, wherein the first, second and third mRNAs are fully modified with N1-methylpseudouridine.

19. The method of claim 15, wherein the first, second and third mRNAs are formulated in the same lipid nanoparticle.

20. The method of claim 19, wherein the first, second and third mRNAs are formulated in the lipid nanoparticle at a mass ratio of OX40L:IL-23:IL-36gamma of 1:1:2.

* * * * *

SEQUENCE LISTING

```
<160> NUMBER OF SEQ ID NOS: 198

<210> SEQ ID NO 1
<211> LENGTH: 328
<212> TYPE: PRT
<213> ORGANISM: Homo sapiens
<220> FEATURE:
<221> NAME/KEY: misc_feature
<222> LOCATION: (1)..(328)
<223> OTHER INFORMATION: Amino acid sequence of human IL-23 IL-12p40
      subunit (Precursor)

<400> SEQUENCE: 1

Met Cys His Gln Gln Leu Val Ile Ser Trp Phe Ser Leu Val Phe Leu
1               5                   10                  15
```

Ala Ser Pro Leu Val Ala Ile Trp Glu Leu Lys Lys Asp Val Tyr Val
20 25 30

Val Glu Leu Asp Trp Tyr Pro Asp Ala Pro Gly Glu Met Val Val Leu
35 40 45

Thr Cys Asp Thr Pro Glu Glu Asp Gly Ile Thr Trp Thr Leu Asp Gln
50 55 60

Ser Ser Glu Val Leu Gly Ser Gly Lys Thr Leu Thr Ile Gln Val Lys
65 70 75 80

Glu Phe Gly Asp Ala Gly Gln Tyr Thr Cys His Lys Gly Gly Glu Val
85 90 95

Leu Ser His Ser Leu Leu Leu Leu His Lys Lys Glu Asp Gly Ile Trp
100 105 110

Ser Thr Asp Ile Leu Lys Asp Gln Lys Glu Pro Lys Asn Lys Thr Phe
115 120 125

Leu Arg Cys Glu Ala Lys Asn Tyr Ser Gly Arg Phe Thr Cys Trp Trp
130 135 140

Leu Thr Thr Ile Ser Thr Asp Leu Thr Phe Ser Val Lys Ser Ser Arg
145 150 155 160

Gly Ser Ser Asp Pro Gln Gly Val Thr Cys Gly Ala Ala Thr Leu Ser
165 170 175

Ala Glu Arg Val Arg Gly Asp Asn Lys Glu Tyr Glu Tyr Ser Val Glu
180 185 190

Cys Gln Glu Asp Ser Ala Cys Pro Ala Ala Glu Glu Ser Leu Pro Ile
195 200 205

Glu Val Met Val Asp Ala Val His Lys Leu Lys Tyr Glu Asn Tyr Thr
210 215 220

Ser Ser Phe Phe Ile Arg Asp Ile Ile Lys Pro Asp Pro Pro Lys Asn
225 230 235 240

Leu Gln Leu Lys Pro Leu Lys Asn Ser Arg Gln Val Glu Val Ser Trp
245 250 255

Glu Tyr Pro Asp Thr Trp Ser Thr Pro His Ser Tyr Phe Ser Leu Thr
260 265 270

Phe Cys Val Gln Val Gln Gly Lys Ser Lys Arg Glu Lys Lys Asp Arg
275 280 285

Val Phe Thr Asp Lys Thr Ser Ala Thr Val Ile Cys Arg Lys Asn Ala
290 295 300

Ser Ile Ser Val Arg Ala Gln Asp Arg Tyr Tyr Ser Ser Ser Trp Ser
305 310 315 320

Glu Trp Ala Ser Val Pro Cys Ser
325

<210> SEQ ID NO 2
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: TNFSF4 isoform 2

<400> SEQUENCE: 2

Met Val Ser His Arg Tyr Pro Arg Ile Gln Ser Ile Lys Val Gln Phe
1 5 10 15

Thr Glu Tyr Lys Lys Glu Lys Gly Phe Ile Leu Thr Ser Gln Lys Glu
20 25 30

Asp Glu Ile Met Lys Val Gln Asn Asn Ser Val Ile Ile Asn Cys Asp

```
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130


<210> SEQ ID NO 3
<211> LENGTH: 306
<212> TYPE: PRT
<213> ORGANISM: Homo sapiens
<220> FEATURE:
<221> NAME/KEY: misc_feature
<222> LOCATION: (1)..(306)
<223> OTHER INFORMATION: Amino acid sequence of human IL-23 IL-12p40
      subunit (Mature)

<400> SEQUENCE: 3

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
```

245 250 255

Gly Lys Ser Lys Arg Glu Lys Lys Asp Arg Val Phe Thr Asp Lys Thr
260 265 270

Ser Ala Thr Val Ile Cys Arg Lys Asn Ala Ser Ile Ser Val Arg Ala
275 280 285

Gln Asp Arg Tyr Tyr Ser Ser Ser Trp Ser Glu Trp Ala Ser Val Pro
290 295 300

Cys Ser
305

<210> SEQ ID NO 4
<211> LENGTH: 189
<212> TYPE: PRT
<213> ORGANISM: Homo sapiens
<220> FEATURE:
<221> NAME/KEY: misc_feature
<222> LOCATION: (1)..(189)
<223> OTHER INFORMATION: Amino acid sequence of human IL-23 IL-23p19 subunit (Precursor)

<400> SEQUENCE: 4

Met Leu Gly Ser Arg Ala Val Met Leu Leu Leu Leu Leu Pro Trp Thr
1 5 10 15

Ala Gln Gly Arg Ala Val Pro Gly Gly Ser Ser Pro Ala Trp Thr Gln
20 25 30

Cys Gln Gln Leu Ser Gln Lys Leu Cys Thr Leu Ala Trp Ser Ala His
35 40 45

Pro Leu Val Gly His Met Asp Leu Arg Glu Glu Gly Asp Glu Glu Thr
50 55 60

Thr Asn Asp Val Pro His Ile Gln Cys Gly Asp Gly Cys Asp Pro Gln
65 70 75 80

Gly Leu Arg Asp Asn Ser Gln Phe Cys Leu Gln Arg Ile His Gln Gly
85 90 95

Leu Ile Phe Tyr Glu Lys Leu Leu Gly Ser Asp Ile Phe Thr Gly Glu
100 105 110

Pro Ser Leu Leu Pro Asp Ser Pro Val Gly Gln Leu His Ala Ser Leu
115 120 125

Leu Gly Leu Ser Gln Leu Leu Gln Pro Glu Gly His His Trp Glu Thr
130 135 140

Gln Gln Ile Pro Ser Leu Ser Pro Ser Gln Pro Trp Gln Arg Leu Leu
145 150 155 160

Leu Arg Phe Lys Ile Leu Arg Ser Leu Gln Ala Phe Val Ala Val Ala
165 170 175

Ala Arg Val Phe Ala His Gly Ala Ala Thr Leu Ser Pro
180 185

<210> SEQ ID NO 5
<211> LENGTH: 170
<212> TYPE: PRT
<213> ORGANISM: Homo sapiens
<220> FEATURE:
<221> NAME/KEY: misc_feature
<222> LOCATION: (1)..(170)
<223> OTHER INFORMATION: Amino acid sequence of human IL-23 IL-23p19 subunit (Mature)

<400> SEQUENCE: 5

Arg Ala Val Pro Gly Gly Ser Ser Pro Ala Trp Thr Gln Cys Gln Gln
1 5 10 15

-continued

```
Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170


<210> SEQ ID NO 6
<211> LENGTH: 986
<212> TYPE: DNA
<213> ORGANISM: Homo sapiens
<220> FEATURE:
<221> NAME/KEY: misc_feature
<222> LOCATION: (1)..(986)
<223> OTHER INFORMATION: Nucleotide sequence  of human IL-23 IL-12p40
      subunit (Precursor)

<400> SEQUENCE: 6

atgtgtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagtta                                         986


<210> SEQ ID NO 7
```

<211> LENGTH: 920
<212> TYPE: DNA
<213> ORGANISM: Homo sapiens
<220> FEATURE:
<221> NAME/KEY: misc_feature
<222> LOCATION: (1)..(920)
<223> OTHER INFORMATION: Nucleotide sequence of human IL-23 IL-12p40 subunit (Mature)

<400> SEQUENCE: 7
atatgggaac tgaagaaaga tgtttatgtc gtagaattgg attggtatcc ggatgcccct 60
ggagaaatgg tggtcctcac ctgtgacacc cctgaagaag atggtatcac ctggaccttg 120
gaccagagca gtgaggtctt aggctctggc aaaaccctga ccatccaagt caaagagttt 180
ggagatgctg gccagtacac ctgtcacaaa ggaggcgagg ttctaagcca ttcgctcctg 240
ctgcttcaca aaaaggaaga tggaatttgg tccactgata ttttaaagga ccagaaagaa 300
cccaaaaata agacctttct aagatgcgag gccaagaatt attctggacg tttcacctgc 360
tggtggctga cgacaatcag tactgatttg acattcagtg tcaaaagcag cagaggctct 420
tctgaccccc aaggggtgac gtgcggagct gctacactct ctgcagagag agtcagaggg 480
gacaacaagg agtatgagta ctcagtggag tgccaggagg acagtgcctg cccagctgct 540
gaggagagtc tgcccattga ggtcatggtg gatgccgttc acaagctcaa gtatgaaaac 600
tacaccagca gcttcttcat cagggacatc atcaaacctg acccacccaa gaacttgcag 660
ctgaagccat taaagaattc tcggcaggtg gaggtcagct gggagtaccc tgacacctgg 720
agtactccac attcctactt ctccctgaca ttctgcgttc aggtccaggg caagagcaag 780
agagaaaaga aagatagagt cttcacggac aagacctcag ccacggtcat ctgccgcaaa 840
aatgccagca ttagcgtgcg ggcccaggac cgctactata gctcatcttg gagcgaatgg 900
gcatctgtgc cctgcagtta 920

<210> SEQ ID NO 8
<211> LENGTH: 567
<212> TYPE: DNA
<213> ORGANISM: Homo sapiens
<220> FEATURE:
<221> NAME/KEY: misc_feature
<222> LOCATION: (1)..(567)
<223> OTHER INFORMATION: Nucleotide sequence of human IL-23 IL-23p19 subunit (Precursor)

<400> SEQUENCE: 8
atgctgggga gcagagctgt aatgctgctg ttgctgctgc cctggacagc tcagggcaga 60
gctgtgcctg ggggcagcag ccctgcctgg actcagtgcc agcagctttc acagaagctc 120
tgcacactgg cctggagtgc acatccacta gtgggacaca tggatctaag agaagaggga 180
gatgaagaga ctacaaatga tgttccccat atccagtgtg gagatggctg tgacccccaa 240
ggactcaggg acaacagtca gttctgcttg caaaggatcc accagggtct gatttttat 300 gagaagctgc taggatcgga tattttcaca ggggagcctt ctctgctccc tgatagccct 360
gtggcgcagc ttcatgcctc cctactgggc ctcagccaac tcctgcagcc tgagggtcac 420
cactgggaga ctcagcagat tccaagcctc agtcccagcc agccatggca gcgtctcctt 480
ctccgcttca aaatccttcg cagcctccag gcctttgtgg ctgtagccgc ccgggtcttt 540
gcccatggag cagcaaccct gagtccc 567

<210> SEQ ID NO 9
<211> LENGTH: 510

<212> TYPE: DNA
<213> ORGANISM: Homo sapiens
<220> FEATURE:
<221> NAME/KEY: misc_feature
<222> LOCATION: (1)..(510)
<223> OTHER INFORMATION: Nucleotide sequence of human IL-23 IL-23p19
subunit (Mature)

<400> SEQUENCE: 9

```
agagctgtgc ctgggggcag cagccctgcc tggactcagt gccagcagct ttcacagaag     60

ctctgcacac tggcctggag tgcacatcca ctagtgggac acatggatct aagagaagag    120

ggagatgaag agactacaaa tgatgttccc catatccagt gtggagatgg ctgtgacccc    180

caaggactca gggacaacag tcagttctgc ttgcaaagga tccaccaggg tctgattttt    240

tatgagaagc tgctaggatc ggatattttc acaggggagc cttctctgct ccctgatagc    300

cctgtggcgc agcttcatgc ctccctactg ggcctcagcc aactcctgca gcctgagggt    360

caccactggg agactcagca gattccaagc ctcagtccca gccagccatg gcagcgtctc    420

cttctccgct tcaaaatcct tcgcagcctc caggcctttg tggctgtagc cgcccgggtc    480

tttgcccatg gagcagcaac cctgagtccc                                     510
```

<210> SEQ ID NO 10
<211> LENGTH: 169
<212> TYPE: PRT
<213> ORGANISM: Homo sapiens
<220> FEATURE:
<221> NAME/KEY: misc_feature
<222> LOCATION: (1)..(169)
<223> OTHER INFORMATION: Amino acid sequence of IL-36-gamma (Precursor)

<400> SEQUENCE: 10

```
Met Arg Gly Thr Pro Gly Asp Ala Asp Gly Gly Gly Arg Ala Val Tyr
1               5                   10                  15

Gln Ser Met Cys Lys Pro Ile Thr Gly Thr Ile Asn Asp Leu Asn Gln
            20                  25                  30

Gln Val Trp Thr Leu Gln Gly Gln Asn Leu Val Ala Val Pro Arg Ser
        35                  40                  45

Asp Ser Val Thr Pro Val Thr Val Ala Val Ile Thr Cys Lys Tyr Pro
    50                  55                  60

Glu Ala Leu Glu Gln Gly Arg Gly Asp Pro Ile Tyr Leu Gly Ile Gln
65                  70                  75                  80

Asn Pro Glu Met Cys Leu Tyr Cys Glu Lys Val Gly Glu Gln Pro Thr
                85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
        115                 120                 125

Thr Leu Glu Ser Val Ala Phe Pro Asp Trp Phe Ile Ala Ser Ser Lys
    130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```

<210> SEQ ID NO 11
<211> LENGTH: 507
<212> TYPE: DNA
<213> ORGANISM: Homo sapiens
<220> FEATURE:

<221> NAME/KEY: misc_feature
<222> LOCATION: (1)..(507)
<223> OTHER INFORMATION: Nucleotide sequence of IL-36-gamma (Precursor)

<400> SEQUENCE: 11
atgagaggca ctccaggaga cgctgatggt ggaggaaggg ccgtctatca atcaatgtgt 60
aaacctatta ctgggactat taatgatttg aatcagcaag tgtggaccct tcagggtcag 120
aaccttgtgg cagttccacg aagtgacagt gtgaccccag tcactgttgc tgttatcaca 180
tgcaagtatc cagaggctct tgagcaaggc agaggggatc ccatttattt gggaatccag 240
aatccagaaa tgtgtttgta ttgtgagaag gttggagaac agcccacatt gcagctaaaa 300
gagcagaaga tcatggatct gtatggccaa cccgagcccg tgaaaccctt cctttctac 360 cgtgccaaga ctggtaggac ctccaccctt gagtctgtgg ccttcccgga ctggttcatt 420
gcctcctcca agagagacca gcccatcatt ctgacttcag aacttgggaa gtcatacaac 480
actgcctttg aattaaatat aaatgac 507

<210> SEQ ID NO 12
<211> LENGTH: 152
<212> TYPE: PRT
<213> ORGANISM: Homo sapiens
<220> FEATURE:
<221> NAME/KEY: misc_feature
<222> LOCATION: (1)..(152)
<223> OTHER INFORMATION: Amino acid sequence of IL-36-gamma (Mature)

<400> SEQUENCE: 12

Ser Met Cys Lys Pro Ile Thr Gly Thr Ile Asn Asp Leu Asn Gln Gln
1 5 10 15

Val Trp Thr Leu Gln Gly Gln Asn Leu Val Ala Val Pro Arg Ser Asp
20 25 30

Ser Val Thr Pro Val Thr Val Ala Val Ile Thr Cys Lys Tyr Pro Glu
35 40 45

Ala Leu Glu Gln Gly Arg Gly Asp Pro Ile Tyr Leu Gly Ile Gln Asn
50 55 60

Pro Glu Met Cys Leu Tyr Cys Glu Lys Val Gly Glu Gln Pro Thr Leu
65 70 75 80

Gln Leu Lys Glu Gln Lys Ile Met Asp Leu Tyr Gly Gln Pro Glu Pro
85 90 95

Val Lys Pro Phe Leu Phe Tyr Arg Ala Lys Thr Gly Arg Thr Ser Thr
100 105 110

Leu Glu Ser Val Ala Phe Pro Asp Trp Phe Ile Ala Ser Ser Lys Arg
115 120 125

Asp Gln Pro Ile Ile Leu Thr Ser Glu Leu Gly Lys Ser Tyr Asn Thr
130 135 140

Ala Phe Glu Leu Asn Ile Asn Asp
145 150

<210> SEQ ID NO 13
<211> LENGTH: 456
<212> TYPE: DNA
<213> ORGANISM: Homo sapiens
<220> FEATURE:
<221> NAME/KEY: misc_feature
<222> LOCATION: (1)..(456)
<223> OTHER INFORMATION: Nucleotide sequence of IL-36-gamma (Mature)
(CCDS2108.1, nt 52-507)

<400> SEQUENCE: 13

-continued

```
tcaatgtgta aacctattac tgggactatt aatgatttga atcagcaagt gtggaccctt      60

cagggtcaga accttgtggc agttccacga agtgacagtg tgaccccagt cactgttgct     120

gttatcacat gcaagtatcc agaggctctt gagcaaggca gaggggatcc catttatttg     180

ggaatccaga atccagaaat gtgtttgtat tgtgagaagg ttggagaaca gcccacattg     240

cagctaaaag agcagaagat catggatctg tatggccaac ccgagcccgt gaaacccttc     300

cttttctacc gtgccaagac tggtaggacc tccacccttg agtctgtggc cttcccggac     360

tggttcattg cctcctccaa gagagaccag cccatcattc tgacttcaga acttgggaag     420

tcatacaaca ctgcctttga attaaatata aatgac                               456
```

```
<210> SEQ ID NO 14
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: Amino acid sequence of IgKV4 signal peptide

<400> SEQUENCE: 14

Met Val Leu Gln Thr Gln Val Phe Ile Ser Leu Leu Leu Trp Ile Ser
1               5                   10                  15

Gly Ala Tyr Gly
            20


<210> SEQ ID NO 15
<211> LENGTH: 60
<212> TYPE: DNA
<213> ORGANISM: Homo sapiens
<220> FEATURE:
<221> NAME/KEY: misc_feature
<222> LOCATION: (1)..(60)
<223> OTHER INFORMATION: Nucleotide sequence of IgKV4 signal peptide
      (IMGT Z00023, nt 1-60)

<400> SEQUENCE: 15

atggtgttgc agacccaggt cttcatttct ctgttgctct ggatctctgg tgcctacggg      60


<210> SEQ ID NO 16
<211> LENGTH: 172
<212> TYPE: PRT
<213> ORGANISM: Artificial Sequence
<220> FEATURE:
<223> OTHER INFORMATION: Synthetic: hIGKV4-hIL-36g construct (protein)

<400> SEQUENCE: 16

Met Val Leu Gln Thr Gln Val Phe Ile Ser Leu Leu Leu Trp Ile Ser
1               5                   10                  15

Gly Ala Tyr Gly Ser Met Cys Lys Pro Ile Thr Gly Thr Ile Asn Asp
            20                  25                  30

Leu Asn Gln Gln Val Trp Thr Leu Gln Gly Gln Asn Leu Val Ala Val
        35                  40                  45

Pro Arg Ser Asp Ser Val Thr Pro Val Thr Val Ala Val Ile Thr Cys
    50                  55                  60

Lys Tyr Pro Glu Ala Leu Glu Gln Gly Arg Gly Asp Pro Ile Tyr Leu
65                  70                  75                  80

Gly Ile Gln Asn Pro Glu Met Cys Leu Tyr Cys Glu Lys Val Gly Glu
                85                  90                  95

Gln Pro Thr Leu Gln Leu Lys Glu Gln Lys Ile Met Asp Leu Tyr Gly
            100                 105                 110
```

```
Gln Pro Glu Pro Val Lys Pro Phe Leu Phe Tyr Arg Ala Lys Thr Gly
        115                 120                 125

Arg Thr Ser Thr Leu Glu Ser Val Ala Phe Pro Asp Trp Phe Ile Ala
    130                 135                 140

Ser Ser Lys Arg Asp Gln Pro Ile Ile Leu Thr Ser Glu Leu Gly Lys
145                 150                 155                 160

Ser Tyr Asn Thr Ala Phe Glu Leu Asn Ile Asn Asp
                165                 170


<210> SEQ ID NO 17
<211> LENGTH: 516
<212> TYPE: DNA
<213> ORGANISM: Artificial Sequence
<220> FEATURE:
<223> OTHER INFORMATION: Synthetic: hIGKV4-hIL-36g construct (RNA)

<400> SEQUENCE: 17

atggtgttgc agacccaggt cttcatttct ctgttgctct ggatctctgg tgcctacggg     60

tcaatgtgta aacctattac tgggactatt aatgatttga atcagcaagt gtggaccctt    120

cagggtcaga accttgtggc agttccacga agtgacagtg tgaccccagt cactgttgct    180

gttatcacat gcaagtatcc agaggctctt gagcaaggca gaggggatcc catttatttg    240

ggaatccaga atccagaaat gtgtttgtat tgtgagaagg ttggagaaca gcccacattg    300

cagctaaaag agcagaagat catggatctg tatggccaac ccgagcccgt gaaacccttc    360

cttttctacc gtgccaagac tggtaggacc tccacccttg agtctgtggc cttcccggac    420

tggttcattg cctcctccaa gagagaccag cccatcattc tgacttcaga acttgggaag    480

tcatacaaca ctgcctttga attaaatata aatgac                              516


<210> SEQ ID NO 18
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 18

atgtgtcacc agcagttggt catctcttgg ttttccctgg tatttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaga ccctgaccat ccaagtcaaa    240

gagtttggag atgctggcca gtacacctgt cacaaaggag gcgaggttct aagccattcg    300

ctcctgctgc ttcacaagaa ggaagatgga atttggtcca ctgatatttt aaaggaccag    360

aaagaaccca agaataagac ctttctaaga tgcgaggcca agaattattc tggacgtttc    420

acctgctggt ggctgacgac aatcagtact gatttgacat tcagtgtcaa gagcagcaga    480

ggctcttctg acccgcaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gagaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840
```

agcaagagag agaagaaaga tagagtcttc acggacaaga cctcagccac ggtcatctgc 900
cgcaagaatg ccagcattag cgtgcgggcc caggaccgct actatagctc atcttggagc 960
gaatgggcat ctgtgccctg cagtggcgga ggtggcggag ggagcagagc tgtgcctggc 1020
ggcagcagcc ctgcctggac tcagtgccag cagctttcac agaagctctg cacactggcc 1080
tggagtgcac atccactagt gggacacatg gatctaagag aagagggaga tgaagagact 1140
acaaatgatg ttccccatat ccagtgtgga gatggctgtg acccgcaagg actcagggac 1200
aacagtcagt tctgcttgca aaggatccac cagggtctga tcttttatga gaagctgcta 1260
ggatcggata ttttcacagg ggagccttct ctgctccctg atagccctgt gggccagctt 1320
catgcctccc tactgggcct cagccaactc ctgcagcctg agggtcacca ctgggagact 1380
cagcagattc caagcctcag tcccagccag ccatggcagc gtctccttct ccgcttcaag 1440
atccttcgca gcctccaggc ctttgtggct gtagccgccc gggtctttgc ccatggagca 1500
gcaaccctga gtccc 1515

<210> SEQ ID NO 19
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 19
atgtgtcacc agcagttggt catctcttgg ttttccctgg tatttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaga ccctgaccat ccaagtcaaa 240
gagtttggag atgctggcca gtacacctgt cacaaaggag gcgaggttct aagccattcg 300
ctcctgctgc ttcacaagaa ggaagatgga atttggtcca ctgatatttt aaaggaccag 360
aaagaaccca agaataagac ctttctaaga tgcgaggcca agaattattc tggacgtttc 420
acctgctggt ggctgacgac aatcagtact gatttgacat tcagtgtcaa gagcagcaga 480
ggctcttctg acccccaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gagaactaca ccagcagctt cttcatcagg gacatcatca aacctgaccc acccaagaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag agaagaaaga tagagtcttc acggacaaga cctcagccac ggtcatctgc 900
cgcaagaatg ccagcattag cgtgcgggcc caggaccgct actatagctc atcttggagc 960
gaatgggcat ctgtgccctg cagtggcgga gggggcggag ggagcagagc tgtgcctggg 1020
ggcagcagcc ctgcctggac tcagtgccag cagctttcac agaagctctg cacactggcc 1080
tggagtgcac atccactagt gggacacatg gatctaagag aagagggaga tgaagagact 1140
acaaatgatg ttccccatat ccagtgtgga gatggctgtg acccccaagg actcagggac 1200
aacagtcagt tctgcttgca aaggatccac cagggtctga tcttttatga gaagctgcta 1260
ggatcggata ttttcacagg ggagccttct ctgctccctg atagccctgt gggccagctt 1320
catgcctccc tactgggcct cagccaactc ctgcagcctg agggtcacca ctgggagact 1380
cagcagattc caagcctcag tcccagccag ccatggcagc gtctccttct ccgcttcaag 1440
atccttcgca gcctccaggc ctttgtggct gtagccgccc gggtctttgc ccatggagca 1500
gcaaccctga gtccc 1515

<210> SEQ ID NO 20
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 20
atgtgtcacc agcagttggt catctcttgg ttttccctgg tttttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaaa ccctgaccat ccaagtcaaa 240
gagtttggag atgctggcca gtacacctgt cacaaaggag gcgaggttct aagccattcg 300
ctcctgctgc ttcacaaaaa ggaagatgga atttggtcca ctgatatttt aaaggaccag 360
aaagaaccca aaaataagac ctttctaaga tgcgaggcca agaattattc tggacgtttc 420
acctgctggt ggctgacgac aatcagtact gatttgacat tcagtgtcaa aagcagcaga 480
ggctcttctg acccccaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gaaaactaca ccagcagctt cttcatcagg gacatcatca aacctgaccc acccaagaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag aaaagaaaga tagagtcttc acggacaaga cctcagccac ggtcatctgc 900
cgcaaaaatg ccagcattag cgtgcgggcc caggaccgct actatagctc atcttggagc 960
gaatgggcat ctgtgccctg cagtggcgga gggggcggag ggagcagagc tgtgcctggg 1020
ggcagcagcc ctgcctggac tcagtgccag cagctttcac agaagctctg cacactggcc 1080
tggagtgcac atccactagt gggacacatg gatctaagag aagagggaga tgaagagact 1140
acaaatgatg ttccccatat ccagtgtgga gatggctgtg acccccaagg actcagggac 1200
aacagtcagt tctgcttgca aaggatccac cagggtctga ttttttatga gaagctgcta 1260
ggatcggata ttttcacagg ggagccttct ctgctccctg atagccctgt gggccagctt 1320
catgcctccc tactgggcct cagccaactc ctgcagcctg agggtcacca ctgggagact 1380
cagcagattc caagcctcag tcccagccag ccatggcagc gtctccttct ccgcttcaaa 1440
atccttcgca gcctccaggc ctttgtggct gtagccgccc gggtctttgc ccatggagca 1500
gcaaccctga gtccc 1515

<210> SEQ ID NO 21
<211> LENGTH: 183
<212> TYPE: PRT
<213> ORGANISM: Homo sapiens
<220> FEATURE:
<221> NAME/KEY: misc_feature
<222> LOCATION: (1)..(183)
<223> OTHER INFORMATION: Tumor necrosis factor ligand superfamily member
      4 isoform 1

<400> SEQUENCE: 21

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 22
<211> LENGTH: 85
<212> TYPE: RNA
<213> ORGANISM: Artificial Sequence
<220> FEATURE:
<223> OTHER INFORMATION: Synthetic: miR-122

<400> SEQUENCE: 22
ccuuagcaga gcuguggagu gugacaaugg uguuuguguc uaaacuauca aacgccauua 60
ucacacuaaa uagcuacugc uaggc 85

<210> SEQ ID NO 23
<211> LENGTH: 22
<212> TYPE: RNA
<213> ORGANISM: Artificial Sequence
<220> FEATURE:
<223> OTHER INFORMATION: Synthetic: miR-122-3p

<400> SEQUENCE: 23
aacgccauua ucacacuaaa ua 22

<210> SEQ ID NO 24
<211> LENGTH: 22
<212> TYPE: RNA
<213> ORGANISM: Artificial Sequence
<220> FEATURE:
<223> OTHER INFORMATION: Synthetic: miR-122-3p binding site

<400> SEQUENCE: 24
uauuuagugu gauaauggcg uu 22

<210> SEQ ID NO 25

<211> LENGTH: 22
<212> TYPE: RNA
<213> ORGANISM: Artificial Sequence
<220> FEATURE:
<223> OTHER INFORMATION: Synthetic: miR-122-5p

<400> SEQUENCE: 25
uggaguguga caaugguguu ug 22

<210> SEQ ID NO 26
<211> LENGTH: 22
<212> TYPE: RNA
<213> ORGANISM: Artificial Sequence
<220> FEATURE:
<223> OTHER INFORMATION: Synthetic: miR-122-5p binding site

<400> SEQUENCE: 26
caaacaccau ugucacacuc ca 22

<210> SEQ ID NO 27
<211> LENGTH: 47
<212> TYPE: RNA
<213> ORGANISM: Artificial Sequence
<220> FEATURE:
<223> OTHER INFORMATION: Synthetic: 5UTR-001

<400> SEQUENCE: 27
gggaaauaag agagaaaaga agaguaagaa gaaauauaag agccacc 47

<210> SEQ ID NO 28
<211> LENGTH: 47
<212> TYPE: RNA
<213> ORGANISM: Artificial Sequence
<220> FEATURE:
<223> OTHER INFORMATION: Synthetic: 5UTR-002

<400> SEQUENCE: 28
gggagaucag agagaaaaga agaguaagaa gaaauauaag agccacc 47

<210> SEQ ID NO 29
<211> LENGTH: 145
<212> TYPE: RNA
<213> ORGANISM: Artificial Sequence
<220> FEATURE:
<223> OTHER INFORMATION: Synthetic: 5UTR-003

<400> SEQUENCE: 29
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 30
<211> LENGTH: 42
<212> TYPE: RNA
<213> ORGANISM: Artificial Sequence
<220> FEATURE:
<223> OTHER INFORMATION: Synthetic: 5UTR-004

<400> SEQUENCE: 30
gggagacaag cuuggcauuc cgguacuguu gguaaagcca cc 42

<210> SEQ ID NO 31
<211> LENGTH: 47
<212> TYPE: RNA
<213> ORGANISM: Artificial Sequence
<220> FEATURE:
<223> OTHER INFORMATION: Synthetic: 5UTR-005

<400> SEQUENCE: 31
gggagaucag agagaaaaga agaguaagaa gaaauauaag agccacc 47

<210> SEQ ID NO 32
<211> LENGTH: 145
<212> TYPE: RNA
<213> ORGANISM: Artificial Sequence
<220> FEATURE:
<223> OTHER INFORMATION: Synthetic: 5UTR-006

<400> SEQUENCE: 32
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 33
<211> LENGTH: 42
<212> TYPE: RNA
<213> ORGANISM: Artificial Sequence
<220> FEATURE:
<223> OTHER INFORMATION: Synthetic: 5UTR-007

<400> SEQUENCE: 33
gggagacaag cuuggcauuc cgguacuguu gguaaagcca cc 42

<210> SEQ ID NO 34
<211> LENGTH: 47
<212> TYPE: RNA
<213> ORGANISM: Artificial Sequence
<220> FEATURE:
<223> OTHER INFORMATION: Synthetic: 5UTR-008

<400> SEQUENCE: 34
gggaauuaac agagaaaaga agaguaagaa gaaauauaag agccacc 47

<210> SEQ ID NO 35
<211> LENGTH: 47
<212> TYPE: RNA
<213> ORGANISM: Artificial Sequence
<220> FEATURE:
<223> OTHER INFORMATION: Synthetic: 5UTR-009

<400> SEQUENCE: 35
gggaaauuag acagaaaaga agaguaagaa gaaauauaag agccacc 47

<210> SEQ ID NO 36
<211> LENGTH: 47
<212> TYPE: RNA
<213> ORGANISM: Artificial Sequence
<220> FEATURE:
<223> OTHER INFORMATION: Synthetic: 5UTR-010

<400> SEQUENCE: 36
gggaaauaag agaguaaaga acaguaagaa gaaauauaag agccacc 47

<210> SEQ ID NO 37
<211> LENGTH: 47
<212> TYPE: RNA
<213> ORGANISM: Artificial Sequence
<220> FEATURE:
<223> OTHER INFORMATION: Synthetic: 5UTR-011

<400> SEQUENCE: 37
gggaaaaaag agagaaaaga agacuaagaa gaaauauaag agccacc 47

<210> SEQ ID NO 38
<211> LENGTH: 47
<212> TYPE: RNA
<213> ORGANISM: Artificial Sequence
<220> FEATURE:
<223> OTHER INFORMATION: Synthetic: 5UTR-012

<400> SEQUENCE: 38
gggaaauaag agagaaaaga agaguaagaa gauauauaag agccacc 47

<210> SEQ ID NO 39
<211> LENGTH: 47
<212> TYPE: RNA
<213> ORGANISM: Artificial Sequence
<220> FEATURE:
<223> OTHER INFORMATION: Synthetic: 5UTR-013

<400> SEQUENCE: 39
gggaaauaag agacaaaaca agaguaagaa gaaauauaag agccacc 47

<210> SEQ ID NO 40
<211> LENGTH: 47
<212> TYPE: RNA
<213> ORGANISM: Artificial Sequence
<220> FEATURE:
<223> OTHER INFORMATION: Synthetic: 5UTR-014

<400> SEQUENCE: 40
gggaaauuag agaguaaaga acaguaagua gaauuaaaag agccacc 47

<210> SEQ ID NO 41
<211> LENGTH: 47
<212> TYPE: RNA
<213> ORGANISM: Artificial Sequence
<220> FEATURE:
<223> OTHER INFORMATION: Synthetic: 5UTR-015

<400> SEQUENCE: 41
gggaaauaag agagaauaga agaguaagaa gaaauauaag agccacc 47

<210> SEQ ID NO 42
<211> LENGTH: 47
<212> TYPE: RNA
<213> ORGANISM: Artificial Sequence
<220> FEATURE:
<223> OTHER INFORMATION: Synthetic: 5UTR-016

<400> SEQUENCE: 42
gggaaauaag agagaaaaga agaguaagaa gaaaauuaag agccacc 47

<210> SEQ ID NO 43
<211> LENGTH: 47
<212> TYPE: RNA
<213> ORGANISM: Artificial Sequence
<220> FEATURE:
<223> OTHER INFORMATION: Synthetic: 5UTR-017

<400> SEQUENCE: 43
gggaaauaag agagaaaaga agaguaagaa gaaauuuaag agccacc 47

<210> SEQ ID NO 44
<211> LENGTH: 47

<212> TYPE: RNA
<213> ORGANISM: Artificial Sequence
<220> FEATURE:
<223> OTHER INFORMATION: Synthetic: 5UTR-018

<400> SEQUENCE: 44
gggaaauaag agagaaaaga agaguaagaa gaaauauaag agccacc 47

<210> SEQ ID NO 45
<211> LENGTH: 371
<212> TYPE: RNA
<213> ORGANISM: Artificial Sequence
<220> FEATURE:
<223> OTHER INFORMATION: Synthetic: 3UTR-001

<400> SEQUENCE: 45
gcgccugccc accugccacc gacugcugga acccagccag ugggagggcc uggcccacca 60
gaguccugcu cccucacucc ucgccccgcc cccugucccca gagucccacc ugggggcucu 120
cuccacccuu cucagaguuc caguuucaac cagaguucca accaaugggc uccauccucu 180
ggauucuggc caaugaaaua ucucccuggc aggguccucu ucuuuuccca gagcuccacc 240
ccaaccagga gcucuaguua auggagagcu cccagcacac ucggagcuug ugcuuugucu 300
ccacgcaaag cgauaaauaa aagcauuggu ggccuuuggu cuuugaauaa agccugagua 360
ggaagucuag a 371

<210> SEQ ID NO 46
<211> LENGTH: 568
<212> TYPE: RNA
<213> ORGANISM: Artificial Sequence
<220> FEATURE:
<223> OTHER INFORMATION: Synthetic: 3UTR-002

<400> SEQUENCE: 46
gccccugccg cucccacccc cacccaucug ggccccgggu ucaagagaga gcggggucug 60
aucucgugua gccauauaga guuugcuucu gagugucugc uuuguuuagu agaggugggc 120
aggaggagcu gaggggcugg ggcuggggug uugaaguugg cuuugcaugc ccagcgaugc 180
gccucccugu gggaugucau cacccuggga accgggagug gcccuuggcu cacuguguuc 240
ugcaugguuu ggaucugaau uaauuguccu uucuucuaaa ucccaaccga acuucuucca 300
accuccaaac uggcuguaac cccaaaucca agccauuaac uacaccugac aguagcaauu 360
gucugauuaa ucacuggccc cuugaagaca gcagaauguc ccuuugcaau gaggaggaga 420
ucugggcugg gcgggccagc uggggaagca uuugacuauc uggaacuugu gugugccucc 480
ucagguaugg cagugacuca ccugguuuua auaaaacaac cugcaacauc ucauggucuu 540
ugaauaaagc cugaguagga agucuaga 568

<210> SEQ ID NO 47
<211> LENGTH: 289
<212> TYPE: RNA
<213> ORGANISM: Artificial Sequence
<220> FEATURE:
<223> OTHER INFORMATION: Synthetic: 3UTR-003

<400> SEQUENCE: 47
acacacucca ccuccagcac gcgacuucuc aggacgacga aucuucucaa uggggggcg 60 gcugagcucc agccaccccg cagucacuuu cuuuguaaca acuuccguug cugccaucgu 120
aaacugacac aguguuuaua acguguacau acauuaacuu auuaccucau uuuguuauuu 180
uucgaaacaa agcccugugg aagaaaaugg aaaacuugaa gaagcauuaa agucauucug 240
uuaagcugcg uaaaaugguc uugaauaaag ccugaguagg aagucuaga 289

<210> SEQ ID NO 48
<211> LENGTH: 379
<212> TYPE: RNA
<213> ORGANISM: Artificial Sequence
<220> FEATURE:
<223> OTHER INFORMATION: Synthetic: 3UTR-004

<400> SEQUENCE: 48
caucacauuu aaaagcaucu cagccuacca ugagaauaag agaaagaaaa ugaagaucaa 60
aagcuuauuc aucuguuuuu cuuuuucguu gguguaaagc caacacccug ucuaaaaaac 120
auaaauuucu uuaaucauuu ugccucuuuu cucugugcuu caauuaauaa aaaauggaaa 180
gaaucuaaua gagugguaca gcacuguuau uuuucaaaga uguguugcua uccugaaaau 240
ucuguagguu cuguggaagu uccaguguuc ucucuuauuc cacuucggua gaggauuucu 300
aguuucuugu gggcuaauua aauaaaucau uaauacucuu cuaauggucu uugaauaaag 360
ccugaguagg aagucuaga 379

<210> SEQ ID NO 49
<211> LENGTH: 118
<212> TYPE: RNA
<213> ORGANISM: Artificial Sequence
<220> FEATURE:
<223> OTHER INFORMATION: Synthetic: 3UTR-005

<400> SEQUENCE: 49
gcugccuucu gcggggcuug ccuucuggcc augcccuucu ucucucccuu gcaccuguac 60
cucuuggucu uugaauaaag ccugaguagg aaggcggccg cucgagcaug caucuaga 118

<210> SEQ ID NO 50
<211> LENGTH: 908
<212> TYPE: RNA
<213> ORGANISM: Artificial Sequence
<220> FEATURE:
<223> OTHER INFORMATION: Synthetic: 3UTR-006

<400> SEQUENCE: 50
gccaagcccu ccccauccca uguauuuauc ucuauuuaau auuuaugucu auuuaagccu 60
cauauuuaaa gacagggaag agcagaacgg agccccaggc cucugugucc uucccugcau 120
uucugaguuu cauucuccug ccuguagcag ugagaaaaag cuccuguccu cccaucccca 180
ggacugggag guagauaggu aaauaccaag uauuuauuac uaugacugcu ccccagcccu 240
ggcucugcaa ugggcacugg gaugagccgc ugugagcccc ugguccugag gguccccacc 300
ugggacccuu gagaguauca ggucucccac gugggagaca agaaaucccu guuuaauauu 360
uaaacagcag uguuccccau cugggguccuu gcaccccuca cucuggccuc agccgacugc 420
acagcggccc cugcaucccc uuggcuguga ggccccugga caagcagagg uggccagagc 480
ugggaggcau ggcccugggg ucccacgaau uugcugggga aucucguuuu ucuucuuaag 540
acuuuuggga caugguuuga cucccgaaca ucaccgacgc gucuccuguu uuucugggug 600
gccucgggac accugcccug cccccacgag ggucaggacu gugacucuuu uuagggccag 660
gcaggugccu ggacauuugc cuugcuggac ggggacuggg gaugugggag ggagcagaca 720
ggaggaauca ugucaggccu gugugugaaa ggaagcucca cugucacccu ccaccucuuc 780 acccccacu caccaguguc cccuccacug ucacauugua acugaacuuc aggauaauaa 840
aguguuugcc uccauggucu uugaauaaag ccugaguagg aaggcggccg cucgagcaug 900
caucuaga 908

<210> SEQ ID NO 51
<211> LENGTH: 835
<212> TYPE: RNA
<213> ORGANISM: Artificial Sequence
<220> FEATURE:
<223> OTHER INFORMATION: Synthetic: 3UTR-007

<400> SEQUENCE: 51
acucaaucua aauuaaaaaa gaaagaaauu ugaaaaaacu uucucuuugc cauuucuucu 60
ucuucuuuuu uaacugaaag cugaauccuu ccauuucuuc ugcacaucua cuugcuuaaa 120
uugugggcaa aagagaaaaa gaaggauuga ucagagcauu gugcaauaca guuucauuaa 180
cuccuucccc cgcuccccca aaaauuugaa uuuuuuuuuc aacacucuua caccuguuau 240
ggaaaauguc aaccuuugua agaaaaccaa aauaaaaauu gaaaaauaaa aaccauaaac 300
auuugcacca cuuguggcuu uugaauaucu uccacagagg gaaguuuaaa acccaaacuu 360
ccaaagguuu aaacuaccuc aaaacacuuu cccaugagug ugauccacau uguuaggugc 420
ugaccuagac agagaugaac ugagguccuu guuuuguuuu guucauaaua caaaggugcu 480
aauuaauagu auuucagaua cuugaagaau guugauggug cuagaagaau uugagaagaa 540
auacuccugu auugaguugu aucgugugu guauuuuuua aaaaauuuga uuuagcauuc 600
auauuuucca ucuuauuccc aauuaaaagu augcagauua uuugcccaaa ucuucuucag 660
auucagcauu uguucuuugc cagucucauu uucaucuucu uccaugguuc cacagaagcu 720
uuguuucuug ggcaagcaga aaaauuaaau uguaccuauu uuguauaugu gagauguuua 780
aauaaauugu gaaaaaaaug aaauaaagca uguuugguuu uccaaaagaa cauau 835

<210> SEQ ID NO 52
<211> LENGTH: 297
<212> TYPE: RNA
<213> ORGANISM: Artificial Sequence
<220> FEATURE:
<223> OTHER INFORMATION: Synthetic: 3UTR-008

<400> SEQUENCE: 52
cgccgccgcc cgggccccgc agucgagggu cgugagccca ccccguccau ggugcuaagc 60
gggcccgggu cccacacggc cagcaccgcu gcucacucgg acgacgcccu gggccugcac 120
cucuccagcu ccucccacgg gguccccgua gccccggccc ccgcccagcc ccaggucucc 180
ccaggcccuc cgcaggcugc ccggccuccc ucccccugca gccaucccaa ggcuccugac 240
cuaccuggcc ccugagcucu ggagcaagcc cugacccaau aaaggcuuug aacccau 297

<210> SEQ ID NO 53
<211> LENGTH: 602
<212> TYPE: RNA
<213> ORGANISM: Artificial Sequence
<220> FEATURE:
<223> OTHER INFORMATION: Synthetic: 3UTR-009

<400> SEQUENCE: 53
ggggcuagag cccucuccgc acagcgugga gacggggcaa ggaggggggu uauuaggauu 60
ggugguuuug uuuugcuuug uuuaaagccg ugggaaaaug gcacaacuuu accucugugg 120
gagaugcaac acugagagcc aaggggugg aguugggaua auuuuuauau aaaagaaguu 180

-continued uuuccacuuu gaauugcuaa aaguggcauu uuuccuaugu gcagucacuc cucucauuuc 240
uaaaauaggg acguggccag gcacggugge ucaugccugu aaucccagca cuuugggagg 300
ccgaggcagg cggcucacga ggucaggaga ucgagacuau ccuggcuaac acgguaaaac 360
ccugucucua cuaaaaguac aaaaaauuag cugggcgugg uggugggcac cuguaguccc 420
agcuacucgg gaggcugagg caggagaaag gcaugaaucc aagaggcaga gcuugcagug 480
agcugagauc acgccauugc acuccagccu gggcaacagu guuaagacuc ugucucaaau 540
auaaauaaau aaauaaauaa auaaauaaau aaauaaaaau aaagcgagau guugcccuca 600
aa 602

<210> SEQ ID NO 54
<211> LENGTH: 785
<212> TYPE: RNA
<213> ORGANISM: Artificial Sequence
<220> FEATURE:
<223> OTHER INFORMATION: Synthetic: 3UTR-010

<400> SEQUENCE: 54
ggcccugccc cgucggacug cccccagaaa gccuccugcc cccugccagu gaaguccuuc 60
agugagcccc uccccagcca gcccuucccu ggccccgccg gauguauaaa uguaaaaaug 120
aaggaauuac auuuuauaug ugagcgagca agccggcaag cgagcacagu auuauuucuc 180
cauccccucc cugccugcuc cuuggcaccc ccaugcugcc uucagggaga caggcaggga 240
gggcuugggg cugcaccucc uacccuccca ccagaacgca ccccacuggg agagcuggug 300
gugcagccuu ccccucccug uauaagacac uuugccaagg cucuccccuc ucgccccauc 360
ccugcuugcc cgcucccaca gcuuccugag ggcuaauucu gggaagggag aguucuuugc 420
ugccccuguc uggaagacgu ggcucugggu gagguaggcg ggaaaggaug gaguguuuua 480
guucuugggg gaggccaccc caaaccccag ccccaacucc aggggcaccu augagauggc 540
caugcucaac ccccucccca gacaggcccu cccugucucc agggccccca ccgagguucc 600
cagggcugga gacuuccucu gguaaacauu ccuccagccu ccccucccu ggggacgcca 660 aggaggaggg ccacacccag gaagggaaag cgggcagccc cguuuugggg acgugaacgu 720
uuuaauaauu uuugcugaau uccuuuacaa cuaaauaaca cagauauugu uauaaauaaa 780
auugu 785

<210> SEQ ID NO 55
<211> LENGTH: 3001
<212> TYPE: RNA
<213> ORGANISM: Artificial Sequence
<220> FEATURE:
<223> OTHER INFORMATION: Synthetic: 3UTR-011

<400> SEQUENCE: 55
auauuaagga ucaagcuguu agcuaauaau gccaccucug caguuuuggg aacaggcaaa 60
uaaaguauca guauacaugg ugauguacau cuguagcaaa gcucuuggag aaaaugaaga 120
cugaagaaag caaagcaaaa acuguauaga gagauuuuuc aaaagcagua aucccucaau 180
uuuaaaaaag gauugaaaau ucuaaauguc uuucugugca uauuuuuugu guuaggaauc 240
aaaaguauuu uauaaaagga gaaagaacag ccucauuuua gauguagucc uguuggauuu 300
uuuaugccuc cucaguaacc agaaauguuu uaaaaaacua aguguuuagg auuucaagac 360
aacauuauac auggcucuga aauaucugac acaauguaaa cauugcaggc accugcauuu 420
uauguuuuuu uuuucaacaa augugacuaa uuugaaacuu uuaugaacuu cugagcuguc 480

-continued

```
cccuugcaau ucaaccgcag uuugaauuaa ucauaucaaa ucaguuuuaa uuuuuuaaau    540
uguacuucag agucuauauu ucaagggcac auuuucucac uacuauuuua auacauuaaa    600
ggacuaaaua aucuuucaga gaugcuggaa acaaaucauu ugcuuuauau guuucauuag    660
aauaccaaug aaacauacaa cuugaaaauu aguaauagua uuuuugaaga ucccauuucu    720
aauuggagau cucuuuaauu ucgaucaacu uauaaugugu aguacuauau uaagugcacu    780
ugaguggaau ucaacauuug acuaauaaaa ugaguucauc auguuggcaa gugauguggc    840
aauuaucucu ggugacaaaa gaguaaaauc aaauauuucu gccuguuaca aauaucaagg    900
aagaccugcu acuaugaaau agaugacauu aaucugucuu cacuguuuau aauacggaug    960
gauuuuuuuu caaaucagug uguguuuuga ggucuuaugu aauugaugac auuugagaga   1020
aaugguggcu uuuuuuagcu accucuuugu ucauuuaagc accaguaaag aucaugucuu   1080
uuuauagaag uguagauuuu cuuugugacu uugcuaucgu gccuaaagcu cuaaauauag   1140
gugaaugugu gaugaauacu cagauuauuu gucucucuau auaauuaguu ugguacuaag   1200
uuucucaaaa aauuauuaac acaugaaaga caaucucuaa accagaaaaa gaaguaguac   1260
aaauuuuguu acuguaaugc ucgcguuuag ugaguuuaaa acacacagua ucuuuugguu   1320
uuauaaucag uuucuauuuu gcugugccug agauuaagau cuguguaugu gugugugugu   1380
gugugugcgu uuguguguua aagcagaaaa gacuuuuuua aaaguuuuaa gugauaaaug   1440
caauuuguua auugaucuua gaucacuagu aaacucaggg cugaauuaua ccauguauau   1500
ucuauuagaa gaaaguaaac accaucuuua uuccugcccu uuuucuucuc ucaaaguagu   1560
uguaguuaua ucuagaaaga agcaauuuug auuucuugaa aagguaguuc cugcacucag   1620
uuuaaacuaa aaauaaucau acuuggauuu uauuuauuuu ugucauagua aaaauuuuaa   1680
uuuauauaua uuuuuauuua guauuaucuu auucuuugcu auuugccaau ccuuugucau   1740
caauuguguu aaaugaauug aaaauucaug cccuguucau uuuauuuuac uuuauugguu   1800
aggauauuua aaggauuuuu guauauauaa uuucuuaaau uaauauucca aaagguuagu   1860
ggacuuagau uauaaauuau ggcaaaaauc uaaaaacaac aaaaaugauu uuuauacauu   1920
cuauuucauu auuccucuuu uuccaauaag ucauacaauu gguagauaug acuuauuuua   1980
uuuuuguauu auucacuaua ucuuuaugau auuuaaguau aaauaauuaa aaaaauuuau   2040
uguaccuuau agucugucac caaaaaaaaa aaauuaucug uagguaguga aaugcuaaug   2100
uugauuuguc uuuaagggcu uguuaacuau ccuuuauuuu cucauuuguc uuaaauuagg   2160
aguuuguguu uaaauuacuc aucuaagcaa aaaauguaua uaaaucccau uacuggguau   2220
auacccaaag gauuauaaau caugcugcua uaaagacaca ugcacacgua uguuuauugc   2280
agcacuauuc acaauagcaa agacuuggaa ccaacccaaa uguccaucaa ugauagacuu   2340
gauuaagaaa augugcacau auacaccaug gaauacuaug cagccauaaa aaaggaugag   2400
uucauguccu uuguagggac auggauaaag cuggaaacca ucauucugag caaacuauug   2460
caaggacaga aaaccaaaca cugcauguuc ucacucauag gugggaauug aacaaugaga   2520
acacuuggac acaaggüggg gaacaccaca caccagggcc ugucaugggg ugggggggagu   2580
ggggagggau agcauuagga gauauaccua auguaaauga ugaguuaaug ggugcagcac   2640
accaacaugg cacauguaua cauauguagc aaaccugcac guugugcaca uguacccuag   2700
aacuuaaagu auaauuaaaa aaaaaaagaa aacagaagcu auuuauaaag aaguuauuug   2760
cugaaauaaa ugugaucuuu cccauuaaaa aaauaaagaa auuuuggggu aaaaaaacac   2820
```

aauauauugu auucuugaaa aauucuaaga gaguggaugu gaaguguucu caccacaaaa 2880
gugauaacua auugagguaa ugcacauauu aauuagaaag auuuugucau uccacaaugu 2940
auauauacuu aaaaauaugu uauacacaau aaauacauac auuaaaaaau aaguaaaugu 3000
a 3001

<210> SEQ ID NO 56
<211> LENGTH: 1037
<212> TYPE: RNA
<213> ORGANISM: Artificial Sequence
<220> FEATURE:
<223> OTHER INFORMATION: Synthetic: 3UTR-012

<400> SEQUENCE: 56
cccacccugc acgccggcac caaacccugu ccucccaccc cuccccacuc aucacuaaac 60
agaguaaaau gugaugcgaa uuuucccgac caaccugauu cgcuagauuu uuuuuaagga 120
aaagcuugga aagccaggac acaacgcugc ugccugcuuu gugcaggguc cuccggggcu 180
cagcccugag uuggcaucac cugcgcaggg cccucugggg cucagcccug agcuaguguc 240
accugcacag ggcccucuga ggcucagccc ugagcuggcg ucaccugugc agggcccucu 300
ggggcucagc ccugagcugg ccucaccugg guuccccacc ccgggcucuc cugcccugcc 360
cuccugcccg cccucccucc ugccugcgca gcuccuuccc uaggcaccuc ugugcugcau 420
cccaccagcc ugagcaagac gcccucucgg ggccugugcc gcacuagccu cccucuccuc 480
uguccccaua gcugguuuuu cccaccaauc cucaccuaac aguuacuuua caauuaaacu 540
caaagcaagc ucuucuccuc agcuuggggc agccauuggc cucugucucg uuuugggaaa 600
ccaaggucag gaggccguug cagacauaaa ucucggcgac ucggccccgu cuccugaggg 660
uccugcuggu gaccggccug gaccuuggcc cuacagcccu ggaggccgcu gcugaccagc 720
acugaccccg accucagaga guacucgcag ggcgcuggc ugcacucaag acccucgaga 780
uuaacggugc uaaccccguc ugcuccuccc ucccgcagag acuggggccu ggacuggaca 840
ugagagcccc uuggugccac agagggcugu gucuuacuag aaacaacgca aaccucuccu 900
uccucagaau agugaugugu ucgacguuuu aucaaaggcc cccuuucuau guucauguua 960
guuuugcucc uucuguguuu uuuucugaac cauauccaug uugcugacuu uuccaaauaa 1020
agguuuucac uccucuc 1037

<210> SEQ ID NO 57
<211> LENGTH: 577
<212> TYPE: RNA
<213> ORGANISM: Artificial Sequence
<220> FEATURE:
<223> OTHER INFORMATION: Synthetic: 3UTR-013

<400> SEQUENCE: 57
agaggccugc cuccagggcu ggacugaggc cugagcgcuc cugccgcaga gcuggccgcg 60
ccaaauaaug ucucugugag acucgagaac uuucauuuuu uuccaggcug guucggauuu 120
gggguggauu uugguuuugu uccccuccuc cacucucccc cacccccucc ccgcccuuuu 180
uuuuuuuuuu uuuuaaacug guauuuuauc uuugauucuc cuucagcccu caccccuggu 240
ucucaucuuu cuugaucaac aucuuuucuu gccucugucc ccuucucuca ucucuuagcu 300
ccccuccaac cuggggggca guggugugga gaagccacag gccugagauu ucaucugcuc 360
uccuuccugg agcccagagg agggcagcag aagggggugg ugucuccaac cccccagcac 420
ugaggaagaa cggggcucuu cucauuucac ccccucccuuu cuccccugcc cccaggacug 480
ggccacuucu gggugggggca gugggguccca gauuggcuca cacugagaau guaagaacua 540
caaacaaaau uucuauuaaa uuaaauuuug ugucucc 577

<210> SEQ ID NO 58
<211> LENGTH: 2212
<212> TYPE: RNA
<213> ORGANISM: Artificial Sequence
<220> FEATURE:
<223> OTHER INFORMATION: Synthetic: 3UTR-014

<400> SEQUENCE: 58 cuccccuccau cccaaccugg cuccccuccca cccaaccaac uuuccccccca acccggaaac 60 agacaagcaa cccaaacuga acccccucaa aagccaaaaa augggagaca auuucacaug 120
gacuuuggaa aauauuuuuu ucccuuugcau ucaucucuca aacuuaguuu uuaucuuuga 180
ccaaccgaac augaccaaaa accaaaagug cauucaaccu uaccaaaaaa aaaaaaaaaa 240
aaagaauaaa uaaauaacuu uuuaaaaaag gaagcuuggu ccacuugcuu gaagacccau 300 gcgggggguaa gucccuuucu gcccguuggg cuuaugaaac cccaaugcug cccuuucugc 360
uccuuucucc acacccccccu uggggccucc ccuccacucc uucccaaauc ugucucccca 420
gaagacacag gaaacaaugu auugucugcc cagcaaucaa aggcaaugcu caaacaccca 480
aguggccccc acccucagcc cgcuccugcc cgcccagcac ccccaggccc ugggggaccu 540
gggguucuca gacugccaaa gaagccuugc caucuggcgc ucccauggcu cuugcaacau 600
cuccccuucg uuuuugaggg ggucaugccg ggggagccac cagcccccuca cuggguucgg 660 aggagaguca ggaagggcca cgacaaagca gaaacaucgg auuuggggaa cgcgugucaa 720
ucccuugugc cgcagggcug ggcgggagag acuguucugu uccuugugua acuguguugc 780
ugaaagacua ccucguucuu gucuugaugu gucaccgggg caacugccug ggggcgggga 840
ugggggcagg guggaagcgg cuccccauuu uauaccaaag gugcuacauc uaugugaugg 900 guggggguggg gagggaauca cuggugcuau agaaauugag augccccccc aggccagcaa 960
auguuccuuu uuguucaaag ucuauuuuua uuccuugaua uuuuucuuuu uuuuuuuuuu 1020
uuuuugugga uggggacuug ugaauuuuuc uaaaggugcu auuuaacaug ggaggagagc 1080
gugugcggcu ccagcccagc ccgcugcuca cuuuccaccc ucucuccacc ugccucuggc 1140
uucucaggcc ucugcucucc gaccucucuc cucugaaacc cuccuccaca gcugcagccc 1200
auccucccgg cucccuccua gucuguccug cguccucugu ccccggguuu cagagacaac 1260
uucccaaagc acaaagcagu uuuucccccu aggggguggga ggaagcaaaa gacucuguac 1320
cuauuuugua uguguauaau aauuugagau guuuuuaauu auuuugauug cuggaauaaa 1380
gcauguggaa augacccaaa cauaauccgc aguggccucc uaauuuccuu cuuuggaguu 1440
gggggagggg uagacauggg gaaggggcuu uggggugaug ggcuugccuu ccauuccugc 1500
ccuuucccuc cccacuauuc ucuucuagau cccuccauaa ccccacuccc cuuucucuca 1560
cccuucuuau accgcaaacc uuucuacuuc cucuuucauu uucuauucuu gcaauuuccu 1620
ugcaccuuuu ccaaauccuc uucuccccug caauaccaua caggcaaucc acgugcacaa 1680
cacacacaca cacucuucac aucuggggguu guccaaaccu cauacccacu ccccuucaag 1740
cccauccacu cuccaccccc uggaugcccu gcacuuggug gcggugggau gcucauggau 1800
acugggaggg ugaggggagu ggaacccgug aggaggaccu gggggccucu ccuugaacug 1860
acaugaaggg ucaucuggcc ucugcucccu ucucacccac gcugaccucc ugccgaagga 1920
gcaacgcaac aggagagggg ucugcugagc cuggcgaggg ucugggaggg accaggagga 1980
aggcgugcuc ccugcucgcu guccuggccc ugggggagug agggagacag acaccuggga 2040
gagcuguggg gaaggcacuc gcaccgugcu cuugggaagg aaggagaccu ggcccugcuc 2100
accacggacu gggugccucg accuccugaa uccccagaac acaacccccc ugggcugggg 2160
uggucugggg aaccaucgug cccccgccuc ccgccuacuc cuuuuuaagc uu 2212

<210> SEQ ID NO 59
<211> LENGTH: 729
<212> TYPE: RNA
<213> ORGANISM: Artificial Sequence
<220> FEATURE:
<223> OTHER INFORMATION: Synthetic: 3UTR-015

<400> SEQUENCE: 59
uuggccaggc cugacccucu uggaccuuuc uucuuugccg acaaccacug cccagcagcc 60
ucugggaccu cgggguccca gggaacccag uccagccucc uggcuguuga cuucccauug 120
cucuuggagc caccaaucaa agagauucaa agagauuccu gcaggccaga ggcggaacac 180
accuuuaugg cuggggcucu ccgugguguu cuggacccag ccccuggaga caccauucac 240
uuuuacugcu uuguagugac ucgugcucuc caaccugucu uccugaaaaa ccaaggcccc 300
cuucccccac cucuuccaug ggugagacu ugagcagaac aggggcuucc ccaaguugcc 360
cagaaagacu gucuggguga gaagccaugg ccagagcuuc ucccaggcac agguguugca 420
ccagggacuu cugcuucaag uuuuggggua aagacaccug gaucagacuc caagggcugc 480
ccugagucug ggacuucugc cuccauggcu ggucaugaga gcaaaccgua guccccugga 540
gacagcgacu ccagagaacc ucuugggaga cagaagaggc aucugugcac agcucgaucu 600
ucuacuugcc uguggggagg ggagugacag guccacacac cacacugggu cacccugucc 660
uggaugccuc ugaagagagg gacagaccgu cagaaacugg agaguuucua uuaaagguca 720
uuuaaacca 729

<210> SEQ ID NO 60
<211> LENGTH: 847
<212> TYPE: RNA
<213> ORGANISM: Artificial Sequence
<220> FEATURE:
<223> OTHER INFORMATION: Synthetic: 3UTR-016

<400> SEQUENCE: 60
uccuccggga ccccagcccu caggauuccu gaugcuccaa ggcgacugau gggcgcugga 60
ugaaguggca cagucagcuu cccugggggc uggugucaug uugggcuccu ggggcggggg 120
cacggccugg cauuucacgc auugcugcca ccccaggucc accugucucc acuuucacag 180
ccuccaaguc uguggcucuu cccuucuguc cuccgagggg cuugccuucu cucgugucca 240
gugaggugcu cagugaucgg cuuaacuuag agaagcccgc cccucccccu ucuccgucug 300
ucccaagagg gucugcucug agccugcguu ccuagguggc ucggccucag cugccugggu 360
uguggccgcc cuagcauccu guaugcccac agcuacugga auccccgcug cugcuccggg 420
ccaagcuucu gguugauuaa ugagggcaug ggugguccc ucaagaccuu ccccuaccuu 480
uuguggaacc agugaugccu caaagacagu guccccucca cagcugggug ccaggggcag 540
gggauccuca guauagccgg ugaacccuga uaccaggagc cugggccucc cugaaccccu 600
ggcuuccagc caucucaucg ccagccuccu ccuggaccuc uuggccccca gccccuuccc 660
cacacagccc cagaaggguc ccagagcuga ccccacucca ggaccuaggc ccagccccuc 720
agccucaucu ggagccccug aagaccaguc ccacccaccu uucuggccuc aucugacacu 780
gcuccgcauc cugcugugug uccuguucca uguuccgguu ccauccaaau acacuuucug 840
gaacaaa 847

<210> SEQ ID NO 61
<211> LENGTH: 110
<212> TYPE: RNA
<213> ORGANISM: Artificial Sequence
<220> FEATURE:
<223> OTHER INFORMATION: Synthetic: 3UTR-017

<400> SEQUENCE: 61
gcuggagccu cgguggccau gcuucuugcc ccuugggccu ccccccagcc ccuccucccc 60
uuccugcacc cguacccccg uggucuuuga auaaagucug agugggcggc 110

<210> SEQ ID NO 62
<211> LENGTH: 116
<212> TYPE: RNA
<213> ORGANISM: Artificial Sequence
<220> FEATURE:
<223> OTHER INFORMATION: Synthetic: 3UTR-018

<400> SEQUENCE: 62
uaauaggcug gagccucggu ggccaugcuu cuugccccuu gggccucccc ccagccccuc 60
cuccccuucc ugcacccgua cccccguggu cuuugaauaa agucugagug ggcggc 116

<210> SEQ ID NO 63
<211> LENGTH: 138
<212> TYPE: RNA
<213> ORGANISM: Artificial Sequence
<220> FEATURE:
<223> OTHER INFORMATION: Synthetic: 3UTR-018 + miR-122-5p binding site

<400> SEQUENCE: 63
uaauaggcug gagccucggu ggccaugcuu cuugccccuu gggccucccc ccagccccuc 60
cuccccuucc ugcacccgua ccccccaaac accauuguca cacuccagug gucuuugaau 120
aaagucugag ugggcggc 138

<210> SEQ ID NO 64
<211> LENGTH: 138
<212> TYPE: RNA
<213> ORGANISM: Artificial Sequence
<220> FEATURE:
<223> OTHER INFORMATION: Synthetic: 3UTR-018 + miR-122-3p binding site

<400> SEQUENCE: 64
uaauaggcug gagccucggu ggccaugcuu cuugccccuu gggccucccc ccagccccuc 60
cuccccuucc ugcacccgua cccccuauuu agugugauaa uggcguugug gucuuugaau 120
aaagucugag ugggcggc 138

<210> SEQ ID NO 65
<211> LENGTH: 198
<212> TYPE: PRT
<213> ORGANISM: Mus musculus
<220> FEATURE:
<221> NAME/KEY: misc_feature
<222> LOCATION: (1)..(198)
<223> OTHER INFORMATION: TNFSF4

<400> SEQUENCE: 65

-continued

```
Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60

Gly Ala Val Thr Arg Cys Glu Asp Gly Gln Leu Phe Ile Ser Ser Tyr
65                  70                  75                  80

Lys Asn Glu Tyr Gln Thr Met Glu Val Gln Asn Asn Ser Val Val Ile
                85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
        115                 120                 125

Ile Pro Met Leu Asn Asp Gly Arg Arg Ile Val Phe Thr Val Val Ala
    130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro Leu
        195
```

<210> SEQ ID NO 66
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: TNFSF4, ORF

<400> SEQUENCE: 66

```
auggaaaggg uccaaccccu ggaagagaau gugggaaaug cagccaggcc aagauucgag      60

aggaacaagc uauugcuggu ggccucugua auucagggac uggggcugcu ccugugcuuc     120

accuacaucu gccugcacuu cucugcucuu cagguaucac aucgguaucc ucgaauucaa     180

aguaucaaag uacaauuuac cgaauauaag aaggagaaag guuucauccu cacuucccaa     240

aaggaggaug aaaucaugaa ggugcagaac aacucaguca ucaucaacug ugaugggguuu    300

uaucucaucu cccugaaggg cuacuucucc caggaaguca acauuagccu ucauuaccag     360

aaggaugagg agccccucuu ccaacugaag aaggucaggu cugucaacuc cuugauggug     420

gccucucuga cuuacaaaga caaagucuac uugaauguga ccacugacaa uaccucccug     480

gaugacuucc augugaaugg cggagaacug auucuuaucc aucaaaaucc ugugaauuc      540

ugugguccuu                                                            549
```

<210> SEQ ID NO 67
<211> LENGTH: 3484
<212> TYPE: RNA
<213> ORGANISM: Homo sapiens
<220> FEATURE:
<221> NAME/KEY: misc_feature
<222> LOCATION: (1)..(3484)

-continued

<223> OTHER INFORMATION: TNFSF4, transcript variant 1, mRNA

<400> SEQUENCE: 67

```
ggcccuggga ccuuugccua uuuucugauu gauaggcuuu guuuugucuu uaccuccuuc      60
uuucuggggga aaacuucagu uuuaucgcac guuccccuuu uccauaucuu caucuucccu     120
cuacccagau ugugaagaug gaaagggucc aaccccugga agagaaugug ggaaaugcag     180
ccaggccaag auucgagagg aacaagcuau ugcugguggc cucuguaauu cagggacugg     240
ggcugcuccu gugcuucacc uacaucugcc ugcacuucuc ugcucuucag guaucacauc     300
gguauccucg aauucaaagu aucaaaguac aauuuaccga auauaagaag gagaaagguu     360
ucauccucac uucccaaaag gaggaugaaa ucaugaaggu gcagaacaac ucagucauca     420
ucaacuguga uggguuuuau cucaucuccc ugaagggcua cuucucccag gaagucaaca     480
uuagccuuca uuaccagaag gaugaggagc cccucuucca acugaagaag gucaggucug     540
ucaacuccuu gaugguggcc ucucugacuu acaaagacaa agucuacuug aaugugacca     600
cugacaauac cucccuggau gacuuccaug ugaauggcgg agaacugauu cuuauccauc     660
aaaauccugg ugaauucugu guccuuugag gggcugaugg caauaucuaa aaccaggcac     720
cagcaugaac accaagcugg ggguggacag ggcauggauu cuucauugca agugaaggag     780
ccucccagcu cagccacgug ggaugugaca agaagcagau ccuggcccuc ccgcccccac     840
cccucaggga uauuuaaaac uuauuuuaua uaccaguuaa ucuuauuuau ccuuauauuu     900
ucuaaauugc cuagccguca caccccaaga uugccuugag ccuacuaggc accuuuguga     960
gaaagaaaaa auagaugccu cuucuucaag augcauuguu ucuauugguc aggcaauugu    1020
cauaauaaac uuaugucauu gaaaacggua ccugacuacc auuugcugga aauuugacau    1080
guguguggca uuaucaaaau gaagaggagc aaggagugaa ggaguggggu uaugaaucug    1140
ccaaaggugg uaugaaccaa ccccuggaag ccaaagcggc cucuccaagg uuaaauugau    1200
ugcaguuugc auauugccua aauuuaaacu uucucauuug guggggguuc aaaagaagaa    1260
ucagcuugug aaaaaucagg acuugaagag agccgucuaa gaaauaccac gugcuuuuuu    1320
ucuuuaccau uuugcuuucc cagccuccaa acauaguuaa uagaaauuuc ccuucaaaga    1380
acugucuggg gaugugaugc uuugaaaaau cuaaucagug acuuaagaga gauuuucuug    1440
uauacaggga gagugagaua acuuauugug aaggguuagc uuuacuguac aggauagcag    1500
ggaacuggac aucucagggu aaaagucagu acggauuuua auagccuggg gaggaaaaca    1560
cauucuuugc cacagacagg caaagcaaca caugcucauc cuccugccua ugcugagaua    1620
cgcacucagc uccaugucuu guacacacag aaacauugcu gguuucaaga aaugaggaga    1680
uccuauuauc aaauucaauc ugaugucaaa uagcacuaag aaguuauugu gccuuaugaa    1740
aaauaaugau cucugucuag aaauaccaua gaccauauau agucucacau ugauaauuga    1800
aacuagaagg gucuauaauc agccuaugcc agggcuucaa uggaauagua uccccuuaug    1860
uuuaguugaa augucccuu aacuugauau aauguguuau gcuuauggcg cuguggacaa    1920
ucugauuuuu caugucaacu uuccagauga uuuguaacuu cucugugcca aaccuuuuau    1980
aaacauaaau uuuugagaua uguauuuuaa aauuguagca cauguuuccc ugacauuuuc    2040
aauagaggau acaacaucac agaaucuuuc uggaugauuc uguguuauca aggaauugua    2100
cugugcuaca auuaucucua gaaucuccag aaagguggag ggcuguucgc ccuuacacua    2160
aauggucuca guuggauuuu uuuuuccugu uuucuauuuc cucuuaagua caccuucaac    2220
uauauuccca ucccucuauu uuaaucuguu augaaggaag guaaauaaaa augcuaaaua    2280
```

```
gaagaaauug uagguaaggu aagaggaauc aaguucugag uggcugccaa ggcacucaca   2340

gaaucauaau cauggcuaaa uauuuaugga gggccuacug uggaccaggc acugggcuaa   2400

auacuuacau uuacaagaau cauucugaga cagauauuca augauaucug gcuucacuac   2460

ucagaagauu gugugugugu uugugugugu gugugugugu guauuucacu uuuuguuauu   2520

gaccauguuc ugcaaaauug caguuacuca gugagugaua uccgaaaaag uaaacguuua   2580

ugacuauagg uaauauuuaa gaaaaugcau gguucauuuu uaaguuugga auuuuuaucu   2640

auauuucuca cagaugugca gugcacaugc aggccuaagu auauguugug uguguuguuu   2700

gucuuugaug ucauggucc cucucuuagg ugcucacucg cuuugggugc accuggccug   2760

cucuucccau guuggccucu gcaaccacac agggauauuu cugcuaugca ccagccucac   2820

uccaccuucc uuccaucaaa aauaugugug ugugucucag ucccuguaag ucauguccuu   2880

cacagggaga auuaacccuu cgauauacau ggcagaguuu ugugggaaaa gaauugaaug   2940

aaaagucagg agaucagaau uuuaaauuug acuuagccac uaacuagcca uguaaccuug   3000

ggaaagucau uucccauuuc ugggucuugc uuuucuuucu guuaaaugag aggaauguua   3060

aauaucuaac aguuuagaau cuuaugcuua caguguuauc ugugaaugca cauauuaaau   3120

gucuauguuc uuguugcuau gagucaagga guguaaccuu cuccuuuacu auguugaaug   3180

uauuuuuuuc uggacaagcu uacaucuucc ucagccaucu uugugagucc uucaagagca   3240

guuaucaauu guuaguuaga uauuuucuau uuagagaaug cuuaagggau uccaaucccg   3300

auccaaauca uaauuuguuc uuaaguauac ugggcagguc cccuauuuua agucauaauu   3360

uuguauuuag ugcuuuccug gcucucagag aguauuaaua uugauauuaa uaauauaguu   3420

aauaguaaua uugcuauuua cauggaaaca aauaaaagau cucagaauuc acuaaaaaaa   3480

aaaa                                                                3484
```

<210> SEQ ID NO 68
<211> LENGTH: 1609
<212> TYPE: RNA
<213> ORGANISM: Mus musculus
<220> FEATURE:
<221> NAME/KEY: misc_feature
<222> LOCATION: (1)..(1609)
<223> OTHER INFORMATION: Mus musculus Tnfsf4, mRNA

<400> SEQUENCE: 68

```
auugcuuuuu gucuccuguu cugggaccuu uaucuucuga cccgcaggcu ugacuuugcc     60

cuuauuggcu ccuuuguggu gaagagcagu cuucccccag guucccccgcc acagcuguau    120

cuccucugca ccccgacugc agagauggaa ggggaagggg uucaaccccu ggaugagaau    180

cuggaaaacg gaucaaggcc aagauucaag uggaagaaga cgcuaaggcu gguggucucu    240

gggaucaagg gagcagggau gcuucugugc uucaucuaug ucugccugca acucucuucc    300

ucuccggcaa aggacccucc aauccaaaga cucagaggag caguuaccag augugaggau    360

gggcaacuau ucaucagcuc auacaagaau gaguaucaaa cuauggaggu gcagaacaau    420

ucgguuguca ucaagugcga ugggcuuuau aucaucuacc ugaagggcuc cuuuuuccag    480

gaggucaaga uugaccuuca uuuccgggag gaucauaauc ccaucucuau uccaaugcug    540

aacgaugguc gaaggauugu cuucacugug guggccucuu uggcuuucaa agauaaaguu    600

uaccugacug uaaaugcucc ugauacucuc ugcgaacacc uccagauaaa ugauggggag    660

cugauuguug uccagcuaac gccuggauac ugugcuccug aaggaucuua ccacagcacu    720
```

```
gugaaccaag uaccacugug aauuccacuc ugagggugga cgggacacag guucuuucuc    780

gagagagaug agugcauccu gcucaugaga ugugacugaa ugcagagccu acccuacuuc    840

cucacucagg gauauuuaaa ucaugucuua cauaacaguu gaccucucau ucccaggauu    900

gccuugagcc ugcuaagagc uguucuggga augaaaaaaa aaauaaaugu cucuucaaga    960

cacauugcuu cugucgguca gaagcucauc guaauaaaca ucugccacug aaaauggcgc   1020

uugauugcua ucuucuagaa uuuugauguu gucaaaagaa agcaaaacau ggaaagggug   1080

guguccaccg gccaguagga gcuggagugc ucucuucaag guuaagguga uagaaguuua   1140

cauguugccu aaaacugucu cucaucucau gggggcuug gaaagaagau uaccccgugg   1200

aaagcaggac uugaagauga cuguuuaagc aacaaggugc acucuuuucc uggccccuga   1260

auacacauaa aagacaacuu ccuucaaaga acuaccuagg gacuaugaua cccaccaaag   1320

aaccacguca gcgaugcaaa gaaaaccagg agagcuuugu uuauuuugca gaguauacga   1380

gagauuuuac ccugagggcu auuuuuauua uacaggauga gagugaacug gaugucucag   1440

gauaaaggcc aagaaggauu uuucacaguc ugagcaagac uguuuuugua gguucucucu   1500

ccaaaacuuu uagguaaauu uuugauaauu uuaaaauuuu uaguuauauu uuuggaccau   1560

uuucaauaga agauugaaac auuuccagau gguuucauau ccccacaag               1609


<210> SEQ ID NO 69
<211> LENGTH: 737
<212> TYPE: RNA
<213> ORGANISM: Homo sapiens
<220> FEATURE:
<221> NAME/KEY: misc_feature
<222> LOCATION: (1)..(737)
<223> OTHER INFORMATION: mRNA sequence: Human OX40L with 5'-UTR, 3'-UTR,
      and miR-122 binding site

<400> SEQUENCE: 69

gggaaauaag agagaaaaga agaguaagaa gaaauauaag agccaccaug gaaagggucc     60

aaccccugga agagaaugug ggaaaugcag ccaggccaag auucgagagg aacaagcuau    120

ugcugguggc cucuguaauu cagggacugg ggcugcuccu gugcuucacc uacaucugcc    180

ugcacuucuc ugcucuucag guaucacauc gguauccucg aauucaaagu aucaaaguac    240

aauuuaccga auauaagaag gagaaagguu ucauccucac uucccaaaag gaggaugaaa    300

ucaugaaggu gcagaacaac ucagucauca ucaacuguga uggguuuuau cucaucuccc    360

ugaagggcua cuucucccag gaagucaaca uuagccuuca uuaccagaag gaugaggagc    420

cccucuucca acugaagaag gucaggucug ucaacuccuu gaugguggcc ucucugacuu    480

acaaagacaa agucuacuug aaugugacca cugacaauac cucccuggau gacuuccaug    540

ugaauggcgg agaacugauu cuuauccauc aaaauccugg ugaauucugu guccuuugau    600

aauaggcugg agccucggug gccaugcuuc uugccccuug ggccuccccc cagccccucc    660

uccccuuccu gcacccguac ccccaaaca ccauugucac acuccagugg ucuuugaaua    720

aagucugagu gggcggc                                                   737


<210> SEQ ID NO 70
<211> LENGTH: 782
<212> TYPE: RNA
<213> ORGANISM: Artificial Sequence
<220> FEATURE:
<223> OTHER INFORMATION: Synthetic: mRNA sequence: murine OX40L with
      5'-UTR, 3'-UTR, and miR-122 binding site

<400> SEQUENCE: 70
```

-continued

```
gggaaauaag agagaaaaga agaguaagaa gaaauauaag agccaccaug gaaggggaag     60

ggguucaacc ccuggaugag aaucuggaaa acggaucaag gccaagauuc aaguggaaga    120

agacgcuaag gcugguggue ucugggauca agggagcagg gaugcuucug ugcuucaucu    180

augucugccu gcaacucucu uccucuccgg caaaggaccc uccaauccaa agacucagag    240

gagcaguuac cagaugugag gaugggcaac uauucaucag cucauacaag aaugaguauc    300

aaacuaugga ggugcagaac aauucgguug ucaucaagug cgaugggcuu uauaucaucu    360

accugaaggg cuccuuuuuc caggagguca agauugaccu ucauuuccgg gaggaucaua    420

aucccaucuc uauuccaaug cugaacgaug gucgaaggau ugucuucacu gugguggccu    480

cuuuggcuuu caaagauaaa guuuaccuga cuguaaaugc uccugauacu cucugcgaac    540

accuccagau aaaugauggg gagcugauug uuguccagcu aacgccugga uacugugcuc    600

cugaaggauc uuaccacagc acugugaacc aaguaccacu gugauaauag gcuggagccu    660

cgguggccau gcuucuugcc ccuugggccu ccccccagcc ccuccucccc uuccugcacc    720

cguacccccc aaacaccauu gucacacucc aguggucuuu gaauaaaguc ugagugggcg    780

gc                                                                   782
```

<210> SEQ ID NO 71
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 71

```
atgtgtcacc agcagttggt catctcttgg ttttccctgg tatttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaga ccctgaccat ccaagtcaaa    240

gagtttggag atgctggcca gtacacctgt cacaaaggag gcgaggttct aagccattcg    300

ctcctgctgc ttcacaagaa ggaagatgga atttggtcca ctgatatttt aaaggaccag    360

aaagaaccca agaataagac ctttctaaga tgcgaggcca agaattattc tggacgtttc    420

acctgctggt ggctgacgac aatcagtact gatttgacat tcagtgtcaa gagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gagaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag agaagaaaga tagagtcttc acggacaaga cctcagccac ggtcatctgc    900

cgcaagaatg ccagcattag cgtgcgggcc caggaccgct actatagctc atcttggagc    960

gaatgggcat ctgtgccctg cagtggcgga gggggcggag ggagcagagc tgtgcctggg   1020

ggcagcagcc ctgcctggac tcagtgccag cagctttcac agaagctctg cacactggcc   1080

tggagtgcac atccactagt gggacacatg gatctaagag aagagggaga tgaagagact   1140

acaaatgatg ttccccatat ccagtgtgga gatggctgtg acccccaagg actcagggac   1200
```

aacagtcagt tctgcttgca aaggatccac cagggtctga tcttttatga gaagctgcta 1260
ggatcggata ttttcacagg ggagccttct ctgctccctg atagccctgt gggccagctt 1320
catgcctccc tactgggcct cagccaactc ctgcagcctg agggtcacca ctgggagact 1380
cagcagattc caagcctcag tcccagccag ccatggcagc gtctccttct ccgcttcaag 1440
atccttcgca gcctccaggc ctttgtggct gtagccgccc gggtctttgc ccatggagca 1500
gcaaccctga gtccc 1515

<210> SEQ ID NO 72
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 72
atgtgtcacc agcagttggt catctcttgg ttttccctgg tatttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaga ccctgaccat ccaagtcaaa 240
gagtttggag atgctggcca gtacacctgt cacaaaggag gcgaggttct aagccattcg 300
ctcctgctgc ttcacaagaa ggaagatgga atttggtcca ctgatatttt aaaggaccag 360
aaagaaccca agaataagac ctttctaaga tgcgaggcca agaattattc tggacgtttc 420
acctgctggt ggctgacgac aatcagtact gatttgacat tcagtgtcaa gagcagcaga 480
ggctcttctg acccgcaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gagaactaca ccagcagctt cttcatcagg gacatcatca aacctgaccc acccaagaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag agaagaaaga tagagtcttc acggacaaga cctcagccac ggtcatctgc 900
cgcaagaatg ccagcattag cgtgcgggcc caggaccgct actatagctc atcttggagc 960
gaatgggcat ctgtgccctg cagtggcgga ggtggcggag ggagcagagc tgtgcctggc 1020
ggcagcagcc ctgcctggac tcagtgccag cagctttcac agaagctctg cacactggcc 1080
tggagtgcac atccactagt gggacacatg gatctaagag aagagggaga tgaagagact 1140
acaaatgatg ttccccatat ccagtgtgga gatggctgtg acccgcaagg actcagggac 1200
aacagtcagt tctgcttgca aaggatccac cagggtctga tcttttatga gaagctgcta 1260
ggatcggata ttttcacagg ggagccttct ctgctccctg atagccctgt gggccagctt 1320
catgcctccc tactgggcct cagccaactc ctgcagcctg agggtcacca ctgggagact 1380
cagcagattc caagcctcag tcccagccag ccatggcagc gtctccttct ccgcttcaag 1440
atccttcgca gcctccaggc ctttgtggct gtagccgccc gggtctttgc ccatggagca 1500
gcaaccctga gtccc 1515

<210> SEQ ID NO 73
<211> LENGTH: 1575
<212> TYPE: DNA
<213> ORGANISM: Artificial Sequence
<220> FEATURE:
<223> OTHER INFORMATION: Synthetic: Codon optimized murine IL-23 sequence

<400> SEQUENCE: 73

```
atgtgtcctc agaagctaac catctcctgg tttgccatcg ttttgctggt gtctccactc      60
atggccatgt gggagctgga gaaagacgtt tatgttgtag aggtggactg gactcccgat     120
gcccctggag aaacagtgaa cctcacctgt gacacgcctg aagaagatga catcacctgg     180
acctcagacc agagacatgg agtcataggc tctggaaaga ccctgaccat cactgtcaaa     240
gagttcctag atgctggcca gtacacctgc cacaaaggag gcgagactct gagccactca     300
catctgctgc tccacaagaa ggaaaatgga atttggtcca ctgaaatttt aaaaaatttc     360
aaaaacaaga ctttcctgaa gtgtgaagca ccaaattact ccggacggtt cacgtgctca     420
tggctggtgc aaagaaacat ggacttgaag ttcaacatca agagcagtag cagttcccct     480
gactctcggg cagtgacatg tggaatggcg tctctgtctg cagagaaggt cacactggac     540
caaagggact atgagaagta ttcagtgtcc tgccaggagg atgtcacctg cccaactgcc     600
gaggagaccc tgcccattga actggcgttg gaagcacggc agcagaataa atatgagaac     660
tacagcacca gcttcttcat cagggacatc atcaaaccag acccgcccaa gaacttgcag     720
atgaagcctt tgaagaactc acaggtggag gtcagctggg agtaccctga ctcctggagc     780
actccccatt cctacttctc cctcaagttc tttgttcgaa tccagcgcaa gaaagaaaag     840
atgaaggaga cagaggaggg gtgtaaccag aaaggtgcgt tcctcgtaga gaagacatct     900
accgaagtcc aatgcaaagg cgggaatgtc tgcgtgcaag ctcaggatcg ctattacaat     960
tcctcatgca gcaagtgggc atgtgttccc tgcagggtcc gatccggagg cggagggagc    1020
ggaggcggag ggagcggagg cggagggagc gtgcctagga gtagcagtcc tgactgggct    1080
cagtgccagc agctctctcg gaatctctgc atgctagcct ggaacgcaca tgcaccagcg    1140
ggacatatga atctactaag agaagaagag gatgaagaga ctaaaaataa tgtgccccgt    1200
atccagtgtg aagatggttg tgacccacaa ggactcaagg acaacagcca gttctgcttg    1260
caaaggatcc gccaaggtct ggctttttat aagcacctgc ttgactctga catcttcaaa    1320
ggggagcctg ctctactccc tgatagcccc atggagcaac ttcacacctc cctactagga    1380
ctcagccaac tcctccagcc agaggatcac ccccgggaga cccaacagat gcccagcctg    1440
agttctagtc agcagtggca gcgcccccttt ctccgttcca agatccttcg aagcctccag    1500
gcctttttgg ccatagctgc ccgggtcttt gcccacggag cagcaactct gactgagccc    1560
ttagtgccaa cagct                                                     1575
```

<210> SEQ ID NO 74
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 74

```
atgtgccacc agcagctcgt gatcagctgg ttcagcctag tgttcctcgc cagcccactc      60
gtggccatct gggagctcaa gaaggacgtc tacgtagtag agctcgactg gtacccggac     120
gccccgggag agatggtcgt gctcacctgc gacaccccgg aagaggacgg catcacctgg     180
accctcgacc agagctccga ggtgctcggc agcggtaaga ccctgaccat ccaggtgaag     240
gagttcggcg acgccggcca atacacctgc cacaagggcg gcgaggtgct gagccactcc     300
```

ctgctgctcc tgcataagaa ggaggatgga atctggtcca ccgacatcct caaggaccag 360
aaggagccta agaacaagac cttcctccgg tgcgaggcca agaactactc gggccgattc 420
acctgttggt ggctgactac cattagcacc gacctcacct tcagcgtcaa gagcagcagg 480
ggcagcagcg accctcaggg cgtgacctgc ggcgccgcca ccctgagcgc cgaaagggtg 540
aggggcgaca acaaggagta cgaatatagc gtggagtgcc aggaggacag cgcctgcccg 600
gccgccgagg agagcctgcc tatcgaggtc atggtcgacg ccgtgcacaa gctgaagtac 660
gagaactaca ccagcagctt cttcatccgg gacatcatca agccggaccc accgaagaac 720
ctgcaactca agccactgaa gaacagccgg caggtggagg tgtcctggga gtaccctgac 780
acctggagca caccgcactc ctatttctcc ctgaccttct gtgtgcaagt gcagggcaag 840
agcaagaggg agaagaagga ccgggtgttc accgataaga cctccgccac cgtgatctgc 900
aggaagaacg cctccatcag cgtgagggcc caagacagat attacagcag ctcatggtcc 960
gagtgggcct ccgtcccatg ctccggcggc ggaggaggag gaagcagggc cgtcccaggc 1020
ggctctagcc ctgcctggac ccaatgccag cagctgagcc agaagctgtg cactctggcc 1080
tggtccgccc acccgctggt gggccacatg gatctgcgcg aggagggcga cgaggaaacc 1140
accaacgacg tcccgcatat ccagtgcggc gacggctgcg atccacaggg cctgagggac 1200
aactcccagt tctgcctgca gagaatccac cagggactga tcttctacga gaagctgctg 1260
ggcagcgaca tattcaccgg cgaaccgagc ctgctccctg acagcccggt gggccagctg 1320
catgccagcc tgctgggcct gtcacagctg ctgcagccgg agggccatca ctgggagact 1380
caacagatcc ctagcctcag ccctagccag ccgtggcagc ggctgctgct caggttcaag 1440
atcctgagga gcctgcaggc cttcgtggcg gtggccgccc gagtgttcgc ccacggcgcc 1500
gcgaccctgt ccccg 1515

<210> SEQ ID NO 75
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 75
atgtgccacc aacaactcgt gatctcctgg ttcagcctcg ttttcctcgc aagcccactc 60
gtggctatct gggaactcaa gaaggacgtg tacgtggtgg agctcgactg gtacccggac 120
gccccgggcg agatggtggt gctcacctgc gataccccgg aggaggacgg catcacctgg 180
accctcgacc agtccagcga agtgctggga tccggcaaga ccctgaccat ccaggtgaag 240
gagttcggcg atgccggcca atacacctgc cacaagggcg gcgaggtcct ctcccacagc 300
ctgctgctgc tccacaagaa ggaggacggc atatggagca ccgacatcct gaaggaccag 360
aaggaaccta agaacaagac cttcctgcga tgcgaggcca agaactacag cggcagattc 420
acctgctggt ggttaactac cataagcaca gacctgacct tcagcgtaaa gagcagcaga 480
ggcagcagcg acccgcaggg cgtgacctgc ggcgccgcca ccctgtccgc cgagcgggtg 540
cggggcgaca acaaggagta tgagtactca gtggaatgcc aggaggacag cgcctgcccg 600
gccgccgagg aaagcctgcc tatcgaggtg atggtggacg ccgtgcacaa gctgaagtac 660
gagaactaca ccagcagctt cttcatcagg gacatcatca agccggaccc gccgaagaac 720
ctgcaactga agccgctgaa gaacagccgg caagtggagg tgtcctggga gtacccggac 780
acctggagca ccccgcatag ctatttcagc ctcaccttct gcgtgcaagt ccagggcaag 840
tccaagcggg agaagaagga cagggtgttc accgacaaga cttccgccac tgtgatctgc 900
cgcaagaacg cgagcatctc cgtgagggcg caggataggt attatagcag cagctggtcg 960
gagtgggcct ccgtgccttg ctccggcgga ggcggcggag gctcgagagc cgtcccaggc 1020
ggcagctccc cagcctggac ccagtgccag cagctgagcc agaagctctg caccctcgcc 1080
tggagtgccc acccactggt gggccacatg gacctccgcg aggaaggcga cgaggaaacc 1140
accaatgacg tgccgcatat ccagtgtggc gacggctgcg accctcaggg tctgagggat 1200
aacagccagt tctgcctcca gcggatccat cagggcctga tcttctacga gaagctgctg 1260
ggcagcgata tcttcaccgg cgagccgtcc ctgctgccgg acagcccggt gggccagctc 1320
cacgccagcc tgctgggcct cagccagctg ctccagcctg aaggccacca ttgggagact 1380
cagcagatcc cgagcctgag cccgagccag ccgtggcaga gactgctgct ccgtttcaag 1440
atcctcaggt cgctgcaggc cttcgtggcc gtggccgcta gggtgttcgc ccacggcgcc 1500
gccaccctgt cccct 1515

<210> SEQ ID NO 76
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 76
atgtgtcatc agcagctcgt gatcagctgg ttcagcctcg tgttcctcgc aagcccgctc 60
gtcgccatct gggagctcaa gaaggacgtg tacgttgtgg agctcgactg gtacccggac 120
gccccgggcg agatggtggt gctcacctgc gacaccccgg aggaggacgg catcacctgg 180
acgctggacc agagcagcga ggtgctgggc agcggcaaga cgctgaccat ccaggtgaag 240
gaattcggcg atgccggcca gtacacctgc cacaagggcg gcgaggttct gagccactca 300
ctgctgctcc tccacaagaa ggaggacggc atctggagca ccgacatcct gaaggaccag 360
aaggagccta agaacaagac cttcctgcgg tgcgaggcca agaattacag cggacggttc 420
acatgctggt ggctgaccac catcagcacc gacctgacct tcagcgtcaa gtccagccgg 480
ggctcaagcg acccgcaggg cgtgacctgc ggcgccgcca ccctgagcgc cgagagggtc 540
agaggcgaca acaaggagta cgaatacagc gtggagtgtc aggaggactc ggcctgcccg 600
gccgctgagg aatccctgcc gatcgaagta atggtggacg ctgtgcacaa gctgaagtac 660
gagaactaca ccagcagctt cttcatcagg gacatcatca agccagaccc tcctaagaac 720
ctccagctga agcctctgaa gaacagccgg caggtggagg tgagctggga gtatccggac 780
acctggtcca ccccgcactc ctacttcagc cttacattct gcgtgcaggt gcagggcaag 840
agcaagaggg agaagaagga tagggtcttc accgacaaga ccagcgccac cgtcatctgc 900
agaaagaacg cctctatctc cgtcagggcc caggatcgct actacagcag cagctggagc 960
gagtgggctt ccgtcccttg ctcaggtggc ggtggcggcg gcagcagggc cgtcccgggt 1020
ggcagctcgc cggcctggac ccagtgccag caactctcgc agaagctgtg taccctggcc 1080
tggtcggccc atccgctggt gggccacatg gacctgaggg aggagggcga tgaggagacg 1140
accaatgatg tgcctcacat ccagtgtggc gacggctgcg accctcaagg cctgagggac 1200
aatagccagt tctgcctgca gaggatccat cagggcctga tcttctacga gaagctgctg 1260
ggcagcgaca ttttcaccgg cgagccgagc ctcctgccgg acagccctgt gggtcaactg 1320

```
cacgccagcc tcctgggcct gtcccaactg ctgcagccgg agggccacca ctgggaaacc   1380

cagcagatcc caagcctgtc cccgagccaa ccgtggcagc gcctgctgct gcggttcaag   1440

atcctgagaa gcctccaggc tttcgtggca gtcgccgcca gggtgttcgc ccacggcgcc   1500

gccaccctgt cccct                                                    1515
```

<210> SEQ ID NO 77
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 77

```
atgtgccacc agcagctcgt gattagctgg ttcagcctcg tgttcctcgc cagcccgctc     60

gtggccatct gggagcttaa gaaggacgtg tacgtggtgg agctcgactg gtacccagac    120

gcgccgggcg agatggtggt ccttacctgc gacaccccgg aagaggacgg tattacctgg    180

accctggatc agtctagcga ggtgctggga tcaggcaaga ccctcaccat ccaggtcaag    240

gagttcggcg acgccggcca gtatacgtgc cacaagggag gcgaggtgct gagccattcg    300

ctgctgctcc tgcacaagaa ggaggatggc atctggagca ccgacattct caaggaccag    360

aaggagccga agaacaagac cttcctcagg tgcgaagcaa agaattactc cggacgcttc    420

acctgctggt ggctgacaac catcagcacc gacctgacgt tcagcgtcaa gtccagcagg    480

ggcagcagcg acccgcaggg cgtgacctgc ggcgctgcca ccctcagcgc cgagcgagtt    540

aggggcgaca acaaggagta cgagtactcc gtggagtgcc aggaggactc cgcttgcccg    600

gccgccgagg agtccctccc tatcgaggtg atggtcgacg ccgtgcacaa gctgaagtat    660

gagaactaca ccagctcatt cttcatcaga gacatcatca agccagaccc gccgaagaac    720

ctccagctga agcctctgaa gaacagcagg caggtggagg tgtcctggga gtacccggac    780

acctggtcca ccccgcactc ctacttcagc ctgaccttct gcgtgcaggt ccaaggcaag    840

agcaagcggg agaagaagga ccgcgtgttc accgacaaga cctccgccac ggtcatatgc    900

aggaagaacg ccagcatcag cgtcagagcc caggatagat actactcgag ctcctggtcc    960

gagtgggcga gcgtgccgtg cagcggcgga ggcggtggcg gctcccgagc cgttccaggc   1020

ggctctagcc cggcatggac gcagtgccag cagctctccc agaagctgtg taccctggcc   1080

tggagcgccc acccactggt gggtcacatg gacctgaggg aggagggcga cgaggaaacc   1140

accaatgatg tgccgcacat ccagtgcggc gacggctgcg atcctcaggg cctgcgggac   1200

aactcccagt tctgcttaca aaggatccac cagggcctga tcttctacga gaagctcctg   1260

ggctccgaca tcttcaccgg cgagccaagc ctcctgccgg acagtccggt gggccagctg   1320

cacgcctccc tgctgggcct gagccaactg ctgcagccgg agggccacca ctgggagaca   1380

cagcagatac ctagcctgtc cccaagccag ccttggcagc gcctgctgct gcgcttcaag   1440

atcctgagaa gcttgcaggc cttcgtggcc gtggccgccc gggtgttcgc ccacggcgcc   1500

gcaaccctga gccca                                                    1515
```

<210> SEQ ID NO 78
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 78

```
atgtgtcacc agcagctcgt aatctcctgg ttcagcctcg tgttcctcgc ctccccgctc      60

gtggctatct gggagctcaa gaaggacgtg tacgtggtcg agctcgactg gtacccagac     120

gcgccgggcg agatggtggt gctcacctgc gacacccctg aggaggacgg catcacctgg     180

accttagacc agagctccga ggtgctcggc agcggcaaga cactcactat ccaagtgaag     240

gagttcggcg atgccggcca gtacacgtgc cacaagggcg gcgaggtgct gagccatagc     300

ctgctgctgc tgcacaagaa ggaagacggc atttggagca ccgacatcct gaaggaccag     360

aaggagccga agaacaagac cttcctgcgc tgcgaggcca agaactactc cggccgattc     420

acctgttggt ggctgacaac catcagcact gacctgacct tctccgtcaa gtcatcccgc     480

ggcagcagcg atccgcaggg cgtcacctgc ggagccgcca ccctgtccgc cgagagggtg     540

cgcggcgaca acaaggagta cgagtactcc gtggagtgcc aggaggatag cgcctgccca     600

gccgccgagg agtccctgcc aatcgaggtg atggtggacg ccgtgcataa gctcaagtat     660

gagaactaca ccagcagctt cttcataagg gacatcatca agccggaccc tccgaagaac     720

ctgcaactga agccgctcaa gaacagcagg caagtggagg tgtcctggga atacccggat     780

acctggagca ccccgcactc ctacttctcc ctgaccttct gcgttcaggt gcaaggaaag     840

agcaagcggg agaagaagga ccgggtgttc accgacaaga ccagcgccac cgtgatctgc     900

cgcaagaatg ccagcatcag cgtaagagcc caggacaggt actacagctc gtcctggtcc     960

gagtgggcct cggtgccgtg tagcggcggc ggaggcggtg gcagcagggc cgtcccaggc    1020

ggctcctcac cagcctggac acagtgccag caactgagcc agaagctgtg taccctggcc    1080

tggagcgccc acccgctggt gggccatatg gacctgcggg aggagggcga cgaggagacg    1140

accaacgatg tgccacacat ccagtgcggt gatggatgcg atccacaggg cctgagggac    1200

aacagccagt tctgcctgca gagaatccac cagggcctga tcttctacga gaagctgctg    1260

ggaagcgata ttttcactgg agaaccgagc cttttgccgg atagccctgt gggtcagctc    1320

cacgccagcc tgctgggtct gtcccagctg ctccagccgg agggccacca ctgggaaacc    1380

cagcagatcc cgagcctgtc cccaagccag ccatggcaac ggctgctgct taggttcaag    1440

atcctgagaa gcttacaggc cttcgtggcc gtggccgcca gggtgttcgc ccacggcgcc    1500

gcgaccctga gcccg                                                     1515
```

<210> SEQ ID NO 79
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 79

```
atgtgccacc agcagttggt gatcagctgg ttcagcctcg tgttcctcgc cagcccactc      60

gtcgccatct gggagttgaa gaaggacgtg tacgtggtgg agctcgactg gtacccggac     120

gccccgggcg agatggtggt gctcacctgc gacaccccgg aggaggacgg catcacgtgg     180

accctggacc agagcagcga ggtcctgggc agcggcaaga ccctcaccat ccaggtgaag     240

gagttcggcg acgccggcca gtacacctgc cacaagggcg gagaagtgct gagccattcc     300

ctgctgctgc tgcataagaa ggaggatggc atttggagca ctgacatcct caaggaccag     360

aaggagccga agaacaagac attcctgcga tgcgaggcca agaattacag cggtaggttc     420

acctgctggt ggcttacgac catcagcaca gacctgacgt tctccgtgaa gtccagcagg     480
```

ggcagcagcg atccgcaggg cgtgacctgc ggcgccgcca ccctgagcgc cgagcgggtg 540
agaggagaca acaaggagta tgaatacagc gtggaatgtc aggaggactc ggcctgcccg 600
gctgccgagg agagcctgcc aatcgaggtg atggtggatg ccgtgcacaa gctgaagtac 660
gagaactaca ccagcagctt cttcatccgt gacatcatca agccggaccc gccgaagaac 720
ctgcagctga agccgctcaa gaactcccga caggtggaag tgtcctggga gtatccagac 780
acctggtcaa ccccgcactc ctacttctcc ctcacattct gcgtgcaggt gcagggcaag 840
agcaagcgcg agaagaagga tagggtgttc accgacaaga cgagcgcgac cgtgatctgc 900
aggaagaacg ccagcatcag cgtgcgggcc caggacaggt actacagctc ctcctggagc 960
gaatgggcct ccgtcccgtg ctcaggcggt ggcggcggcg gctcgcgggc cgtgccggga 1020
ggcagcagtc ctgcatggac ccagtgccaa cagctgagcc agaagctctg cacattggcc 1080
tggagcgccc acccgctggt gggccacatg gacctcagag aggagggcga cgaagaaacc 1140
accaacgacg tgccgcacat ccagtgcggc gacggctgcg accctcaggg tctgcgggac 1200
aatagccaat tctgcctcca gcgcatccat cagggcctga tcttctacga gaagcttctg 1260
ggaagcgaca tcttcaccgg cgagccgagc ctgctgccgg acagcccggt gggccagctg 1320
cacgcctccc tcctgggcct gagccagctg ctgcaaccag agggccatca ctgggaaacc 1380
cagcagatcc ctagcctgag cccgagccag ccgtggcaga ggctgctcct gcggttcaag 1440
atcctcagga gcctgcaggc cttcgtggcc gtggcggccc gggtgttcgc ccacggcgcc 1500
gccaccctca gccca 1515

<210> SEQ ID NO 80
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 80
atgtgccacc aacagctcgt gatcagctgg ttcagcctcg tgttcctcgc cagcccgctc 60
gtggccatct gggagctcaa gaaggacgtg tacgtcgtcg aactcgactg gtacccggac 120
gcgccgggcg aaatggtggt gctaacctgc gacaccccgg aagaggacgg catcacctgg 180
accctggacc aatcaagcga ggtgctgggt agcggaaaga ccctcaccat ccaggtgaag 240
gagttcggcg acgccggcca atacacgtgt cacaagggcg gcgaggtgct gagccacagc 300
ctcctactgc tgcacaagaa ggaggacggt atctggagca ccgacatact gaaggaccag 360
aaggagccga agaacaagac cttcctgcgc tgcgaggcca agaactactc tggcaggttc 420
acctgctggt ggctcaccac catcagcacc gacctgacct tcagcgtcaa gagctcccgg 480
ggcagtagcg atccgcaggg cgtgacctgc ggcgccgcca ccctcagcgc cgagcgcgtc 540
cgcggcgaca acaaggagta cgagtacagc gtggagtgcc aggaggactc cgcctgcccg 600
gccgccgagg agagcctccc gatcgaggtc atggtggacg ccgtgcacaa gctgaagtat 660
gagaattaca cctcctcctt cttcatccgg gatatcataa agccggaccc gccgaagaac 720
ttacagctga agcctctgaa gaacagcagg caggtggagg tgagctggga gtatccggac 780
acctggagca ccccgcactc ctatttcagc ctgaccttct gcgtccaagt gcagggcaag 840
agcaagaggg agaagaagga cagggtgttc acggacaaga ccagcgccac cgtaatctgt 900
aggaagaacg ccagcatcag cgtgcgagcc caggacaggt actactccag tagctggtcc 960

```
gagtgggcct ccgtgccatg tagcggaggc ggcggcggcg gcagccgggc cgtgccagga   1020

ggaagctctc cggcctggac ccagtgccaa cagctgagcc agaagctgtg caccctggcc   1080

tggagcgccc acccgctcgt gggccacatg gatctgcggg aggagggcga cgaggaaact   1140

accaacgacg tgccacacat ccagtgcggc gacggctgcg acccacaggg actgagggac   1200

aattcccagt tctgcctcca gcggatccac cagggcctga tcttctacga gaagctcctg   1260

ggcagcgata tcttcaccgg tgagccttcc ctgctgccgg attcccctgt gggccagctc   1320

catgcctctc tgctgggcct cagccagctg ctgcaaccgg agggacacca ttgggagacg   1380

cagcaaatcc ctagcctgag cccgagccaa ccatggcaaa ggctcctgct gaggttcaag   1440

atcctgcgca gcctgcaggc cttcgtggcc gtcgccgccc gggtgttcgc ccacggcgcc   1500

gccacgctga gcccg                                                    1515
```

```
<210> SEQ ID NO 81
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 81
```

```
atgtgccacc agcagctcgt gataagctgg ttcagcctcg tcttcctcgc gagcccgctc     60

gtcgccatct gggaactcaa gaaggacgtg tacgtggtgg agctcgattg gtacccggac    120

gccccgggtg agatggtggt cctcacctgc gacaccccgg aggaggacgg catcacgtgg    180

actctggacc agagcagcga agtgctcggc tcgggtaaga ctctgaccat ccaggtgaag    240

gagttcggtg acgccggcca gtacacctgc cataagggcg gagaggtgct ctcccacagc    300

ctgctgctgc tgcacaagaa ggaagacggt atctggagca ccgatatcct gaaggaccag    360

aaggagccga agaacaagac cttcctgcgg tgtgaggcca agaactacag cggcagattc    420

acctgttggt ggctgaccac catctcgacc gacctgacat tcagcgtgaa gtcctccagg    480

ggtagcagcg acccgcaggg cgtgacctgc ggcgccgcca ccctgtccgc cgagcgggtg    540

cgcggcgaca acaaggagta cgagtactcc gtggagtgcc aggaggacag cgcctgccca    600

gcggcggagg agagcctccc tatcgaagtg atggtggacg ccgtacacaa gctgaagtat    660

gagaattaca ccagcagctt cttcatccgg gacataatca agccggatcc accgaagaat    720

ctgcagctga agccactgaa gaacagccgg caggtggagg tgagctggga gtacccggac    780

acctggtcca cccctcacag ctacttcagc ctgaccttct gtgtgcaggt ccagggcaag    840

tccaagcgcg agaagaagga ccgagtgttc accgacaaga cctcggccac cgtgatctgc    900

cgtaagaacg catctatcag cgtgcgggcc caggaccggt actacagctc cagttggagc    960

gaatgggcca gcgtgccttg ctccggcggc ggcggcggcg gaagcagggc cgtgccgggc   1020

ggcagctccc cagcatggac ccagtgccag caactgagcc agaagctgtg caccctcgcc   1080

tggtctgccc acccgctggt gggccacatg gatctgcggg aggagggcga tgaggaaacc   1140

accaacgacg tgccgcacat ccagtgcggc gacggatgcg accctcaagg cctgagagac   1200

aacagccagt tctgcctgca gcgaatccac cagggcctga tcttctacga gaagctgctg   1260

ggcagcgaca tcttcaccgg cgagccgagc ctgctgccgg acagcccggt gggccaactg   1320

cacgccagcc tgctgggact gtcccaactg ctgcagccgg aaggccacca ctgggagaca   1380

cagcagatcc cgagcctgag cccttcccag ccgtggcaga ggctgctgct gaggttcaag   1440

atcctccgtt ctctacaggc cttcgtggcc gtggcggcca gagtgttcgc ccacggcgcc   1500
```

gctacgctct ccccg 1515

<210> SEQ ID NO 82
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 82
atgtgccacc agcagctcgt gatcagctgg ttctccttgg tgttcctcgc atccccactc 60
gtggccatct gggagctcaa gaaggacgtg tacgtggtgg agctcgactg gtacccggac 120
gccccaggcg agatggtggt gctcacctgt gacaccccgg aggaggacgg catcacttgg 180
accctggacc aaagctctga ggtcctgggc tccggcaaga cgctcaccat ccaggtgaag 240
gagttcggcg atgccggcca gtacacctgc cacaagggcg gcgaggtgct gagccacagc 300
ctgctgctgc tgcacaagaa ggaggacggc atctggtcca ccgatattct taaggaccag 360
aaggagccga agaacaagac gttcctgcgg tgcgaggcca agaactacag cggcagattc 420
acctgctggt ggctcactac catcagcacc gacctgacct tcagcgtgaa gtcctccagg 480
ggcagctccg acccgcaggg agtcacctgc ggcgccgcca ccctgagtgc ggaacgggtg 540
agaggagaca acaaggagta cgagtactcc gtggaatgtc aggaggacag cgcctgcccg 600
gccgccgagg agagcctgcc gatcgaggtc atggtggacg ccgtgcataa gctgaagtac 660
gagaactaca ccagcagctt cttcatccgg gacatcatca agccggaccc gccgaagaac 720
ctgcagctga agccgctgaa gaactcccga caggtggagg ttagctggga gtacccggac 780
acctggagca ccccacacag ctacttcagc ctcaccttct gcgtgcaggt ccagggcaag 840
agcaagaggg agaagaagga cagggtgttc accgacaaga ccagcgccac agtgatctgt 900
agaaagaacg ccagcatctc cgtgcgcgcc caggaccgct actacagcag cagctggagc 960
gagtgggcta gcgtcccatg ctccggtggc ggtggcggcg gcagcagagc cgtgccgggc 1020
ggcagcagcc cagcctggac acagtgtcag cagctctccc agaagctgtg caccctcgcc 1080
tggagcgccc acccgctggt gggccacatg gatctcaggg aggagggcga cgaagaaacc 1140
accaacgacg tgccgcacat ccagtgtggc gatggatgcg acccgcaggg cctgagggac 1200
aacagccagt tctgcctgca gcggatccac cagggcctga tcttctatga gaagctgctg 1260
ggctcagaca ttttcaccgg cgaaccaagc ctcctgccgg acagcccggt gggacagctg 1320
cacgcctccc tgctgggcct gagccagctg ctccagccgg agggccacca ctgggaaacg 1380
cagcagatcc cgagcctctc cccaagccag ccatggcaga ggctcctgct ccgcttcaag 1440
atcctgcggt ccctgcaggc cttcgtggcc gtggccgcga gggtcttcgc ccacggcgcc 1500
gccaccctga gccct 1515

<210> SEQ ID NO 83
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 83
atgtgccacc agcagctcgt gatcagctgg ttcagcctcg tgttccttgc ctccccgctc 60
gtggccatct gggagctcaa gaaggacgtc tacgtggtgg agttggactg gtatccagac 120

```
gccccgggcg agatggtggt gcttacctgc gataccccag aggaggatgg cattacctgg    180

accctggacc agagcagcga agtgctgggc agcggcaaga ccctgaccat ccaggtgaag    240

gagttcggcg acgccggcca atacacctgc cacaagggcg gcgaggtgct gagccacagc    300

ctgctgcttc tgcacaagaa ggaggatggc atctggagca cagacatcct caaggaccag    360

aaggagccga agaacaagac cttccttagg tgcgaggcca agaactactc cggccggttc    420

acctgctggt ggctcaccac catttccacc gacctgacct tcagcgtcaa gagcagccgg    480

ggatcctctg atccgcaggg cgtgacctgc ggcgccgcca ccctgagcgc cgaacgcgtg    540

aggggcgaca acaaggagta cgagtattca gtcgagtgcc aggaggacag cgcctgcccg    600

gccgccgagg agagcctgcc gatcgaagtc atggtggacg ccgtgcacaa gctaaagtac    660

gagaactaca ccagctcctt cttcatcagg gacatcatca agcctgaccc gccaaagaac    720

ctgcagctga agccgctgaa gaactccagg caggtggagg tcagctggga gtaccctgac    780

acctggagca ccccgcactc ctacttctcg ctcaccttct gcgtgcaagt gcagggcaag    840

tccaagaggg agaagaagga ccgggtgttc accgacaaga ccagcgccac cgtgatatgc    900

aggaagaacg ccagcatctc cgtccgggct caggacaggt actacagctc cagctggagc    960

gaatgggcct ccgtcccgtg cagcggcggc ggtggcggcg gtagccgtgc cgtcccaggc   1020

ggaagctccc ctgcctggac acagtgtcag cagctgtccc agaagctgtg caccctggcc   1080

tggtccgccc atccgctcgt gggccatatg gacctcaggg aggagggcga cgaggaaaca   1140

accaacgatg tgccgcatat ccaatgcggc gacggctgcg atccgcaggg cctgcgggat   1200

aacagccaat tctgcctgca gagaatccac cagggactga tcttctacga gaagctgctg   1260

ggcagcgaca tcttcacagg cgaacctagc ctgctgccag actctcctgt gggtcagctg   1320

cacgccagcc tgctgggcct ctcccagctc ctgcaaccgg agggccacca ctgggagacg   1380

cagcagatcc caagcctcag cccgtcccag ccgtggcaga ggctgctcct gcgcttcaag   1440

atcctgcgca gcctgcaggc cttcgtcgcg gtggcggccc gtgtgttcgc gcacggcgcc   1500

gccaccctgt cccca                                                     1515
```

```
<210> SEQ ID NO 84
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 84

atgtgccacc agcagctcgt catcagctgg ttcagcctcg tgttcctcgc cagcccgctc     60

gtggccattt gggagctcaa gaaggacgtg tacgtggtcg agctcgattg gtacccggac    120

gccccaggag agatggtcgt cctcacctgc gacaccccgg aggaggacgg catcacctgg    180

accctcgacc aaagctccga ggtgctcggc agcggcaaga ccctgacaat ccaggtgaag    240

gagttcggtg acgccggcca gtacacctgc cataagggcg gcgaggtgct gagccacagc    300

ctgctgctgc tgcacaagaa ggaggacggc atctggtcta ccgacatcct gaaggaccag    360

aaggagccga agaataagac tttcctgagg tgcgaggcca agaactactc cggccgcttc    420

acctgttggt ggctgaccac tatctcgacc gacctgacct tcagcgtgaa gtcctcgcgg    480

ggctcctccg acccgcaggg cgtgacctgc ggcgccgcca ctctgtccgc tgagagggtc    540

aggggcgaca acaaggagta cgagtacagc gtcgagtgtc aggaggacag cgcctgcccg    600

gccgccgagg agtccctgcc gattgaggtc atggtggacg cggtgcacaa gctgaagtat    660
```

gagaactata ccagctcctt cttcatccgg gacattatca agccggaccc gccgaagaac 720
ctgcagctga agccgctgaa gaactcccgc caggtcgagg tgtcctggga gtatcctgac 780
acctggtcca ccccgcactc ctacttcagc ctgaccttct gcgtgcaggt gcaaggcaag 840
agcaagcgag agaagaagga tagagtgttc accgacaaga ccagcgccac cgtgatttgc 900
agaaagaacg ccagcatctc cgtgcgcgcc caggaccgct actacagcag cagctggtcc 960
gagtgggcca gcgtgccatg cagcggcgga ggcggaggcg gtagccgcgc cgtgccaggc 1020
ggaagctccc cggcgtggac ccagtgccag cagctgagcc agaagctctg cacactggcc 1080
tggtccgccc atccactcgt gggccacatg gacctccggg aggagggaga cgaggaaacg 1140
acgaacgacg tgccgcacat ccagtgcggc gacggctgcg acccgcaggg actgcgggac 1200
aactcccagt tctgcctgca gaggatccat cagggtctga tcttctacga gaagctgctg 1260
ggcagcgaca tcttcaccgg cgaaccaagc ctgctgcctg actcccctgt gggccagctg 1320
cacgcctccc tgctgggcct gtcccagctg ctccagccgg agggccacca ctgggaaacc 1380
caacaaatcc cgagcctgag cccatcccag ccgtggcagc gcctgctgct gaggttcaag 1440
atcctgcgct ccctgcaggc cttcgtcgcc gtggccgcca gagtattcgc ccacggcgcc 1500
gccaccctga gcccg 1515

<210> SEQ ID NO 85
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 85
atgtgccacc agcagctcgt catcagctgg ttctccctcg tgttcctcgc gagccctctc 60
gtggccatct gggaactcaa gaaggacgtg tacgtggtgg agctcgactg gtatccagac 120
gccccgggcg aaatggtggt gctcacttgt gacaccccgg aggaggacgg tatcacctgg 180
accctggacc agtccagcga ggtcctgggc agcggcaaga cgctgaccat ccaggtgaag 240
gagttcggcg acgccggaca gtacacctgc cataagggcg gagaggtgct cagccattcc 300
ctgctcctgc tgcacaagaa ggaggacggc atatggagca cggacatact gaaggaccag 360
aaggagccta agaacaagac cttcctgaga tgcgaggcca agaactactc cggtcggttc 420
acctgttggt ggctcaccac catctccacc gacctgacct tcagcgtgaa gtcctccaga 480
ggctccagcg acccgcaggg cgtcacctgc ggcgccgcca ccctgtccgc cgagagggtg 540
aggggcgaca ataaggagta cgagtacagc gtggaatgtc aagaggatag cgcctgcccg 600
gccgccgagg aaagcctgcc aatcgaggtg atggtggatg ccgtgcacaa gctgaagtat 660
gagaactaca ccagctcctt cttcatcagg gacatcatca agccggaccc gccgaagaac 720
ctgcagctca agccactgaa gaacagcaga caggtggagg tgtcctggga gtacccggac 780
acatggagca ccccgcactc ctacttctcc ctcaccttct gcgtccaggt gcagggcaag 840
agcaagcggg agaagaagga cagggtgttc accgataaga cctccgccac agtgatctgc 900
cgcaagaacg cctccatcag cgtgagggcc caggacagat actacagctc cagctggagc 960
gagtgggcca gcgtcccatg cagcggcggc ggaggcggcg gcagcagagc cgtgccgggc 1020
ggcagctccc cagcatggac acagtgccag cagctgagcc agaagctctg caccctcgcc 1080
tggtcggccc acccgctggt gggccacatg gacctgcgcg aggaaggcga cgaggaaacc 1140

```
acgaacgacg tgccgcacat ccagtgcggc gacggctgcg acccgcaggg cctccgtgat   1200

aacagccagt tctgcctgca gaggatccac cagggcctga tcttctacga gaagctgctg   1260

ggctccgaca tcttcactgg cgagccgagc ctgctcccag atagcccagt gggacagctg   1320

cacgccagcc tgctgggcct ctcccagctg ctccaaccgg agggccatca ctgggaaacc   1380

cagcagatcc cgagcctgtc cccgagtcag ccatggcaga gactgctgct gaggttcaag   1440

atcctgcggt ccctgcaggc cttcgtggcc gtggccgcca gagtgttcgc ccacggcgcc   1500

gccaccctca gccca                                                     1515
```

<210> SEQ ID NO 86
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 86

```
atgtgccacc agcagctcgt gatcagctgg ttcagccttg tgttcttggc cagcccccctt     60

gtggccatct gggagttaaa gaaggacgtg tacgtggtgg agttagactg gtaccccgac    120

gcccccggcg agatggtggt gctcacctgc gacacccccg aggaggacgg catcacctgg    180

accctggacc agagcagcga ggtgctgggc agcggcaaga ccctgaccat ccaggtgaag    240

gagttcggcg acgccggcca gtacacctgc cacaagggcg gcgaagtgct gagccacagc    300

ctgctgctcc tgcacaagaa ggaagatggc atctggagca ccgacatcct gaaggaccag    360

aaggagccca agaacaagac cttcctgcgg tgcgaggcca agaactacag cggccggttc    420

acctgctggt ggctgaccac catcagcacc gatctgacct tcagcgtcaa gtccagccgg    480

ggcagcagcg acccccaggg cgtgacctgt ggcgccgcca ccctgagcgc cgagcgggtg    540

cggggcgaca acaaggagta cgagtacagc gtggagtgcc aggaggacag cgcctgcccc    600

gccgccgagg agagcctgcc catcgaggtg atggtggacg ccgtgcacaa gctgaagtac    660

gagaactaca cctccagctt cttcatccgg gacatcatca agcccgaccc ccctaagaac    720

ctgcagctga agcccctgaa gaacagccgg caggtggagg tgagctggga gtacccagac    780

acatggagca caccccacag ctacttctcc ttgaccttct gcgtgcaggt gcagggcaag    840

agcaagcggg agaagaagga tcgggtgttc accgacaaga ccagcgccac cgtgatctgc    900

cggaagaacg ccagcatcag cgtgcgggcc caggaccggt actactcttc ttcgtggagc    960

gagtgggcca gcgtgccctg cagcggcggc ggaggaggcg gcagcagagc cgtgccgggc   1020

ggcagttccc ccgcctggac tcagtgccag caactgagcc agaagctgtg caccctggcc   1080

tggagcgccc acccactggt gggccacatg gacctgagag aggagggcga cgaggagacg   1140

accaacgacg tgccccacat ccagtgcggc gacggctgcg acccacaggg tctgcgagac   1200

aacagccagt tctgcctgca gaggatccac cagggcttga tcttctacga gaagctgctg   1260

ggaagcgaca tcttcaccgg cgagccttcc ctgctgcccg acagccccgt cggccagctg   1320

cacgccagcc tcctgggcct gtcccagctg ctccagcccg agggccacca ctgggaaacc   1380

cagcagatcc caagcctgag ccccagccag ccctggcaga gactgctgct gcggttcaag   1440

atcctgcgga gcctgcaggc cttcgtggcc gtggccgcca gagtcttcgc ccacggagcc   1500

gccacactaa gcccc                                                     1515
```

<210> SEQ ID NO 87
<211> LENGTH: 1515

<212> TYPE: DNA
<213> ORGANISM: Artificial Sequence
<220> FEATURE:
<223> OTHER INFORMATION: Synthetic: Codon optimized human IL-23 sequence

<400> SEQUENCE: 87
atgtgccacc agcagcttgt gatcagctgg ttcagccttg tgttcctcgc cagcccctta 60
gtggccatct gggagctcaa gaaggacgtg tacgtggtgg agctcgactg gtaccccgac 120
gcccccggcg agatggtggt gctaacctgc gacacccccg aggaggacgg catcacctgg 180
accctggacc agagcagcga ggtgctgggc agcggcaaga ccctgaccat ccaggtgaag 240
gagttcggcg acgccggcca gtacacctgc cacaagggcg gcgaggtcct gagccacagc 300
ctgttgctcc tgcacaagaa ggaagacggt atctggagca ccgacatcct gaaggaccag 360
aaggagccca agaacaagac cttcctgcgg tgcgaggcca agaactacag cggccggttc 420
acctgctggt ggctgaccac catctccacc gacctgacct tcagcgtgaa gtccagccgg 480
ggcagcagcg acccccaggg cgtgacatgc ggcgccgcca ccctgagcgc cgagcgggtg 540
cggggcgaca acaaggagta cgagtacagc gtggagtgcc aggaggacag cgcctgcccc 600
gccgccgagg agagcctgcc catcgaggtg atggtggacg ccgtgcacaa gctgaagtac 660
gagaactaca caagcagctt cttcatccgg gacatcatca agcccgaccc ccctaagaac 720
ctgcagctga agcccctgaa gaacagccgg caggtggagg tgagctggga gtaccctgac 780
acctggtcta ccccccacag ctacttcagc ctcaccttct gcgtgcaggt gcagggcaag 840
agcaagcggg agaagaagga tcgggtgttc accgacaaga ccagcgccac cgtgatctgc 900
cggaagaacg ccagcatcag cgtgcgggcc caggaccggt actacagcag ctcttggagc 960
gagtgggcca gcgtgccctg cagcggcggt ggcggcggcg gaagcagagc cgtgccaggc 1020
ggctctagcc ccgcatggac ccagtgtcaa cagctgagcc agaagctgtg caccctggcc 1080
tggagcgccc accctttggt gggccacatg gacctgagag aggagggcga cgaggaaacg 1140
accaacgacg tgccccacat ccagtgcggc gacggctgtg accctcaggg cctgcgggac 1200
aacagccagt tctgcctgca gaggatccac cagggattga tcttctacga gaagctcctg 1260
ggctctgaca tcttcaccgg cgagccaagc ctgctccccg acagccccgt gggacagctg 1320
cacgcctccc tgctgggcct gtcacagctc cttcagcccg agggccacca ctgggagaca 1380
cagcagatcc catctctgag ccccagccag ccctggcaga gactgttgct gcggttcaag 1440
atcctgcgga gcctgcaggc cttcgtggcc gtggccgcca gggtgttcgc ccacggagca 1500
gccacactgt ccccc 1515

<210> SEQ ID NO 88
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 88
atgtgccacc agcagcttgt gatcagctgg ttcagcttag tgttcctcgc cagcccctta 60
gtggccatct gggagctcaa gaaggacgtg tacgtggtgg agcttgactg gtaccccgac 120
gcccccggcg agatggtggt gctcacctgc gacacccccg aggaggacgg catcacctgg 180
accctggacc agagcagcga ggtgctgggc agcggcaaga ccctgaccat ccaggtgaag 240
gagttcggcg acgccggcca gtacacctgc cacaagggcg gcgaggttct tagccacagc 300

-continued

```
ctgctgcttc tgcacaagaa ggaggatggc atctggagca ccgacatcct gaaggaccag    360

aaggagccca agaacaagac cttcctgcgg tgcgaggcca agaactacag cggccggttc    420

acctgctggt ggctgaccac catctctacc gacctgacct tcagcgttaa gagcagccgg    480

ggcagcagcg acccccaggg cgtaacctgc ggcgccgcca ccctgagcgc cgagcgggtg    540

cggggcgaca acaaggagta cgagtacagc gtggagtgcc aggaggacag cgcctgcccc    600

gccgccgagg agagcctgcc catcgaggtg atggtggacg ccgtgcacaa gctgaagtac    660

gagaactata cctctagctt cttcatccgg gacatcatca agcccgaccc cccaaagaac    720

ctgcagctga agcccctgaa gaacagccgg caggtggagg tgagctggga gtaccctgac    780

acatggagca cacccccacag ctacttcagt ctgacattct gcgtgcaggt gcagggcaag    840

agcaagcggg agaagaagga tcgggtgttc accgacaaga ccagcgccac cgtgatctgc    900

cggaagaacg ccagcatcag cgtgcgggcc caggaccggt actacagcag ctcctggagc    960

gagtgggcca gcgtgccctg cagcggcggc ggaggaggcg gcagcagagc cgtgccaggc   1020

ggctcctctc ccgcgtggac ccagtgccag cagttgagcc agaagctgtg caccctggca   1080

tggtccgccc acccactggt gggccacatg gacctcaggg aggagggcga cgaggagaca   1140

accaacgacg tgccccacat ccagtgcggc gacggctgcg acccacaggg cctgagagac   1200

aacagccagt tctgtctgca gagaatccac cagggactga tcttctacga gaagctgctc   1260

ggctccgaca tcttcaccgg cgagcctagc ctcctgcccg acagccccgt gggacagctg   1320

cacgccagtt tgttgggcct gtcacaactg ctgcagcccg agggccacca ctgggagacg   1380

cagcagatcc ctagcctgag ccccagccag ccctggcagc ggttactgct gcggttcaag   1440

atcctgcgga gcctgcaggc cttcgtggcc gtggccgccc gcgtgttcgc ccacggagcg   1500

gccacactga gcccc                                                    1515
```

<210> SEQ ID NO 89
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 89

```
atgtgccacc agcagctcgt gatcagctgg ttcagccttg tgttcctcgc cagccccctc     60

gtggccatct gggagctcaa gaaggacgtg tacgtcgtcg agctcgactg gtaccccgac    120

gcccccggcg agatggtcgt cctcacctgc gacacccccg aggaggacgg catcacctgg    180

accctcgacc agtcctccga ggtcctcggc tccggcaaga ccctcaccat ccaggtcaag    240

gagttcggcg acgccggcca gtacacctgc cacaagggcg gagaggttct gtcccactcc    300

ctgctgctac tccacaagaa ggaggatggc atctggtcca ccgacatcct caaggaccag    360

aaggagccca agaacaagac cttcctccgc tgcgaggcca agaactactc cggccgcttc    420

acctgctggt ggctcaccac catctccaca gacctcacct tctccgtcaa gtcctcccgc    480

ggctcctccg acccccaggg cgttacctgc ggcgccgcca ccctctccgc cgagcgcgtc    540

cgcggcgaca acaaggagta cgagtactcc gtcgagtgcc aggaggactc cgcctgcccc    600

gccgccgagg agtccctccc catcgaggtc atggtcgacg ccgtccacaa gctcaagtac    660

gagaactaca ccagctcctt cttcatccgc gacatcatca agcctgaccc tcctaagaat    720

ctccagctca agcccctcaa gaactcccgc caggtcgagg tgtcctggga atatccagac    780

acctggagca ccccccactc ctacttctcc ctgaccttct gcgtccaggt ccagggcaag    840
```

```
tccaagcgcg agaagaagga tcgcgtcttc accgacaaga catccgccac cgtcatctgc    900

cgcaagaacg cctccatctc cgtccgcgcc caggaccgct actactcctc ctcttggtcc    960

gagtgggcct ccgtcccctg ctccggcgga ggcggcggtg gatcccgcgc cgtccctggc   1020

ggcagctccc cagcttggac ccagtgtcag cagctctccc agaagctctg caccctcgcc   1080

tggagcgccc accccctcgt cggccacatg gacctcaggg aggagggcga cgaggagaca   1140

accaacgacg tcccccacat ccagtgcggc gacggctgcg acccacaggg acttagagac   1200

aactcccagt tctgcctcca gcgcatccac cagggcctca tcttctacga gaagcttttg   1260

ggatccgaca tcttcactgg cgagcctagc ctgctgccgg actcccctgt gggccagctc   1320

cacgcgtctc tgctgggcct gagtcagctc ctccagcccg agggccacca ctgggaaacc   1380

cagcagatcc cttccttgtc cccctcccag ccctggcagc gcctcctgct gcggttcaag   1440

atcctgagat ccctccaggc cttcgtcgcc gtcgccgccc gggtcttcgc ccatggcgct   1500

gctacactga gcccc                                                    1515
```

```
<210> SEQ ID NO 90
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 90
```

```
atgtgccacc agcagctcgt gatcagctgg ttcagcctcg tgttcctagc cagcccccctt     60

gtggccatct gggagctcaa gaaggacgtg tacgtcgtcg agctcgactg gtaccccgac    120

gcccccggcg agatggtcgt cctcacctgc gacacccccg aggaggacgg catcacctgg    180

accctcgacc agtcctccga ggtcctcggc tccggcaaga ccctcaccat ccaggtcaag    240

gagttcggcg acgccggcca gtacacctgc cacaagggcg gcgaggtgct gtcccactcc    300

ctgctgctgc tccacaagaa ggaggatggc atctggtcca ccgacatcct caaggaccag    360

aaggagccca agaacaagac cttcctccgc tgcgaggcca agaactactc cggccgcttc    420

acctgctggt ggctcaccac catcagcacc gacctcacct tctccgtcaa gtcctcccgc    480

ggctcctccg acccccaggg cgtgacatgc ggcgccgcca ccctctccgc cgagcgcgtc    540

cgcggcgaca acaaggagta cgagtactcc gtcgagtgcc aggaggactc cgcctgcccc    600

gccgccgagg agtccctccc catcgaggtc atggtcgacg ccgtccacaa gctcaagtac    660

gagaactaca ccagtagctt cttcatccgc gacatcatca agcctgaccc tccaaagaac    720

ctccagctca agcccctcaa gaactcccgc caggtcgaag tgtcctggga gtacccagac    780

acctggtcaa ctccccactc ctacttcagc cttacgttct gcgtccaggt ccagggcaag    840

tccaagcgcg agaagaagga tcgcgtcttc accgacaaga cttccgccac cgtcatctgc    900

cgcaagaacg cctccatctc cgtccgcgcc caggaccgct actacagctc ctcttggtcc    960

gagtgggcct ccgtcccctg ctccggaggc ggtggcggcg gatcccgcgc cgtcccaggc   1020

ggaagctccc ccgcatggac ccagtgtcag cagctctccc agaagctctg caccctcgcc   1080

tggtccgccc accccctcgt cggccacatg gacctgcgcg aggagggcga cgaggagaca   1140

accaacgacg tcccccacat ccagtgcggc gacggctgcg atccacaggg cctgagggac   1200

aactcccagt tctgcctcca gcgcatccac cagggactca tcttctacga gaagctgctg   1260

ggaagcgaca tattcaccgg cgagccttcc ttgctgccag actcccctgt gggccagctc   1320
```

cacgcctccc tcctgggcct ctcccaactg ctccagcccg agggccacca ctgggagaca 1380
cagcagatcc catccctgtc cccctcccag ccctggcagc gcctgctact gcgcttcaag 1440
atcctgagat ccctccaggc cttcgtcgcc gtcgccgcca gagtgttcgc ccatggagcc 1500
gccacactga gcccc 1515

<210> SEQ ID NO 91
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 91
atgtgccacc agcagctggt gatcagctgg ttcagcctgg tgttcctggc cagccccctg 60
gtggccatct gggagctgaa gaaggacgtg tacgtggtgg agctggactg gtaccccgac 120
gcccccggcg agatggtggt gctgacctgc gacacccccg aggaggacgg catcacctgg 180
accctggacc agagcagcga ggtgctgggc agcggcaaga ccctgaccat ccaggtgaag 240
gagttcggcg acgccggcca gtacacctgc cacaagggcg gcgaggtgct gagccacagc 300
ctgctgctgc tgcacaagaa ggaggacggc atctggagca ccgacatcct gaaggaccag 360
aaggagccca agaacaagac cttcctgcgg tgcgaggcca agaactacag cggccggttc 420
acctgctggt ggctgaccac catcagcacc gacctgacct tcagcgtgaa gagcagccgg 480
ggcagcagcg acccccaggg cgtgacctgc ggcgccgcca ccctgagcgc cgagcgggtg 540
cggggcgaca acaaggagta cgagtacagc gtggagtgcc aggaggacag cgcctgcccc 600
gccgccgagg agagcctgcc catcgaggtg atggtggacg ccgtgcacaa gctgaagtac 660
gagaactaca ccagcagctt cttcatccgg gacatcatca agcccgaccc ccccaagaac 720
ctgcagctga agcccctgaa gaacagccgg caggtggagg tgagctggga gtaccccgac 780
acctggagca ccccccacag ctacttcagc ctgaccttct gcgtgcaggt gcagggcaag 840
agcaagcggg agaagaagga ccgggtgttc accgacaaga ccagcgccac cgtgatctgc 900
cggaagaacg ccagcatcag cgtgcgggcc caggaccggt actacagcag cagctggagc 960
gagtgggcca gcgtgccctg cagcggcggc ggcggcggcg gcagccgggc cgtgcccggc 1020
ggcagcagcc ccgcctggac ccagtgccag cagctgagcc agaagctgtg caccctggcc 1080
tggagcgccc accccctggt gggccacatg gacctgcggg aggagggcga cgaggagacc 1140
accaacgacg tgccccacat ccagtgcggc gacggctgcg acccccaggg cctgcgggac 1200
aacagccagt tctgcctgca gcggatccac cagggcctga tcttctacga gaagctgctg 1260
ggcagcgaca tcttcaccgg cgagcccagc ctgctgcccg acagccccgt gggccagctg 1320
cacgccagcc tgctgggcct gagccagctg ctgcagcccg agggccacca ctgggagacc 1380
cagcagatcc ccagcctgag ccccagccag ccctggcagc ggctgctgct gcggttcaag 1440
atcctgcgga gcctgcaggc cttcgtggcc gtggccgccc gggtgttcgc ccacggcgcc 1500
gccaccctga gcccc 1515

<210> SEQ ID NO 92
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 92
atgtgccacc agcagctggt gatcagctgg ttcagcctgg tgttcctggc cagccccctg 60
gtggccatct gggagctgaa gaaggacgtg tacgtggtgg agctggactg gtacccggac 120
gcgccggggg agatggtggt gctgacgtgc gacacgccgg aggaggacgg gatcacgtgg 180
acgctggacc agagcagcga ggtgctgggg agcgggaaga cgctgacgat ccaggtgaag 240
gagttcgggg acgcggggca gtacacgtgc cacaaggggg gggaggtgct gagccacagc 300
ctgctgctgc tgcacaagaa ggaggacggg atctggagca cggacatcct gaaggaccag 360
aaggagccga agaacaagac gttcctgagg tgcgaggcga agaactacag cgggaggttc 420
acgtgctggt ggctgacgac gatcagcacg gacctgacgt tcagcgtgaa gagcagcagg 480
gggagcagcg acccgcaggg ggtgacgtgc ggggcggcga cgctgagcgc ggagagggtg 540 agggggggaca acaaggagta cgagtacagc gtggagtgcc aggaggacag cgcgtgcccg 600
gcggcggagg agagcctgcc gatcgaggtg atggtggacg cggtgcacaa gctgaagtac 660
gagaactaca cgagcagctt cttcatcagg gacatcatca agccggaccc gccgaagaac 720
ctgcagctga agccgctgaa gaacagcagg caggtggagg tgagctggga gtacccggac 780
acgtggagca cgccgcacag ctacttcagc ctgacgttct gcgtgcaggt gcaggggaag 840
agcaagaggg agaagaagga cagggtgttc acggacaaga cgagcgcgac ggtgatctgc 900
aggaagaacg cgagcatcag cgtgagggcg caggacaggt actacagcag cagctggagc 960
gagtgggcga gcgtgccgtg cagcgggggg gggggggggg ggagcagggc ggtgccgggg 1020
gggagcagcc cggcgtggac gcagtgccag cagctgagcc agaagctgtg cacgctggcg 1080
tggagcgcgc acccgctggt ggggcacatg gacctgaggg aggaggggga cgaggagacg 1140
acgaacgacg tgccgcacat ccagtgcggg gacgggtgcg acccgcaggg gctgagggac 1200
aacagccagt tctgcctgca gaggatccac caggggctga tcttctacga gaagctgctg 1260
gggagcgaca tcttcacggg ggagccgagc ctgctgccgg acagcccggt ggggcagctg 1320
cacgcgagcc tgctggggct gagccagctg ctgcagccgg aggggcacca ctgggagacg 1380
cagcagatcc cgagcctgag cccgagccag ccgtggcaga ggctgctgct gaggttcaag 1440
atcctgagga gcctgcaggc gttcgtggcg gtggcggcga gggtgttcgc gcacggggcg 1500
gcgacgctga gcccg 1515

<210> SEQ ID NO 93
<211> LENGTH: 1515
<212> TYPE: DNA
<213> ORGANISM: Artificial Sequence
<220> FEATURE:
<223> OTHER INFORMATION: Synthetic: Codon optimized human IL-23 sequence

<400> SEQUENCE: 93
atgtgccacc agcagctggt gatcagctgg ttcagcctgg tgttcctggc cagccccctg 60
gtggccatct gggagctgaa gaaggacgtg tacgtcgtcg agctcgactg gtaccccgac 120
gcccccggcg agatggtcgt cctcacctgc gacacccccg aggaggacgg catcacctgg 180
accctcgacc agtcctccga ggtcctcggc tccggcaaga ccctcaccat ccaggtcaag 240
gagttcggcg acgccggcca gtacacctgc cacaagggcg gcgaggtcct ctcccactcc 300
ctcctcctcc tccacaagaa ggaggacggc atctggtcca ccgacatcct caaggaccag 360
aaggagccca agaacaagac cttcctccgc tgcgaggcca agaactactc cggccgcttc 420
acctgctggt ggctcaccac catctccacc gacctcacct tctccgtcaa gtcctcccgc 480

```
ggctcctccg acccccaggg cgtcacctgc ggcgccgcca ccctctccgc cgagcgcgtc    540
cgcggcgaca acaaggagta cgagtactcc gtcgagtgcc aggaggactc cgcctgcccc    600
gccgccgagg agtccctccc catcgaggtc atggtcgacg ccgtccacaa gctcaagtac    660
gagaactaca cctcctcctt cttcatccgc gacatcatca agcccgaccc ccccaagaac    720
ctccagctca agcccctcaa gaactcccgc caggtcgagg tctcctggga gtaccccgac    780
acctggtcca ccccccactc ctacttctcc ctcaccttct gcgtccaggt ccagggcaag    840
tccaagcgcg agaagaagga ccgcgtcttc accgacaaga cctccgccac cgtcatctgc    900
cgcaagaacg cctccatctc cgtccgcgcc caggaccgct actactcctc ctcctggtcc    960
gagtgggcct ccgtcccctg ctccggcggc ggcggcggcg gctcccgcgc cgtccccggc   1020
ggctcctccc ccgcctggac ccagtgccag cagctctccc agaagctctg caccctcgcc   1080
tggtccgccc accccctcgt cggccacatg gacctccgcg aggagggcga cgaggagacc   1140
accaacgacg tcccccacat ccagtgcggc gacggctgcg acccccaggg cctccgcgac   1200
aactcccagt tctgcctcca gcgcatccac cagggcctca tcttctacga gaagctcctc   1260
ggctccgaca tcttcaccgg cgagccctcc ctcctccccg actcccccgt cggccagctc   1320
cacgcctccc tcctcggcct ctcccagctc ctccagcccg agggccacca ctgggagacc   1380
cagcagatcc cctccctctc cccctcccag ccctggcagc gcctcctcct ccgcttcaag   1440
atcctccgct ccctccaggc cttcgtcgcc gtcgccgccc gcgtcttcgc ccacggcgcc   1500
gccaccctct ccccc                                                    1515
```

<210> SEQ ID NO 94
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 94

```
atggtgttgc agacccaggt cttcatttct ctgttgctct ggatctctgg tgcctacggg     60
tcaatgtgta aacctattac tgggactatt aatgatttga atcagcaagt gtggaccctt    120
cagggtcaga accttgtggc agttccacga agtgacagtg tgaccccagt cactgttgct    180
gttatcacat gcaagtatcc agaggctctt gagcaaggca gaggggatcc catttatttg    240
ggaatccaga atccagaaat gtgtttgtat tgtgagaagg ttggagaaca gcccacattg    300
cagctaaaag agcagaagat catggatctg tatggccaac ccgagcccgt gaaacccttc    360
cttttctacc gtgccaagac tggtaggacc tccacccttg agtctgtggc cttcccggac    420
tggttcattg cctcctccaa gagagaccag cccatcattc tgacttcaga acttgggaag    480
tcatacaaca ctgcctttga attaaatata aatgac                              516
```

<210> SEQ ID NO 95
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 95

```
atggtgctcc agacccaggt gttcatctcc ttgctcttgt ggatcagtgg cgcttacgga     60
tcaatgtgca agcctattac cggcaccatc aacgacttaa accagcaggt ttggaccctc    120
cagggccaga acctcgttgc cgtgcctcgc agcgacagcg tgacccctgt caccgtggcc    180
```

-continued gtgatcacgt gtaagtaccc tgaagcactg gagcagggca gaggcgaccc aatttatctc 240
ggaatccaga acccggagat gtgcctgtac tgcgagaagg tgggcgaaca gcctaccctg 300
cagctgaagg agcagaagat catggatctg tatggacagc ctgagccggt gaagccgttc 360
ctgttctaca gagcgaagac tggaaggaca agcaccctag agagcgtcgc cttcccggac 420
tggttcatcg ccagctcaaa gagggatcag cctatcattc tgacgtcaga gcttggcaag 480
agctacaaca ccgccttcga gcttaatatc aacgac 516

<210> SEQ ID NO 96
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 96
atggtgcttc agacccaggt gttcatcagc ctactcctct ggatcagcgg cgcctacggc 60
agcatgtgca agcccatcac cggcaccatc aacgacttaa accagcaggt gtggaccctc 120
cagggccaga accttgtggc cgtgccccgg agcgacagcg tgaccccggt gaccgttgct 180
gtgatcacct gcaagtaccc cgaggccctg gagcagggcc ggggcgaccc catctacctg 240
ggcatccaga accccgagat gtgcctgtac tgcgagaagg tgggcgagca gcccactttg 300
cagctgaagg agcagaagat catggacctg tacggccagc ccgagcccgt gaagcccttc 360
ctgttctacc gggccaagac cggccggacc agcaccctgg agagcgtggc cttccccgac 420
tggttcatcg ccagcagcaa gcgggaccag ccgatcatcc tgaccagcga gctgggcaag 480
agctacaaca ccgccttcga gctgaatatc aatgac 516

<210> SEQ ID NO 97
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 97
atggtgctcc agacgcaggt gttcatcagc ttgcttcttt ggatcagcgg agcctacggc 60
tccatgtgca agcctatcac aggcaccatc aacgacttaa accagcaggt gtggaccctc 120
cagggtcaga acttagtggc cgtgcctcgg agcgacagcg tcacgcctgt gaccgtggcc 180
gtaataacct gtaagtatcc tgaggccctg gaacagggca ggggagatcc aatatacctg 240
ggcatccaga accctgagat gtgtctctac tgcgagaagg tgggcgaaca gcctaccttg 300
cagctgaagg agcagaagat aatggacctg tacggacagc cagaaccagt caagccgttc 360
ctgttctata gagccaagac cggtagaacc tccacgctcg agtccgtggc attccctgac 420
tggttcatcg cctccagcaa gcgcgaccag ccgatcatac tgacctctga gttgggcaag 480
agctataaca ccgccttcga gctgaatatc aatgac 516

<210> SEQ ID NO 98
<211> LENGTH: 516
<212> TYPE: DNA
<213> ORGANISM: Artificial Sequence
<220> FEATURE:
<223> OTHER INFORMATION: Synthetic: Codon optimized:  hIGKV4-hIL-36g

<400> SEQUENCE: 98

-continued atggtgcttc agacccaggt gttcatcagc ttgctcctct ggatcagcgg cgcctacggc 60
agcatgtgca agcccatcac cggcaccatc aacgacctca accagcaggt ctggaccctc 120
cagggccaga acctcgtcgc cgtgcctcgc tccgactccg tcacccctgt cacggtggcc 180
gtgatcacct gcaagtaccc cgaggccctc gagcagggcc gcggcgaccc catctacctc 240
ggcatccaga accccgagat gtgcctctac tgcgagaagg tcggcgagca gcccactctg 300
cagctcaagg agcagaagat catggacctc tacggccagc ccgagcccgt caagcccttc 360
ctcttctacc gcgccaagac cggccgcacc tccaccctcg agtccgtcgc cttccccgac 420
tggttcatcg cctcctccaa gcgcgaccag cctattatcc tcacctccga gctcggcaag 480
tcctacaaca ccgccttcga gctcaacatc aatgac 516

<210> SEQ ID NO 99
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g
<400> SEQUENCE: 99
atggtgctcc agacccaggt gttcattagc ctattacttt ggatatccgg cgcttacggc 60
agcatgtgca agcctatcac cggcaccatc aacgacctca accagcaggt ttggacactc 120
cagggccaga accttgtggc cgtgcctaga tccgactctg ttacccctgt tacagtggct 180
gtgatcactt gcaagtaccc ggaagccctg gagcagggca ggggagatcc tatctatctg 240
ggtatccaga acccagaaat gtgcctttat tgcgagaagg tgggcgagca gcctacactt 300
cagctgaagg aacagaagat catggacctc tacggacagc cagaaccagt gaagcctttc 360
ctgttctacc gagccaagac cggccggacc agcaccctgg agagcgtggc gttccctgat 420
tggttcatcg cctctagcaa gagggaccaa cctatcatct taaccagtga gctgggcaag 480
agctacaaca cggccttcga gctcaacatt aatgat 516

<210> SEQ ID NO 100
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g
<400> SEQUENCE: 100
atggtgctcc agacccaggt gttcatcagc ctattgctct ggatcagcgg cgcctacggc 60
agcatgtgca agcccatcac cggcaccatc aacgacttga accagcaggt gtggaccttg 120
cagggccaga acctcgtggc cgtgccccgg agcgacagcg tgacgccagt gaccgtggcg 180
gtcatcacct gcaagtaccc cgaggccctg gagcagggcc ggggcgaccc catctacctg 240
ggcatccaga accccgagat gtgcctgtac tgcgagaagg tgggcgagca gcccaccctt 300
cagctgaagg agcagaagat catggacctg tacggccagc ccgagcccgt gaagcccttc 360
ctgttctacc gggccaagac cggccggacc agcaccctgg agagcgtggc cttccccgac 420
tggttcatcg ccagcagcaa gcgggaccag cctatcatcc tgaccagcga gctgggcaag 480
agctacaaca ccgccttcga gctgaatatc aatgac 516

<210> SEQ ID NO 101
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 101
atggtgctcc agacacaggt gttcatctct ctcctcctct ggatatccgg agcctacggc 60
tcaatgtgta agcctatcac cggcactatc aacgatttaa atcagcaggt gtggaccctt 120
cagggccaga acctcgtggc agtgccgaga agcgacagcg tgaccccggt gaccgtggcc 180
gtgatcactt gtaagtaccc agaggccctg gagcagggtc gcggcgaccc aatctatctg 240
ggtattcaga accctgagat gtgcctgtat tgcgagaagg tgggcgaaca gccgacgctg 300
cagctcaagg agcagaagat catggattta tacggccagc ctgagccggt gaagccattc 360
ctgttctaca gggccaagac gggcaggact tccaccttgg agagcgtggc tttcccggac 420
tggttcattg catcttccaa gagggaccag cctattatcc tgacaagcga gctgggcaag 480
tcatacaaca ccgccttcga gctgaacatt aatgac 516

<210> SEQ ID NO 102
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 102
atggtgctcc agacccaggt gttcatcagc ttgctcctct ggatcagcgg cgcctacggc 60
agcatgtgca agcccatcac cggcaccatc aacgacttga accagcaggt gtggaccttg 120
cagggccaga acctcgtggc cgtgccccgg agcgacagcg tgactcctgt gaccgtggcg 180
gtgatcacct gcaagtaccc cgaggccctg gagcagggcc ggggcgaccc catctacctg 240
ggcatccaga accccgagat gtgcctgtac tgcgagaagg tgggcgagca gcccaccctc 300
cagctgaagg agcagaagat catggacctg tacggccagc ccgagcccgt gaagcccttc 360
ctgttctacc gggccaagac cggccggacc agcaccctgg agagcgtggc cttccccgac 420
tggttcatcg ccagcagcaa gcgggaccag cctatcatcc tgaccagcga gctgggcaag 480
agctacaaca ccgccttcga gctgaatatc aacgac 516

<210> SEQ ID NO 103
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 103
atggtgcttc agacacaggt cttcattagc ctcttattat ggatatccgg cgcttacggc 60
tctatgtgca agcctattac cggcacaatc aacgatttga accagcaagt gtggaccctc 120
cagggccaga atttggtggc cgtgccgaga tccgatagcg tgaccccagt gaccgtggct 180
gtgattacct gtaagtaccc tgaagctctg gagcagggca ggggcgaccc aatttacctc 240
ggcatccaga accctgagat gtgtctgtac tgtgagaagg tgggcgagca gccaacttta 300
caactcaagg aacagaagat catggacctc tacggccagc cagagccggt taagcctttc 360
ctgttctata gagccaagac tggcaggacc agtaccctgg agtcagtggc tttccctgat 420
tggttcattg cctccagcaa gcgggatcag ccaattattc tgaccagcga gctgggaaag 480
agctacaaca ccgcgttcga gctgaacatc aacgat 516

<210> SEQ ID NO 104
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 104
atggtgctcc agacccaggt gttcatcagc ttgctcttgt ggatcagcgg cgcctacggc 60
agcatgtgca agcccatcac cggcaccatc aacgacctca accagcaggt ctggaccctc 120
cagggccaga acctcgtcgc cgtgcctcgc tccgactccg tcactccagt cacagtggct 180
gtgatcacct gcaagtaccc cgaggccctc gagcagggcc gcggcgaccc catctacctc 240
ggcatccaga accccgagat gtgcctctac tgcgagaagg tcggcgagca gcccaccttg 300
cagctcaagg agcagaagat catggacctc tacggccagc ccgagcccgt caagcccttc 360
ctcttctacc gcgccaagac cggccgcacc tccaccctcg agtccgtcgc cttccccgac 420
tggttcatcg cctcctccaa gcgcgaccag cctattatcc tcacctccga gctcggcaag 480
tcctacaaca ccgccttcga gctcaatatc aacgac 516

<210> SEQ ID NO 105
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 105
atggtcctcc agacccaagt cttcatctcc ttgttgctct ggatcagcgg ggcctacggc 60
tctatgtgta agcccattac cggcaccatc aacgacctca accaacaggt ctggaccctt 120
cagggtcaga acctcgtcgc cgtgcccaga tccgactccg tgacccctgt caccgtggcc 180
gtgatcacct gcaaatatcc cgaggccctg gagcaggggc gcggcgaccc catatacctg 240
ggcatccaga accccgagat gtgcctctac tgcgagaagg tgggcgaaca gcccaccctc 300
cagctgaagg agcagaagat catggacctg tacggccagc ccgagcccgt gaagcccttc 360
ctgttctata gggccaagac cggccgcacc tccaccctgg agtccgtggc cttccccgat 420
tggtttattg ccagtagcaa gagggaccag cccatcatcc tcaccagcga actgggcaag 480
agctacaaca ccgccttcga gctgaacatc aatgac 516

<210> SEQ ID NO 106
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 106
atggtgctcc agacacaggt gttcatcagc ctcctcctct ggatcagcgg ggcctacggc 60
agcatgtgca agcccatcac aggcaccatc aacgacctca atcagcaagt ctggaccctc 120
cagggtcaga acctcgtggc cgtgccccgc agcgacagcg tgacgcccgt gacagtggcc 180
gtcatcacgt gcaaataccc cgaagccctg gagcagggcc gtggcgaccc tatctacctg 240
ggcatacaga accccgagat gtgcctgtac tgcgagaagg tgggtgagca gcccaccctg 300
caactgaagg agcagaagat catggacctc tacggacaac cggagcccgt gaaacccttc 360
ctgttctaca gggccaagac cgggaggacc tccaccctgg aaagcgtggc ctttcccgac 420
tggtttatcg ccagctccaa gagggaccaa cccatcatcc tcaccagcga gctgggcaag 480
tcttacaaca ccgcctttga gctgaacatc aatgat 516

<210> SEQ ID NO 107
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 107
atggtgctcc agacccaggt gttcatcagc ctcctcctct ggatcagcgg ggcctacggg 60
agcatgtgca agcccatcac cgggaccatc aacgacctca accagcaggt ctggacgctc 120
caggggcaga atctcgtggc cgtgcccaga tccgacagcg tgaccccggt gaccgtggcc 180
gtcatcacct gtaagtaccc ggaggccctg gaacagggcc gaggtgaccc catctatctg 240
ggtatccaga atccggagat gtgcctgtac tgcgagaagg tgggcgagca gcccaccctg 300
cagctgaagg agcagaagat catggacctg tacggccaac ccgagcccgt gaagcccttc 360
ctgttttaca gggccaagac cggccggacg agcaccctgg agagcgtggc ctttcccgac 420
tggttcatcg ccagtagcaa gagggaccaa cccatcatcc tgacctccga gctgggcaag 480
agctacaata ccgccttcga gctcaacatc aatgat 516

<210> SEQ ID NO 108
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 108
atggtcctac agacccaagt gttcatcagc ctccttctct ggatcagcgg agcctacggc 60
tccatgtgta agcccatcac cggcactatc aacgacctca atcagcaggt gtggacactc 120
cagggccaga acctcgtggc cgtgcccaga agcgacagcg tgaccccggt caccgtcgcc 180
gtgatcacct gcaaatatcc cgaggccctg gagcagggcc gaggggaccc catctacctc 240
gggatccaga acccggagat gtgtctgtat tgtgagaagg tcggcgagca acctaccctg 300
cagctgaagg agcagaagat catggacctg tacggccagc ccgagccggt gaaaccgttc 360
ctgttctacc gggccaagac cggcagaacc agcaccctgg aaagcgtggc ctttcccgac 420
tggttcatcg cgagcagtaa acgggaccaa cccatcatcc tgaccagcga gctgggcaag 480
agctacaaca ccgcgtttga gctgaacatc aacgac 516

<210> SEQ ID NO 109
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 109
atggtgctac agacccaggt gttcatcagc ctcctacttt ggatcagcgg ggcgtacggc 60
agcatgtgca aacccatcac aggaaccatc aacgacctta accagcaggt ctggacactc 120
cagggccaga acctcgtggc cgtgcccagg agcgattccg tcacgcccgt gaccgtggct 180
gtgatcacct gcaagtaccc cgaggccctg gagcaggggc gaggggaccc catctacctg 240
ggcatccaga accccgagat gtgcctgtac tgcgagaagg tcggtgaaca gcccaccctc 300
caactcaagg agcagaagat tatggacctg tacggccagc cagagcccgt gaagccattt 360
ctgttctata gggccaagac cggccgcacc tccaccctgg agtccgtggc cttccccgac 420
tggttcatcg ccagcagcaa acgggaccag cccatcattc tgaccagcga actgggcaag 480
agctacaata ccgccttcga gcttaatatc aatgac 516

<210> SEQ ID NO 110
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 110
atggtgctcc aaactcaggt gttcatcagc ctcctcctct ggatcagcgg ggcgtacggc 60
agcatgtgta agcccatcac cggcaccatc aacgacctca accagcaagt gtggaccttg 120
cagggccaga atctcgtggc cgtgcccagg tccgacagcg tgacgcccgt gactgtggcc 180
gtcatcacct gcaaatatcc ggaggcgctg gagcagggca gaggcgatcc catctatctc 240
gggatccaga accccgagat gtgcctgtat tgcgagaagg tcggcgagca gcccaccctc 300
cagctgaagg agcagaagat catggacctg tatggccagc ccgagcccgt gaagcccttc 360
ctgttctacc gggcgaagac cggccgcacc tccaccctgg aaagcgtggc cttccccgat 420
tggttcatcg cgtccagcaa gagggaccag ccgatcatcc tgacctcaga gctgggcaag 480
tcctacaaca ccgccttcga gctgaatatc aacgac 516

<210> SEQ ID NO 111
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 111
atggtgctcc agacccaggt gttcataagc ctcctcctct ggatcagcgg cgcctacggc 60
tctatgtgca agcccatcac cgggaccatc aacgacctca accagcaggt gtggacccta 120
cagggccaga acctcgtggc cgtgccccgg agcgactctg tgactcccgt caccgtggcc 180
gtcatcacct gcaagtaccc cgaggccctg gagcagggca ggggcgaccc gatctatctg 240
ggcatccaga atcccgagat gtgcctctac tgcgagaagg tgggcgaaca gcccaccctc 300
cagctgaagg agcagaagat aatggatctg tacggtcagc ccgagcccgt gaagccgttc 360
ctgttctacc gggccaagac gggaaggaca agcaccctgg agagcgtggc atttcccgac 420
tggttcatcg ccagctccaa gagggatcag cccataatcc tgaccagcga gctgggcaag 480
agctacaaca ccgccttcga gctgaatatc aacgac 516

<210> SEQ ID NO 112
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 112
atggtgctcc agacccaagt cttcatcagc ctcctcctct ggatctccgg cgcctacggg 60
agcatgtgca agcccatcac gggcaccatc aacgacctca atcagcaggt ctggaccctc 120
cagggtcaga acctcgtggc cgtccccagg tccgacagcg tgaccccggt gaccgtggcc 180
gtgatcacct gcaagtaccc cgaggcgctg gagcaaggcc ggggcgaccc catctacctg 240
ggtatccaga accccgagat gtgcctgtac tgtgagaaag tgggcgagca gcccacactg 300
cagctgaagg agcagaagat catggatctg tacggtcagc ccgagcccgt gaaacccttc 360
ctgttttaca gggccaagac cggcaggacc agcaccctgg agagcgtggc cttcccggac 420
tggttcatcg ccagcagtaa gagggaccaa cccataatac tgaccagcga gctcggcaag 480
agctacaata ccgccttcga gctgaatatc aacgac 516

<210> SEQ ID NO 113
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 113
atggtgttgc agacacaggt gttcatcagc ctcctcctct ggatcagcgg cgcttacggc 60
agcatgtgca agcccatcac cggcaccatc aacgatctca atcagcaggt gtggaccctc 120
cagggccaga atctcgtagc cgttcccaga agcgacagcg tgacgcccgt cacggtggct 180
gtgatcacgt gcaaataccc agaggcactc gagcagggca gaggcgatcc tatctacctg 240
ggaatccaga accccgagat gtgcctgtac tgcgagaagg tcggagagca gcctaccctg 300
caactgaagg agcagaagat aatggacctg tacggacagc ccgagcccgt gaagccattt 360
ctgttctaca gagccaagac cggaagaaca agcacactgg aaagcgtggc atttcctgac 420
tggttcattg ccagctccaa gcgggaccag cccataatcc tcacctctga gctgggcaag 480
agctacaaca ccgccttcga gctgaacatc aacgac 516

<210> SEQ ID NO 114
<211> LENGTH: 516
<212> TYPE: DNA
<213> ORGANISM: Artificial Sequence
<220> FEATURE:
<223> OTHER INFORMATION: Synthetic: Codon optimized hIGKV4-hIL-36g

<400> SEQUENCE: 114
atggtgctcc agacacaggt gttcatcagc ctcctcctct ggatcagtgg cgcgtacgga 60
tcaatgtgca agcccatcac aggcaccatt aacgatctca accagcaggt gtggaccctc 120
cagggccaga acctcgtggc cgtgcccagg tccgacagcg tgactcctgt cacagtagcc 180
gtgatcacct gcaagtaccc cgaggcactt gagcagggcc ggggcgaccc catctacctg 240
gggatccaga accctgagat gtgtctgtac tgcgagaaag tgggcgagca gcccacactg 300
cagctcaagg agcagaagat catggatctg tatggccagc ccgagcccgt gaagcctttc 360
ctgttttatc gcgccaagac aggacggact tcaaccttgg aatccgtggc tttccccgac 420
tggttcatcg cgtcttccaa gagggaccag cctatcattc ttacctcaga gctgggcaaa 480
tcatataaca cagctttcga gctgaacatc aatgac 516

<210> SEQ ID NO 115
<211> LENGTH: 516
<212> TYPE: DNA
<213> ORGANISM: Artificial Sequence
<220> FEATURE:
<223> OTHER INFORMATION: Synthetic: Codon optimized murine mIL-2-mIL-36g

<400> SEQUENCE: 115
atgtacagca tgcagctcgc atcctgtgtc acattgacac ttgtgctcct tgtcaacagc 60
ggaagagaaa ctcctgactt tggggaggtt tttgacttgg accagcaggt gtggatcttt 120
cgtaatcagg cccttgtgac agttccacga agccacagag taaccccagt cagcgtgact 180
atcctcccat gcaagtaccc agagtctctt gaacaggaca aagggattgc catttatttg 240
ggaattcaga atccagataa atgcctgttt tgtaaggaag ttaatggaca ccctactttg 300
ctgctaaagg aagagaagat tttggatttg taccaccacc ctgagccaat gaagccattc 360
ctgttttacc acacccggac aggtggaaca tccacctttg aatcagtggc tttccctggc 420
cactatattg cctcctccaa gactggcaac cccatcttcc tcacatcaaa gaagggagaa 480
tattacaaca ttaacttcaa tttagatata aagtct 516

<210> SEQ ID NO 116
<211> LENGTH: 549
<212> TYPE: DNA
<213> ORGANISM: Artificial Sequence
<220> FEATURE:
<223> OTHER INFORMATION: Synthetic: Codon optimized human OX40L

<400> SEQUENCE: 116
atggaaaggg tccaacccct ggaagagaat gtgggaaatg cagccaggcc aagattcgag 60
aggaacaagc tattgctggt ggcctctgta attcagggac tggggctgct cctgtgcttc 120
acctacatct gcctgcactt ctctgctctt caggtatcac atcggtatcc tcgaattcaa 180
agtatcaaag tacaatttac cgaatataag aaggagaaag gtttcatcct cacttcccaa 240
aaggaggatg aaatcatgaa ggtgcagaac aactcagtca tcatcaactg tgatgggttt 300
tatctcatct ccctgaaggg ctacttctcc caggaagtca acattagcct tcattaccag 360
aaggatgagg agcccctctt ccaactgaag aaggtcaggt ctgtcaactc cttgatggtg 420
gcctctctga cttacaaaga caaagtctac ttgaatgtga ccactgacaa tacctccctg 480
gatgacttcc atgtgaatgg cggagaactg attcttatcc atcaaaatcc tggtgaattc 540
tgtgtcctt 549

<210> SEQ ID NO 117
<211> LENGTH: 594
<212> TYPE: DNA
<213> ORGANISM: Artificial Sequence
<220> FEATURE:
<223> OTHER INFORMATION: Synthetic: Codon optimized mouse OX40L

<400> SEQUENCE: 117
atggaagggg aaggggttca acccctggat gagaatctgg aaaacggatc aaggccaaga 60
ttcaagtgga agaagacgct aaggctggtg gtctctggga tcaagggagc agggatgctt 120
ctgtgcttca tctatgtctg cctgcaactc tcttcctctc cggcaaagga ccctccaatc 180
caaagactca gaggagcagt taccagatgt gaggatgggc aactattcat cagctcatac 240
aagaatgagt atcaaactat ggaggtgcag aacaattcgg ttgtcatcaa gtgcgatggg 300
ctttatatca tctacctgaa gggctccttt ttccaggagg tcaagattga ccttcatttc 360
cgggaggatc ataatcccat ctctattcca atgctgaacg atggtcgaag gattgtcttc 420
actgtggtgg cctctttggc tttcaaagat aaagtttacc tgactgtaaa tgctcctgat 480
actctctgcg aacacctcca gataaatgat ggggagctga ttgttgtcca gctaacgcct 540
ggatactgtg ctcctgaagg atcttaccac agcactgtga accaagtacc actg 594

<210> SEQ ID NO 118
<211> LENGTH: 92
<212> TYPE: RNA
<213> ORGANISM: Artificial Sequence
<220> FEATURE:
<223> OTHER INFORMATION: Synthetic: 5UTR-019

<400> SEQUENCE: 118
ucaagcuuuu ggacccucgu acagaagcua auacgacuca cuauagggaa auaagagaga 60
aaagaagagu aagaagaaau auaagagcca cc 92

<210> SEQ ID NO 119
<211> LENGTH: 118
<212> TYPE: RNA
<213> ORGANISM: Artificial Sequence
<220> FEATURE:
<223> OTHER INFORMATION: Synthetic: 3UTR-019

<400> SEQUENCE: 119
ugauaauagg cuggagccuc gguggccaug cuucuugccc cuugggccuc cccccagccc 60
cuccuccccu uccugcaccc guacccccug gucuuugaau aaagucugag ugggcggc 118

<210> SEQ ID NO 120
<211> LENGTH: 141
<212> TYPE: RNA
<213> ORGANISM: Artificial Sequence
<220> FEATURE:
<223> OTHER INFORMATION: Synthetic: 3UTR-019 + miR-122 binding site

<400> SEQUENCE: 120
ugauaauagg cuggagccuc gguggccaug cuucuugccc cuugggccuc cccccagccc 60
cuccuccccu uccugcaccc guacccccca aacaccauug ucacacucca guggucuuug 120
aauaaagucu gagugggcgg c 141

<210> SEQ ID NO 121
<211> LENGTH: 549
<212> TYPE: RNA
<213> ORGANISM: Artificial Sequence
<220> FEATURE:
<223> OTHER INFORMATION: Synthetic: Codon-optimized sequence 1 for ENSP
281834

<400> SEQUENCE: 121
auggagagag ugcagccccu ggaggagaac gugggcaacg ccgccagacc cagauucgag 60
agaaacaagc ugcugcuggu ggccagcgug auccagggcc ugggccugcu gcugugcuuc 120
accuacaucu gccugcacuu cagcgcccug caggugagcc acagauaccc cagaauccag 180
agcaucaagg ugcaguucac cgaguacaag aaggagaagg gcuucauccu gaccagccag 240
aaggaggacg agaucaugaa ggugcagaac aacagcguga ucaucaacug cgacggcuuc 300
uaccugauca gccugaaggg cuacuucagc caggagguga acaucagccu gcacuaccag 360
aaggacgagg agccccuguu ccagcugaag aaggugagaa gcgugaacag ccugauggug 420
gccagccuga ccuacaagga caagguguac cugaacguga ccaccgacaa caccagccug 480
gacgacuucc acgugaacgg cggcgagcug auccugaucc accagaaccc cggcgaguuc 540
ugcgugcug 549

<210> SEQ ID NO 122
<211> LENGTH: 549

<212> TYPE: RNA
<213> ORGANISM: Artificial Sequence
<220> FEATURE:
<223> OTHER INFORMATION: Synthetic: Codon-optimized sequence 2 for ENSP 281834

<400> SEQUENCE: 122
auggagcgug ugcagccucu ugaggagaau gugggaaaug cagcccggcc ucgauucgaa 60
cguaauaaac uccugcucgu ggccuccgug auccagggguc ucgguuuauu gcuguguuuu 120
accuauauau gcuuacacuu uagugcauua caggucucac accgguaccc ucgcauucag 180
ucuauaaaag ugcaguuuac cgaguauaag aaggagaaag guuuuauacu gacuucucag 240
aaagaggacg agaucaugaa ggugcagaau aauagcguca uuaucaacug cgauggauuc 300
uaucuaauuu cccuaaaggg guacuucagc caggagguca auauaucacu gcacuaucaa 360
aaggacgagg agccccuguu ucaacugaag aaagugcgau caguuaacuc ucugaugguu 420
gccucucuga ccuauaagga caaagucuac uugaacguga caacugacaa caccucacug 480
gaugacuuuc augugaaugg gggggaacug auucuuaucc aucagaaucc aggagaauuc 540
ugugugcuc 549

<210> SEQ ID NO 123
<211> LENGTH: 549
<212> TYPE: RNA
<213> ORGANISM: Artificial Sequence
<220> FEATURE:
<223> OTHER INFORMATION: Synthetic: Codon-optimized sequence 3 for ENSP 281834

<400> SEQUENCE: 123
auggagcggg ugcagccccu ggaggagaau gugggcaaug cugcccggcc cagguuugaa 60
agaaacaagc ugcugcuggu ggccagcguc auccagggcc ugggccugcu gcugugcuuc 120
accuacaucu gccugcacuu cagcgcccug caggugagcc accgcuaccc ccgcauccag 180
agcaucaagg ugcaguucac agaguacaag aaggagaagg gcuucauccu gaccagccag 240
aaggaggaug agaucaugaa ggugcagaac aacagcguca ucaucaacug ugauggcuuc 300
uaccugauca gccugaaggg cuacuucagc caggagguga acaucagccu gcacuaccag 360
aaggaugagg agccccucuu ccagcugaag aaggugcgcu cugugaacag ccugauggug 420
gccagccuga ccuacaagga caagguguac cugaauguga ccacagacaa caccagccug 480
gaugacuucc acgugaaugg aggagagcug auccugaucc accagaaccc uggagaguuc 540
ugugugcug 549

<210> SEQ ID NO 124
<211> LENGTH: 549
<212> TYPE: RNA
<213> ORGANISM: Artificial Sequence
<220> FEATURE:
<223> OTHER INFORMATION: Synthetic: Codon-optimized sequence 4 for ENSP 281834

<400> SEQUENCE: 124
auggagcggg ugcagccccu ggaggagaac guggggcaacg ccgcccgccc gcguuuugag 60
cgaaauaagu uacugcuugu ugcaucugug auacaggggu uggguuuacu ucuuugcuuu 120
acauauauuu gucuccacuu uagugcgcuu cagguauccc aucgguaccc gcgcauccag 180
ucaaucaagg uccaguucac ugaauauaaa aaggagaaag gauucauucu gacuucacaa 240
aaagaggacg aaaucaugaa agugcagaac aacucuguaa uuauaaacug cgaugggguuc 300

```
uaucugauca gucugaaggg auauuuuagc caggaaguaa auauuucacu acauuaucag    360

aaggacgaag aaccacuuuu ucaacugaag aaaguccggu ccgugaacuc ccugaugguu    420

gcuagccuua ccuacaagga uaaagucuau uuaaacguca caacagauaa cacuagccuc    480

gacgauuucc augugaacgg aggugaacug auauugaucc aucaaaaccc cggcgaguuc    540

ugcguuuua                                                            549
```

<210> SEQ ID NO 125
<211> LENGTH: 549
<212> TYPE: RNA
<213> ORGANISM: Artificial Sequence
<220> FEATURE:
<223> OTHER INFORMATION: Synthetic: Codon-optimized sequence 5 for ENSP 281834

<400> SEQUENCE: 125

```
auggagcggg uccagccccu cgaggagaac guugguaaug ccgcacgucc cagguuugaa     60

cgcaacaagc ugcuguuggu ggccagcguc auucaggggc uggguuuguu gcugugcuuc    120

acuuacaucu gucugcauuu uagugcacuc caggugcccc accgcuaccc ccguauccaa    180

uccauuaaag uccaauuuac cgaauacaaa aaagagaagg guuucauucu uaccucccag    240

aaggaggaug aaauuaugaa ggugcagaac aauucuguua ucaucaacug ugacggauuc    300

uaucugauuu cacugaaggg auacuuuucc caggagguga acaucagucu gcauuaucag    360

aaggacgaag aaccgcuuuu ucaacugaag aagguuagga gugugaacuc cuuaauggua    420

gccagccuga cauauaagga caagguauau cugaacguca ccacugauaa caccucuuua    480

gacgauuuuc auguaaaugg gggagaauug auacucauuc accagaaucc gggugaguuu    540

uguguucug                                                            549
```

<210> SEQ ID NO 126
<211> LENGTH: 399
<212> TYPE: RNA
<213> ORGANISM: Artificial Sequence
<220> FEATURE:
<223> OTHER INFORMATION: Synthetic: Codon-optimized sequence 1 for ENSP 356691

<400> SEQUENCE: 126

```
auggugagcc acagauaccc cagaauccag agcaucaagg ugcaguucac cgaguacaag     60

aaggagaagg gcuucauccu gaccagccag aaggaggacg agaucaugaa ggugcagaac    120

aacagcguga ucaucaacug cgacggcuuc uaccugauca gccugaaggg cuacuucagc    180

caggagguga acaucagccu gcacuaccag aaggacgagg agccccuguu ccagcugaag    240

aaggugagaa gcgugaacag ccugauggug gccagccuga ccuacaagga caagguguac    300

cugaacguga ccaccgacaa caccagccug gacgacuucc acgugaacgg cggcgagcug    360

auccugaucc accagaaccc cggcgaguuc ugcgugcug                           399
```

<210> SEQ ID NO 127
<211> LENGTH: 399
<212> TYPE: RNA
<213> ORGANISM: Artificial Sequence
<220> FEATURE:
<223> OTHER INFORMATION: Synthetic: Codon-optimized sequence 2 for ENSP 356691

<400> SEQUENCE: 127

```
augguuucuc accguuaccc acggauccag ucuaucaagg uucaguuuac cgaguacaaa     60
```

aaggaaaaag gguucauccu caccucucag aaagaggacg aaaucaugaa ggugcagaau 120
aacucuguaa ucauuaauug cgacgguuuu uaucugauuu cacugaaggg cuacuuuagu 180
caggaaguua auauuaguuu gcacuaccaa aaggacgagg agccucucuu ccaacuaaaa 240
aagguaagau ccguuaauuc ccuuauggug gccuccuuaa cuuauaagga caaggugua u 300 cugaauguga ccacagauaa cacaucccug gacgacuuuc auguaaaugg cggcgaguua 360
auucugauac accagaaccc uggcgaguuc ugcgugcug 399

<210> SEQ ID NO 128
<211> LENGTH: 399
<212> TYPE: RNA
<213> ORGANISM: Artificial Sequence
<220> FEATURE:
<223> OTHER INFORMATION: Synthetic: Codon-optimized sequence 3 for ENSP 356691

<400> SEQUENCE: 128
auggugagcc accgcuaccc ccgcauccag agcaucaagg ugcaguucac agaguacaag 60
aaggagaagg gcuucauccu gaccagccag aaggaggaug agaucaugaa ggugcagaac 120
aacagcguca ucaucaacug ugauggcuuc uaccugauca gccugaaggg cuacuucagc 180
caggagguga acaucagccu gcacuaccag aaggaugagg agccccucuu ccagcugaag 240
aaggugcgcu cugugaacag ccugauggug gccagccuga ccuacaagga caagguguac 300
cugaauguga ccacagacaa caccagccug gaugacuucc acgugaaugg aggagagcug 360
auccugaucc accagaaccc uggagaguuc ugugugcug 399

<210> SEQ ID NO 129
<211> LENGTH: 399
<212> TYPE: RNA
<213> ORGANISM: Artificial Sequence
<220> FEATURE:
<223> OTHER INFORMATION: Synthetic: Codon-optimized sequence 4 for ENSP 356691

<400> SEQUENCE: 129
auggugagcc accgguaccc ccggauccag agcaucaagg ugcaguucac cgaauacaag 60
aaggagaagg guuuuauccu gacgagccag aaggaagacg agauuaugaa gguccaaaac 120
aacucaguca ucauaaacug cgauggauuu uaccugaucu cucugaaagg guacuucucc 180
caggaaguga auauuagcuu gcacuaucaa aaagaugagg agccucuauu ccagcucaag 240
aaggucagaa gcgucaauag ucugaugguc gcaucauuaa ccuauaaaga caaaguauau 300
cuaaauguga cgacagacaa uacaucccuc gaugauuuuc acgucaacgg aggcgaacuc 360
auucugaucc accagaaucc aggggaauuu ugcgugcug 399

<210> SEQ ID NO 130
<211> LENGTH: 399
<212> TYPE: RNA
<213> ORGANISM: Artificial Sequence
<220> FEATURE:
<223> OTHER INFORMATION: Synthetic: Codon-optimized sequence 5 for ENSP 356691

<400> SEQUENCE: 130
auggucucac accgguaccc ccguauccag aguauuaagg ugcaauucac ggaguauaaa 60
aaagaaaagg gauucauucu gacgucucag aaggaagaug agaucaugaa gguccagaac 120
aauucuguga ucauuaauug cgauggauuu uaucugauuu cacuuaaagg auauuuuucc 180
caggagguua auaucaguuu gcacuaucag aaagacgagg agccauuauu ccagcugaag 240
aaggugagau cagugaauag ccugaugguu gcgucacuga cguauaaaga caaaguuuau 300
cuaaacguua ccacugauaa uacaucccuu gaugauuuuc augugaacgg gggugaacug 360
auccuuauac accagaaccc cggagaguuc uguguguug 399

<210> SEQ ID NO 131
<211> LENGTH: 399
<212> TYPE: RNA
<213> ORGANISM: Artificial Sequence
<220> FEATURE:
<223> OTHER INFORMATION: Synthetic: Codon-optimized sequence 1 for ENSP 439704

<400> SEQUENCE: 131
auggugagcc acagauaccc cagaauccag agcaucaagg ugcaguucac cgaguacaag 60
aaggagaagg gcuucauccu gaccagccag aaggaggacg agaucaugaa ggugcagaac 120
aacagcguga ucaucaacug cgacggcuuc uaccugauca gccugaaggg cuacuucagc 180 caggaggug a acaucagccu gcacuaccag aaggacgagg agccccuguu ccagcugaag 240
aaggugagaa gcgugaacag ccugauggug gccagccuga ccuacaagga caagguguac 300
cugaacguga ccaccgacaa caccagccug gacgacuucc acgugaacgg cggcgagcug 360
auccugaucc accagaaccc cggcgaguuc ugcgugcug 399

<210> SEQ ID NO 132
<211> LENGTH: 399
<212> TYPE: RNA
<213> ORGANISM: Artificial Sequence
<220> FEATURE:
<223> OTHER INFORMATION: Synthetic: Codon-optimized sequence 2 for ENSP 439704

<400> SEQUENCE: 132
auggugucac accgguaccc ucggauccag ucuauuaaag uucaauuuac ggaguacaag 60
aaagaaaaag gcuuuauccu uacaagccaa aaggaagacg agaucaugaa agugcaaaac 120 aacagugug a uuauaaauug ugauggcuuc uaccuuauua gucugaaggg cuacuuuagu 180
caggaaguca auauuagccu acacuaccag aaagacgagg agccccucuu ucaacugaaa 240
aaggugcgcu ccgugaauuc guugauggu c gccucucuga ccuacaaaga uaaggugua u 300 cuuaacguua cuaccgacaa uacuagucug gacgacuuuc acgucaacgg aggcgaacuu 360
auucugaucc accagaaccc cggcgaauuc ugcgugcug 399

<210> SEQ ID NO 133
<211> LENGTH: 399
<212> TYPE: RNA
<213> ORGANISM: Artificial Sequence
<220> FEATURE:
<223> OTHER INFORMATION: Synthetic: Codon-optimized sequence 3 for ENSP 439704

<400> SEQUENCE: 133
auggugagcc accgcuaccc ccgcauccag agcaucaagg ugcaguucac agaguacaag 60
aaggagaagg gcuucauccu gaccagccag aaggaggaug agaucaugaa ggugcagaac 120
aacagcguca ucaucaacug ugauggcuuc uaccugauca gccugaaggg cuacuucagc 180 caggaggug a acaucagccu gcacuaccag aaggaugagg agccccucuu ccagcugaag 240
aaggugcgcu cugugaacag ccugauggug gccagccuga ccuacaagga caagguguac 300
cugaauguga ccacagacaa caccagccug gaugacuucc acgugaaugg aggagagcug 360
auccugaucc accagaaccc uggagaguuc ugugugcug 399

<210> SEQ ID NO 134
<211> LENGTH: 399
<212> TYPE: RNA
<213> ORGANISM: Artificial Sequence
<220> FEATURE:
<223> OTHER INFORMATION: Synthetic: Codon-optimized sequence 4 for ENSP 439704

<400> SEQUENCE: 134
auggugagcc accgguaccc ccggauccag agcaucaagg ugcaguucac agaguacaag 60
aaggagaagg gauuuauucu cacaagucag aaagaagaug agaucaugaa gguucagaac 120
aacucaguca uuauuaauug cgacggauuc uaucucauua gccucaaagg cuauuucagc 180
caggagguca auaucagccu gcacuaccag aaggaugagg aaccucucuu ucagcugaaa 240
aaaguccgcu cugugaauuc ccucaugguc gcuucccuga ccuacaagga uaaaguuuau 300
uugaacguua caacagauaa uacaucgcug gacgacuucc augugaaugg uggcgaacua 360
auucuaauac accaaaaucc aggcgaauuu uguguccuu 399

<210> SEQ ID NO 135
<211> LENGTH: 399
<212> TYPE: RNA
<213> ORGANISM: Artificial Sequence
<220> FEATURE:
<223> OTHER INFORMATION: Synthetic: Codon-optimized sequence 5 for ENSP 439704

<400> SEQUENCE: 135
augguauccc auagauaccc acguauucaa agcauuaagg ugcaguucac agaguacaaa 60
aaggagaagg guuucauacu gacgucacag aaggaggacg agauaaugaa ggugcagaau 120
aauagaguga ucaucaauug ugauggauuc uauuugauca gccucaaagg uuauuucuca 180
caggaaguca acauuucccu gcacuaccag aaggacgaag agccuuuguu ucagcugaag 240
aaggugcgcu cagugaacag uuugauggua gccucccuaa cuuauaaaga uaaaguuuau 300
cugaacguga caaccgauaa cacaucccug gacgacuuuc acgucaaugg aggugaguua 360
auccugaucc aucagaaucc cggagaauuc ugcguucuu 399

<210> SEQ ID NO 136
<211> LENGTH: 5
<212> TYPE: PRT
<213> ORGANISM: Artificial Sequence
<220> FEATURE:
<223> OTHER INFORMATION: Synthetic: linker

<400> SEQUENCE: 136

Gly Gly Gly Gly Ser
1 5

<210> SEQ ID NO 137
<211> LENGTH: 6
<212> TYPE: PRT
<213> ORGANISM: Artificial Sequence
<220> FEATURE:
<223> OTHER INFORMATION: Synthetic: linker

<400> SEQUENCE: 137

Gly Gly Gly Gly Gly Ser 1 5

<210> SEQ ID NO 138
<211> LENGTH: 7
<212> TYPE: PRT
<213> ORGANISM: Artificial Sequence
<220> FEATURE:
<223> OTHER INFORMATION: Synthetic: linker

<400> SEQUENCE: 138

Gly Gly Gly Gly Gly Gly Ser
1 5

<210> SEQ ID NO 139
<211> LENGTH: 8
<212> TYPE: PRT
<213> ORGANISM: Artificial Sequence
<220> FEATURE:
<223> OTHER INFORMATION: Synthetic: linker

<400> SEQUENCE: 139

Gly Gly Gly Gly Gly Gly Gly Ser
1 5

<210> SEQ ID NO 140
<211> LENGTH: 505
<212> TYPE: PRT
<213> ORGANISM: Homo sapiens
<220> FEATURE:
<221> NAME/KEY: misc_feature
<222> LOCATION: (1)..(505)
<223> OTHER INFORMATION: Amino Acid sequence of human IL-23 (IL-12p40 subunit and IL-23p19 subunit linked by GS Linker)

<400> SEQUENCE: 140

Met Cys His Gln Gln Leu Val Ile Ser Trp Phe Ser Leu Val Phe Leu
1 5 10 15

Ala Ser Pro Leu Val Ala Ile Trp Glu Leu Lys Lys Asp Val Tyr Val
20 25 30

Val Glu Leu Asp Trp Tyr Pro Asp Ala Pro Gly Glu Met Val Val Leu
35 40 45

Thr Cys Asp Thr Pro Glu Glu Asp Gly Ile Thr Trp Thr Leu Asp Gln
50 55 60

Ser Ser Glu Val Leu Gly Ser Gly Lys Thr Leu Thr Ile Gln Val Lys
65 70 75 80

Glu Phe Gly Asp Ala Gly Gln Tyr Thr Cys His Lys Gly Gly Glu Val
85 90 95

Leu Ser His Ser Leu Leu Leu Leu His Lys Lys Glu Asp Gly Ile Trp
100 105 110

Ser Thr Asp Ile Leu Lys Asp Gln Lys Glu Pro Lys Asn Lys Thr Phe
115 120 125

Leu Arg Cys Glu Ala Lys Asn Tyr Ser Gly Arg Phe Thr Cys Trp Trp
130 135 140

Leu Thr Thr Ile Ser Thr Asp Leu Thr Phe Ser Val Lys Ser Ser Arg
145 150 155 160

Gly Ser Ser Asp Pro Gln Gly Val Thr Cys Gly Ala Ala Thr Leu Ser
165 170 175

Ala Glu Arg Val Arg Gly Asp Asn Lys Glu Tyr Glu Tyr Ser Val Glu
180 185 190

Cys Gln Glu Asp Ser Ala Cys Pro Ala Ala Glu Glu Ser Leu Pro Ile
195 200 205

```
Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Gly Gly Ser Arg
                325                 330                 335

Ala Val Pro Gly Gly Ser Ser Pro Ala Trp Thr Gln Cys Gln Gln Leu
            340                 345                 350

Ser Gln Lys Leu Cys Thr Leu Ala Trp Ser Ala His Pro Leu Val Gly
        355                 360                 365

His Met Asp Leu Arg Glu Glu Gly Asp Glu Glu Thr Thr Asn Asp Val
    370                 375                 380

Pro His Ile Gln Cys Gly Asp Gly Cys Asp Pro Gln Gly Leu Arg Asp
385                 390                 395                 400

Asn Ser Gln Phe Cys Leu Gln Arg Ile His Gln Gly Leu Ile Phe Tyr
                405                 410                 415

Glu Lys Leu Leu Gly Ser Asp Ile Phe Thr Gly Glu Pro Ser Leu Leu
            420                 425                 430

Pro Asp Ser Pro Val Gly Gln Leu His Ala Ser Leu Leu Gly Leu Ser
        435                 440                 445

Gln Leu Leu Gln Pro Glu Gly His His Trp Glu Thr Gln Gln Ile Pro
    450                 455                 460

Ser Leu Ser Pro Ser Gln Pro Trp Gln Arg Leu Leu Leu Arg Phe Lys
465                 470                 475                 480

Ile Leu Arg Ser Leu Gln Ala Phe Val Ala Val Ala Ala Arg Val Phe
                485                 490                 495

Ala His Gly Ala Ala Thr Leu Ser Pro
            500                 505
```

<210> SEQ ID NO 141
<211> LENGTH: 1515
<212> TYPE: RNA
<213> ORGANISM: Homo sapiens
<220> FEATURE:
<221> NAME/KEY: misc_feature
<222> LOCATION: (1)..(1515)
<223> OTHER INFORMATION: Nucleotide sequence (ORF) of human IL-23 (IL-12p40 subunit and IL-23p19 subunit linked by GS Linker)

<400> SEQUENCE: 141

```
augugucacc agcaguuggu caucucuugg uuuucccugg uauuucuggc aucuccccuc      60

guggccauau gggaacugaa gaaagauguu uaugucguag aauuggauug guauccggau     120

gccccuggag aaaugguggu ccucaccugu gacaccccug aagaagaugg uaucaccugg     180

accuuggacc agagcaguga ggucuuaggc ucuggcaaga cccugaccau ccaagucaaa     240
```

```
gaguuuggag augcuggcca guacaccugu cacaaaggag gcgagguucu aagccauucg    300

cuccugcugc uucacaagaa ggaagaugga auuuggucca cugauauuuu aaaggaccag    360

aaagaaccca agaauaagac cuuucuaaga ugcgaggcca agaauuauuc uggacguuuc    420

accugcuggu ggcugacgac aaucaguacu gauuugacau ucagugucaa gagcagcaga    480

ggcucuucug acccccaagg ggugacgugc ggagcugcua cacucucugc agagagaguc    540

agaggggaca acaaggagua ugaguacuca guggagugcc aggaggacag ugccugccca    600

gcugcugagg agagucugcc cauugagguc augguggaug ccguucacaa gcucaaguau    660

gagaacuaca ccagcagcuu cuucaucagg gacaucauca aaccugaccc acccaagaac    720

uugcagcuga agccauuaaa gaauucucgg cagguggagg ucagcuggga guacccugac    780

accuggagua cuccacauuc cuacuucucc cugacauucu gcguucaggu ccagggcaag    840

agcaagagag agaagaaaga uagagucuuc acggacaaga ccucagccac ggucaucugc    900

cgcaagaaug ccagcauuag cgugcgggcc caggaccgcu acuauagcuc aucuuggagc    960

gaaugggcau cugugcccug caguggcgga gggggcggag ggagcagagc ugugccuggg   1020

ggcagcagcc cugccuggac ucagugccag cagcuuucac agaagcucug cacacuggcc   1080

uggagugcac auccacuagu gggacacaug gaucuaagag aagagggaga ugaagagacu   1140

acaaaugaug uuccccauau ccagugugga gauggcugug acccccaagg acucagggac   1200

aacagucagu ucugcuugca aaggauccac cagggucuga ucuuuuauga gaagcugcua   1260

ggaucggaua uuuucacagg ggagccuucu cugcucccug auagcccugu gggccagcuu   1320

caugccuccc uacugggccu cagccaacuc cugcagccug agggucacca cugggagacu   1380

cagcagauuc caagccucag ucccagccag ccauggcagc gucuccuucu ccgcuucaag   1440

auccuucgca gccuccaggc cuuuguggcu guagccgccc gggucuuugc ccauggagca   1500

gcaacccuga guccc                                                    1515
```

```
<210> SEQ ID NO 142
<211> LENGTH: 1807
<212> TYPE: RNA
<213> ORGANISM: Homo sapiens
<220> FEATURE:
<221> NAME/KEY: misc_feature
<223> OTHER INFORMATION: Every A,C G and U = AMP, CMP, GMP and N1-psi
      -UMP, respectively
<220> FEATURE:
<221> NAME/KEY: misc_feature
<222> LOCATION: (1)..(1)
<223> OTHER INFORMATION: 7MeGpppG2'OMe at 5' end
<220> FEATURE:
<221> NAME/KEY: misc_feature
<222> LOCATION: (1)..(1807)
<223> OTHER INFORMATION: Full-length mRNA Nucleotide sequence (5 UTR,
      ORF, 3 UTR, mir-122-5p  polyA tail) of human IL-23 (IL-12p40
      subunit and IL-23p19 subunit linked by GS Linker)

<400> SEQUENCE: 142

ggaaauaaga gagaaaagaa gaguaagaag aaauauaaga gccaccaugu gucaccagca     60

guuggucauc ucuugguuuu cccugguauu ucuggcaucu ccccucgugg ccauauggga    120

acugaagaaa gauguuuaug ucguagaauu ggauugguau ccggaugccc cuggagaaau    180

gguggucuc accugugaca ccccugaaga agaugguauc accuggaccu uggaccagag    240

cagugagguc uuaggcucug gcaagacccu gaccauccaa gucaaagagu uuggagaugc    300

uggccaguac accugucaca aaggaggcga gguucuaagc cauucgcucc ugcugcuuca    360

caagaaggaa gauggaauuu gguccacuga uauuuuaaag gaccagaaag aacccaagaa    420
```

uaagaccuuu cuaagaugcg aggccaagaa uuauucugga cguuucaccu gcugguggcu 480
gacgacaauc aguacugauu ugacauucag ugucaagagc agcagaggcu cuucugaccc 540
ccaaggggug acgugcggag cugcuacacu cucugcagag agagucagag gggacaacaa 600
ggaguaugag uacucagugg agugccagga ggacagugcc ugcccagcug cugaggagag 660
ucugcccauu gaggucaugg uggaugccgu ucacaagcuc aaguaugaga acuacaccag 720
cagcuucuuc aucagggaca ucaucaaacc ugacccaccc aagaacuugc agcugaagcc 780
auuaaagaau ucucggcagg uggaggucag cugggaguac ccugacaccu ggaguacucc 840
acauuccuac uucucccuga cauucugcgu ucagguccag ggcaagagca agagagagaa 900
gaaagauaga gucuucacgg acaagaccuc agccacgguc aucugccgca agaaugccag 960
cauuagcgug cgggcccagg accgcuacua uagcucaucu uggagcgaau gggcaucugu 1020
gcccugcagu ggcggagggg gcggagggag cagagcugug ccugggggca gcagcccugc 1080
cuggacucag ugccagcagc uuucacagaa gcucugcaca cuggccugga gugcacaucc 1140
acuaguggga cacauggauc uaagagaaga gggagaugaa gagacuacaa augauguucc 1200
ccauauccag uguggagaug gcugugaccc ccaaggacuc agggacaaca gucaguucug 1260
cuugcaaagg auccaccagg gucugaucuu uuaugagaag cugcuaggau cggauauuuu 1320
cacaggggag ccuucucugc ucccugauag cccugugggc cagcuucaug ccucccuacu 1380
gggccucagc caacuccugc agccugaggg ucaccacugg gagacucagc agauuccaag 1440
ccucaguccc agccagccau ggcagcgucu ccuucuccgc uucaagaucc uucgcagccu 1500
ccaggccuuu guggcuguag ccgcccgggu cuuugcccau ggagcagcaa cccugagucc 1560
cugauaauag gcuggagccu cgguggccau gcuucuugcc ccuugggccu ccccccagcc 1620
ccuccucccc uuccugcacc cguacccccc aaacaccauu gucacacucc aguggucuuu 1680
gaauaaaguc ugagugggcg gcaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaucuag 1807

<210> SEQ ID NO 143
<211> LENGTH: 516
<212> TYPE: RNA
<213> ORGANISM: Homo sapiens
<220> FEATURE:
<221> NAME/KEY: misc_feature
<222> LOCATION: (1)..(516)
<223> OTHER INFORMATION: Human IL-36-gamma mRNA (ORF)

<400> SEQUENCE: 143
augguguugc agacccaggu cuucauuucu cuguugcucu ggaucucugg ugccuacggg 60
ucaaugugua aaccuauuac ugggacuauu aaugauuuga aucagcaagu guggacccuu 120
cagggucaga accuuguggc aguuccacga agugacagug ugaccccagu cacuguugcu 180
guuaucacau gcaaguaucc agaggcucuu gagcaaggca gaggggaucc cauuuauuug 240
ggaauccaga auccagaaau guguuuguau ugugagaagg uuggagaaca gcccacauug 300
cagcuaaaag agcagaagau cauggaucug uauggccaac ccgagcccgu gaaacccuuc 360
cuuuucuacc gugccaagac ugguaggacc uccacccuug agucuguggc cuucccggac 420
ugguucauug ccuccuccaa gagagaccag cccaucauuc ugacuucaga acuugggaag 480
ucauacaaca cugccuuuga auuaaauaua aaugac 516

<210> SEQ ID NO 144
<211> LENGTH: 808
<212> TYPE: RNA
<213> ORGANISM: Homo sapiens
<220> FEATURE:
<221> NAME/KEY: misc_feature
<223> OTHER INFORMATION: Every A,C G and U = AMP, CMP, GMP and N1-psi -UMP, respectively
<220> FEATURE:
<221> NAME/KEY: misc_feature
<222> LOCATION: (1)..(1)
<223> OTHER INFORMATION: 7MeGpppG2'OMe at 5' end
<220> FEATURE:
<221> NAME/KEY: misc_feature
<222> LOCATION: (1)..(808)
<223> OTHER INFORMATION: Full-length mRNA Nucleotide sequence (5 UTR, ORF, 3 UTR, mir-122-5p polyA tail) of human IL-36-gamma

<400> SEQUENCE: 144

```
ggaaauaaga gagaaaagaa gaguaagaag aaauauaaga gccaccaugg uguugcagac     60

ccaggucuuc auuucucugu ugcucuggau cucuggugcc uacgggucaa uguguaaacc    120

uauuacuggg acuauuaaug auuugaauca gcaagugugg acccuucagg gucagaaccu    180

uguggcaguu ccacgaagug acagugugac cccagucacu guugcuguua ucacaugcaa    240

guauccagag gcucuugagc aaggcagagg ggaucccauu uauuugggaa uccagaaucc    300

agaaaugugu uuguauugug agaagguugg agaacagccc acauugcagc uaaaagagca    360

gaagaucaug gaucuguaug gccaacccga gcccgugaaa cccuuccuuu ucuaccgugc    420

caagacuggu aggaccucca cccuugaguc uguggccuuc ccggacuggu ucauugccuc    480

cuccaagaga gaccagccca ucauucugac uucagaacuu gggaagucau acaacacugc    540

cuuugaauua aauauaaaug acugauaaua ggcuggagcc ucgguggcca ugcuucuugc    600

cccuugggcc ucccccagc cccuccuccc cuuccugcac ccguaccccc caaacaccau    660

ugucacacuc caguggucuu ugaauaaagu cugagugggc ggcaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaucuag                                       808
```

<210> SEQ ID NO 145
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: Human OX40L mRNA (ORF)

<400> SEQUENCE: 145

```
auggaaaggg uccaaccccu ggaagagaau gugggaaaug cagccaggcc aagauucgag     60

aggaacaagc uauugcuggu ggccucugua auucagggac uggggcugcu ccugugcuuc    120

accuacaucu gccugcacuu cucugcucuu cagguaucac aucgguaucc ucgaauucaa    180

aguaucaaag uacaauuuac cgaauauaag aaggagaaag guuucauccu cacuucccaa    240

aaggaggaug aaaucaugaa ggugcagaac aacucaguca ucaucaacug ugaugggguuu    300

uaucucaucu cccugaaggg cuacuucucc caggaaguca acauuagccu ucauuaccag    360

aaggaugagg agccccucuu ccaacugaag aaggucaggu cugucaacuc cuugauggug    420

gccucucuga cuuacaaaga caaagucuac uugaauguga ccacugacaa uaccucccug    480

gaugacuucc augugaaugg cggagaacug auucuuaucc aucaaaaucc uggugaauuc    540
```

```
ugugucccuu                                                            549


<210> SEQ ID NO 146
<211> LENGTH: 841
<212> TYPE: RNA
<213> ORGANISM: Homo sapiens
<220> FEATURE:
<221> NAME/KEY: misc_feature
<223> OTHER INFORMATION: Every A,C G and U = AMP, CMP, GMP and N1-psi
      -UMP, respectively
<220> FEATURE:
<221> NAME/KEY: misc_feature
<222> LOCATION: (1)..(1)
<223> OTHER INFORMATION: 7MeGpppG2'OMe at 5' end
<220> FEATURE:
<221> NAME/KEY: misc_feature
<222> LOCATION: (1)..(841)
<223> OTHER INFORMATION: Full-length mRNA Nucleotide sequence (5 UTR,
      ORF, 3 UTR, miR-122-5p polyA tail) of human OX40L

<400> SEQUENCE: 146

ggaaauaaga gagaaaagaa gaguaagaag aaauauaaga gccaccaugg aaagggucca      60

accccuggaa gagaaugugg gaaaugcagc caggccaaga uucgagagga acaagcuauu     120

gcugguggcc ucuguaauuc agggacuggg gcugcuccug ugcuucaccu acaucugccu     180

gcacuucucu gcucuucagg uaucacaucg guauccucga auucaaagua ucaaaguaca     240

auuuaccgaa uauaagaagg agaaagguuu cauccucacu ucccaaaagg aggaugaaau     300

caugaaggug cagaacaacu cagucaucau caacugugau ggguuuuauc ucaucucccu     360

gaagggcuac uucucccagg aagucaacau uagccuucau uaccagaagg augaggagcc     420

ccucuuccaa cugaagaagg ucaggucugu caacuccuug augguggccu cucugacuua     480

caaagacaaa gucuacuuga augugaccac ugacaauacc ucccuggaug acuuccaugu     540

gaauggcgga gaacugauuc uuauccauca aaauccuggu gaauucugug uccuuugaua     600

auaggcugga gccucggugg ccaugcuucu ugccccuugg gccucccccc agccccuccu     660

ccccuuccug cacccguacc ccccaaacac cauugucaca cuccaguggu cuuugaauaa     720

agucugagug ggcggcaaaa aaaaaaaaaa aaaaaaaaaa aaaaaaaaaa aaaaaaaaaa     780

aaaaaaaaaa aaaaaaaaaa aaaaaaaaaa aaaaaaaaaa aaaaaaaaaa aaaaaaucua     840

g                                                                     841


<210> SEQ ID NO 147
<211> LENGTH: 193
<212> TYPE: PRT
<213> ORGANISM: Homo sapiens
<220> FEATURE:
<221> NAME/KEY: misc_feature
<222> LOCATION: (1)..(193)
<223> OTHER INFORMATION: Human IL 18 isoform 1

<400> SEQUENCE: 147

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80
```

Thr Ile Phe Ile Ile Ser Met Tyr Lys Asp Ser Gln Pro Arg Gly Met
85 90 95

Ala Val Thr Ile Ser Val Lys Cys Glu Lys Ile Ser Thr Leu Ser Cys
100 105 110

Glu Asn Lys Ile Ile Ser Phe Lys Glu Met Asn Pro Pro Asp Asn Ile
115 120 125

Lys Asp Thr Lys Ser Asp Ile Ile Phe Phe Gln Arg Ser Val Pro Gly
130 135 140

His Asp Asn Lys Met Gln Phe Glu Ser Ser Ser Tyr Glu Gly Tyr Phe
145 150 155 160

Leu Ala Cys Glu Lys Glu Arg Asp Leu Phe Lys Leu Ile Leu Lys Lys
165 170 175

Glu Asp Glu Leu Gly Asp Arg Ser Ile Met Phe Thr Val Gln Asn Glu
180 185 190

Asp

<210> SEQ ID NO 148
<211> LENGTH: 579
<212> TYPE: DNA
<213> ORGANISM: Homo sapiens
<220> FEATURE:
<221> NAME/KEY: misc_feature
<222> LOCATION: (1)..(579)
<223> OTHER INFORMATION: Nucleotide sequence of IL-18 isoform 1 (Precursor)

<400> SEQUENCE: 148
atggctgctg aaccagtaga agacaattgc atcaactttg tggcaatgaa atttattgac 60
aatacgcttt actttatagc tgaagatgat gaaaacctgg aatcagatta ctttggcaag 120
cttgaatcta aattatcagt cataagaaat ttgaatgacc aagttctctt cattgaccaa 180
ggaaatcggc ctctatttga agatatgact gattctgact gtagagataa tgcaccccgg 240
accatattta ttataagtat gtataaagat agccagccta gaggtatggc tgtaactatc 300
tctgtgaagt gtgagaaaat ttcaactctc tcctgtgaga acaaaattat ttcctttaag 360
gaaatgaatc ctcctgataa catcaaggat acaaaaagtg acatcatatt ctttcagaga 420
agtgtcccag gacatgataa taagatgcaa tttgaatctt catcatacga aggatacttt 480
ctagcttgtg aaaaagagag agaccttttt aaactcattt tgaaaaaaga ggatgaattg 540
ggggatagat ctataatgtt cactgttcaa aacgaagac 579

<210> SEQ ID NO 149
<211> LENGTH: 157
<212> TYPE: PRT
<213> ORGANISM: Homo sapiens
<220> FEATURE:
<221> NAME/KEY: misc_feature
<222> LOCATION: (1)..(157)
<223> OTHER INFORMATION: Amino acid sequence of IL-18 isoform 1 (Mature)

<400> SEQUENCE: 149

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile

```
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 150

<400> SEQUENCE: 150

000


<210> SEQ ID NO 151
<211> LENGTH: 189
<212> TYPE: PRT
<213> ORGANISM: Homo sapiens
<220> FEATURE:
<221> NAME/KEY: misc_feature
<222> LOCATION: (1)..(189)
<223> OTHER INFORMATION: Amino acid sequence of isoform 2,
      Delta3pro-IL-18, 27-30 missing (Precursor)

<400> SEQUENCE: 151

Met Ala Ala Glu Pro Val Glu Asp Asn Cys Ile Asn Phe Val Ala Met
1               5                   10                  15

Lys Phe Ile Asp Asn Thr Leu Tyr Phe Ile Glu Asn Leu Glu Ser Asp
            20                  25                  30

Tyr Phe Gly Lys Leu Glu Ser Lys Leu Ser Val Ile Arg Asn Leu Asn
        35                  40                  45

Asp Gln Val Leu Phe Ile Asp Gln Gly Asn Arg Pro Leu Phe Glu Asp
    50                  55                  60

Met Thr Asp Ser Asp Cys Arg Asp Asn Ala Pro Arg Thr Ile Phe Ile
65                  70                  75                  80

Ile Ser Met Tyr Lys Asp Ser Gln Pro Arg Gly Met Ala Val Thr Ile
                85                  90                  95

Ser Val Lys Cys Glu Lys Ile Ser Thr Leu Ser Cys Glu Asn Lys Ile
            100                 105                 110

Ile Ser Phe Lys Glu Met Asn Pro Pro Asp Asn Ile Lys Asp Thr Lys
        115                 120                 125

Ser Asp Ile Ile Phe Phe Gln Arg Ser Val Pro Gly His Asp Asn Lys
    130                 135                 140

Met Gln Phe Glu Ser Ser Ser Tyr Glu Gly Tyr Phe Leu Ala Cys Glu
145                 150                 155                 160

Lys Glu Arg Asp Leu Phe Lys Leu Ile Leu Lys Lys Glu Asp Glu Leu
                165                 170                 175

Gly Asp Arg Ser Ile Met Phe Thr Val Gln Asn Glu Asp
            180                 185


<210> SEQ ID NO 152
```

<400> SEQUENCE: 152

000

<210> SEQ ID NO 153
<211> LENGTH: 157
<212> TYPE: PRT
<213> ORGANISM: Homo sapiens
<220> FEATURE:
<221> NAME/KEY: misc_feature
<222> LOCATION: (1)..(157)
<223> OTHER INFORMATION: Amino acid sequence of IL-18 isoform 2 (Mature)

<400> SEQUENCE: 153

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 154

<400> SEQUENCE: 154

000

<210> SEQ ID NO 155
<211> LENGTH: 531
<212> TYPE: DNA
<213> ORGANISM: Artificial Sequence
<220> FEATURE:
<223> OTHER INFORMATION: Synthetic: Codon optimized sequence

<400> SEQUENCE: 155

```
atgtacagga tgcaactcct gtcttgcatt gcactaagtc ttgcacttgt cacaaacagt      60

tactttggca agcttgaatc taaattatca gtcataagaa atttgaatga ccaagttctc     120

ttcattgacc aaggaaatcg gcctctattt gaagatatga ctgattctga ctgtagagat     180

aatgcacccc ggaccatatt tattataagt atgtataaag atagccagcc tagaggtatg     240

gctgtaacta tctctgtgaa gtgtgagaag atttcaactc tctcctgtga gaacaagatt     300

atttccttta aggaaatgaa tcctcctgat aacatcaagg atacaaagag tgacatcata     360

ttctttcaga gaagtgtccc aggacatgat aataagatgc aatttgaatc ttcatcatac     420

gaaggatact ttctagcttg tgagaaagag agagacctgt ttaaactcat tttgaagaaa     480
```

gaggatgaat tgggcgatag atctataatg ttcactgttc agaacgaaga c 531

<210> SEQ ID NO 156
<211> LENGTH: 546
<212> TYPE: DNA
<213> ORGANISM: Artificial Sequence
<220> FEATURE:
<223> OTHER INFORMATION: Synthetic: Codon optimized sequence

<400> SEQUENCE: 156
atggaaatct gcagaggcct ccgcagtcac ctaatcactc tcctcctctt cctgttccat 60
tcagagacga tctgctactt tggcaagctt gaatctaaat tatcagtcat aagaaatttg 120
aatgaccaag ttctcttcat tgaccaagga aatcggcctc tatttgaaga tatgactgat 180
tctgactgta gagataatgc accccggacc atatttatta taagtatgta taaagatagc 240
cagcctagag gtatggctgt aactatctct gtgaagtgtg agaagatttc aactctctcc 300
tgtgagaaca agattatttc ctttaaggaa atgaatcctc ctgataacat caaggataca 360
aagagtgaca tcatattctt tcagagaagt gtcccaggac atgataataa gatgcaattt 420
gaatcttcat catacgaagg atactttcta gcttgtgaga aagagagaga cctgtttaaa 480
ctcattttga agaaagagga tgaattgggc gatagatcta taatgttcac tgttcagaac 540
gaagac 546

<210> SEQ ID NO 157
<211> LENGTH: 546
<212> TYPE: DNA
<213> ORGANISM: Artificial Sequence
<220> FEATURE:
<223> OTHER INFORMATION: Synthetic: Codon optimized sequence

<400> SEQUENCE: 157
atggaaatct gcagaggcct ccgcagtcac ctaatcactc tcctcctctt cctgttccat 60
tcagagacga tctgctactt tggcaagctt gaatctaaat tatcagtcat aagaaatttg 120
aatgaccaag ttctcttcat tgaccaagga aatcggcctc tatttgaaga tatgactgat 180
tctgactgta gagataatgc accccggacc atatttatta taagtatgta taaagatagc 240
cagcctagag gtatggctgt aactatctct gtgaagtgtg agaaaatttc aactctctcc 300
tgtgagaaca aaattatttc ctttaaggaa atgaatcctc ctgataacat caaggataca 360
aagagtgaca tcatattctt tcagagaagt gtcccaggac atgataataa gatgcaattt 420
gaatcttcat catacgaagg atactttcta gcttgtgaga aagagagaga ccttttttaaa 480 ctcattttga agaaagagga tgaattgggg gatagatcta taatgttcac tgttcaaaac 540
gaagac 546

<210> SEQ ID NO 158
<211> LENGTH: 531
<212> TYPE: DNA
<213> ORGANISM: Artificial Sequence
<220> FEATURE:
<223> OTHER INFORMATION: Synthetic: Codon optimized sequence

<400> SEQUENCE: 158
atggcctgga ccgttctcct cctcggcctc ctctctcact gcacaggctc tgtgacctcc 60
tactttggca agcttgaatc taaattatca gtcataagaa atttgaatga ccaagttctc 120
ttcattgacc aaggaaatcg gcctctattt gaagatatga ctgattctga ctgtagagat 180
aatgcacccc ggaccatatt tattataagt atgtataaag atagccagcc tagaggtatg 240
gctgtaacta tctctgtgaa gtgtgagaaa atttcaactc tctcctgtga gaacaaaatt 300
atttccttta aggaaatgaa tcctcctgat aacatcaagg atacaaagag tgacatcata 360
ttctttcaga gaagtgtccc aggacatgat aataagatgc aatttgaatc ttcatcatac 420
gaaggatact ttctagcttg tgagaaagag agagaccttt ttaaactcat tttgaagaaa 480
gaggatgaat tgggggatag atctataatg ttcactgttc aaaacgaaga c 531

<210> SEQ ID NO 159
<211> LENGTH: 531
<212> TYPE: DNA
<213> ORGANISM: Artificial Sequence
<220> FEATURE:
<223> OTHER INFORMATION: Synthetic: Codon optimized sequence

<400> SEQUENCE: 159
atgtacagga tgcaactcct gtcttgcatt gcactaagtc ttgcacttgt cacaaacagt 60
tactttggca agcttgaatc taaattatca gtcataagaa atttgaatga ccaagttctc 120
ttcattgacc aaggaaatcg gcctctattt gaagatatga ctgattctga ctgtagagat 180
aatgcacccc ggaccatatt tattataagt atgtataaag atagccagcc tagaggtatg 240
gctgtaacta tctctgtgaa gtgtgagaaa atttcaactc tctcctgtga gaacaaaatt 300
atttccttta aggaaatgaa tcctcctgat aacatcaagg atacaaagag tgacatcata 360
ttctttcaga gaagtgtccc aggacatgat aataagatgc aatttgaatc ttcatcatac 420
gaaggatact ttctagcttg tgagaaagag agagaccttt ttaaactcat tttgaagaaa 480
gaggatgaat tgggggatag atctataatg ttcactgttc aaaacgaaga c 531

<210> SEQ ID NO 160
<211> LENGTH: 531
<212> TYPE: DNA
<213> ORGANISM: Artificial Sequence
<220> FEATURE:
<223> OTHER INFORMATION: Synthetic: Codon optimized sequence

<400> SEQUENCE: 160
atgtacagga tgcaactcct gtcttgcatt gcactaagtc ttgcacttgt cacaaacagt 60
tactttggca agcttgaatc taaattatca gtcataagaa atttgaatga ccaagttctc 120
ttcattgacc aaggaaatcg gcctctattt gaagatatga ctgattctga ctgtagagat 180
aatgcacccc ggaccatatt tattataagt atgtataaag atagccagcc tagaggtatg 240
gctgtaacta tctctgtgaa gtgtgagaaa atttcaactc tctcctgtga gaacaaaatt 300
atttccttta aggaaatgaa tcctcctgat aacatcaagg atacaaaaag tgacatcata 360
ttctttcaga gaagtgtccc aggacatgat aataagatgc aatttgaatc ttcatcatac 420
gaaggatact ttctagcttg tgaaaaagag agagaccttt ttaaactcat tttgaaaaaa 480
gaggatgaat tgggggatag atctataatg ttcactgttc aaaacgaaga c 531

<210> SEQ ID NO 161
<211> LENGTH: 579
<212> TYPE: DNA
<213> ORGANISM: Homo sapiens
<220> FEATURE:
<221> NAME/KEY: misc_feature
<222> LOCATION: (1)..(579)
<223> OTHER INFORMATION: human IL-18 nucleotide sequence

<400> SEQUENCE: 161

-continued

```
atggctgctg aaccagtaga agacaattgc atcaactttg tggcaatgaa atttattgac     60

aatacgcttt actttatagc tgaagatgat gaaaacctgg aatcagatta ctttggcaag    120

cttgaatcta aattatcagt cataagaaat ttgaatgacc aagttctctt cattgaccaa    180

ggaaatcggc ctctatttga agatatgact gattctgact gtagagataa tgcaccccgg    240

accatattta ttataagtat gtataaagat agccagccta gaggtatggc tgtaactatc    300

tctgtgaagt gtgagaaaat ttcaactctc tcctgtgaga acaaaattat ttcctttaag    360

gaaatgaatc ctcctgataa catcaaggat acaaaaagtg acatcatatt ctttcagaga    420

agtgtcccag gacatgataa taagatgcaa tttgaatctt catcatacga aggatacttt    480

ctagcttgtg aaaaagagag agaccttttt aaactcattt tgaaaaaaga ggatgaattg    540

ggggatagat ctataatgtt cactgttcaa aacgaagac                           579
```

<210> SEQ ID NO 162
<211> LENGTH: 531
<212> TYPE: DNA
<213> ORGANISM: Artificial Sequence
<220> FEATURE:
<223> OTHER INFORMATION: Synthetic: Codon optimized murine IL-18

<400> SEQUENCE: 162

```
atgtacagca tgcagctcgc atcctgtgtc acattgacac ttgtgctcct tgtcaacagc     60

aactttggcc gacttcactg tacaaccgca gtaatacgga atataaatga ccaagttctc    120

ttcgttgaca aaagacagcc tgtgttcgag gatatgactg atattgatca aagtgccagt    180

gaaccccaga ccagactgat aatatacatg tacaaagaca gtgaagtaag aggactggct    240

gtgaccctct ctgtgaagga tagtaaaatg tctaccctct cctgtaagaa caagatcatt    300

tcctttgagg aaatggatcc acctgaaaat attgatgata tacaaagtga tctcatattc    360

tttcagaaac gtgttccagg acacaacaag atggagtttg aatcttcact gtatgaagga    420

cactttcttg cttgccaaaa ggaagatgat gctttcaaac tcattctgaa aaaaaaggat    480

gaaaatgggg ataaatctgt aatgttcact ctcactaact tacatcaaag t             531
```

<210> SEQ ID NO 163
<211> LENGTH: 25
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (6)..(25)
<223> OTHER INFORMATION: Repeats of "Glu Ala Ala Ala Lys" may or may not be present

<400> SEQUENCE: 163

```
Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25
```

<210> SEQ ID NO 164
<211> LENGTH: 15
<212> TYPE: PRT
<213> ORGANISM: Artificial Sequence
<220> FEATURE:
<223> OTHER INFORMATION: Synthetic: linker

<400> SEQUENCE: 164

-continued

Glu Ala Ala Ala Lys Glu Ala Ala Ala Lys Glu Ala Ala Ala Lys
1 5 10 15

<210> SEQ ID NO 165
<211> LENGTH: 5
<212> TYPE: PRT
<213> ORGANISM: Artificial Sequence
<220> FEATURE:
<223> OTHER INFORMATION: Synthetic: linker

<400> SEQUENCE: 165

Gly Gly Gly Gly Gly
1 5

<210> SEQ ID NO 166
<211> LENGTH: 6
<212> TYPE: PRT
<213> ORGANISM: Artificial Sequence
<220> FEATURE:
<223> OTHER INFORMATION: Synthetic: linker

<400> SEQUENCE: 166

Gly Gly Gly Gly Gly Gly
1 5

<210> SEQ ID NO 167
<211> LENGTH: 7
<212> TYPE: PRT
<213> ORGANISM: Artificial Sequence
<220> FEATURE:
<223> OTHER INFORMATION: Synthetic: linker

<400> SEQUENCE: 167

Gly Gly Gly Gly Gly Gly Gly
1 5

<210> SEQ ID NO 168
<211> LENGTH: 8
<212> TYPE: PRT
<213> ORGANISM: Artificial Sequence
<220> FEATURE:
<223> OTHER INFORMATION: Synthetic: linker

<400> SEQUENCE: 168

Gly Gly Gly Gly Gly Gly Gly Gly
1 5

<210> SEQ ID NO 169
<211> LENGTH: 16
<212> TYPE: PRT
<213> ORGANISM: Artificial Sequence
<220> FEATURE:
<223> OTHER INFORMATION: Synthetic: linker

<400> SEQUENCE: 169

Gly Gly Gly Gly Ser Leu Val Pro Arg Gly Ser Gly Gly Gly Gly Ser
1 5 10 15

<210> SEQ ID NO 170
<211> LENGTH: 6
<212> TYPE: PRT
<213> ORGANISM: Artificial Sequence
<220> FEATURE:
<223> OTHER INFORMATION: Synthetic: linker

<400> SEQUENCE: 170

Gly Ser Gly Ser Gly Ser 1 5

<210> SEQ ID NO 171
<211> LENGTH: 15
<212> TYPE: PRT
<213> ORGANISM: Artificial Sequence
<220> FEATURE:
<223> OTHER INFORMATION: Synthetic: linker

<400> SEQUENCE: 171

Gly Gly Gly Gly Ser Leu Val Pro Arg Gly Ser Gly Gly Gly Gly
1 5 10 15

<210> SEQ ID NO 172
<211> LENGTH: 11
<212> TYPE: PRT
<213> ORGANISM: Artificial Sequence
<220> FEATURE:
<223> OTHER INFORMATION: Synthetic: linker

<400> SEQUENCE: 172

Gly Gly Ser Gly Gly His Met Gly Ser Gly Gly
1 5 10

<210> SEQ ID NO 173
<211> LENGTH: 11
<212> TYPE: PRT
<213> ORGANISM: Artificial Sequence
<220> FEATURE:
<223> OTHER INFORMATION: Synthetic: linker

<400> SEQUENCE: 173

Gly Gly Ser Gly Gly Ser Gly Gly Ser Gly Gly
1 5 10

<210> SEQ ID NO 174
<211> LENGTH: 5
<212> TYPE: PRT
<213> ORGANISM: Artificial Sequence
<220> FEATURE:
<223> OTHER INFORMATION: Synthetic: linker

<400> SEQUENCE: 174

Gly Gly Ser Gly Gly
1 5

<210> SEQ ID NO 175
<211> LENGTH: 8
<212> TYPE: PRT
<213> ORGANISM: Artificial Sequence
<220> FEATURE:
<223> OTHER INFORMATION: Synthetic: linker

<400> SEQUENCE: 175

Gly Ser Gly Ser Gly Ser Gly Ser
1 5

<210> SEQ ID NO 176
<211> LENGTH: 18
<212> TYPE: PRT
<213> ORGANISM: Artificial Sequence
<220> FEATURE:
<223> OTHER INFORMATION: Synthetic: linker

<400> SEQUENCE: 176

Gly Gly Gly Ser Glu Gly Gly Gly Ser Glu Gly Gly Gly Ser Glu Gly
1 5 10 15

Gly Gly

<210> SEQ ID NO 177
<211> LENGTH: 8
<212> TYPE: PRT
<213> ORGANISM: Artificial Sequence
<220> FEATURE:
<223> OTHER INFORMATION: Synthetic: linker

<400> SEQUENCE: 177

Ala Ala Gly Ala Ala Thr Ala Ala
1 5

<210> SEQ ID NO 178
<211> LENGTH: 5
<212> TYPE: PRT
<213> ORGANISM: Artificial Sequence
<220> FEATURE:
<223> OTHER INFORMATION: Synthetic: linker

<400> SEQUENCE: 178

Gly Gly Ser Ser Gly
1 5

<210> SEQ ID NO 179
<211> LENGTH: 11
<212> TYPE: PRT
<213> ORGANISM: Artificial Sequence
<220> FEATURE:
<223> OTHER INFORMATION: Synthetic: linker

<400> SEQUENCE: 179

Gly Ser Gly Gly Gly Thr Gly Gly Gly Ser Gly
1 5 10

<210> SEQ ID NO 180
<211> LENGTH: 12
<212> TYPE: PRT
<213> ORGANISM: Artificial Sequence
<220> FEATURE:
<223> OTHER INFORMATION: Synthetic: linker

<400> SEQUENCE: 180

Gly Ser Gly Ser Gly Ser Gly Ser Gly Gly Ser Gly
1 5 10

<210> SEQ ID NO 181
<211> LENGTH: 14
<212> TYPE: PRT
<213> ORGANISM: Artificial Sequence
<220> FEATURE:
<223> OTHER INFORMATION: Synthetic: linker

<400> SEQUENCE: 181

Gly Ser Gly Gly Ser Gly Ser Gly Gly Ser Gly Gly Ser Gly
1 5 10

<210> SEQ ID NO 182
<211> LENGTH: 14
<212> TYPE: PRT
<213> ORGANISM: Artificial Sequence
<220> FEATURE:
<223> OTHER INFORMATION: Synthetic: linker

<400> SEQUENCE: 182

Gly Ser Gly Gly Ser Gly Gly Ser Gly Gly Ser Gly Gly Ser 1 5 10

<210> SEQ ID NO 183
<211> LENGTH: 1596
<212> TYPE: RNA
<213> ORGANISM: Homo sapiens
<220> FEATURE:
<221> NAME/KEY: misc_feature
<222> LOCATION: (1)..(1596)
<223> OTHER INFORMATION: mRNA ORF for human IL-12

<400> SEQUENCE: 183
augugccacc agcagcuggu gaucagcugg uucagccugg uguuccuggc cagcccccug 60
guggccaucu gggagcugaa gaaggacgug uacguggugg aguuggauug guaccccgac 120
gcccccggcg agaugguggu gcugaccugc gacacccccg aggaggacgg caucaccugg 180
acccuggacc agagcagcga ggugcugggc agcggcaaga cccugaccau ccaggugaag 240
gaguucggcg acgccggcca guacaccugc cacaagggcg gcgaggugcu gagccacagc 300
cugcugcugc ugcacaagaa ggaggacggc aucuggagca ccgacauccu gaaggaccag 360
aaggagccca agaacaagac cuuccugaga ugcgaggcca agaacuacag cggcagauuc 420
accugcuggu ggcugaccac caucagcacc gaccugaccu ucagcgugaa gagcagcaga 480
ggcagcagcg acccccaggg cgugaccugc ggcgccgcca cccugagcgc cgagagagug 540
agaggcgaca acaaggagua cgaguacagc guggagugcc aggaagauag cgccugcccc 600
gccgccgagg agagccugcc caucgaggug augguggacg ccgugcacaa gcugaaguac 660
gagaacuaca ccagcagcuu cuucaucaga gauaucauca agcccgaccc ccccaagaac 720
cugcagcuga agccccugaa gaacagccgg cagguggagg ugagcuggga guaccccgac 780
accuggagca ccccccacag cuacuucagc cugaccuucu gcgugcaggu gcagggcaag 840
agcaagagag agaagaaaga uagaguguuc accgacaaga ccagcgccac cgugaucugc 900
agaaagaacg ccagcaucag cgugagagcc caagauagau acuacagcag cagcuggagc 960
gagugggcca gcgugcccug cagcggcggc ggcggcggcg gcagcagaaa ccugcccgug 1020
gccacccccg accccggcau guuccccugc cugcaccaca gccagaaccu gcugagagcc 1080
gugagcaaca ugcugcagaa ggcccggcag acccuggagu ucuaccccug caccagcgag 1140
gagaucgacc acgaagauau caccaaagau aagaccagca ccguggaggc cugccugccc 1200
cuggagcuga ccaagaacga gagcugccug aacagcagag agaccagcuu caucaccaac 1260
ggcagcugcc uggccagcag aaagaccagc uucaugaugg cccugugccu gagcagcauc 1320
uacgaggacc ugaagaugua ccagguggag uucaagacca ugaacgccaa gcugcugaug 1380
gaccccaagc ggcagaucuu ccuggaccag aacaugcugg ccgugaucga cgagcugaug 1440
caggcccuga acuucaacag cgagaccgug ccccagaaga gcagccugga ggagcccgac 1500
uucuacaaga ccaagaucaa gcugugcauc cugcugcacg ccuucagaau cagagccgug 1560
accaucgaca gagugaugag cuaccugaac gccagc 1596

<210> SEQ ID NO 184
<211> LENGTH: 306
<212> TYPE: PRT
<213> ORGANISM: Artificial Sequence
<220> FEATURE:
<223> OTHER INFORMATION: Synthetic: Wildtype IL12B without signal amino acids

<400> SEQUENCE: 184

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 185
<211> LENGTH: 918
<212> TYPE: DNA
<213> ORGANISM: Artificial Sequence
<220> FEATURE:
<223> OTHER INFORMATION: Synthetic: Wildtype IL12B without signal nucleic acids

<400> SEQUENCE: 185

```
atatgggaac tgaagaaaga tgtttatgtc gtagaattgg attggtatcc ggatgcccct      60

ggagaaatgg tggtcctcac ctgtgacacc cctgaagaag atggtatcac ctggaccttg     120

gaccagagca gtgaggtctt aggctctggc aaaaccctga ccatccaagt caaagagttt     180

ggagatgctg gccagtacac ctgtcacaaa ggaggcgagg ttctaagcca ttcgctcctg     240
```

-continued

```
ctgcttcaca aaaaggaaga tggaatttgg tccactgata ttttaaagga ccagaaagaa    300

cccaaaaata agacctttct aagatgcgag gccaagaatt attctggacg tttcacctgc    360

tggtggctga cgacaatcag tactgatttg acattcagtg tcaaaagcag cagaggctct    420

tctgaccccc aaggggtgac gtgcggagct gctacactct ctgcagagag agtcagaggg    480

gacaacaagg agtatgagta ctcagtggag tgccaggagg acagtgcctg cccagctgct    540

gaggagagtc tgcccattga ggtcatggtg gatgccgttc acaagctcaa gtatgaaaac    600

tacaccagca gcttcttcat cagggacatc atcaaacctg acccacccaa gaacttgcag    660

ctgaagccat taaagaattc tcggcaggtg gaggtcagct gggagtaccc tgacacctgg    720

agtactccac attcctactt ctccctgaca ttctgcgttc aggtccaggg caagagcaag    780

agagaaaaga aagatagagt cttcacggac aagacctcag ccacggtcat ctgccgcaaa    840

aatgccagca ttagcgtgcg ggcccaggac cgctactata gctcatcttg gagcgaatgg    900

gcatctgtgc cctgcagt                                                  918
```

```
<210> SEQ ID NO 186
<211> LENGTH: 197
<212> TYPE: PRT
<213> ORGANISM: Artificial Sequence
<220> FEATURE:
<223> OTHER INFORMATION: Synthetic: Wildtype IL12A without signal amino
      acids

<400> SEQUENCE: 186

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 187
<211> LENGTH: 591
<212> TYPE: DNA
<213> ORGANISM: Artificial Sequence
```

<220> FEATURE:
<223> OTHER INFORMATION: Synthetic: Wildtype IL12A without signal nucleic acids

<400> SEQUENCE: 187
agaaacctcc ccgtggccac tccagaccca ggaatgttcc catgccttca ccactcccaa 60
aacctgctga gggccgtcag caacatgctc cagaaggcca gacaaactct agaattttac 120
ccttgcactt ctgaagagat tgatcatgaa gatatcacaa aagataaaac cagcacagtg 180
gaggcctgtt taccattgga attaaccaag aatgagagtt gcctaaattc cagagagacc 240
tctttcataa ctaatgggag ttgcctggcc tccagaaaga cctcttttat gatggccctg 300
tgccttagta gtatttatga agacttgaag atgtaccagg tggagttcaa gaccatgaat 360
gcaaagcttc tgatggatcc taagaggcag atctttctag atcaaaacat gctggcagtt 420
attgatgagc tgatgcaggc cctgaatttc aacagtgaga ctgtgccaca aaaatcctcc 480
cttgaagaac cggattttta taaaactaaa atcaagctct gcatacttct tcatgctttc 540
agaattcggg cagtgactat tgatagagtg atgagctatc tgaatgcttc c 591

<210> SEQ ID NO 188
<211> LENGTH: 22
<212> TYPE: PRT
<213> ORGANISM: Artificial Sequence
<220> FEATURE:
<223> OTHER INFORMATION: Synthetic: Wildtype IL12B signal peptide amino acids

<400> SEQUENCE: 188

Met Cys His Gln Gln Leu Val Ile Ser Trp Phe Ser Leu Val Phe Leu
1 5 10 15

Ala Ser Pro Leu Val Ala
20

<210> SEQ ID NO 189
<211> LENGTH: 66
<212> TYPE: DNA
<213> ORGANISM: Artificial Sequence
<220> FEATURE:
<223> OTHER INFORMATION: Synthetic: Wildtype IL12B signal peptide nucleoic acids

<400> SEQUENCE: 189
atgtgtcacc agcagttggt catctcttgg ttttccctgg tttttctggc atctcccctc 60
gtggcc 66

<210> SEQ ID NO 190
<211> LENGTH: 10
<212> TYPE: PRT
<213> ORGANISM: Artificial Sequence
<220> FEATURE:
<223> OTHER INFORMATION: Synthetic: linker

<400> SEQUENCE: 190

Gly Gly Ser Gly Gly Gly Gly Ser Gly Gly
1 5 10

<210> SEQ ID NO 191
<211> LENGTH: 8
<212> TYPE: PRT
<213> ORGANISM: Artificial Sequence
<220> FEATURE:
<223> OTHER INFORMATION: Synthetic: linker

<400> SEQUENCE: 191

Gly Gly Ser Gly Gly Gly Gly Gly
1               5

<210> SEQ ID NO 192
<211> LENGTH: 8
<212> TYPE: PRT
<213> ORGANISM: Artificial Sequence
<220> FEATURE:
<223> OTHER INFORMATION: Synthetic: linker

<400> SEQUENCE: 192

Gly Ser Gly Ser Gly Ser Gly Ser
1               5

<210> SEQ ID NO 193
<211> LENGTH: 2100
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(2100)
<223> OTHER INFORMATION: For every repeat of "GGGGGGGGGG GGGGGGGGGG S", at least one "G" is present and the others may be absent; the repeat of "GGGGGGGGGG GGGGGGGGGG S" is present at least once and may repeat up to 100 times or be absent

<400> SEQUENCE: 193

Gly Gly Gly Gly Gly Gly Gly Gly Gly Gly Gly Gly Gly Gly Gly Gly
1               5                   10                  15

Gly Gly Gly Gly Ser Gly Gly Gly Gly Gly Gly Gly Gly Gly Gly Gly
            20                  25                  30

Gly Gly Gly Gly Gly Gly Gly Gly Gly Ser Gly Gly Gly Gly Gly Gly
        35                  40                  45

Gly Gly Gly Gly Gly Gly Gly Gly Gly Gly Gly Gly Gly Gly Ser Gly
    50                  55                  60

Gly Gly Gly Gly Gly Gly Gly Gly Gly Gly Gly Gly Gly Gly Gly Gly
65                  70                  75                  80

Gly Gly Gly Ser Gly Gly Gly Gly Gly Gly Gly Gly Gly Gly Gly Gly
                85                  90                  95

Gly Gly Gly Gly Gly Gly Gly Gly Ser Gly Gly Gly Gly Gly Gly Gly
            100                 105                 110

Gly Gly Gly Gly Gly Gly Gly Gly Gly Gly Gly Gly Gly Ser Gly Gly
        115                 120                 125

Gly Gly Gly Gly Gly Gly Gly Gly Gly Gly Gly Gly Gly Gly Gly Gly
    130                 135                 140

Gly Gly Ser Gly Gly Gly Gly Gly Gly Gly Gly Gly Gly Gly Gly Gly
145                 150                 155                 160

Gly Gly Gly Gly Gly Gly Gly Ser Gly Gly Gly Gly Gly Gly Gly Gly
                165                 170                 175

Gly Gly Gly Gly Gly Gly Gly Gly Gly Gly Gly Gly Ser Gly Gly Gly
            180                 185                 190

Gly Gly Gly Gly Gly Gly Gly Gly Gly Gly Gly Gly Gly Gly Gly Gly
        195                 200                 205

Gly Ser Gly Gly Gly Gly Gly Gly Gly Gly Gly Gly Gly Gly Gly Gly
    210                 215                 220

Gly Gly Gly Gly Gly Gly Ser Gly Gly Gly Gly Gly Gly Gly Gly Gly
225                 230                 235                 240

-continued

```
Gly Gly Gly Gly Gly Gly Gly Gly Gly Gly Gly Ser Gly Gly Gly Gly
                245                 250                 255

Gly Gly Gly Gly Gly Gly Gly Gly Gly Gly Gly Gly Gly Gly Gly Gly
            260                 265                 270

Ser Gly Gly Gly Gly Gly Gly Gly Gly Gly Gly Gly Gly Gly Gly Gly
        275                 280                 285

Gly Gly Gly Gly Gly Ser Gly Gly Gly Gly Gly Gly Gly Gly Gly Gly
    290                 295                 300

Gly Gly Gly Gly Gly Gly Gly Gly Gly Gly Ser Gly Gly Gly Gly Gly
305                 310                 315                 320

Gly Gly Gly Gly Gly Gly Gly Gly Gly Gly Gly Gly Gly Gly Gly Ser
                325                 330                 335

Gly Gly Gly Gly Gly Gly Gly Gly Gly Gly Gly Gly Gly Gly Gly Gly
            340                 345                 350

Gly Gly Gly Gly Ser Gly Gly Gly Gly Gly Gly Gly Gly Gly Gly Gly
        355                 360                 365

Gly Gly Gly Gly Gly Gly Gly Gly Gly Ser Gly Gly Gly Gly Gly Gly
    370                 375                 380

Gly Gly Gly Gly Gly Gly Gly Gly Gly Gly Gly Gly Gly Gly Ser Gly
385                 390                 395                 400

Gly Gly Gly Gly Gly Gly Gly Gly Gly Gly Gly Gly Gly Gly Gly Gly
                405                 410                 415

Gly Gly Gly Ser Gly Gly Gly Gly Gly Gly Gly Gly Gly Gly Gly Gly
            420                 425                 430

Gly Gly Gly Gly Gly Gly Gly Gly Ser Gly Gly Gly Gly Gly Gly Gly
        435                 440                 445

Gly Gly Gly Gly Gly Gly Gly Gly Gly Gly Gly Gly Gly Ser Gly Gly
    450                 455                 460

Gly Gly Gly Gly Gly Gly Gly Gly Gly Gly Gly Gly Gly Gly Gly Gly
465                 470                 475                 480

Gly Gly Ser Gly Gly Gly Gly Gly Gly Gly Gly Gly Gly Gly Gly Gly
                485                 490                 495

Gly Gly Gly Gly Gly Gly Gly Ser Gly Gly Gly Gly Gly Gly Gly Gly
            500                 505                 510

Gly Gly Gly Gly Gly Gly Gly Gly Gly Gly Gly Gly Ser Gly Gly Gly
        515                 520                 525

Gly Gly Gly Gly Gly Gly Gly Gly Gly Gly Gly Gly Gly Gly Gly Gly
    530                 535                 540

Gly Ser Gly Gly Gly Gly Gly Gly Gly Gly Gly Gly Gly Gly Gly Gly
545                 550                 555                 560

Gly Gly Gly Gly Gly Gly Ser Gly Gly Gly Gly Gly Gly Gly Gly Gly
                565                 570                 575

Gly Gly Gly Gly Gly Gly Gly Gly Gly Gly Gly Ser Gly Gly Gly Gly
            580                 585                 590

Gly Gly Gly Gly Gly Gly Gly Gly Gly Gly Gly Gly Gly Gly Gly Gly
        595                 600                 605

Ser Gly Gly Gly Gly Gly Gly Gly Gly Gly Gly Gly Gly Gly Gly Gly
    610                 615                 620

Gly Gly Gly Gly Gly Ser Gly Gly Gly Gly Gly Gly Gly Gly Gly Gly
625                 630                 635                 640

Gly Gly Gly Gly Gly Gly Gly Gly Gly Gly Ser Gly Gly Gly Gly Gly
                645                 650                 655
```

-continued

Gly Gly Gly Gly Gly Gly Gly Gly Gly Gly Gly Gly Gly Gly Gly Ser
660 665 670

Gly Gly Gly Gly Gly Gly Gly Gly Gly Gly Gly Gly Gly Gly Gly Gly
675 680 685

Gly Gly Gly Gly Ser Gly Gly Gly Gly Gly Gly Gly Gly Gly Gly Gly
690 695 700

Gly Gly Gly Gly Gly Gly Gly Gly Gly Ser Gly Gly Gly Gly Gly Gly
705 710 715 720

Gly Gly Gly Gly Gly Gly Gly Gly Gly Gly Gly Gly Gly Gly Ser Gly
725 730 735

Gly Gly Gly Gly Gly Gly Gly Gly Gly Gly Gly Gly Gly Gly Gly Gly
740 745 750

Gly Gly Gly Ser Gly Gly Gly Gly Gly Gly Gly Gly Gly Gly Gly Gly
755 760 765

Gly Gly Gly Gly Gly Gly Gly Gly Ser Gly Gly Gly Gly Gly Gly Gly
770 775 780

Gly Gly Gly Gly Gly Gly Gly Gly Gly Gly Gly Gly Gly Ser Gly Gly
785 790 795 800

Gly Gly Gly Gly Gly Gly Gly Gly Gly Gly Gly Gly Gly Gly Gly Gly
805 810 815

Gly Gly Ser Gly Gly Gly Gly Gly Gly Gly Gly Gly Gly Gly Gly Gly
820 825 830

Gly Gly Gly Gly Gly Gly Gly Ser Gly Gly Gly Gly Gly Gly Gly Gly
835 840 845

Gly Gly Gly Gly Gly Gly Gly Gly Gly Gly Gly Gly Ser Gly Gly Gly
850 855 860

Gly Gly Gly Gly Gly Gly Gly Gly Gly Gly Gly Gly Gly Gly Gly Gly
865 870 875 880

Gly Ser Gly Gly Gly Gly Gly Gly Gly Gly Gly Gly Gly Gly Gly Gly
885 890 895

Gly Gly Gly Gly Gly Gly Ser Gly Gly Gly Gly Gly Gly Gly Gly Gly
900 905 910

Gly Gly Gly Gly Gly Gly Gly Gly Gly Gly Gly Ser Gly Gly Gly Gly
915 920 925

Gly Gly Gly Gly Gly Gly Gly Gly Gly Gly Gly Gly Gly Gly Gly Gly
930 935 940

Ser Gly Gly Gly Gly Gly Gly Gly Gly Gly Gly Gly Gly Gly Gly Gly
945 950 955 960

Gly Gly Gly Gly Gly Ser Gly Gly Gly Gly Gly Gly Gly Gly Gly Gly
965 970 975

Gly Gly Gly Gly Gly Gly Gly Gly Gly Gly Ser Gly Gly Gly Gly Gly
980 985 990

Gly Gly Gly Gly Gly Gly Gly Gly Gly Gly Gly Gly Gly Gly Gly Ser
995 1000 1005

Gly Gly Gly Gly Gly Gly Gly Gly Gly Gly Gly Gly Gly Gly Gly
1010 1015 1020

Gly Gly Gly Gly Gly Ser Gly Gly Gly Gly Gly Gly Gly Gly Gly
1025 1030 1035

Gly Gly Gly Gly Gly Gly Gly Gly Gly Gly Gly Ser Gly Gly Gly
1040 1045 1050

Gly Gly Gly Gly Gly Gly Gly Gly Gly Gly Gly Gly Gly Gly Gly
1055 1060 1065

Gly Gly Ser Gly Gly Gly Gly Gly Gly Gly Gly Gly Gly Gly Gly

```
    1070                1075                1080

Gly Gly  Gly Gly Gly Gly Gly  Gly Ser Gly Gly Gly  Gly Gly Gly
    1085                1090                1095

Gly Gly  Gly Gly Gly Gly Gly  Gly Gly Gly Gly Gly  Gly Gly Ser
    1100                1105                1110

Gly Gly  Gly Gly Gly Gly Gly  Gly Gly Gly Gly Gly  Gly Gly Gly
    1115                1120                1125

Gly Gly  Gly Gly Gly Ser Gly  Gly Gly Gly Gly Gly  Gly Gly Gly
    1130                1135                1140

Gly Gly  Gly Gly Gly Gly Gly  Gly Gly Gly Gly Ser  Gly Gly Gly
    1145                1150                1155

Gly Gly  Gly Gly Gly Gly Gly  Gly Gly Gly Gly Gly  Gly Gly Gly
    1160                1165                1170

Gly Gly  Ser Gly Gly Gly Gly  Gly Gly Gly Gly Gly  Gly Gly Gly
    1175                1180                1185

Gly Gly  Gly Gly Gly Gly Gly  Gly Ser Gly Gly Gly  Gly Gly Gly
    1190                1195                1200

Gly Gly  Gly Gly Gly Gly Gly  Gly Gly Gly Gly Gly  Gly Gly Ser
    1205                1210                1215

Gly Gly  Gly Gly Gly Gly Gly  Gly Gly Gly Gly Gly  Gly Gly Gly
    1220                1225                1230

Gly Gly  Gly Gly Gly Ser Gly  Gly Gly Gly Gly Gly  Gly Gly Gly
    1235                1240                1245

Gly Gly  Gly Gly Gly Gly Gly  Gly Gly Gly Gly Ser  Gly Gly Gly
    1250                1255                1260

Gly Gly  Gly Gly Gly Gly Gly  Gly Gly Gly Gly Gly  Gly Gly Gly
    1265                1270                1275

Gly Gly  Ser Gly Gly Gly Gly  Gly Gly Gly Gly Gly  Gly Gly Gly
    1280                1285                1290

Gly Gly  Gly Gly Gly Gly Gly  Gly Ser Gly Gly Gly  Gly Gly Gly
    1295                1300                1305

Gly Gly  Gly Gly Gly Gly Gly  Gly Gly Gly Gly Gly  Gly Gly Ser
    1310                1315                1320

Gly Gly  Gly Gly Gly Gly Gly  Gly Gly Gly Gly Gly  Gly Gly Gly
    1325                1330                1335

Gly Gly  Gly Gly Gly Ser Gly  Gly Gly Gly Gly Gly  Gly Gly Gly
    1340                1345                1350

Gly Gly  Gly Gly Gly Gly Gly  Gly Gly Gly Gly Ser  Gly Gly Gly
    1355                1360                1365

Gly Gly  Gly Gly Gly Gly Gly  Gly Gly Gly Gly Gly  Gly Gly Gly
    1370                1375                1380

Gly Gly  Ser Gly Gly Gly Gly  Gly Gly Gly Gly Gly  Gly Gly Gly
    1385                1390                1395

Gly Gly  Gly Gly Gly Gly Gly  Gly Ser Gly Gly Gly  Gly Gly Gly
    1400                1405                1410

Gly Gly  Gly Gly Gly Gly Gly  Gly Gly Gly Gly Gly  Gly Gly Ser
    1415                1420                1425

Gly Gly  Gly Gly Gly Gly Gly  Gly Gly Gly Gly Gly  Gly Gly Gly
    1430                1435                1440

Gly Gly  Gly Gly Gly Ser Gly  Gly Gly Gly Gly Gly  Gly Gly Gly
    1445                1450                1455

Gly Gly  Gly Gly Gly Gly Gly  Gly Gly Gly Gly Ser  Gly Gly Gly
    1460                1465                1470
```

```
Gly Gly Gly Gly Gly Gly Gly Gly Gly Gly Gly Gly Gly Gly Gly
    1475                1480                1485

Gly Gly Ser Gly Gly Gly Gly Gly Gly Gly Gly Gly Gly Gly Gly
    1490                1495                1500

Gly Gly Gly Gly Gly Gly Gly Gly Ser Gly Gly Gly Gly Gly Gly
    1505                1510                1515

Gly Gly Gly Gly Gly Gly Gly Gly Gly Gly Gly Gly Gly Gly Ser
    1520                1525                1530

Gly Gly Gly Gly Gly Gly Gly Gly Gly Gly Gly Gly Gly Gly Gly
    1535                1540                1545

Gly Gly Gly Gly Gly Ser Gly Gly Gly Gly Gly Gly Gly Gly Gly
    1550                1555                1560

Gly Gly Gly Gly Gly Gly Gly Gly Gly Gly Gly Ser Gly Gly Gly
    1565                1570                1575

Gly Gly Gly Gly Gly Gly Gly Gly Gly Gly Gly Gly Gly Gly Gly
    1580                1585                1590

Gly Gly Ser Gly Gly Gly Gly Gly Gly Gly Gly Gly Gly Gly Gly
    1595                1600                1605

Gly Gly Gly Gly Gly Gly Gly Gly Ser Gly Gly Gly Gly Gly Gly
    1610                1615                1620

Gly Gly Gly Gly Gly Gly Gly Gly Gly Gly Gly Gly Gly Gly Ser
    1625                1630                1635

Gly Gly Gly Gly Gly Gly Gly Gly Gly Gly Gly Gly Gly Gly Gly
    1640                1645                1650

Gly Gly Gly Gly Gly Ser Gly Gly Gly Gly Gly Gly Gly Gly Gly
    1655                1660                1665

Gly Gly Gly Gly Gly Gly Gly Gly Gly Gly Gly Ser Gly Gly Gly
    1670                1675                1680

Gly Gly Gly Gly Gly Gly Gly Gly Gly Gly Gly Gly Gly Gly Gly
    1685                1690                1695

Gly Gly Ser Gly Gly Gly Gly Gly Gly Gly Gly Gly Gly Gly Gly
    1700                1705                1710

Gly Gly Gly Gly Gly Gly Gly Gly Ser Gly Gly Gly Gly Gly Gly
    1715                1720                1725

Gly Gly Gly Gly Gly Gly Gly Gly Gly Gly Gly Gly Gly Gly Ser
    1730                1735                1740

Gly Gly Gly Gly Gly Gly Gly Gly Gly Gly Gly Gly Gly Gly Gly
    1745                1750                1755

Gly Gly Gly Gly Gly Ser Gly Gly Gly Gly Gly Gly Gly Gly Gly
    1760                1765                1770

Gly Gly Gly Gly Gly Gly Gly Gly Gly Gly Gly Ser Gly Gly Gly
    1775                1780                1785

Gly Gly Gly Gly Gly Gly Gly Gly Gly Gly Gly Gly Gly Gly Gly
    1790                1795                1800

Gly Gly Ser Gly Gly Gly Gly Gly Gly Gly Gly Gly Gly Gly Gly
    1805                1810                1815

Gly Gly Gly Gly Gly Gly Gly Gly Ser Gly Gly Gly Gly Gly Gly
    1820                1825                1830

Gly Gly Gly Gly Gly Gly Gly Gly Gly Gly Gly Gly Gly Gly Ser
    1835                1840                1845

Gly Gly Gly Gly Gly Gly Gly Gly Gly Gly Gly Gly Gly Gly Gly
    1850                1855                1860
```

```
Gly Gly  Gly Gly Gly Ser Gly  Gly Gly Gly Gly Gly  Gly Gly Gly
    1865                 1870                 1875

Gly Gly  Gly Gly Gly Gly Gly  Gly Gly Gly Gly Ser  Gly Gly Gly
    1880                 1885                 1890

Gly Gly  Gly Gly Gly Gly Gly  Gly Gly Gly Gly Gly  Gly Gly Gly
    1895                 1900                 1905

Gly Gly  Ser Gly Gly Gly Gly  Gly Gly Gly Gly Gly  Gly Gly Gly
    1910                 1915                 1920

Gly Gly  Gly Gly Gly Gly Gly  Gly Ser Gly Gly Gly  Gly Gly Gly
    1925                 1930                 1935

Gly Gly  Gly Gly Gly Gly Gly  Gly Gly Gly Gly Gly  Gly Gly Ser
    1940                 1945                 1950

Gly Gly  Gly Gly Gly Gly Gly  Gly Gly Gly Gly Gly  Gly Gly Gly
    1955                 1960                 1965

Gly Gly  Gly Gly Gly Ser Gly  Gly Gly Gly Gly Gly  Gly Gly Gly
    1970                 1975                 1980

Gly Gly  Gly Gly Gly Gly Gly  Gly Gly Gly Gly Ser  Gly Gly Gly
    1985                 1990                 1995

Gly Gly  Gly Gly Gly Gly Gly  Gly Gly Gly Gly Gly  Gly Gly Gly
    2000                 2005                 2010

Gly Gly  Ser Gly Gly Gly Gly  Gly Gly Gly Gly Gly  Gly Gly Gly
    2015                 2020                 2025

Gly Gly  Gly Gly Gly Gly Gly  Gly Ser Gly Gly Gly  Gly Gly Gly
    2030                 2035                 2040

Gly Gly  Gly Gly Gly Gly Gly  Gly Gly Gly Gly Gly  Gly Gly Ser
    2045                 2050                 2055

Gly Gly  Gly Gly Gly Gly Gly  Gly Gly Gly Gly Gly  Gly Gly Gly
    2060                 2065                 2070

Gly Gly  Gly Gly Gly Ser Gly  Gly Gly Gly Gly Gly  Gly Gly Gly
    2075                 2080                 2085

Gly Gly  Gly Gly Gly Gly Gly  Gly Gly Gly Gly Ser
    2090                 2095                 2100


<210> SEQ ID NO 194
<211> LENGTH: 4
<212> TYPE: PRT
<213> ORGANISM: Artificial Sequence
<220> FEATURE:
<223> OTHER INFORMATION: Synthetic: linker

<400> SEQUENCE: 194

Gly Gly Gly Ser
1


<210> SEQ ID NO 195
<211> LENGTH: 15
<212> TYPE: PRT
<213> ORGANISM: Artificial Sequence
<220> FEATURE:
<223> OTHER INFORMATION: Synthetic: linker

<400> SEQUENCE: 195

Glu Ala Ala Ala Lys Glu Ala Ala Ala Lys Glu Ala Ala Ala Lys
1               5                   10                  15


<210> SEQ ID NO 196
<211> LENGTH: 40
<212> TYPE: PRT
<213> ORGANISM: Artificial Sequence
```

-continued

```
<220> FEATURE:
<223> OTHER INFORMATION: Synthetic: linker
<220> FEATURE:
<221> NAME/KEY: misc_feature
<222> LOCATION: (2)..(40)
<223> OTHER INFORMATION: Gly may or may not be present

<400> SEQUENCE: 196

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly
        35                  40


<210> SEQ ID NO 197
<211> LENGTH: 20
<212> TYPE: DNA
<213> ORGANISM: Artificial Sequence
<220> FEATURE:
<223> OTHER INFORMATION: Synthetic: oligonucleotide
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 197

gnnnnwncrn ctcncnnwnd                                                  20


<210> SEQ ID NO 198
<211> LENGTH: 18
<212> TYPE: DNA
<213> ORGANISM: Artificial Sequence
<220> FEATURE:
<223> OTHER INFORMATION: Synthetic: oligonucleotide

<400> SEQUENCE: 198

attgggcacc cgtaaggg                                                    18
```